US008892364B2

(12) United States Patent
Glaser et al.

(10) Patent No.: US 8,892,364 B2
(45) Date of Patent: Nov. 18, 2014

(54) STABILIZED POLYPEPTIDE COMPOSITIONS

(75) Inventors: Scott Glaser, San Diego, CA (US); Stephen Demarest, San Diego, CA (US); Brian Robert Miller, San Diego, CA (US); William B. Snyder, Escondido, CA (US); Xiufeng Wu, San Diego, CA (US); Norman Wang, Honolulu, HI (US); Lisa J. Croner, San Diego, CA (US); Alexey Alexandrovich Lugovskoy, Woburn, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1748 days.

(21) Appl. No.: 11/894,057

(22) Filed: Aug. 17, 2007

(65) Prior Publication Data

US 2011/0301331 A1    Dec. 8, 2011

Related U.S. Application Data

(63) Continuation of application No. 11/725,970, filed on Mar. 19, 2007, now Pat. No. 7,951,918.

(60) Provisional application No. 60/783,622, filed on Mar. 17, 2006, provisional application No. 60/812,688, filed on Jun. 9, 2006, provisional application No. 60/873,802, filed on Dec. 8, 2006, provisional application No. 60/873,996, filed on Dec. 8, 2006.

(51) Int. Cl.
| | | |
|---|---|---|
| *G06F 17/00* | (2006.01) | |
| *C07K 16/00* | (2006.01) | |
| *C12N 5/10* | (2006.01) | |
| *G06F 19/16* | (2011.01) | |
| *G06F 19/22* | (2011.01) | |

(52) U.S. Cl.
CPC ............... *G06F 19/16* (2013.01); *G06F 19/22* (2013.01); *C07K 2317/34* (2013.01)
USPC ........ 702/19; 702/20; 530/387.3; 435/252.31

(58) Field of Classification Search
CPC ..................... C07K 2317/60; C07K 2317/515; C07K 2317/622
See application file for complete search history.

(56) References Cited

U.S. PATENT DOCUMENTS

| | | | |
|---|---|---|---|
| 5,637,481 A | 6/1997 | Ledbetter et al. | |
| 5,747,654 A | 5/1998 | Pastan et al. | |
| 5,854,027 A | 12/1998 | Steipe et al. | |
| 5,917,021 A | 6/1999 | Lee | |
| 5,958,784 A | 9/1999 | Benner et al. | |
| 5,990,275 A | 11/1999 | Whitlow et al. | |
| 6,132,992 A | 10/2000 | Ledbetter et al. | |
| 6,147,203 A | 11/2000 | Pastan et al. | |
| 6,262,238 B1 | 7/2001 | Steipe et al. | |
| 6,377,893 B1 | 4/2002 | Benner | |
| 6,482,919 B2 | 11/2002 | Ledbetter et al. | |
| 6,558,672 B1 | 5/2003 | Pastan et al. | |
| 7,799,902 B2 | 9/2010 | Browning et al. | |
| 2002/0012989 A1 | 1/2002 | Ledbetter et al. | |
| 2003/0219876 A1 | 11/2003 | Ledbetter et al. | |
| 2005/0038609 A1 | 2/2005 | Benner | |
| 2005/0163782 A1 | 7/2005 | Glaser et al. | |
| 2008/0050370 A1 | 2/2008 | Glaser et al. | |
| 2009/0048122 A1 | 2/2009 | Glaser et al. | |
| 2009/0130105 A1 | 5/2009 | Glaser et al. | |
| 2009/0155255 A1 | 6/2009 | Glaser et al. | |
| 2009/0162380 A1 | 6/2009 | Glaser et al. | |

FOREIGN PATENT DOCUMENTS

| | | |
|---|---|---|
| EP | 0610046 B1 | 12/2005 |
| WO | WO-88/01649 | 3/1988 |
| WO | WO-93/11161 | 6/1993 |
| WO | WO-96/02574 | 2/1996 |
| WO | WO 98/41641 A1 | 9/1998 |
| WO | WO 03/025018 A2 | 3/2003 |
| WO | WO 03/075129 | 9/2003 |
| WO | WO-03/075129 A2 | 9/2003 |
| WO | WO 2004/058191 A2 | 7/2004 |
| WO | WO 2005/121177 A2 | 12/2005 |

OTHER PUBLICATIONS

Hugo et al. Protein Science (2002), 11:2697-2705.*
Choulier et al. Proteins: Structure, Function, and Genetics 41:475-484, 2000.*
Yang et al J. Mol. Biol. (2000) 301, 665-678.*
Jennings et al. J. Mol. Biol., vol. 303:433-446 2000.*
Eddy et al. Bioinformatics, 14 (9), 755-763, 1998.*
Brown M. et al. "Tolerance to single, but not multiple, amino acid replacements in antibody VH CDR2," *J. Immunol.* 156:3285-3291, Williams & Wilkins Co., United States (1996).
Caldas C. et al. "Humanization of the anti-CD18 antibody 6.7: an unexpected effect of a framework residue in binding to antigen" *Mol. Immunol.* 39: 941-952, Pergamon Press, United States (2003).
Caronti B. et al. "Anti-beta 2-glycoprotein I antibodies bind to central nervous system." *J. Neurol. Sci.* 156: 211-9, Elsevier, Inc., The Netherlands (1998).
Halaby D.M. et al. "The immunoglobulin fold family: sequence analysis and 3D structure comparisons." *Protein Engineering* 12: 563-571, Oxford University Press, United Kingdom (1999).
Harrison A. et al. "Recognizing the fold of a protein structure." *Bioinformatics* 19:1 748-59, Oxford University Press, United Kingdom (2003).
Jung S. et al. "Selection for improved protein stability by phage display." *J. Mol. Biol.* 294: 163-80, Academic Press, United Kingdom (1999).
Lu D. et al. "Acquired antagonistic activity of a bispecific diabody directed against two different epitopes on vascular endothelial growth factor receptor 2." *J. Immunol. Methods.* 230:159-171, Elsevier, Inc., The Netherlands (1999).

(Continued)

*Primary Examiner* — Michael Borin
(74) *Attorney, Agent, or Firm* — Sterne, Kessler, Goldstein & Fox P.L.L.C.

(57) ABSTRACT

The invention is based, at least in part, on the development of stabilized binding molecules that consist of or comprise a stabilized scFv and methods for making such stabilized molecules.

22 Claims, 97 Drawing Sheets

(56) References Cited

OTHER PUBLICATIONS

Mok Y.K.. et al. "Dramatic stabilization of an SH3 domain by a single substitution: roles of the folded and unfolded states." *J. Mol. Biol.* 307: 913-28, Academic Press, United Kingdom (2001).

Roguska M.A. et al. "Humanization of murine monoclonal antibodies through variable domain resurfacing." *Proc. Natl. Acad. Sci. USA* 91: 969-973, National Academy of Sciences, United States (1994).

Song L.P. et al. "A new model of trispecific antibody resulting the cytotoxicity directed against tumor cells." *Sheng Wu Hua Xue Yu Sheng Wu Wu Li Xue Bao* [*Acta Biochimica et Biophysica Sinica*] (Shanghai) 35:503-510, Shanghai Institute of Biochemistry, Academia Sinica, China (2003).

Todorovska A. et al., "Design and application of diabodies, triabodies and tetrabodies for cancer targeting," *J. Immunol. Methods* 248: 47-66, Elsevier, Inc., The Netherlands (2001).

Tse E. et al. "Intracellular antibody capture technology: application to selection of intracellular antibodies recognizing the BCR-ABL oncogenic protein." *J. Mol. Biol.* 317: 85-94, Academic Press, United Kingdom (2002).

Vajdos, F.F., et al. "Comprehensive functional maps of the antigen-binding site of an anti-ErbB2 antibody obtained with shotgun scanning mutagenesis" *J. Mol. Biol.* 320: 415-428 Academic Press, United Kingdom (2002).

Van Spriel A.B. et al., "Immunotherapeutic perspective for bispecific antibodies," *Immunol. Today* 21:391-397, Elsevier, Inc., The Netherlands (2000).

Young N.M. et al. "Thermal stabilization of single-chain Fv antibody fragment by introduction of a disulfide bond," FEBS Lett. 377:135-139, Elsevier Science B.V., The Netherlands (1995).

Office Action mailed on Nov. 13, 2009 in U.S. Appl. No. 11/725,970, inventors Glaser et al., filed Mar. 19, 2007.

Final Office Action mailed on May 26, 2010 in U.S. Appl. No. 11/725,970, inventors Glaser et al., filed Mar. 19, 2007.

Advisory Action Before the Filing of an Appeal Brief mailed on Oct. 14, 2010 in U.S. Appl. No. 11/725,970, inventors Glaser et al., filed Mar. 19, 2007.

Office Action mailed on Feb. 3, 2010 in U.S. Appl. No. 11/894,025, inventors Glaser et al., filed Aug. 17, 2007.

Final Office Action mailed on Jul. 20, 2010 in U.S. Appl. No. 11/894,025, inventors Glaser et al., filed Aug. 17, 2007.

Advisory Action Bedore the Filing of an Appeal Brief mailed on Nov. 8, 2010 in U.S. Appl. No. 11/894,025, inventors Glaser et al., filed Aug. 17, 2007.

Eurasian Search Report for Application No. 200802005/26, filed Oct. 17, 2008.

Hugo N. et al. "VL position 34 is a key determinant for the engineering of stable antibodies with fast dissociation rates." *Protein Engineering* 16: 381-386, Oxford University Press, United Kingdom (2003).

Rigden D.J. "Use of covariance analysis for the prediction of structural domain boundaries from multiple protein sequence alignments." *Protein Engineering* 15: 65-77, Oxford University Press, United Kingdom (2002).

Altschuh, D. et al., "Modulation of the enzymatic activity of papain by interdomain residues remote from the active site," *Protein Enginering*, vol. 7(6):769-775 (1994).

Altschuh, T. et al., "Coordinated amino acid changes in homologous protein families," *Protein Engineering*, vol. 2(3):190-199 (1998).

Altshuh, D. et al., "Correlation of Co-ordinated Amino Acid Substitutions with Function in Viruses Related to Tobacco Mosaic Virus," *J. Mol. Biol.*, vol. 193:693-707 (1987).

Arndt, M.A. et al., "Generation of a highly stable, internalizing anti-CD22 single-chain Fv fragment for targeting non-Hodgkin's lymphoma," *International Journal of Cancer*, vol. 107:822-9 (2003).

Bera, Tapan K. et al., "Bivalent Disulfide-stabilized Fragment Variable Immunotoxin Directed against Mesotheliomas and Ovarian Cancer," *Molecular Cancer Therapeutics*, vol. 1:79-84 (2001).

Bivalent Disulfide-Stabilized Fragment Variable Immunotoxin Directed Against Mesotheliomas and Ovarian Cancer, Mol. Cancer Therapeutics, vol. 1, 79-84, 2001.

Chatellier, Jean et al., "Functional Mapping of Conserved Residues Located at the VL and VH Domain Interface of a Fab," *J. Mol. Biol.*, vol. 264:1-6 (1996).

Chelvanayagam, Gareth et al., "An analysis of simultaneous variation in protein structures," *Protein Engineering*, vol. 10(4):307-316 (1997).

Choulier, Laurence et al., "Covariance analysis of protein families: The case of the variable domains of antibodies," *Proteins: Structure, Function, and Genetics*, vol. 41:475-484 (2002).

Choulier, Laurence et al., "Kinetic Analysis of the Effect on Fab Binding of Identical Substitutions in a Peptide and Its Parent Protein," *Biochemistry*, vol. 38:3530-3537 (1999).

Coloma, M.J. et al., "Design and production of novel tetravalent bispecific antibodies," *Nature Biotechnology*, vol. 15(2):159-63 (1997).

Davidson, Alan, "Multiple Sequence Alignment as a Guideline for Protein Engineering Strategies," *Methods in Molecular Biology*, vol. 340:171-181 (2006).

Demarest, S.J. et al., "Engineering stability into the *Escherichia coli* secreted Fabs leads to increased functional expression," *Protein Engng. Des. Select*, vol. 19(7):325-36 (2006).

Demarest, S.J. et al., Optimization of the antibody CH3 domain using residue frequency analysis of IgG sequences. *J. Mol. Biol.*, vol. 335:41-48 (2004).

Desplancq, D. et al., "Multimerization behaviour of single chain Fv variants for the tumour-binding antibody B72.3," *Protein Engineering*, vol. 7(8):1027-33, 1994.

Ewert, S. et al., "Stability improvement of antibodies for extracellular and intracellular applications: CDR grafting to stable frameworks and structure-based framework engineering," *Methods.*, vol. 34:184-199 (2004).

Göbel, Ulrike et al., "Correlated Mutations and Residue Contacts in Proteins," *Proteins: Structure, Function, and Genetics*, vol. 18:309-317 (1994).

Govindarajan, Sridhar et al., "Systematic Variation of Amino Acid Substitutes for Stringent Assessment of Pairwise Covariation," *J. Mol. Biol.*, vol. 328:1061-1069 (2003).

Hugo, N. et al., "VL position 34 is a key determinant for the engineering of the stable antibodies with fast dissociation rates," Protein Engineering, vol. 16(5):381-386 (2003).

Hugo, Nicolas et al., "Functional aspects of co-variant surface charges in an antibody fragment," *Protein Science*, vol. 11:2697-2705 (2002).

Khalifa, Myriam Ben et al., "Effects on interaction kinetics of mutations at the VH-VL interface of Fabs depend on the structural context," *Journal of Molecular Recognition*, vol. 13:127-139 (2000).

Knappik, A. et al., "Fully synthetic human combinatorial antibody libraries (HuCAL) based on modular consensus frameworks and CDRs randomized with trinucleotides," *J. Mol. Biol.*, vol. 296: 57-86 (2000).

Krishnadev, O. et al., "PRODOC: a resource for the comparison of tethered protein domain architectures with in-built information on remotely related domain families," *Nucleic Acids Research*, vol. 33:W126-W129 (2005).

Larson, Stefan M. et al., "Analysis of Covariation in an SH3 Domain Sequence Alignment: Applications in Tertiary Contact Prediction and Design of Compensating Hydrophobic Core Substitutions," *J. Mol. Biol.*, vol. 303:433-446 (2000).

Liu, Yanshun et al., "3D domain swapping: As domains continue to swap," *Protein Science*, vol. 11:1285-1299 (2002).

Magliery, Thomas J. et al., "Beyond Consensus: Stastical Free Energies Reveal Hidden Interactions in the Design of a TPR Motif," *J. Mol. Biol.*, vol. 343,731-745 (2004).

Nellis, David F. et al., "Preclinical Manufacture of an Anti-HER2 scFv-PEG-DSPE, Liposome-Inserting Conjugate. 1. Gram-Scale Production and Purification," *Biotechnol. Prog.*, vol. 21:205-220 (2005).

Nellis, David F. et al., "Preclinical Manufacture of Anti-HER2 Liposome-Inserting, scFv-PEG-Lipid Conjugate. 2. Conjugate Micelle Identity, Purity, Stability, and Potency Analysis," *Biotechnol. Prog.*, vol. 21:221-232 (2005).

(56) References Cited

OTHER PUBLICATIONS

Nikolova, Penka V. et al., "Semirational design of active tumor suppressor p53 DNA binding domain with enhanced stability," *Proc. Natl. Acad. Sci. USA*, vol. 95:14675-14680 (1998).

Ortiz, Angel R. et al., "Ab Initio Folding of Proteins Using Restraints Derived From Evolutionary Information," *Proteins: Structure, Function, and Genetics Suppl.*, vol. 3:177-185 (1999).

Pollack, David D. et al., "Coevolving Protein Residues: Maximum Likelihood Identification and Relationship to Structure," *J. Mol. Biol.*, vol. 287:187-198 (1999).

Pollock, D.D, et al., "Effectiveness of correlation analysis in identifying protein residues undergoing correlated evolution," *Protein Engineering*, vol. 10(6):647-657 (1997).

Rauffer, Nathalie et al., "Structure-Activity Relationships for the Interaction Between Cyclosporin A Derivatives and the Fab Fragment of a Monoclonal Antibody," *Molecular Immunology*, vol. 31(12):913-922 (1994).

Rauffer-Bruyere, Nathalie et al., "Cooperative Effects of Mutations in a Recombinant Fab on the Kinetics of Antigen Binding," *Molecular Immunology*, vol. 34(2):165-173 (1997).

Reiter, Yoram et al., "Engineering antibody Fv fragments for cancer detection and therapy: Disulfide-stabilized Fv fragments," *Nature Biotechnology*, vol. 14:1239-1245 (1996).

Renard, Martial et al., "Knowledge-based Design of Reagentless Flourescent Biosensors from Recombinant Antibodies," *J. Mol. Biol.* vol. 318:429-442 (2002).

Röthlisberger, D. et al., "Domain interactions in the Fab fragment: a comparative evaluation of the single-chain Fv and Fab format engineered with variable domains of different stability," *J. Mol. Biol.*, vol. 347:773-789 (2005).

Socolich, Michael et al., "Evolutionary information for specifying a protein fold," *Nature*, vol. 437:512-518 (2005).

Steipe, B. et al., "Sequence statistics reliability predict stabilizing mutations in a protein domain," *J. Mol. Biol.*, vol. 240:188-192 (1994).

Steipe, B., "Consensus-based engineering for protein stability: from intrabodies to thermostable enzymes," *Methods Enzymol.*, vol. 388:176-186 (2004).

Suel, Gurol M. et al., "Evolutionarily conserved networks of residues mediate allosteric communication in proteins," *Nature Structural Biology*, vol. 10(1):59-67 (2003).

Valencia, Alfonso et al., "Computational methods for the prediction of protein interactions," *Current Opinion in Structural Biology*, vol. 12:368-373 (2002).

Vernet, Thierry et al., "Correlation of Co-ordinated Amino Acid Changes at the Two-domain Interface of Cysteine Proteases with Protein Stability," *J. Mol. Biol.*, vol. 224:501-509 (1992).

Wall, J.G. et al., "The hierarchy of mutations influencing the folding of antibody domains in *Escherichia coli*," *Protein Engng.*, vol. 12:605-611 (1999).

Weidenhaupt, Marianne et al., "Functional mapping of conserved, surface-exposed charges of antibody variable domains," *Journal of Molecular Recognition*, vol. 15:94-103 (2002).

Wörn, A. et al., "Stability engineering of antibody single chain Fv fragments," *J. Mol. Biol.*, vol. 305:989-1010 (2001).

Wrabl, James O. et al., "Gaps in Structurally Similar Proteins: Towards Improvement of Multiple Sequence Alignment," *Proteins: Structure, Function, and Bioinformatics*, vol. 54:71-87 (2004).

Invitation to Pay Additional Fees for Application No. PCT/US2007/006883, dated Feb. 22, 2008.

International Search Report for Application No. PCT/US2007/006883, dated Sep. 5, 2008.

Written Opinion for Application No. PCT/US2007/006883, dated Jan. 21, 2009.

\* cited by examiner

CAGGTCCAACTGGTGCAGTCTGGAGCTGAGGTGAAGAAGCCTGGGTC
CTCAGTGAAGGTGTCCTGCAAGGCTTCTGGCTACACTTTCACAACCT
ACTATTTGCACTGGGTGAGGCAGGCCCCTGGACAGGGACTTGAGTGG
ATGGGATGGATTTATCCTGGAAATGTTCATGCTCAGTACAATGAGAA
GTTCAAGGGCAGGGTCACAATCACTGCAGACAAATCCACCAGCACAG
CCTACATGGAGCTCAGCAGCCTGAGGTCTGAAGATACTGCGGTCTAT
TACTGTGCAAGATCCTGGGAAGGTTTTCCTTACTGGGGCCAAGGGAC
CACGGTCACCGTCTCCTCA**GGTGGGGGCGGATCTGGGGGCGGCGGAT
CCGGTGGTGGTGGTAGT**GACATTCAGATGACCCAGTCTCCTAGCTCC
CTGTCCGCCTCAGTAGGAGACAGGGTCACCATCACCTGCAAGGCCAG
TCAGAATGTGGGTATTAATGTAGCCTGGTATCAACAGAAACCAGGGA
AGGCTCCTAAATCACTGATTTCCTCGGCCTCCTACCGGTACAGTGGA
GTCCCTTCCAGATTCAGCGGCAGTGGATCTGGACAGATTTCACTCT
CACCATCAGCAGCCTCCAGCCTGAAGACTTCGCAACCTATTTCTGTC
AGCAATATGACACCTATCCATTCACGTTCGGCCAGGGTACCAAGGTG
GAGATCAAA (SEQ ID NO: 3)

*Fig. 1A*

QVQLVQSGAEVKKPGSSVKVSCKASGYTFTTYYLHWVRQAPGQG
LEWMGWIYPGNVHAQYNEKFKGRVTITADKSTSTAYMELSSLRS
EDTAVYYCARSWEGFPYWGQGTTVTVSSGGGGSGGGGSGGGGSD
IQMTQSPSSLSASVGDRVTITCKASQNVGINVAWYQQKPGKAPK
SLISSASYRYSGVPSRFSGSGSGTDFTLTISSLQPEDFATYFCQ
QYDTYPFTFGQGTKVEIK (SEQ ID NO: 4)

*Fig. 1B*

CAGGTCCAACTGGTGCAGTCTGGAGCTGAGGTGAAGAAGCCTGGGTC
CTCAGTGAAGGTGTCCTGCAAGGCTTCTGGCTACACTTTCACAACCT
ACTATTTGCACTGGGTGAGGCAGGCCCCTGGACAGTGCCTTGAGTGG
ATGGGATGGATTTATCCTGGAAATGTTCATGCTCAGTACAATGAGAA
GTTCAAGGGCAGGGTCACAATCACTGCAGACAAATCCACCAGCACAG
CCTACATGGAGCTCAGCAGCCTGAGGTCTGAAGATACTGCGGTCTAT
TACTGTGCAAGATCCTGGGAAGGTTTTCCTTACTGGGGCCAAGGGAC
CACGGTCACCGTCTCCTCA**GGTGGGGGCGGATCTGGGGGCGGCGGAT
CCGGTGGTGGTGGTAGT**GACATTCAGATGACCCAGTCTCCTAGCTCC
CTGTCCGCCTCAGTAGGAGACAGGGTCACCATCACCTGCAAGGCCAG
TCAGAATGTGGGTATTAATGTAGCCTGGTATCAACAGAAACCAGGGA
AGGCTCCTAAATCACTGATTTCCTCGGCCTCCTACCGGTACAGTGGA
GTCCCTTCCAGATTCAGCGGCAGTGGATCTGGGACAGATTTCACTCT
CACCATCAGCAGCCTCCAGCCTGAAGACTTCGCAACCTATTTCTGTC
AGCAATATGACACCTATCCATTCACGTTCGGCTGCGGTACCAAGGTG
GAGATCAAA    (SEQ ID NO: 9)

*Fig. 3A*

QVQLVQSGAEVKKPGSSVKVSCKASGYTFTTYYLHWVRQAPGQ*C*LE
WMGWIYPGNVHAQYNEKFKGRVTITADKSTSTAYMELSSLRSEDTA
VYYCARSWEGFPYWGQGTTVTVSSGGGGSGGGGSGGGGSDIQMTQS
PSSLSASVGDRVTIT*C*KASQNVGINVAWYQQKPGKAPKSLISSASY
RYSGVPSRFSGSGSGTDFTLTISSLQPEDFATYFCQQYDTYPFTFG
CGTKVEIK    (SEQ ID NO:10)

*Fig. 3B*

CAGGTCCAACTGGTGCAGTCTGGAGCTGAGGTGAAGAAGCCTGGGTC
CTCAGTGAAGGTGTCCTGCAAGGCTTCTGGCTACACTTTCACAACCT
ACTATTTGCACTGGGTGAGGCAGGCCCCTGGACAGGGACTTGAGTGG
ATGGGATGGATTTATCCTGGAAATGTTCATGCTCAGTACAATGAGAA
GTTCAAGGGCAGGGTCACAATCACTGCAGACAAATCCACCAGCACAG
CCTACATGGAGCTCAGCAGCCTGAGGTCTGAAGATACTGCGGTCTAT
TACTGTGCAAGATCCTGGGAAGGTTTTCCTTACTGGGGCCAAGGGAC
CACGGTCACCGTCTCCTCA<u>GGCGGTGGAGGGTCCGGTGGGGCGGAT
CTGGGGGCGGCGGATCCGGTGGTGGTGGTAGT</u>GACATTCAGATGACC
CAGTCTCCTAGCTCCCTGTCCGCCTCAGTAGGAGACAGGGTCACCAT
CACCTGCAAGGCCAGTCAGAATGTGGGTATTAATGTAGCCTGGTATC
AACAGAAACCAGGGAAGGCTCCTAAATCACTGATTTCCTCGGCCTCC
TACCGGTACAGTGGAGTCCCTTCCAGATTCAGCGGCAGTGGATCTGG
GACAGATTTCACTCTCACCATCAGCAGCCTCCAGCCTGAAGACTTCG
CAACCTATTTCTGTCAGCAATATGACACCTATCCATTCACGTTCGGC
CAGGGTACCAAGGTGGAGATCAAA (SEQ ID NO:14)

*Fig. 4A*

QVQLVQSGAEVKKPGSSVKVSCKASGYTFTTYYLHWVRQAPGQGL
EWMGWIYPGNVHAQYNEKFKGRVTITADKSTSTAYMELSSLRSED
TAVYYCARSWEGFPYWGQGTTVTVSS<u>GGGGSGGGGSGGGGSGGGG</u>
SDIQMTQSPSSLSASVGDRVTITCKASQNVGINVAWYQQKPGKAP
KSLISSASYRYSGVPSRFSGSGSGTDFTLTISSLQPEDFATYFCQ
QYDTYPFTFGQGTKVEIK (SEQ ID NO:15)

*Fig. 4B*

CAGGTCCAACTGGTGCAGTCTGGAGCTGAGGTGAAGAAGCCTGGGTCC
TCAGTGAAGGTGTCCTGCAAGGCTTCTGGCTACACTTTCACAACCTAC
TATTTGCACTGGGTGAGGCAGGCCCCTGGACAGGGACTTGAGTGGATG
GGATGGATTTATCCTGGAAATGTTCATGCTCAGTACAATGAGAAGTTC
AAGGGCAGGGTCACAATCACTGCAGACAAATCCACCAGCACAGCCTAC
ATGGAGCTCAGCAGCCTGAGGTCTGAAGATACTGCGGTCTATTACTGT
GCAAGATCCTGGGAAGGTTTTCCTTACTGGGGCCAAGGGACCACGGTC
ACCGTCTCCTCA<u>GGAGGGGGCGGTTCAGGCGGTGGAGGGTCCGGTGGG
GGCGGATCTGGGGGCGGCGGATCCGGTGGTGGTGGTAGT</u>GACATTCAG
ATGACCCAGTCTCCTAGCTCCCTGTCCGCCTCAGTAGGAGACAGGGTC
ACCATCACCTGCAAGGCCAGTCAGAATGTGGGTATTAATGTAGCCTGG
TATCAACAGAAACCAGGGAAGGCTCCTAAATCACTGATTTCCTCGGCC
TCCTACCGGTACAGTGGAGTCCCTTCCAGATTCAGCGGCAGTGGATCT
GGGACAGATTTCACTCTCACCATCAGCAGCCTCCAGCCTGAAGACTTC
GCAACCTATTTCTGTCAGCAATATGACACCTATCCATTCACGTTCGGC
CAGGGTACCAAGGTGGAGATCAAA (SEQ ID NO:16)

*Fig. 5A*

QVQLVQSGAEVKKPGSSVKVSCKASGYTFTTYYLHWVRQAPGQGLEWMGWIYPGN
VHAQYNEKFKGRVTITADKSTSTAYMELSSLRSEDTAVYYCARSWEGFPYWGQGTT
VTVSS<u>GGGGSGGGGSGGGGSGGGGSGGGGS</u>DIQMTQSPSSLSASVGDRVTITCKA
SQNVGINVAWYQQKPGKAPKSLISSASYRYSGVPSRFSGSGSGTDFTLTISSLQPEDFA
TYFCQQYDTYPFTFGQGTKVEIK (SEQ ID NO:17)

*Fig. 5B*

Lane
1 – conventional BHA10 scFv
2 – BHA10 scFv $V_H44/V_L100$
3 – BHA10 scFv $(Gly_4Ser)_4$ linker
4 – BHA10 scFv $V_H44/V_L100$ and $(Gly_4Ser)_4$ linker CAGGTCCAACTGGTGCAGTCTGGAGCTGAGGTGAAGAAGCCTGGGTC
CTCAGTGAAGGTGTCCTGCAAGGCTTCTGGCTACACTTTCACAACCT
ACTATTTGCACTGGGTGAGGCAGGCCCCTGGACAGTGCCTTGAGTGG
ATGGGATGGATTTATCCTGGAAATGTTCATGCTCAGTACAATGAGAA
GTTCAAGGGCAGGGTCACAATCACTGCAGACAAATCCACCAGCACAG
CCTACATGGAGCTCAGCAGCCTGAGGTCTGAAGATACTGCGGTCTAT
TACTGTGCAAGATCCTGGGAAGGTTTTCCTTACTGGGGCCAAGGGAC
CACGGTCACCGTCTCCTCA<u>GGCGGTGGAGGGTCCGGTGGGGCGGAT
CTGGGGGCGGCGGATCCGGTGGTGGTGGTAGT</u>GACATTCAGATGACC
CAGTCTCCTAGCTCCCTGTCCGCCTCAGTAGGAGACAGGGTCACCAT
CACCTGCAAGGCCAGTCAGAATGTGGGTATTAATGTAGCCTGGTATC
AACAGAAACCAGGGAAGGCTCCTAAATCACTGATTTCCTCGGCCTCC
TACCGGTACAGTGGAGTCCCTTCCAGATTCAGCGGCAGTGGATCTGG
GACAGATTTCACTCTCACCATCAGCAGCCTCCAGCCTGAAGACTTCG
CAACCTATTTCTGTCAGCAATATGACACCTATCCATTCACGTTCGGC
TGCGGTACCAAGGTGGAGATCAAA (SEQ ID NO:18)

*Fig. 7A*

QVQLVQSGAEVKKPGSSVKVSCKASGYTFTTYYLHWVRQAPGQCL
EWMGWIYPGNVHAQYNEKFKGRVTITADKSTSTAYMELSSLRSED
TAVYYCARSWEGFPYWGQGTTVTVSSGGGGSGGGGSGGGGSGGGG
SDIQMTQSPSSLSASVGDRVTITCKASQNVGINVAWYQQKPGKAP
KSLISSASYRYSGVPSRFSGSGSGTDFTLTISSLQPEDFATYFCQ
QYDTYPFTFGCGTKVEIK (SEQ ID NO:19)

| Pos# | MFR | P(i) | SMFR | P(i) | SR | S(i) | SR/MFR | Kabat# | VH1cons | Chothia |
|---|---|---|---|---|---|---|---|---|---|---|
| 9 | G | 0.593 | P | 0.220 | A | 0.169 | 0.285 | 9 | A | no data |
| 11 | L | 0.745 | V | 0.186 | V | 0.186 | 0.25 | 11 | V | P(7),A(7),T(3), S(32),V(10),L(41) |
| 12 | V | 0.796 | K | 0.101 | K | 0.101 | 0.127 | 12 | K | T(3),G(3),K(6),A(22),V(57),L(4) |
| 16 | G | 0.491 | Q | 0.152 | S | 0.033 | 0.068 | 16 | S | D(15), R(2),E(26),Q(17),G(19),A(14) |
| 18 | L | 0.728 | V | 0.186 | V | 0.186 | 0.255 | 18 | V | A(14),I(2),S(4),T(2), V(52),L(29) |
| 20 | L | 0.813 | V | 0.101 | V | 0.101 | 0.125 | 20 | V | V(4),L(42),I(38),M(14) |
| 45 | K | 0.830 | Q | 0.135 | Q | 0.135 | 0.163 | 43 | Q | S(3),T(7), R(6),K(38),Q(33),N(2),H(3),G(3) |
| 50 | V | 0.559 | I | 0.186 | M | 0.084 | 0.151 | 48 | M | W(7),V(15),L(41),I(30),M(9) |
| 74 | F | 0.610 | A | 0.118 | V | 0.118 | 0.194 | 67 | V | I(4),A(17),T(4),V(8),L(4),F(61) |
| 78 | R | 0.559 | K | 0.169 | A | 0.118 | 0.212 | 71 | A | G(34),A(9),S(3), R(22),K(8),V(16),L(4) |
| 80 | N | 0.627 | T | 0.203 | K | 0.118 | 0.189 | 73 | K | G(42),K(17),D(3),N(15),T(18) |
| 82 | K | 0.661 | S | 0.118 | T | 0.033 | 0.051 | 75 | T | no data |
| 87 | L | 0.847 | M | 0.118 | M | 0.118 | 0.14 | 80 | M | L(76),M(20),F(3) |
| 88 | Q | 0.694 | E | 0.067 | E | 0.067 | 0.097 | 81 | E | E(7),Q(40),K(13),N(2),S(2),T(33) |

Fig. 11B

| Pos# | MFR | P(i) | SMFR | P(i) | SR | S(i) | SR/MFR | Kabat# | Vk1cons | Chothia |
|---|---|---|---|---|---|---|---|---|---|---|
| 3 | V | 0.72 | Q | 0.16 | Q | 0.16 | 0.222 | 3 | Q | no data |
| 13 | V | 0.64 | A | 0.16 | A | 0.16 | 0.25 | 13 | A | K(6),G(4),A(22),T(3),V(51),L(4) |
| 48 | Q | 0.82 | K | 0.16 | K | 0.16 | 0.195 | 42 | K | R(6),H(3),K(40),(Q33),G(3),T(7) |
| 52 | L | 0.76 | R | 0.08 | S | 0.02 | 0.026 | 46 | L | Y(2),W(53),R(6),G(2),T(4),V(15),L(32) |
| 55 | Y | 0.88 | E | 0.04 | S | 0.02 | 0.022 | 49 | Y | no data |
| 56 | W | 0.3 | L | 0.12 | S | 0.12 | 0.4 | 50 | A | no data |
| 70 | D | 0.68 | S | 0.18 | S | 0.18 | 0.264 | 60 | S | G(34),D(22),N(2),A(12),S(27),V(2) |
| 95 | V | 0.58 | T | 0.16 | T | 0.16 | 0.275 | 85 | T | L(3),D(6),T(27),V(44),I(8),M(9) |
| 97 | Y | 0.84 | F | 0.14 | F | 0.14 | 0.166 | 87 | Y | Y(79),F(19) |

N_L-terminal LTβR/TRAILR2
"N_L-Hercules"
C-terminal LTβR/TRAILR2
"C-Hercules"
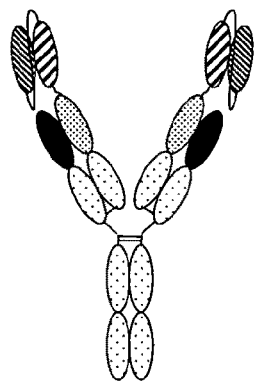
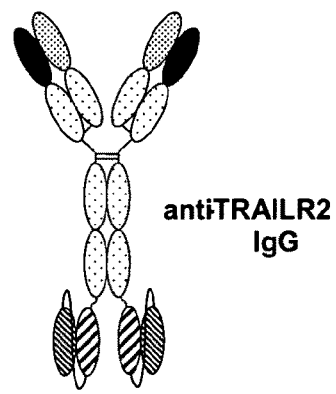
antiTRAILR2
IgG
Stable BHA10 scFv
V_L  V_H
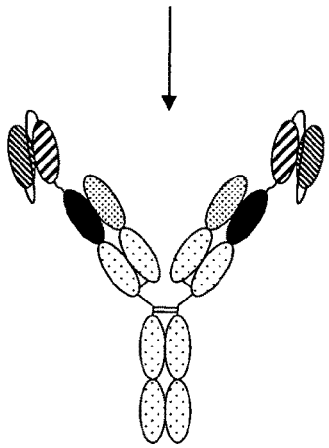
N_H-terminal LTβR/TRAILR2
"N_H-Hercules"
*Fig. 13*

CAACTTGTGCTCACTCAGTCATCTTCAGTCTCTTTCTCCCTGGGAGC
CTCAGCAAAACTCACGTGCACCTTGAGTAGTCAGCACAGTACGTACA
CCATTGAATGGTATCAGCAACAGCCCCTCAAGCCTCCTAAGTATGTG
ATGGAGCTTAAGAAAGATGGAAGCCACAGCACAGGTGATGGGATTCC
TGATCGCTTCTCTGGATCCAGCTCTGGTGCTGATCGCTACCTTAGCA
TTTCCAACATCCAGCCTGAAGATGAAGCAATATACATCTGTGGTGTG
GGTGATACAATTAAGGAACAATTTGTGTATGTTTTCGGCGGTGGAAC
CAAGGTCGAAATCAAACGTACGGTGGCTGCACCATCTGTCTTCATCT
TCCCGCCATCTGATGAGCAGTTGAAATCTGGAACTGCCTCTGTTGTG
TGCCTGCTGAATAACTTCTATCCCAGAGAGGCCAAAGTACAGTGGAA
GGTGGATAACGCCCTCCAATCGGGTAACTCCCAGGAGAGTGTCACAG
AGCAGGACAGCAAGGACAGCACCTACAGCCTCAGCAGCACCCTGACG
CTGAGCAAAGCAGACTACGAGAAACACAAAGTCTACGCCTGCGAAGT
CACCCATCAGGGCCTGAGCTCGCCCGTCACAAAGAGCTTCAACAGGG
GAGAGTGTTGA    (SEQ ID NO:28)

Fig. 15A

QLVLTQSSSVSFSLGASAKLTCTLSSQHSTYTIEWYQQQPLKPPK
YVMELKKDGSHSTGDGIPDRFSGSSSGADRYLSISNIQPEDEAIY
ICGVGDTIKEQFVYVFGGGTKVEIKRTVAAPSVFIFPPSDEQLKS
GTASVVCLLNNFYPREAKVQWKVDNALQSGNSQESVTEQDSKDST
YSLSSTLTLSKADYEKHKVYACEVTHQGLSSPVTKSFNRGEC
(SEQ ID NO:29)

Fig. 15B

```
CAGGTCCAACTGGTGCAGTCTGGAGCTGAGGTGAAGAAGCCTGGGTCCTCAGTGAAGGT
GTCCTGCAAGGCTTCTGGCTACACTTTCACAACCTACTATTTGCACTGGGTGAGGCAGG
CCCCTGGACAGGGACTTGAGTGGATGGGATGGATTTATCCTGGAAATGTTCATGCTCAG
TACAATGAGAAGTTCAAGGGCAGGGTCACAATCACTGCAGACAAATCCACCAGCACAGC
CTACATGGAGCTCAGCAGCCTGAGGTCTGAAGATACTGCGGTCTATTACTGTGCAAGAT
CCTGGGAAGGTTTTCCTTACTGGGGCCAAGGGACCACGGTCACCGTCTCCTCAGGTGGG
GGCGGATCTGGGGGCGGCGGATCCGGTGGTGGTGGTAGTGACATTCAGATGACCCAGTC
TCCTAGCTCCCTGTCCGCCTCAGTAGGAGACAGGGTCACCATCACCTGCAAGGCCAGTC
AGAATGTGGGTATTAATGTAGCCTGGTATCAACAGAAACCAGGGAAGGCTCCTAAATCA
CTGATTTCCTCGGCCTCCTACCGGTACAGTGGAGTCCCTTCCAGATTCAGCGGCAGTGG
ATCTGGGACAGATTTCACTCTCACCATCAGCAGCCTCCAGCCTGAAGACTTCGCAACCT
ATTTCTGTCAGCAATATGACACCTATCCATTCACGTTCGGCCAGGGTACCAAGGTGGAG
ATCAAAGGCGGTGGAGGGTCCGGTGGAGGGGCTCTGGAGGGGCGGTTCAGGGGCGG
TGGATCGGGGGGAGGTGGCTCCCAGATCCAGTTGGTGCAGTCTGGACCTGAGCTGAAGA
AGCCTGGAGAGACAGTCAAGATCTCCTGCAAGGCTTCTGGTTTTACCTTCACAGACTAT
TCAATACACTGGGTGAAACAGGCTCCAGGAAAGGGTTTAAAGTGGATGGGCTGGATAAA
CACTGAGACTGGTGAGCCAACATATACAGATGACTTCAAGGGACGATTTGCCTTCTCTT
TGGTGACCTCTGCCACCACTGCCTATTTGCAGATCAACAACCTCAACAATGAGGACACG
GCTACATTTTTCTGTGCTAGATTCATCTATGATCCTTATTGGGGTTTGCTTACTGGGG
CCAGGGGACTCTGGTCACTGTCTCCGCAGCTAGCACCAAGGGCCCATCGGTCTTCCCCC
TGGCACCCTCCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAATCACAAGCCC
AGCAACACCAAGGTGGACAAGAAAGTTGAGCCCAAATCTTGTGACAAAACTCACACATG
CCCACCGTGCCCAGCACCTGAACTCCTGGGGGGACCGTCAGTCTTCCTCTTCCCCCCAA
AACCCAAGGACACCCTCATGATCTCCCGGACCCCTGAGGTCACATGCGTGGTGGTGGAC
GTGAGCCACGAAGACCCTGAGGTCAAGTTCAACTGGTACGTGGACGGCGTGGAGGTGCA
TAATGCCAAGACAAAGCCGCGGGAGGAGCAGTACAACAGCACGTACCGTGTGGTCAGCG
TCCTCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCCCCG
AGAACCACAGGTGTACACCCTGCCCCCATCCCGGGATGAGCTGACCAAGAACCAGGTCA
GCCTGACCTGCCTGGTCAAAGGCTTCTATCCCAGCGACATCGCCGTGGAGTGGGAGAGC
AATGGGCAGCCGGAGAACAACTACAAGACCACGCCTCCCGTGCTGGACTCCGACGGCTC
CTTCTTCCTCTACAGCAAGCTCACCGTGGACAAGAGCAGGTGGCAGCAGGGGAACGTCT
TCTCATGCTCCGTGATGCATGAGGCTCTGCACAACCACTACACGCAGAAGAGCCTCTCC
CTGTCTCCGGGTTGA     (SEQ ID NO:30)
```

*Fig. 16*

QVQLVQSGAEVKKPGSSVKVSCKASGYTFTTYYLHWVRQAPGQGL
EWMGWIYPGNVHAQYNEKFKGRVTITADKSTSTAYMELSSLRSED
TAVYYCARSWEGFPYWGQGTTVTVSSGGGGSGGGGSGGGGSDIQM
TQSPSSLSASVGDRVTITCKASQNVGINVAWYQQKPGKAPKSLIS
SASYRYSGVPSRFSGSGSGTDFTLTISSLQPEDFATYFCQQYDTY
PFTFGQGTKVEIKGGGGSGGGGSGGGGSGGGGSGGGGSQIQLVQS
GPELKKPGETVKISCKASGFTFTDYSIHWVKQAPGKGLKWMGWIN
TETGEPTYTDDFKGRFAFSLVTSATTAYLQINNLNNEDTATFFCA
RFIYDPYWGFAYWGQGTLVTVSAASTKGPSVFPLAPSSKSTSGGT
AALGCLVKDYFPEPVTVSWNSGALTSGVHTFPAVLQSSGLYSLSS
VVTVPSSSLGTQTYICNVNHKPSNTKVDKKVEPKSCDKTHTCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFLYSK
LTVDKSRWQQGNVFSCSVMHEALHNHYTQKSLSLSPG (SEQ ID
NO:31)

*Fig. 17*

CAGGTCCAACTGGTGCAGTCTGGAGCTGAGGTGAAGAAGCCTGGGTCCTCAGTGAAGGTG
TCCTGCAAGGCTTCTGGCTACACTTTCACAACCTACTATTTGCACTGGGTGAGGCAGGCC
CCTGGACAGGGACTTGAGTGGATGGGATGGATTTATCCTGGAAATGTTCATGCTCAGTAC
AATGAGAAGTTCAAGGGCAGGGTCACAATCACTGCAGACAAATCCACCAGCACAGCCTAC
ATGGAGCTCAGCAGCCTGAGGTCTGAAGATACTGCGGTCTATTACTGTGCAAGATCCTGG
GAAGGTTTTCCTTACTGGGGCCAAGGGACCACGGTCACCGTCTCCTCAGGCGGTGGAGGG
TCCGGTGGGGGCGGATCTGGGGGCGGCGGATCCGGTGGTGGTGGTAGTGACATTCAGATG
ACCCAGTCTCCTAGCTCCCTGTCCGCCTCAGTAGGAGACAGGGTCACCATCACCTGCAAG
GCCAGTCAGAATGTGGGTATTAATGTAGCCTGGTATCAACAGAAACCAGGGAAGGCTCCT
AAATCACTGATTTCCTCGGCCTCCTACCGGTACAGTGGAGTCCCTTCCAGATTCAGCGGC
AGTGGATCTGGGACAGATTTCACTCTCACCATCAGCAGCCTCCAGCCTGAAGACTTCGCA
ACCTATTTCTGTCAGCAATATGACACCTATCCATTCACGTTCGGCCAGGGTACCAAGGTG
GAGATCAAAGGCGGTGGAGGGTCCGGTGGAGGGGGCTCTGGAGGGGCGGTTCAGGGGGC
GGTGGATCGGGGGGAGGTGGCTCCCAGATCCAGTTGGTGCAGTCTGGACCTGAGCTGAAG
AAGCCTGGAGAGACAGTCAAGATCTCCTGCAAGGCTTCTGGTTTTACCTTCACAGACTAT
TCAATACACTGGGTGAAACAGGCTCCAGGAAAGGGTTTAAAGTGGATGGGCTGGATAAAC
ACTGAGACTGGTGAGCCAACATATACAGATGACTTCAAGGGACGATTTGCCTTCTCTTTG
GTGACCTCTGCCACCACTGCCTATTTGCAGATCAACAACCTCAACAATGAGGACACGGCT
ACATTTTTCTGTGCTAGATTCATCTATGATCCTTATTGGGGGTTTGCTTACTGGGGCCAG
GGGACTCTGGTCACTGTCTCCGCAGCTAGCACCAAGGGCCCATCGGTCTTCCCCCTGGCA
CCCTCCTCCAAGAGCACCTCTGGGGGCACAGCGGCCCTGGGCTGCCTGGTCAAGGACTAC
TTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAACACC
AAGGTGGACAAGAAAGTTGAGCCCAAATCTTGTGACAAAACTCACACATGCCCACCGTGC
CCAGCACCTGAACTCCTGGGGGGACCGTCAGTCTTCCTCTTCCCCCCAAAACCCAAGGAC
ACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACA
AAGCCGCGGGAGGAGCAGTACAACAGCACGTACCGTGTGGTCAGCGTCCTCACCGTCCTG
CACCAGGACTGGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAG
CTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTTGA
(SEQ ID NO:32)

*Fig. 18*

QVQLVQSGAEVKKPGSSVKVSCKASGYTFTTYYLHWVRQAPGQGLEW
MGWIYPGNVHAQYNEKFKGRVTITADKSTSTAYMELSSLRSEDTAVY
YCARSWEGFPYWGQGTTVTVSSGGGGSGGGGSGGGGSGGGGSDIQMT
QSPSSLSASVGDRVTITCKASQNVGINVAWYQQKPGKAPKSLISSAS
YRYSGVPSRFSGSGSGTDFTLTISSLQPEDFATYFCQQYDTYPFTFG
QGTKVEIKGGGGSGGGGSGGGGSGGGGSGGGGSQIQLVQSGPELKKP
GETVKISCKASGFTFTDYSIHWVKQAPGKGLKWMGWINTETGEPTYT
DDFKGRFAFSLVTSATTAYLQINNLNNEDTATFFCARFIYDPYWGFA
YWGQGTLVTVSAASTKGPSVFPLAPSSKSTSGGTAALGCLVKDYFPE
PVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAK
GQPREPQVYTLPPSRDELTKNQVSLTCLVKGFYPSDIAVEWESNGQP
ENNYKTTPPVLDSDGSFFLYSKLTVDKSRWQQGNVFSCSVMHEALHN
HYTQKSLSLSPG     (SEQ ID NO:33)

*Fig. 19*

CAGGTCCAACTGGTGCAGTCTGGAGCTGAGGTGAAGAAGCCTGGGTCCTCAGTG
AAGGTGTCCTGCAAGGCTTCTGGCTACACTTTCACAACCTACTATTTGCACTGG
GTGAGGCAGGCCCCTGGACAGTGCCTTGAGTGGATGGGATGGATTTATCCTGGA
AATGTTCATGCTCAGTACAATGAGAAGTTCAAGGGCAGGGTCACAATCACTGCA
GACAAATCCACCAGCACAGCCTACATGGAGCTCAGCAGCCTGAGGTCTGAAGAT
ACTGCGGTCTATTACTGTGCAAGATCCTGGGAAGGTTTTCCTTACTGGGGCCAA
GGGACCACGGTCACCGTCTCCTCAGGTGGGGCGGATCTGGGGCGGCGGATCC
GGTGGTGGTGGTAGTGACATTCAGATGACCCAGTCTCCTAGCTCCCTGTCCGCC
TCAGTAGGAGACAGGGTCACCATCACCTGCAAGGCCAGTCAGAATGTGGGTATT
AATGTAGCCTGGTATCAACAGAAACCAGGGAAGGCTCCTAAATCACTGATTTCC
TCGGCCTCCTACCGGTACAGTGGAGTCCCTTCCAGATTCAGCGGCAGTGGATCT
GGGACAGATTTCACTCTCACCATCAGCAGCCTCCAGCCTGAAGACTTCGCAACC
TATTTCTGTCAGCAATATGACACCTATCCATTCACGTTCGGCTGCGGTACCAAG
GTGGAGATCAAAGGCGGTGGAGGGTCCGGTGGAGGGGGCTCTGGAGGGGCGGT
TCAGGGGGCGGTGGATCGGGGGGAGGTGGCTCCCAGATCCAGTTGGTGCAGTCT
GGACCTGAGCTGAAGAAGCCTGGAGAGACAGTCAAGATCTCCTGCAAGGCTTCT
GGTTTTACCTTCACAGACTATTCAATACACTGGGTGAAACAGGCTCCAGGAAAG
GGTTTAAAGTGGATGGGCTGGATAAACACTGAGACTGGTGAGCCAACATATACA
GATGACTTCAAGGGACGATTTGCCTTCTCTTTGGTGACCTCTGCCACCACTGCC
TATTTGCAGATCAACAACCTCAACAATGAGGACACGGCTACATTTTTCTGTGCT
AGATTCATCTATGATCCTTATTGGGGGTTTGCTTACTGGGGCCAGGGGACTCTG
GTCACTGTCTCCGCAGCTAGCACCAAGGGCCCATCGGTCTTCCCCCTGGCACCC
TCCTCCAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAGCGGC
GTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTG
AATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCG
TCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAG
TTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCAC
CAGGACTGGCTGAATGGCAAGGAGTACAAGTGCAAGGTCTCCAAC
(SEQ ID NO:34)

*Fig. 20*

QVQLVQSGAEVKKPGSSVKVSCKASGYTFTTYYLHWVRQAPGQCLE
WMGWIYPGNVHAQYNEKFKGRVTITADKSTSTAYMELSSLRSEDTA
VYYCARSWEGFPYWGQGTTVTVSSGGGGSGGGGSGGGGSDIQMTQS
PSSLSASVGDRVTITCKASQNVGINVAWYQQKPGKAPKSLISSASY
RYSGVPSRFSGSGSGTDFTLTISSLQPEDFATYFCQQYDTYPFTFG
CGTKVEIKGGGGSGGGGSGGGGSGGGGSGGGGSQIQLVQSGPELKK
PGETVKISCKASGFTFTDYSIHWVKQAPGKGLKWMGWINTETGEPT
YTDDFKGRFAFSLVTSATTAYLQINNLNNEDTATFFCARFIYDPYW
GFAYWGQGTLVTVSAASTKGPSVFPLAPSSKSTSGGTAALGCLVKD
YFPEPVTVSWNSGALTSGVHTFPAVLQSSGLYSLSSVVTVPSSSLG
TQTYICNVNHKPSNTKVDKKVEPKSCDKTHTCPPCPAPELLGGPSV
FLFPPKPKDTLMISRTPEVTCVVVDVSHEDPEVKFNWYVDGVEVHN
AKTKPREEQYNSTYRVVSVLTVLHQDWLNGKEYKCKVSNKALPAPI
EKTISKAKGQPREPQVYTLPPSRDELTKNQVSLTCLVKGFYPSDIA
VEWESNGQPENNYKTTPPVLDSDGSFFLYSKLTVDKSRWQQGNVFS
CSVMHEALHNHYTQKSLSLSPG (SEQ ID NO:35)

*Fig. 21*

```
CAGGTCCAACTGGTGCAGTCTGGAGCTGAGGTGAAGAAGCCTGGGTCCTCAGTGAAGGTGT
CCTGCAAGGCTTCTGGCTACACTTTCACAACCTACTATTTGCACTGGGTGAGGCAGGCCCC
TGGACAGTGCCTTGAGTGGATGGGATGGATTTATCCTGGAAATGTTCATGCTCAGTACAAT
GAGAAGTTCAAGGGCAGGGTCACAATCACTGCAGACAAATCCACCAGCACAGCCTACATGG
AGCTCAGCAGCCTGAGGTCTGAAGATACTGCGGTCTATTACTGTGCAAGATCCTGGGAAGG
TTTTCCTTACTGGGGCCAAGGGACCACGGTCACCGTCTCCTCAGGCGGTGGAGGGTCCGGT
GGGGGCGGATCTGGGGGCGGCGGATCCGGTGGTGGTGGTAGTGACATTCAGATGACCCAGT
CTCCTAGCTCCCTGTCCGCCTCAGTAGGAGACAGGGTCACCATCACCTGCAAGGCCAGTCA
GAATGTGGGTATTAATGTAGCCTGGTATCAACAGAAACCAGGGAAGGCTCCTAAATCACTG
ATTTCCTCGGCCTCCTACCGGTACAGTGGAGTCCCTTCCAGATTCAGCGGCAGTGGATCTG
GGACAGATTTCACTCTCACCATCAGCAGCCTCCAGCCTGAAGACTTCGCAACCTATTTCTG
TCAGCAATATGACACCTATCCATTCACGTTCGGCTGCGGTACCAAGGTGGAGATCAAAGGC
GGTGGAGGGTCCGGTGGAGGGGGCTCTGGAGGGGCGGTTCAGGGGGCGGTGGATCGGGGG
GAGGTGGCTCCCAGATCCAGTTGGTGCAGTCTGGACCTGAGCTGAAGAAGCCTGGAGAGAC
AGTCAAGATCTCCTGCAAGGCTTCTGGTTTTACCTTCACAGACTATTCAATACACTGGGTG
AAACAGGCTCCAGGAAAGGGTTTAAAGTGGATGGGCTGGATAAACACTGAGACTGGTGAGC
CAACATATACAGATGACTTCAAGGGACGATTTGCCTTCTCTTTGGTGACCTCTGCCACCAC
TGCCTATTTGCAGATCAACAACCTCAACAATGAGGACACGGCTACATTTTTCTGTGCTAGA
TTCATCTATGATCCTTATTGGGGGTTTGCTTACTGGGGCCAGGGGACTCTGGTCACTGTCT
CCGCAGCTAGCACCAAGGGCCCATCGGTCTTCCCCCTGGCACCCTCCTCCAAGAGCACCTC
TGGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACCCAGAC
CTACATCTGCAACGTGAATCACAAGCCCAGCAACACCAAGGTGGACAAGAAAGTTGAGCCC
AAATCTTGTGACAAAACTCACACATGCCCACCGTGCCCAGCACCTGAACTCCTGGGGGGAC
CGTCAGTCTTCCTCTTCCCCCCAAAACCCAAGGACACCCTCATGATCTCCCGGACCCCTGA
GGTCACATGCGTGGTGGTGGACGTGAGCCACGAAGACCCTGAGGTCAAGTTCAACTGGTAC
GTGGACGGCGTGGAGGTGCATAATGCCAAGACAAAGCCGCGGGAGGAGCAGTACAACAGCA
CGTACCGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGATGAGCTGACCA
AGAACCAGGTCAGCCTGACCTGCCTGGTCAAAGGCTTCTATCCCAGCGACATCGCCGTGGA
GTGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCAGAAGAGCCT
CTCCCTGTCTCCGGGTTGA      (SEQ ID NO:36)
```

*Fig. 22*

QVQLVQSGAEVKKPGSSVKVSCKASGYTFTTYYLHWVRQAPGQCLEW
MGWIYPGNVHAQYNEKFKGRVTITADKSTSTAYMELSSLRSEDTAVY
YCARSWEGFPYWGQGTTVTVSSGGGGSGGGGSGGGGSGGGGSDIQMT
QSPSSLSASVGDRVTITCKASQNVGINVAWYQQKPGKAPKSLISSAS
YRYSGVPSRFSGSGSGTDFTLTISSLQPEDFATYFCQQYDTYPFTFG
CGTKVEIKGGGGSGGGGSGGGGSGGGGSGGGGSQIQLVQSGPELKKP
GETVKISCKASGFTFTDYSIHWVKQAPGKGLKWMGWINTETGEPTYT
DDFKGRFAFSLVTSATTAYLQINNLNNEDTATFFCARFIYDPYWGFA
YWGQGTLVTVSAASTKGPSVFPLAPSSKSTSGGTAALGCLVKDYFPE
PVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAK
GQPREPQVYTLPPSRDELTKNQVSLTCLVKGFYPSDIAVEWESNGQP
ENNYKTTPPVLDSDGSFFLYSKLTVDKSRWQQGNVFSCSVMHEALHN
HYTQKSLSLSPG     (SEQ ID NO:37)

*Fig. 23*

```
CAGATCCAGTTGGTGCAGTCTGGACCTGAGCTGAAGAAGCCTGGAGAGACAGTCAAG
ATCTCCTGCAAGGCTTCTGGTTTTACCTTCACAGACTATTCAATACACTGGGTGAAA
CAGGCTCCAGGAAAGGGTTTAAAGTGGATGGGCTGGATAAACACTGAGACTGGTGAG
CCAACATATACAGATGACTTCAAGGGACGATTTGCCTTCTCTTTGGTGACCTCTGCC
ACCACTGCCTATTTGCAGATCAACAACCTCAACAATGAGGACACGGCTACATTTTTC
TGTGCTAGATTCATCTATGATCCTTATTGGGGGTTTGCTTACTGGGCCAGGGGACT
CTGGTCACTGTCTCCGCAGCTAGCACCAAGGGCCCATCGGTCTTCCCCCTGGCACCC
TCCTCCAAGAGCACCTCTGGGGGCACAGCGGCCCTGGGCTGCCTGGTCAAGGACTAC
TTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTGGTGACC
GTGCCCTCCAGCAGCTTGGGCACCCAGACCTACATCTGCAACGTGAATCACAAGCCC
AGCAACACCAAGGTGGACAAGAAAGTTGAGCCCAAATCTTGTGACAAAACTCACACA
TGCCCACCGTGCCCAGCACCTGAACTCCTGGGGGGACCGTCAGTCTTCCTCTTCCCC
CCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTG
GAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGATGAGCTG
ACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGC
AGGTGGCAGCAGGGGAACGTCTTCTCATGCTCCGTGATGCATGAGGCTCTGCACAAC
CACTACACGCAGAAGAGCCTCTCCCTGTCTCCGGGTAAATCCGGCGGGGTGGATCC
GGTGGAGGGGGCTCCGGCGGTGGCGGGTCCCAGGTCCAACTGGTGCAGTCTGGAGCT
GAGGTGAAGAAGCCTGGGTCCTCAGTGAAGGTGTCCTGCAAGGCTTCTGGCTACACT
TTCACAACCTACTATTTGCACTGGGTGAGGCAGGCCCCTGGACAGGGACTTGAGTGG
ATGGGATGGATTTATCCTGGAAATGTTCATGCTCAGTACAATGAAGTTCAAGGGC
AGGGTCACAATCACTGCAGACAAATCCACCAGCACAGCCTACATGGAGCTCAGCAGC
CTGAGGTCTGAAGATACTGCGGTCTATTACTGTGCAAGATCCTGGGAAGGTTTTCCT
TACTGGGGCCAAGGGACCACGGTCACCGTCTCCTCAGGTGGGGCGGATCTGGGGGC
GGCGGGTCCGGTGGTGGTGGTAGTGACATTCAGATGACCCAGTCTCCTAGCTCCCTG
TCCGCCTCAGTAGGAGACAGGGTCACCATCACCTGCAAGGCCAGTCAGAATGTGGGT
ATTAATGTAGCCTGGTATCAACAGAAACCAGGGAAGGCTCCTAAATCACTGATTTCC
TCGGCCTCCTACCGGTACAGTGGAGTCCCTTCCAGATTCAGCGGCAGTGGATCTGGG
ACAGATTTCACTCTCACCATCAGCAGCCTCCAGCCTGAAGACTTCGCAACCTATTTC
TGTCAGCAATATGACACCTATCCATTCACGTTCGGCCAGGGTACCAAGGTGGAGATC
AAATGA      (SEQ ID NO:44)
```

*Fig. 24*

QIQLVQSGPELKKPGETVKISCKASGFTFTDYSIHWVKQAPGKG
LKWMGWINTETGEPTYTDDFKGRFAFSLVTSATTAYLQINNLNN
EDTATFFCARFIYDPYWGFAYWGQGTLVTVSAASTKGPSVFPLA
PSSKSTSGGTAALGCLVKDYFPEPVTVSWNSGALTSGVHTFPAV
LQSSGLYSLSSVVTVPSSSLGTQTYICNVNHKPSNTKVDKKVEP
KSCDKTHTCPPCPAPELLGGPSVFLFPPKPKDTLMISRTPEVTC
VVVDVSHEDPEVKFNWYVDGVEVHNAKTKPREEQYNSTYRVVSV
LTVLHQDWLNGKEYKCKVSNKALPAPIEKTISKAKGQPREPQVY
TLPPSRDELTKNQVSLTCLVKGFYPSDIAVEWESNGQPENNYKT
TPPVLDSDGSFFLYSKLTVDKSRWQQGNVFSCSVMHEALHNHYT
QKSLSLSPGKSGGGGSGGGGSGGGGSQVQLVQSGAEVKKPGSSV
KVSCKASGYTFTTYYLHWVRQAPGQGLEWMGWIYPGNVHAQYNE
KFKGRVTITADKSTSTAYMELSSLRSEDTAVYYCARSWEGFPYW
GQGTTVTVSSGGGGSGGGGSGGGGSDIQMTQSPSSLSASVGDRV
TITCKASQNVGINVAWYQQKPGKAPKSLISSASYRYSGVPSRFS
GSGSGTDFTLTISSLQPEDFATYFCQQYDTYPFTFGQGTKVEIK
(SEQ ID NO:45)

*Fig. 25*

CAGATCCAGTTGGTGCAGTCTGGACCTGAGCTGAAGAAGCCTGGAGAGACAGTCAAGATC
TCCTGCAAGGCTTCTGGTTTTACCTTCACAGACTATTCAATACACTGGGTGAAACAGGCT
CCAGGAAAGGGTTTAAAGTGGATGGGCTGGATAAACACTGAGACTGGTGAGCCAACATAT
ACAGATGACTTCAAGGGACGATTTGCCTTCTCTTTGGTGACCTCTGCCACCACTGCCTAT
TTGCAGATCAACAACCTCAACAATGAGGACACGGCTACATTTTTCTGTGCTAGATTCATC
TATGATCCTTATTGGGGGTTTGCTTACTGGGGCCAGGGGACTCTGGTCACTGTCTCCGCA
GCTAGCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAAAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGAGCAGTACAAC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGATGAG
CTGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATCCGGCGGGGGTGGATCCGGTGGAGGGGGC
TCCGGCGGTGGCGGGTCCCAGGTCCAACTGGTGCAGTCTGGAGCTGAGGTGAAGAAGCCT
GGGTCCTCAGTGAAGGTGTCCTGCAAGGCTTCTGGCTACACTTTCACAACCTACTATTTG
CACTGGGTGAGGCAGGCCCCTGGACAGGGACTTGAGTGGATGGGATGGATTTATCCTGGA
AATGTTCATGCTCAGTACAATGAGAAGTTCAAGGGCAGGGTCACAATCACTGCAGACAAA
TCCACCAGCACAGCCTACATGGAGCTCAGCAGCCTGAGGTCTGAAGATACTGCGGTCTAT
TACTGTGCAAGATCCTGGGAAGGTTTTCCTTACTGGGGCCAAGGGACCACGGTCACCGTC
TCCTCAGGCGGTGGAGGGTCCGGTGGGGCGGATCTGGGGCGGCGGGTCCGGTGGTGGT
GGTAGTGACATTCAGATGACCCAGTCTCCTAGCTCCCTGTCCGCCTCAGTAGGAGACAGG
GTCACCATCACCTGCAAGGCCAGTCAGAATGTGGGTATTAATGTAGCCTGGTATCAACAG
AAACCAGGGAAGGCTCCTAAATCACTGATTTCCTCGGCCTCCTACCGGTACAGTGGAGTC
CCTTCCAGATTCAGCGGCAGTGGATCTGGGACAGATTTCACTCTCACCATCAGCAGCCTC
CAGCCTGAAGACTTCGCAACCTATTTCTGTCAGCAATATGACACCTATCCATTCACGTTC
GGCCAGGGTACCAAGGTGGAGATCAAATGA    (SEQ ID NO:46)

*Fig. 26*

QIQLVQSGPELKKPGETVKISCKASGFTFTDYSIHWVKQAPGKGLKW
MGWINTETGEPTYTDDFKGRFAFSLVTSATTAYLQINNLNNEDTATF
FCARFIYDPYWGFAYWGQGTLVTVSAASTKGPSVFPLAPSSKSTSGG
TAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNK
ALPAPIEKTISKAKGQPREPQVYTLPPSRDELTKNQVSLTCLVKGFY
PSDIAVEWESNGQPENNYKTTPPVLDSDGSFFLYSKLTVDKSRWQQG
NVFSCSVMHEALHNHYTQKSLSLSPGKSGGGGSGGGGSGGGGSQVQL
VQSGAEVKKPGSSVKVSCKASGYTFTTYYLHWVRQAPGQGLEWMGWI
YPGNVHAQYNEKFKGRVTITADKSTSTAYMELSSLRSEDTAVYYCAR
SWEGFPYWGQGTTVTVSSGGGGSGGGGSGGGGSGGGGSDIQMTQSPS
SLSASVGDRVTITCKASQNVGINVAWYQQKPGKAPKSLISSASYRYS
GVPSRFSGSGSGTDFTLTISSLQPEDFATYFCQQYDTYPFTFGQGTK
VEIK      (SEQ ID NO:47)

*Fig. 27*

CAGATCCAGTTGGTGCAGTCTGGACCTGAGCTGAAGAAGCCTGGAGAGACAGTCAAGAT
CTCCTGCAAGGCTTCTGGTTTTACCTTCACAGACTATTCAATACACTGGGTGAAACAGG
CTCCAGGAAAGGGTTTAAAGTGGATGGGCTGGATAAACACTGAGACTGGTGAGCCAACA
TATACAGATGACTTCAAGGGACGATTTGCCTTCTCTTTGGTGACCTCTGCCACCACTGC
CTATTTGCAGATCAACAACCTCAACAATGAGGACACGGCTACATTTTTCTGTGCTAGAT
TCATCTATGATCCTTATTGGGGGTTTGCTTACTGGGGCCAGGGGACTCTGGTCACTGTC
TCCGCAGCTAGCACCAAGGGCCCATCGGTCTTCCCCCTGGCACCCTCCTCCAAGAGCAC
CTCTGGGGGCACAGCGGCCCTGGGCTGCCTGGTCAAGGACTACTTCCCCGAACCGGTGA
CGGTGTCGTGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGCAGCTTGGG
CACCCAGACCTACATCTGCAACGTGAATCACAAGCCCAGCAACACCAAGGTGGACAAGA
AAGTTGAGCCCAAATCTTGTGACAAAACTCACACATGCCCACCGTGCCCAGCACCTGAA
CTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAGG
TCAAGTTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCCCAGCCCCCA
TCGAGAAAACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTGGTCAAAGG
CTTCTATCCCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTACAGCAAGCTC
ACCGTGGACAAGAGCAGGTGGCAGCAGGGGAACGTCTTCTCATGCTCCGTGATGCATGA
GGCTCTGCACAACCACTACACGCAGAAGAGCCTCTCCCTGTCTCCGGGTAAATCCGGCG
GGGGTGGATCCGGTGGAGGGGGCTCCGGCGGTGGCGGGTCCCAGGTCCAACTGGTGCAG
TCTGGAGCTGAGGTGAAGAAGCCTGGGTCCTCAGTGAAGGTGTCCTGCAAGGCTTCTGG
CTACACTTTCACAACCTACTATTTGCACTGGGTGAGGCAGGCCCCTGGACAGTGCCTTG
AGTGGATGGGATGGATTTATCCTGGAAATGTTCATGCTCAGTACAATGAGAAGTTCAAG
GGCAGGGTCACAATCACTGCAGACAAATCCACCAGCACAGCCTACATGGAGCTCAGCAG
CCTGAGGTCTGAAGATACTGCGGTCTATTACTGTGCAAGATCCTGGGAAGGTTTTCCTT
ACTGGGGCCAAGGGACCACGGTCACCGTCTCCTCAGGTGGGGGCGGATCTGGGGGCGGC
GGGTCCGGTGGTGGTGGTAGTGACATTCAGATGACCCAGTCTCCTAGCTCCCTGTCCGC
CTCAGTAGGAGACAGGGTCACCATCACCTGCAAGGCCAGTCAGAATGTGGGTATTAATG
TAGCCTGGTATCAACAGAAACCAGGGAAGGCTCCTAAATCACTGATTTCCTCGGCCTCC
TACCGGTACAGTGGAGTCCCTTCCAGATTCAGCGGCAGTGGATCTGGGACAGATTTCAC
TCTCACCATCAGCAGCCTCCAGCCTGAAGACTTCGCAACCTATTTCTGTCAGCAATATG
ACACCTATCCATTCACGTTCGGCTGCGGTACCAAGGTGGAGATCAAATGA
(SEQ ID NO:48)

*Fig. 28*

QIQLVQSGPELKKPGETVKISCKASGFTFTDYSIHWVKQAPGKGLK
WMGWINTETGEPTYTDDFKGRFAFSLVTSATTAYLQINNLNNEDTA
TFFCARFIYDPYWGFAYWGQGTLVTVSAASTKGPSVFPLAPSSKST
SGGTAALGCLVKDYFPEPVTVSWNSGALTSGVHTFPAVLQSSGLYS
LSSVVTVPSSSLGTQTYICNVNHKPSNTKVDKKVEPKSCDKTHTCP
PCPAPELLGGPSVFLFPPKPKDTLMISRTPEVTCVVVDVSHEDPEV
KFNWYVDGVEVHNAKTKPREEQYNSTYRVVSVLTVLHQDWLNGKEY
KCKVSNKALPAPIEKTISKAKGQPREPQVYTLPPSRDELTKNQVSL
TCLVKGFYPSDIAVEWESNGQPENNYKTTPPVLDSDGSFFLYSKLT
VDKSRWQQGNVFSCSVMHEALHNHYTQKSLSLSPGKSGGGGSGGGG
SGGGGSQVQLVQSGAEVKKPGSSVKVSCKASGYTFTTYYLHWVRQA
PGQCLEWMGWIYPGNVHAQYNEKFKGRVTITADKSTSTAYMELSSL
RSEDTAVYYCARSWEGFPYWGQGTTVTVSSGGGGSGGGGSGGGGSD
IQMTQSPSSLSASVGDRVTITCKASQNVGINVAWYQQKPGKAPKSL
ISSASYRYSGVPSRFSGSGSGTDFTLTISSLQPEDFATYFCQQYDT
YPFTFGCGTKVEIK    (SEQ ID NO:49)

*Fig. 29*

```
CAGATCCAGTTGGTGCAGTCTGGACCTGAGCTGAAGAAGCCTGGAGAGACAGTCAAG
ATCTCCTGCAAGGCTTCTGGTTTTACCTTCACAGACTATTCAATACACTGGGTGAAA
CAGGCTCCAGGAAAGGGTTTAAAGTGGATGGGCTGGATAAACACTGAGACTGGTGAG
CCAACATATACAGATGACTTCAAGGGACGATTTGCCTTCTCTTTGGTGACCTCTGCC
ACCACTGCCTATTTGCAGATCAACAACCTCAACAATGAGGACACGGCTACATTTTTC
TGTGCTAGATTCATCTATGATCCTTATTGGGGGTTTGCTTACTGGGGCCAGGGGACT
CTGGTCACTGTCTCCGCAGCTAGCACCAAGGGCCCATCGGTCTTCCCCCTGGCACCC
TCCTCCAAGAGCACCTCTGGGGGCACAGCGGCCCTGGGCTGCCTGGTCAAGGACTAC
TTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTGGTGACC
GTGCCCTCCAGCAGCTTGGGCACCCAGACCTACATCTGCAACGTGAATCACAAGCCC
AGCAACACCAAGGTGGACAAGAAAGTTGAGCCCAAATCTTGTGACAAAACTCACACA
TGCCCACCGTGCCCAGCACCTGAACTCCTGGGGGGACCGTCAGTCTTCCTCTTCCCC
CCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTG
GAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAG
TGCAAGGTCTCCAACAAAGCCCTCCCAGCCCCATCGAGAAACCATCTCCAAAGCC
AAAGGGCAGCCCCGAGAACCACAGGTGTACACCCTGCCCCCATCCCGGGATGAGCTG
ACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGC
AGGTGGCAGCAGGGGAACGTCTTCTCATGCTCCGTGATGCATGAGGCTCTGCACAAC
CACTACACGCAGAAGAGCCTCTCCCTGTCTCCGGGTAAATCCGGCGGGGGTGGATCC
GGTGGAGGGGGCTCCGGCGGTGGCGGGTCCCAGGTCCAACTGGTGCAGTCTGGAGCT
GAGGTGAAGAAGCCTGGGTCCTCAGTGAAGGTGTCCTGCAAGGCTTCTGGCTACACT
TTCACAACCTACTATTTGCACTGGGTGAGGCAGGCCCCTGGACAGTGCCTTGAGTGG
ATGGGATGGATTTATCCTGGAAATGTTCATGCTCAGTACAATGAAGTTCAAGGGC
AGGGTCACAATCACTGCAGACAAATCCACCAGCACAGCCTACATGGAGCTCAGCAGC
CTGAGGTCTGAAGATACTGCGGTCTATTACTGTGCAAGATCCTGGGAAGGTTTTCCT
TACTGGGGCCAAGGGACCACGGTCACCGTCTCCTCAGGCGGTGGAGGGTCCGGTGGG
GGCGGATCTGGGGGCGGCGGGTCCGGTGGTGGTGGTAGTGACATTCAGATGACCCAG
TCTCCTAGCTCCCTGTCCGCCTCAGTAGGAGACAGGGTCACCATCACCTGCAAGGCC
AGTCAGAATGTGGGTATTAATGTAGCCTGGTATCAACAGAAACCAGGGAAGGCTCCT
AAATCACTGATTTCCTCGGCCTCCTACCGGTACAGTGGAGTCCCTTCCAGATTCAGC
GGCAGTGGATCTGGGACAGATTTCACTCTCACCATCAGCAGCCTCCAGCCTGAAGAC
TTCGCAACCTATTTCTGTCAGCAATATGACACCTATCCATTCACGTTCGGCTGCGGT
ACCAAGGTGGAGATCAAATGA    (SEQ ID NO:50)
```

*Fig. 30*

```
QIQLVQSGPELKKPGETVKISCKASGFTFTDYSIHWVKQAPGKGLK
WMGWINTETGEPTYTDDFKGRFAFSLVTSATTAYLQINNLNNEDTA
TFFCARFIYDPYWGFAYWGQGTLVTVSAASTKGPSVFPLAPSSKST
SGGTAALGCLVKDYFPEPVTVSWNSGALTSGVHTFPAVLQSSGLYS
LSSVVTVPSSSLGTQTYICNVNHKPSNTKVDKKVEPKSCDKTHTCP
PCPAPELLGGPSVFLFPPKPKDTLMISRTPEVTCVVVDVSHEDPEV
KFNWYVDGVEVHNAKTKPREEQYNSTYRVVSVLTVLHQDWLNGKEY
KCKVSNKALPAPIEKTISKAKGQPREPQVYTLPPSRDELTKNQVSL
TCLVKGFYPSDIAVEWESNGQPENNYKTTPPVLDSDGSFFLYSKLT
VDKSRWQQGNVFSCSVMHEALHNHYTQKSLSLSPGKSGGGGSGGGG
SGGGGSQVQLVQSGAEVKKPGSSVKVSCKASGYTFTTYYLHWVRQA
PGQCLEWMGWIYPGNVHAQYNEKFKGRVTITADKSTSTAYMELSSL
RSEDTAVYYCARSWEGFPYWGQGTTVTVSSGGGGSGGGGSGGGGSG
GGGSDIQMTQSPSSLSASVGDRVTITCKASQNVGINVAWYQQKPGK
APKSLISSASYRYSGVPSRFSGSGSGTDFTLTISSLQPEDFATYFC
QQYDTYPFTFGCGTKVEIK
```

(SEQ ID NO:51)

*Fig. 31*

1. Mark 12 Marker
2. N- Hercules VH44:VL100 non-reduced
3. N- Hercules VH44:VL100 reduced
4. Mark 12 Marker
5. N- Hercules VH44:VL100/$(G_4/S)_4$ non-reduced
6. N- Hercules VH44:VL100/$(G_4/S)_4$ reduced 1. Mark 12 Marker
2. C-Hercules VH44:VL100 non-reduced
3. C-Hercules VH44:VL100 reduced
4. C-Hercules VH44:VL100/$(G_4/S)_4$ non-reduced
5. C-Hercules VH44:VL100/$(G_4/S)_4$ reduced Stabilized sc(Fv)2 Tetravalent CH2 Domain-Deleted Bispecific Antibody
(Stabilized C-scFv Tetravalent CH2 Domain- Deleted Bispecific Antibody)
bispecific C-scFv Tetravalent CH2 Domain Deleted antibody)

V = Variable
C = Constant
L = Light
H = Heavy
HCP = Hinge Connecting Peptide
), ↶ = (G$_4$S)4 linkers Stabilized N$_H$-scFv Tetravalent CH2 Domain-
Deleted Bispecific Antibody V = Variable
C = Constant
L = Light
H = Heavy
HCP = Hinge Connecting Peptide ⟩ = (G$_4$S)$_4$ linker ⟩ = (G$_4$S)$_4$G$_3$AS flexible linker A.
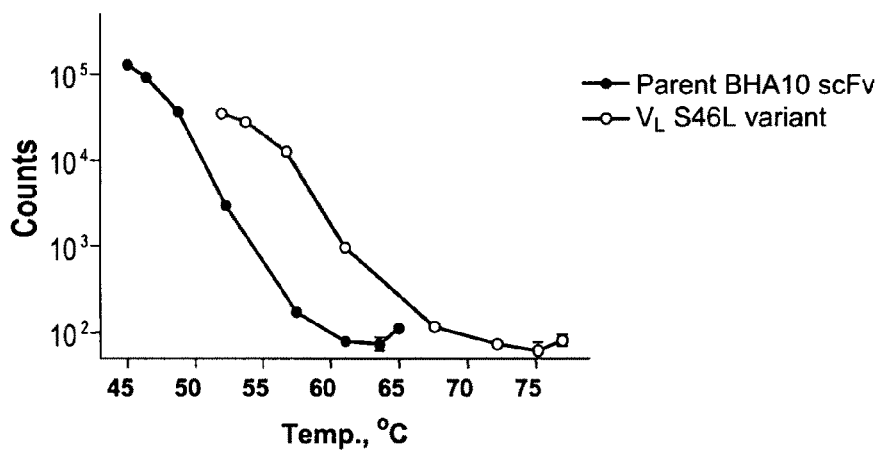
B.
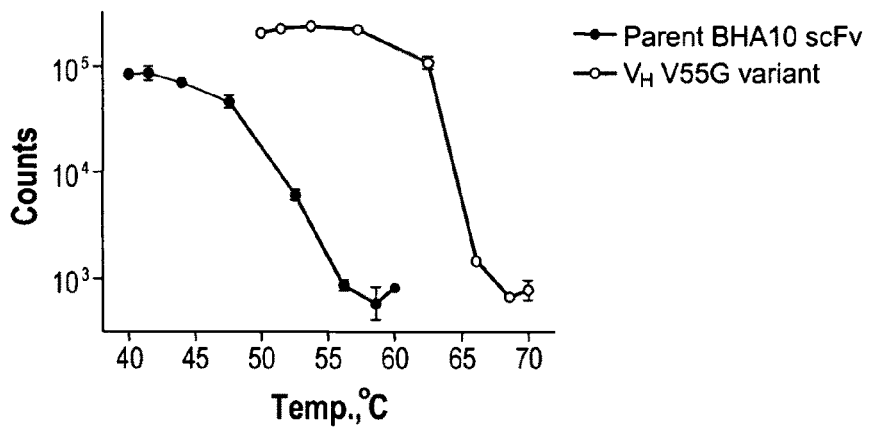
C.
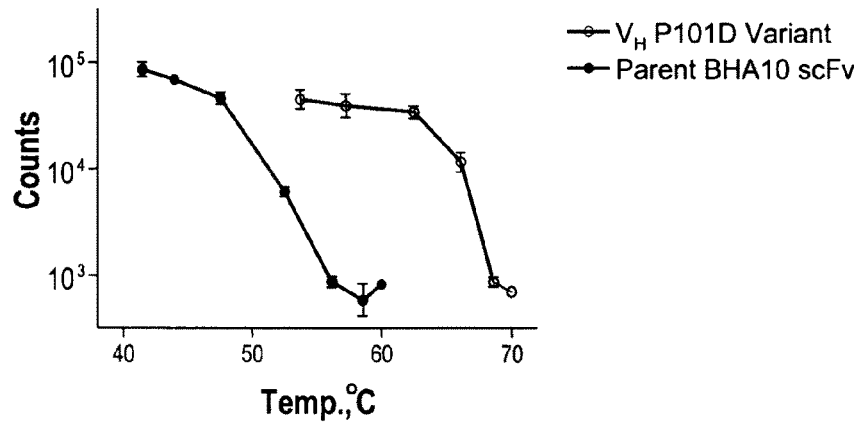
*Fig. 50*

CAGATCCAGTTGGTGCAGTCTGGACCTGAGCTGAAGAAGCCTGGAGAGACAGTCAAGAT
CTCCTGCAAGGCTTCTGGTTTTACCTTCACAGACTATTCAATACACTGGGTGAAACAGG
CTCCAGGAAAGGGTTTAAAGTGGATGGGCTGGATAAACACTGAGACTGGTGAGCCAACA
TATACAGATGACTTCAAGGGACGATTTGCCTTCTCTTTGGTGACCTCTGCCACCACTGC
CTATTTGCAGATCAACAACCTCAACAATGAGGACACGGCTACATTTTTCTGTGCTAGAT
TCATCTATGATCCTTATTGGGGGTTTGCTTACTGGGGCCAGGGGACTCTGGTCACTGTC
TCCGCAGCTAGCACCAAGGGCCCATCGGTCTTCCCCCTGGCACCCTCCTCCAAGAGCAC
CTCTGGGGGCACAGCGGCCCTGGGCTGCCTGGTCAAGGACTACTTCCCCGAACCGGTGA
CGGTGTCGTGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGCAGCTTGGG
CACCCAGACCTACATCTGCAACGTGAATCACAAGCCCAGCAACACCAAGGTGGACAAGA
AAGTTGAGCCCAAATCTTGTGACAAAACTCACACATGCCCACCGTGCCCAGCACCTGAA
CTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAGG
TCAAGTTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCCCAGCCCCCA
TCGAGAAAACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTGGTCAAAGG
CTTCTATCCCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTACAGCAAGCTC
ACCGTGGACAAGAGCAGGTGGCAGCAGGGGAACGTCTTCTCATGCTCCGTGATGCATGA
GGCTCTGCACAACCACTACACGCAGAAGAGCCTCTCCCTGTCTCCGGGTAAATCCGGCG
GGGGTGGATCCGGTGGAGGGGCTCCGGCGGTGGCGGGTCCCAGGTCCAACTGGTGCAG
TCTGGAGCTGAGGTGAAGAAGCCTGGGGAGTCAGTGAAGGTGTCCTGCAAGGCTTCTGG
CTACACTTTCACAACCTACTATTTGCACTGGGTGAGGCAGGCCCCTGGACAGGGACTTG
AGTGGATGGGATGGATTTATCCTGGAAATGTTCATGCTCAGTACAATGAGAAGTTCAAG
GGCAGGGTCACAATCACTGCAGACAAATCCACCAGCACAGCCTACATGGAGCTCAGCAG
CCTGAGGTCTGAAGATACTGCGGTCTATTACTGTGCAAGATCCTGGGAAGGTTTTCCTT
ACTGGGGCCAAGGGACCACGGTCACCGTCTCCTCAGGCGGTGGAGGGTCCGGTGGGGC
GGATCTGGGGGCGGCGGGTCCGGTGGTGGTGGTAGTGACATTCAGATGACCCAGTCTCC
TAGCTCCCTGTCCGCCTCAGTAGGAGACAGGGTCACCATCACCTGCAAGGCCAGTCAGA
ATGTGGGTATTAATGTAGCCTGGTATCAACAGAAACCAGGGAAGGCTCCTAAATTACTG
ATTTCCTCGGCCTCCTACCGGTACAGTGGAGTCCCTTCCAGATTCAGCGGCAGTGGATC
TGGGACAGATTTCACTCTCACCATCAGCAGCCTCCAGCCTGAAGACTTCGCAACCTATT
TCTGTCAGCAATATGACACCTATCCATTCACGTTCGGCCAGGGTACCAAGGTGGAGATC
AAATGA     (SEQ ID NO: 52)

*Fig. 61*

QIQLVQSGPELKKPGETVKISCKASGFTFTDYSIHWVKQAPGKG
LKWMGWINTETGEPTYTDDFKGRFAFSLVTSATTAYLQINNLNN
EDTATFFCARFIYDPYWGFAYWGQGTLVTVSAASTKGPSVFPLA
PSSKSTSGGTAALGCLVKDYFPEPVTVSWNSGALTSGVHTFPAV
LQSSGLYSLSSVVTVPSSSLGTQTYICNVNHKPSNTKVDKKVEP
KSCDKTHTCPPCPAPELLGGPSVFLFPPKPKDTLMISRTPEVTC
VVVDVSHEDPEVKFNWYVDGVEVHNAKTKPREEQYNSTYRVVSV
LTVLHQDWLNGKEYKCKVSNKALPAPIEKTISKAKGQPREPQVY
TLPPSRDELTKNQVSLTCLVKGFYPSDIAVEWESNGQPENNYKT
TPPVLDSDGSFFLYSKLTVDKSRWQQGNVFSCSVMHEALHNHYT
QKSLSLSPGKSGGGGSGGGGSGGGGSQVQLVQSGAEVKKPGESV
KVSCKASGYTFTTYYLHWVRQAPGQGLEWMGWIYPGNVHAQYNE
KFKGRVTITADKSTSTAYMELSSLRSEDTAVYYCARSWEGFPYW
GQGTTVTVSSGGGGSGGGGSGGGGSGGGGSDIQMTQSPSSLSAS
VGDRVTITCKASQNVGINVAWYQQKPGKAPKLLISSASYRYSGV
PSRFSGSGSGTDFTLTISSLQPEDFATYFCQQYDTYPFTFGQGT
KVEIK     (SEQ ID NO: 53)

*Fig. 62*

CAGATCCAGTTGGTGCAGTCTGGACCTGAGCTGAAGAAGCCTGGAGAGACAGTCAAG
ATCTCCTGCAAGGCTTCTGGTTTTACCTTCACAGACTATTCAATACACTGGGTGAAA
CAGGCTCCAGGAAAGGGTTTAAAGTGGATGGGCTGGATAAACACTGAGACTGGTGAG
CCAACATATACAGATGACTTCAAGGGACGATTTGCCTTCTCTTTGGTGACCTCTGCC
ACCACTGCCTATTTGCAGATCAACAACCTCAACAATGAGGACACGGCTACATTTTTC
TGTGCTAGATTCATCTATGATCCTTATTGGGGGTTTGCTTACTGGGCCAGGGGACT
CTGGTCACTGTCTCCGCAGCTAGCACCAAGGGCCCATCGGTCTTCCCCCTGGCACCC
TCCTCCAAGAGCACCTCTGGGGGCACAGCGGCCCTGGGCTGCCTGGTCAAGGACTAC
TTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTGGTGACC
GTGCCCTCCAGCAGCTTGGGCACCCAGACCTACATCTGCAACGTGAATCACAAGCCC
AGCAACACCAAGGTGGACAAGAAAGTTGAGCCCAAATCTTGTGACAAAACTCACACA
TGCCCACCGTGCCCAGCACCTGAACTCCTGGGGGGACCGTCAGTCTTCCTCTTCCCC
CCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTG
GAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGATGAGCTG
ACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGC
AGGTGGCAGCAGGGGAACGTCTTCTCATGCTCCGTGATGCATGAGGCTCTGCACAAC
CACTACACGCAGAAGAGCCTCTCCCTGTCTCCGGGTAAATCCGGCGGGGTGGATCC
GGTGGAGGGGGCTCCGGCGGTGGCGGGTCCAGGTCCAACTGGTGCAGTCTGGAGCT
GAGGTGAAGAAGCCTGGGGAGTCAGTGAAGGTGTCCTGCAAGGCTTCTGGCTACACT
TTCACAACCTACTATTTGCACTGGGTGAGGCAGGCCCCTGGACAGTGCCTTGAGTGG
ATGGGATGGATTTATCCTGGAAATGTTCATGCTCAGTACAATGAAGTTCAAGGGC
AGGGTCACAATCACTGCAGACAAATCCACCAGCACAGCCTACATGGAGCTCAGCAGC
CTGAGGTCTGAAGATACTGCGGTCTATTACTGTGCAAGATCCTGGGAAGGTTTTCCT
TACTGGGGCCAAGGGACCACGGTCACCGTCTCCTCAGGCGGTGGAGGGTCCGGTGGG
GGCGGATCTGGGGGCGGCGGGTCCGGTGGTGGTGGTAGTGACATTCAGATGACCCAG
TCTCCTAGCTCCCTGTCCGCCTCAGTAGGAGACAGGGTCACCATCACCTGCAAGGCC
AGTCAGAATGTGGGTATTAATGTAGCCTGGTATCAACAGAAACCAGGGAAGGCTCCT
AAATTACTGATTTCCTCGGCCTCCTACCGGTACAGTGGAGTCCCTTCCAGATTCAGC
GGCAGTGGATCTGGGACAGATTTCACTCTCACCATCAGCAGCCTCCAGCCTGAAGAC
TTCGCAACCTATTTCTGTCAGCAATATGACACCTATCCATTCACGTTCGGCTGCGGT
ACCAAGGTGGAGATCAAATGA     (SEQ ID NO: 54)

*Fig. 63*

QIQLVQSGPELKKPGETVKISCKASGFTFTDYSIHWVKQAPGKGLK
WMGWINTETGEPTYTDDFKGRFAFSLVTSATTAYLQINNLNNEDTA
TFFCARFIYDPYWGFAYWGQGTLVTVSAASTKGPSVFPLAPSSKST
SGGTAALGCLVKDYFPEPVTVSWNSGALTSGVHTFPAVLQSSGLYS
LSSVVTVPSSSLGTQTYICNVNHKPSNTKVDKKVEPKSCDKTHTCP
PCPAPELLGGPSVFLFPPKPKDTLMISRTPEVTCVVVDVSHEDPEV
KFNWYVDGVEVHNAKTKPREEQYNSTYRVVSVLTVLHQDWLNGKEY
KCKVSNKALPAPIEKTISKAKGQPREPQVYTLPPSRDELTKNQVSL
TCLVKGFYPSDIAVEWESNGQPENNYKTTPPVLDSDGSFFLYSKLT
VDKSRWQQGNVFSCSVMHEALHNHYTQKSLSLSPGKSGGGGSGGGG
SGGGGSQVQLVQSGAEVKKPGESVKVSCKASGYTFTTYYLHWVRQA
PGQCLEWMGWIYPGNVHAQYNEKFKGRVTITADKSTSTAYMELSSL
RSEDTAVYYCARSWEGFPYWGQGTTVTVSSGGGGSGGGGSGGGGSG
GGGSDIQMTQSPSSLSASVGDRVTITCKASQNVGINVAWYQQKPGK
APKLLISSASYRYSGVPSRFSGSGSGTDFTLTISSLQPEDFATYFC
QQYDTYPFTFGCGTKVEIK (SEQ ID NO: 55)

*Fig. 64*

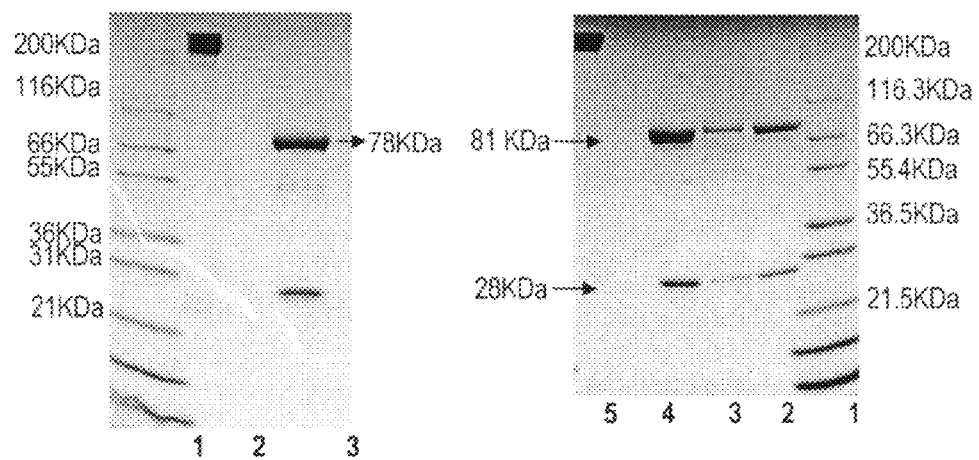
*Fig. 66A*  *Fig. 66B*

```
GAGGTGCAGCTGGTGGAGTCTGGGGGCGGCTTGGCAAAGCCTGGGGGGTCCCTGAGACTCT
CCTGCGCAGCCTCCGGGTTCAGGTTCACCTTCAATAACTACTACATGGACTGGGTCCGCCA
GGCTCCAGGGCAGGGGCTGGAGTGGGTCTCACGTATTAGTAGTAGTGGTGATCCCACATGG
TACGCAGACTCCGTGAAGGGCAGATTCACCATCTCCAGAGAGAACGCCAAGAACACACTGT
TTCTTCAAATGAACAGCCTGAGAGCTGAGGACACGGCTGTCTATTACTGTGCGAGCTTGAC
TACAGGGTCTGACTCCTGGGGCCAGGGAGTCCTGGTCACCGTCTCCTCAGCTAGCACCAAG
GGCCCATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAGGCGC
CCTGACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAACGTGA
ATCACAAGCCCAGCAACACCAAGGTGGACAAGAAAGTTGAGCCCAAATCTTGTGACAAAAC
TCACACATGCCCACCGTGCCCAGCACCTGAACTCCTGGGGGGACCGTCAGTCTTCCTCTTC
CCCCCAAAACCCAAGGACACCCTCATGATCTCCCGGACCCCTGAGGTCACATGCGTGGTGG
TGGACGTGAGCCACGAAGACCCTGAGGTCAAGTTCAACTGGTACGTGGACGGCGTGGAGGT
GCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGGCAGCCCCGAGA
ACCACAGGTGTACACCCTGCCCCCATCCCGGGATGAGCTGACCAAGAACCAGGTCAGCCTG
ACCTGCCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCTTCCT
CTACAGCAAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCTCCGGGTA
AATCCGGCGGGGGTGGATCCGGTGGAGGGGGCTCCGGCGGTGGCGGGTCCGACATCCAGAT
GACCCAGTCTCCATCTTCCCTGTCTGCATCTGTAGGGGACAGAGTCACCATCACTTGCAGG
GCAAGTCAGGACATTAGGTATTATTTAAATTGGTATCAGCAGAAACCAGGAAAAGCTCCTA
AGCTCCTGATCTATGTTGCATCCAGTTTGCAAAGTGGGGTCCCATCAAGGTTCAGCGGCAG
TGGATCTGGGACAGAGTTCACTCTCACCGTCAGCAGCCTGCAGCCTGAAGATTTTGCGACT
TATTACTGTCTACAGGTTTATAGTACCCCTCGGACGTTCGGCCAAGGGACCAAGGTGGAAA
TCAAAGGTGGGGCGGATCTGGGGCGGCGGGTCCGGTGGTGGTGGTAGTGAGGTGCAGCT
GGTGGAGTCTGGGGGCGGCTTGGCAAAGCCTGGGGGGTCCCTGAGACTCTCCTGCGCAGCC
TCCGGGTTCAGGTTCACCTTCAATAACTACTACATGGACTGGGTCCGCCAGGCTCCAGGGC
AGGGGCTGGAGTGGGTCTCACGTATTAGTAGTAGTGGTGATCCCACATGGTACGCAGACTC
CGTGAAGGGCAGATTCACCATCTCCAGAGAGAACGCCAAGAACACACTGTTTCTTCAAATG
AACAGCCTGAGAGCTGAGGACACGGCTGTCTATTACTGTGCGAGCTTGACTACAGGGTCTG
ACTCCTGGGGCCAGGGAGTCCTGGTCACCGTCTCCTCATGA          (SEQ ID NO:63)
```

Fig. 80

EVQLVESGGGLAKPGGSLRLSCAASGFRFTFNNYYMDWVRQAPGQGLEWVSRIS
SSGDPTWYADSVKGRFTISRENAKNTLFLQMNSLRAEDTAVYYCASLTTGSDSW
GQGVLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEA
LHNHYTQKSLSLSPGKSGGGGSGGGGSGGGGSDIQMTQSPSSLSASVGDRVTIT
CRASQDIRYYLNWYQQKPGKAPKLLIYVASSLQSGVPSRFSGSGSGTEFTLTVS
SLQPEDFATYYCLQVYSTPRTFGQGTKVEIKGGGGSGGGGSGGGGSEVQLVESG
GGLAKPGGSLRLSCAASGFRFTFNNYYMDWVRQAPGQGLEWVSRISSSGDPTWY
ADSVKGRFTISRENAKNTLFLQMNSLRAEDTAVYYCASLTTGSDSWGQGVLVTV
SS* (SEQ ID NO:64)

*Fig. 81*

GACATCCAGATGACCCAGTCTCCATCTTCCCTGTCTGCATCTGTAGGGGAC
AGAGTCACCATCACTTGCAGGGCAAGTCAGGACATTAGGTATTATTTAAAT
TGGTATCAGCAGAAACCAGGAAAAGCTCCTAAGCTCCTGATCTATGTTGCA
TCCAGTTTGCAAAGTGGGGTCCCATCAAGGTTCAGCGGCAGTGGATCTGGG
ACAGAGTTCACTCTCACCGTCAGCAGCCTGCAGCCTGAAGATTTTGCACT
TATTACTGTCTACAGGTTTATAGTACCCCTCGGACGTTCGGCCAAGGGACC
AAGGTGGAAATCAAACGTACGGTGGCTGCACCATCTGTCTTCATCTTCCCG
CCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCC
CTCCAATCGGGTAACTCCCAGGAGAGTGTCACAGAGCAGGACAGCAAGGAC
AGCACCTACAGCCTCAGCAGCACCCTGACGCTGAGCAAAGCAGACTACGAG
AAACACAAAGTCTACGCCTGCGAAGTCACCCATCAGGGCCTGAGCTCGCCC
GTCACAAAGAGCTTCAACAGGGGAGAGTGTTGA (SEQ ID NO:65)

*Fig. 82A*

DIQMTQSPSSLSASVGDRVTITCRASQDIRYYLNWYQQKPGKAPKLLIYVA
SSLQSGVPSRFSGSGSGTEFTLTVSSLQPEDFATYYCLQVYSTPRTFGQGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC  (SEQ ID NO:66)

*Fig. 82B*

```
GACATCCAGATGACCCAGTCTCCATCTTCCCTGTCTGCATCTGTAGGGGAC
AGAGTCACCATCACTTGCAGGGCAAGTCAGGACATTAGGTATTATTTAAAT
TGGTATCAGCAGAAACCAGGAAAAGCTCCTAAGCTCCTGATCTATGTTGCA
TCCAGTTTGCAAAGTGGGGTCCCATCAAGGTTCAGCGGCAGTGGATCTGGG
ACAGAGTTCACTCTCACCGTCAGCAGCCTGCAGCCTGAAGATTTTGCACT
TATTACTGTCTACAGGTTTATAGTACCCCTCGGACGTTCGGCCAAGGGACC
AAGGTGGAAATCAAAGGCGGTGGCGGGTCCGGTGGGGTGGCTCCGGGGGC
GGTGGCTCCGAGGTGCAGCTGGTGGAGTCTGGGGGCGGCTTGGCAAAGCCT
GGGGGGTCCCTGAGACTCTCCTGCGCAGCCTCCGGGTTCAGGTTCACCTTC
AATAACTACTACATGGACTGGGTCCGCCAGGCTCCAGGGCAGGGGCTGGAG
TGGGTCTCACGTATTAGTAGTAGTGGTGATCCCACATGGTACGCAGACTCC
GTGAAGGGCAGATTCACCATCTCCAGAGAGAACGCCAAGAACACACTGTTT
CTTCAAATGAACAGCCTGAGAGCTGAGGACACGGCTGTCTATTACTGTGCG
AGCTTGACTACAGGGTCTGACTCCTGGGGCCAGGGAGTCCTGGTCACCGTC
TCCTCATGA      (SEQ ID NO:67)
```

*Fig. 83A*

```
DIQMTQSPSSLSASVGDRVTITCRASQDIRYYLNWYQQKPGKAPKLLIYV
ASSLQSGVPSRFSGSGSGTEFTLTVSSLQPEDFATYYCLQVYSTPRTFGQ
GTKVEIKGGGGSGGGGSGGGGSEVQLVESGGGLAKPGGSLRLSCAASGFR
FTFNNYYMDWVRQAPGQGLEWVSRISSSGDPTWYADSVKGRFTISRENAK
NTLFLQMNSLRAEDTAVYYCASLTTGSDSWGQGVLVTVSS*
(SEQ ID NO:68)
```

*Fig. 83B*

GAGGTGCAGCTGGTGGAGTCTGGGGGCGGCTTGGCAAAGCCTGGGGGGTCCCT
GAGACTCTCCTGCGCAGCCTCCGGGTTCAGGTTCACCTTCAATAACTACTACA
TGGACTGGGTCCGCCAGGCTCCAGGGCAGGGGCTGGAGTGGGTCTCACGTATT
AGTAGTAGTGGTGATCCCACATGGTACGCAGACTCCGTGAAGGGCAGATTCAC
CATCTCCAGAGAGAACGCCAAGAACACACTGTTTCTTCAAATGAACAGCCTGA
GAGCTGAGGACACGGCTGTCTATTACTGTGCGAGCTTGACTACAGGGTCTGAC
TCCTGGGGCCAGGGAGTCCTGGTCACCGTCTCCTCAGGCGGTGGCGGGTCCGG
TGGGGGTGGCTCCGGGGCGGTGGCTCCGACATCCAGATGACCCAGTCTCCAT
CTTCCCTGTCTGCATCTGTAGGGACAGAGTCACCATCACTTGCAGGGCAAGT
CAGGACATTAGGTATTATTTAAATTGGTATCAGCAGAAACCAGGAAAAGCTCC
TAAGCTCCTGATCTATGTTGCATCCAGTTTGCAAAGTGGGGTCCCATCAAGGT
TCAGCGGCAGTGGATCTGGGACAGAGTTCACTCTCACCGTCAGCAGCCTGCAG
CCTGAAGATTTTGCGACTTATTACTGTCTACAGGTTTATAGTACCCCTCGGAC
GTTCGGCCAAGGGACCAAGGTGGAAATCAAATGA        (SEQ ID NO:69)

Fig. 84A

EVQLVESGGGLAKPGGSLRLSCAASGFRFTFNNYYMDWVRQAPGQGLEWVSRIS
SSGDPTWYADSVKGRFTISRENAKNTLFLQMNSLRAEDTAVYYCASLTTGSDSW
GQGVLVTVSSGGGGSGGGGSGGGGSDIQMTQSPSSLSASVGDRVTITCRASQDI
RYYLNWYQQKPGKAPKLLIYVASSLQSGVPSRFSGSGSGTEFTLTVSSLQPEDF
ATYYCLQVYSTPRTFGQGTKVEIK*
(SEQ ID NO:70)

MKKLLFAIPLVVPFYSHSQVQLVQSGAEVKKPGSSVKVSCKASGYTF
TTYYLHWVRQAPGQGLEWMGWIYPGNVHAQYNEKFKGRVTITADKST
STAYMELSSLRSEDTAVYYCARSWEGFPYWGQGTTVTVSSGGGGSGG
GGSGGGGSGGGGSDIQMTQSPSSLSASVGDRVTITCKASQNVGINVA
WYQQKPGKAPKSLISSASYRYSGVPSRFSGSGSGTDFTLTISSLQPE
DFATYFCQQYDTYPFTFGQGTKVEIK*DDDDKSFLEQKLISEEDLNSA*
*VDHHHHHH*\* (SEQ ID NO: 137)

B

MKKLLFAIPLVVPFYSHSQVQLVQSGAEVKKPGSSVKVSCKASGYTF
TTYYLHWVRQAPGQGLEWMGWIYPGNGHAQYNEKFKGRVTITADKST
STAYMELSSLRSEDTAVYYCARSWEGFPYWGQGTTVTVSSGGGGSGG
GGSGGGGSGGGGSDIQMTQSPSSLSASVGDRVTITCKASQNVGINVA
WYQQKPGKAPKSLISSASYRYSGVPSRFSGSGSGTDFTLTISSLQPE
DFATYFCQQYDTYPFTFGQGTKVEIK*DDDDKSFLEQKLISEEDLNSA*
*VDHHHHHH*\* (SEQ ID NO: 138)

*Fig. 94*

SEQUENCE LISTING

<160> NUMBER OF SEQ ID NOS: 161

<210> SEQ ID NO 1
<211> LENGTH: 28
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 1
cagtagcatg caggtccaac tggtgcag                                        28

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gttctagaaa gcttttgtcg tcgtcgtctt tgatctccac cttggtaccc tg            52

<210> SEQ ID NO 3
<211> LENGTH: 714
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3
caggtccaac tggtgcagtc tggagctgag gtgaagaagc ctgggtcctc agtgaaggtg    60
tcctgcaagg cttctggcta cactttcaca acctactatt tgcactgggt gaggcaggcc   120
cctggacagg gacttgagtg gatgggatgg atttatcctg gaaatgttca tgctcagtac   180
aatgagaagt tcaagggcag ggtcacaatc actgcagaca atccaccag cacagcctac    240 atggagctca gcagcctgag gtctgaagat actgcggtct attactgtgc aagatcctgg   300
gaaggttttc cttactgggg ccaagggacc acggtcaccg tctcctcagg tggggcgga   360 tctgggggcg gcggatccgg tggtggtggt agtgacattc agatgaccca gtctcctagc   420
tccctgtccg cctcagtagg agacagggtc accatcacct gcaaggccag tcagaatgtg   480
ggtattaatg tagcctggta tcaacagaaa ccagggaagg ctcctaaatc actgatttcc   540
tcggcctcct accggtacag tggagtccct tccagattca gcggcagtgg atctgggaca   600
gatttcactc tcaccatcag cagcctccag cctgaagact cgcaaccta tttctgtcag   660 caatatgaca cctatccatt cacgttcggc cagggtacca aggtggagat caaa         714

<210> SEQ ID NO 4
<211> LENGTH: 238
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60
```

-continued

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Trp Glu Gly Phe Pro Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Asp Ile Gln Met Thr Gln Ser Pro Ser Ser Leu Ser Ala
130                 135                 140

Ser Val Gly Asp Arg Val Thr Ile Thr Cys Lys Ala Ser Gln Asn Val
145                 150                 155                 160

Gly Ile Asn Val Ala Trp Tyr Gln Gln Lys Pro Gly Lys Ala Pro Lys
                165                 170                 175

Ser Leu Ile Ser Ser Ala Ser Tyr Arg Tyr Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Phe Cys Gln Gln Tyr Asp Thr
    210                 215                 220

Tyr Pro Phe Thr Phe Gly Gln Gly Thr Lys Val Glu Ile Lys
225                 230                 235

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcaggcccct ggacagtgcc ttgagtggat gggatg                               36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
catcccatcc actcaaggca ctgtccaggg gcctgc                               36

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctatccatt cacgttcggc tgcggtacca aggtggagat c                         41

<210> SEQ ID NO 8
<211> LENGTH: 41
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 8
gatctccacc ttggtaccgc agccgaacgt gaatggatag g                    41

<210> SEQ ID NO 9
<211> LENGTH: 714
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 9
caggtccaac tggtgcagtc tggagctgag gtgaagaagc ctgggtcctc agtgaaggtg    60
tcctgcaagg cttctggcta cactttcaca acctactatt tgcactgggt gaggcaggcc   120
cctggacagt gccttgagtg gatgggatgg atttatcctg gaaatgttca tgctcagtac   180
aatgagaagt tcaagggcag ggtcacaatc actgcagaca aatccaccag cacagcctac   240
atggagctca gcagcctgag gtctgaagat actgcggtct attactgtgc aagatcctgg   300
gaaggttttc cttactgggg ccaagggacc acggtcaccg tctcctcagg tggggcgga    360 tctgggggcg gcggatccgg tggtggtggt agtgacattc agatgaccca gtctcctagc   420
tccctgtccg cctcagtagg agacaggtc accatcacct gcaaggccag tcagaatgtg    480
ggtattaatg tagcctggta tcaacagaaa ccagggaagg ctcctaaatc actgatttcc   540
tcggcctcct accggtacag tggagtccct tccagattca gcggcagtgg atctgggaca   600
gatttcactc tcaccatcag cagcctccag cctgaagact cgcaaccta tttctgtcag    660 caatatgaca cctatccatt cacgttcggc tgcggtacca aggtggagat caaa          714

<210> SEQ ID NO 10
<211> LENGTH: 238
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Cys Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Ser Gly Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Lys Ala Ser Gln Asn Val
145                 150                 155                 160

Gly Ile Asn Val Ala Trp Tyr Gln Gln Lys Pro Gly Lys Ala Pro Lys
                165                 170                 175

Ser Leu Ile Ser Ser Ala Ser Tyr Arg Tyr Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Phe Cys Gln Gln Tyr Asp Thr
    210                 215                 220

Tyr Pro Phe Thr Phe Gly Cys Gly Thr Lys Val Glu Ile Lys
225                 230                 235

<210> SEQ ID NO 11
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aagggaccac ggtcaccgtc tcctcaggcg gtggagggtc cggtgggggc ggatctgggg      60
gcggcggatc cggtggtggt ggtag                                           85

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttttgttcta gaaaactttt gtcgtcg                                         27

<210> SEQ ID NO 13
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagggaccac ggtcaccgtc tcctcaggag ggggcggttc aggcggtgga gggtccggtg      60
ggggcggatc tgggggcggc ggatc                                           85

<210> SEQ ID NO 14
<211> LENGTH: 729
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 14
caggtccaac tggtgcagtc tggagctgag gtgaagaagc ctgggtcctc agtgaaggtg      60
tcctgcaagg cttctggcta cactttcaca acctactatt tgcactgggt gaggcaggcc     120
cctggacagg gacttgagtg gatgggatgg atttatcctg gaaatgttca tgctcagtac     180

```
aatgagaagt tcaagggcag ggtcacaatc actgcagaca atccaccag cacagcctac    240 atggagctca gcagcctgag gtctgaagat actgcggtct attactgtgc aagatcctgg    300
gaaggttttc cttactgggg ccaagggacc acggtcaccg tctcctcagg cggtggaggg    360
tccggtgggg gcggatctgg gggcggcgga tccggtggtg gtggtagtga cattcagatg    420
acccagtctc ctagctccct gtccgcctca gtaggagaca gggtcaccat cacctgcaag    480
gccagtcaga atgtgggtat taatgtagcc tggtatcaac agaaaccagg gaaggctcct    540
aaatcactga tttcctcggc ctcctaccgg tacagtggag tcccttccag attcagcggc    600
agtggatctg ggacagattt cactctcacc atcagcagcc tccagcctga agacttcgca    660
acctatttct gtcagcaata tgacacctat ccattcacgt tcggccaggg taccaaggtg    720
gagatcaaa                                                            729
```

<210> SEQ ID NO 15
<211> LENGTH: 243
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Gly Ile Asn Val Ala Trp Tyr Gln Gln Lys Pro
                165                 170                 175

Gly Lys Ala Pro Lys Ser Leu Ile Ser Ser Ala Ser Tyr Arg Tyr Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Phe Cys
    210                 215                 220

Gln Gln Tyr Asp Thr Tyr Pro Phe Thr Phe Gly Gln Gly Thr Lys Val
225                 230                 235                 240

Glu Ile Lys
```

<210> SEQ ID NO 16
<211> LENGTH: 744
<212> TYPE: DNA
<213> ORGANISM: Artificial Sequence
<220> FEATURE:
<223> OTHER INFORMATION: Description of Artificial Sequence: Synthetic construct

<400> SEQUENCE: 16

```
caggtccaac tggtgcagtc tggagctgag gtgaagaagc ctgggtcctc agtgaaggtg      60
tcctgcaagg cttctggcta cactttcaca acctactatt tgcactgggt gaggcaggcc     120
cctggacagg gacttgagtg gatgggatgg atttatcctg gaaatgttca tgctcagtac     180
aatgagaagt tcaagggcag ggtcacaatc actgcagaca aatccaccag cacagcctac     240
atggagctca gcagcctgag gtctgaagat actgcggtct attactgtgc aagatcctgg     300
gaaggttttc cttactgggg ccaagggacc acggtcaccg tctcctcagg aggggcggt      360
tcaggcggtg gagggtccgg tggggcgga tctgggggcg cggatccgg tggtggtggt      420
agtgacattc agatgaccca gtctcctagc tccctgtccg cctcagtagg agacagggtc     480
accatcacct gcaaggccag tcagaatgtg ggtattaatg tagcctggta tcaacagaaa     540
ccagggaagg ctcctaaatc actgatttcc tcggcctcct accggtacag tggagtccct     600
tccagattca gcggcagtgg atctgggaca gatttcactc tcaccatcag cagcctccag     660
cctgaagact tcgcaaccta tttctgtcag caatatgaca cctatccatt cacgttcggc     720
cagggtacca aggtggagat caaa                                            744
```

<210> SEQ ID NO 17
<211> LENGTH: 248
<212> TYPE: PRT
<213> ORGANISM: Artificial Sequence
<220> FEATURE:
<223> OTHER INFORMATION: Description of Artificial Sequence: Synthetic construct

<400> SEQUENCE: 17

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Lys Ala Ser Gln Asn Val Gly Ile Asn Val Ala Trp
                165                 170                 175
```

```
Tyr Gln Gln Lys Pro Gly Lys Ala Pro Lys Ser Leu Ile Ser Ser Ala
            180                 185                 190

Ser Tyr Arg Tyr Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
210                 215                 220

Ala Thr Tyr Phe Cys Gln Gln Tyr Asp Thr Tyr Pro Phe Thr Phe Gly
225                 230                 235                 240

Gln Gly Thr Lys Val Glu Ile Lys
                245

<210> SEQ ID NO 18
<211> LENGTH: 729
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 18
caggtccaac tggtgcagtc tggagctgag gtgaagaagc ctgggtcctc agtgaaggtg     60
tcctgcaagg cttctggcta cactttcaca acctactatt tgcactgggt gaggcaggcc    120
cctggacagt gccttgagtg gatgggatgg atttatcctg gaaatgttca tgctcagtac    180
aatgagaagt tcaagggcag ggtcacaatc actgcagaca atccaccag cacagcctac     240 atggagctca gcagcctgag gtctgaagat actgcggtct attactgtgc aagatcctgg    300
gaaggttttc cttactgggg ccaagggacc acggtcaccg tctcctcagg cggtggaggg    360
tccggtgggg gcggatctgg gggcggcgga tccggtggtg gtggtagtga cattcagatg    420
acccagtctc ctagctccct gtccgcctca gtaggagaca gggtcaccat cacctgcaag    480
gccagtcaga atgtgggtat taatgtagcc tggtatcaac agaaaccagg gaaggctcct    540
aaatcactga tttcctcggc ctcctaccgg tacagtggag tcccttccag attcagcggc    600
agtggatctg ggacagattt cactctcacc atcagcagcc tccagcctga agacttcgca    660
acctatttct gtcagcaata tgacacctat ccattcacgt tcggctgcgg taccaaggtg    720
gagatcaaa                                                            729

<210> SEQ ID NO 19
<211> LENGTH: 243
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Cys Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Gly Ile Asn Val Ala Trp Tyr Gln Gln Lys Pro
                165                 170                 175

Gly Lys Ala Pro Lys Ser Leu Ile Ser Ser Ala Ser Tyr Arg Tyr Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Phe Cys
    210                 215                 220

Gln Gln Tyr Asp Thr Tyr Pro Phe Thr Phe Gly Cys Gly Thr Lys Val
225                 230                 235                 240

Glu Ile Lys

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ser Gly Gly Gly Gly Ser Gly Gly Gly Gly Ser Gly
1               5                   10                  15

Gly Gly Gly Ser
            20

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 22

His His His His His His
1               5

<210> SEQ ID NO 23
```

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Ser Gly Gly Gly Ser Gly Gly Gly Gly Ser Gly
1               5                   10                  15

Gly Gly Gly Ser Gly Gly Gly Ala Ser
            20                  25

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Gly Gly Ser
1               5

<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atgaaaaaac tgctgttcgc gattccgctg gtggtgccgt tctatagcca tagt            54

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Lys Lys Leu Leu Phe Ala Ile Pro Leu Val Val Pro Phe Tyr Ser
1               5                   10                  15

His Ser

<210> SEQ ID NO 27
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gacgacgacg acaaaagctt tctagaacaa aaactcatct cagaagagga tctgaatagc      60
gccgtcgacc atcatcatca tcatcattga                                       90

<210> SEQ ID NO 28
<211> LENGTH: 669
<212> TYPE: DNA
<213> ORGANISM: Artificial Sequence
<220> FEATURE:
```

<223> OTHER INFORMATION: Description of Artificial Sequence: Synthetic
      construct

<400> SEQUENCE: 28

| caacttgtgc tcactcagtc atcttcagtc tctttctccc tgggagcctc agcaaaactc | 60 |
| acgtgcacct tgagtagtca gcacagtacg tacaccattg aatggtatca gcaacagccc | 120 |
| ctcaagcctc ctaagtatgt gatggagctt aagaaagatg aagccacag cacaggtgat | 180 |
| gggattcctg atcgcttctc tggatccagc tctggtgctg atcgctacct tagcatttcc | 240 |
| aacatccagc ctgaagatga agcaatatac atctgtggtg tgggtgatac aattaaggaa | 300 |
| caatttgtgt atgttttcgg cggtggaacc aaggtcgaaa tcaaacgtac ggtggctgca | 360 |
| ccatctgtct tcatcttccc gccatctgat gagcagttga atctggaac tgcctctgtt | 420 |
| gtgtgcctgc tgaataactt ctatcccaga gaggccaaag tacagtggaa ggtgataac | 480 |
| gccctccaat cgggtaactc ccaggagagt gtcacagagc aggacagcaa ggacagcacc | 540 |
| tacagcctca gcagcaccct gacgctgagc aaagcagact acgagaaaca caaagtctac | 600 |
| gcctgcgaag tcacccatca gggcctgagc tcgcccgtca caaagagctt caacagggga | 660 |
| gagtgttga | 669 |

<210> SEQ ID NO 29
<211> LENGTH: 222
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 29

Gln Leu Val Leu Thr Gln Ser Ser Val Ser Phe Ser Leu Gly Ala
1               5                   10                  15

Ser Ala Lys Leu Thr Cys Thr Leu Ser Ser Gln His Ser Thr Tyr Thr
                20                  25                  30

Ile Glu Trp Tyr Gln Gln Pro Leu Lys Pro Pro Lys Tyr Val Met
            35                  40                  45

Glu Leu Lys Lys Asp Gly Ser His Ser Thr Gly Asp Gly Ile Pro Asp
        50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Thr Ile Lys Glu Gln Phe Val Tyr Val Phe Gly Gly Gly Thr Lys Val
            100                 105                 110

Glu Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 30
<211> LENGTH: 2139
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 30

| | | | | | |
|---|---|---|---|---|---|
| caggtccaac | tggtgcagtc | tggagctgag | gtgaagaagc | ctgggtcctc | agtgaaggtg | 60 |
| tcctgcaagg | cttctggcta | cactttcaca | acctactatt | tgcactgggt | gaggcaggcc | 120 |
| cctggacagg | gacttgagtg | gatgggatgg | atttatcctg | gaaatgttca | tgctcagtac | 180 |
| aatgagaagt | tcaagggcag | ggtcacaatc | actgcagaca | aatccaccag | cacagcctac | 240 |
| atggagctca | gcagcctgag | gtctgaagat | actgcggtct | attactgtgc | aagatcctgg | 300 |
| gaaggttttc | cttactgggg | ccaagggacc | acggtcaccg | tctcctcagg | tggggcgga | 360 |
| tctgggggcg | gcggatccgg | tggtggtggt | agtgacattc | agatgaccca | gtctcctagc | 420 |
| tccctgtccg | cctcagtagg | agacaggtc | accatcacct | gcaaggccag | tcagaatgtg | 480 |
| ggtattaatg | tagcctggta | tcaacagaaa | ccagggaagg | ctcctaaatc | actgatttcc | 540 |
| tcggcctcct | accggtacag | tggagtccct | tccagattca | gcggcagtgg | atctgggaca | 600 |
| gatttcactc | tcaccatcag | cagcctccag | cctgaagact | tcgcaaccta | tttctgtcag | 660 |
| caatatgaca | cctatccatt | cacgttcggc | cagggtacca | aggtggagat | caaaggcggt | 720 |
| ggagggtccg | gtggaggggg | ctctggaggg | ggcggttcag | gggcggtgg | atcgggggga | 780 |
| ggtggctccc | agatccagtt | ggtgcagtct | ggacctgagc | tgaagaagcc | tggagagaca | 840 |
| gtcaagatct | cctgcaaggc | ttctggtttt | accttcacag | actattcaat | acactgggtg | 900 |
| aaacaggctc | caggaaaggg | tttaaagtgg | atgggctgga | taaacactga | gactggtgag | 960 |
| ccaacatata | cagatgactt | caagggacga | tttgccttct | ctttggtgac | ctctgccacc | 1020 |
| actgccattt | gcagatcaa | caacctcaac | aatgaggaca | cggctacatt | tttctgtgct | 1080 |
| agattcatct | atgatcctta | ttgggggttt | gcttactggg | gccagggac | tctggtcact | 1140 |
| gtctccgcag | ctagcaccaa | gggcccatcg | gtcttccccc | tggcaccctc | ctccaagagc | 1200 |
| acctctgggg | gcacagcggc | cctgggctgc | ctggtcaagg | actacttccc | cgaaccggtg | 1260 |
| acggtgtcgt | ggaactcagg | cgccctgacc | agcggcgtgc | acaccttccc | ggctgtccta | 1320 |
| cagtcctcag | gactctactc | cctcagcagc | gtggtgaccg | tgccctccag | cagcttgggc | 1380 |
| acccagacct | acatctgcaa | cgtgaatcac | aagcccagca | acaccaaggt | ggacaagaaa | 1440 |
| gttgagccca | atcttgtga | caaaactcac | acatgcccac | cgtgcccagc | acctgaactc | 1500 |
| ctggggggac | cgtcagtctt | cctcttcccc | ccaaaaccca | aggacaccct | catgatctcc | 1560 |
| cggacccctg | aggtcacatg | cgtggtggtg | gacgtgagcc | acgaagaccc | tgaggtcaag | 1620 |
| ttcaactggt | acgtggacgg | cgtggaggtg | cataatgcca | agacaaagcc | gcgggaggag | 1680 |
| cagtacaaca | gcacgtaccg | tgtggtcagc | gtcctcaccg | tcctgcacca | ggactggctg | 1740 |
| aatggcaagg | agtacaagtg | caaggtctcc | aacaaagccc | tcccagcccc | catcgagaaa | 1800 |
| accatctcca | aagccaaagg | gcagccccga | gaaccacagg | tgtacaccct | gcccccatcc | 1860 |
| cgggatgagc | tgaccaagaa | ccaggtcagc | ctgacctgcc | tggtcaaagg | cttctatccc | 1920 |
| agcgacatcg | ccgtggagtg | ggagagcaat | gggcagccgg | agaacaacta | caagaccacg | 1980 |

-continued

```
cctcccgtgc tggactccga cggctccttc ttcctctaca gcaagctcac cgtggacaag    2040
agcaggtggc agcagggaa cgtcttctca tgctccgtga tgcatgaggc tctgcacaac    2100
cactacacgc agaagagcct ctccctgtct ccgggttga                            2139
```

<210> SEQ ID NO 31
<211> LENGTH: 712
<212> TYPE: PRT
<213> ORGANISM: Artificial Sequence
<220> FEATURE:
<223> OTHER INFORMATION: Description of Artificial Sequence: Synthetic construct

<400> SEQUENCE: 31

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Ser Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Lys Ala Ser Gln Asn Val
145                 150                 155                 160

Gly Ile Asn Val Ala Trp Tyr Gln Gln Lys Pro Gly Lys Ala Pro Lys
                165                 170                 175

Ser Leu Ile Ser Ser Ala Ser Tyr Arg Tyr Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Phe Cys Gln Gln Tyr Asp Thr
    210                 215                 220

Tyr Pro Phe Thr Phe Gly Gln Gly Thr Lys Val Glu Ile Lys Gly Gly
225                 230                 235                 240

Gly Gly Ser Gly Gly Gly Ser Gly Gly Gly Ser Gly Gly
                245                 250                 255

Gly Ser Gly Gly Gly Ser Gln Ile Gln Leu Val Gln Ser Gly Pro
            260                 265                 270

Glu Leu Lys Lys Pro Gly Glu Thr Val Lys Ile Ser Cys Lys Ala Ser
        275                 280                 285

Gly Phe Thr Phe Thr Asp Tyr Ser Ile His Trp Val Lys Gln Ala Pro
    290                 295                 300

Gly Lys Gly Leu Lys Trp Met Gly Trp Ile Asn Thr Glu Thr Gly Glu
305                 310                 315                 320

Pro Thr Tyr Thr Asp Asp Phe Lys Gly Arg Phe Ala Phe Ser Leu Val
```

```
                325                 330                 335
Thr Ser Ala Thr Thr Ala Tyr Leu Gln Ile Asn Asn Leu Asn Asn Glu
            340                 345                 350
Asp Thr Ala Thr Phe Phe Cys Ala Arg Phe Ile Tyr Asp Pro Tyr Trp
            355                 360                 365
Gly Phe Ala Tyr Trp Gly Gln Gly Thr Leu Val Thr Val Ser Ala Ala
            370                 375                 380
Ser Thr Lys Gly Pro Ser Val Phe Pro Leu Ala Pro Ser Ser Lys Ser
385                 390                 395                 400
Thr Ser Gly Gly Thr Ala Ala Leu Gly Cys Leu Val Lys Asp Tyr Phe
                405                 410                 415
Pro Glu Pro Val Thr Val Ser Trp Asn Ser Gly Ala Leu Thr Ser Gly
            420                 425                 430
Val His Thr Phe Pro Ala Val Leu Gln Ser Ser Gly Leu Tyr Ser Leu
            435                 440                 445
Ser Ser Val Val Thr Val Pro Ser Ser Ser Leu Gly Thr Gln Thr Tyr
            450                 455                 460
Ile Cys Asn Val Asn His Lys Pro Ser Asn Thr Lys Val Asp Lys Lys
465                 470                 475                 480
Val Glu Pro Lys Ser Cys Asp Lys Thr His Thr Cys Pro Pro Cys Pro
                485                 490                 495
Ala Pro Glu Leu Leu Gly Gly Pro Ser Val Phe Leu Phe Pro Pro Lys
            500                 505                 510
Pro Lys Asp Thr Leu Met Ile Ser Arg Thr Pro Glu Val Thr Cys Val
            515                 520                 525
Val Val Asp Val Ser His Glu Asp Pro Glu Val Lys Phe Asn Trp Tyr
530                 535                 540
Val Asp Gly Val Glu Val His Asn Ala Lys Thr Lys Pro Arg Glu Glu
545                 550                 555                 560
Gln Tyr Asn Ser Thr Tyr Arg Val Val Ser Val Leu Thr Val Leu His
                565                 570                 575
Gln Asp Trp Leu Asn Gly Lys Glu Tyr Lys Cys Lys Val Ser Asn Lys
            580                 585                 590
Ala Leu Pro Ala Pro Ile Glu Lys Thr Ile Ser Lys Ala Lys Gly Gln
            595                 600                 605
Pro Arg Glu Pro Gln Val Tyr Thr Leu Pro Pro Ser Arg Asp Glu Leu
            610                 615                 620
Thr Lys Asn Gln Val Ser Leu Thr Cys Leu Val Lys Gly Phe Tyr Pro
625                 630                 635                 640
Ser Asp Ile Ala Val Glu Trp Glu Ser Asn Gly Gln Pro Glu Asn Asn
                645                 650                 655
Tyr Lys Thr Thr Pro Pro Val Leu Asp Ser Asp Gly Ser Phe Phe Leu
            660                 665                 670
Tyr Ser Lys Leu Thr Val Asp Lys Ser Arg Trp Gln Gln Gly Asn Val
            675                 680                 685
Phe Ser Cys Ser Val Met His Glu Ala Leu His Asn His Tyr Thr Gln
            690                 695                 700
Lys Ser Leu Ser Leu Ser Pro Gly
705                 710

<210> SEQ ID NO 32
<211> LENGTH: 2154
<212> TYPE: DNA
<213> ORGANISM: Artificial Sequence
```

<220> FEATURE:
<223> OTHER INFORMATION: Description of Artificial Sequence: Synthetic
      construct

<400> SEQUENCE: 32

```
caggtccaac tggtgcagtc tggagctgag gtgaagaagc ctgggtcctc agtgaaggtg      60
tcctgcaagg cttctggcta cactttcaca acctactatt tgcactgggt gaggcaggcc     120
cctggacagg gacttgagtg gatgggatgg atttatcctg gaaatgttca tgctcagtac     180
aatgagaagt tcaagggcag ggtcacaatc actgcagaca aatccaccag cacagcctac     240
atggagctca gcagcctgag gtctgaagat actgcggtct attactgtgc aagatcctgg     300
gaaggttttc cttactgggg ccaagggacc acggtcaccg tctcctcagg cggtggaggg     360
tccggtgggg gcggatctgg gggcggcgga tccggtggtg gtggtagtga cattcagatg     420
acccagtctc ctagctccct gtccgcctca gtaggagaca gggtcaccat cacctgcaag     480
gccagtcaga atgtgggtat taatgtagcc tggtatcaac agaaaccagg gaaggctcct     540
aaatcactga tttcctcggc ctcctaccgg tacagtggag tcccttccag attcagcggc     600
agtggatctg gacagattt cactctcacc atcagcagcc tccagcctga agacttcgca     660
acctatttct gtcagcaata tgacacctat ccattcacgt tcggcaggg taccaaggtg     720
gagatcaaag gcggtggagg gtccggtgga ggggctctg aggggggcgg ttcaggggc     780
ggtggatcgg ggggaggtgg ctcccagatc agttggtgc agtctggacc tgagctgaag     840
aagcctggag agacagtcaa gatctcctgc aaggcttctg gttttacctt cacagactat     900
tcaatacact gggtgaaaca ggctccagga aagggtttaa agtggatggg ctggataaac     960
actgagactg gtgagccaac atatacagat gacttcaagg gacgatttgc cttctctttg    1020
gtgacctctg ccaccactgc ctatttgcag atcaacaacc tcaacaatga ggacacggct    1080
acatttttct gtgctagatt catctatgat ccttattggg ggtttgctta ctggggccag    1140
gggactctgg tcactgtctc cgcagctagc accaagggcc catcggtctt cccctggca    1200
ccctcctcca agagcacctc tgggggcaca gcggccctgg gctgcctggt caaggactac    1260
ttccccgaac cggtgacggt gtcgtggaac tcaggcgccc tgaccagcgg cgtgcacacc    1320
ttcccggctg tcctacagtc ctcaggactc tactccctca gcagcgtggt gaccgtgccc    1380
tccagcagct gggcacccca gacctacatc tgcaacgtga atcacaagcc cagcaacacc    1440
aaggtggaca agaaagttga gcccaaatct tgtgacaaaa ctcacacatg cccaccgtgc    1500
ccagcacctg aactcctggg gggaccgtca gtcttcctct tccccccaaa acccaaggac    1560
accctcatga tctcccggac ccctgaggtc acatgcgtgg tggtggacgt gagccacgaa    1620
gaccctgagg tcaagttcaa ctggtacgtg gacggcgtgg aggtgcataa tgccaagaca    1680
aagccgcggg aggagcagta caacagcacg taccgtgtgg tcagcgtcct caccgtcctg    1740
caccaggact ggctgaatgg caaggagtac aagtgcaagg tctccaacaa agccctccca    1800
gcccccatcg agaaaaccat ctccaaagcc aaagggcagc ccgagaacca caggtgtac    1860
accctgcccc catcccggga tgagctgacc aagaaccagg tcagcctgac ctgcctggtc    1920
aaaggcttct atcccagcga catcgccgtg gagtgggaga gcaatgggca gccggagaac    1980
aactacaaga ccacgcctcc cgtgctggac tccgacggct ccttcttcct ctacagcaag    2040
ctcaccgtgg acaagagcag gtggcagcag gggaacgtct tctcatgctc cgtgatgcat    2100
gaggctctgc acaaccacta cacgcagaag agcctctccc tgtctccggg ttga          2154
```

```
<210> SEQ ID NO 33
<211> LENGTH: 717
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 33
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Ser Gly Gly Gly Gly Ser Gly Gly
        115                 120                 125

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Lys
145                 150                 155                 160

Ala Ser Gln Asn Val Gly Ile Asn Val Ala Trp Tyr Gln Gln Lys Pro
                165                 170                 175

Gly Lys Ala Pro Lys Ser Leu Ile Ser Ser Ala Ser Tyr Arg Tyr Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Phe Cys
    210                 215                 220

Gln Gln Tyr Asp Thr Tyr Pro Phe Thr Phe Gly Gln Gly Thr Lys Val
225                 230                 235                 240

Glu Ile Lys Gly Gly Gly Gly Ser Gly Gly Gly Gly Ser Gly Gly Gly
                245                 250                 255

Gly Ser Gly Gly Gly Gly Ser Gly Gly Gly Gly Ser Gln Ile Gln Leu
            260                 265                 270

Val Gln Ser Gly Pro Glu Leu Lys Lys Pro Gly Glu Thr Val Lys Ile
        275                 280                 285

Ser Cys Lys Ala Ser Gly Phe Thr Phe Thr Asp Tyr Ser Ile His Trp
290                 295                 300

Val Lys Gln Ala Pro Gly Lys Gly Leu Lys Trp Met Gly Trp Ile Asn
305                 310                 315                 320

Thr Glu Thr Gly Glu Pro Thr Tyr Thr Asp Asp Phe Lys Gly Arg Phe
                325                 330                 335

Ala Phe Ser Leu Val Thr Ser Ala Thr Thr Ala Tyr Leu Gln Ile Asn
            340                 345                 350

Asn Leu Asn Asn Glu Asp Thr Ala Thr Phe Phe Cys Ala Arg Phe Ile
        355                 360                 365

```
Tyr Asp Pro Tyr Trp Gly Phe Ala Tyr Trp Gly Gln Gly Thr Leu Val
    370                 375                 380

Thr Val Ser Ala Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
            420                 425                 430

Ala Leu Thr Ser Gly Val His Thr Phe Pro Ala Val Leu Gln Ser Ser
        435                 440                 445

Gly Leu Tyr Ser Leu Ser Ser Val Val Thr Val Pro Ser Ser Ser Leu
    450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys Asp Lys Thr His Thr
                485                 490                 495

Cys Pro Pro Cys Pro Ala Pro Glu Leu Leu Gly Gly Pro Ser Val Phe
            500                 505                 510

Leu Phe Pro Pro Lys Pro Lys Asp Thr Leu Met Ile Ser Arg Thr Pro
        515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
        595                 600                 605

Lys Ala Lys Gly Gln Pro Arg Glu Pro Gln Val Tyr Thr Leu Pro Pro
    610                 615                 620

Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn His Tyr Thr Gln Lys Ser Leu Ser Leu Ser Pro Gly
705                 710                 715

<210> SEQ ID NO 34
<211> LENGTH: 1773
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 34
caggtccaac tggtgcagtc tggagctgag gtgaagaagc ctgggtcctc agtgaaggtg     60
```

```
tcctgcaagg cttctggcta cactttcaca acctactatt tgcactgggt gaggcaggcc      120
cctggacagt gccttgagtg gatgggatgg atttatcctg gaaatgttca tgctcagtac      180
aatgagaagt tcaagggcag ggtcacaatc actgcagaca atccaccag cacagcctac       240
atggagctca gcagcctgag gtctgaagat actgcggtct attactgtgc aagatcctgg      300
gaaggttttc cttactgggg ccaagggacc acggtcaccg tctcctcagg tggggcgga       360
tctgggggcg gcggatccgg tggtggtggt agtgacattc agatgaccca gtctcctagc      420
tccctgtccg cctcagtagg agacagggtc accatcacct gcaaggccag tcagaatgtg      480
ggtattaatg tagcctggta tcaacagaaa ccagggaagg ctcctaaatc actgatttcc      540
tcggcctcct accggtacag tggagtccct tccagattca gcggcagtgg atctgggaca      600
gatttcactc tcaccatcag cagcctccag cctgaagact tcgcaaccta tttctgtcag      660
caatatgaca cctatccatt cacgttcggc tgcggtacca aggtggagat caaaggcggt      720
ggagggtccg gtggagggg ctctggaggg gcggttcag ggggcggtgg atcgggggga       780
ggtggctccc agatccagtt ggtgcagtct ggacctgagc tgaagaagcc tggagagaca      840
gtcaagatct cctgcaaggc ttctggtttt accttcacag actattcaat acactgggtg      900
aaacaggctc caggaaaggg tttaaagtgg atgggctgga taaacactga gactggtgag      960
ccaacatata cagatgactt caagggacga tttgccttct ctttggtgac ctctgccacc     1020
actgccatt tgcagatcaa caacctcaac aatgaggaca cggctacatt tttctgtgct      1080
agattcatct atgatcctta ttgggggttt gcttactggg gccaggggac tctggtcact     1140
gtctccgcag ctagcaccaa gggcccatcg gtcttccccc tggcaccctc ctccaagagc     1200
acctctgggg gcacagcggc cctgggctgc ctggtcaagg actacttccc cgaaccggtg     1260
acggtgtcgt ggaactcagg cgccctgacc agcggcgtgc acaccttccc ggctgtccta     1320
cagtcctcag gactctactc cctcagcagc gtggtgaccg tgccctccag cagcttgggc     1380
acccagacct acatctgcaa cgtgaatcac aagcccagca acaccaaggt ggacaagaaa     1440
gttgagccca atcttgtga caaaactcac acatgcccac cgtgcccagc acctgaactc     1500
ctggggggac cgtcagtctt cctcttcccc ccaaaaccca aggacaccct catgatctcc     1560
cggacccctg aggtcacatg cgtggtggtg gacgtgagcc acgaagaccc tgaggtcaag     1620
ttcaactggt acgtggacgg cgtggaggtg cataatgcca agacaaagcc gcggaggag     1680
cagtacaaca gcacgtaccg tgtggtcagc gtcctcaccg tcctgcacca ggactggctg     1740
aatggcaagg agtacaagtg caaggtctcc aac                                  1773
```

<210> SEQ ID NO 35
<211> LENGTH: 712
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Cys Leu Glu Trp Met
        35                  40                  45

Gly Trp Ile Tyr Pro Gly Asn Val His Ala Gln Tyr Asn Glu Lys Phe

-continued

```
            50                  55                  60
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Trp Glu Gly Phe Pro Tyr Trp Gly Gln Gly Thr Thr Val
                100                 105                 110

Thr Val Ser Ser Gly Gly Gly Gly Ser Gly Gly Gly Gly Ser Gly Gly
                115                 120                 125

Gly Gly Ser Asp Ile Gln Met Thr Gln Ser Pro Ser Ser Leu Ser Ala
130                 135                 140

Ser Val Gly Asp Arg Val Thr Ile Thr Cys Lys Ala Ser Gln Asn Val
145                 150                 155                 160

Gly Ile Asn Val Ala Trp Tyr Gln Gln Lys Pro Gly Lys Ala Pro Lys
                165                 170                 175

Ser Leu Ile Ser Ser Ala Ser Tyr Arg Tyr Ser Gly Val Pro Ser Arg
                180                 185                 190

Phe Ser Gly Ser Gly Ser Gly Thr Asp Phe Thr Leu Thr Ile Ser Ser
                195                 200                 205

Leu Gln Pro Glu Asp Phe Ala Thr Tyr Phe Cys Gln Gln Tyr Asp Thr
210                 215                 220

Tyr Pro Phe Thr Phe Gly Cys Gly Thr Lys Val Glu Ile Lys Gly Gly
225                 230                 235                 240

Gly Gly Ser Gly Gly Gly Gly Ser Gly Gly Gly Gly Ser Gly Gly Gly
                245                 250                 255

Gly Ser Gly Gly Gly Gly Ser Gln Ile Gln Leu Val Gln Ser Gly Pro
                260                 265                 270

Glu Leu Lys Lys Pro Gly Glu Thr Val Lys Ile Ser Cys Lys Ala Ser
                275                 280                 285

Gly Phe Thr Phe Thr Asp Tyr Ser Ile His Trp Val Lys Gln Ala Pro
                290                 295                 300

Gly Lys Gly Leu Lys Trp Met Gly Trp Ile Asn Thr Glu Thr Gly Glu
305                 310                 315                 320

Pro Thr Tyr Thr Asp Asp Phe Lys Gly Arg Phe Ala Phe Ser Leu Val
                325                 330                 335

Thr Ser Ala Thr Thr Ala Tyr Leu Gln Ile Asn Asn Leu Asn Asn Glu
                340                 345                 350

Asp Thr Ala Thr Phe Phe Cys Ala Arg Phe Ile Tyr Asp Pro Tyr Trp
                355                 360                 365

Gly Phe Ala Tyr Trp Gly Gln Gly Thr Leu Val Thr Val Ser Ala Ala
                370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
                405                 410                 415

Pro Glu Pro Val Thr Val Ser Trp Asn Ser Gly Ala Leu Thr Ser Gly
                420                 425                 430

Val His Thr Phe Pro Ala Val Leu Gln Ser Ser Gly Leu Tyr Ser Leu
                435                 440                 445

Ser Ser Val Val Thr Val Pro Ser Ser Ser Leu Gly Thr Gln Thr Tyr
                450                 455                 460

Ile Cys Asn Val Asn His Lys Pro Ser Asn Thr Lys Val Asp Lys Lys
465                 470                 475                 480
```

Val Glu Pro Lys Ser Cys Asp Lys Thr His Thr Cys Pro Pro Cys Pro
            485                 490                 495

Ala Pro Glu Leu Leu Gly Gly Pro Ser Val Phe Leu Phe Pro Pro Lys
        500                 505                 510

Pro Lys Asp Thr Leu Met Ile Ser Arg Thr Pro Glu Val Thr Cys Val
        515                 520                 525

Val Val Asp Val Ser His Glu Asp Pro Glu Val Lys Phe Asn Trp Tyr
        530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Ala Leu Pro Ala Pro Ile Glu Lys Thr Ile Ser Lys Ala Lys Gly Gln
        595                 600                 605

Pro Arg Glu Pro Gln Val Tyr Thr Leu Pro Pro Ser Arg Asp Glu Leu
    610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
        675                 680                 685

Phe Ser Cys Ser Val Met His Glu Ala Leu His Asn His Tyr Thr Gln
    690                 695                 700

Lys Ser Leu Ser Leu Ser Pro Gly
705                 710

<210> SEQ ID NO 36
<211> LENGTH: 2154
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 36
caggtccaac tggtgcagtc tggagctgag gtgaagaagc tgggtcctc agtgaaggtg      60 tcctgcaagg cttctggcta cactttcaca acctactatt tgcactgggt gaggcaggcc    120
cctggacagt gccttgagtg gatgggatgg atttatcctg aaatgttca tgctcagtac     180 aatgagaagt tcaagggcag ggtcacaatc actgcagaca atccaccag cacagcctac     240 atggagctca gcagcctgag gtctgaagat actgcggtct attactgtgc aagatcctgg    300
gaaggttttc cttactgggg ccaagggacc acggtcaccg tctcctcagg cggtggaggg    360
tccggtgggg gcggatctgg gggcggcgga tccggtggtg gtggtagtga cattcagatg    420
acccagtctc ctagctccct gtccgcctca gtaggagaca gggtcaccat cacctgcaag    480
gccagtcaga atgtgggtat taatgtagcc tggtatcaac agaaaccagg gaaggctcct    540
aaatcactga tttcctcggc ctcctaccgg tacagtggag tcccttccag attcagcggc    600
agtggatctg ggacagattt cactctcacc atcagcagcc tccagcctga agacttcgca    660

-continued

```
acctatttct gtcagcaata tgacacctat ccattcacgt tcggctgcgg taccaaggtg    720
gagatcaaag gcggtggagg gtccggtgga gggggctctg gagggggcgg ttcaggggggc   780
ggtggatcgg ggggaggtgg ctcccagatc cagttggtgc agtctggacc tgagctgaag    840
aagcctggag agacagtcaa gatctcctgc aaggcttctg gttttacctt cacagactat    900
tcaatacact gggtgaaaca ggctccagga aagggtttaa agtggatggg ctggataaac    960
actgagactg gtgagccaac atatacagat gacttcaagg gacgatttgc cttctctttg    1020
gtgacctctg ccaccactgc ctatttgcag atcaacaacc tcaacaatga ggacacggct    1080
acatttttct gtgctagatt catctatgat ccttattggg ggtttgctta ctggggccag    1140
gggactctgg tcactgtctc cgcagctagc accaagggcc catcggtctt ccccctggca    1200
ccctcctcca agagcacctc tgggggcaca gcggccctgg gctgcctggt caaggactac    1260
ttccccgaac cggtgacggt gtcgtggaac tcaggcgccc tgaccagcgg cgtgcacacc    1320
ttcccggctg tcctacagtc ctcaggactc tactccctca gcagcgtggt gaccgtgccc    1380
tccagcagct tgggcaccca gacctacatc tgcaacgtga atcacaagcc cagcaacacc    1440
aaggtggaca gaaagttga gcccaaatct tgtgacaaaa ctcacacatg cccaccgtgc     1500
ccagcacctg aactcctggg gggaccgtca gtcttcctct tccccccaaa acccaaggac    1560
accctcatga tctcccggac ccctgaggtc acatgcgtgg tggtggacgt gagccacgaa    1620
gaccctgagg tcaagttcaa ctggtacgtg gacggcgtgg aggtgcataa tgccaagaca    1680
aagccgcggg aggagcagta caacagcacg taccgtgtgg tcagcgtcct caccgtcctg    1740
caccaggact ggctgaatgg caaggagtac aagtgcaagg tctccaacaa agccctccca    1800
gcccccatcg agaaaaccat ctccaaagcc aagggcagc cccgagaacc acaggtgtac     1860
accctgcccc catcccggga tgagctgacc aagaaccagg tcagcctgac ctgcctggtc    1920
aaaggcttct atcccagcga catcgccgtg gagtgggaga gcaatgggca gccggagaac    1980
aactacaaga ccacgcctcc cgtgctggac tccgacggct ccttcttcct ctacagcaag    2040
ctcaccgtgg acaagagcag gtggcagcag gggaacgtct tctcatgctc cgtgatgcat    2100
gaggctctgc acaaccacta cacgcagaag agcctctccc tgtctccggg ttga          2154
```

<210> SEQ ID NO 37
<211> LENGTH: 717
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 37

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Cys Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Ser Trp Glu Gly Phe Pro Tyr Trp Gln Gly Thr Thr Val
            100                 105                 110
Thr Val Ser Ser Gly Gly Gly Ser Gly Gly Gly Ser Gly Gly
        115                 120                 125
Gly Gly Ser Gly Gly Gly Ser Asp Ile Gln Met Thr Gln Ser Pro
    130                 135                 140
Ser Ser Leu Ser Ala Ser Val Gly Asp Arg Val Thr Ile Thr Cys Lys
145                 150                 155                 160
Ala Ser Gln Asn Val Gly Ile Asn Val Ala Trp Tyr Gln Gln Lys Pro
            165                 170                 175
Gly Lys Ala Pro Lys Ser Leu Ile Ser Ser Ala Ser Tyr Arg Tyr Ser
            180                 185                 190
Gly Val Pro Ser Arg Phe Ser Gly Ser Gly Ser Gly Thr Asp Phe Thr
        195                 200                 205
Leu Thr Ile Ser Ser Leu Gln Pro Glu Asp Phe Ala Thr Tyr Phe Cys
        210                 215                 220
Gln Gln Tyr Asp Thr Tyr Pro Phe Thr Phe Gly Cys Gly Thr Lys Val
225                 230                 235                 240
Glu Ile Lys Gly Gly Gly Gly Ser Gly Gly Gly Gly Ser Gly Gly Gly
            245                 250                 255
Gly Ser Gly Gly Gly Gly Ser Gly Gly Gly Gly Ser Gln Ile Gln Leu
        260                 265                 270
Val Gln Ser Gly Pro Glu Leu Lys Lys Pro Gly Glu Thr Val Lys Ile
        275                 280                 285
Ser Cys Lys Ala Ser Gly Phe Thr Phe Thr Asp Tyr Ser Ile His Trp
290                 295                 300
Val Lys Gln Ala Pro Gly Lys Gly Leu Lys Trp Met Gly Trp Ile Asn
305                 310                 315                 320
Thr Glu Thr Gly Glu Pro Thr Tyr Thr Asp Asp Phe Lys Gly Arg Phe
                325                 330                 335
Ala Phe Ser Leu Val Thr Ser Ala Thr Thr Ala Tyr Leu Gln Ile Asn
            340                 345                 350
Asn Leu Asn Asn Glu Asp Thr Ala Thr Phe Phe Cys Ala Arg Phe Ile
        355                 360                 365
Tyr Asp Pro Tyr Trp Gly Phe Ala Tyr Trp Gly Gln Gly Thr Leu Val
        370                 375                 380
Thr Val Ser Ala Ala Ser Thr Lys Gly Pro Ser Val Phe Pro Leu Ala
385                 390                 395                 400
Pro Ser Ser Lys Ser Thr Ser Gly Gly Thr Ala Ala Leu Gly Cys Leu
            405                 410                 415
Val Lys Asp Tyr Phe Pro Glu Pro Val Thr Val Ser Trp Asn Ser Gly
            420                 425                 430
Ala Leu Thr Ser Gly Val His Thr Phe Pro Ala Val Leu Gln Ser Ser
        435                 440                 445
Gly Leu Tyr Ser Leu Ser Ser Val Val Thr Val Pro Ser Ser Ser Leu
        450                 455                 460
Gly Thr Gln Thr Tyr Ile Cys Asn Val Asn His Lys Pro Ser Asn Thr
465                 470                 475                 480
Lys Val Asp Lys Lys Val Glu Pro Lys Ser Cys Asp Lys Thr His Thr
            485                 490                 495
Cys Pro Pro Cys Pro Ala Pro Glu Leu Leu Gly Gly Pro Ser Val Phe
        500                 505                 510
Leu Phe Pro Pro Lys Pro Lys Asp Thr Leu Met Ile Ser Arg Thr Pro
```

```
                   515                 520                 525
Glu Val Thr Cys Val Val Asp Val Ser His Glu Asp Pro Glu Val
    530                 535                 540
Lys Phe Asn Trp Tyr Val Asp Gly Val Glu Val His Asn Ala Lys Thr
545                 550                 555                 560
Lys Pro Arg Glu Glu Gln Tyr Asn Ser Thr Tyr Arg Val Val Ser Val
                565                 570                 575
Leu Thr Val Leu His Gln Asp Trp Leu Asn Gly Lys Glu Tyr Lys Cys
            580                 585                 590
Lys Val Ser Asn Lys Ala Leu Pro Ala Pro Ile Glu Lys Thr Ile Ser
        595                 600                 605
Lys Ala Lys Gly Gln Pro Arg Glu Pro Gln Val Tyr Thr Leu Pro Pro
    610                 615                 620
Ser Arg Asp Glu Leu Thr Lys Asn Gln Val Ser Leu Thr Cys Leu Val
625                 630                 635                 640
Lys Gly Phe Tyr Pro Ser Asp Ile Ala Val Glu Trp Glu Ser Asn Gly
                645                 650                 655
Gln Pro Glu Asn Asn Tyr Lys Thr Thr Pro Pro Val Leu Asp Ser Asp
            660                 665                 670
Gly Ser Phe Phe Leu Tyr Ser Lys Leu Thr Val Asp Lys Ser Arg Trp
        675                 680                 685
Gln Gln Gly Asn Val Phe Ser Cys Ser Val Met His Glu Ala Leu His
    690                 695                 700
Asn His Tyr Thr Gln Lys Ser Leu Ser Leu Ser Pro Gly
705                 710                 715

<210> SEQ ID NO 38
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gggggtggat ccggtggagg gggctccggc ggtggcgggt cccaggtcca actggtgcag      60
tctg                                                                  64

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgggggcggc gggtccggtg gtggtggtag                                      30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
taccaccacc accggacccg ccgcccccag                                      30
```

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
gttaacggat cctcatttga tctccacctt gg                32

<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
tccggcgggg gtggatccgg tggagggggc tccggcggtg gcgggtcc                48

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Ser Gly Gly Gly Gly Ser Gly Gly Gly Gly Ser Gly Gly Gly Gly Ser
 1               5                  10                  15

<210> SEQ ID NO 44
<211> LENGTH: 2115
<212> TYPE: DNA
<213> ORGANISM: Artificial Sequence
<220> FEATURE:
<223> OTHER INFORMATION: Description of Artificial Sequence: Synthetic
construct

<400> SEQUENCE: 44
cagatccagt tggtgcagtc tggacctgag ctgaagaagc ctggagagac agtcaagatc        60
tcctgcaagg cttctggttt taccttcaca gactattcaa tacactgggt gaaacaggct       120
ccaggaaagg gtttaaagtg gatgggctgg ataaacactg agactggtga gccaacatat       180
acagatgact caagggacg atttgccttc tctttggtga cctctgccac cactgcctat       240
ttgcagatca caacctcaa caatgaggac acggctacat ttttctgtgc tagattcatc        300
tatgatcctt attgggggtt tgcttactgg ggccagggga ctctggtcac tgtctccgca       360
gctagcacca agggcccatc ggtcttcccc ctggcaccct cctccaagag cacctctggg       420
ggcacagcgg ccctgggctg cctggtcaag gactacttcc ccgaaccggt gacggtgtcg       480
tggaactcag gcgccctgac cagcggcgtg cacaccttcc cggctgtcct acagtcctca       540
ggactctact ccctcagcag cgtggtgacc gtgccctcca gcagcttggg cacccagacc       600
tacatctgca acgtgaatca caagcccagc aacaccaagg tggacaagaa agttgagccc       660
aaatcttgtg acaaaactca cacatgccca ccgtgcccag cacctgaact cctgggggga       720
ccgtcagtct tcctcttccc cccaaaaccc aaggacaccc tcatgatctc ccggaccct        780 gaggtcacat gcgtggtggt ggacgtgagc cacgaagacc ctgaggtcaa gttcaactgg       840

-continued

```
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tccggcgggg gtggatccgg tggaggggc    1380 tccggcggtg gcgggtccca ggtccaactg gtgcagtctg gagctgaggt gaagaagcct   1440
gggtcctcag tgaaggtgtc ctgcaaggct tctggctaca ctttcacaac ctactatttg   1500
cactgggtga ggcaggcccc tggacaggga cttgagtgga tgggatggat ttatcctgga   1560
aatgttcatg ctcagtacaa tgagaagttc aagggcaggg tcacaatcac tgcagacaaa   1620
tccaccagca cagcctacat ggagctcagc agcctgaggt ctgaagatac tgcggtctat   1680
tactgtgcaa gatcctggga aggttttcct tactggggcc aagggaccac ggtcaccgtc   1740
tcctcaggtg ggggcggatc tggggcggc gggtccggtg gtggtggtag tgacattcag   1800
atgacccagt ctcctagctc cctgtccgcc tcagtaggag acagggtcac catcacctgc   1860
aaggccagtc agaatgtggg tattaatgta gcctggtatc aacagaaacc agggaaggct   1920
cctaaatcac tgatttcctc ggcctcctac cggtacagtg gagtcccttc cagattcagc   1980
ggcagtggat ctgggacaga tttcactctc accatcagca gcctccagcc tgaagacttc   2040
gcaacctatt tctgtcagca atatgacacc tatccattca cgttcggcca gggtaccaag   2100
gtggagatca aatga                                                    2115
```

<210> SEQ ID NO 45
<211> LENGTH: 704
<212> TYPE: PRT
<213> ORGANISM: Artificial Sequence
<220> FEATURE:
<223> OTHER INFORMATION: Description of Artificial Sequence: Synthetic construct

<400> SEQUENCE: 45

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Pro Thr Tyr Thr Asp Asp Phe
    50                  55                  60

Lys Gly Arg Phe Ala Phe Ser Leu Val Thr Ser Ala Thr Ala Tyr
65                  70                  75                  80

Leu Gln Ile Asn Asn Leu Asn Asn Glu Asp Thr Ala Thr Phe Phe Cys
            85                  90                  95

Ala Arg Phe Ile Tyr Asp Pro Tyr Trp Gly Phe Ala Tyr Trp Gly Gln
            100                 105                 110

Gly Thr Leu Val Thr Val Ser Ala Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Gly Gly Gly Gly Ser Gly Gly Gly Ser Gly Gly Gly
    450                 455                 460

Gly Ser Gln Val Gln Leu Val Gln Ser Gly Ala Glu Val Lys Lys Pro
465                 470                 475                 480

Gly Ser Ser Val Lys Val Ser Cys Lys Ala Ser Gly Tyr Thr Phe Thr
                485                 490                 495

Thr Tyr Tyr Leu His Trp Val Arg Gln Ala Pro Gly Gln Gly Leu Glu
            500                 505                 510

Trp Met Gly Trp Ile Tyr Pro Gly Asn Val His Ala Gln Tyr Asn Glu
        515                 520                 525

Lys Phe Lys Gly Arg Val Thr Ile Thr Ala Asp Lys Ser Thr Ser Thr
    530                 535                 540

Ala Tyr Met Glu Leu Ser Ser Leu Arg Ser Glu Asp Thr Ala Val Tyr
```

|  |  |  |  |  |  |  |  |  |  |  |  |  |  |  |
|---|---|---|---|---|---|---|---|---|---|---|---|---|---|---|
| 545 | | | | | 550 | | | | | 555 | | | | 560 |
| Tyr | Cys | Ala | Arg | Ser | Trp | Glu | Gly | Phe | Pro | Tyr | Trp | Gly | Gln | Gly |
| | | | | 565 | | | | | 570 | | | | | 575 |
| Thr | Thr | Val | Thr | Val | Ser | Ser | Gly | Gly | Gly | Gly | Ser | Gly | Gly | Gly |
| | | | 580 | | | | | 585 | | | | | 590 | |
| Ser | Gly | Gly | Gly | Gly | Ser | Asp | Ile | Gln | Met | Thr | Gln | Ser | Pro | Ser |
| | | | 595 | | | | | 600 | | | | | 605 | |
| Ser | Leu | Ser | Ala | Ser | Val | Gly | Asp | Arg | Val | Thr | Ile | Thr | Cys | Lys |
| | | 610 | | | | | 615 | | | | | 620 | | |
| Ala | Ser | Gln | Asn | Val | Gly | Ile | Asn | Val | Ala | Trp | Tyr | Gln | Gln | Lys |
| | | | 625 | | | | | 630 | | | | | 635 | |
| Pro | Gly | Lys | Ala | Pro | Lys | Ser | Leu | Ile | Ser | Ser | Ala | Ser | Tyr | Arg |
| | | | 640 | | | | | 645 | | | | | 650 | |
| Tyr | Ser | Gly | Val | Pro | Ser | Arg | Phe | Ser | Gly | Ser | Gly | Ser | Gly | Thr |
| | | | 655 | | | | 660 | | | | | 665 | | |
| Asp | Phe | Thr | Leu | Thr | Ile | Ser | Ser | Leu | Gln | Pro | Glu | Asp | Phe | Ala |
| | | | 670 | | | | 675 | | | | | 680 | | |
| Thr | Tyr | Phe | Cys | Gln | Gln | Tyr | Asp | Thr | Tyr | Pro | Phe | Thr | Phe | Gly |
| | | | 685 | | | | 690 | | | | | 695 | | |
| Gln | Gly | Thr | Lys | Val | Glu | Ile | Lys |
| | | 700 | | | | | |

<210> SEQ ID NO 46
<211> LENGTH: 2130
<212> TYPE: DNA
<213> ORGANISM: Artificial Sequence
<220> FEATURE:
<223> OTHER INFORMATION: Description of Artificial Sequence: Synthetic construct

<400> SEQUENCE: 46

```
cagatccagt tggtgcagtc tggacctgag ctgaagaagc tggagagaca agtcaagatc      60
tcctgcaagg cttctggttt taccttcaca gactattcaa tacactgggt gaaacaggct     120
ccaggaaagg gtttaaagtg gatgggctgg ataaacactg agactggtga gccaacatat     180
acagatgact tcaagggacg atttgccttc tctttggtga cctctgccac cactgcctat     240
ttgcagatca caaccctcaa caatgaggac acggctacat ttttctgtgc tagattcatc     300
tatgatcctt attgggggtt tgcttactgg ggccagggga ctctggtcac tgtctccgca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggaccccT     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgccccccat ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
```

```
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tccggcgggg gtggatccgg tggagggggc    1380
tccggcggtg gcgggtccca ggtccaactg gtgcagtctg gagctgaggt gaagaagcct    1440
gggtcctcag tgaaggtgtc ctgcaaggct tctggctaca ctttcacaac ctactatttg    1500
cactgggtga ggcaggcccc tggacaggga cttgagtgga tgggatggat ttatcctgga    1560
aatgttcatg ctcagtacaa tgagaagttc aagggcaggg tcacaatcac tgcagacaaa    1620
tccaccagca cagcctacat ggagctcagc agcctgaggt ctgaagatac tgcggtctat    1680
tactgtgcaa gatcctggga aggttttcct tactggggcc aagggaccac ggtcaccgtc    1740
tcctcaggcg gtggagggtc cggtgggggc ggatctgggg gcggcgggtc cggtggtggt    1800
ggtagtgaca ttcagatgac ccagtctcct agctccctgt ccgcctcagt aggagacagg    1860
gtcaccatca cctgcaaggc cagtcagaat gtgggtatta atgtagcctg gtatcaacag    1920
aaaccaggga aggctcctaa atcactgatt tcctcggcct cctaccggta cagtggagtc    1980
ccttccagat tcagcggcag tggatctggg acagatttca ctctcaccat cagcagcctc    2040
cagcctgaag acttcgcaac ctatttctgt cagcaatatg acacctatcc attcacgttc    2100
ggccagggta ccaaggtgga gatcaaatga                                     2130
```

<210> SEQ ID NO 47
<211> LENGTH: 709
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 47

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Pro Thr Tyr Thr Asp Asp Phe
    50                  55                  60

Lys Gly Arg Phe Ala Phe Ser Leu Val Thr Ser Ala Thr Thr Ala Tyr
65                  70                  75                  80

Leu Gln Ile Asn Asn Leu Asn Asn Glu Asp Thr Ala Thr Phe Phe Cys
                85                  90                  95

Ala Arg Phe Ile Tyr Asp Pro Tyr Trp Gly Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

-continued

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Gly Gly Gly Ser Gly Gly Gly Ser Gly Gly Gly
    450                 455                 460

Gly Ser Gln Val Gln Leu Val Gln Ser Gly Ala Glu Val Lys Lys Pro
465                 470                 475                 480

Gly Ser Ser Val Lys Val Ser Cys Lys Ala Ser Gly Tyr Thr Phe Thr
                485                 490                 495

Thr Tyr Tyr Leu His Trp Val Arg Gln Ala Pro Gly Gln Gly Leu Glu
            500                 505                 510

Trp Met Gly Trp Ile Tyr Pro Gly Asn Val His Ala Gln Tyr Asn Glu
        515                 520                 525

Lys Phe Lys Gly Arg Val Thr Ile Thr Ala Asp Lys Ser Thr Ser Thr
530                 535                 540

Ala Tyr Met Glu Leu Ser Ser Leu Arg Ser Glu Asp Thr Ala Val Tyr
545                 550                 555                 560

Tyr Cys Ala Arg Ser Trp Glu Gly Phe Pro Tyr Trp Gly Gln Gly Thr
                565                 570                 575

Thr Val Thr Val Ser Ser Gly Gly Gly Gly Ser Gly Gly Gly Gly Ser
            580                 585                 590

Gly Gly Gly Gly Ser Gly Gly Gly Gly Ser Asp Ile Gln Met Thr Gln
        595                 600                 605
```

```
Ser Pro Ser Ser Leu Ser Ala Ser Val Gly Asp Arg Val Thr Ile Thr
    610                 615                 620
Cys Lys Ala Ser Gln Asn Val Gly Ile Asn Val Ala Trp Tyr Gln Gln
625                 630                 635                 640
Lys Pro Gly Lys Ala Pro Lys Ser Leu Ile Ser Ser Ala Ser Tyr Arg
                645                 650                 655
Tyr Ser Gly Val Pro Ser Arg Phe Ser Gly Ser Gly Ser Gly Thr Asp
                660                 665                 670
Phe Thr Leu Thr Ile Ser Ser Leu Gln Pro Glu Asp Phe Ala Thr Tyr
            675                 680                 685
Phe Cys Gln Gln Tyr Asp Thr Tyr Pro Phe Thr Phe Gly Gln Gly Thr
        690                 695                 700
Lys Val Glu Ile Lys
705

<210> SEQ ID NO 48
<211> LENGTH: 2115
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 48
cagatccagt tggtgcagtc tggacctgag ctgaagaagc tggagagaca agtcaagatc      60
tcctgcaagg cttctggttt taccttcaca gactattcaa tacactgggt gaaacaggct     120
ccaggaaagg gtttaaagtg gatgggctgg ataaacactg agactggtga gccaacatat     180
acagatgact tcaagggacg atttgccttc tctttggtga cctctgccac cactgcctat     240
ttgcagatca acaacctcaa caatgaggac acggctacat ttttctgtgc tagattcatc     300
tatgatcctt attgggggtt tgcttactgg ggccagggga ctctggtcac tgtctccgca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggggga    720 ccgtcagtct tcctcttccc cccaaaaccc aaggacaccc tcatgatctc ccggaccccct    780 gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tccggcgggg gtggatccgg tgaggggggc    1380
tccggcggtg gcgggtccca ggtccaactg gtgcagtctg gagctgaggt gaagaagcct    1440
```

```
gggtcctcag tgaaggtgtc ctgcaaggct tctggctaca ctttcacaac ctactatttg    1500
cactgggtga ggcaggcccc tggacagtgc cttgagtgga tgggatggat ttatcctgga    1560
aatgttcatg ctcagtacaa tgagaagttc aagggcaggg tcacaatcac tgcagacaaa    1620
tccaccagca cagcctacat ggagctcagc agcctgaggt ctgaagatac tgcggtctat    1680
tactgtgcaa gatcctggga aggttttcct tactggggcc aagggaccac ggtcaccgtc    1740
tcctcaggtg ggggcggatc tggggcggc ggtccggtg gtggtggtag tgacattcag    1800
atgacccagt ctcctagctc cctgtccgcc tcagtaggag acagggtcac catcacctgc    1860
aaggccagtc agaatgtggg tattaatgta gcctggtatc aacagaaacc agggaaggct    1920
cctaaatcac tgatttcctc ggcctcctac cggtacagtg gagtcccttc agattcagc    1980 ggcagtggat ctgggacaga tttcactctc accatcagca gcctccagcc tgaagacttc    2040
gcaacctatt tctgtcagca atatgacacc tatccattca cgttcggctg cggtaccaag    2100
gtggagatca aatga                                                    2115
```

<210> SEQ ID NO 49
<211> LENGTH: 704
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 49

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Pro Thr Tyr Thr Asp Asp Phe
    50                  55                  60

Lys Gly Arg Phe Ala Phe Ser Leu Val Thr Ser Ala Thr Thr Ala Tyr
65                  70                  75                  80

Leu Gln Ile Asn Asn Leu Asn Asn Glu Asp Thr Ala Thr Phe Phe Cys
                85                  90                  95

Ala Arg Phe Ile Tyr Asp Pro Tyr Trp Gly Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
```

```
            225                 230                 235                 240
Pro Ser Val Phe Leu Phe Pro Lys Pro Lys Asp Thr Leu Met Ile
                    245                 250                 255

Ser Arg Thr Pro Glu Val Thr Cys Val Val Asp Val Ser His Glu
                    260                 265                 270

Asp Pro Glu Val Lys Phe Asn Trp Tyr Val Asp Gly Val Glu Val His
                    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                    325                 330                 335

Lys Thr Ile Ser Lys Ala Lys Gly Gln Pro Arg Glu Pro Gln Val Tyr
                    340                 345                 350

Thr Leu Pro Pro Ser Arg Asp Glu Leu Thr Lys Asn Gln Val Ser Leu
                    355                 360                 365

Thr Cys Leu Val Lys Gly Phe Tyr Pro Ser Asp Ile Ala Val Glu Trp
                    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                    435                 440                 445

Gly Lys Ser Gly Gly Gly Ser Gly Gly Gly Ser Gly Gly Gly
                    450                 455                 460

Gly Ser Gln Val Gln Leu Val Gln Ser Gly Ala Glu Val Lys Lys Pro
465                 470                 475                 480

Gly Ser Ser Val Lys Val Ser Cys Lys Ala Ser Gly Tyr Thr Phe Thr
                    485                 490                 495

Thr Tyr Tyr Leu His Trp Val Arg Gln Ala Pro Gly Gln Cys Leu Glu
                    500                 505                 510

Trp Met Gly Trp Ile Tyr Pro Gly Asn Val His Ala Gln Tyr Asn Glu
                    515                 520                 525

Lys Phe Lys Gly Arg Val Thr Ile Thr Ala Asp Lys Ser Thr Ser Thr
                    530                 535                 540

Ala Tyr Met Glu Leu Ser Ser Leu Arg Ser Glu Asp Thr Ala Val Tyr
545                 550                 555                 560

Tyr Cys Ala Arg Ser Trp Glu Gly Phe Pro Tyr Trp Gly Gln Gly Thr
                    565                 570                 575

Thr Val Thr Val Ser Ser Gly Gly Gly Ser Gly Gly Gly Gly Ser
                    580                 585                 590

Gly Gly Gly Gly Ser Asp Ile Gln Met Thr Gln Ser Pro Ser Ser Leu
                    595                 600                 605

Ser Ala Ser Val Gly Asp Arg Val Thr Ile Thr Cys Lys Ala Ser Gln
                    610                 615                 620

Asn Val Gly Ile Asn Val Ala Trp Tyr Gln Gln Lys Pro Gly Lys Ala
625                 630                 635                 640

Pro Lys Ser Leu Ile Ser Ser Ala Ser Tyr Arg Tyr Ser Gly Val Pro
                    645                 650                 655
```

```
Ser Arg Phe Ser Gly Ser Gly Ser Thr Asp Phe Thr Leu Thr Ile
        660                 665                 670

Ser Ser Leu Gln Pro Glu Asp Phe Ala Thr Tyr Phe Cys Gln Gln Tyr
    675                 680                 685

Asp Thr Tyr Pro Phe Thr Phe Gly Cys Gly Thr Lys Val Glu Ile Lys
    690                 695                 700

<210> SEQ ID NO 50
<211> LENGTH: 2130
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 50
cagatccagt tggtgcagtc tggacctgag ctgaagaagc tggagagac agtcaagatc      60 tcctgcaagg cttctggttt taccttcaca gactattcaa tacactgggt gaaacaggct     120
ccaggaaagg gtttaaagtg gatgggctgg ataaacactg agactggtga gccaacatat     180
acagatgact tcaagggacg atttgccttc tctttggtga cctctgccac cactgcctat     240
ttgcagatca acaacctcaa caatgaggac acggctacat ttttctgtgc tagattcatc     300
tatgatcctt attgggggtt tgcttactgg ggccagggga ctctggtcac tgtctccgca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tccggcgggg gtggatccgg tggagggggc    1380
tccggcggtg gcgggtccca ggtccaactg gtgcagtctg gagctgaggt gaagaagcct    1440
gggtcctcag tgaaggtgtc ctgcaaggct tctggctaca ctttcacaac ctactatttg    1500
cactgggtga ggcaggcccc tggacagtgc cttgagtgga tgggatggat ttatcctgga    1560
aatgttcatg ctcagtacaa tgagaagttc aagggcaggg tcacaatcac tgcagacaaa    1620
tccaccagca cagcctacat ggagctcagc agcctgaggt ctgaagatac tgcggtctat    1680
tactgtgcaa gatcctggga aggttttcct tactgggggcc aagggaccac ggtcaccgtc    1740
```

-continued

```
tcctcaggcg gtggagggtc cggtgggggc ggatctgggg gcggcgggtc cggtggtggt    1800
ggtagtgaca ttcagatgac ccagtctcct agctccctgt ccgcctcagt aggagacagg    1860
gtcaccatca cctgcaaggc cagtcagaat gtgggtatta atgtagcctg gtatcaacag    1920
aaaccaggga aggctcctaa atcactgatt tcctcggcct cctaccggta cagtggagtc    1980
ccttccagat tcagcggcag tggatctggg acagatttca ctctcaccat cagcagcctc    2040
cagcctgaag acttcgcaac ctatttctgt cagcaatatg acacctatcc attcacgttc    2100
ggctgcggta ccaaggtgga gatcaaatga                                      2130
```

```
<210> SEQ ID NO 51
<211> LENGTH: 709
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 51

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Pro Thr Tyr Thr Asp Asp Phe
    50                  55                  60

Lys Gly Arg Phe Ala Phe Ser Leu Val Thr Ser Ala Thr Ala Ala Tyr
65                  70                  75                  80

Leu Gln Ile Asn Asn Leu Asn Asn Glu Asp Thr Ala Thr Phe Phe Cys
                85                  90                  95

Ala Arg Phe Ile Tyr Asp Pro Tyr Trp Gly Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys Ser Gly Gly Gly Ser Gly Gly Gly Ser Gly Gly Gly
450                 455                 460

Gly Ser Gln Val Gln Leu Val Gln Ser Gly Ala Glu Val Lys Lys Pro
465                 470                 475                 480

Gly Ser Ser Val Lys Val Ser Cys Lys Ala Ser Gly Tyr Thr Phe Thr
                485                 490                 495

Thr Tyr Tyr Leu His Trp Val Arg Gln Ala Pro Gly Gln Cys Leu Glu
            500                 505                 510

Trp Met Gly Trp Ile Tyr Pro Gly Asn Val His Ala Gln Tyr Asn Glu
                515                 520                 525

Lys Phe Lys Gly Arg Val Thr Ile Thr Ala Asp Lys Ser Thr Ser Thr
530                 535                 540

Ala Tyr Met Glu Leu Ser Ser Leu Arg Ser Glu Asp Thr Ala Val Tyr
545                 550                 555                 560

Tyr Cys Ala Arg Ser Trp Glu Gly Phe Pro Tyr Trp Gly Gln Gly Thr
                565                 570                 575

Thr Val Thr Val Ser Ser Gly Gly Gly Gly Ser Gly Gly Gly Gly Ser
            580                 585                 590

Gly Gly Gly Gly Ser Gly Gly Gly Gly Ser Asp Ile Gln Met Thr Gln
                595                 600                 605

Ser Pro Ser Ser Leu Ser Ala Ser Val Gly Asp Arg Val Thr Ile Thr
610                 615                 620

Cys Lys Ala Ser Gln Asn Val Gly Ile Asn Val Ala Trp Tyr Gln Gln
625                 630                 635                 640

Lys Pro Gly Lys Ala Pro Lys Ser Leu Ile Ser Ser Ala Ser Tyr Arg
                645                 650                 655

Tyr Ser Gly Val Pro Ser Arg Phe Ser Gly Ser Gly Ser Gly Thr Asp
            660                 665                 670

Phe Thr Leu Thr Ile Ser Ser Leu Gln Pro Glu Asp Phe Ala Thr Tyr
                675                 680                 685

Phe Cys Gln Gln Tyr Asp Thr Tyr Pro Phe Thr Phe Gly Cys Gly Thr
690                 695                 700

Lys Val Glu Ile Lys
```

<210> SEQ ID NO 52
<211> LENGTH: 2130
<212> TYPE: DNA
<213> ORGANISM: Artificial Sequence
<220> FEATURE:
<223> OTHER INFORMATION: Description of Artificial Sequence: Synthetic construct

<400> SEQUENCE: 52

```
cagatccagt tggtgcagtc tggacctgag ctgaagaagc ctggagagac agtcaagatc      60
tcctgcaagg cttctggttt taccttcaca gactattcaa tacactgggt gaaacaggct     120
ccaggaaagg gtttaaagtg gatgggctgg ataaacactg agactggtga gccaacatat     180
acagatgact tcaagggacg atttgccttc tctttggtga cctctgccac cactgcctat     240
ttgcagatca caacctcaa caatgaggac acggctacat ttttctgtgc tagattcatc      300
tatgatcctt attgggggtt tgcttactgg ggccagggga ctctggtcac tgtctccgca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tccggcgggg gtggatccgg tggagggggc    1380
tccggcggtg gcgggtccca ggtccaactg gtgcagtctg gagctgaggt gaagaagcct    1440
gggagtcag tgaaggtgtc ctgcaaggct tctggctaca ctttcacaac ctactatttg    1500
cactgggtga ggcaggcccc tggacaggga cttgagtgga tgggatggat ttatcctgga    1560
aatgttcatg ctcagtacaa tgagaagttc aagggcaggg tcacaatcac tgcagacaaa    1620
tccaccagca cagcctacat ggagctcagc agcctgaggt ctgaagatac tgcggtctat    1680
tactgtgcaa gatcctggga aggttttcct tactggggcc aagggaccac ggtcaccgtc    1740
tcctcaggcg gtgagggtc cggtggggc ggatctgggg gcgcgggtc cggtggtggt    1800
ggtagtgaca ttcagatgac ccagtctcct agctccctgt ccgcctcagt aggagacagg    1860
gtcaccatca cctgcaaggc cagtcagaat gtgggtatta atgtagcctg gtatcaacag    1920
aaaccaggga aggctcctaa attactgatt tcctcggcct cctaccggta cagtggagtc    1980
```

```
ccttccagat tcagcggcag tggatctggg acagatttca ctctcaccat cagcagcctc    2040
cagcctgaag acttcgcaac ctatttctgt cagcaatatg acacctatcc attcacgttc    2100
ggccagggta ccaaggtgga gatcaaatga                                     2130
```

<210> SEQ ID NO 53
<211> LENGTH: 709
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 53

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Pro Thr Tyr Thr Asp Asp Phe
    50                  55                  60

Lys Gly Arg Phe Ala Phe Ser Leu Val Thr Ser Ala Thr Thr Ala Tyr
65                  70                  75                  80

Leu Gln Ile Asn Asn Leu Asn Asn Glu Asp Thr Ala Thr Phe Phe Cys
                85                  90                  95

Ala Arg Phe Ile Tyr Asp Pro Tyr Trp Gly Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Gly Gly Gly Gly Ser Gly Gly Gly Gly Ser Gly Gly Gly
    450                 455                 460

Gly Ser Gln Val Gln Leu Val Gln Ser Gly Ala Glu Val Lys Lys Pro
465                 470                 475                 480

Gly Glu Ser Val Lys Val Ser Cys Lys Ala Ser Gly Tyr Thr Phe Thr
                485                 490                 495

Thr Tyr Tyr Leu His Trp Val Arg Gln Ala Pro Gly Gln Gly Leu Glu
            500                 505                 510

Trp Met Gly Trp Ile Tyr Pro Gly Asn Val His Ala Gln Tyr Asn Glu
        515                 520                 525

Lys Phe Lys Gly Arg Val Thr Ile Thr Ala Asp Lys Ser Thr Ser Thr
    530                 535                 540

Ala Tyr Met Glu Leu Ser Ser Leu Arg Ser Glu Asp Thr Ala Val Tyr
545                 550                 555                 560

Tyr Cys Ala Arg Ser Trp Glu Gly Phe Pro Tyr Trp Gly Gln Gly Thr
                565                 570                 575

Thr Val Thr Val Ser Ser Gly Gly Gly Gly Ser Gly Gly Gly Gly Ser
            580                 585                 590

Gly Gly Gly Gly Ser Gly Gly Gly Gly Ser Asp Ile Gln Met Thr Gln
        595                 600                 605

Ser Pro Ser Ser Leu Ser Ala Ser Val Gly Asp Arg Val Thr Ile Thr
    610                 615                 620

Cys Lys Ala Ser Gln Asn Val Gly Ile Asn Val Ala Trp Tyr Gln Gln
625                 630                 635                 640

Lys Pro Gly Lys Ala Pro Lys Leu Leu Ile Ser Ser Ala Ser Tyr Arg
                645                 650                 655

Tyr Ser Gly Val Pro Ser Arg Phe Ser Gly Ser Gly Ser Gly Thr Asp
            660                 665                 670

Phe Thr Leu Thr Ile Ser Ser Leu Gln Pro Glu Asp Phe Ala Thr Tyr
        675                 680                 685

Phe Cys Gln Gln Tyr Asp Thr Tyr Pro Phe Thr Phe Gly Gln Gly Thr
    690                 695                 700

Lys Val Glu Ile Lys
705

<210> SEQ ID NO 54
<211> LENGTH: 2130
<212> TYPE: DNA
<213> ORGANISM: Artificial Sequence
<220> FEATURE:
```

<223> OTHER INFORMATION: Description of Artificial Sequence: Synthetic construct

<400> SEQUENCE: 54

```
cagatccagt tggtgcagtc tggacctgag ctgaagaagc ctggagagac agtcaagatc      60
tcctgcaagg cttctggttt taccttcaca gactattcaa tacactgggt gaaacaggct     120
ccaggaaagg gtttaaagtg gatgggctgg ataaacactg agactggtga gccaacatat     180
acagatgact tcaagggacg atttgccttc tctttggtga cctctgccac cactgcctat     240
ttgcagatca caacctcaa caatgaggac acggctacat ttttctgtgc tagattcatc      300
tatgatcctt attgggggtt tgcttactgg ggccagggga ctctggtcac tgtctccgca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggaccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggatgag     1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tccggcgggg gtggatccgg tggagggggc    1380
tccggcggtg cgggtccca ggtccaactg gtgcagtctg gagctgaggt gaagaagcct     1440
ggggagtcag tgaaggtgtc ctgcaaggct tctggctaca ctttcacaac ctactatttg    1500
cactgggtga ggcaggcccc tggacagtgc cttgagtgga tgggatggat ttatcctgga    1560
aatgttcatg ctcagtacaa tgagaagttc aagggcaggg tcacaatcac tgcagacaaa    1620
tccaccagca cagcctacat ggagctcagc agcctgaggt ctgaagatac tgcggtctat    1680
tactgtgcaa gatcctggga aggttttcct tactggggcc aagggaccac ggtcaccgtc    1740
tcctcaggcg gtggagggtc cggtggggc ggatctgggg gcggcgggtc cggtggtggt     1800
ggtagtgaca ttcagatgac ccagtctcct agctccctgt ccgcctcagt aggagacagg    1860
gtcaccatca cctgcaaggc cagtcagaat gtgggtatta atgtagcctg gtatcaacag    1920
aaaccaggga aggctcctaa attactgatt tcctcggcct cctaccggta cagtggagtc    1980
ccttccagat tcagcggcag tggatctggg acagatttca ctctcaccat cagcagcctc    2040
cagcctgaag acttcgcaac ctatttctgt cagcaatatg acacctatcc attcacgttc    2100
ggctgcggta ccaaggtgga gatcaaatga                                     2130
```

<210> SEQ ID NO 55

```
<211> LENGTH: 709
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 55

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Pro Thr Tyr Thr Asp Asp Phe
    50                  55                  60

Lys Gly Arg Phe Ala Phe Ser Leu Val Thr Ser Ala Thr Thr Ala Tyr
65                  70                  75                  80

Leu Gln Ile Asn Asn Leu Asn Asn Glu Asp Thr Ala Thr Phe Phe Cys
                85                  90                  95

Ala Arg Phe Ile Tyr Asp Pro Tyr Trp Gly Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
```

```
                370                 375                 380
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Gly Gly Gly Ser Gly Gly Gly Ser Gly Gly Gly
    450                 455                 460

Gly Ser Gln Val Gln Leu Val Gln Ser Gly Ala Glu Val Lys Lys Pro
465                 470                 475                 480

Gly Glu Ser Val Lys Val Ser Cys Lys Ala Ser Gly Tyr Thr Phe Thr
                485                 490                 495

Thr Tyr Tyr Leu His Trp Val Arg Gln Ala Pro Gly Gln Cys Leu Glu
            500                 505                 510

Trp Met Gly Trp Ile Tyr Pro Gly Asn Val His Ala Gln Tyr Asn Glu
        515                 520                 525

Lys Phe Lys Gly Arg Val Thr Ile Thr Ala Asp Lys Ser Thr Ser Thr
530                 535                 540

Ala Tyr Met Glu Leu Ser Ser Leu Arg Ser Glu Asp Thr Ala Val Tyr
545                 550                 555                 560

Tyr Cys Ala Arg Ser Trp Glu Gly Phe Pro Tyr Trp Gly Gln Gly Thr
                565                 570                 575

Thr Val Thr Val Ser Ser Gly Gly Gly Gly Ser Gly Gly Gly Gly Ser
            580                 585                 590

Gly Gly Gly Gly Ser Gly Gly Gly Ser Asp Ile Gln Met Thr Gln
        595                 600                 605

Ser Pro Ser Ser Leu Ser Ala Ser Val Gly Asp Arg Val Thr Ile Thr
    610                 615                 620

Cys Lys Ala Ser Gln Asn Val Gly Ile Asn Val Ala Trp Tyr Gln Gln
625                 630                 635                 640

Lys Pro Gly Lys Ala Pro Lys Leu Leu Ile Ser Ser Ala Ser Tyr Arg
                645                 650                 655

Tyr Ser Gly Val Pro Ser Arg Phe Ser Gly Ser Gly Ser Gly Thr Asp
            660                 665                 670

Phe Thr Leu Thr Ile Ser Ser Leu Gln Pro Glu Asp Phe Ala Thr Tyr
        675                 680                 685

Phe Cys Gln Gln Tyr Asp Thr Tyr Pro Phe Thr Phe Gly Cys Gly Thr
690                 695                 700

Lys Val Glu Ile Lys
705

<210> SEQ ID NO 56
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gggggtggat ccggtggagg gggctccggc ggtggcgggt cccaggtcca actggtgcag    60
tctg                                                                64
```

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
gttaacggat cctcatttga tctccacctt gg    32

<210> SEQ ID NO 58
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Asp Asp Asp Asp Lys Ser Phe Leu Glu Gln Lys Leu Ile Ser Glu Glu
1               5                   10                  15

Asp Leu Asn Ser Ala Val Asp His His His His His His
            20                  25

<210> SEQ ID NO 59
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
atggcctgga ctcctctctt cttcttcttt gttcttcatt gctcagggtc tttctcc    57

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Met Ala Trp Thr Pro Leu Phe Phe Phe Phe Val Leu His Cys Ser Gly
1               5                   10                  15

Ser Phe Ser

<210> SEQ ID NO 61
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
atgggttgga gcctcatctt gctcttcctt gtcgctgttg ctacgcgtgt cctgtcc    57

<210> SEQ ID NO 62
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 62

Met Gly Trp Ser Leu Ile Leu Leu Phe Leu Val Ala Val Ala Thr Arg
1               5                   10                  15

Val Leu Ser

<210> SEQ ID NO 63
<211> LENGTH: 2115
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 63
gaggtgcagc tggtggagtc tgggggcggc ttggcaaagc ctgggggggtc cctgagactc     60 tcctgcgcag cctccgggtt caggttcacc ttcaataact actacatgga ctgggtccgc    120
caggctccag ggcaggggct ggagtgggtc tcacgtatta gtagtagtgg tgatcccaca    180
tggtacgcag actccgtgaa gggcagattc accatctcca gagagaacgc caagaacaca    240
ctgtttcttc aaatgaacag cctgagagct gaggacacgg ctgtctatta ctgtgcgagc    300
ttgactacag ggtctgactc ctggggccag ggagtcctgg tcaccgtctc ctcagctagc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc    600 tgcaacgtga atcacaagcc cagcaacacc aaggtggaca gaaagttga gcccaaatct    660 tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaatccggc ggggtggat ccggtggagg gggctccggc   1380
ggtggcgggt ccgacatcca gatgacccag tctccatctt ccctgtctgc atctgtaggg   1440
gacagagtca ccatcacttg cagggcaagt caggacatta gtattatttt aaattggtat   1500
cagcagaaac aggaaaagc tcctaagctc ctgatctatg ttgcatccag tttgcaaagt   1560
ggggtcccat caaggttcag cggcagtgga tctgggacag agttcactct caccgtcagc   1620
agcctgcagc ctgaagattt tgcgacttat tactgtctac aggtttatag taccccctcgg   1680 acgttcggcc aagggaccaa ggtggaaatc aaagtggggg cggatctgg gggcggcggg   1740
```

-continued

```
tccggtggtg gtggtagtga ggtgcagctg gtggagtctg ggggcggctt ggcaaagcct    1800 gggggggtccc tgagactctc ctgcgcagcc tccgggttca ggttcacctt caataactac    1860
tacatggact gggtccgcca ggctccaggg caggggctgg agtgggtctc acgtattagt    1920
agtagtggtg atcccacatg gtacgcagac tccgtgaagg gcagattcac catctccaga    1980
gagaacgcca agaacacact gtttcttcaa atgaacagcc tgagagctga ggacacggct    2040
gtctattact gtgcgagctt gactacaggg tctgactcct ggggccaggg agtcctggtc    2100
accgtctcct catga                                                     2115
```

<210> SEQ ID NO 64
<211> LENGTH: 704
<212> TYPE: PRT
<213> ORGANISM: Artificial Sequence
<220> FEATURE:
<223> OTHER INFORMATION: Description of Artificial Sequence: Synthetic construct

<400> SEQUENCE: 64

```
Glu Val Gln Leu Val Glu Ser Gly Gly Gly Leu Ala Lys Pro Gly Gly
  1               5                  10                  15

Ser Leu Arg Leu Ser Cys Ala Ala Ser Gly Phe Arg Phe Thr Phe Asn
             20                  25                  30

Asn Tyr Tyr Met Asp Trp Val Arg Gln Ala Pro Gly Gln Gly Leu Glu
         35                  40                  45

Trp Val Ser Arg Ile Ser Ser Gly Asp Pro Thr Trp Tyr Ala Asp
     50                  55                  60

Ser Val Lys Gly Arg Phe Thr Ile Ser Arg Glu Asn Ala Lys Asn Thr
 65                  70                  75                  80

Leu Phe Leu Gln Met Asn Ser Leu Arg Ala Glu Asp Thr Ala Val Tyr
                 85                  90                  95

Tyr Cys Ala Ser Leu Thr Thr Gly Ser Asp Ser Trp Gly Gln Gly Val
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Ser Gly Gly Gly Gly Ser Gly Gly Gly Gly Ser Gly Gly Gly Gly Ser
450                 455                 460

Asp Ile Gln Met Thr Gln Ser Pro Ser Ser Leu Ser Ala Ser Val Gly
465                 470                 475                 480

Asp Arg Val Thr Ile Thr Cys Arg Ala Ser Gln Asp Ile Arg Tyr Tyr
                485                 490                 495

Leu Asn Trp Tyr Gln Gln Lys Pro Gly Lys Ala Pro Lys Leu Leu Ile
            500                 505                 510

Tyr Val Ala Ser Ser Leu Gln Ser Gly Val Pro Ser Arg Phe Ser Gly
        515                 520                 525

Ser Gly Ser Gly Thr Glu Phe Thr Leu Thr Val Ser Ser Leu Gln Pro
530                 535                 540

Glu Asp Phe Ala Thr Tyr Tyr Cys Leu Gln Val Tyr Ser Thr Pro Arg
545                 550                 555                 560

Thr Phe Gly Gln Gly Thr Lys Val Glu Ile Lys Gly Gly Gly Gly Ser
                565                 570                 575

Gly Gly Gly Gly Ser Gly Gly Gly Ser Glu Val Gln Leu Val Glu
            580                 585                 590

Ser Gly Gly Gly Leu Ala Lys Pro Gly Gly Ser Leu Arg Leu Ser Cys
        595                 600                 605

Ala Ala Ser Gly Phe Arg Phe Thr Phe Asn Asn Tyr Tyr Met Asp Trp
610                 615                 620

Val Arg Gln Ala Pro Gly Gln Gly Leu Glu Trp Val Ser Arg Ile Ser
625                 630                 635                 640

Ser Ser Gly Asp Pro Thr Trp Tyr Ala Asp Ser Val Lys Gly Arg Phe
                645                 650                 655

Thr Ile Ser Arg Glu Asn Ala Lys Asn Thr Leu Phe Leu Gln Met Asn
            660                 665                 670

Ser Leu Arg Ala Glu Asp Thr Ala Val Tyr Tyr Cys Ala Ser Leu Thr
        675                 680                 685

Thr Gly Ser Asp Ser Trp Gly Gln Gly Val Leu Val Thr Val Ser Ser
690                 695                 700
```

```
<210> SEQ ID NO 65
<211> LENGTH: 645
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 65
gacatccaga tgacccagtc tccatcttcc ctgtctgcat ctgtagggga cagagtcacc      60
atcacttgca gggcaagtca ggacattagg tattatttaa attggtatca gcagaaacca     120
ggaaaagctc ctaagctcct gatctatgtt gcatccagtt tgcaaagtgg ggtcccatca     180
aggttcagcg gcagtggatc tgggacagag ttcactctca ccgtcagcag cctgcagcct     240
gaagattttg cgacttatta ctgtctacag gtttatagta cccctcggac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc      600
ctgagctcgc ccgtcacaaa gagcttcaac aggggagagt gttga                    645

<210> SEQ ID NO 66
<211> LENGTH: 214
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Tyr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Glu Asp Phe Ala Thr Tyr Tyr Cys Leu Gln Val Tyr Ser Thr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 67
<211> LENGTH: 723
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 67

```
gacatccaga tgacccagtc tccatcttcc ctgtctgcat ctgtagggga cagagtcacc     60
atcacttgca gggcaagtca ggacattagg tattatttaa attggtatca gcagaaacca    120
ggaaaagctc ctaagctcct gatctatgtt gcatccagtt tgcaaagtgg ggtcccatca    180
aggttcagcg gcagtggatc tgggacagag ttcactctca ccgtcagcag cctgcagcct    240
gaagattttg cgacttatta ctgtctacag gtttatagta cccctcggac gttcggccaa    300
gggaccaagg tggaaatcaa aggcggtggc gggtccggtg ggtggctc cggggggcgt     360
ggctccgagg tgcagctggt ggagtctggg gcggcttgg caaagcctgg ggggtccctg    420
agactctcct gcgcagcctc cgggttcagg ttcaccttca ataactacta catggactgg    480
gtccgccagg ctccagggca ggggctggag tgggtctcac gtattagtag tagtggtgat    540
cccacatggt acgcagactc cgtgaagggc agattcacca ctccagaga gaacgccaag    600
aacacactgt ttcttcaaat gaacagcctg agagctgagg acacggctgt ctattactgt    660
gcgagcttga ctacagggtc tgactcctgg ggccaggag tcctggtcac cgtctcctca    720
tga                                                                   723
```

<210> SEQ ID NO 68
<211> LENGTH: 240
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Tyr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Glu Asp Phe Ala Thr Tyr Tyr Cys Leu Gln Val Tyr Ser Thr Pro Arg
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Ala Lys Pro Gly Gly Ser Leu Arg Leu Ser Cys

Ala Ala Ser Gly Phe Arg Phe Thr Phe Asn Asn Tyr Tyr Met Asp Trp
145                 150                 155                 160

Val Arg Gln Ala Pro Gly Gln Gly Leu Glu Trp Val Ser Arg Ile Ser
                165                 170                 175

Ser Ser Gly Asp Pro Thr Trp Tyr Ala Asp Ser Val Lys Gly Arg Phe
            180                 185                 190

Thr Ile Ser Arg Glu Asn Ala Lys Asn Thr Leu Phe Leu Gln Met Asn
        195                 200                 205

Ser Leu Arg Ala Glu Asp Thr Ala Val Tyr Tyr Cys Ala Ser Leu Thr
    210                 215                 220

Thr Gly Ser Asp Ser Trp Gly Gln Gly Val Leu Val Thr Val Ser Ser
225                 230                 235                 240

<210> SEQ ID NO 69
<211> LENGTH: 723
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 69
gaggtgcagc tggtggagtc tgggggcggc ttggcaaagc ctggggggtc cctgagactc      60
tcctgcgcag cctccgggtt caggttcacc ttcaataact actacatgga ctgggtccgc     120
caggctccag gcaggggct ggagtgggtc tcacgtatta gtagtagtgg tgatcccaca      180
tggtacgcag actccgtgaa gggcagattc accatctcca gagagaacgc caagaacaca     240
ctgtttcttc aaatgaacag cctgagagct gaggacacgg ctgtctatta ctgtgcgagc     300
ttgactacag ggtctgactc ctggggccag ggagtcctgg tcaccgtctc ctcaggcggt     360
ggcgggtccg gtggggtgg ctccggggc ggtggctccg acatccagat gacccagtct      420
ccatcttccc tgtctgcatc tgtagggac agagtcacca tcacttgcag ggcaagtcag     480
gacattaggt attatttaaa ttggtatcag cagaaaccag gaaaagctcc taagctcctg     540
atctatgttg catccagttt gcaaagtggg gtcccatcaa ggttcagcgg cagtggatct     600
gggacagagt tcactctcac cgtcagcagc ctgcagcctg aagattttgc gacttattac     660
tgtctacagg tttatagtac ccctcggacg ttcggccaag gaccaaggt ggaaatcaaa     720 tga                                                                   723

<210> SEQ ID NO 70
<211> LENGTH: 240
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 70

Glu Val Gln Leu Val Glu Ser Gly Gly Gly Leu Ala Lys Pro Gly Gly
1               5                   10                  15

Ser Leu Arg Leu Ser Cys Ala Ala Ser Gly Phe Arg Phe Thr Phe Asn
            20                  25                  30

Asn Tyr Tyr Met Asp Trp Val Arg Gln Ala Pro Gly Gln Gly Leu Glu
        35                  40                  45

Trp Val Ser Arg Ile Ser Ser Ser Gly Asp Pro Thr Trp Tyr Ala Asp
    50                  55                  60

Ser Val Lys Gly Arg Phe Thr Ile Ser Arg Glu Asn Ala Lys Asn Thr
65                  70                  75                  80

Leu Phe Leu Gln Met Asn Ser Leu Arg Ala Glu Asp Thr Ala Val Tyr
            85                  90                  95

Tyr Cys Ala Ser Leu Thr Thr Gly Ser Asp Ser Trp Gly Gln Gly Val
        100                 105                 110

Leu Val Thr Val Ser Ser Gly Gly Gly Ser Gly Gly Gly Gly Ser
    115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Ile Arg Tyr Tyr Leu Asn Trp Tyr Gln Gln Lys Pro Gly Lys Ala
                165                 170                 175

Pro Lys Leu Leu Ile Tyr Val Ala Ser Ser Leu Gln Ser Gly Val Pro
            180                 185                 190

Ser Arg Phe Ser Gly Ser Gly Ser Gly Thr Glu Phe Thr Leu Thr Val
        195                 200                 205

Ser Ser Leu Gln Pro Glu Asp Phe Ala Thr Tyr Tyr Cys Leu Gln Val
    210                 215                 220

Tyr Ser Thr Pro Arg Thr Phe Gly Gln Gly Thr Lys Val Glu Ile Lys
225                 230                 235                 240

<210> SEQ ID NO 71
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgctggtggt gccgttctat agccatagtg acatccagat gacc                    44

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtggtcgact ttgatttcca c                                             21

<210> SEQ ID NO 73
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cgctggtggt gccgttctat agccatagtg aggtgcagct ggtggag                 47

<210> SEQ ID NO 74
<211> LENGTH: 24
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 74
gtggtcgact gaggagacgg tgac                                            24

<210> SEQ ID NO 75
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggcatatgaa aaactgctg ttcgcgattc cgctggtggt gccgttctat ag             52

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gaggtgcagc tggtgcagtc tggggggcggc ttg                                 33

<210> SEQ ID NO 77
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gagtctgggg gcggcrrcgc aaagcctggg ggg                                  33

<210> SEQ ID NO 78
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78 gtctggggggc ggcttgrhgm agcctggggg gtccctg                             37

<210> SEQ ID NO 79
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gttcaggttc accttcagca actactacat ggac                                 34

<210> SEQ ID NO 80
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
caataactac tacatgmrct gggtccgcca ggctc                            35

<210> SEQ ID NO 81
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cgccaggctc cagggarggg gctggagtgg gtc                              33

<210> SEQ ID NO 82
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gggctggagt gggtcgsccg tattagtagt agtg                             34

<210> SEQ ID NO 83
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gagtgggtct cacgtatgag tagtagtggt gatc                             34

<210> SEQ ID NO 84
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggtattattt aaattggtat gcccagaaac caggaaaag                        39

<210> SEQ ID NO 85
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gtattagtag tagtggtrgc cccacatggt acgcag                           36

<210> SEQ ID NO 86
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gtagtagtgg tgatrvcaca tggtacgcag ac					32

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gtggtgatcc cacawactac gcagactccg tg					32

<210> SEQ ID NO 88
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gattcaccat ctccagarac aacgccaaga acacac					36

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
catctccaga gagaacagca agaacacact gtttc					35

<210> SEQ ID NO 90
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gccaagaaca cactgkhcct tcaaatgaac agc					33

<210> SEQ ID NO 91
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gaacacactg tttcttgaaa tgaacagcct gagag					35

<210> SEQ ID NO 92
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
caaatgaaca gcctgagagg cgaggacacg gctgtc								36

<210> SEQ ID NO 93
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gagctgagga cacggctrsc tattactgtg cg									32

<210> SEQ ID NO 94
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gtctattact gtgcgargtt gactacaggg tctg								34

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cagtctccat cttccggctc tgcatctgta ggg								33

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ccctgtctgc atctrscggg gacagagtca cc									32

<210> SEQ ID NO 97
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ctgtagggga cagactgacc atcacttgca gg									32

<210> SEQ ID NO 98
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggggacagag tcaccctgac ttgcagggca ag                                      32

<210> SEQ ID NO 99
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gacagagtca ccatcagctg cagggcaagt cag                                     33

<210> SEQ ID NO 100
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gcagggcaag tcagrgcatt aggtattatt taaattg                                 37

<210> SEQ ID NO 101
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gcaagtcagg acattmkcta ttatttaaat tgg                                     33

<210> SEQ ID NO 102
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aattggtatc agcaggcccc aggaaaagct cc                                      32

<210> SEQ ID NO 103
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ccaggaaaag ctcctsrcct cctgatctat gttg                                    34

<210> SEQ ID NO 104
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(19)

<223> OTHER INFORMATION: a, c, g or t

<400> SEQUENCE: 104
ctaagctcct gatctatnnk gcatccagtt tgcaaag                37

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ctatgttgca tccagtcgcc aaagtggggt ccc                33

<210> SEQ ID NO 106
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cagtttgcaa agtgggtccc catcaaggtt cagc                34

<210> SEQ ID NO 107
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cagtggatct gggacagact tcactctcac cgtc                34

<210> SEQ ID NO 108
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gagttcactc tcaccatcag cagcctgcag cc                32

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cagcagcctg cagrgcgaag attttgcgac                30

<210> SEQ ID NO 110
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ctgcagcctg aagatrscgc gacttattac tg            32

<210> SEQ ID NO 111
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cctgaagatt ttgcggacta ttactgtcta cag           33

<210> SEQ ID NO 112
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gcgacttatt actgtsmrca ggtttatagt acc           33

<210> SEQ ID NO 113
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gtttatagta cccctmwaac gttcggccaa ggg           33

<210> SEQ ID NO 114
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114 gtaccccteg gacgtggggc caagggacca ag            32

<210> SEQ ID NO 115
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gctccagggc aggggtgcga gtgggtctca cg            32

<210> SEQ ID NO 116
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gtacccctcg gacgtgcggc caagggacca ag 32

<210> SEQ ID NO 117
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cttgactaca gggtcttgct cctggggcca gggag 35

<210> SEQ ID NO 118
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ggaaaagctc ctaagtgcct gatctatgtt gc 32

<210> SEQ ID NO 119
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gactacaggg tctgactgct ggggccaggg agtc 34

<210> SEQ ID NO 120
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ggaaaagctc ctaagtgcct gatctatgtt gc 32

<210> SEQ ID NO 121
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
caggctccag ggcagtgcct ggagtgggtc tcac 34

<210> SEQ ID NO 122
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cctcggacgt tcggctgcgg gaccaaggtg gaaatc          36

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(18)
<223> OTHER INFORMATION: a, c, g or t

<400> SEQUENCE: 123
gtaccggtag gaggcmnnrk aaatcagtga tttagg          36

<210> SEQ ID NO 124
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gggaaggctc ctaaattact gatttcctcg gcc          33

<210> SEQ ID NO 125
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)
<223> OTHER INFORMATION: a, c, g or t

<400> SEQUENCE: 125
ggacaccttc actgacbncc caggcttctt cac          33

<210> SEQ ID NO 126
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gatcctggga aggttttgac tactggggcc aagggac          37

<210> SEQ ID NO 127
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gggtcctcag tgaagwtrtc ctgcaaggct tctg          34

<210> SEQ ID NO 128
<211> LENGTH: 34

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
cagggacttg agtggvkkgg atggatttat cctg                            34

<210> SEQ ID NO 129
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)
<223> OTHER INFORMATION: a, c, g or t

<400> SEQUENCE: 129
gaagttcaag ggcaggnyca caatcactgc agac                            34

<210> SEQ ID NO 130
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggatggattt atcctggaaa tggtcatgct cagtacaatg ag                   42

<210> SEQ ID NO 131
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)
<223> OTHER INFORMATION: a, c, g or t

<400> SEQUENCE: 131
ggtggtagtg acattvnsat gacccagtct cctagc                          36

<210> SEQ ID NO 132
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ggcggtggag ggtccggtgg aggggctct ggagggggcg gttcaggggg cggtggatcg   60
gggggaggtg gctcc                                                 75

<210> SEQ ID NO 133
<211> LENGTH: 25
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 133

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 134
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
agagagacgc gtgtcctgtc ccaggtccaa ctggtgcag                              39

<210> SEQ ID NO 135
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
agccacctcc ccccgatcca ccgcccctg aaccgccccc tccagagccc cctccaccgg         60
accctccacc gcctttgatc tccaccttg                                         89

<210> SEQ ID NO 136
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
agagagagat cttgactgtc tctccaggct tcttcagctc aggtccagac tgcaccaact        60
ggatctggga gccacctccc ccgatccac                                         90

<210> SEQ ID NO 137
<211> LENGTH: 290
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 137

Met Lys Lys Leu Leu Phe Ala Ile Pro Leu Val Val Pro Phe Tyr Ser
1               5                   10                  15

His Ser Gln Val Gln Leu Val Gln Ser Gly Ala Glu Val Lys Lys Pro
            20                  25                  30

Gly Ser Ser Val Lys Val Ser Cys Lys Ala Ser Gly Tyr Thr Phe Thr
        35                  40                  45

Thr Tyr Tyr Leu His Trp Val Arg Gln Ala Pro Gly Gln Gly Leu Glu
    50                  55                  60

Trp Met Gly Trp Ile Tyr Pro Gly Asn Val His Ala Gln Tyr Asn Glu
65                  70                  75                  80
```

```
Lys Phe Lys Gly Arg Val Thr Ile Thr Ala Asp Lys Ser Thr Ser Thr
                 85                  90                  95

Ala Tyr Met Glu Leu Ser Ser Leu Arg Ser Glu Asp Thr Ala Val Tyr
            100                 105                 110

Tyr Cys Ala Arg Ser Trp Glu Gly Phe Pro Tyr Trp Gly Gln Gly Thr
        115                 120                 125

Thr Val Thr Val Ser Ser Gly Gly Gly Gly Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Lys Ala Ser Gln Asn Val Gly Ile Asn Val Ala Trp Tyr Gln Gln
            180                 185                 190

Lys Pro Gly Lys Ala Pro Lys Ser Leu Ile Ser Ser Ala Ser Tyr Arg
        195                 200                 205

Tyr Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Phe Cys Gln Gln Tyr Asp Thr Tyr Pro Phe Thr Phe Gly Gln Gly Thr
                245                 250                 255

Lys Val Glu Ile Lys Asp Asp Asp Lys Ser Phe Leu Glu Gln Lys
            260                 265                 270

Leu Ile Ser Glu Glu Asp Leu Asn Ser Ala Val Asp His His His His
        275                 280                 285

His His
    290

<210> SEQ ID NO 138
<211> LENGTH: 290
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 138

Met Lys Lys Leu Leu Phe Ala Ile Pro Leu Val Val Pro Phe Tyr Ser
1               5                   10                  15

His Ser Gln Val Gln Leu Val Gln Ser Gly Ala Glu Val Lys Lys Pro
            20                  25                  30

Gly Ser Ser Val Lys Val Ser Cys Lys Ala Ser Gly Tyr Thr Phe Thr
        35                  40                  45

Thr Tyr Tyr Leu His Trp Val Arg Gln Ala Pro Gly Gln Gly Leu Glu
    50                  55                  60

Trp Met Gly Trp Ile Tyr Pro Gly Asn Gly His Ala Gln Tyr Asn Glu
65                  70                  75                  80

Lys Phe Lys Gly Arg Val Thr Ile Thr Ala Asp Lys Ser Thr Ser Thr
                85                  90                  95

Ala Tyr Met Glu Leu Ser Ser Leu Arg Ser Glu Asp Thr Ala Val Tyr
            100                 105                 110

Tyr Cys Ala Arg Ser Trp Glu Gly Phe Pro Tyr Trp Gly Gln Gly Thr
        115                 120                 125

Thr Val Thr Val Ser Ser Gly Gly Gly Gly Ser Gly Gly Gly Gly Ser
130                 135                 140
```

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Lys Ala Ser Gln Asn Val Gly Ile Asn Val Ala Trp Tyr Gln Gln
            180                 185                 190

Lys Pro Gly Lys Ala Pro Lys Ser Leu Ile Ser Ser Ala Ser Tyr Arg
        195                 200                 205

Tyr Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Phe Cys Gln Gln Tyr Asp Thr Tyr Pro Phe Thr Phe Gly Gln Gly Thr
                245                 250                 255

Lys Val Glu Ile Lys Asp Asp Asp Lys Ser Phe Leu Glu Gln Lys
            260                 265                 270

Leu Ile Ser Glu Glu Asp Leu Asn Ser Ala Val Asp His His His
        275                 280                 285

His His
    290

<210> SEQ ID NO 139
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Val Lys Leu Thr Val Ser Gln Gly Gln Pro Val Lys Leu Asn Cys Ser
1               5                   10                  15

Val Glu Gly Glu Glu Pro Asp Ile Gln Trp Val Lys Asp Gly Ala Val
            20                  25                  30

Val

<210> SEQ ID NO 140
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Val Leu Gln Ser Val Ala Gly Gln Thr Leu Thr Val Arg Cys Gln
1               5                   10                  15

Tyr Pro Pro Thr Gly Ser Leu Tyr Glu Lys Lys Gly Trp Cys Lys Glu
            20                  25                  30

Ala Ser Ala Leu Val Cys Ile Arg Leu Val Thr Ser
        35                  40

<210> SEQ ID NO 141
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Leu Lys Ile Gln Ala Tyr Phe Asn Glu Thr Ala Asp Leu Pro Cys Gln
1               5                   10                  15

Ala Asn Ser Gln Asn Gln Ser Leu Ser Glu Leu Val Val Phe Trp Gln
            20                  25                  30

Asp Gln Glu Asn Leu Val Leu Asn Glu Val
        35                  40

<210> SEQ ID NO 142
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Val Val Arg Val Pro Thr Ala Thr Leu Val Arg Val Val Gly Thr Glu
1               5                   10                  15

Leu Val Ile Pro Cys Asn Val Ser Asp Tyr Asp Gly Pro Ser Glu Gln
            20                  25                  30

Asn Phe Asp Trp Ser Phe Ser Ser Leu Gly Ser Ser Phe Val Glu Leu
        35                  40                  45

Ala Ser Thr
    50

<210> SEQ ID NO 143
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Leu Thr Gln Gln Asp Gly Gly Met Ser Val Ala Glu Gly Gln Ala
1               5                   10                  15

Leu Leu Leu Pro Cys Gly Ala Thr Leu Gly Gly Pro Asn Leu Ser Val
            20                  25                  30

Val Trp Val Ser Pro Arg Gln Glu Asp Leu Val Ala
        35                  40

<210> SEQ ID NO 144
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Leu Arg Val Ser Pro Lys Asn Pro Arg Val Pro Lys Ser His Thr
1               5                   10                  15

Leu Glu Leu His Cys Glu Ser Gln Cys Asp Ser His Leu Lys Tyr Ser
            20                  25                  30

Leu Lys Leu Ser Trp Ser Lys Asp Gly Glu Ala Phe Glu
        35                  40                  45

<210> SEQ ID NO 145
<211> LENGTH: 44
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 145

Val Val Pro Thr Val His Arg Asn Val Thr Val Ser Arg Gly Glu Pro
1               5                   10                  15

Val Thr Leu Asn Cys Ser Ile Asn Met Thr Asn Ile Thr Gln Ile Ser
            20                  25                  30

Trp Arg Lys Asp Thr Leu Ile Phe Val Tyr Leu Ala
        35                  40

<210> SEQ ID NO 146
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

His Gln Gln Gln Ile Gly Val Glu Gly Lys Glu Val Ile Leu Asn Cys
1               5                   10                  15

Lys Thr His Asp Lys Asp Val Thr Trp Lys Tyr Lys Tyr Asp Thr Gly
            20                  25                  30

Ser Ala Ile Ile Ile Ile Gln
        35

<210> SEQ ID NO 147
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Val Ala Ser Gln Gly Gly His Val Glu Ser Val Tyr Leu Tyr Gly Thr
1               5                   10                  15

Val Glu Leu Pro Cys Glu Phe Pro Phe Val Thr Gly Pro Gln Asp Leu
            20                  25                  30

Val Met Thr Trp Leu Lys Val Val Gln Asp Ser Glu Asn Val Val Val
        35                  40                  45

His Ser Tyr
        50

<210> SEQ ID NO 148
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Ile Thr Ala Pro Lys Asp Leu Tyr Val Val Glu Tyr Gly Ser Asn
1               5                   10                  15

Val Thr Met Glu Cys Arg Phe Pro Val Glu Arg Glu Asp Leu Leu Ala
            20                  25                  30

Leu Val Val Tyr Trp Glu Lys Glu Asp Glu Gln Val Ile Gln Phe Val
        35                  40                  45

Ala Gly Glu
```

```
<210> SEQ ID NO 149
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Lys Ile Glu Ala Pro Val Asn Val Ile Val Gln Arg Gly Leu Cys Val
1               5                   10                  15

Leu Ile Pro Cys Asn Phe Thr Val Gly Pro Lys Tyr Asn Leu Thr Lys
            20                  25                  30

Asp Ala Ile Gly Ile Trp Tyr Lys Gly His Pro Asn Asp Pro Val Ala
        35                  40                  45

Ala Ser
    50

<210> SEQ ID NO 150
<211> LENGTH: 49
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Gly Ala Val Pro Glu Glu Leu His Lys His Pro Gly Gln Thr Leu
1               5                   10                  15

Leu Leu Gln Cys Gln Tyr Ser Pro Lys Arg Gly Pro Tyr Gln Pro Lys
            20                  25                  30

Ser Trp Cys Gln Gln Thr Ser Pro Ser Arg Cys Thr Leu Leu Val Thr
        35                  40                  45

Ser

<210> SEQ ID NO 151
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ser Leu Ser Asp Ser Val Ser Ser Ala Val Leu Gly Ser Ser Ala Lys
1               5                   10                  15

Leu Ile Cys Gln Phe Thr Pro Val Val Asp Ala Lys Asn Val Glu Ile
            20                  25                  30

Arg Trp Phe Thr Arg Ser Phe Arg Pro Tyr Val His Gln Tyr
        35                  40                  45

<210> SEQ ID NO 152
<211> LENGTH: 49
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Val Gly Thr Gln Arg Pro Ile Glu Leu His Leu Gly Glu Leu Arg Gly
```

```
                1               5                   10                  15
Ser Ile Thr Ile Pro Cys Pro Pro Gly Asp Ser Trp Gly Gly Thr Arg
                20                  25                  30

Arg Leu Trp Cys Arg Val Gly Arg Ser Arg Cys Ile Leu Ile Ala Asp
            35                  40                  45

Thr

<210> SEQ ID NO 153
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Leu Val Pro Val Pro Asn Val Thr Val Ser Pro Gly Glu Thr Ala
1               5                   10                  15

Ile Leu Ser Cys Leu Val Leu Ser Glu Ala Pro Tyr Asn Leu Thr Trp
            20                  25                  30

Val Arg Asp Trp Arg Val Leu
        35

<210> SEQ ID NO 154
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Met Val Glu Gln Met Asp Asn Lys Thr Val Val Ser Gly Lys Pro Val
1               5                   10                  15

Thr Phe Leu Cys Asn Tyr Ile Leu Ser Met Arg Val Arg Gln Val Leu
            20                  25                  30

Trp Lys Lys Thr Ala Glu Gln Gly Asp Thr Ala Ile Val Ala Ser
        35                  40                  45

<210> SEQ ID NO 155
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Gln Met Val Ser Glu Pro Gly Lys Asn Ile Thr Leu Thr Cys Glu
1               5                   10                  15

Pro Arg Glu Asn His Leu Leu Glu Glu Val Ser Trp Glu Lys Ile Gln
            20                  25                  30

Pro Gln Gln Ile Asp Leu Leu Ile Ser Cys
        35                  40

<210> SEQ ID NO 156
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<221> NAME/KEY: MOD_RES
<222> LOCATION: (6)..(10)
<223> OTHER INFORMATION: Region may or may not be present
<220> FEATURE:
<221> NAME/KEY: MOD_RES
<222> LOCATION: (11)..(15)
<223> OTHER INFORMATION: Region may or may not be present
<220> FEATURE:
<221> NAME/KEY: MOD_RES
<222> LOCATION: (16)..(20)
<223> OTHER INFORMATION: Region may or may not be present
<220> FEATURE:
<221> NAME/KEY: MOD_RES
<222> LOCATION: (21)..(25)
<223> OTHER INFORMATION: Region may or may not be present
<220> FEATURE:
<221> NAME/KEY: MOD_RES
<222> LOCATION: (26)..(30)
<223> OTHER INFORMATION: Region may or may not be present

<400> SEQUENCE: 156

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 157
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(11)
<223> OTHER INFORMATION: Region may or may not be present
<220> FEATURE:
<221> NAME/KEY: MOD_RES
<222> LOCATION: (12)..(16)
<223> OTHER INFORMATION: Region may or may not be present
<220> FEATURE:
<221> NAME/KEY: MOD_RES
<222> LOCATION: (17)..(21)
<223> OTHER INFORMATION: Region may or may not be present
<220> FEATURE:
<221> NAME/KEY: MOD_RES
<222> LOCATION: (22)..(26)
<223> OTHER INFORMATION: Region may or may not be present
<220> FEATURE:
<221> NAME/KEY: MOD_RES
<222> LOCATION: (27)..(31)
<223> OTHER INFORMATION: Region may or may not be present

<400> SEQUENCE: 157

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

<210> SEQ ID NO 158
<211> LENGTH: 4
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: MOD_RES
<222> LOCATION: (1)
<223> OTHER INFORMATION: Suc-beta-Ala

<400> SEQUENCE: 158

```
Ala Leu Ala Leu
1

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 159

His His His His His
1               5

<210> SEQ ID NO 160
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(20)
<223> OTHER INFORMATION: Region may or may not be present
<220> FEATURE:
<221> NAME/KEY: MOD_RES
<222> LOCATION: (21)..(25)
<223> OTHER INFORMATION: Region may or may not be present

<400> SEQUENCE: 160

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 161
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Gly Gly Gly
1
```

STABILIZED POLYPEPTIDE COMPOSITIONS

RELATED APPLICATIONS

This application is a continuation of U.S. patent application Ser. No. 11/725,970, filed on Mar. 19, 2007, which claims the benefit of priority to the following U.S. provisional patent applications, each of which is hereby incorporated by reference in its entirety for all purposes:
1) U.S. provisional patent application No. 60/783,622, filed on Mar. 17, 2006, entitled "STABILIZED POLYPEPTIDES AND METHODS FOR EVALUATING AND INCREASING THE STABILITY OF SAME";
2) U.S. provisional patent application No. 60/812,688, filed on Jun. 9, 2006, entitled "STABILIZED POLYPEPTIDES AND METHODS FOR EVALUATING AND INCREASING THE STABILITY OF SAME";
3) U.S. provisional patent application No. 60/873,802, filed on Dec. 8, 2006, entitled "METHODS FOR EVALUATING AND ENHANCING BIOPHYSICAL PROPERTIES OF POLYPEPTIDES"; and
4) U.S. provisional patent application No. 60/873,996, filed on Dec. 8, 2006, entitled "STABILIZED POLYPEPTIDE COMPOSITIONS".

The contents of any patents, patent applications, and references cited throughout this specification are hereby incorporated by reference in their entireties.

BACKGROUND OF THE INVENTION

Protein stability is now recognized as a central issue for the development and scale up of proteins, e.g, antibody molecules. The heavy and light chain variable domain sequences of antibodies are under selective pressure and can vary significantly in sequence from one antibody to another (Wu and Kabat, 1970). There are a large number of functional germline variable heavy (~40; Tomlinson et al., 1992; Tomlinson et al., 1994; Matsuda and Honjo, 1996), variable kappa (~40; Meindl et al., 1989; Cox et al., 1994; Barbie and Lefranc, 1998) and variable lambda (~30; Williams et al., 1996; Kawasaki, et al., 1997) genes embedded within the human genome. The ability of the immune system to create many combinations of heavy chain and light chain variable domain germlines is one mechanism for creating antibody diversity (Edelman, 1959; Frañek, 1961). Additional diversity is derived by the insertion of a variable connecting peptide region, the J-connecting peptide (plus D-connecting peptide for heavy chains), between the variable domains and the constant domains (Leder, 1982). Subsequent to germline antibody selection against a specific antigen, B-cells expressing a single antibody with selected variable domain germlines and (D-)J-connecting peptides undergo the process of hypersomatic mutation within the variable heavy and light chain domains to increase antibody affinity towards the antigen (Leder, 1982; Tomlinson et al., 1996). Hypersomatic insertions or deletions within variable domains are also commonly observed, although at a much lower frequency than hypersomatic mutation (de Wildt et al., 1999). Thus, a mature antibody selected against a particular antigen will have highly unique variable domain sequences which are not necessarily optimized for stability.

Poor stability can affect the ability of an antibody or antibody domain to fold properly when expressed in various cellular systems, e.g., in bacterial or mammalian expression systems. Misfolding or poor stability can also result in fractional populations of non-functional material (Martsev et al., 1998) and/or antibodies with the tendency to form large soluble aggregates which are potentially dangerous or immunogenic when used therapeutically. Other stability problems include impeded refolding, degradation, impaired avidity, aggregation, or loss of activity following storage.

Stability problems are not limited to naturally occurring antibodies, but may occur in engineered antigen binding molecules as well, such as recombinant antibody libraries (Hoogenboom, 2005), antibody fragments (Holt et al., 2003; Todorovska et al., 2001; Worn and Plückthun, 2001; Reiter and Pastan, 1996) and engineered or humanized therapeutic antibodies for manufacturing and clinical purposes (Ewert et al., 2004; Carter and Merchant, 1997). In addition, multivalent forms of antibodies, such as bispecific molecules may have stability problems. While bispecific antibodies are desirable because of their therapeutic utility in humans, their production is unpredictable. For example, bispecific antibodies may result in substantial decrease in thermal stability, product yield, or in the formation of low molecular weight aggregates.

Unnatural changes to the $V_H$ and $V_L$ domains may also arise when humanizing rodent antibodies. Humanization is generally performed by grafting rodent complementarity determining regions (CDRs) onto the most similar human germline variable domain (Hurle and Gross, 1994). The germlines chosen for humanization may not be used with great frequency by the immune system and changes within the human frameworks are often necessary to achieve adequate antigen binding.

Unstable proteins suffer from many problems, including one or more of: unsuitability for scale-up production in bioreactors (e.g., because of low yield, significant levels of unwanted byproducts such as unassembled product, and/or aggregated material), difficulties in protein purification, and unsuitability for pharmaceutical preparation and use (e.g., owing to significant levels of breakdown product, poor product quality, and/or unfavorable pharmacokinetic properties). Instability within the variable domains of antibodies, Fabs, Fvs, or single-chain Fvs (scFvs) may result in many of these problems. scFv constructs in particular have demonstrated problems with stability, solubility, expression, aggregation, breakdown products, and overall manufacturability in both bacterial and in mammalian expression systems (see Worn and Pluckthun, 2001). Additionally, incorporation of scFv molecules into otherwise stable recombinant antibody products often imparts these generally undesirable traits to the new recombinant design.

Accordingly, there is a need for improved methods of predicting the stability of proteins, such as antibodies, and for improved, stable antigen binding molecules that are suitable for scalable production. There is also a need for improved methods that allow for scalable production of a population of stable antigen binding molecules that are suitable for pharmaceutical applications.

SUMMARY OF THE INVENTION

The invention is based, at least in part, on the development of improved polypeptide compositions, e.g. improved binding molecules, comprising or consisting of scFv molecules with improved stability and methods for making the same.

In one aspect, the invention pertains to a population of stabilized scFv molecules, wherein the stabilized scFv molecules comprise
i) a scFv linker interposed between a $V_H$ domain and a $V_L$ domain, wherein the $V_H$ and $V_L$ domains are linked by a disulfide bond between an amino acid in the $V_H$ domain and an amino acid in the $V_L$ domain, and wherein the $V_H$ and $V_L$ domains of the scFv molecules have Tm values of greater than 55° C.; or ii) a scFv linker interposed between a $V_H$ domain and a $V_L$ domain, wherein the $V_H$ and $V_L$ domains are linked by a disulfide bond between an amino acid in the $V_H$ and an amino acid in the $V_L$ domain, and wherein scFv molecules have a $T_{50}$ of greater than 49° C.

In another aspect, the invention pertains to stabilized scFv molecule wherein the stabilized scFv molecule comprises
a. a scFv linker having the amino acid sequence $(Gly_4Ser)_n$ interposed between a $V_H$ domain and a $V_L$ domain, wherein the $V_H$ and $V_L$ domains are linked by a disulfide bond between $V_H$ amino acid 44 and $V_L$ amino acid 100;
ii) a $V_H$ domain and a $V_L$ domain wherein the molecule has at least one substitution selected from a group consisting of:
a) substitution of an amino acid at Kabat position 13 of VH;
b) substitution of an amino acid at Kabat position 16 of VH;
c) substitution of an amino acid at Kabat position 46 of VL;
d) substitution of an amino acid at Kabat position 49 of VL;
e) substitution of an amino acid at Kabat position 50 of VL;
f) substitution of amino acids at Kabat positions 49 and 50 of VL;
g) substitution of amino acid at Kabat position 101 of VH;
h) substitution of amino acid at Kabat position 20 of VH;
i) substitution of amino acid at Kabat position 48 of VH;
j) substitution of amino acid at Kabat position 3 of VL;
k) substitution of amino acid at Kabat position 55 of VH;
l) substitution of amino acid at Kabat position 67 of VH;
m) substitution of amino acid at Kabat position 6 of VH;
n) substitution of amino acid at Kabat position 32 of VH;
o) substitution of amino acid at Kabat position 49 of VH;
p) substitution of amino acid at Kabat position 43 of VH;
q) substitution of amino acid at Kabat position 72 of VH;
r) substitution of amino acid at Kabat position 79 of VH;
s) substitution of amino acid at Kabat position 50 of VL;
t) substitution of amino acid at Kabat position 75 of VL;
u) substitution of amino acid at Kabat position 80 of VL;
v) substitution of amino acid at Kabat position 83 of VL; or
iii) a $V_H$ domain and a $V_L$ domain with a stabilized interface between VH and VL of the scFv wherein the molecule has at least one substitution at an amino acid position directly within the interface and/or at an amino acid position that scaffolds the interaction between VH and VL, wherein the at least one amino acid position is selected from a group consisting of: 47H, 37H, 45H, 46H, 51H, 59H, 109H, 14H, 26H, 27H, 40H, 69H, 103H, 29H, 38H, 44H, 49H, 55H, 63H, 54H, 68H, 72H, 74H, 79H, 82bH, 8H, 32H, 39H, 41H, 62H, 85H, 91H, 24H, 60H, 37L, 36L, 44L, 59L, 57L, 64L, 46L, 48L, 63L, 67L, 68L, 39L, 45L, 47L, 54L, 56L, 79L, 85L, 98L, 58L, 74L, 77L, 83L, 89L, and 104L, according to Kabat numbering, and wherein the stabilized scFv molecule has a $T_{50}$ greater than that of a scFv molecule lacking the substitution.

In another aspect, the invention pertains to a stabilized scFv molecule comprising a $(Gly_4Ser)_4$ scFv linker interposed between a $V_H$ domain and a $V_L$ domain, wherein the $V_H$ and $V_L$ domains are linked by a disulfide bond between an amino acid in the $V_H$ and an amino acid in the $V_L$ domain.

In another embodiment, the invention pertains to a stabilized scFv molecule comprising a $V_H$ domain and a $V_L$ domain wherein the molecule has at least one set of substitutions selected from the group consisting of:
 a) a substitution of an amino acid at Kabat position 16 of VH, e.g., with a glutamate or glutamine and a substitution of an amino acid at Kabat position 46 of VL, e.g., with a lysine;
 b) a substitution of an amino acid at Kabat position 16 of VH, e.g., with a glutamate or glutamine; a substitution of an amino acid at Kabat position 46 of VL, e.g., with a lysine; and a substitution of an amino acid at Kabat position 55 of VH, e.g., with a glycine; and
 c) a substitution of an amino acid at Kabat position 16 of VH, e.g., with a glutamate or glutamine; a substitution of an amino acid at Kabat position 46 of VL, e.g., with a lysine; a substitution of an amino acid at Kabat position 55 of VH, e.g., with a glycine; and substitution of an amino acid at Kabat position 101 of VH, e.g., with an aspartic acid.

In another embodiment, the stabilized scFv molecule has a stability equivalent to that of a conventional Fab fragment under conditions of thermal challenge.

In one embodiment, the stability is assessed by measuring the ability to bind to a target molecule.

In one embodiment, the scFv molecule comprises an amino acid sequence encoded by a nucleotide sequence selected from the group consisting of SEQ ID NOs:9, 14, 16, and 18.

In one embodiment, the scFv molecule comprises an amino acid sequence selected from the group consisting of SEQ ID NOs:10, 15, 17, and 19.

In another embodiment, the invention pertains to a fusion protein comprising a stabilized scFv molecule.

In one embodiment, the fusion protein comprises at least two antigen binding sites.

In another aspect, the invention pertains to a population of stabilized multivalent antigen binding molecules, wherein the stabilized binding molecules comprise at least one stabilized scFv molecule comprising a scFv linker interposed between a $V_H$ domain and a $V_L$ domain, wherein the $V_H$ and $V_L$ domains are linked by a disulfide bond between an amino acid in the $V_H$ and an amino acid in the $V_L$ domain, and wherein the population of stabilized binding molecules comprise monomeric, soluble proteins of which not more than 10% is present in aggregated form.

In one embodiment, the stabilized multivalent antigen binding molecules are expressed in CHO or NS0 cells.

In another aspect, the invention pertains to a population of stabilized multivalent antigen binding molecules, wherein each multivalent antigen binding molecule comprises
i) at least one scFv molecule comprising a scFv linker interposed between a $V_H$ domain and a $V_L$ domain, wherein the $V_H$ and $V_L$ domains are linked by a disulfide bond between an amino acid in the $V_H$ and an amino acid in the $V_L$ domain, and wherein the $V_H$ and $V_L$ domains of the at least one scFv molecule have a Tm of greater than 55° C.; or
ii) at least one scFv molecule comprising a scFv linker interposed between a $V_H$ domain and a $V_L$ domain, wherein the $V_H$ and $V_L$ domains are linked by a disulfide bond between an amino acid in the $V_H$ and an amino acid in the $V_L$ domain, and wherein the at least one scFv molecule of the multivalent antigen binding molecule has a $T_{50}$ of greater than 49° C.

In another embodiment, the invention pertains to a stabilized multivalent antigen binding molecule comprising
i) at least one stabilized scFv molecule, wherein the stabilized scFv molecule comprises a $(Gly_4Ser)_n$ scFv linker interposed between a $V_H$ domain and a $V_L$ domain and wherein the $V_H$ and $V_L$ domains are linked by a disulfide bond;
ii) at least one stabilized scFv molecule comprising a scFv linker having the amino acid sequence $(Gly_4Ser)_n$ interposed between a $V_H$ domain and a $V_L$ domain, wherein the $V_H$ and $V_L$ domains are linked by a disulfide bond between $V_H$ amino acid 44 and $V_L$ amino acid 100;
iii) at least one stabilized scFv molecule, wherein the stabilized scFv molecule comprises at least one substitution selected from a group consisting of:
 a) substitution of an amino acid at Kabat position 13 of VH;
 b) substitution of an amino acid at Kabat position 16 of VH;

c) substitution of an amino acid at Kabat position 46 of VL;
d) substitution of an amino acid at Kabat position 49 of VL;
e) substitution of an amino acid at Kabat position 50 of VL;
f) substitution of amino acids at Kabat positions 49 and 50 of VL;
g) substitution of amino acid at Kabat position 101 of VH;
h) substitution of amino acid at Kabat position 20 of VH;
i) substitution of amino acid at Kabat position 48 of VH;
j) substitution of amino acid at Kabat position 3 of VL;
k) substitution of amino acid at Kabat position 55 of VH;
l) substitution of amino acid at Kabat position 67 of VH;
m) substitution of amino acid at Kabat position 6 of VH;
n) substitution of amino acid at Kabat position 32 of VH;
o) substitution of amino acid at Kabat position 49 of VH;
p) substitution of amino acid at Kabat position 43 of VH;
q) substitution of amino acid at Kabat position 72 of VH;
r) substitution of amino acid at Kabat position 79 of VH;
s) substitution of amino acid at Kabat position 50 of VL;
t) substitution of amino acid at Kabat position 75 of VL;
u) substitution of amino acid at Kabat position 80 of VH;
v) substitution of amino acid at Kabat position 83 of VH; or iv) a $V_H$ domain and a $V_L$ domain with a stabilized interface between VH and VL of the scFv wherein the molecule has at least one substitution at an amino acid position directly within the interface and/or at an amino acid position that scaffolds the interaction between VH and VL, wherein the at least one amino acid position is selected from a group consisting of: 47H, 37H, 45H, 46H, 51H, 59H, 109H, 14H, 26H, 27H, 40H, 69H, 103H, 29H, 38H, 44H, 49H, 55H, 63H, 54H, 68H, 72H, 74H, 79H, 82bH, 8H, 32H, 39H, 41H, 62H, 85H, 91H, 24H, 60H, 37L, 36L, 44L, 59L, 57L, 64L, 46L, 48L, 63L, 67L, 68L, 39L, 45L, 47L, 54L, 56L, 79L, 85L, 98L, 58L, 74L, 77L, 83L, 89L, and 104L, according to Kabat numbering, In another aspect, the invention pertains to a stabilized multivalent antigen binding molecule comprising at least one stabilized scFv molecule comprising a (Gly$_4$Ser)$_4$ scFv linker interposed between a $V_H$ domain and a $V_L$ domain, wherein the $V_H$ and $V_L$ domains are linked by a disulfide bond between an amino acid in the $V_H$ and an amino acid in the $V_L$ domain.

ii) at least one stabilized scFv molecule comprising a scFv linker having the amino acid sequence (Gly$_4$Ser)$_n$ interposed between a $V_H$ domain and a $V_L$ domain, wherein the $V_H$ and $V_L$ domains are linked by a disulfide bond between $V_H$ amino acid 44 and $V_L$ amino acid 100; or iii) at least one stabilized scFv molecule, wherein the stabilized scFv molecule comprises at least one substitution selected from a group consisting of:
a) substitution of an amino acid (e.g., glutamine) at Kabat position 3 of VL, e.g., with an alanine, a serine, a valine, an aspartic acid, or a glycine;
b) substitution of an amino acid (e.g., serine) at Kabat position 46 of VL, e.g., with leucine;
c) substitution of an amino acid (e.g., serine) at Kabat position 49 of VL, e.g., with tyrosine or serine;
d) substitution of an amino acid (e.g., serine or valine) at Kabat position 50 of VL, e.g., with serine, threonine, and arginine, aspartic acid, glycine, or lysine;
e) substitution of amino acids (e.g., serine) at Kabat position 49 and (e.g., serine) at Kabat position 50 of VL, respectively with tyrosine and serine; tyrosine and threonine; tyrosine and arginine; tyrosine and glysine; serine and arginine; or serine and lysine;
f) substitution of an amino acid (e.g., valine) at Kabat position 75 of VL, e.g., with isoleucine;
g) substitution of an amino acid (e.g., proline) at Kabat position 80 of VL, e.g., with serine or glycine;
h) substitution of an amino acid (e.g., phenylalanine) at Kabat position 83 of VL, e.g., with serine, alanine, glycine, or threonine;
i) substitution of an amino acid (e.g., glutamic acid) at Kabat position 6 of VH, e.g., with glutamine;
j) substitution of an amino acid (e.g., lysine) at Kabat position 13 of VH, e.g., with glutamate;
k) substitution of an amino acid (e.g., serine) at Kabat position 16 of VH, e.g., with glutamate or glutamine;
l) substitution of an amino acid (e.g., valine) at Kabat position 20 of VH, e.g., with an isoleucine;
m) substitution of an amino acid (e.g., asparagine) at Kabat position 32 of VH, e.g., with serine;
n) substitution of an amino acid (e.g., glutamine) at Kabat position 43 of VH, e.g, with lysine or arginine;
o) substitution of an amino acid (e.g., methionine) at Kabat position 48 of VH, e.g., with an isoleucine or a glycine;
p) substitution of an amino acid (e.g., serine) at Kabat position 49 of VH, e.g, with glycine or alanine;
q) substitution of an amino acid (e.g., valine) at Kabat position 55 of VH, e.g., with a glycine;
r) substitution of an amino acid (e.g., valine) at Kabat position 67 of VH, e.g., with an isoleucine or a leucine;
s) substitution of an amino acid (e.g., glutamic acid) at Kabat position 72 of VH, e.g., with aspartate or asparagine;
t) substitution of an amino acid (e.g., phenylalanine) at Kabat position 79 of VH, e.g., with serine, valine, or tyrosine; and
u) substitution of an amino acid (e.g., proline) at Kabat position 101 of VH, e.g., with an aspartic acid.

In another aspect, the invention pertains to a multivalent antigen binding molecule comprising at least one stabilized scFv molecule, wherein the stabilized scFv molecule comprises at least one set of substitutions selected from the group consisting of:
a) a substitution of an amino acid at Kabat position 16 of VH, e.g., with a glutamate or glutamine and a substitution of an amino acid at Kabat position 46 of VL, e.g., with a lysine;
b) a substitution of an amino acid at Kabat position 16 of VH, e.g., with a glutamate or glutamine; a substitution of an amino acid at Kabat position 46 of VL, e.g., with a lysine; and a substitution of an amino acid at Kabat position 55 of VH, e.g., with a glycine; and
c) a substitution of an amino acid at Kabat position 16 of VH, e.g., with a glutamate or glutamine; a substitution of an amino acid at Kabat position 46 of VL, e.g., with a lysine; a substitution of an amino acid at Kabat position 55 of VH, e.g., with a glycine; and substitution of an amino acid at Kabat position 101 of VH, e.g., with an aspartic acid.

In one embodiment, at least one stabilized scFv molecule is genetically fused to an antibody. In another embodiment, two stabilized scFv molecules are genetically fused to an antibody.

In one embodiment, at least one stabilized scFv molecule is genetically fused to the carboxy terminus of the light or heavy chain of the antibody.

In one embodiment, at least one stabilized scFv molecule is genetically fused to the amino terminus of a light chain or heavy chain of the antibody.

In one embodiment, a binding molecule of the invention comprises at least one binding site that binds to a molecule preferentially expressed on cancer cells In one embodiment, the $V_H$ domain of a scFv molecule of the invention is derived from the BHA10 antibody.

In one embodiment, the $V_L$ domain of a scFv molecule of the invention is derived from the BHA10 antibody.

In one embodiment a binding molecule of the invention comprises at least one binding site that is specific for a molecule selected from the group consisting of HER1, HER3, CD80, CD86, PD-1, CTLA4, B7-H4, RON, CD200, CD4, BAFR, EGFR, IGFR, VEGFR, a member of the TNF family of receptors, a Tie receptor, MET, IGF1, IGF2, TNF, a TNF ligand, IL-6, TWEAK, Fn14, CD20, CD23, CRIPTO, HGF, alpha4beta1 integrin, alpha5beta1 integrin, alpha6beta4 integrin, and alphaVbeta6 integrin.

In one embodiment, a binding molecule of the invention comprises at least one binding site that binds to a molecule involved in modulating immune responses. In one embodiment, the molecule is an Fc receptor.

In one embodiment, a binding molecule of the invention comprises at least one binding site that binds to a molecule involved in modulating angiogenesis. In one embodiment, a binding molecule of the invention binds to VEGF or angiopoitin.

In one embodiment, a binding molecule of the invention comprises at least one binding site that binds to a neurological target.

In one embodiment, a binding molecule of the invention is multispecific. In one embodiment, a binding molecule of the invention is bispecific.

In another embodiment, a binding molecule of the invention binds to two members of the TNF receptor family. In one embodiment, a binding molecule of the invention binds to LTβR and Trail R2. In one embodiment, a binding molecule of the invention comprises a BHA10 scFv molecule genetically fused a 14A2 antibody.

In one embodiment, a binding molecule of the invention comprises a heavy chain having a sequence selected from the group consisting of SEQ ID NO:33, SEQ ID NO:35, SEQ ID NO:37, SEQ ID NO:47, SEQ ID NO:49, SEQ ID NO:51, SEQ ID NO:53, and SEQ ID NO:55.

In one embodiment, a binding molecule of the invention comprises a nucleotide sequence encoding a polypeptide of the molecule of any one of claims 4-8, 11, 12, and 18-22.

In one embodiment, the invention pertains to a nucleic acid molecule comprising a nucleotide sequence which encodes the stabilized scFv molecule or binding molecule comprising a stabilized scFv molecule of the invention.

In one embodiment, the nucleic acid molecule is in a vector. In another embodiment, the invention pertains to a host cell comprising such a vector.

In one embodiment, the host cell is a mammalian host cell, e.g., a CHO cell or an NS0 cell.

In one embodiment, the invention pertains to a population of binding molecules comprising scFv molecules, the population having at least 10% fewer aggregates relative to a host cell which expresses a population of binding molecules comprising conventional scFv molecules.

In one aspect, the invention pertains to a method of producing a stabilized binding molecule, comprising culturing a host cell under conditions such that the stabilized binding molecule is produced.

In one embodiment, at least 10 mg of the stabilized binding molecule is produced for every liter of the host cell culture medium and wherein not more than 10% of the binding molecule is present in aggregate form.

In one aspect, the invention pertains to a method of treating a subject that would benefit from treatment with a binding molecule of the invention comprising administering the binding molecule to the subject such that treatment occurs.

In one embodiment, the subject is suffering from a disease or disorder selected from the group consisting of cancer, an autoimmune disease or disorder, and a neurological disease or disorder.

In one aspect, the invention pertains to a method of stabilizing an scFv molecule comprising genetically fusing a $V_H$ domain and a $V_L$ domain using a $(Gly_4Ser)_n$ scFv linker and engineering the $V_H$ domain to comprise a cysteine at amino acid 44 and engineering the $V_L$ domain to comprise a cysteine at amino acid 100 to form a stabilized scFv molecule.

In one aspect, the invention pertains to a method of making a stabilized multivalent antibody comprising a stabilized scFv molecule, the method comprising genetically fusing a stabilized scFv molecule to the amino terminus or the carboxy terminus of a light or heavy chain of an antibody molecule.

In one embodiment, the invention pertains to a method of making a stabilized scFv molecule comprising substituting at least one amino acid in the VH/VL interface of the scFv molecule and/or at least one amino acid that scaffolds the VH/VL interface of the scFv molecule substitution(s) simultaneously improve the thermal stability of both the VH and VL domains of the scFv molecule as compared to a conventional scFv molecule.

In yet another embodiment, the invention pertains to a method of making a stabilized scFv molecule comprising substituting at least one amino acid in the VH domain or VL domain that covaries with two or more amino acids at the interface between the VH and VL domains.

In yet another embodiment, the invention pertains to a method of making a stabilized fusion protein comprising an scFv molecule comprising substituting at least one amino acid in the VH/VL interface of the scFv molecule and/or at least one amino acid in the VH/VL scaffold of the scFv molecule and genetically fusing the scFv molecule to a polypeptide to thereby make a stabilized fusion protein.

In yet another embodiment, the invention pertains to a method of improving the stability of a multivalent molecule comprising at least one scFv molecule, the method comprising introducing at least one stabilizing mutation into the at least one scFv molecule to thereby improve the stability of the multivalent molecule.

In yet another embodiment, the invention pertains to a method of improving the stability of an scFv molecule comprising introducing at least one stabilizing mutation into the scFv molecule to thereby improve the stability of an scFv molecule.

In yet another aspect, the invention pertains to a method for large scale manufacture of a stabilized fusion protein, the method comprising:

(a) conducting a thermal stability test of an scFv molecule to determine the thermal stability of a candidate scFv molecule;

(b) comparing the thermal stability of the candidate scFv molecule with a suitable control to identify stabilized scFv molecules having increased thermal stability relative to the control, (c) selecting the stabilized scFv molecules identified in step (b);

(d) genetically fusing at least one stabilized scFv molecule to a protein to form a stabilized fusion protein;

(e) transfecting a mammalian host cell with a nucleic acid molecule encoding the stabilized fusion protein, (f) culturing the host cell of step (f) under conditions such that the stabilized fusion protein is expressed;

wherein the stabilized fusion protein is expressed with not more than 10% protein aggregation when grown in 10L or more of culture medium.

In yet another aspect, the invention pertains to a method of determining the thermal stability of a protein fold from an immunoglobulin (Ig) superfamily polypeptide comprising a candidate sequence of amino acids, the method comprising the steps of:

a) providing an alignment of a curated reference set of sequences corresponding to an Ig fold of the polypeptide;

b) calculating covariation between amino acid residues of the sequences of the alignment to generate covariation data;

c) determining a sequence position specific covariation score for amino acid positions within the candidate sequence from covariations within the covariation data; and d) storing or outputting the amino acid position specific sequence covariation score as a measure of the stability of the polypeptide.

In one embodiment, the method comprises repeating at least steps c) and d) for a plurality of immunoglobulin (Ig) superfamily polypeptides. In yet another embodiment, the method further comprises the step of selecting from amongst the plurality of immunoglobulin (Ig) superfamily polypeptides an Ig superfamily polypeptide for production, based on the sequence position specific covariation scores of the candidate sequences.

In another embodiment, the method further comprises the step of producing the selected Ig superfamily polypeptide and preparing it for therapeutic use.

In another embodiment, the Ig superfamily polypeptide derived from a protein selected from the group consisting of an immunoglobulin or antigen-binding fragment thereof, an immunoglobulin receptor, a cell adhesion protein, an integrin, an allergen, a T-cell receptor, and a major histocompatibility complex (MHC).

In one embodiment, the Ig superfamily polypeptide is selected from the group consisting of a heavy chain variable region ($V_H$), a light chain variable region ($V_L$), and a single chain antibody (scFv).

In another embodiment, the Ig fold is selected from the group consisting of a V-class fold, an I-class fold, a C1-class fold, and a C2-class fold.

In one embodiment, the curated reference set or the alignment has a diversity of at least 50%.

In one embodiment, each sequence of the alignment has less than 90% identity with every other sequence of the alignment.

In another embodiment, at least one sequence is from a mammalian species and at least one sequence is from a non-mammalian species.

In one embodiment, residues of the candidate sequence are assigned positive position specific covariation scores for satisfying positive covariations found at corresponding positions in the alignment.

In one embodiment, the residues of the candidate sequence are assigned negative position specific covariation scores for satisfying negative covariations found at corresponding positions in the alignment.

In one embodiment, the positive covariation has a phi association coefficient ($\Phi$) of about +0.25 to about +1.0.

In one embodiment, the negative covariation has a phi association coefficient ($\Phi$) of about −0.25 to about −1.0.

In one embodiment, the alignment is selected from the group consisting of a structure-based sequence alignment, a sequence-based sequence alignment, and a structure-based structural alignment.

In one embodiment, the position specific covariation score is determined for all possible residue pairs at each residue position of the alignment.

In one embodiment, the alignment is obtained by (i) generating a Hidden Markov Model (HMM) from an initial alignment; (ii) acquiring additional sequences with the HMM; and (iii) aligning the additional sequences with the initial alignment.

In one aspect, the invention pertains to a computer program or computer program product or computer readable medium having a set of instructions executable by a processor which when executed cause the processor to perform a method of the invention.

In yet another embodiment, the invention pertains to a computer program or computer program product or computer readable medium suitable for use in an electronic device comprising data corresponding to the alignment of the method of the invention.

In yet another embodiment, the invention pertains to a computer program or computer program product or computer readable medium suitable for use in an electronic device comprising the covariation data of a method of the invention.

In one embodiment, the invention pertains to a device arranged to carry out the method of the invention.

In one aspect, the invention pertains to a system in a computing device, comprising:

(i) an initial sequence collection process;

(ii) a storage location capable of holding sequence data from the alignment of any one of claims 58-74;

(iii) an analysis facility, which programmatically analyses covariation between pairs of residues within the alignment to obtain covariation data;

(iv) an output device interfaced with said electronic device, said output device outputting said covariation data.

In one embodiment, the invention pertains to a medium in a computing device holding executable steps for carrying out a method comprising any of the steps of the method of the invention.

In yet another embodiment, the display of residue usage frequency data comprises a matrix comprising (i) contiguous residue positions corresponding to the polypeptide sequence; and (ii) residue usage frequencies for a residue type at each residue position.

In yet another embodiment, the residue usage frequency is symbolically depicted.

In one embodiment, all 20 natural amino acids, gaps, and ambiguous residues are represented. In one embodiment, residue use frequency is correlated with symbol size.

In one embodiment, residue use frequency is positively correlated with symbol size.

In one embodiment, (i) the residue positions are displayed in columns; and (ii) the residue usage frequencies are displayed in rows.

In another embodiment, covariation among the covariant residues is depicted by a network overlay.

In one aspect, the invention pertains to a graphical user interface comprising a graphical display of:

(i) a grid layout comprising a collection of residue usage frequency data for a reference set of polypeptide sequences; and (ii) a co variation overlay.

In one embodiment, the interface further comprises: (iii) a display of a sequence of interest.

In one aspect, the invention pertains to a method for producing an immunoglobulin (Ig) superfamily polypeptide with an improved biophysical property, said method comprising the steps of:

a) providing an alignment of a curated reference set of sequences corresponding to an Ig fold of the polypeptide;

b) calculating covariation between residues of the sequences of the alignment to identify covarying residues;

c) substituting a residue of the polypeptide that fails to satisfy a covariation with the covarying residue found at a corresponding position in the alignment.

In another embodiment, the biophysical property is selected from the group consisting of thermal stability, pH unfolding profile, stable removal of glycosylation, solubility, biochemical function, and combinations thereof.

In one embodiment, the biochemical function is selected from the group consisting of recognition of a protein target or a chemical moiety, which chemical moiety is selected from the group consisting of phosphate, methyl, acetyl, lipid, detergent, metal ion, halogen, RNA, DNA, oligonucleotide, and oligonucleoside.

In one embodiment, the Ig superfamily polypeptide is derived from a protein selected from the group consisting of an antibody or antigen-binding fragment thereof, an immunoglobulin receptor, a cell adhesion protein, an integrin, an allergen, a T-cell receptor, and a major histocompatibility complex (MHC) molecule.

In one embodiment, the Ig superfamily polypeptide is selected from the group consisting of a heavy chain variable region ($V_H$), a light chain variable region ($V_L$), and a single chain antibody (sFv).

In one embodiment, the Ig fold is selected from the group consisting of a V-class fold, an I-class fold, a C1-class fold, and a C2-class fold.

In another embodiment, the Ig superfamily polypeptide is a modified antibody selected from the group consisting of a domain antibody, a humanized antibody, a human antibody, a non-human monoclonal antibody, a chimeric antibody, a bispecific antibody, a scFv-containing antibody, and a domain-deleted antibody.

In one embodiment, the covarying residues are part of a structural feature selected from the group consisting of a disulfide bond, a salt bridge, a portion of a ligand binding pocket or surface, and a network of van Der Waals, hydrogen bond, and/or charge-charge interactions.

In another embodiment, the invention pertains to a method for producing an antibody or modified antibody with an improved stability, said method comprising the steps of:
a) providing a high-resolution structural model of a template antibody that is experimentally validated as stable;
b) using the structural model to identify a VH/VL interface and/or interface scaffolding residue in the template antibody;
c) using a homology model to identify a corresponding VH/VL interface residue of the antibody or modified antibody that is important for stabilizing the interface; and
d) substituting the corresponding VH/VL interface residue in the antibody or modified antibody with the interface residue from the template protein.

In one embodiment, the interface residue of the template protein buries at least 10 $Å^2$ of surface area in the interface.

In one embodiment, the modified antibody is selected from the group consisting of a domain antibody, a humanized antibody, a human antibody, a non-human monoclonal antibody, a chimeric antibody, a bispecific antibody, a scFv-containing antibody, and a domain-deleted antibody.

In another embodiment, the invention pertains to a polypeptide produced by the method of the invention.

In one embodiment, the polypeptide exhibits an improvement in a biophysical property selected from the group consisting of thermal stability, pH unfolding profile, stable removal of glycosylation, solubility, biochemical function, and combinations thereof.

In one embodiment, the biochemical function is ligand binding affinity or specificity.

In another aspect, the invention pertains to a method for producing a library comprising stabilized scFv molecules, the method comprising:
(a) providing a reference set of sequences corresponding to a variable domain sequence of a scFv molecule;
(b) identifying an amino acid within the variable domain which is absent or found at low frequencies at a corresponding position in the reference set; and
(c) combining this information with covariation data suggesting that modifying the amino acid identified with low frequency in the reference set may satisfy existing covariation restraints within the variable domain; and
(d) substituting the amino acid of step (b) with a candidate stabilizing amino acid to thereby produce a library comprising stabilized scFv molecules.

In one embodiment, the amino acid of step (b) has a consensus score of less than 0.5. In another embodiment, the amino acid of step (b) is present within less than 10% of the sequences in the reference set. In another embodiment, the amino acid of step (b) is a non-consensus residue.

In one embodiment, the candidate stabilizing amino acid is found at a corresponding position within the reference set.

In yet another embodiment, the candidate stabilizing amino acid is a consensus amino acid.

In one embodiment, the candidate stabilizing amino acid is identified by an analysis of a 3-D structure of the variable region sequence. In another embodiment, the stabilizing amino acid is identified by a side-chain repacking calculation.

In yet another aspect, the invention pertains to a method for producing a stabilized scFv molecule, the method comprising:
(a) providing a scFv library designed according to the method of claim 56,
(b) screening the scFv library with a thermal challenge assay to identify candidate scFv molecules,
(c) comparing the thermal stability of a candidate scFv molecule of the scFv library with a suitable control,
whereby an increase in thermal stability of a candidate scFv molecule relative to the control identifies the candidate scFv molecule as a stabilized scFv molecule.

In another embodiment, the invention pertains to a stabilized scFv molecule identified using a method of the invention or a fusion protein comprising a stabilized scFv molecule of the invention.

In another aspect, the invention pertains to a method for predicting the stability of a candidate protein comprising an amino acid sequence having candidate domain sequences, the method comprising:
(a) providing a reference set of amino acid sequences corresponding to a candidate domain sequence of the candidate protein;
(b) determining residue frequencies at individual amino acid positions within the test domain sequence to obtain a consensus score; and
(c) using the consensus score to predict the stability of the candidate protein,
wherein the consensus score is correlated with the stability of the candidate protein.

In another aspect, the invention pertains to a method for predicting the stability of a candidate protein, the method comprising:
(a) providing a reference set of sequences corresponding to a test domain sequence of the candidate protein;

(b) determining residue frequencies at individual amino acid positions within the test domain sequence to obtain a consensus score; and (c) using the consensus score to predict the stability of the candidate protein, wherein the consensus score is correlated with the stability of the candidate protein.

In another embodiment, the invention pertains to a method for predicting the stability of a candidate protein, the method comprising:

(a) providing a reference set of sequences corresponding to a test domain sequence of the candidate protein;

(b) determining residue frequencies at amino acid positions within the test domain sequence to obtain a consensus score;

(c) determining residue frequencies at corresponding amino acid positions within the sequences of the reference set to determine an average consensus score;

(d) comparing the consensus score with the average consensus score to determine a sequence score; and (e) using the sequence score to predict the stability of the candidate protein, wherein the consensus score is directly correlated with the stability of the candidate protein.

In yet another embodiment, the invention pertains to a method for predicting the stability of a candidate antibody or candidate modified antibody, the method comprising:

(a) providing a reference set of VH domain sequences corresponding to a test VH domain sequence of the candidate antibody or modified antibody;

(b) determining residue frequencies at amino acid positions within the test VH domain sequence to obtain a consensus score;

(c) determining residue frequencies at corresponding amino acid positions within the sequences of the reference set to determine an average consensus score;

(d) comparing the consensus score with the average consensus score to determine a sequence score; and (e) using the sequence score to predict the stability of the candidate antibody or modified antibody, wherein the consensus score is directly correlated with the stability of the candidate antibody or modified antibody.

In one embodiment, the reference set comprises protein sequences from proteins with the same class of protein fold as the candidate protein.

In another embodiment, the reference set comprises orthologous sequences.

In one embodiment, the reference set comprises human sequences, e.g., human VH sequences, e.g., of the same Kabat class.

In one embodiment, the reference set comprises human VH germline sequences.

In one embodiment, the test domain sequence is a portion of the domain sequence of the candidate protein.

In one embodiment, the consensus score is determined for each position of the test sequence to obtain a total consensus score, wherein the total consensus score is correlated with protein stability.

In another embodiment, the total consensus score is calculated using the formula:

$$\text{score} = \sum_i \frac{h_i(r)}{c_i(r)}$$

wherein:

$c_i(r)$ equals the consensus residue frequency at an amino acid position of the consensus sequence, $h_i(r)$ equals the test residue frequency of an amino acid position of the test sequence, and i equals the number of amino acid positions within the test sequence.

In one embodiment, the stability of the protein is determined by comparing the consensus score of the candidate protein with a consensus score of a suitable control.

In another embodiment, the stability of the protein is determined by comparing the consensus score of the candidate protein with the perfect consensus score of the candidate protein.

In yet another embodiment, stability is determined by comparing the sequence score of the candidate protein with a suitable control.

In another embodiment, stability is determined by comparing the sequence score of the candidate antibody or modified antibody with a suitable control.

In one embodiment, the protein is a multi-domain protein, and wherein the target domain sequence is derived from the least stable domain of the multi-domain protein.

In still another embodiment, the protein is a modified antibody selected from the group consisting of a camelid antibody, humanized antibody, a human antibody, a non-human monoclonal antibody, a chimeric antibody, a bispecific antibody, a scFv-containing antibody, and a domain-deleted antibody.

In another embodiment, the invention pertains to a method for selecting a candidate protein for expression, comprising determining the stability of the candidate protein using the method of the invention, wherein the candidate protein is selected for expression if its consensus score or sequence score is predictive of high stability.

In another embodiment, the invention pertains to a method for selecting a candidate protein for expression, comprising determining the stability of the candidate protein using the method of the invention, wherein the candidate protein is selected for expression if its sequence position specific covariation score is predictive of high stability.

In another embodiment, the invention pertains to a method for selecting an acceptor immunoglobulin variable region test sequence for use in the humanization of a donor antibody, the method comprising determining the stability of the candidate sequence using the method of the invention, wherein the candidate sequence is selected if its sequence score is predictive of high stability.

In yet another embodiment, the invention pertains to a method for selecting an acceptor immunoglobulin variable region test sequence for use in the humanization of a donor antibody, the method comprising determining the stability of the candidate sequence using the method of the invention, wherein the candidate sequence is selected if its position specific covariation score is predictive of high stability.

In another embodiment, the test sequence is a human germline sequence.

BRIEF DESCRIPTION OF THE DRAWINGS

FIG. 1A shows the DNA sequence (SEQ ID NO:3) encoding a conventional BHA10 scFv construct comprising a (Gly4Ser)3 linker (indicated in bold type). FIG. 1B shows the amino acid sequence (SEQ ID NO:4) of the conventional BHA10 scFv construct.

FIG. 2 depicts the results of differential scanning calorimetry (DSC) measurements with purified conventional Fab or scFv fragments of BHA10.

FIG. 3A depicts the DNA sequence (SEQ ID NO:9) encoding a stabilized VH44/VL100 disulfide-stabilized BHA10 scFv construct comprising a (Gly4Ser)$_3$ linker (indicated in bold type). FIG. 3B shows the amino acid sequence (SEQ ID NO:10) of the VH44/VL100 disulfide-stabilized BHA10 scFv construct. The cysteine residues forming the VH44/VL100 disulfide bond are indicated in bold and italicized type.

FIG. 4A depicts the DNA sequence (SEQ ID NO:14) encoding a stabilized BHA10 scFv comprising a (Gly$_4$Ser)$_4$ linker (indicated in bold type). FIG. 4B shows the amino acid sequence (SEQ ID NO:15) of the (Gly$_4$Ser)$_4$ BHA10 scFv construct. Annotation is the same as in FIG. 4A.

FIG. 5A depicts the DNA sequence (SEQ ID NO:16) encoding a BHA10 scFv comprising a (Gly$_4$Ser)$_5$ linker (indicated in bold type). FIG. 5B depicts the amino acid sequence (SEQ ID NO:17) of the (Gly$_4$Ser)$_5$ BHA10 scFv construct. Annotation is the same as in FIG. 5A.

FIG. 7A depicts the DNA sequence (SEQ ID NO:18) encoding a VH44/VL100 disulfide-stabilized BHA10 scFv comprising a (Gly$_4$Ser)$_4$ linker (indicated in bold type). FIG. 7B depicts the amino acid sequence (SEQ ID NO:19) of the VH44/VL100 disulfide+(Gly$_4$Ser)4-stabilized BHA10 scFv. Annotation is the same as in FIG. 7A. The cysteine residues forming the VH44/VL100 disulfide bond are indicated in bold and italicized type.

FIG. 11 depicts the results of residue frequency analysis of the BHA10 VH and VL domains. FIG. 11A lists BHA10 VH library positions for screening based on residue frequency analysis of IgG variable domain sequences. FIG. 11B lists BHA10 VL library positions for screening based on residue frequency analysis of IgG variable domain sequences.

FIG. 13 depicts exemplary stabilized LTβR/TRAIL-R2 bispecific antibodies ("Hercules" antibodies) of the invention. The Hercules antibodies are formed by the fusion of a stabilized BHA10 scFv molecule of the invention to an 14A2 IgG antibody. The scFv molecule may be fused to the C-terminus or N-terminus of the heavy chain (C-Hercules or N$_H$-Hercules) or to the N-terminus of the light chain (N$_L$-Hercules).

FIG. 15A depicts the DNA sequence (SEQ ID NO:28) of a chimeric 14A2 light chain comprising signal peptide (underlined). FIG. 15B shows the amino acid sequence (SEQ ID NO:29) of chimeric 14A2 light chain.

FIG. 16 depicts the DNA sequence (SEQ ID NO:30) of the heavy chain of a conventional BHA10 scFv N$_H$-Hercules.

FIG. 17 depicts the amino acid sequence (SEQ ID NO:31) of the heavy chain of a conventional BHA10 scFv N$_H$-Hercules.

FIG. 18 depicts the DNA sequence (SEQ ID NO:32) of the heavy chain of a BHA10 scFv (Gly$_4$Ser)$_4$ N$_H$-Hercules.

FIG. 19 depicts the amino acid sequence (SEQ ID NO:33) of the heavy chain of a BHA10 scFv (Gly$_4$Ser)$_4$ N$_H$-Hercules.

FIG. 20 depicts the DNA sequence (SEQ ID NO:34) of the heavy chain of a BHA10 scFv V$_H$44:V$_L$100 N-Hercules.

FIG. 21 depicts the amino acid sequence (SEQ ID NO:35) of the heavy chain of a BHA10 scFv V$_H$44:V$_L$100 N$_H$-Hercules.

FIG. 22 depicts the DNA sequence (SEQ ID NO:36) of the heavy chain of a BHA10 scFv V$_H$44:V$_L$100/(Gly$_4$Ser)$_4$N$_H$-Hercules.

FIG. 23 depicts the amino acid sequence (SEQ ID NO:37) of the heavy chain of a BHA10 scFv V$_H$44:V$_L$100/(Gly$_4$Ser)$_4$ N$_H$-Hercules.

FIG. 24 depicts the DNA sequence (SEQ ID NO:44) of the heavy chain of a conventional BHA10 scFv C-Hercules.

FIG. 25 depicts the amino acid sequence (SEQ ID NO:45) of the heavy chain of a conventional BHA10 scFv C-Hercules.

FIG. 26 depicts the DNA sequence (SEQ ID NO:46) of the heavy chain of a BHA10 scFv (Gly$_4$Ser)$_4$ C-Hercules.

FIG. 27 depicts the amino acid sequence (SEQ ID NO:47) of the heavy chain of a BHA10 scFv (Gly$_4$Ser)$_4$ C-Hercules.

FIG. 28 depicts the DNA sequence (SEQ ID NO:48) of the heavy chain of a BHA10 scFv V$_H$44:V$_L$100 C-Hercules.

FIG. 29 depicts the amino acid sequence (SEQ ID NO:49) of the heavy chain of a BHA10 scFv V$_H$44:V$_L$100 C-Hercules.

FIG. 30 depicts the DNA sequence (SEQ ID NO:50) of the heavy chain of a BHA10 scFv V$_H$44:V$_L$100/(Gly$_4$Ser)$_4$C-Hercules.

FIG. 31 depicts the amino acid sequence (SEQ ID NO:51) of the heavy chain of a BHA10 scFv V$_H$44:V$_L$100/(Gly$_4$Ser)$_4$ C-Hercules.

FIG. 33 depicts the results of an ELISA to evaluate the binding activity of the stabilized Hercules antibodies of the invention to LTβR_receptors.

FIG. 34 depicts the results of an ELISA to evaluate the binding activity of the stabilized Hercules antibodies of the invention to TRAIL R2 receptors.

FIG. 36 depicts the results of SDS-PAGE analysis of purified stabilized Hercules bispecific antibodies.

FIG. 41 depicts the effects of stabilized N- and C-Hercules bispecific and monospecific antibodies on tumor cell growth.

FIG. 50 depicts T50 curves of wild-type BHA10 scFv (closed circles) versus BHA10 scFVs containing the VL_S46L (FIG. 50A, open circles), VH_V55G (FIG. 50B, open circles), and VH P101D (open circles) (FIG. 50C) stabilizing mutations.

FIG. 56A) or C-terminal Hercules (XWU036; FIG. 56B) to TRAIL-R2 and LTβR receptors.

FIG. 61 depicts the heavy chain DNA sequence (SEQ ID NO:52) for C-Hercules BHA10 scFv $V_H$ S16E+$V_L$ S46L bispecific antibody.

FIG. 62 depicts the heavy chain amino acid sequence (SEQ ID NO:53) for C-Hercules BHA10 scFv $V_H$ S16E+$V_L$ S46L bispecific antibody.

FIG. 63 depicts the heavy chain DNA sequence (SEQ ID NO:54) for C-Hercules BHA10 scFv $V_H44$-$V_L100N_H$ S16E+$V_L$ S46L bispecific antibody.

FIG. 64 depicts the heavy chain amino acid sequence (SEQ ID NO:55) for C-Hercules BHA10 scFv $V_H44$-$V_L100$/$V_H$ S16E+$V_L$ S46L bispecific antibody.

FIG. 66 depicts SDS-PAGE gels of purified C-terminal Hercules with the $V_H$ S16E+$V_L$ S46L BHA10 scFv (FIG. 66A) and purified C-terminal Hercules with the $V_H44$:$V_L100$/$V_H$ S16E+$V_L$ S46L BHA10 scFv (FIG. 66B).

FIG. 72 depicts 2-dimensional plots comparing sequence scores for 18 BIIB antibodies with the corresponding Fab $T_M$s as measured by DSC.

FIG. 80 (SEQ ID NO:63) shows the single-stranded DNA sequence of heavy chain C-terminal tetravalent PRIMATIZED® p5E8 antibody comprising a conventional scFv.

FIG. 81 (SEQ ID NO:64) shows the amino acid sequence of heavy chain C-terminal tetravalent PRIMATIZED® p5E8 antibody comprising a conventional scFv.

FIG. 82A (SEQ ID NO:65) shows the single-stranded DNA sequence of PRIMATIZED® p5E8 light chain. Signal peptide sequence is shown as underlined. FIG. 82B (SEQ ID NO:66) shows the amino acid sequence of PRIMATIZED® p5E8 light chain.

FIG. 83A (SEQ ID NO:67) shows single-stranded DNA sequence of conventional PRIMATIZED® p5E8 (VL/VH) scFv. Signal peptide sequence is shown as underlined. FIG. 83B (SEQ ID NO:68) shows amino acid sequence of conventional PRIMATIZED® p5E8 (VL/VH) scFv.

FIG. 84A (SEQ ID NO:69) shows single-stranded DNA sequence of conventional PRIMATIZED® p5E8 (VH/VL) scFv. FIG. 84B (SEQ ID NO:70) shows amino acid sequence of conventional PRIMATIZED® p5E8 (VH/VL) scFv.

FIGS. 94A and 94B shows the amino acid sequences of the stabilized BHA10 scFVs containing the S46L(VL) stabilizing mutation (SEQ ID NO:137), and the V55G(VH) stabilizing mutation (SEQ ID NO:138). The stabilizing mutation is indicated by the boxed residue. The leader sequence, gly/ser connecting peptide, and CH1 domain are indicated by the underlined, bolded, and italicized residues, respectively.

DETAILED DESCRIPTION OF THE INVENTION

Figure 2A:
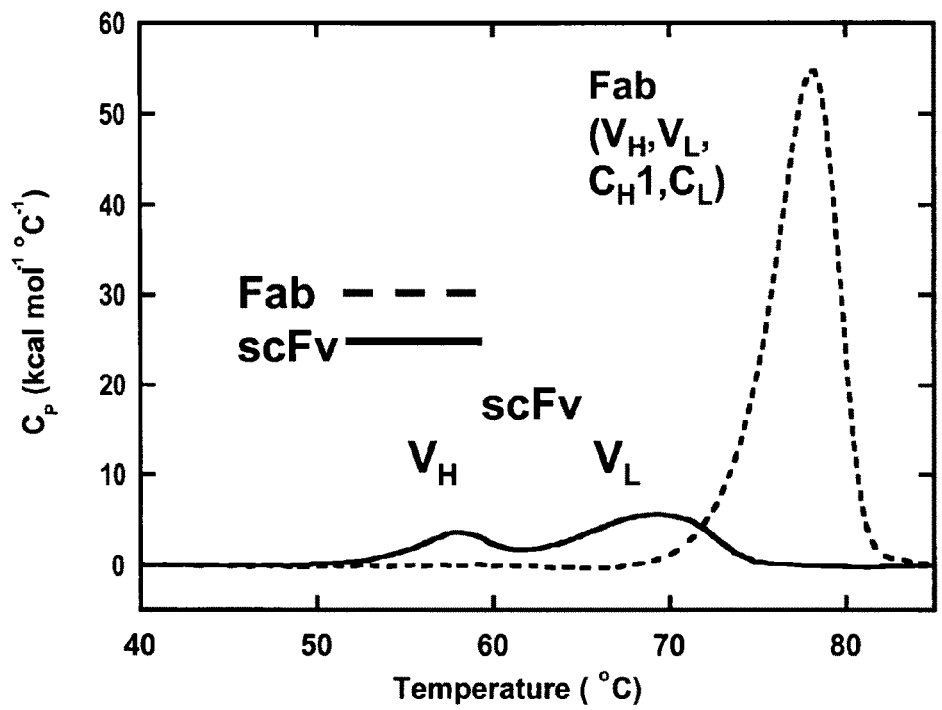
FIG. 2A depicts the results of a DSC study comparing the unfolding of conventional Fab and scFv fragments of BHA10.

The invention is based, at least in part, on the development of stabilized target binding molecules that consist of or comprise a stabilized scFv molecule and methods for making such stabilized binding molecules. In addition, the instant invention provides methods for designing stable proteins, such as antibody molecules.

The stabilized scFv molecules of the instant invention are especially useful in producing stable multispecific, e.g., bispecific molecules. The stabilized binding molecules of the invention, e.g., multispecific binding molecules can be stably expressed in culture, are suitable for large scale production, and are stable in vivo.

The invention is also based, at least in part, on the development of stabilized binding molecules that consist of or comprise a stabilized scFv molecule and methods for making such stabilized binding molecules. In addition, the instant invention provides methods for designing stable proteins and for predicting the stability of proteins, such as antibody molecules.

Before further description of the invention, for convenience, certain terms are described below:

I. DEFINITIONS

As used herein the term "scFv molecule" includes binding molecules which consist of one light chain variable domain (VL) or portion thereof, and one heavy chain variable domain (VH) or portion thereof, wherein each variable domain (or portion thereof) is derived from the same or different antibodies. scFv molecules preferably comprise an scFv linker interposed between the VH domain and the VL domain. scFv molecules are known in the art and are described, e.g., in U.S. Pat. No. 5,892,019, Ho et al. 1989. *Gene* 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

A "scFv linker" as used herein refers to a moiety interposed between the VL and VH domains of the scFv. scFv linkers preferably maintain the scFv molecule in a antigen binding conformation. In one embodiment, an scFv linker comprises or consists of an scFv linker peptide. In certain embodiments, an scFv linker peptide comprises or consists of a gly-ser connecting peptide. In other embodiments, an scFv linker comprises a disulfide bond.

As used herein, the term "gly-ser connecting peptide" refers to a peptide that consists of glycine and serine residues. An exemplary gly/ser connecting peptide comprises the amino acid sequence $(Gly_4Ser)_n$. In one embodiment, n=1. In one embodiment, n=2. In another embodiment, n=3. In a preferred embodiment, n=4, i.e., $(Gly_4Ser)_4$. In another embodiment, n=5. In yet another embodiment, n=6. Another exemplary gly/ser connecting peptide comprises the amino acid sequence $Ser(Gly_4Ser)_n$. In one embodiment, n=1. In one embodiment, n=2. In a preferred embodiment, n=3. In another embodiment, n=4. In another embodiment, n=5. In yet another embodiment, n=6.

As used herein the term "disulfide bond" refers to the covalent bond formed between two sulfur atoms. The amino acid cysteine comprises a thiol group that can form a disulfide bond or bridge with a second thiol group.

As used herein the term "conventional scFv molecule" refers to an scFv molecule which is not a stabilized scFv molecule. For example, a typical conventional scFv molecule lacks stabilizing mutations and comprises a VH and a VL domain linked by a $(G_4S)_3$ linker.

A "stabilized scFv molecule" of the invention is an scFv molecule comprising at least one change or alteration as compared to a conventional scFv molecule which results in stabilization of the scFv molecule. As used herein, the term "stabilizing mutation" includes a mutation which confers enhanced protein stability (e.g. thermal stability) to the scFv molecule and/or to a larger protein comprising said scFv molecule. In one embodiment, the stabilizing mutation comprises the substitution of a destabilizing amino acid with a replacement amino acid that confers enhanced protein stability (herein a "stabilizing amino acid"). In one embodiment, the stabilizing mutation is one in which the length of an scFv linker has been optimized. In one embodiment, a stabilized scFv molecule of the invention comprises one or more amino acid substitutions. For example, in one embodiment, a stabilizing mutation comprises a substitution of at least one amino acid residue which substitution results in an increase in stability of the VH and VL interface of an scFv molecule. In one embodiment, the amino acid is within the interface. In another embodiment, the amino acid is one which scaffolds the interaction between VH and VL. In another embodiment, a stabilizing mutation comprises substituting at least one amino acid in the VH domain or VL domain that covaries with two or more amino acids at the interface between the VH and VL domains. In another embodiment, the stabilizing mutation is one in which at least one cysteine residue is introduced (i.e., is engineered into one or more of the VH or VL domain) such that the VH and VL domains are linked by at least one disulfide bond between an amino acid in the VH and an amino acid in the VL domain. In certain preferred embodiments, a stabilized scFv molecule of the invention is one in which both the length of the scFv linker is optimized and at least one amino acid residue is substituted and/or the VH and VL domains are linked by a disulfide bond between an amino acid in the VH and an amino acid in the VL domain. In one embodiment, more than one of the stabilizing mutations described herein may be made in an scFv molecule.

In one embodiment, one or more stabilizing mutations made to an scFv molecule simultaneously improves the thermal stability of both the VH and VL domains of the scFv molecule as compared to a conventional scFv molecule.

Preferably, a population of one or more of the stabilized scFv molecules of the invention is expressed as a population of monomeric, soluble proteins. In one embodiment, no more than 10% is present in aggregated form. In one embodiment, the stabilized scFv molecules of the population may comprise the same stabilizing mutation or a combination of stabilizing mutations. In other embodiments, the individual stabilized scFv molecules of the population comprise different stabilizing mutations.

The subject stabilized scFv molecules may be used alone to bind to a target molecule or may be linked to another polypeptide to form stabilized binding molecules which comprise a stabilized scFv molecule. For example, a binding molecule of the invention may comprise an scFv molecule linked to a second scFv molecule or a non-scFv molecule, e.g., that imparts target binding specificity, such as an antibody.

As used herein the term "protein stability" refers to an art-recognized measure of the maintenance of one or more physical properties of a protein in response to an environmental condition (e.g. an elevated or lowered temperature). In one embodiment, the physical property is the maintenance of the covalent structure of the protein (e.g. the absence of proteolytic cleavage, unwanted oxidation or deamidation). In another embodiment, the physical property is the presence of the protein in a properly folded state (e.g. the absence of soluble or insoluble aggregates or precipitates). In one embodiment, stability of a protein is measured by assaying a biophysical property of the protein, for example thermal stability, pH unfolding profile, stable removal of glycosylation, solubility, biochemical function (e.g., ability to bind to a protein (e.g., a ligand, a receptor, an antigen, etc.) or chemical moiety, etc.), and/or combinations thereof. In another embodiment, biochemical function is demonstrated by the binding affinity of an interaction. In one embodiment, a measure of protein stability is thermal stability, i.e., resistance to thermal challenge. Stability can be measured using methods known in the art and/or described herein.

The VL and VH domains of an scFv molecule are derived from one or more antibody molecules. It will also be understood by one of ordinary skill in the art that the variable regions of the scFv molecules of the invention may be modified such that they vary in amino acid sequence from the antibody molecule from which they were derived. For example, in one embodiment, nucleotide or amino acid substitutions leading to conservative substitutions or changes at amino acid residues may be made (e.g., in CDR and/or framework residues). Alternatively or in addition, mutations may be made to CDR amino acid residues to optimize antigen binding using art recognized techniques. The binding molecules of the invention maintain the ability to bind to antigen.

As used herein the term "derived from" a designated protein refers to the origin of the polypeptide. In one embodiment, the polypeptide or amino acid sequence which is derived from a particular starting polypeptide is a variable region sequence (e.g. a VH or VL) or sequence related thereto (e.g. a CDR or framework region). In one embodiment, the amino acid sequence which is derived from a particular starting polypeptide is not contiguous. For example, in one embodiment, one, two, three, four, five, or six CDRs are derived from a starting antibody. In one embodiment, the polypeptide or amino acid sequence that is derived from a particular starting polypeptide or amino acid sequence has an amino acid sequence that is essentially identical to that of the starting sequence or a portion thereof, wherein the portion consists of at least 3-5 amino acids, 5-10 amino acids, at least 10-20 amino acids, at least 20-30 amino acids, or at least 30-50 amino acids, or which is otherwise identifiable to one of ordinary skill in the art as having its origin in the starting sequence.

An isolated nucleic acid molecule encoding a stabilized scFv molecule or a portion thereof can be created by introducing one or more nucleotide substitutions, additions or deletions into the nucleotide sequence of a conventional scFv molecule or an immunoglobulin from which it is derived such that one or more amino acid substitutions, additions or deletions are introduced into the encoded protein. Mutations may be introduced by standard techniques, such as site-directed mutagenesis and PCR-mediated mutagenesis. In one embodiment, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, an amino acid residue in an immunoglobulin polypeptide may be replaced with another amino acid residue from the same side chain family. In another embodiment, a string of amino acids can be replaced with a structurally similar string that differs in order and/or composition of side chain family members. In another embodiment, a mutation is introduced in order to introduce at least one cysteine molecule into the VH and into the VL domain and, thereby, introduce a disulfide bond into the scFv molecule. In another embodiment, an amino acid of a conventional scFv molecule may be substituted with an amino acid having similar physical (e.g., spatial) or functional properties. Preferably, amino acids substituted into conventional scFv molecules are compatible with the integrity of the $V_L/V_H$ interface, CDR conformations, and $V_H$ and/or $V_L$ folding.

Alternatively, in another embodiment, mutations may be introduced randomly along all or part of the immunoglobulin coding sequence.

The stabilized scFv molecules of the invention or polypeptides comprising the stabilized scFv molecules are binding molecules, i.e., they bind to a target molecule of interest, e.g., an antigen. When a stabilized scFv molecule of the invention is fused to a second molecule, the second molecule may also impart a binding specificity to the fusion protein.

The binding molecules of the invention consist of scFv molecules (e.g., a VH and a VL domain joined by an scFv linker) or comprise a stabilized scFv molecule of the invention.

In one embodiment, the binding molecules of the invention are monovalent, i.e., comprise one target binding site (e.g., as in the case of an scFv molecule). In one embodiment, the binding molecules of the invention are multivalent, i.e., comprise more than one target binding site. In another embodiment, the binding molecules comprise at least two binding sites. In one embodiment, the binding molecules comprise two binding sites. In one embodiment, the binding molecules comprise three binding sites. In another embodiment, the binding molecules comprise four binding sites. In another embodiment, the binding molecules comprise greater than four binding sites.

In one embodiment, the binding molecules of the invention are monomers. In another embodiment, the binding molecules of the invention are multimers. For example, in one embodiment, the binding molecules of the invention are dimers. In one embodiment, the dimers of the invention are homodimers, comprising two identical monomeric subunits. In another embodiment, the dimers of the invention are heterodimers, comprising two non-identical monomeric subunits. The subunits of the dimer may comprise one or more polypeptide chains. For example, in one embodiment, the dimers comprise at least two polypeptide chains. In one embodiment, the dimers comprise two polypeptide chains. In another embodiment, the dimers comprise four polypeptide chains (e.g., as in the case of antibody molecules).

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different molecules, e.g., different antigens, or different epitopes on the same molecule).

The term "specificity" refers to the ability to specifically bind (e.g., immunoreact with) a given target. A polypeptide may be monospecific and contain one or more binding sites which specifically bind a target or a polypeptide may be multispecific (e.g., bispecific or trispecific) and contain two or more binding sites which specifically bind the same or different targets. Specific binding may be imparted by a stabilized scFv molecule of the invention and/or a non-scFv moiety to which a stabilized scFv molecule of the invention is linked.

In one embodiment, a binding molecule of the invention is multispecific. For example, in one embodiment, a multispecific binding molecule of the invention is a bispecific molecule (e.g., antibody, minibody, domain deleted antibody, or fusion protein, single domain antibodies (e.g., camelid, shark, human) comprising at least one stabilized scFv molecule) having binding specificity for at least two targets, e.g., more than one target molecule or more than one epitope on the same target molecule. In one embodiment, a multispecific molecule has at least one binding site specific for a molecule targeted for reduction or elimination and a target molecule on a cell. In another embodiment, a multispecific molecule has at least one target binding site specific for a molecule targeted for reduction or elimination and at least one binding site specific for a drug. In yet another embodiment, a multispecific molecule has at least one binding site specific for a molecule targeted for reduction or elimination and at least one binding site specific for a prodrug.

In one embodiment, a multispecific molecule comprises one specificity for a soluble molecule and one specifity for a cell surface molecule. In another embodiment, a multispecific molecule has two binding specificities for two targets present on one or more soluble molecules. In another embodiment, a multispecific molecule has two binding specificities for two targets present on one or more cell surface molecules (which may be present on one or more cells).

In one embodiment, the binding molecules have at least one target binding site specific for a molecule which mediates a biological effect (e.g., which modulates cellular activation (e.g., by binding to a cell surface receptor and resulting in transmission or inhibition of an activating or inhibitory signal), which results in death of the cell (e.g., by a cell signal induced pathway, by complement fixation or exposure to a payload present on the binding molecule), or which modulates a disease or disorder in a subject (e.g., by mediating or promoting cell killing, by promoting lysis of a fibrin clot or promoting clot formation, or by modulating the amount of a substance which is bioavailable (e.g., by enhancing or reducing the amount of a ligand such as TNFα in the subject)).

In another embodiment, the binding molecules of the invention bind at least one target that transduces a signal to a cell, e.g., by binding to a cell surface receptor, such as a TNF family receptor. By "transduces a signal" it is meant that by binding to the cell, the binding molecule converts the extracellular influence on the cell surface receptor into a cellular response, e.g., by modulating a signal transduction pathway.

In one embodiment, the binding molecules bind at least one target binding site specific for a molecule targeted for reduction or elimination, e.g., a cell surface antigen or a soluble antigen. In one embodiment, the binding of the binding molecule to the target results in reduction or elimination of the target, e.g., from a tissue or from the circulation. In another embodiment, the binding molecules have at least one binding site specific for a molecule that can be used to detect the presence of a target molecule (e.g., to detect a contaminant or diagnose a condition or disorder). In yet another embodiment, a binding molecule of the invention comprises at least one binding site that targets the binding molecule to a specific site in a subject (e.g., to a tumor cell or blood clot).

In a preferred embodiment, a multispecific molecule is a tetravalent antibody that has four binding sites. A tetravalent molecule may be bispecific and bivalent for each specificity. Further description of exemplary bispecific molecules is provided below.

Preferred binding molecules of the invention comprise framework and constant region amino acid sequences derived from a human amino acid sequence. However, binding polypeptides may comprise framework and/or constant region sequences derived from another mammalian species. For example, binding molecules comprising murine sequences may be appropriate for certain applications. In one embodiment, a primate framework region (e.g., non-human primate), heavy chain portion, and/or hinge portion may be included in the subject binding molecules. In one embodiment, one or more murine amino acids may be present in the framework region of a binding polypeptide, e.g., a human or non-human primate framework amino acid sequence may comprise one or more amino acid back mutations in which the corresponding murine amino acid residue is present and/or may comprise one or mutations to a different amino acid residue not found in the starting murine antibody. Preferred binding molecules of the invention are less immunogenic than murine antibodies.

A "fusion" or chimeric protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A fusion protein may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a genotypically distinct entity from that of the entity to which it is being compared. For instance, a heterologous polynucleotide or antigen may be derived from a different species, different cell type of an individual, or the same or different type of cell of distinct individuals.

The term "ligand binding domain" or "ligand binding portion" as used herein refers to any native receptor (e.g., cell surface receptor) or any region or derivative thereof retaining at least a qualitative ligand binding ability, and preferably the biological activity of a corresponding native receptor.

The term "receptor binding domain" or "receptor binding portion" as used herein refers to any native ligand or any region or derivative thereof retaining at least a qualitative receptor binding ability, and preferably the biological activity of a corresponding native ligand.

In one embodiment, the binding molecules of the invention are stabilized "antibody" or "immunoglobulin" molecules, e.g., naturally occurring antibody or immunoglobulin molecules (or an antiben binding fragment thereof) or genetically engineered antibody molecules that bind antigen in a manner similar to antibody molecules and that comprise an scFv molecule of the invention. As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "immunoglobulin" comprises five distinct classes of that can be distinguished biochemically. All five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

Stabilizing mutations to scFv molecules may be made to amino acids in the CDR and/or in the framework regions of an scFv variable heavy and/or variable light chain. As used herein the term "variable region CDR amino acid residues" includes amino acids in a CDR or complementarity determining region as identified using sequence or structure based methods. As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein the term "variable region framework (FR) amino acid residues" refers to those amino acids in the framework region of an Ig chain. The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments, the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As previously indicated, the subunit structures and three dimensional configuration of the constant regions of the various immunoglobulin classes are well known. As used herein, the term "VH domain" includes the amino terminal variable domain of an immunoglobulin heavy chain. As used herein, the term "VL domain" includes the amino terminal variable domain of an immunoglobulin light chain.

The term "fragment" refers to a part or portion of a polypeptide (e.g., an antibody or an antibody chain) comprising fewer amino acid residues than an intact or complete polypeptide. The term "antigen-binding fragment" refers to a polypeptide fragment of an immunoglobulin or antibody that binds antigen or competes with intact antibody (i.e., with the intact antibody from which they were derived) for antigen binding (i.e., specific binding). As used herein, the term "fragment" of an antibody molecule includes antigen-binding fragments of antibodies, for example, an antibody light chain (VL), an antibody heavy chain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

As used herein, the term "binding site" comprises a region of a polypeptide which is responsible for selectively binding to a target molecule of interest (e.g. an antigen, ligand, receptor, substrate or inhibitor). Binding domains comprise at least one target binding site. Exemplary binding domains include an antibody variable domain, a receptor binding domain of a ligand, a ligand binding domain of a receptor or an enzymatic domain.

Binding molecules of the invention can be made using techniques that are known in the art. In one embodiment, the polypeptides of the invention are "recombinantly produced," i.e., are produced using recombinant DNA technology. Exemplary techniques for making such molecules are discussed in more detail below.

In one embodiment, a binding molecule of the invention is a naturally occurring antibody to which a stabilized scFv molecule has been fused. In one embodiment, a binding molecule of the invention is a modified antibody to which a stabilized scFv molecule has been fused. As used herein, the term "modified antibody" includes synthetic forms of antibodies which are altered such that they are not naturally occurring. In another embodiment, a binding molecule of the invention is a fusion protein comprising at least one scFv molecule.

In preferred embodiments, a polypeptide of the invention will not elicit a deleterious immune response in a human.

In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Exemplary modifications include additions, deletions or substitutions of one or more amino acids in one or more domains. Such changes may be included to optimize effector function, half-life, etc.

As used herein, the term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the binding molecules of the invention are made using such methods.

As used herein, the terms "linked," "fused" or "fusion" are used interchangeably. These terms refer to the joining together of two more elements or components, by whatever means including chemical conjugation or recombinant means. Preferably the polypeptides which are fused are genetically fused, i.e., are fused using recombinant DNA technology. An "in-frame fusion" refers to the joining of two or more open reading frames (ORFs) to form a continuous longer ORF, in a manner that maintains the correct reading frame of the original ORFs. Thus, the resulting fusion protein is a single protein containing two or more segments that correspond to polypeptides encoded by the original ORFs (which segments are not normally so joined in nature.) Although the reading frame is thus made continuous throughout the fused segments, the segments may be physically or spatially separated by, for example, in-frame scFv linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

As used herein, the phrase "subject that would benefit from administration of a binding molecule" includes subjects, such as mammalian subjects, that would benefit from administration of a binding molecule used, e.g., for detection of an antigen recognized by a binding molecule (e.g., for a diagnostic procedure) and/or from treatment with a binding molecule to reduce or eliminate the target recognized by the binding molecule. For example, in one embodiment, the subject may benefit from reduction or elimination of a soluble or particulate molecule from the circulation or serum (e.g., a toxin or pathogen) or from reduction or elimination of a population of cells expressing the target (e.g., tumor cells). As described in more detail herein, the binding molecule can be used in unconjugated form or can be conjugated, e.g., to a detectable moiety, a drug, prodrug, or an isotope.

The term "TNF receptor" or "TNF receptor family member" refers to any receptor belonging to the Tumor Necrosis Factor ("TNF") superfamily of receptors. Members of the TNF Receptor Superfamily ("TNFRSF") are characterized by an extracellular region with two or more cysteine-rich domains (~40 amino acids each) arranged as cysteine knots (see Dempsey et al., *Cytokine Growth Factor Rev.* (2003). 14(3-4):193-209). Upon binding their cognate TNF ligands, TNF receptors transduce signals by interacting directly or indirectly with cytoplasmic adapter proteins known as TRAFs (TNF receptor associate factors). TRAFs can induce the activation of several kinase cascades that ultimately lead to the activation of signal transduction pathways such as NF-KappaB, INK, ERK, p38 and PI3K, which in turn regulate cellular processes ranging from immune function and tissue differentiation to apoptosis.

The nucleotide and amino acid sequences of several TNF receptors family members are known in the art and include at least 29 human genes: TNFRSF1A (TNFR1, also known as DR1, CD120a, TNF-R-I p55, TNF-R, TNFR1, TNFAR, TNF-R55, p55TNFR, p55R, or TNFR60, GenBank GI No. 4507575; see also U.S. Pat. No. 5,395,760)), TNFRSF1B (CD120b, also known as p75, TNF-R, TNF-R-II, TNFR80, TNFR2,TNF-R75, TNFBR, or p75TNFR; GenBank GI No. 4507577), TNFRSF3 (Lymphotoxin Beta Receptor (LTβR), also known as TNFR2-RP, CD18, TNFR-RP, TNFCR, or TNF-R-III; GI Nos. 4505038 and 20072212), TNFRSF4 (OX40, also known as ACT35, TXGP1L, or CD134 antigen; GI Nos. 4507579 and 8926702), TNFRSF5 (CD40, also known as p50 or Bp50; GI Nos. 4507581 and 23312371), TNFRSF6 (FAS, also known as FAS-R, DcR-2, DR2, CD95, APO-1, or APT1; GenBank GI Nos. 4507583, 23510421, 23510423, 23510425, 23510427, 23510429, 23510431, and 23510434)), TNFRSF6B (DcR3, DR3; GenBank GI Nos. 4507569, 23200021, 23200023, 23200025, 23200027, 23200029, 23200031, 23200033, 23200035, 23200037, and 23200039), TNFRSF7 (CD27, also known as Tp55 or S152; GenBank GI No. 4507587), TNFRSF8 (CD30, also known as Ki-1, or D1S166E; GenBank GI Nos. 4507589 and 23510437), TNFRSF9 (4-1-BB, also known as CD137 or ILA; GI Nos. 5730095 and 728738), TNFRSF10A (TRAIL-R1, also known as DR4 or Apo2; GenBank GI No. 21361086), TNFRSF10B (TRAIL-R2, also known as DR5, KILLER, TRICK2A, or TRICKB; GenBank GI Nos. 22547116 and 22547119), TNFRSF10C (TRAIL-R3, also known as DcR1, LIT, or TRID; GenBank GI No. 22547121), TNFRSF10D (TRAIL-R4, also known as DcR2 or TRUNDD), TNFRSF11A (RANK; GenBank GI No. 4507565; see U.S. Pat. Nos. 6,562,948; 6,537,763; 6,528,482; 6,479,635; 6,271,349; 6,017,729), TNFRSF11B (Osteoprotegerin (OPG), also known as OCIF or TR1; GI Nos. 38530116, 22547122 and 33878056), TNFRSF12 (Translocating chain-Association Membrane Protein (TRAMP), also known as DR3, WSL-1, LARD, WSL-LR, DDR3, TR3, APO-3, Fn14, or TWEAKR; GenBank GI No. 7706186; US Patent Application Publication No. 2004/0033225A1), TNFRSF12L (DR3L), TNFRSF13B (TACI; GI No. 6912694), TNFRSF13C (BAFFR; GI No. 16445027), TNFRSF14 (Herpes Virus Entry Mediator (HVEM), also known as ATAR, TR2, LIGHTR, or HVEA; GenBank GI Nos. 23200041, 12803895, and 3878821), TNFRSF16 (Low-Affinity Nerve Growth Factor Receptor (LNGFR), also known as Neurotrophin Receptor or p75(NTR); GenBank GI Nos. 128156 and 4505393), TNFRSF17 (BCM, also known as BCMA; GI No. 23238192), TNFRSF18 (AITR, also known as GITR; GenBank GI Nos. 4759246, 23238194 and 23238197), TNFRSF19 (Troy/Trade, also known as TAJ; GenBank GI Nos. 23238202 and 23238204), TNFRSF20 (RELT, also known as FLJ14993; GI Nos. 21361873 and 23238200), TNFRSF21 (DR6), TNFRSF22 (SOBa, also known as Tnfrh2 or 2810028K06Rik), and TNFRSF23 (mSOB, also known as Tnfrh1). Other TNF family members include EDAR1 (Ectodysplasin A Receptor, also known as Downless (DL), ED3, EDS, ED1R, EDA3, EDA1R, EDA-A1R; GenBank GI No. 11641231; U.S. Pat. No. 6,355,782), XEDAR (also known as EDA-A2R; GenBank GI No. 11140823); and CD39 (GI Nos. 2135580 and 765256).

The term "TNF ligand" or "TNF ligand family member" refers to a ligand belonging to the Tumor Necrosis Factor (TNF) superfamily. TNF ligands bind to distinct receptors of the TNF receptor superfamily and exhibit 15-25% amino acid sequence homology with each other (Gaur et al., *Biochem. Pharmacol.* (2003), 66(8):1403-8). The nucleotide and amino acid sequences of several TNF Receptor (Ligand) Superfamily ("TNFSF") members are known in the art and include at least 16 human genes: TNFSF1 (also known as Lymphotoxin-α (LTA), TNFβ or LT, GI No.:34444 and 6806893), TNFSF2 (also known as TNF, TNFα, or DIF; GI No. 25952111), TNFSF3 (also known as Lymphotoxin-β (LTB), TNFC, or p33), TNFSF4 (also known as OX-40L, gp34, CD134L, or tax-transcriptionally activated glycoprotein 1, 34kD (TXGP1); GI No. 4507603), TNFSF5 (also known as CD40LG, IMD3, HIGM1, CD40L, hCD40L, TRAP, CD154, or gp39; GI No. 4557433), TNFSF6 (also known as FasL or APT1LG1; GenBank GI No. 4557329), TNFSF7 (also known as CD70, CD27L, or CD27LG; GI No. 4507605), TNFSF8 (also known as CD30LG, CD30L, or CD153; GI No. 4507607), TNFSF9 (also known as 4-1BB-L or ILA ligand; GI No. 4507609), TNFSF10 (also known as TRAIL, Apo-2L, or TL2; GI No. 4507593), TNFSF11 (also known as TRANCE, RANKL, OPGL, or ODF; GI Nos. 4507595 and 14790152), TNFSF12 (also known as Fn14L, TWEAK, DR3LG, or APO3L; GI Nos. 4507597 and 23510441), TNFSF13 (also known as APRIL), TNFSF14 (also known as LIGHT, LTg, or HVEM-L; GI Nos. 25952144 and 25952147), TNFSF15 (also known as TL1 or VEGI), or TNFSF16 (also known as AITRL, TL6, hGITRL, or GITRL; GI No. 4827034). Other TNF ligand family members include EDAR1 & XEDAR ligand (ED1; GI No. 4503449; Monreal et al. (1998) *Am J Hum Genet.* 63:380), Troy/Trade ligand, BAFF (also known as TALL1; GI No. 5730097), and NGF ligands (e.g. NGF-β (GI No. 4505391), NGF-2/NTF3; GI No. 4505469), NTF5 (GI No. 5453808)), BDNF (GI Nos. 25306267, 25306235, 25306253, 25306257, 25306261, 25306264; IFRD1 (GI No. 4504607)).

The term "Tm", also referred to as the "transition temperature", is the temperature at which 50% of a macromolecule, e.g., binding molecule, becomes denatured, and is considered to be the standard parameter for describing the thermal stability of a protein.

As used herein the term "scaffolding residue" refers to amino acid residues or residue positions that are not in an interface (e.g., the VH/VL interface) but that are important in maintaining the interface. These amino acid residues do not physically interact with the interface residues on the opposing domain or contribute surface area to the interface, but are nonetheless important for providing proper structural context for interface residues. Such amino acid residues scaffold the interaction between VH and VL.

Two or more amino acid residue positions within a candidate polypeptide sequence that normally occur together are said to "covary" ("covarying residue positions" or "covariant residue positions"). Covariance between two or more amino acid positions is observed when the type of amino acid found at a first amino acid position is dependent on the type of amino acid found at another amino acid position. That is, when one particular amino acid is found at a first position within a sequence, a second particular amino acid is usually found at a second position within the sequence.

Figure 73:
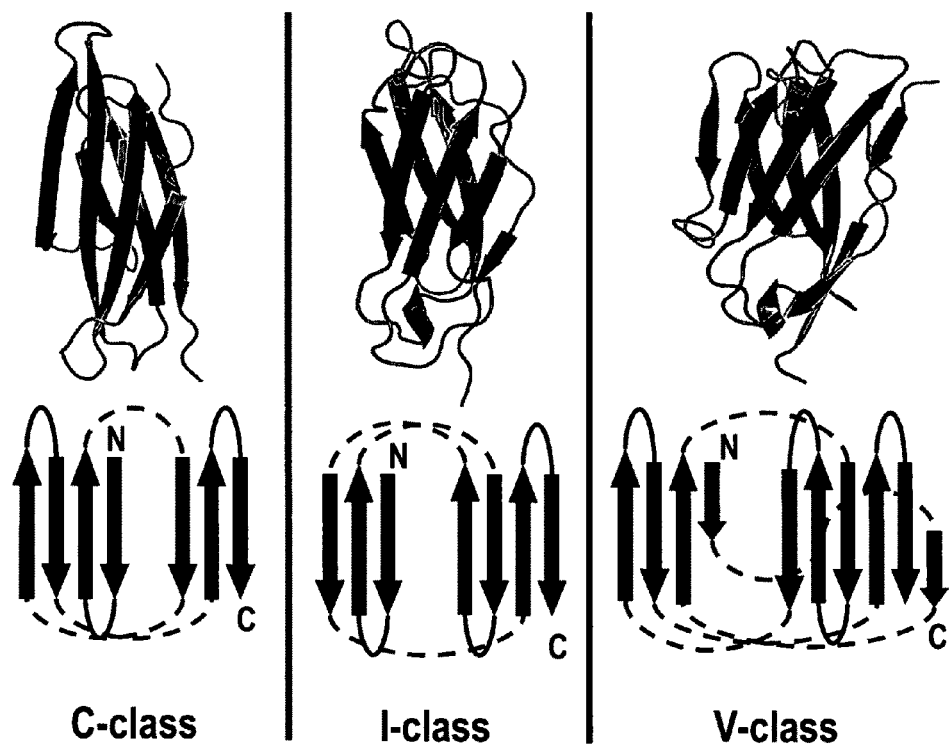
FIG. 73 depicts representative structures for the V-class, C-class, and I-class of Ig folds.

As used herein the term "Ig fold" includes a protein domain found in proteins belonging to the immunoglobulin superfamily of proteins. As is well known in the art, the Ig fold is a distinguishing feature of the immunoglobulin superfamily (see, e.g. Bork, P., Holm, L. & Sander, C. 1994. The Immunoglobulin Fold. *J. Mol. Biol.* 242, 309-320). Representative structures for each class of Ig fold are depicted in FIG. 73.

II. Stabilized scFv Molecules

In one embodiment, a binding molecule of the invention is a stabilized scFv molecule. The stabilized scFv molecules of the invention may comprise an scFv linker interposed between a $V_H$ domain and a $V_L$ domain, wherein the $V_H$ and $V_L$ domains are linked by a disulfide bond between an amino acid in the $V_H$ and an amino acid in the $V_L$ domain. In other embodiments, the stabilized scFv molecules of the invention comprise an scFv linker having an optimized length or composition. In yet other embodiments, the stabilized scFv molecules of the invention comprise a $V_H$ or $V_L$ domain having at least one stabilizing amino acid substitution(s). In yet another embodiment, a stabilized scFv molecule of the invention comprises at least two of the above listed stabilizing features.

The stabilized scFv molecules of the invention have improved stability. In one embodiment, populations of the stabilized scFv molecules of the invention or polypeptides comprising the same are expressed as a monomeric, soluble protein of which is no more than 10% in dimeric, tetrameric, or otherwise aggregated form. In another embodiment, populations of the stabilized scFv molecules of the invention have VH and VL domains with Tm-values greater than 55° C. In another embodiment, populations of the stabilized scFv molecules of the invention have a T50 of greater than 49° C. In another embodiment, populations of the stabilized scFv molecules of the invention have a T50 of greater than 40, 41, 42, 43, 44, 45, 46, 47, or 48° C. In yet another embodiment, populations of the stabilized scFv molecules of the invention have a T50 of greater than 50, 51, 52, 53, 54, 55, 56, 57, 58, or 49° C. The scFv molecules of the invention bind to a target molecule of interest.

The VH and VL domains used to make an scFv may be derived from the same or from different antibodies. In another embodiment, a VH or VL for use in a stabilized scFv of the invention may comprise one or more CDRs which bind to a target of interest, while the remainder of the VH or VL domain is derived from a different antibody or is synthetic. In a preferred embodiment, a binding molecule of the invention comprises at least one CDR of an antibody, e.g., an antibody known in the art to bind to a target of interest. In another embodiment, a binding molecule of the invention comprises at least two CDRs of a given antibody. In another embodiment, a binding molecule of the invention comprises at least three CDRs of a given antibody. In another embodiment, a binding molecule of the invention comprises at least four CDRs of a given antibody. In another embodiment, a binding molecule of the invention comprises at least five CDRs of a given antibody. In another embodiment, a binding molecule of the invention comprises at least six CDRs of a given antibody. In a preferred embodiment, a binding molecule of the invention comprises at least one VH domain of an antibody, e.g., an antibody known in the art to bind to a target of interest. In a preferred embodiment, a binding molecule of the invention comprises at least one VL domain of a given antibody. In another preferred embodiment, a binding molecule of the invention comprises at least one VH domain and one VL domain of an antibody known in the art to bind a target of interest. scFv molecules can be constructed in a VH-linker-VL orientation or VL-linker-VH orientation.

The stability of scFv molecules of the invention or fusion proteins comprising them can be evaluated in reference to the biophysical properties (e.g., thermal stability) of a conventional (non-stabilized) scFv molecule or a binding molecule comprising a conventional scFv molecule. In one embodiment, the binding molecules of the invention have a thermal stability that is greater than about 0.1, about 0.25, about 0.5, about 0.75, about 1, about 1.25, about 1.5, about 1.75, about 2, about 3, about 4, about 5, about 6, about 7, about 8, about 9, or about 10 degrees Celsius than a control binding molecule (eg. a conventional scFv molecule). Stabilized scFv molecules of the invention include those identified using methods of the invention as described in Section VIII infra.

In other embodiments, the stabilized scFv molecules of the invention comprise an scFv linker with an optimized length and/or amino acid composition. Preferred scFv linkers of the invention improve the thermal stability of a binding molecule of the invention by at least about 2° C. or 3° C. as compared to a conventional binding molecule. In one embodiment, a binding molecule of the invention has a 1° C. improved thermal stability as compared to a conventional binding molecule. In another embodiment, a binding molecule of the invention has a 2° C. improved thermal stability as compared to a conventional binding molecule. In another embodiment, a binding molecule of the invention has a 4, 5, 6° C. improved thermal stability as compared to a conventional binding molecule. Comparisons can be made, for example, between the scFv molecules of the invention and scFv molecules made using prior art methods or between scFv molecules and fab fragments of an antibody from which the scFv VH and VL were derived. Thermal stability can be measured using methods known in the art. For example, in one embodiment, Tm can be measured. Methods for measuring Tm and other methods of determining protein stability are described in more detail below.

In one embodiment, the scFv linker consists of the amino acid sequence $(Gly_4Ser)_4$ or comprises a $(Gly_4Ser)_4$ sequence. Other exemplary linkers comprise or consist of $(Gly_4Ser)_3$ and $(Gly_4Ser)_5$ sequences. scFv linkers of the invention can be of varying lengths. In one embodiment, an scFv linker of the invention is from about 5 to about 50 amino acids in length. In another embodiment, an scFv linker of the invention is from about 10 to about 40 amino acids in length. In another embodiment, an scFv linker of the invention is from about 15 to about 30 amino acids in length. In another embodiment, an scFv linker of the invention is from about 17 to about 28 amino acids in length. In another embodiment, an scFv linker of the invention is from about 19 to about 26 amino acids in length. In another embodiment, an scFv linker of the invention is from about 21 to about 24 amino acids in length.

scFv linkers can be introduced into polypeptide sequences using techniques known in the art. For example, in one embodiment, PCR mutagenesis can be used. Modifications can be confirmed by DNA sequence analysis. Plasmid DNA can be used to transform host cells for stable production of the polypeptides produced.

In certain embodiments, the stabilized scFv molecules of the invention comprise at least one disulfide bond which links an amino acid in the VL domain with an amino acid in the VH domain. Cysteine residues are necessary to provide disulfide bonds. Disulfide bonds can be included man scFv molecule of the invention, e.g., to connect FR4 of VL and FR2 of VH or to connect FR2 of VL and FR4 of VH. Exemplary positions for disulfide bonding include: 43, 44, 45, 46, 47, 103, 104, 105, and 106 of VH and 42, 43, 44, 45, 46, 98, 99, 100, and 101 of VL, Kabat numbering. Exemplary combinations of amino acid positions which are mutated to cysteine residues include: VH44-VL100, VH105-VL43, VH105-VL42, VH44-VL101, VH106-VL43, VH104-VL43, VH44-VL99, VH45-VL98, VH46-VL98, VH103-VL43, VH103-VL44, and VH103-VL45.

In one embodiment, a disulfide bond links $V_H$ amino acid 44 and $V_L$ amino acid 100.

Modifications of the genes which encode the VH and VL domains may be accomplished using techniques known in the art, for example, site-directed mutagenesis.

In one embodiment, a stabilized scFv molecule of the invention comprises an scFv linker having the amino acid sequence $(Gly_4Ser)_4$ interposed between a $V_H$ domain and a $V_L$ domain, wherein the $V_H$ and $V_L$ domains are linked by a disulfide bond between an amino acid in the $V_H$ at amino acid position 44 and an amino acid in the $V_L$ at amino acid position 100.

In other embodiments the stabilized scFv molecules of the invention comprise one or more stabilizing mutations within a variable domain (VH or VL) of the scFv. In one embodiment, the stabilizing mutation is selected from the group consisting of:
  a) substitution of an amino acid (e.g., glutamine) at Kabat position 3 of VL, e.g., with an alanine, a serine, a valine, an aspartic acid, or a glycine;

b) substitution of an amino acid (e.g., serine) at Kabat position 46 of VL, e.g., with leucine;
c) substitution of an amino acid (e.g., serine) at Kabat position 49 of VL, e.g., with tyrosine or serine;
d) substitution of an amino acid (e.g., serine or valine) at Kabat position 50 of VL, e.g., with serine, threonine, and arginine, aspartic acid, glycine, or lysine;
e) substitution of amino acids (e.g., serine) at Kabat position 49 and (e.g., serine) at Kabat position 50 of VL, respectively with tyrosine and serine; tyrosine and threonine; tyrosine and arginine; tyrosine and glysine; serine and arginine; or serine and lysine;
f) substitution of an amino acid (e.g., valine) at Kabat position 75 of VL, e.g., with isoleucine;
g) substitution of an amino acid (e.g., proline) at Kabat position 80 of VL, e.g., with serine or glycine;
h) substitution of an amino acid (e.g., phenylalanine) at Kabat position 83 of VL, e.g., with serine, alanine, glycine, or threonine;
i) substitution of an amino acid (e.g., glutamic acid) at Kabat position 6 of VH, e.g., with glutamine;
j) substitution of an amino acid (e.g., lysine) at Kabat position 13 of VH, e.g., with glutamate;
k) substitution of an amino acid (e.g., serine) at Kabat position 16 of VH, e.g., with glutamate or glutamine;
l) substitution of an amino acid (e.g., valine) at Kabat position 20 of VH, e.g., with an isoleucine;
m) substitution of an amino acid (e.g., asparagine) at Kabat position 32 of VH, e.g., with serine;
n) substitution of an amino acid (e.g., glutamine) at Kabat position 43 of VH, e.g, with lysine or arginine;
o) substitution of an amino acid (e.g., methionine) at Kabat position 48 of VH, e.g., with an isoleucine or a glycine;
p) substitution of an amino acid (e.g., serine) at Kabat position 49 of VH, e.g, with glycine or alanine;
q) substitution of an amino acid (e.g., valine) at Kabat position 55 of VH, e.g., with a glycine;
r) substitution of an amino acid (e.g., valine) at Kabat position 67 of VH, e.g., with an isoleucine or a leucine;
s) substitution of an amino acid (e.g., glutamic acid) at Kabat position 72 of VH, e.g., with aspartate or asparagine;
t) substitution of an amino acid (e.g., phenylalanine) at Kabat position 79 of VH, e.g., with serine, valine, or tyrosine; and
u) substitution of an amino acid (e.g., proline) at Kabat position 101 of VH, e.g., with an aspartic acid.
v) In an exemplary embodiment, a stabilized scFv molecule of the invention comprises two or more of the stabilizing mutations described in a) through u) above. In an exemplary embodiment, a stabilized scFv molecule of the invention comprises a substitution of an amino acid at Kabat position 49 of VL, e.g., with tyrosine or serine and a substitution of an amino acid at Kabat position 50 of VL, e.g., with, threonine, and arginine, aspartic acid, glycine, or lysine. In another exemplary embodiment, a stabilized scFv molecule of the invention comprises a substitution of an amino acid at Kabat position 16 of VH, e.g., with a glutamate or glutamine and a substitution of an amino acid at Kabat position 46 of VL, e.g., with a lysine. In another embodiment a binding molecule of the invention comprises a substitution of an amino acid at Kabat position 16 of VH, e.g., with a glutamate or glutamine; a substitution of an amino acid at Kabat position 46 of VL, e.g., with a lysine; and a substitution of an amino acid at Kabat position 55 of VH, e.g., with a glycine. In another embodiment a binding molecule of the invention comprises a substitution of an amino acid at Kabat position 16 of VH, e.g., with a glutamate or glutamine; a substitution of an amino acid at Kabat position 46 of VL, e.g., with a lysine; a substitution of an amino acid at Kabat position 55 of VH, e.g., with a glycine; and substitution of an amino acid at Kabat position 101 of VH, e.g., with an aspartic acid. In another embodiment, a binding molecule of the invention comprises a substitution of an amino acid at Kabat position 6 of VH, e.g., with glutamine. In another embodiment, a binding molecule of the invention comprises a substitution of an amino acid at Kabat position 13 of VH, e.g., with glutamate. In another embodiment, a binding molecule of the invention comprises a substitution of an amino acid at Kabat position 16 of VH, e.g., with glutamate or glutamine. In another embodiment, a binding molecule of the invention comprises a substitution of an amino acid at Kabat position 20 of VH, e.g., with an isoleucine; In another embodiment, a binding molecule of the invention comprises a substitution of an amino acid at Kabat position 32 of VH, e.g., with serine. In another embodiment, a binding molecule of the invention comprises a substitution of an amino acid at Kabat position 43 of VH, e.g, with lysine or arginine. In another embodiment, a binding molecule of the invention comprises a substitution of an amino acid at Kabat position 48 of VH, e.g., with an isoleucine or a glycine. In another embodiment, a binding molecule of the invention comprises a substitution of an amino acid at Kabat position substitution 49 of VH, e.g, with glycine or alanine. In another embodiment, a binding molecule of the invention comprises a substitution of an amino acid at Kabat position 55 of VH, e.g., with a glycine. In another embodiment, a binding molecule of the invention comprises a substitution of an amino acid at Kabat position 67 of VH, e.g., with an isoleucine or a leucine. In another embodiment, a binding molecule of the invention comprises a substitution of an amino acid at Kabat position 72 of VH, e.g., with aspartate or asparagine. In another embodiment, a binding molecule of the invention comprises a substitution of an amino acid at Kabat position 79 of VH, e.g., with serine, valine, or tyrosine. In another embodiment, a binding molecule of the invention comprises a substitution of an amino acid at Kabat position 101 of VH, e.g., with an aspartic acid.

In another exemplary embodiment, a stabilized scFv molecule of the invention comprises one or more of the stabilizing amino acid substitutions described herein and an scFv linker with an optimized length or composition (e.g. $(Gly_4Ser)_4$). In another exemplary embodiment, a stabilized scFv molecule of the invention comprises one or more of the amino acid substitution described herein and a disulfide bind which links an amino acid in the VL domain with an amino acid in the VH domain (e.g. VH44-VL100). In yet another exemplary embodiment, a stabilized scFv molecule of the invention comprises one or more of the amino acid substitutions described herein, an scFv linker with an optimized length or composition (e.g. $(Gly_4Ser)_4$), and a disulfide bind which links an amino acid in the VL domain with an amino acid in the VH domain (e.g. VH44-VL100).

Stabilized scFv molecules may be expressed using art recognized techniques. For example, in one embodiment, such molecules may be expressed using an expression vector appropriate for expression in a cellular expression system, e.g., a bacterial or mammalian expression system.

In one embodiment, scFv molecules may be expressed in *E. coli*, e.g., using a vector appropriate for periplasmic expression. Additional sequences may be included to optimize expression, e.g., a signal sequence and/or a tag to facilitate purification and/or detection of the scFv.

In one embodiment, additives, such as 1-2% triton (e.g., triton x-100) or 1-2% glysine or a combination thereof (e.g., 1% glycine and 1% triton) may be added to facilitate secretion from the periplasm into the medium.

III. Methods for Predicting/Determining Protein Stability

In certain aspects, the invention provides methods for predicting, a priori, potentional biophysical problems with proteins selected for large-scale expression, e.g. therapeutic proteins or industrial enzymes. In certain exemplary aspects, the methods of the invention allow one skilled in the art to avoid expressing protein sequences that are predicted to have inherently poor stability when recombinantly expressed, for example, in mammalian cells. In alternative aspects, the methods of the invention may be employed to identify a variant of a protein sequence that is predicted to have improved biophysical properties, including, but not limited to improved stability, improved stability to changes in pH, and enhanced biochemical function.

In certain aspects, the invention provides computational methods for predicting a biophysical property of (e.g., thermal stability) a candidate proteins, or a sequence variant or homolog thereof, based on the polypeptide sequence (e.g. amino acid sequence) of the candidate protein. In other aspects, the methods of the invention employ structural modeling to predict the stability of the candidate protein or to identify homologs or variants of the candidate protein with known exemplary stability that can be used to improve the stability of a candidate protein, e.g., an scFv molecule.

a. Covariation Analysis

In certain exemplary aspects, the invention provides an improved computational method termed "covariation analysis" for predicting a biophysical property (e.g. protein stability). As used herein, "covariation analysis" refers to a computational method for identifying two or more amino acid residue positions within a candidate polypeptide sequence that normally occur together, or covary, in homologs of the candidate sequence (herein "covarying residue positions" or "covariant residue positions"). Covariance between two or more amino acid positions is observed when the type of amino acid found at a first amino acid position is dependent on the type of amino acid found at another amino acid position. That is, when one particular amino acid is found at a first position within a sequence, a second particular amino acid is usually found at a second position within the sequence.

Since covariant residues are likely to have coevolved, an observation of covariation indicates that the compatibility of amino acid residues residing at normally covarying positions is likely to be important for functional or structural reasons. Accordingly, the covariation method of the invention can be used to identify one or more covarying residues or groups of residues (e.g. covarying residue pairs) within a polypeptide sequence (e.g. a candidate polypeptide sequence). As used herein, a "covarying residue" (also termed a "linked residue") is an amino acid which is statistically prevalent at a covarying residue position within a polypeptide sequence.

In certain embodiments, the covariation methods of the invention can be used to identify important functional residues in a candidate sequence. Moreover, since the number of covarying residues within a candidate polypeptide is predictive of its stability, the covariation method of the invention can be used to predict the stability candidate protein.

In other certain embodiments, the covariation methods of the invention can be employed to guide successful protein designs. In one exemplary embodiment, the covariation method of the invention can be used to identify covarying amino acids within a candidate sequence. If present, the covarying residues are preferably retained during subsequent engineering of the protein sequence. In another exemplary embodiment, the covariation methods of the invention can be used to identify the amino acid positions of non-covarying residues within a candidate polypeptide sequence wherein corresponding amino acids in other proteins (e.g., proteins corresponding to the sequences of a reference set) are normally covarying amino acids. Once identified, non-covarying residues can be substituted (e.g. using recombinant DNA methodology) with corresponding covarying residues to enhance function or improve the biophysical properties (e.g., stability) of the candidate polypeptide sequence.

Covariant residue positions may be identified by a statistical analysis (e.g., a correlation analysis) of residue positions within a database of related polypeptide sequences (e.g., an aligned reference set or multiple sequence alignment). In preferred embodiments, the covariation analysis involves a statistical comparison of candidate polypeptide sequences against a curated database of diverse polypeptide sequences having the same structural fold (e.g. an Ig fold).

In the novel covariation analysis described herein, the following basic steps are taken to predict the stability of a candidate polypeptide:

1. Providing a set of homologous sequences (herein, a "reference set") corresponding to a sequence of a candidate polypeptide or a domain or portion thereof (herein a "test domain sequence").
2. Aligning the sequences of the reference set to generate an aligned set of homologous sequence (herein, an "aligned set).
3. Determining covariation between two or more residue positions (e.g. at least one pair of amino acids) within the reference set to generate covariation data or a set of covariation data ("covariation dataset").
4. Using the covariation data to predict the stability of the candidate polypeptide.

Step 1: Providing a Reference Set

The covariation methods of the invention employ a set of sequences (a "reference set") which are homologous to (i.e., related to) a sequence of interest or "test sequence". The reference set may comprise a set of homologous sequences having moderate to high degrees of similarity with the test sequence. In certain embodiments, the homologous sequences of the reference set have a moderate to high degree of amino acid sequence similarity. In more preferred embodiments, the homologous sequences of the reference set have a moderate to high degree of structural similarity. In still more preferred embodiments, the homologous sequences of the reference set have a high degree of structural similarity (e.g. they share at least one protein domain or fold). The set of homologous sequences need not be large, as long as a reasonably unbiased selection is obtained.

In exemplary embodiments, the covariation method of the invention employs a curated reference set. As used herein, the term "curated reference set" refers to a reference set in which component sequences have been deleted or additional sequences added according to certain selection criteria. Accordingly, whereas a non-curated reference is generated by unbiased selection of component sequences, a curated database is generated by biased selection. For example, the reference set of homologous sequences may be culled to eliminate certain sequences, e.g. redundant sequence. Alternatively, a curated database may be expanded, e.g. to include a suitable number of non-redundant or non-identical sequences.

In certain embodiments, the curated database comprises at least one hundred sequences (e.g. 100, 150, 200, 250, 300, 400, 500, 750, or more sequences). In one embodiment, the curated database comprises at least one thousand sequences (e.g. 1000, 2000, 3000, 4000, 5000, 6000, 7000, 8000, 9000, or more sequences). In another embodiment, the curated database comprises at least ten thousand sequences (e.g., 10,000, 20,000, 50,000, 100,000, 250,000, 500,000, 750,000 or more sequence. In one embodiment the curated database comprises at least 1 million individual sequences (e.g., 1 million, 2 million, 5 million, 10 million, or more sequences).

In preferred embodiments, the covariation method of the invention employs a curated reference set having at least 50% diversity (e.g. at least 60%, at least 70%, at least 75%, at least 80%, at least 90%, at least 95% diversity, at least 97%, at least 98%, at least 99% or more diversity) in order to minimize artificial or non-informative covariations. As used herein, the term "% diversity" refers to the percentage of sequences in the reference set that are non-redundant or non-identical. As used herein, the term "non-redundant" refers to a sequence which has less than 100% sequence identity with every other sequence in the reference set, i.e., a sequence which differs at least in one amino acid position from every other sequence in the reference set. In certain embodiments, a sequence of the reference set has less than 99%, less than 95%, less than 90%, or less than 85% sequence identity with every other sequence in the reference set. In preferred embodiments, a sequence of the reference set has less than 80% sequence identity with every other sequence in the reference set (e.g. less than 75%, less than 70%, less than 65%, less than 60%, or less than 50% sequence identity). In particularly preferred embodiments, every sequence of the reference set has less than than 80% sequence identity with every other sequence in the reference set. In exemplary embodiments, the sequences of the reference set are curated for the preferred diversity using a filtering tool which culls sequences containing more common sequence types (e.g., a Henikoff sorting tool). When two sequences are equal in length, sorting by Henikoff weight ensures that sequences with rare residue types are retained while sequences with more common residue types are discarded (Henikoff et al., *J. Mol. Biol.*, 243: 574-578 (1994)).

In other preferred embodiments, the reference set comprises sequences encoded by genes which are not evolutionarly close to genes encoding other sequences in the database. For example, to increase diversity, the reference set may comprise one or more ortholog sequences, that is a sequence which is from a different species (e.g., different mammalian species)) but which has the same or similar biochemical function. In one exemplary embodiment, the reference set may comprise one human sequence and at least one non-human sequence (e.g., a non-human mammalian sequence). In another exemplary embodiment, the reference set may comprise at least one sequence for a mammalian species (e.g., a human, chimpanzee, dog, cow, pig, cat, rat, or mouse) and at least one non-mammalian sequence (e.g. a non-mammalian vertebrate sequence (e.g., a teleost or avian sequence), an invertebrate sequence (e.g., an insect (e.g., *Drosophila*) or nematode (e.g., *C. elegans*) sequence), or a fungal, plant, bacterial, or virus sequence). In other embodiments, the reference set may comprise one or more paralog sequences, that is sequences from the same species as a first sequence, but which has the same or similar biochemical function.

In yet other embodiments, the sequences of the reference set are above a certain threshold length. Preferably, the sequences of the reference set are at least 20 residues in length (e.g., 25, 30, or 40 residues in length). More preferably, the sequences of the reference set are at least 50 residues in length (e.g., 60, 65, 70, 75, 80, 85, 90, or 95 residues in length). Still more preferred are sequences of at least 100 residues in length (e.g., 110, 120, 130, 140, 150, 160, 170, 180, or more residues in length). In exemplary embodiments, the sequences of the reference set are curated for the preferred length by filtering using a filtering tool (e.g., a non-gap residue count). Ranking by decreasing non-gap residue count ensures that shorter sequences (e.g., gapped sequences) are filtered out over longer ones.

The sequences can be obtained through sequence-based homology searches for any of the sequence databases known in the art (e.g. NCBI, TIGR databases). In an exemplary embodiment, a standard BLAST search with default parameters may be performed with the test sequence to retrieve homologous sequences of interest. Sequences with a minimum percentage of sequence identity (e.g. greater than 25%, 30%, 35%, 40%, 45% or 50% sequence identity, preferably greater than 30% sequence identity) to the test sequence may be selected for inclusion in the reference set.

In certain preferred embodiments, the reference set is curated to comprise sequences from proteins having the same class of protein fold (e.g., proteins having SH3, TPR, GPCR, serine protease, aspartyl protease, globin, immunoglobulin, or other folds). Such proteins or structures may be identified and collected by bioinformatics techniques known in the art (e.g., be structure-based searching using the Conserved Domain Database (CDD) of the National Institutes of Health), or by searching the ASTRAL database or the RCSB protein database (PDB) using a desired SCOP classification). Preferably, the sequences are derived from proteins whose 3-dimensional structures have been solved at high resolution, for example, by X-ray crystallography.

In preferred embodiments, sequences corresponding to collected structures are filtered using art-recognized techniques to remove erroneously categorized, incomplete, redundant, or domain-swapped structures. In one embodiment, the structures are visually inspected (e.g., using the SwissPDB Viewer) for breaks in the corresponding sequence due to unresolved densities or domain swapping. The PDB files of faulty structures are manually removed from the corresponding set of structures. In another embodiment, sequences (e.g. FASTA sequences) corresponding to the collected structures are filtered to remove any sequences that are 100% identical, or perfect match substrings of remaining sequences. In yet other embodiments, PDB structures with aberrantly long or short amino acid sequences (a hallmark of erroneous structural categorization) are culled from the structure datasets. The length cutoff criteria may be determined, for example, by examining a histogram of all sequence lengths of sequences of the reference set. In still other embodiments, the structures are visually inspected (e.g., using the Swiss PDB viewer) for misfolding. Any structures that do not conform with the standard topology of the protein fold are preferably discarded.

In exemplary embodiments, the curated reference set comprises sequences corresponding to an immunoglobulin-type fold ("Ig fold") of a protein belonging to the immunoglobulin superfamily of proteins. As is well known in the art, the Ig fold is a distinguishing feature of the immunoglobulin superfamily (see, e.g. Bork, P., Holm, L. & Sander, C. 1994. The Immunoglobulin Fold. *J. Mol. Biol.* 242, 309-320). The Ig fold appears often in mammalian proteins and serves as a platform for various functions—particularly protein-protein interactions. For example, all immunoglobulins and most immunoglobulin receptors are composed of multiple Ig-fold domains. Ig folds may be subdivided into several subfamilies including C1, C2, I, and V. Although members of all the subfamilies comprise a two-βsheet, greek-key topology, these subfamilies differ by the number of β-strands on each sheet and by the connections across β-sheets (see, e.g., A F Williams, *Immunology Today,* 8, (1987)). Representative structures for each class of Ig fold are depicted in FIG. 73.

In one embodiment, the reference set comprises an Ig-fold sequence of an immunoglobulin superfamily protein selected from the group consisting of a cell adhesion protein, a integrin, an allergen, a T-cell receptor, a major histocompatibility complex protein (e.g., a MHC Class I or MHC Class II protein), an immunoglobulin receptor (e.g., an Fc gamma receptor (e.g. FcγRI, FcγRIIa)), and an immunoglobulin (e.g., an IgG, IgM, IgA, or IgE immunoglobulin).

In certain preferred embodiments, all of the sequences of the reference set correspond to an Ig-fold or portion thereof. In one embodiment, the Ig-fold is a C1 fold. In another embodiment, the Ig-fold is a C2-fold. In another embodiment, the Ig-fold is a V-fold. In yet another embodiment, the Ig-fold is an I-fold. In another embodiment, all of the sequences of the reference set correspond to a C1 fold. In another embodiment, all of the sequences of the reference set correspond to a C2-fold. In another embodiment, all of the sequences of the reference set correspond to an I-fold. In certain preferred embodiments, the sequences of Ig-fold reference set are within about 75 to about 150 residues in length.

Step 2: Aligning the Reference Set

In the second step, the sequences of the reference set are precisely aligned to generate an aligned set of sequences (or alignment). In one embodiment, the sequences of the reference set are aligned using sequence alignment algorithms (e.g. LALIGN or BLAST and other art-recognized alignments described supra) to create an aligned set of sequences (herein a "sequence-based sequence alignment"). In another embodiment, structures corresponding to the sequences of the reference set are aligned using a structural alignment algorithm (e.g. Secondary Structure Matching (SSM) using the Schrödinger structalign package) to create an aligned set of structures (herein, a "structure alignment"). Preferably, the structure alignment algorithm ensures that core regions (e.g., (β strands) of each structure are aligned, instead of intervening loops. In yet another embodiment, the sequences of the reference set are aligned by structure-based methods (e.g., by matching amino acids from one superimposed structure to that of another superimposed structure based on the shortest distance between the α-carbons of the polypeptide backbones, e.g., using the Schrödinger package).

In another embodiment, the sequences of the reference set are aligned using both sequence-based and structure-based alignment algorithms. Preferably, the structures corresponding to the sequences of the reference set are first aligned using a structure-based alignment algorithm or other structure-guided alignment tools, followed by alignment of the corresponding sequences with a sequence-based algorithm. More preferably, the structures corresponding to the sequences of the reference set are first aligned, followed by alignment of the sequences using a structure-based sequence alignment.

In certain optional embodiments, the aligned set of sequences is further curated. For example, the aligned set of sequences can be expanded (e.g., by non-gap sorting or by Henikoff sorting) to increase its diversity (e.g., to obtain very large sets of homolgous sequences having the same fold). In other embodiments, the aligned set of sequences can be further subjected to several rounds of curation and, optionally, further alignment (e.g. structure-based alignment).

In certain preferred embodiments, the invention provides methods for curating an aligned set containing a relatively small number of sequences in order to enhance its diversity. By increasing the number of sequence in the alignment, the robustness of the covariation analysis is increased. In one embodiment, the methods may employ a heuristically-derived model or profile to search for additional homologous sequences from a large, publically-available, sequence database (e.g., the NR database maintained by the NCBI). The heuristically-derived models may be produced using one or more regression-based algorithms selected from, e.g., a partial least squares regression, a multiple linear regression, an inverse least squares regression, a principal component regression, a variable importance for projection, or the like. In other embodiments, the heuristically-derived model is produced using one or more pattern-based algorithm selected from, e.g., a Hidden Markov model, a Smith Waterman algorithm, neural network, a classification and regression tree, a multivariate adaptive regression spline, or the like. In an exemplary embodiment, the pattern recognition algorithm is a Hidden Markov Model. An HMM is a statistical model where the system being modeled contains hidden parameters which can be extracted using observable parameters and employed for analysis of pattern recognition. For example, art-recognized HMMs may employ predicted secondary structures to search for antibodies of the same fold as a given antibody, rather than antibodies having purely sequence-based relatedness (see e.g., *Proteins* 36(1), 68-76). MetaFam (Silverstein et al. *Nucleic Acids Res* 29(1), 49-51 (2001)), Interpro (Apweiler, et al., *Nucleic Acids Res,* 29(1), 37-40, (2001)), and HMMER (Bateman et al, *Nucleic Acids Res* 27(1), 260-2 (1999)) are exemplary HMM-based pattern recognition tools.

In certain additional embodiments, sequences extracted with a HMM algorithm may be validated for their proper structural class assignment using art-recognized bioinformatics software. An exemplary validation tool is the PFAM classification tool maintained by the Wellcome Trust Sanger Institute and is publicly available on the internet. For example, the PFAM tool 'pfamverify' may be applied to each extracted sequence to confirm that it was correctly classified by the class-specific HMM created from the structure-based structure alignment (Finn et al., *Nucleic Acids Res,* 24 (Database issue), D247-51, (2006). HMM profiles corresponding to a PFAM clan (or related family of proteins, e.g. an Ig-fold clan) may be downloaded from the PFAM website to facilitate scoring of the extracted sequences. Extracted sequences whose scores lay below a recommended cutoff are preferably removed from the reference set.

In other embodiments, sequences extracted with the HMM algorithm may also be aligned using the HMMC algorithm. Since these HMM algorithms are based upon careful structural alignments, this process insures the structure guided alignment of the additional extracted sequences. For example, the HMMER package may be utilized to generate 'mapali' alignments in FASTA output format.

In preferred embodiments, the method of the invention provides a novel HMM which not only finds sequences similar to those of the aligned set, but aligns the new sequences to insure the correct core region alignment. For example, the novel HMM algorithm of the invention can search for separate domains (e.g., Ig-fold domains) within a single protein (e.g., an immunoglobulin superfamily member), extract each domain separately, and add it to the aligned set of sequences. HMM algorithms or profiles may be built from structure-based sequence alignments (e.g., using the HMMER software package which is publically available on the internet, e.g., at www.psc.edu). For each structure-specific HMM search, hit sequences above a criterion score threshold are preferably retained as candidate members of the structural class whose HMM was used. For those hit regions that are subsequences of hit sequence, the exact subsequence hit may be extracted from the full sequence.

In other exemplary embodiments, the invention provides methods for curating the aligned set of sequences in order to reduce its redundancy. For example, while the large number of sequences in a structurally aligned set (e.g., an Ig-fold aligned set) represents a rich source of sequences, some subfamilies (e.g., certain Ig-fold subclasses) may be highly overrepresented, while other are highly under-represented. Over- or under-representation results in significant bias due to close common ancestry and limits the overall usefulness of covariation analyses. Accordingly, in preferred embodiments, the alignment is subjected to further filtering steps to reduce alignment redundancy. In preferred embodiments, at least one sequence with greater than 90% identity to another sequence (e.g., 91%, 92%, 93%, 95%, 96%, 97%, 98%, 99% or more sequence identity) is removed from the alignment. In particularly preferred embodiments, at least one sequence sharing greater than 80% sequence identity with another sequence (e.g., 81%, 82%, 83%, 84%, 87%, 88%, 89%, or 90% sequence identity) is removed from the alignment.

In exemplary embodiments, the invention provides a novel method to reduce redundancy within the alignment. Such methods comprise use of a heuristic algorithm to find and rank sequences of desired sequence identity cutoff. Such methods comprise one of more of the following sequential steps: (1) calculating percent identities for all pairs of sequences in the alignment; (2) grouping identity values into one or more bins of percent identity; (3) ranking the sequences of each bin by decreasing non-gap residue count and/or by Henikoff sequence weight; and (4) removing redundant sequences according to a cutoff criterion (e.g., a % identity cutoff level).

Removal of the redundant sequences can be performed in a number of ways. In one embodiment, ranked sequences are grouped into multiple bins of sequence identity (e.g., a 99% bin, a 98% bin, a 97% bin, etc.). Sequences are then systematically removed by rank (e.g., highest ranked sequences first) from the highest % identity bin (ie., the 99% bin, followed by the 98% bin, followed by the 97% bin, etc.). Identity calculation, grouping and/or ranking steps (Steps (1)-(3)) are optionally repeated after each removal step until the final bin that meets the cutoff criterion is eliminated. In another embodiment, a single bin of ranked sequences is created at the cutoff criterion and sequences are systematically removed by rank from the bin. Identity calculation and/or ranking steps (Step (1) and (3)) are optionally repeated after each removal step.

In preferred embodiments, the cutoff criterion is 90% or higher (e.g., 91%, 92%, 93%, 95%, 96%, 97%, 98%, 99% or more sequence identity). In particularly preferred embodiments, the cutoff criterion is 80% or higher (e.g., 81%, 82%, 83%, 84%, 87%, 88%, 89%, or 90% sequence identity).

In another optional step, the lengths of sequences in the aligned reference set may be truncated. In one embodiment, gapped regions within the alignment may be removed to avoid calculation on these less informative regions. For example, columns that are not match states in an HMM profile used to find the sequences may be removed. In another embodiment, sequences within the alignment which overlap the consensus length of the alignment are cropped to remove the overhanging portion of the sequence. In other embodiment, overlapping sequences are removed from the alignment.

Step 3: Covariation Analysis of the Aligned Set

Once the sequences of the aligned set are compiled, covariation analysis is performed on one or more pairs of amino acid residues in the alignment set. The covariation analysis results in the generation of a novel dataset (herein, a "covariation dataset") describing the statistical significance of correlated residues within the alignments. In certain embodiments, the covariation dataset lists correlations between every possible pair of residues within the alignment.

In preferred embodiments, computation of covariation is a computer-implemented process (e.g., a Java-executable process). Computation of covariation may result in several art-recognized statistical parameters. In one embodiment, the statistical significance (e.g. a $\chi^2$-value) of covariation is calculated using a Chi-square analysis. In another embodiment, the statistical strength (e.g. $\phi$ value) of covariation is calculated. For example, a negative $\phi$ value may be predictive of a negative correlation. That is, the presence of one amino acid at a first position in the alignment favors the absence of another specific amino acid at a second position. Conversely, a positive $\phi$ value may be predictive of a positive correlation, thereby indicating that the amino acid at the first position favors the presence of the amino acid at the second position.

In one embodiment, a $\phi$ value is calculated using formula I:

$$\phi(a_i b_j) = \frac{(a_i b_j * \overline{a_i} \overline{b_j}) - (a_i \overline{b_j} * \overline{a_i} b_j)}{\sqrt{(a_i b_j + \overline{a_i} b_j) * (a_i \overline{b_j} + \overline{a_i} \overline{b_j}) * (a_i b_j + a_i \overline{b_j}) * (\overline{a_i} b_j + \overline{a_i} \overline{b_j})}} \quad (I)$$

wherein $a_i b_j$ is the number of times residues of type "a" or "b" are found in the same sequence at positions i and j, respectively;

$\overline{a}_i \overline{b}_j$ is the number of times both residue types are absent from the same sequence; $a_i \overline{b}_j$ is the number of times a is found present while b is absent; and $\overline{a}_i b_j$ is the number of times a is absent while b is present.

In one embodiment, a 4) value is calculated using the following formula II:

$$\phi(a_i b_j) = \frac{(c * f) - (d * e)}{\sqrt{ghij}} \quad (II)$$

where c through j are defined by the matrix:

| | $a_i$ | $\overline{a}_i$ | Total |
|---|---|---|---|
| $b_j$ | c | d | g |
| $\overline{b}_j$ | e | f | h |
| Total | i | j | | and $c = a_i b_j, d = \overline{a}_i b_j, e - a_i \overline{b}_j, f = \overline{a}_i \overline{b}_j, g = c + d, h = e + f,$ $i = c + e,$ and $j = d + f.$ In certain embodiments, a $\chi^2$-value may be calculated using a "frequency-of-occurrence" based formula. In other embodiments, a $\chi^2$-value is calculated using an "event-based"

formula (Ie. number of occurrences). An exemplary event-based formula is set forth as Formula III:

$$\chi^2 = \frac{[c(i,j) - (p(i) \cdot p(j) \cdot c(t))]^2}{p(i) \cdot p(j) \cdot c(t)} \quad \text{(III)}$$

wherein p(i) and p(j) are the residue frequencies of any two residue types of interest at positions i and j, respectively, in the aligned set of sequences;

c(i,j) is number of times p(i) and p(j) are observed in the same sequence; and c(t) is the number of total sequences in the alignment;
and wherein residue frequencies are defined as the number of times a residue type is observed at a specific position in an alignment divided by the total number of sequences in the alignment.

In certain embodiments, only a natural amino acid residue is considered a "residue type" for the purposes of a covariation calculation. In preferred embodiments, however, a residue type may also include a gap as a distinct residue type, since gaps (especially in loop portion) often help to discriminate one motif from another.

In certain embodiments, the covariation calculation may include a diversity weighting function (e.g., a Henikoff weighing scheme).

In other embodiments, Sequence Average Identities (SAIs) may be used to filter out covarying pairs. For example, SAIs may be used to filter out covariation from pairs with greater than average sequence identity in order to remove potential artifactual covariations arising from closely related sequences. In embodiments where the alignment has been subjected to curation by a high identity threshold (e.g., 80% identity as cutoff criterion), SAI calculations are preferably dispensed with.

In certain embodiments, covarying pairs are not reported by the calculation unless they are observed a minimum number of times (herein, an "event cutoff"). In one embodiment, the event cutoff is 10 or more events. In a more preferred embodiment, the event cutoff about 2 or more, and less than 10, events (e.g., 9, 8, 7, 6, or 5 events).

Step 4: Using Covariation Data to Predict Protein Stability

In certain embodiments, the statistically significant covariations within the covariation dataset are used to search for corresponding covariations within the candidate or test sequence. In particular, the conservation of one or more covariant amino acids of the reference set at corresponding amino acid positions within the candidate or test sequence indicates that these residues are functionally important and are predictive of favorable protein stability. Accordingly, the number of covariant amino acids that are conserved within a candidate or test sequence may be used to predict the stability of the sequence.

In certain exemplary aspects, the relavent covariations may be visualized using a graphical user interface (GUI) of the invention (e.g., the NAPMAP tool described in Section V infra) for analysis of the covariation dataset. Because interpretation of data in the covariation dataset may be cumbersome, the graphical user interface may ease data analysis and facilitate rapid protein designs and functional analyses.

In exemplary embodiments, the presence or absence of covariant residues within the reference set or alignment that are present or absent within the candidate sequence can be used to establish a score which is correlative with protein stability. For example, where a covariant (e.g., positively covariant) pair of residues is found to be retained within the candidate sequence, a first score (e.g. a positive score) can be assigned to the candidate sequence. Conversely, where a covariant (e.g., positively covariant) pair of residues is missing from the candidate sequence, a second score of oppositive sign to the first score (e.g., a negative score) can be assigned to the candidate sequence. In one preferred embodiment, the absence of a negatively covariant pair of residues within a test sequence is assigned a positive score, while the presence of the negatively covariant pair of residues is assigned a negative score. In another preferred embodiment, the presence of a positively covariant pair of residues of a test sequence is assigned a positive score, while the absence of a positively covariant pair test sequence residues is assigned a negative score.

In certain embodiments, covariation scores are generated only for covariations that satisfy a threshold level of statistical significance. In one embodiment, covariation scores are generated only for covariations above (or below) a certain $\chi^2$-value or $\phi$ value. For example, the cutoff for designation of negative covariation score may be a covariation with a phi association coefficient ($\Phi$) of less than +0.2 (about +0.2 to about −1.0), and more preferable less than −0.2. In another exemplary embodiment, a covariation is assigned a positive covariation score if it has a phi association coefficient of greater than −0.2, preferably greater than +0.2. In preferred embodiments, a negative covariation score is assigned to a covariation with a phi association coefficient ($\Phi$) of less than −0.5 (e.g., −0.5, −0.6, −0.7, −0.8, −0.9, or −1.0), and a positive covariation score is assigned to a covariation with a phi association coefficient ($\Phi$) of greater than +0.5 (e.g., +0.5, +0.6, +0.7, +0.8, +0.9, or +1.0), while all other covariations are masked by assigning a neutral score (e.g., zero).

In certain embodiments, the negative or positive covariation score can be weighted to reflect the statistical significance or strength of the corresponding covariation. In one exemplary embodiment, a positive covariation can be assigned a high positive covariation score if its phi association coefficient is also high or a lower positive covariation score its 4) value is low. For example, a candidate sequence having first and second covariations with respective 4) values of +0.5 and +1.0 may be assigned a low positive covariation score (e.g., +1) for the first covariation and a higher positive covariation score for the second covariation (e.g., +2).

In other embodiments, the covariation score is assigned only to those covariations which are validated by a means other than calculated statistical significance. Several non-statistical criteria may be used to validate that the calculated covariations are significant and biologically meaningful. In one embodiment, the covariation is validated by examining whether there is correlation or trend between residues that covary with each other and their proximity to each other within a structural model of the corresponding protein. If said residues are close in proximity (e.g. 30 Å or less, preferably 10 Å or less) to each other in the structure, the predicted covariation is validated as a true covariation. In another embodiment, the covariation is validated by determining whether the covarying amino acids form a connection which is already known to exist within a subset of proteins corresponding to sequences of the reference set (e.g., a known disulfide bond). For example, residues 6-10 at the N-terminus of human or murine IgG variable heavy chain folds are known to adopt very specific conformations based on the conservation of covarying pairs of amino acids (Ewert et al., *Methods, 34*: 184-199 (2004)).

In yet other embodiments, a covariation score of an amino acid in a candidate sequence can be weighted to reflect the number of covariations within the reference set or alignment that is satisfies (or violates). In one embodiment, the candidate sequence is assigned a positive covariation score for each covariation within the reference set or alignment that it satisfies, and a negative covariation score for each covariation within the reference set that it violates. In preferred embodiments, the covariation score for a particular amino acid of a test sequence is the sum total of the positive covariation scores offset by the sum total of the negative covariation scores. For example, where 2 negative covariations and 9 positive covariations are observed within the reference set at amino acid positions corresponding to the amino acid of the candidate sequence, the candidate sequence amino acid may be assigned a total covariation score of 7.

In certain embodiments, a total covariation scores are summed for all the amino acids in a candidate sequence (or portion thereof) to obtain a "sequence covariation score". This sequence covariation score may be employed to predict the stability of the sequence. Generally, a negative sequence covariation score is predictive of low protein stability, whereas a positive sequence covariation score is predictive of high protein stability.

b. Consensus Scoring

In other embodiments, the computational methods of the invention employ a novel scoring technique termed "consensus-based scoring" which compares candidate polypeptide sequences against a database of related polypeptide sequences to identify proteins with potentially low stability. As used herein "consensus-based scoring" refers to calculation of the number of non-consensus amino acids within a protein (e.g., a test protein) based on the information available from sequence compilations of related proteins. The calculation results in a "consensus score" for the protein. As shown in the Examples infra, the consensus score of a protein is highly correlative with its empirically-determined protein stability. Accordingly, an object of the invention is to employ consensus-based scoring to predict protein stability. The greater the deviation of a test protein sequence from a consensus sequence, the higher the consensus score, and the more likely the test protein is to contain amino acids detrimental to its stability.

In the novel consensus scoring approach described herein, the following basic steps are taken to predict the stability of a candidate or test protein:
1. Providing a set of homologous sequences (herein, a "reference set") corresponding to a sequence of a domain (or portion thereof) of the candidate protein (herein a "test domain sequence").
2. Determining the residue frequency at every residue position within the test domain sequence (or portion thereof) to obtain a consensus score.
3. Using the consensus score to predict the stability of the candidate or test protein.

In certain exemplary embodiments, the following optional steps are employed to increase the predictive value of the consensus score:
4. Determining the residue frequency at every corresponding residue position within every sequence of the reference set (or a subset thereof) obtain an average score.
5. Comparing the consensus score to the average consensus score to determine a sequence score.
6. Using the sequence score to predict the stability of the candidate or test protein.

Step 1: Providing a Reference Set

The consensus scoring based methods of the invention employ a set of sequences (a "reference set") which are homologous to (i.e., related to) a sequence of interest or "test sequence". The reference set may comprise a set of homologous sequences having moderate to high degrees of similarity with the test sequence.

The set of homologous sequences may be determined by one skilled in the art to include a suitable number of non-redundant sequences. The set of homologous sequences need not be large, as long as a reasonably unbiased selection is obtained. It is not the number of sequences, but the ratio of frequencies that is important.

Such sequences can be obtained through homology-based searches of any of the sequence databases known in the art (e.g. NCBI, TIGR databases). In an exemplary embodiment, a standard BLAST search with default parameters may be performed with the test sequence to retrieve homologous sequences of interest. Sequences with a minimum percentage of sequence identity (e.g. greater than 25%, 30%, 35%, 40%, 45% or 50% sequence identity, preferably greater than 30% sequence identity) may be selected for inclusion in the reference set. In certain embodiments, those sequences with a high degree of sequence identity (e.g., greater than 85%, 90%, 95%, or 98% sequence identity, preferably greater than 95% sequence identity) are excluded from the reference set to avoid bias.

In certain embodiments, the reference set may be curated to include only those sequences which satisfy one or more criteria for inclusion in the set. For example, in certain embodiments, the reference set may comprise ortholog sequences (e.g. sequences which are from different species (e.g., different mammalian species) but which have the same biochemical function). In other embodiments, the reference set comprises human sequences. In an exemplary embodiment, the set of homologous sequences includes only mammalian germline sequences. In preferred embodiments, the reference set includes sequences from proteins having the same class of protein fold (e.g. a similar protein domain) to the test protein (e.g. proteins having an immunoglobulin-type fold). Such proteins may be identified by bioinformatics techniques known in the art (e.g., be searching the Conserved Domain Database (CDD) of the National Institutes of Health).

Step 2: Determining the Consensus Score of the Test Sequence

Once the sequences of the reference set are compiled, the consensus sequence of the reference set is determined in order to facilitate the consensus scoring method of the invention. As used herein, the term "consensus sequence" refers to a sequence wherein the residue (e.g. amino acid residue) at each position within the sequence corresponds to the most common residue at that position in an aligned set of related sequences (i.e., the reference set).

To determine the consensus sequence, the sequences within the reference set may first be aligned using sequence alignment algorithms known in the art. A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5858-77. Such an algorithm is incorporated into the BLAST programs (version 2.0) of Altschul, et al. (1990) *J. Mol. Biol.* 215:403-10. In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

To determine the consensus sequence of the aligned set of references, the most frequently occurring residue at each position within the aligned set of references is determined. The consensus sequence may be determined visually or it may be determined by computational analysis using a publically available bioinformatics program (e.g., the EMBOSS CONS tool available from the Helix Systems of the National Institute of Health).

The consensus sequence is employed in the methods of the invention to determine a consensus score. In certain embodiments, a consensus score is a numerical value which equates the residue frequency or occurrence within the reference set of the consensus residue at each amino acid position in the consensus sequence (ie. the "consensus residue frequency") with the residue frequency or occurrence within the reference set of the amino acid at the corresponding position in the test sequence (ie. the "test residue frequency"). Residue frequencies at a position within the test or consensus sequence are calculated by summing the number of times the amino acid at that position is present at the corresponding position in the aligned reference set, and dividing the summed value by the total number of sequences within the reference set. In an exemplary embodiment, the consensus score at each amino acid position is calculated by dividing the test residue frequency by the consensus residue frequency to give a non-zero score of between 1 and 0. For example, a residue which is identical to the consensus amino acid at that position is assigned a perfect score of 1, while a consensus score approaches zero, the less common the amino acid is at that position.

In certain preferred embodiments, the consensus score may be summed for each position of the test sequence (or a portion thereof) to obtain a total consensus score. For example, a perfect total consensus score is the number of amino acids in the test sequence, indicating that the test sequence is identical to its corresponding consensus sequence.

An exemplary formula for calculating the total consensus score of a protein is set forth below:

$$\text{score} = \sum_i \frac{h_i(r)}{c_i(r)}$$

wherein $c_i(r)$ equals the consensus residue frequency at an amino acid position of the consensus sequence, $h_i(r)$ equals the test residue frequency of an amino acid position of the test sequence, and i equals the number of amino acid positions within the test sequence.

Step 3: Using the Consensus Score to Predict Protein Stability

The consensus score may then be employed to predict the stability of the test protein. In general, the higher the value of the consensus score, the greater the probability that the test protein will have adequate stability for its intended use. In certain embodiments, the consensus score of the test protein may be compared with the consensus score of a control sequence. In one exemplary embodiment, the control sequence is from a protein which is known to have poor or undesired stability properties (herein, a "negative control"). Accordingly, the test protein is predicted to have improved stability if its consensus score is higher than that of the negative control. In another exemplary embodiment, the control sequence is from a protein which is known to have desirable stability properties (herein, a "positive control"). Accordingly, the test protein is predicted to have improved stability if its consensus score is substantially similar or higher than that of the positive control. In other embodiments, the consensus score of the test sequence may be compared with its hypothetical perfect consensus score, a value which corresponds to the total number of amino acids in the test sequence.

Step 4: Determining the Average Consensus Score of the Reference Set

In certain embodiments, average consensus scores at some or all of the amino acid positions of the sequences within the reference set are determined for comparison with the consensus scores at corresponding positions within the test sequence. In preferred embodiments, the average total consensus score for the reference set is determined for comparison with the total consensus score of the of the test sequence. The average total consensus score for the reference set is the sum of the residue frequencies for all amino acid positions of a sequence within the reference set, divided by the total number of sequences in there reference set.

Step 5: Determining the Sequence Score

In certain embodiments, the sequence score is determined by comparing the average consensus score of the reference set with the consensus score of the test sequence. The differential of these values is the "sequence score" of the test sequence (also referred to herein as the "Δ score"). The sequence score may be determined by subtracting the consensus score from the average consensus score.

Step 6: Using the Sequence Score to Predict Protein Stability

The sequence score provides a measure of the deviation of the consensus score of the test sequence from the average consensus score of the reference set. The Examples infra demonstrate that the sequence score of a protein is highly correlated with the stability (e.g. thermal stability) of the protein. Accordingly, in certain embodiments, the sequence score may also be used to predict the stability of the protein. If the Δ score of the protein is a negative value (ie. the consensus score is lower than the average consensus score), the prediction would be that the stability of the protein of interest will have a lower stability than the majority of proteins within the reference set.

In certain embodiments, the test sequences employed in the methods of the invention are single-domain proteins. As used herein, a "single domain protein" is a protein comprising one or more domains, wherein each of the domains are of the same type (e.g. a variable heavy (VH) domain).

In other embodiments, the test sequences employed in the methods of the invention are multi-domain proteins. As used herein, a "multi-domain protein" is a protein comprising two or more domains, where at least two of the domains are of a different type. For example, antibodies are proteins typically comprising six domains (i.e., VH, VL, CL, CH1, CH2, and CH3). In preferred embodiments, the stability of the least stable domain of a multi-domain protein is predicted using the methods of the invention. The Examples infra demonstrate that the methods of the invention are particularly effective in predicting thermal stability when the least stable domain (or portion thereof) of a multi-domain protein (e.g. the VH domain of an antibody) is employed as a test sequence.

If the least stable domain is not known a priori, it can be determined using experimental methods that are known in the art (e.g. using any of the methods described supra, such as differential scanning calorimetry (DSC), temperature dependent circular dichroism (CD), or fluorescence measurements). Such methods allow for the determination of multiple thermal unfolding transitions where the least stable domain either unfolds first (see FIG. 69A) or limits the overall stability threshold of a multidomain unit that unfolds cooperatively (i.e. a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., *Fold. Des.*, 2: R17-26, 1997). Once the least stable domain is identified, the sequence encoding this domain (or a portion thereof) may be employed as a test sequence in the methods of the invention.

In certain exemplary embodiments, the multi-domain proteins evaluated using the methods of the invention are antibodies. The methods of the invention allow one skilled in the art to exclude the selection of inappropriate variable region domains from among the vast pool of variable region sequences created by the diversity mechanisms of the immune system. In exemplary embodiments, e.g., scFv molecules or antibody molecules comprising variable region (Fv) domains with a relatively high stability (e.g. thermal stability) may be identified using the methods of the invention, and selected. In other exemplary embodiments, human immunoglobulin variable region (Fv) domains having acceptable stability may be identified using the methods of the invention and selected for use as acceptor immunoglobulin chains in the humanization of an antibody. In other exemplary embodiments, the methods of the invention may be employed to screen candidate engineered antibody variable sequences (e.g., humanized VL or VH sequences) for appropriate stability before proceeding with the synthesis of a binding molecule comprising the candidate sequence.

As is known in the art, protein stability varies from one antibody to another based on the many possible variations in natural or engineered antibodies. For example, the selective pressure of the immune system to create diversity within the variable domains of natural antibody can negatively affect their stability or foldability in recombinant expression systems (Knappik and Pluckthun, *Protein Engng.*, 8: 81-89, (1995); Wall and Pluckthun, *Protein Engng*, 12: 605-11 (1999); Knappik et al., *J. Mol. Biol.*, 296: 57-86, (2000); Ewert et al., *J. Mol. Biol.*, 3325: 531-33, (2003)). Antibodies consisting of the same isotype and subclass, human IgG1 being the most commonly used for antibody therapeutics, vary in stability from one another primarily based on differences in their variable domains since the remainder of their sequences are identical. Thermal unfolding of antibody Fab fragments predominantly occurs in a single apparent transition. In most cases, the antibody Fv region limits the overall thermostability of the Fab except in the rare cases where Fv (or single $V_H$ or $V_L$) stability is extremely low or extremely high and the Fv unfolding transition is decoupled from that of the $C_H1/C_L$ region (Shimba, et al., 1995; Röthlisberger et al., 2005).

In certain embodiments, the methods of the invention employ a variable region sequence of an antibody as a test sequence. In certain preferred embodiments, the methods of the invention employ the heavy chain variable domain (VH) (or a portion thereof) as a test sequence. The Examples infra demonstrate that the VH domain is highly predictive of the stability of an antibody comprising said domain.

In certain embodiments, the variable domain test sequence is compared with a reference set comprising, or consisting solely of, variable domain sequences. Said variable domain sequences may be compiled from the Kabat database of immunoglobulin sequences (Kabat et al., "Distribution Files of the Fifth Edition of Sequences of Proteins of Immunological Interest", 1992). In certain preferred embodiments, the reference set may comprise or consist of human immunoglobulin sequences.

In other preferred embodiments, the reference set may comprise, or consist solely of, human germline sequences. In one embodiment, the reference comprises variable domain sequences from the same Kabat subclass of antibody sequences.

In other embodiments, a portion of variable domain (e.g. VH domain) is used as a test sequence in the methods of the invention. An exemplary variable domain portion is a sequence comprising less than all of the framework regions or CDRs of the variable region sequence (e.g. a VH sequence that is truncated to remove CDR3 and FR4). In one embodiment, the VH domain sequences are of the $V_H1$ Kabat germline subclass. In another embodiment, the variable domain sequences are of the $V_H2$ Kabat germline subclass. In another embodiment, the variable domain sequences are of the $V_H3$ Kabat germline subclass. In another embodiment, the variable domain sequences are of the $V_H4$ Kabat germline subclass. In another embodiment, the variable domain sequences are of the $V_H5$ Kabat germline subclass. In another embodiment, the variable domain sequences are of the $V_H7$ Kabat germline subclass.

The methods of invention may be employed with proteins known in the art. In one embodiment, the protein is an antibody or portion thereof. In certain embodiments, the antibody is a humanized antibody. In other embodiments, the antibody is a human antibody. In other embodiments, the antibody is a non-human antibody (e.g., mouse monoclonal antibody). In other embodiments, the antibody is a single-domain antibody (e.g., camelid, shark, human). In yet other embodiments, the antibody is a chimeric antibody. Other exemplary modified antibodies for use in the methods of the invention include domain-deleted antibodies and bispecific binding molecules. Other exemplary antibodies include the scFv-containing antibodies or modified antibodies described supra. In preferred embodiments, the stability of the aforementioned binding proteins is evaluated using a heavy chain variable sequence thereof (or portion thereof) as the test sequence in the methods of the invention.

In one embodiment, of the invention, the data obtained for a given polypeptide are stored or outputted as a measure of the stability of the polypeptide. In one embodiment, the methods described herein can be repeated for a plurality of polypeptides. In one embodiment, a selection of a polypeptide may be made based on the data obtained. In another embodiment, a selected polypeptide may be formulated for therapeutic use.

IV. Methods for Designing/Producing Proteins with Enhanced Biophysical Properties (e.g., Protein Stability)

(a) Covariation Design

In another aspect, the invention provides methods for designing protein variants with an enhanced biophysical property relative to the parent molecule from which it is derived using the results of a covariation analysis. There are many types of protein engineering efforts where covariation data may be used to facilitate design, including but not limited to enhanced protein stability designs, modification of pH unfolding profiles, stable removal of glycosylation, and alteration of biochemical function.

In certain embodiments, the invention provides methods for designing proteins with enhanced stability designs based on the identification of covariation scores (or covariations themselves) that are predictive of enhanced or reduced protein stability according the method of Section III supra. For example, if a sequence belonging to the protein of interest is missing or violates several key covariations, protein designs can be made to correct for this. Modifications can also be included which improve the calculated number of strong covariations observed within a single sequence.

A number of designs have been developed for stabilizing the BHA10 scFv $V_H$ and $V_L$ domains. In particular, initial library screening results for two scFv BHA10 domains validate the ability of the Covariation Analysis Tool for protein stability design. The first example involves the successful prediction of a stabilizing mutation (S46L) within the BHA10 $V_L$ domain that imparts a significant improvement in thermal stability ($\Delta T_{50}$ of +10° C.) as measured by a thermal challenge assay. Mutation from Ser to Leu at position 46 (Kabat numbering system) leads to a positive connection to an existing Tyr at residue 36 which the Tool shows covaries strongly with Leu 46 (FIG. 78). A second example of the utility of the Covariation Analysis Tool is the analytical agreement of the negative effects of a BHA10 $V_H$Q6E mutation. Single residue frequency analysis suggested that mutation to the much more commonly observed Glu at this position would lead to an increase in stability. However, the Covariation Analysis Tool indicated that single mutation to Glu violates several existing covariations present within the BHA10 $V_H$ sequence. To obtain an improvement in stability one must replace several amino acids that preferentially stabilize Glu at this position.

Another example of the predictive value of the Covariation Analysis Tool is shown in FIG. 79. Met 80 was mutated to Leu as part of a single residue library design. It was thought that this single mutation would be highly stabilizing, as Leu is the most frequent amino acid observed at this position within the sequence database. However, covariation analyses indicate that two other amino acids must be mutated (V67F and T70S) in order to achieve covariation harmony.

(b) Interface Design

In yet other aspects, the invention provides methods for enhancing a biophysical property (e.g., protein stability) of a second or candidate protein (e.g., an antibody) using a first protein as a template protein for rational design.

As used herein, the term "template protein", refers to a protein with a desirable biophysical property (e.g., high protein thermal stability) which is used to model the same property in a second protein for an improvement of the biophysical property is also desirable. In preferred embodiments, the template protein is of the same structural class as the second protein (e.g., if the second protein is an antibody, an antibody is employed as a template protein).

In certain embodiments, the template protein is identified as having desirable biophysical property (e.g., protein stability) according to a method of the invention. In one exemplary embodiment, the template protein with desirable stability properties may have been identified from a group of proteins (Such as BIIB1-4, described in Table 20, supra) using experimental methods such as those described in Example 15. This template protein would then serve as a sequence platform for design. In one exemplary embodiment, the template protein is predicted to have an improved biophysical property (e.g, protein stability) by a covariation analysis method of the invention outlined supra. In other exemplary embodiments, the template protein is predicted to be a desirable protein (e.g., a stabilized protein) according to a consensus scoring method as outlined supra. In yet another exemplary embodiment, the template protein is identified according to a screening method of the invention.

In other embodiments, the template protein is a protein designed according to a method of the invention. In one exemplary embodiment, the template protein is designed to have an improved biophysical property (e.g., enhanced protein stability) according to a covariation method of the invention. In another exemplary embodiment, the template protein is designed to have an improved biophysical property according a consensus scoring method.

The methods of this aspect of the invention involve the following steps:

(1) providing structural models of the template protein and the candidate protein;

(2) identifying residues in the template protein that are important for stability; and (3) substituting residues in the candidate protein that correspond to the important residues template protein.

In one embodiment, the template protein structural model is a crystal structure (e.g., an X-ray crystal structure) and the candidate protein is modeled by homology modeling using the structural model of the template protein.

In another embodiment, an important residue is a VH/VL interface residue. As used herein, an "interface residue" is a residue that participates in domain-domain interactions within or among proteins. Preferably, an interface residue resides at the boundary, i.e., the "interface" between two protein domains and contributes its surface area to at least one of the domains (preferably both). The residues that bury significantly more surface area than others at the interface, i.e., the residues which do not expose significantly more of their surface area to the surface of the folded protein, are considered to be more crucial to interface stability. The surface area that each residue contributes to the interface can be determined using art-recognized techniques (e.g., analysis using MOLMOL software). In certain embodiments, the interface residue buries at least 10 $Å^2$ of surface area (e.g, 10 $Å^2$, 15 $Å^2$, 20 $Å^2$, 25 $Å^2$ or more of buried surface area).

Residues of the candidate protein located at amino acid positions corresponding to those of the important residues (e.g., buried interface residues) of the template protein are preferably substituted if they are of a non-identical type. In certain embodiments, only non-conservative substitutions are made. In other embodiments, only conservative substitutions are made.

In exemplary embodiments, the template and candidate proteins are binding molecules (e.g., antibodies or variants thereof (e.g. scFv molecules)). In one embodiment, the interface that is examined is that between one Fc domain (e.g., hinge, CH2, and CH3) and another Fc domain. In another embodiment, the interface is that formed between the $V_H$ domain and the $V_L$ domain.

In preferred embodiments, the designs are focused on the interface between the VH and VL domains of an antibody. Biophysical data (see DSC data—Example 15) suggest that the affinity of VH and VL for one another is marginal in the scFv format (i.e. in the absence of the CH1 and CL domains of the Fab). In particular, VH and VL interactions are not always strong enough (i.e. do not have sufficient affinity to lead to a cooperatively folded single entity. Therefore, improving the stability of the VH/VL interface (ie. increasing the affinity between the VH and VL domains) may be a preferred route to enhancing antibody/scFv stability. By stabilizing the interface, the folding transition of antibody can be turned into a single event, raise the affinity of the domains for one another, and allowing for less dynamic fluctuations that may lead to exposed hydrophobic surface area (as observed by ANS-binding experiments).

In yet other embodiments, the designs may be validated using diffluential scanning calorimetry (DSC) experiments which allow one skilled in the art to non-quantitatively observe real affinity increases between the VH and VL.

(c) Combined Covariation and Interface Design

In yet other aspects of the invention, two or more of the sequence based design tools described herein may be employed for the design of optimized protein variants. In one exemplary embodiment, interface design is employed together with covariation analysis to determine residues or residue positions which are important for protein structure and function, including, for example, protein stability. In one exemplary embodiment, covariation analysis is used to determine residues or residue positions outside an interface (herein, termed "scaffolding residues") that do not physically interact with the interface residues on the opposing domain or contribute surface area to the interface, but are nonetheless important for providing proper structural context for interface residues. For example, covariation analysis may be conducted on residues located within the interface to identify scaffolding residues which covary with the interface residues. Preferably, interface residues which bury a high degree of surface area (e.g., residues that bury at least 40 $Å^2$ of surface area) are selected for covariation analysis. Scaffolding residues which covary with the selected interface residues are then identified using the covariation methods of the invention. Preferably, scaffolding residues which strongly covary (e.g., phi-value of at least 0.25) are selected. In another preferred embodiment, scaffolding residues are selected if they covary with at least two interface residues (e.g., 2, 3, 4, 5, 6, 7, 8, 9, 10 or more interface residues). The greater the number of covariations, the higher the covariation score may be attributed to the scaffolding residue, since the number of covariations is predictive of the contribution made by the scaffolding residue to stabilization of the VH/VL interface.

The methods of this aspect of the invention involve the following steps:
(1) providing structural models of a template protein and a candidate protein;
(2) identifying interface residues (e.g., VH/VL) in the template protein that are important for stability;
(3) identifying scaffolding residues which covary with the interface residues of step (2), e.g., using the Covariation Analysis Tool described herein;
(4) substituting one or more interface residues or scaffolding residues in the candidate protein with the corresponding residues or scaffolding residues identified in steps (2) and (3).

Residues of the candidate protein located at amino acid positions corresponding to those of the important residues (e.g., interface or scaffolding residues) of the template protein are preferably substituted if they are of a non-identical type. In certain embodiments, only non-conservative substitutions are made. In other embodiments, only conservative substitutions are made.

In one embodiment, of the invention, the improved sequence of a given polypeptide is stored or outputted. In another embodiment, a selected polypeptide may be formulated for therapeutic use.

V. Systems, Interfaces, and Computer-Implemented Methods

One aspect of the invention pertains to methods (e.g., computer-implemented methods), apparatus, and software for implementing the selection or design methods of the invention. In exemplary embodiments, the invention provides a computer-implemented method and apparatus for identifying amino acid residues (e.g., covariant amino acid residues) in a candidate sequence. In another embodiment, the invention provides computer-implemented methods and apparatus for ranking one or more test or candidate sequences by a score (e.g., a consensus score or covariation score) which is predictive of a biophysical property (e.g., protein stability, catalytic activity, therapeutic activity, resistance to a pathogen or toxin, toxicity, etc).

The computer implemented methods aspect may be described by the following sequence of operations: (a) receiving data (e.g., sequence or structural data) characterizing a reference set and a test sequence; (b) from the data, calculating a score (e.g., a covariation score or consensus score); (c) ranking the scores to identify one or more sequences or amino acid residues of interest.

In some embodiments, the scores are ranked to identify one or more amino acid residues that are to remain fixed in the test or candidate sequence. In other embodiments, the scores are ranked to identify one or more amino acid residues which are candidates for substitution. In one exemplary embodiment, the computer-implemented method ranks residue positions (or specific residues at certain positions) in order of covariation score. In another exemplary embodiment, the computer implemented method ranks candidate sequences in order of consensus score.

Yet another aspect of the invention pertains to apparatus and machine-readable media on which are provided program instructions and/or arrangements of data for implementing the methods described above. Frequently, the program instructions are provided as code for performing certain method operations. Data, if employed to implement features of this invention, may be provided as data structures, database tables, data objects, or other appropriate arrangements of specified information. Any of the methods or systems of this invention may be represented, in whole or in part, as such program instructions and/or data provided on machine-readable media.

The computer-implemented methods of the invention may include an output device that displays information to a user (e.g., a CRT display, an LCD, a printer, a communication device such as a modem, audio output, and the like). In addition, instructions (e.g. an algorithm) for carrying out the calculation, in part or in whole, can be conferred to a medium suitable for use in an electronic device for carrying out the instructions. Thus, the methods of the invention are amenable to a high throughput approach comprising software (e.g., computer-readable instructions) and hardware (e.g., computers, robotics, and chips). The computer-implemented process is not limited to a particular computer platform, particular processor, or particular high-level programming language.

In certain embodiments, the calculations used in the methods of the invention are carried out by a computer algorithm suitable for use with a computer programming language (e.g. PERL). In exemplary embodiments, the computer algorithm is designed to recognize (i) a sequence alignment of a reference set and/or (ii) one or more test sequences as input for the algorithm.

(i) Computer-Implemented Consensus Scoring

In one aspect of the invention pertains to computer-implemented methods, apparatus, and software for conducting the consensus scoring method of the invention described supra using a computer-implemented algorithm. In exemplary embodiments, the algorithm is designed to perform one or more of the following steps: (1) cutting out each residue position of the alignment as a column and calculating the consensus residue frequency at that position; (2) cutting off each residue position of the test sequence(s) and calculating the test residue frequency at that position, and (3) dividing the test residue frequency by the consensus residue frequency to give a consensus score; and/or (4) summing the consensus score at each position to give a total consensus score. In other embodiments, the algorithm may be designed to perform one or more of the following additional steps: (5) calculating the average consensus score of the reference set, and/or (6) the sequence score of the test sequence.

These aspects of the invention are also embodied in a system for conducting the consensus scoring method of the invention. The system includes (a) a computer that includes a database capable of storing at least one population of reference sets, and (b) system software. The system software includes one or more logic instructions for conducting any of steps (1)-(6) of the computer-implemented consensus scoring method.

The invention also provides a computer program product for conducting the consensus scoring method of the invention. The computer program product includes a computer-readable medium having one or more logic instructions for conducting any of steps (1)-(6).

(ii) Computer-Implemented Covariation Analysis

Another aspect of the invention pertains to computer-implemented methods for conducting the covariation analysis method of the invention as described supra using a computer-implemented algorithm. In exemplary embodiments, the methods perform one or more of the following steps: (1) cutting out each residue position of the aligned set as a column; (2) arranging columns in a matrix; (3) calculating correlation among various columns in the matrix to derive a correlative term; (4) adding correlative terms to linear terms, which correspond to amino acid residues, to generate an expanded predictor matrix; (5) generating a heuristically-derived model (e.g. a hidden Markov model) from the expanded predictor matrix to identify important correlations.

These aspects of the invention are also embodied in a system for conducting the covariation analysis method of the invention. The system includes (a) a computer that includes a database capable of storing at least one population of character string libraries, and (b) system software. The system software includes one or more logic instructions for conducting any of steps (1)-(5) of the computer-implemented method covariation scoring method.

The invention also provides a computer program product for conducting the covariation scoring method of the invention. The computer program product includes a computer-readable medium having one or more logic instructions for conducting any of steps (1)-(5).

(iii) Graphical User Interfaces for Covariation Analysis

In certain exemplary aspects, the invention provides a novel graphical user interface (GUI) for use with the covariation methods of the invention. This covariation analysis tool, termed NAPMAP, assists the user in visualizing covariations in the context of aligned set of sequences. The novel graphical user interface is computer implemented using art-recognized programming languages (e.g. in Java 1.4.2 utilizing the Processing library from processing.org).

(a) Grid Layouts

In one aspect, the graphical user interface of the invention comprises a graphical depiction of an alignment (e.g., a sequence alignment created according to the methods of the invention supra) or data corresponding thereto. A simple form of this display is the grid layout. As used herein, the term "grid layout" (also known as an alignment platform) refers to a matrix in which the properties of an alignment are represented. In one embodiment, the grid layout graphically represents residue positions of the sequences of an alignment. In another embodiment, the grid layout graphically represents residue types of sequences within the alignment. In another embodiment, the grid layout graphically represents the frequency of residue types (or "residue usage frequency") within the alignment. In yet other embodiments, the grid layout represents one or more properties of residues within the alignment (e.g., hydrophobicity, charge, size, pKa, etc.).

In certain exemplary embodiments, the grid layout comprises a representative display of (i) contiguous residue positions corresponding to a sequence of the alignment; and (ii) residue usage frequencies for residue types at each residue position of the alignment sequence. In one embodiment, the residue usage frequency is symbolically depicted (e.g., by a circle or square). In other embodiments, all 20 natural amino acids, gaps, and ambiguous residues are represented. In certain embodiments, the residue positions are displayed in rows and the residue usage frequencies are displayed in columns. In certain embodiments, the residue positions are displayed in columns and the residue usage frequencies are displayed in rows.

Figure 76:
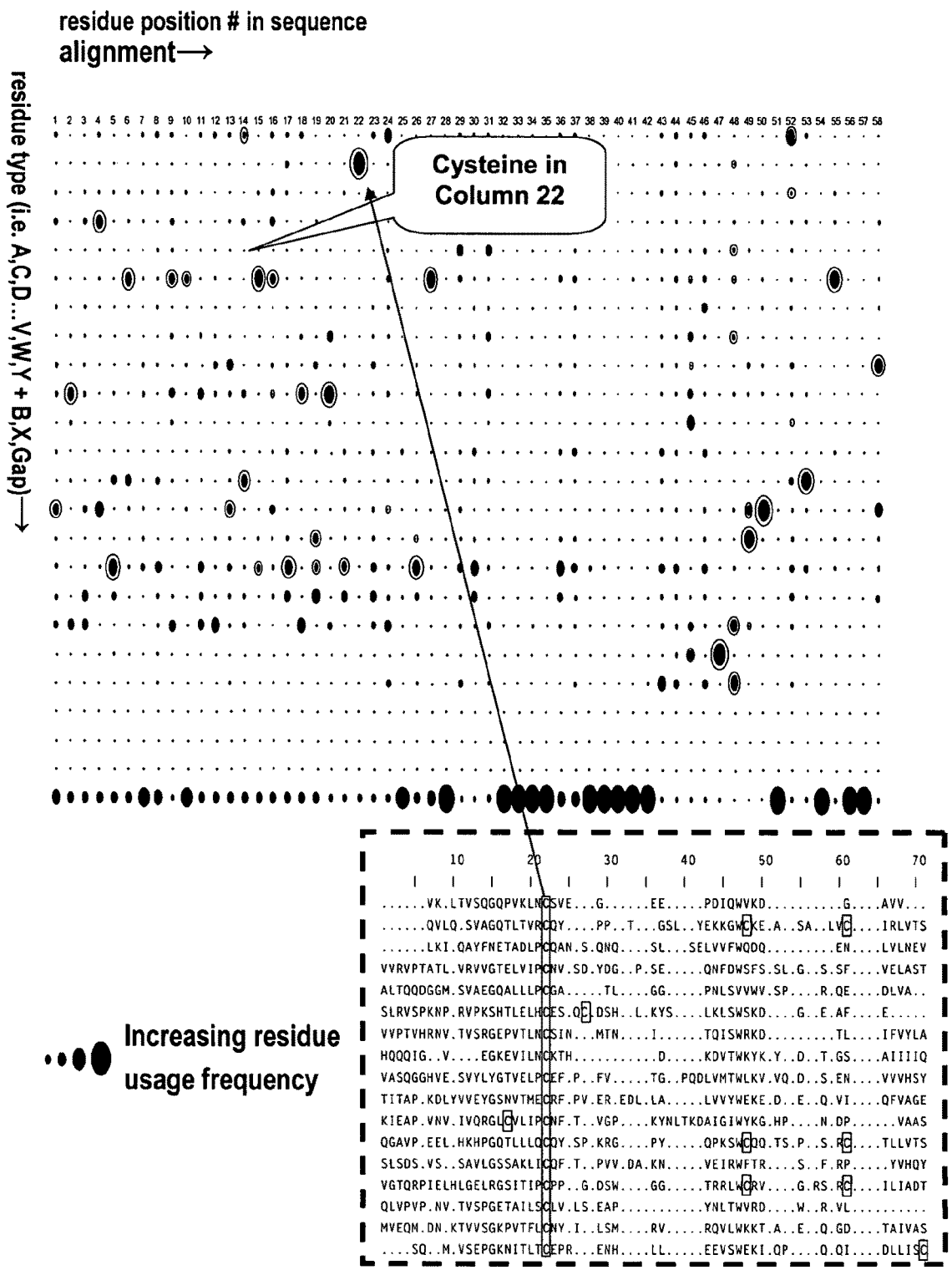
FIG. 76 shows the output of the NAPMAP Visual Tool which includes a portion of the alignment platform on which the covariation analysis is overlayed. The platform displays columns containing all of the amino acids including gaps (residue type) for each position within the V region (residue position #).

In one embodiment, the residue use frequency is correlated (e.g., positively or negatively correlated) with symbol size (e.g., size of circle), so that more conserved residues can be discriminated from less frequently observed residues. For example, residue frequency may be represented as circles of various sizes with circle area proportional to the frequency of its usage. The radius of each circle (R) may be used for drawing the node using an ellipse function calculated according to the following formula (IV)

$$R = \sqrt{\frac{A \cdot \frac{N}{M}}{\pi}} \quad (IV)$$

wherein:
A=desired average area of all nodes
N=number of sequences using this residue
M=the average number of sequences using each residue In an exemplary embodiment, the grid layout comprises a matrix of contiguous columns and rows wherein (i) contiguous columns graphically represent corresponding contiguous residue positions of the alignment; (ii) each of the contiguous rows graphically represent a specific amino acid type; and (iii) the residue usage frequency at each residue position is graphically represented in each cell of the matrix. Preferably all residue types (e.g., all 20 amino acids and/or possible gaps) are represented by a separate row in the grid layout. More preferably, residue usage frequency at each residue position of the alignment is graphically represented in each cell of the matrix with a symbol (e.g., a circle) whose size is correlated (e.g., positively correlated) with residue usage frequency. An exemplary grid layout is depicted in FIG. 76.

(b) Covariation Overlays

In other aspects, the graphical user interface of the invention comprises a graphical depiction of one or more covariations (e.g., covariations identified according to the methods of the invention supra) or data corresponding thereto.

In certain embodiments, the graphical user interface of the invention comprises graphical depicts of both (i) a grid layout; and (ii) one or more covariations. In these embodiments, the grid layout may serve as alignment platform for the display of covariation data. Covariation data may be displayed, for example, by overlaying the grid layout with covariation data. Covariation data arranged in this fashion are termed a "covariation overlay". For example, covariations may be depicted in the covariation overlay as lines or network of lines connecting two or more covarying amino acids that are graphically depicted within the grid layout.

Figure 77:
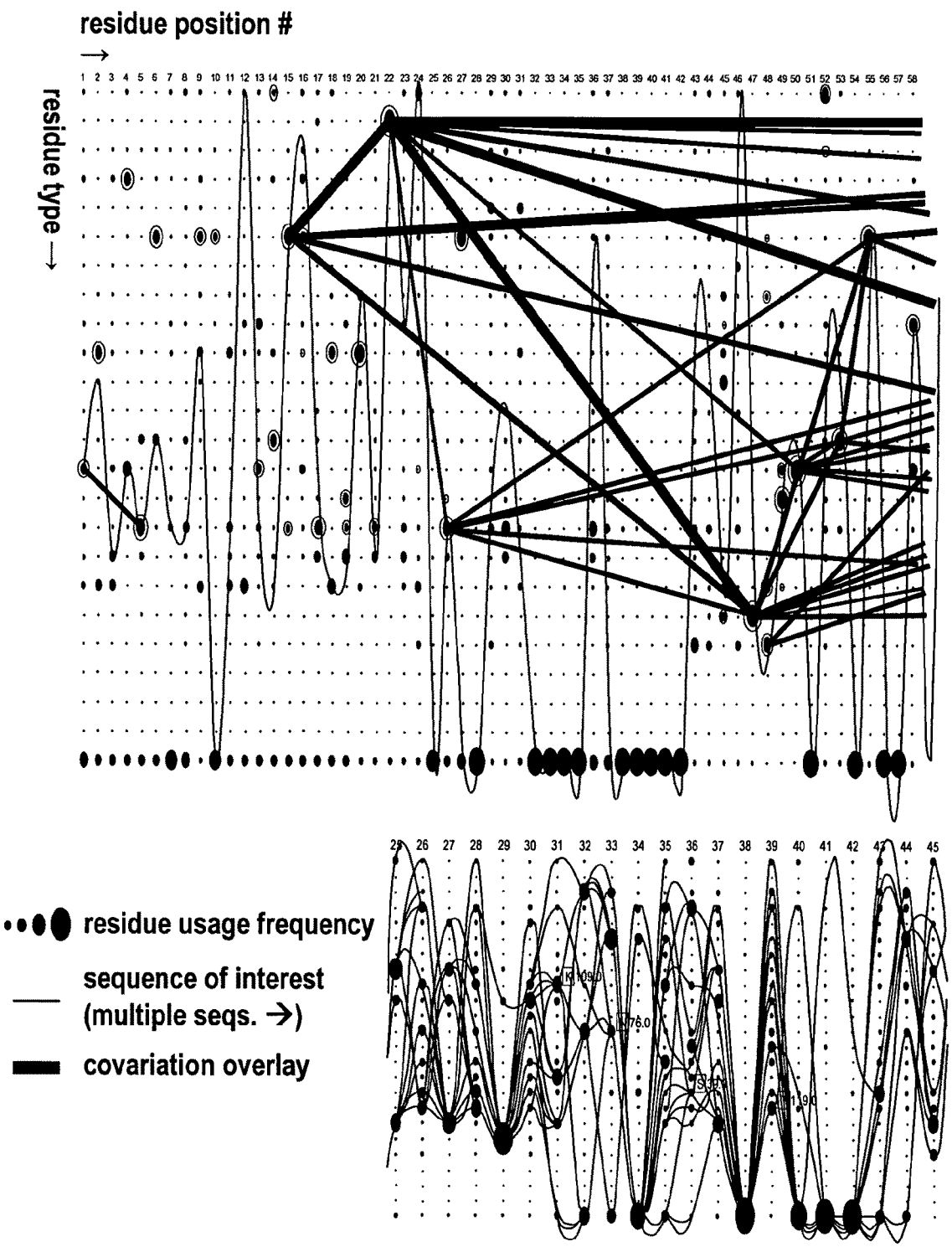
FIG. 77 depicts an overlay of Ig-Fold covariation statistics onto the NAPMAP template. The sequence of interest is shown as a curved line through the relevant amino acids. Covariations are shown as straight bars between the relevant covarying amino acid residues.

The lines of the covariation overlay may be of various thicknesses (e.g., thin lines or bars) or continuities (e.g., dashed or solid, straight or jagged), so long as the connection between two or more covarying amino acids is apparent to the user (see, e.g., FIG. 77, wherein covariations are depicted as semi-transparent bars that connect two covarying amino acids). In certain exemplary embodiments, the graphical representation of the covariation may further represent the statistical significance of the covariation (e.g., its $\phi$ or $\chi^2$-value). In one exemplary embodiment, the thickness of a line within the covariation overlay may be proportional to the statistical significance of the covariation. For example, the line thickness of the covariation overlay may be drawn in proportion to $\phi$ value according to formula V:

$$W=1+(M \cdot \Phi^N) \quad \quad (V)$$

wherein:
W=line thickness
$\Phi$=phi (correlation coefficient)
N=exaggeration multiplier
M=max line thickness In another exemplary embodiment, positive and negative covariations may be graphically discriminated from each other (e.g., by different colored lines or thicknesses). In yet other exemplary embodiments, only covariations above a certain threshold level of statistical significance are displayed to the user. For example, in certain embodiments, $\phi$ value cutoffs may be applied to view only covariations with desired correlation strengths.

(c) Sequence Traces

In other optional aspects, the graphical user interface comprises a graphical depiction of a sequence of interest to aid with possible protein design efforts. The sequence of interest may be the test or candidate sequence (ie., an input sequence) or it may be a sequence in which desirable covariations are integrated (ie., an output sequence). The sequence of interest may be graphically represented as a line.

In one embodiment, the graphical interface comprises both (i) a depiction of a sequence of interest; and (ii) a grid layout (e.g., the sequence of interest is superimposed on the grid layout). In another embodiment, the graphical interface comprises both (i) a depiction of a sequence of interest; and (ii) a covariation overlay (e.g., the sequence of interest is superimposed on the covariation overlay). In yet other embodiments, the graphical interface comprises (i) a depiction of a sequence of the interest; (ii) a covariation overlay; and (iii) a grid layout (e.g., the sequence of interest is superimposed (e.g., traced) on the covariation overlay which is in turn superimposed on the grid layout).

A sequence of interest may be displayed on a grid layout, for example, as a curve connecting adjacent amino acids that are graphically depicted within the grid layout. A sequence of interest displayed in this fashion is termed a "sequence trace". In preferred embodiments, the sequence trace should pass or thread through only one cell (or graphical representation of an amino acid type) for a particular row or column of the grid layout that represents a particular residue position. More preferably, the sequence trace passes through the cell which graphically represents the residue type occurring at a particular residue position within the sequence of interest. The sequence trace may pass though every cell of the grid layout that represent a residue within the sequence of interest, or it may pass through only the cells that represent a portion of the sequence of interest. An exemplary sequence trace of a sequence of interest is depicted in FIG. 77. Sequence traces depicted therein (catmull-rom splines) were drawn using a bezier function. Given two nodes to draw a sequence transition bezier curve, the node pair's previous and next nodes are used as anchor points and the two nodes themselves are used as the first and second control points. For nodes in the first column (representing the first residues of amino acid sequences), the first control point doubles as its anchor point; for nodes in the last column, its second control point double as its anchor point.

In preferred embodiments, the sequence trace plot is rendered interactive for manipulation by the user. For example, the cells within the grid layout (representing can be rendered interactive for selection by the user. In one embodiment, the selected cell can be assigned a particular selection state (e.g., a positive, neutral, or negative selection state). In one exemplary embodiment, a cell representing a particular residue can be positively selected by the user so that the sequence trace can be retraced to pass though the selected cell. For example, if a cell is positively selected by the user, multiple sequence traces can be generated for all sequences of interest (e.g., all sequences within the reference set or alignment) that employ the residue represented by the positively selected cell. In an alternative embodiment, a cell representing a particular residue can be negatively selected by the user so that the sequence trace does not pass through the selected cell. Accordingly, sequence traces can be generated for every sequence of interest (e.g., all sequences within the reference set or alignment) that excludes the residue represented by the negatively selected cell.

Multiple sequences of interest can be graphically displayed, so long as they can be distinguished by the user (e.g., using different line thicknesses or continuities). For example, to compare different sequence alignments, sequences traces representing multiple sequences of interest from two or more alignments can be overlaid on the grid layout (e.g., with different colors, preferably opposing colors) to enable visualization of differential residue usage on a global scale.

(d) Display Modes

The graphical user interface may facilitate any art-recognized functionality. For example, in certain embodiments, the graphical user interface may be capable of panning or zooming on different portions of the grid layout. For example, the viewport size of the grid layout can be changed depending on the user's computer screen resolution and visualization can be zoomed out or panned for viewing an alignment that does not fit in the view port initially.

In preferred embodiments, data masking is employed, for example, to emphasize the most important covariation pairs and/or networks across several pairs. The graphical user interface of the invention may employ one or more display modes for the viewing of covariations (e.g., statistically-significant covariations). Preferably, said display modes are available in an interactive plot when viewing a sequence trace of a sequence of interest. Exemplary Viewermodes are as follows:

Viewermode #1: Only covariations between residues that are also present in the sequence of interest are displayed.

These covariations can be thought of as hypothesized residue-residue interactions (e.g., those found by statistical residue pair frequency analysis) that hold the corresponding protein molecule together and may be important for function.

Viewermode #2: The only covariations displayed are those between residue pairs having only one residue of the residue pair present in the sequence of interest. These covariations are residue-residue interactions that tend to be conserved but are not present in the sequence of interest, and whose absence may be detrimental to protein stability. This viewermode is particularly preferred when the Covariation Analysis Tool is employed for protein design (see Section IV supra).

Viewermode #3: The only covariations displayed are those between residue pairs having neither amino acid member of the covarying pair present in the sequence of interest.

In certain embodiments, all viewermodes are displayed to the user but each in a unique display format. In another embodiment, all viewermodes are separately displayed (e.g., in separate display windows).

Figure 89:
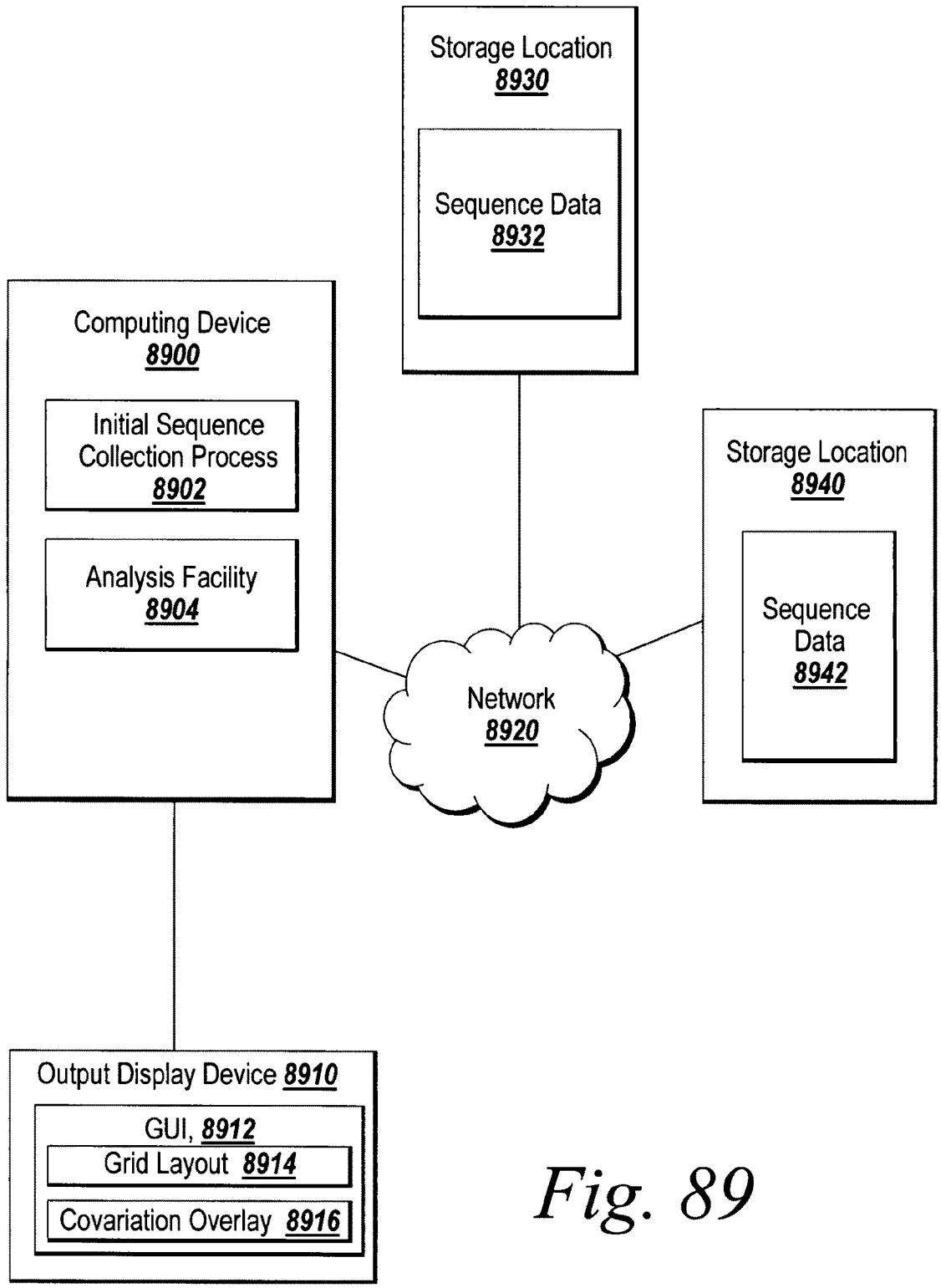
FIG. 89 depicts an exemplary environment suitable for practicing an embodiment of the invention.

FIG. 89 depicts an exemplary environment suitable for practicing an embodiment of the invention. A computing device 8900 supports an initial sequence collection process 8902 and analysis facility 8904. The computing device 8900 may be a workstation, server, laptop, mainframe, PDA or other computing device equipped with one or more processors and able to support the initial sequence collection process 8902 and analysis facility 8904. The computing device 8900 may have a single processor or multiple processors and each of the processors may have one core or multiple cores. The analysis facility 8904 is implemented in software and programmatically analyzes covariation between pairs of residues within alignment to obtain covariation data. The computing device 8900 is in communication with, and outputs data to, an output display device 8910. The Output display device 8910 displays a graphical user interface (GUI) 8912 generated by the analysis facility 8904. The GUI 8912 may include a grid layout 8914 and a covariation overlay 8916. The computing device 8900 may also be in communication over a network 8920 with one or more storage locations 8930 and 8940 that respectively hold sequence data 8932 and 8942. The initial sequence collection process 8902 programmatically retrieves candidate sequences from the sequence data 8932 and 8942 based on user-supplied and/or pre-determined parameters. The retrieved sequence data is analyzed by the analysis facility 8904. It will be appreciated by those skilled in the art that although the initial sequence collection process 8902 and analysis facility 8904 are depicted separately in FIG. 89, they may be implemented as part of an integrated application, process or plug-in. Similarly, it should be appreciated that the initial sequence collection process 8902 and analysis facility may each separately be a task, thread, process, application or plug-in. The computing device 8900 may communicate over the network 8920 with the storage locations 8930 and 8940 using a number of different mediums and configurations. For example, the network 8920 may be arranged as a Local Area Network (LAN), a Wide Area Network (WAN), an intranet, the Internet, and/or may be a wireless network and/or a telephone line, or some other type of network allowing the computing device 8900 to communicate with the storage locations 8930 and 8940. The storage locations 8930 and 8940 may be databases or some other type of storage datastructure hosted by computing devices that are accessible over the network 8920. It should be noted that although components of the present invention are depicted in a particular configuration in FIG. 89, other component configurations are also possible within the scope of the present invention. For example, the initial sequence collection process 8902 and analysis facility 8904 may be located on separate computing devices and/or the sequence data 8932 and 8942 may be located on one or more databases hosted by the computing device 8900.

Figure 90:
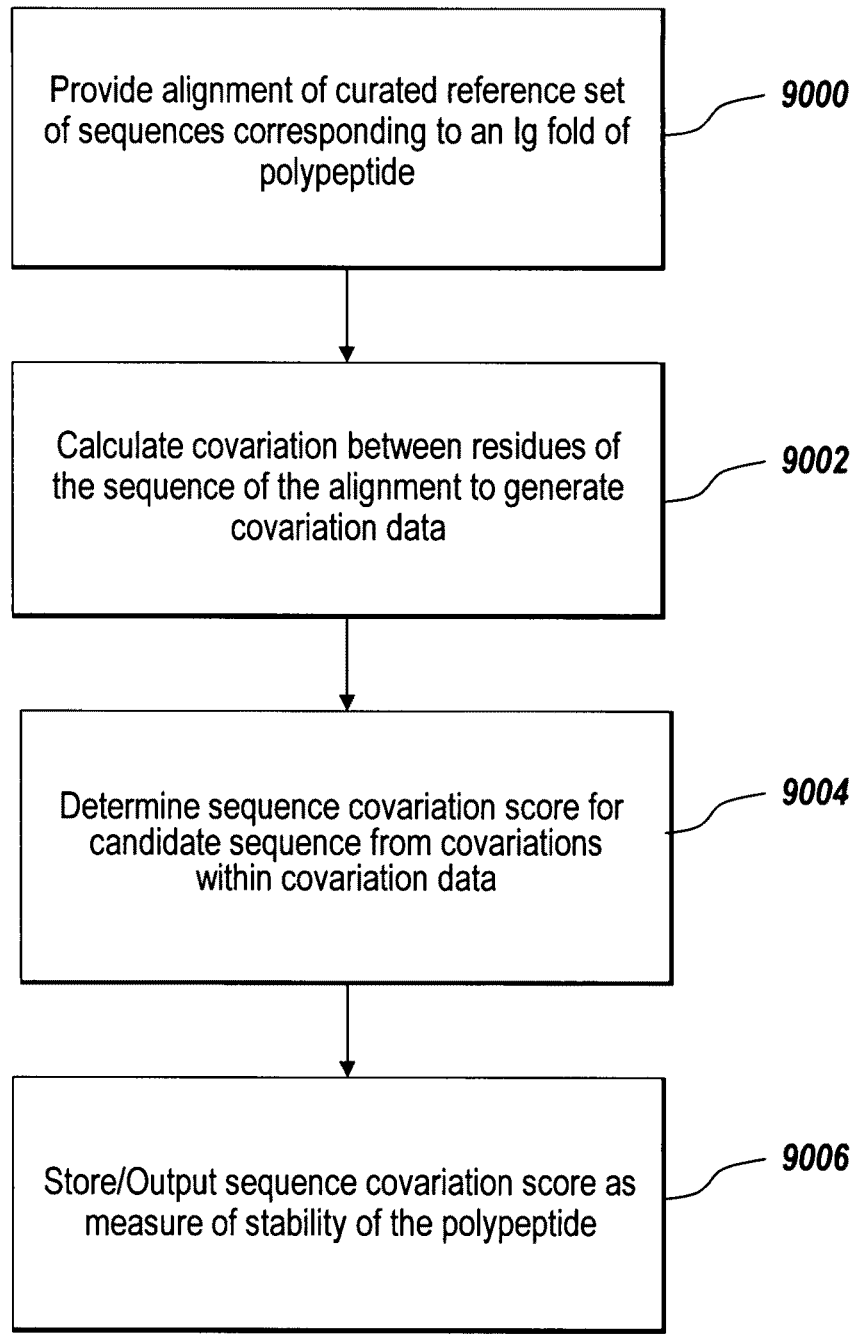
FIG. 90 is a flowchart of an exemplary sequence of steps that may be followed by an embodiment of the invention in order to determine a sequence covariation score that may be used as a measure of the stability of a polypeptide.

FIG. 90 is a flowchart of an exemplary sequence of steps that may be followed by an embodiment of the invention in order to determine a sequence covariation score that may be used as a measure of the stability of a polypeptide. The sequence begins with the initial sequence collection process 8902 providing alignment of a curated reference set of sequences corresponding to an Ig fold of a polypeptide (step 9000). The analysis facility 8904 then calculates covariation between residues of the sequence of the alignment as described herein to generate covariation data (step 9002). The analysis facility 8904 uses the covariation data to determine a sequence covariation score for a candidate sequence from covariations within the covariation data (step 9004). The determined sequence covariation score provides an indicator of the measure of stability of the polypeptide and may be stored and/or output to a user via the GUI 8912 or in some other manner (step 9006).

Figure 91:
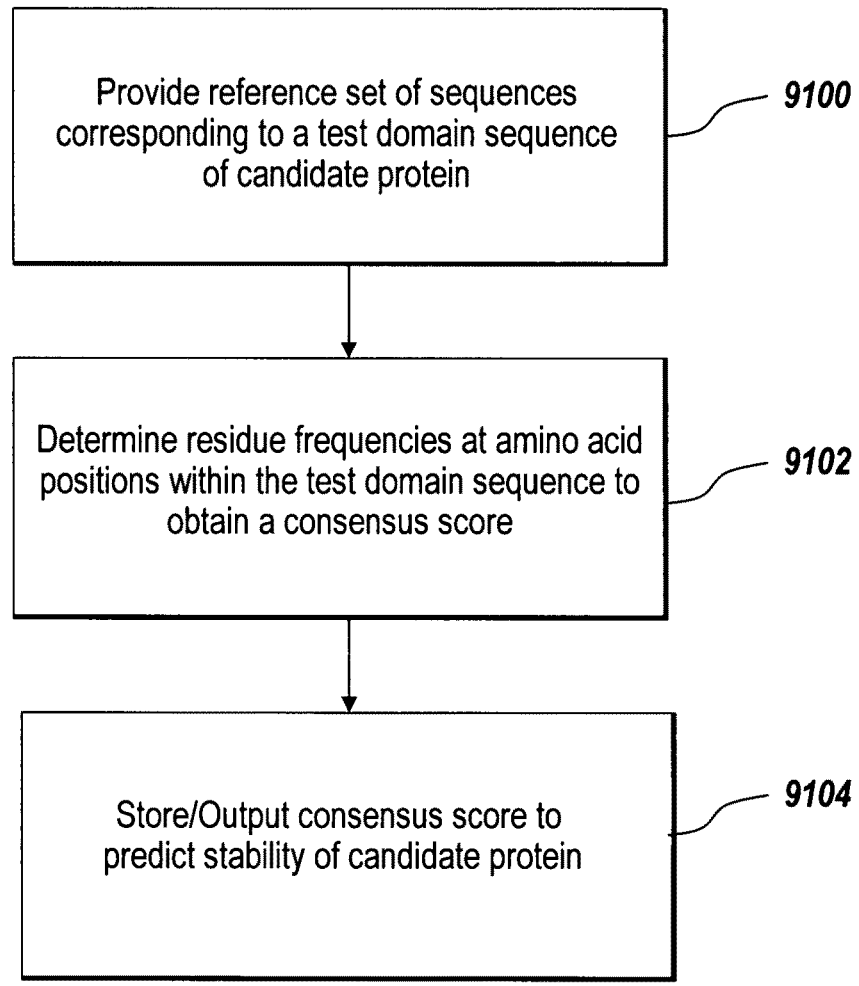
FIG. 91 is a flowchart of an exemplary sequence of steps that may be followed by an embodiment of the invention in order to determine and use a consensus score to predict the stability of a candidate protein.

As noted above, the analysis facility 8904 may also be used to determine a consensus score. FIG. 91 is a flowchart of an exemplary sequence of steps that may be followed by an embodiment of the invention in order to determine and use a consensus score to predict the stability of a candidate protein. The sequence begins by using the initial sequence collection process 8902 to provide a reference set of sequences corresponding to a test domain sequence of a candidate protein (step 9100). The analysis facility 8904 then determines residue frequencies at amino acid positions within the test domain sequence to obtain a consensus score (step 9102). The determined consensus score may then be stored and/or output to a user to provide a prediction of the stability of the candidate protein (step 9104).

Figure 92:
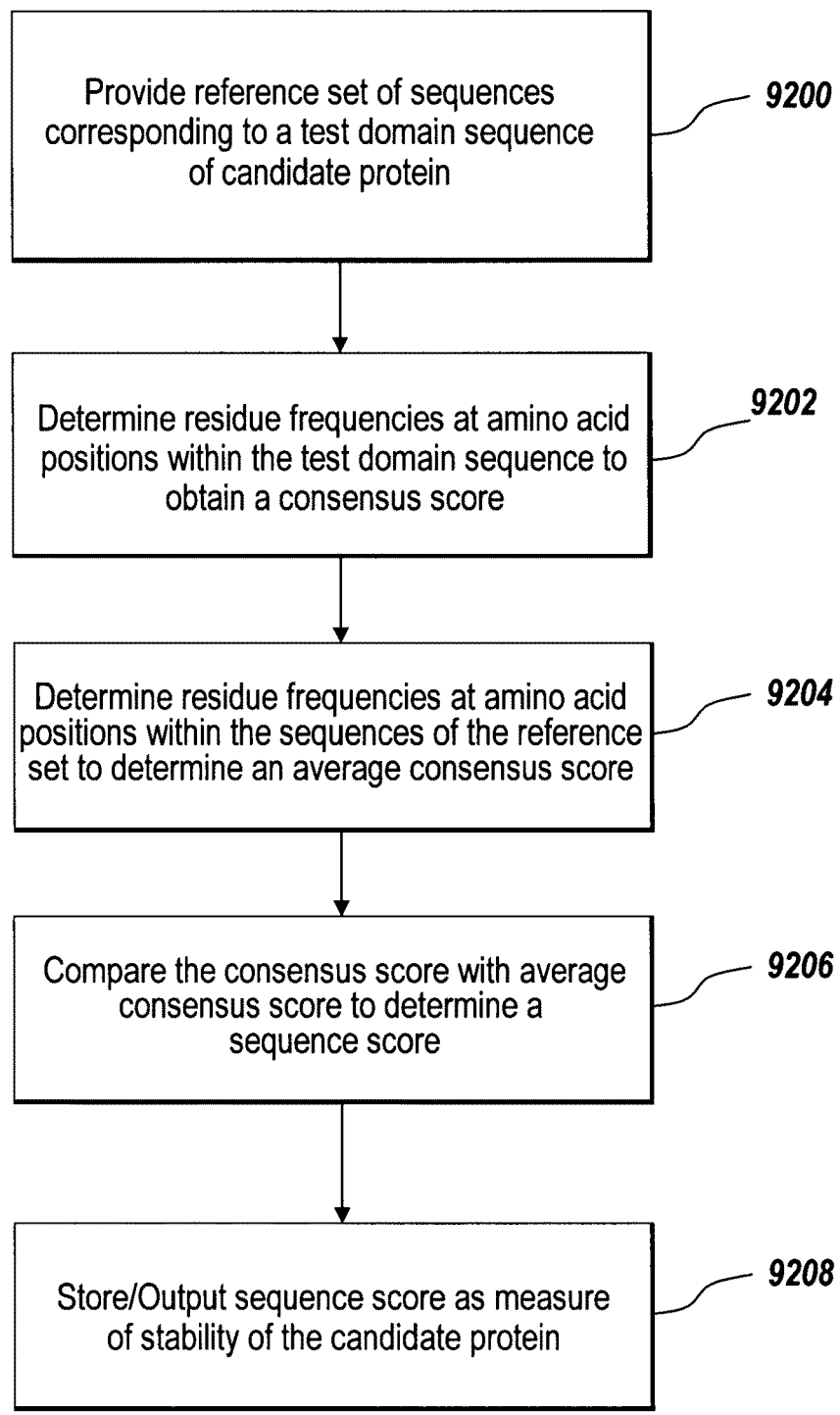
FIG. 92 is a flowchart of an exemplary sequence of steps that may be followed by an embodiment of the invention in order to determine and use an average consensus score as a measure of the stability of a candidate protein.

The analysis facility 8904 may also be used to determine an average consensus score. FIG. 92 is a flowchart of an exemplary sequence of steps that may be followed by an embodiment of the invention in order to determine and use an average consensus score as a measure of the stability of a candidate protein. The sequence begins by using the initial sequence collection process 8902 to provide a reference set of sequences corresponding to a test domain sequence of a candidate protein (step 9200). The analysis facility 8904 then determines residue frequencies at amino acid positions within the test domain sequence to obtain a consensus score (step 9202). The analysis facility 8904 also determines residue frequencies within the sequences of the reference set to determine an average consensus score (step 9204). The consensus score is compared with the average consensus score in order to determine a sequence score (step 9206) and the determined sequence score may then be stored and/or output to a user to provide a prediction of the stability of the candidate protein (step 9206).

Figure 93:
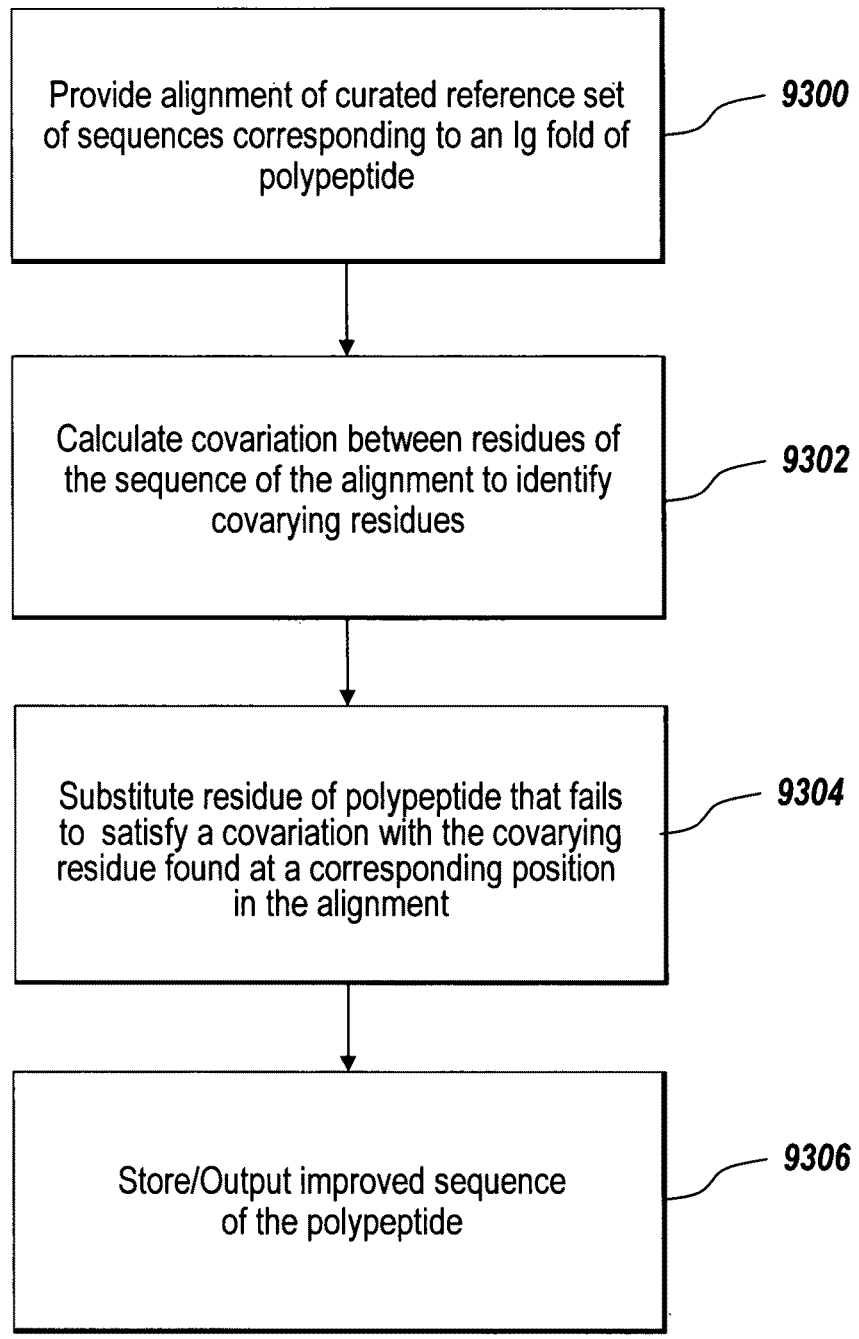
FIG. 93 is a flowchart of an exemplary series of steps that may be followed by an embodiment of the invention in order to use a substitute residue of a polypeptide to determine an improved sequence of the polypeptide.

FIG. 93 is a flowchart of an exemplary series of steps that may be followed by an embodiment of the invention in order to identify and substitute an amino acid residue that fails to satisfy a covariation with the covarying residue found at a corresponding position in the alignment to determine an improved amino acid sequence of the polypeptide. The sequence begins by the initial sequence collection process 8902 providing alignment of a curated reference set of sequences corresponding to an Ig fold of a polypeptide (step 9300). The analysis facility 8904 then calculates covariation between residues of the sequence of the alignment to identify covarying residues (step 9302). The analysis facility 8904 may identify a particular residue of the polypeptide that fails to satisfy a covariation and may substitute a covarying residue found at a corresponding position in the alignment (step 9304) in order to improve the sequence of the polypeptide. The improved sequence may then be stored or output to a user (step 9306).

The present invention may be provided as one or more computer-readable programs embodied on or in one or more mediums. The mediums may be a floppy disk, a hard disk, a compact disc, a digital versatile disc, a flash memory card, a PROM, an MRAM, a RAM, a ROM, or a magnetic tape. In general, the computer-readable programs may be implemented in any programming language. Some examples of languages that can be used include FORTRAN, C, C++, C#, Python or Java. The software programs may be stored on or in one or more mediums as object code. Hardware acceleration may be used and all or a portion of the code may run on a FPGA, an ASIP, or an ASIC. The code may run in a virtualized environment such as in a virtual machine. Multiple virtual machines running the code may be resident on a single processor.

VI. Methods of Evaluating Protein Stability

The stability properties of the compositions of the invention can be analyzed using methods known in the art. Stability parameters acceptable to those in the art may be employed. Exemplary parameters are described in more detail below. In exemplary embodiments, thermal stability is evaluated. In preferred embodiments, the expression levels (e.g., as measured by % yield) of the compositions of the invention are evaluated. In other preferred embodiments, the aggregation levels of the compositions of the invention are evaluated.

In certain embodiments, the stability properties of a composition of an invention are compared with that of a suitable control. Exemplary controls include conventional scFv molecule. A particularly preferred control is a $(Gly_4Ser)_3$ scFv molecule.

In one embodiment, one or more parameters described below are measured. In one embodiment, one or more of these parameters is measured following expression in a mammalian cell. In one embodiment, one or more parameters described below are measured under large scale manufacturing conditions (e.g., expression of scFvs or molecules comprising scFvs in a bioreactor).

a) Thermal Stability

The thermal stability of the compositions of the invention may be analyzed using a number of non-limiting biophysical or biochemical techniques known in the art. In certain embodiments, thermal stability is evaluated by analytical spectroscopy.

An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, *J. Biotechnol.*, 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

In other embodiments, the thermal stability of a composition of the invention is measured biochemically. An exemplary biochemical method for assessing thermal stability is a thermal challenge assay. In a "thermal challenge assay", a composition of the invention is subjected to a range of elevated temperatures for a set period of time. For example, in one embodiment, test scFv molecules or molecules comprising scFv molecules are subject to an range of increasing temperatures, e.g., for 1-1.5 hours. The activity of the protein is then assayed by a relevant biochemical assay. For example, if the protein is a binding protein (e.g. an scFv or scFv-containing polypeptide of the invention) the binding activity of the binding protein may be determined by a functional or quantitative ELISA.

In one embodiment, such an assay may be done in a high-throughput format. In another embodiment, a library of scFv variants may be created using methods known in the art. scFv expression may be induced an scFvs may be subjected to thermal challenge. The challenged test samples may be assayed for binding and those scFvs which are stable may be scaled up and further characterized.

In certain embodiments, thermal stability is evaluated by measuring the melting temperature (Tm) of a composition of the invention using any of the above techniques (e.g. analytical spectroscopy techniques). The melting temperature is the temperature at at the midpoint of a thermal transition curve wherein 50% of molecules of a composition are in a folded state.

In other embodiments, thermal stability is evaluated by measuring the specific heat or heat capacity (Cp) of a composition of the invention using an analytical calorimetric technique (e.g. DSC). The specific heat of a composition is the energy (e.g. in kcal/mol) required to raise by 1° C., the temperature of 1 mol of water. As large Cp is a hallmark of a denatured or inactive protein composition. In certain embodiments, the change in heat capacity ($\Delta Cp$) of a composition is measured by determining the specific heat of a composition before and after its thermal transition. In other embodiments, thermal stability may be evaluated by measuring or determining other parameters of thermodynamic stability including Gibbs free energy of unfolding ($\Delta G$), enthalpy of unfolding ($\Delta H$), or entropy of unfolding ($\Delta S$).

In other embodiments, one or more of the above biochemical assays (e.g. a thermal challenge assay) is used to determine the temperature (ie. the $T_C$ value) at which 50% of the composition retains its activity (e.g. binding activity).

b) % Aggregation

In certain embodiments, the stability of a composition of the invention is determined by measuring its propensity to aggregate. Aggregation can be measured by a number of non-limiting biochemical or biophysical techniques. For example, the aggregation of a composition of the invention may be evaluated using chromatography, e.g. Size-Exclusion Chromatograpy (SEC). SEC separates molecules on the basis of size. A column is filled with semi-solid beads of a polymeric gel that will admit ions and small molecules into their interior but not large ones. When a protein composition is applied to the top of the column, the compact folded proteins (ie. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition of the invention can be determined by comparing the concentration of a fraction with the total concentration of protein applied to the gel. Stable compositions elute from the column as essentially a single fraction and appear as essentially a single peak in the elution profile or chromatogram.

In preferred embodiments, SEC is used in conjunction with in-line light scattering (e.g. classical or dynamic light scattering) to determine the % aggregation of a composition. In certain preferred embodiments, static light scattering is employed to measure the mass of each fraction or peak, independent of the molecular shape or elution position. In other preferred embodiments, dynamic light scattering is employed to measure the hydrodynamic size of a composition. Other exemplary methods for evaluating protein stability include High-Speed SEC (see e.g. Corbett et al., Biochemistry. 23(8):1888-94, 1984).

In a preferred embodiment, the % aggregation is determined by measuring the fraction of protein aggregates within the protein sample. In a preferred embodiment, the % aggregation of a composition is measured by determining the fraction of folded protein within the protein sample.

c) % Yield

In other embodiments, the stability of a composition of the invention is evaluated by measuring the amount of protein that is recovered (herein the "% yield") following expression (e.g. recombinant expression) of the protein. For example, the % yield can be measured by determining milligrams of protein recovered for every ml of host culture media (ie. mg/ml of protein). In a preferred embodiment the % yield is evaluated following expression in a mammalian host cell (e.g. a CHO cell).

d) % Loss

In yet other embodiments, the stability of a composition of the invention is evaluated by monitoring the loss of protein at a range of temperatures (e.g. from −80 to 25° C.) following storage for a defined time period. The amount or concentration of recovered protein can be determined using any protein quantification method known in the art, and compared with the initial concentration of protein. Exemplary protein quantification methods include SDS-PAGE analysis or the Bradford assay for (Bradford, et al., *Anal. Biochem.* 72, 248, (1976)). A preferred method for evaluating % loss employs any of the analytical SEC methods described supra. It will be appreciated that % Loss measurements can be determined under any desired storage condition or storage formulation, including, for example, lyophilized protein preparations.

e) % Proteolysis

In still other embodiments, the stability of a composition of the invention is evaluated by determining the amount of protein that is proteolyzed following storage under standard conditions. In an exemplary embodiment, proteolysis is determined by SDS-PAGE a sample of the protein wherein the amount of intact protein is compared with the amount of low-molecular weight fragments which appear on the SDS-PAGE gel. In another exemplary embodiment, proteolysis is determined by Mass Spectrometry (MS), wherein the amount of protein of the expected molecular weight is compared with the amount of low-molecular weight protein fragments within the sample.

f) Binding Affinity

In still other embodiments, the stability of a composition of the invention may be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

g) Other Binding Studies

In yet other embodiments, the stability of a composition of the invention may be assessed by quantifying the binding of a labeled compound to denatured or unfolded portions of a binding molecule. Such molecules are preferably hydrophobic, as they preferably bind or interact with large hydrophobic patches of amino acids that are normally buried in the interior of the native protein, but which are exposed in a denatured or unfolded binding molecule. An exemplary labeled compound is the hydrophobic fluorescent dye, 1-anilino-8-naphthaline sulfonate (ANS).

VII. Methods for Selecting Stable Proteins

The methods described supra for the prediction of protein stability can be employed to select a candidate protein (e.g. antibodies) for further use. In certain embodiments, the methods of the invention are employed to select a protein for expression. In other embodiments, the methods of the invention are used to select a candidate protein for modification. In exemplary embodiments, the prediction methods of the invention can be employed in the humanization of a non-human donor antibody (e.g. to select an acceptor immunoglobulin).

A candidate protein may be selected based on its total consensus score or sequence score as determined using the methods of the invention. In certain embodiments, the candidate protein is selected if its consensus score is greater than a suitable negative control (e.g. greater than 5%, preferably greater than 10%, more preferably greater than 20%). In other embodiments, the candidate protein is selected if its consensus score is substantially similar to (e.g. within 20%, 10%, or 5%) or greater than (e.g. greater than 5%, preferably greater than 10%, more preferably greater than 20%) a suitable positive control.

In other embodiments, a candidate protein is selected if its consensus score is substantially similar to its ideal or perfect consensus score (e.g. within 30%, preferably within 20%, more preferably within 10%).

In other embodiments, a candidate protein is selected if its sequence score is greater than zero. In one embodiment, the candidate protein is selected if its sequence score is greater than 0.5. In another embodiment, the candidate protein is selected if its sequence score is greater than 1. In other embodiment, the candidate protein is selected if its sequence score is greater than 2. In a preferred embodiment, the candidate protein is selected if its sequence score is greater than 3.

In other embodiments, a candidate protein is selected if its A score is at least −3, at least −2, or at least −1, preferably at least 0, more preferably at least 1.

a. Selecting an Acceptor Immunoglobulin for Antibody Humanization

Humanized antibodies can be produced using recombinant DNA technology, see for example, e.g., Queen et al., *Proc. Natl. Acad. Sci. USA*, (1989), 86:10029-10033; Jones et al., *Nature*, (1986), 321:522-25; Riechmann et al., *Nature*, (1988), 332:323-27; Verhoeyen et al., *Science*, (1988), 239: 1534-36; Orlandi et al., *Proc. Natl. Acad. Sci. USA*, (1989), 86:3833-37; U.S. Pat. Nos. 5,225,539; 5,530,101; 5,585,089; 5,693,761; 5,693,762; 6,180,370. When a preferred nonhuman donor antibody has been selected for humanization, an appropriate human acceptor antibody may be obtained, e.g., from sequence databases of expressed human antibody genes, from germline Ig sequences or a consensus sequence of several human antibodies. The substitution of nonhuman CDRs into a human variable domain framework is most likely to result in retention of their correct spatial orientation if the human variable domain framework adopts the same or similar conformation to the nonhuman variable framework from which the CDRs originated. This is achieved by obtaining the human variable domains from human acceptor antibodies whose framework sequences exhibit a high degree of sequence identity with the nonhuman variable framework domains from which the CDRs were derived. The heavy and light chain variable framework regions can be derived from the same or different human antibody sequences. Preferably the human acceptor antibody retains the canonical and interface residues of the donor antibody. Additionally, the human acceptor antibody preferably has substantial similarity in the length of CDR loops. See Kettleborough et al., *Protein Engineering* 4:758 (1991); Kolbinger et al., *Protein Engineering* 6:971 (1993) and Carter et al., WO 92/22653.

Having identified the CDRs of the donor antibody and appropriate human acceptor antibody, the next step is to determine which, if any, residues from these components should be substituted to optimize the properties of the resulting humanized antibody. Typically, some or all of the amino acids of the nonhuman, donor immunoglobulin light or heavy chain that are required for antigen binding (e.g., one or more CDRs) are used to substitute for the corresponding amino acids from the light or heavy chain of the human acceptor antibody. The human acceptor antibody retains some or all of the amino acids that are not required for antigen binding. When necessary, one or more residues in the human framework regions can be changed to residues at the corresponding positions in the murine antibody so as to preserve the binding affinity of the humanized antibody to the antigen. This change is sometimes called "back mutation." Certain amino acids from the human variable region framework residues are selected for back mutation based on their possible influence on CDR conformation and/or binding to antigen.

In some cases, however, the humanization process results in unnatural changes to the variable domain which confers undesirable instability to the humanized antibody. For example, the acceptor immunoglobulin may have rare sequence variations that confer low stability. This is particularly true of certain germline sequences which may not be used with great frequency by the immune system.

The methods of the invention provide improved methods for humanization. In particular, the methods of the invention allow the skilled artisan to predict which test sequence (e.g. test germline sequence) with a reference set of candidate acceptor sequences (e.g. germline sequences) are suitably stable for use in the humanization of the acceptor sequence. Test acceptor sequences (e.g. germline sequences) which have a score that is predictive of acceptable stability (e.g. have a high consensus score as compared to the average consensus score of the reference set) may be selected as an acceptor immunoglobulin.

VIII. Library Based Methods for Identifying Stabilized scFv molecules

In another aspect, the present invention provides methods of identifying scFv molecules with improved protein stability, e.g. improved thermal stability. The methods of the invention comprise (i) providing a library comprising candidate scFv molecules; and (ii) screening the library to identify candidate scFv molecules with improved protein stability relative to a suitable control (e.g. a control scFv molecule). As used herein, a "candidate scFv molecule" is an scFv molecule formed by introducing one or more candidate stabilizing mutations into the scFv molecule, wherein the effect of the candidate stabilizing mutation on the stability of the scFv molecule is not known a priori, i.e., an scFv molecule into which a mutation has been introduced and which has to be evaluated to determine whether the mutation results in an scFv molecule with increased stability. In one embodiment, a candidate scFv molecule is one formed by introducing one or more candidate stabilizing mutations into a conventional (ie. non-stabilized) scFv molecule. In another embodiment, a candidate scFv molecule is one formed by introducing one or more candidate stabilizing mutations into one of the stabilized scFv molecules described in Section II, supra.

By a "library of candidate scFv molecules" herein is meant at least two non-redundant candidate scFv molecules, with at least about 10 being preferred, at least about 100 being particularly preferred, and at least about 1000 being especially preferred (e.g. at least about $10^4$, $10^5$, $10^6$, $10^7$, or $10^8$ scFv molecules). In one embodiment, the library is randomized, with unspecified mutations generated randomly at any position. In another embodiment, the scFv library is a partially randomized or designed. That is, a specified amino acid residue or class of amino acid residues is introduced randomly at any position of the scFv, or a specified amino acid position is selected for mutagenesis with an unspecified amino acid, a particular class of amino acids, or a specified amino amino acid. In a preferred embodiment, an scFv library is designed by substituting a selected residue of an scFv molecule with an amino acid of a defined class, for example, a hydrophobic amino acid, a basic amino acid, a hydrophilic amino acid, a charged amino acid, a sterically biased (either small or large) amino acid, or a cysteine capable of disulfide bond formation.

In certain embodiments, the scFv library comprises candidate scFv molecules with candidate stabilizing mutation(s) that are introduced within a variable region (VL and/or VH) of the scFv molecule. In other embodiments, the scFv library comprises candidate scFv molecules with candidate stabilizing mutation(s) that are introduced within an scFv linker of the scFv molecule. In other embodiments, the scFv library comprises candidate scFv molecules with candidate stabilizing mutation(s) that are introduced within an scFv linker of the scFv molecule and candidate stabilizing mutation(s) that are introduced within a variable region (VL and/or VH).

a. Design of scFv Libraries

Methods for designing the scFv library may be aided by molecular or computational modeling. In certain embodiments, library design may be carried out in silico. In certain embodiments, the scFv library may be designed by the following two-step method:

1) identifying target amino acid residues in the scFv that when altered by a mutation (e.g, by amino acid substitution), are predicted to result in improved scFv stability (herein "candidate destabilizing residues"); and
2) substituting the target amino acid residues with candidate stabilizing amino acid residues.

Step #1: Identifying Candidate Destabilizing Residues

In certain embodiments, candidate destabilizing amino acid residues may be identified by sequence-based analysis. For example, candidate destabilizing amino acid residues may be identified by comparing a variable region sequence of an scFv with a reference set of variable region sequences, e.g. variable region sequences from naturally-occurring human antibodies, and selecting those variable region amino acid residues of the scFv which are unusual or rare at their corresponding amino acid positions within the reference set. In preferred embodiments, only the framework regions of a variable region sequence of the scFv are analysed, while the complementarity determining regions (CDRs) of the variable region are conserved in order to avoid disrupting the binding activity of the scFv molecule.

In certain embodiments, a candidate destabilizing amino acid residue is one which is absent or found at a low frequency at a corresponding position within a reference set of homologous variable region sequences. Methods for compiling reference sets are described in Sections III-V, supra. In preferred embodiments, the candidate destabilizing amino acid residue is one which is present within less than 10% of the sequences at corresponding positions within the reference set. In more preferred embodiments, the candidate destabilizing amino acid residue is one which is present within less than 5% of the sequences at corresponding positions within the reference set. In particularly preferred embodiments, the candidate destabilizing amino acid residue is one which is present within less than 2% (e.g. 0.5%, 0.75%, or 1%) of the sequences at corresponding positions within the reference set.

In another embodiment, a candidate destabilizing amino acid residue is one which differs from the amino acid present at the corresponding position in a consensus sequence of the reference set of variable region sequences (ie. the consensus amino acid residue). Methods for determining the consensus sequence of the reference set are described in Section III and V, supra.

In another embodiment, a candidate destabilizing amino acid residue is one which has a low consensus score. Methods for determining a consensus score of an amino acid are described in Section III and V, supra. In one embodiment, the candidate destabilizing amino acid residue is one with a consensus score of less than 0.5 (e.g. less than 0.4, less than 0.3, less than 0.2, or less than 0.1). In a preferred embodiment, the candidate destabilizing amino acid residue is one with a consensus score of less than 0.3.

Step #2: Selection of Candidate Stabilizing Mutations

Having identified one or more candidate destabilizing amino acids, the next step is to select one or more candidate stabilizing mutations for each destabilizing amino acid. The scFv library may then be designed to include a representative candidate scFv molecule for each candidate stabilizing mutation that is selected.

In certain embodiments, every natural amino acid variant of a particular destabilizing amino acid is selected as a candidate stabilizing mutation (ie. 19 candidate stabilizing mutations for every destabilizing amino acid).

In more preferred embodiments, a subset of the natural amino acid variants of a particular destabilizing amino acid are selected as candidate stabilizing mutations (ie. 1-18 candidate stabilizing amino acids for every destabilizing amino acid). In one embodiment, the subset of candidate stabilizing mutations comprise substitutions with an amino acid of a defined class, for example, hydrophobic amino acids, basic amino acids, hydrophilic amino acids, charged amino acids, or sterically biased amino acids (either small or large) amino acids.

In one embodiment, a subset of candidate stabilizing mutations include substitutions with amino acids which are present at high frequencies at a position corresponding to that of the destabilizing amino acid within a reference set of homologous variable region sequences. In preferred embodiments, a candidate stabilizing mutation comprises substitution with an amino acid that is present within the database at a frequency of greater than 10%. In more preferred embodiments, the amino acid is present at a frequency greater than 15%. In still more preferred embodiments, the amino acid is present at a frequency of greater than 20%. In yet more preferred embodiments, the amino acid is present at a frequency of greater than 25%.

In another embodiment, a candidate stabilizing mutation is a substitution with the consensus amino acid (ie. most frequent residue) found at the position of the destabilizing amino acid within the reference set.

In another embodiment, a subset of candidate stabilizing mutations comprise substitutions with every amino acid that is found within a reference set of homologous variable region sequences at the position of the destabilizing amino acid. Accordingly, an scFv library may then be designed to include a representative candidate scFv molecule for each candidate stabilizing mutation that is represented in the reference set.

In other embodiments, the subset of candidate stabilizing mutations may be identified or prioritized for screening by an analysis (e.g. visual inspection or computational analysis) of a three-dimensional structure or model of a variable region of the scFv molecule. The three-dimensional structure of a polypeptide influences its biological activity and stability, and that structure can be determined or predicted in a number of ways. Tertiary structure can be predicted using model building of three-dimensional structures of one or more homologous proteins (or protein complexes) that have a known three-dimensional structure. X-ray crystallography is perhaps the best-known way of determining protein structure (accordingly, the term "crystal structure" may be used in place of the term "structure"), but estimates can also be made using circular dichroism, light scattering, or by measuring the absorption and emission of radiant energy. Other useful techniques include neutron diffraction, nuclear magnetic resonance (NMR), and homology modeling. All of these methods are known to those of ordinary skill in the art, and they have been well described in standard textbooks (see, e.g., *Physical Chemistry*, 4th Ed., W. J. Moore, Prentiss-Hall, N.J., 1972, or *Physical Biochemistry*, K. E. Van Holde, Prentiss-Hall, N.J., 1971)) and numerous publications. Any of these techniques can be carried out to determine the structure of a molecule comprising a variable region of an scFv molecule (e.g. an antibody, a Fab, or an scFv molecule itself).

The structure of the variable region may be modeled in silico. For example, the compatability of a candidate stabilizing mutation with the three-dimensional structure may be analyzed by computationally modeling the substitution of a destabilizing mutation with a candidate stabilizing mutation. The candidate stabilizing mutation may be selected for inclusion in the scFv library if it is compatable with the overall structure of the scFv molecule. In one embodiment, the candidate stabilizing mutation may be selected if it does not perturb the native folding or conformation of the variable region of the scFv molecule or one or more complementarity determining regions (CDRs) thereof. In another embodiment, the candidate stabilizing mutation may be selected if it does not perturb the ability of the variable region to form a native VL/VH interface.

In certain embodiments, a candidate stabilizing mutation may be selected by applying a sidechain repacking technique to a structure (e.g. the crystal structure or model) of the variable region. In a sidechain repacking calculation, the candidate stabilizing residues can be modified computationally, and the stability of the resulting mutants is evaluated computationally. The sidechain repacking calculation generates a ranked list of the mutants that have altered stability (i.e., altered intramolecular energy). The number of protein mutants that is evaluated computationally can be very large, since every variable amino acid position can be mutated into all 20 standard amino acids. Exemplary computational algorithms used to rank the results of the computational analysis include dead-end elimination and tree search algorithms (see for example, Lasters et al. (*Protein Eng.* 8:815-822, 1995), Looger and Helling a Mol. Biol. 307:429-445, 2001), and Dahiyat and Mayo (*Protein Sci.* 5:895-903, 1996)). Accordingly, an scFv library may then be designed to include a representative candidate scFv molecule for each of the top-ranked candidate stabilizing mutations in the ranked list of mutations generated by the sidechain repacking calculation. In certain embodiments, at least the top ranked mutation is selected (e.g., the top ranked, the top two ranked, the top three ranked, the top four ranked, or the top five ranked mutations are selected).

b. Construction of scFv Libraries

Having determined the candidate stabilizing mutations to include in the scFv library, one can use any of a variety of available methods to produce candidate scFv molecules comprising the mutations. Such polypeptides can, for example, be produced by recombinant methods. Moreover, because of the degeneracy of the genetic code, a variety of nucleic acid sequences can be used to encode each desired scFv.

Exemplary art recognized methods for making a nucleic acid molecule encoding a candidate scFv molecule include, but are not limited to, preparation by site-directed (or oligonucleotide-mediated) mutagenesis, PCR mutagenesis, and cassette mutagenesis of an earlier prepared DNA encoding the candidate scFv.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the parent DNA is altered by first hybridizing an oligonucleotide encoding the desired mutation to a single strand of such parent DNA. After hybridization, a DNA polymerase is used to synthesize an entire second strand, using the hybridized oligonucleotide as a primer, and using the single strand of the parent DNA as a template. Thus, the oligonucleotide encoding the desired mutation is incorporated in the resulting double-stranded DNA, which may then be ligated into a plasmid or other suitable vector.

PCR mutagenesis is also suitable for making candidate scFv molecules. See Higuchi, in PCR Protocols, pp. 177-183 (Academic Press, 1990); and Vallette et al., *Nuc. Acids Res.* 17:723-583 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. The PCR primers may also be designed to incorporate restriction sites, such that the DNA product of the PCR reaction can be can then be directly ligated into a plasmid or other suitable vector.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the parent DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid.

Representative nucleic acids for each of the candidate scFv molecules may be generated by the above methods. The nucleic acids may then be cloned into expression vectors to form an expression vector library. Host cells may then be transformed with the resulting library of vectors, and the host cells cultured under the appropriate conditions in order to express each candidate scFv molecule.

c. Screening Methods

A scFv library the invention may be screened in an assay (e.g. a high-throughput assay) to identify candidate scFv molecules with desired protein stability. Such an assay may employ any of the methods for evaluating protein stability described in Section VI, supra. A particularly preferred method is a thermal challenge assay.

Such assay methods generally involve comparing the thermal stability of a candidate scFv molecule with that of a suitable control and selecting the candidate scFv molecule if the thermal stability is greater than that of the control. Exemplary suitable controls include conventional scFv molecules, e.g. a (Gly4Ser)$_3$ scFv molecule. Candidate scFv molecules are may be selected if they have a thermal stability that is greater than about 0.1, about 0.25, about 0.5, about 0.75, about 1, about 1.25, about 1.5, about 1.75, about 2, about 3, about 4, about 5, about 6, about 7, about 8, about 9, or about 10 degrees Celsius than that of the control. In an exemplary embodiment, a candidate scFv molecule is selected if it has a thermal stability than is greater than about 3 degrees Celsius than that of the control.

scFv Libraries may be presented in different assay formats. For example, scFv molecules may be presented in solution (e.g., Houghten (1992) *Biotechniques* 13:412-421), on beads (Lam (1991) *Nature* 354:82-84), chips (Fodor (1993) *Nature* 364:555-556), bacteria (Ladner U.S. Pat. No. 5,223,409), spores (Ladner USP '409), or on phage (Scott and Smith (1990) *Science* 249:386-390); (Devlin (1990) *Science* 249: 404-406); (Cwirla et al. (1990) *Proc. Natl. Acad. Sci.* 87:6378-6382); (Felici (1991) *J. Mol. Biol.* 222:301-310); (Ladner supra.).

In certain exemplary embodiments, the candidate scFv molecules are assayed in a solution format. In one embodiment, each sample comprises an aliquot of a solution having candidate scFv molecules with the same candidate stabilizing mutation or mutations. Such a solution can generated by isolating individual host cell colonies from a library of host cells transformed with expression plasmid library and culturing the host cell colony in an appropriate vessel under conditions which facilitate expression of the scFv molecule. In one embodiment, the candidate scFv molecule may be purified from the host cell and resolubilized in an appropriate assay solution. In a more preferred embodiment, the candidate scFv molecule is fused to a cleavable signal peptide sequence such that the scFv molecule is secreted by the host cell into the host cell culture medium. In yet other preferred embodiments, the host cell may be cultured under conditions such that candidate scFv molecule is released into the media, along with host cell proteins.

It may be desirable to automate any of the above assay formats. For example, robotics may be employed to isolate each member of the scFv library (e.g. as individual host cell colonies) in rapid succession so they can be assayed in separate vessels. Examples of assay vessels include microtiter plates (e.g. 96-well microtiter plates), test tubes, and microcentrifuge tubes.

d. Further Optimization of Stabilized scFv Molecules

A stable scFv molecule identified by the above screening methods can be re-modeled and further optimized to further improve its protein stability. Thus, the steps described above can be repeated with a stable scFv molecule identified in an initial round of optimization. Alternatively, the stabilizing mutations from two or more stabilized scFv molecules may be combined in a single scFv molecule to further improve protein stability.

In certain embodiments, the stable scFv molecule identified by the methods of the invention can be further optimized. For example, on or more of the following additional alterations may be made. In one embodiment, a stabilized scFv molecule may be further stabilized by introducing a disulfide bond which links an amino acid in the VL domain with an amino acid in the VH domain. Exemplary disulfide bonds include any the disulfide bonds described in Section II supra. A particularly preferred disulfide bond is VH44-VL100.

In other embodiments, the stable scFv molecule identified by the methods of the invention is further optimized by introducing an scFv linker with an optimized length or composition. Exemplary scFv linkers are described in Section II supra. A particularly preferred scFv linker is (Gly$_4$Ser)$_4$.

In another embodiment, the stable scFv molecule identified by the methods of the invention is further optimized by introducing a stabilizing mutation into at least one of the VH or VL domain.

IX. Methods for Stabilizing Binding Molecules

In other aspects, the invention provides methods for improving the stability properties of binding molecules. These methods generally involve incorporating or appending a stabilized scFv molecule of the invention to the binding molecule. Surprisingly, as shown in the working examples herein, scFv molecules of the invention are not only stable on their own, they also confer improved stability to binding molecules into which they are incorporated. Accordingly, the methods of the invention provide a convenient and reliable means for improving the stability of commercially valuable binding molecules for which large scale manufacturing is often limited by poor protein stability (e.g. multispecific antibodies (e.g. bispecific antibodies) and other modified antibodies).

Stabilized scFv molecules may be incorporated into binding molecules using protein conjugation methodology that is known in the art. In one embodiment, the stabilized scFv is fused directly to an N- or C-terminus of a polypeptide, e.g., an antibody molecule. In another embodiment, a non-peptide linker is employed to link the stabilized scFv to an N- or C-terminus of a polypeptide. In yet other embodiments, a connecting peptide is used to link the stabilized scFv to a polypeptide. In an exemplary embodiment, the connecting peptide is a short gly/ser rich peptide. Exemplary Gly/Ser rich peptides are listed in Table 1 below. Other exemplary connecting peptides are known in the art (see, e.g., International PCT Application Nos. WO 2005/000898 and WO 2005/000899). In one embodiment, a stabilized scFv of the invention is linked to the C-terminal end of a binding molecule, e.g., an antibody molecule, using a S(G$_4$S)$_3$ linker. In another embodiment, a stabilized scFv of the invention is linked to the N-terminal end of a binding molecule, e.g., an antibody molecule, using a (G$_4$S)$_5$ linker.

TABLE 1

Connecting Peptides

| Linker | SEQ ID NO | DNA or Amino Acid Sequence |
|---|---|---|
| (Gly$_4$Ser)$_5$ | 132 | 5'-GGCGGTGGAGGGTCCGGTGGAGGGGGCTCTGGA GGGGGCGGTTCAGGGGGCGGTGGATCGGGGGG AGGTGGCTCC-3' |
|  | 133 | GGGGSGGGGSGGGGSGGGGSGGGGS |
| Ser(Gly$_4$Ser)$_3$ | 42 | 5'-TCCGGCGGGGTGGATCCGGTGGAGGGGGCTCC GGCGGTGGCGGGTCC-3' |
|  | 43 | SGGGGSGGGGSGGGGS |

In one embodiment, at least one stabilized scFv molecule is appended to an antibody molecule to make a bispecific molecule. In another embodiment, two stabilized scFv molecules are appended to an antibody molecule to make a bispecific molecule.

In certain embodiments, stabilized binding molecules of the invention result in increased yield as compared to conventional scFv molecules or binding molecules comprising conventional scFv molecules. Methods for evaluating yield are described in Section VI, supra. In one embodiment, a stabilized binding molecule produced by the methods of the invention has an increase in yield of at least 1% relative to the unstabilized binding molecule. In other embodiments, the stabilized binding molecule has an increase in yield of at least 2%, at least 5%, at least 10%, at least 20%, at least 30%, at least 50%, at least 75%, or at least 100%, relative to the unstabilized binding molecule.

In certain embodiments, binding molecules of the invention result in reduced aggregation as compared to conventional scFv molecules or binding molecules comprising conventional scFv molecules. Methods for evaluating aggregation are described in Section VI, supra. In one embodiment, a stabilized binding molecule produced by the methods of the invention has a decrease in aggregation of at least 1% relative to the unstabilized binding molecule. In other embodiments, the stabilized binding molecule has a decrease in aggregation of at least 2%, at least 5%, at least 10%, at least 20%, at least 30%, at least 50%, at least 75%, or at least 100%, relative to the unstabilized binding molecule.

In other embodiments, binding molecules of the invention result in increased long-term stability or shelf-life as compared to conventional scFv molecules or binding molecules comprising conventional scFv molecules. Methods for evaluating shelf-life include % loss or % proteolysis as described in Section VI, supra. In one embodiment, a stabilized binding molecule produced by the methods of the invention has an increase in shelf life of at least 1 day relative to the unstabilized binding molecule. This means that a preparation of binding molecules has substantially the same amount of stable binding molecules as present on the previous day. In other embodiments, the stabilized binding molecule has an increase in shelf life of at least 2 days, at least 5 days, at least 1 week, at least 2 weeks, at least 1 month, at least 2 months, at least 6 months, or at least 1 year, relative to the unstabilized binding molecule.

In other embodiments, binding molecules of the invention result improved stability e.g., when expressed in a particular host cell type, as compared to conventional scFv molecules or binding molecules comprising conventional scFv molecules. In exemplary embodiments, the methods of the invention result in the production of binding molecules which have increased stability (e.g. increased yield) when the binding molecule is expressed in a host cell, e.g., a bacterial or eukaryotic (e.g., yeast or mammalian) host cell. Exemplary mammalian host cells include Chinese Hamster Ovary (CHO) cells, HELA (human cervical carcinoma) cells, CVI (monkey kidney line) cells, COS (a derivative of CVI with SV40 T antigen) cells, R1610 (Chinese hamster fibroblast) cells, BALBC/3T3 (mouse fibroblast) cells, HAK (hamster kidney line) cells, SP2/O (mouse myeloma) cells, BFA-1c1BPT cells (bovine endothelial cells), RAJI (human lymphocyte) cells and 293 cells (human kidney). In a preferred embodiment, two stabilized scFv molecules are appended to an antibody molecule to create a stabilized bispecific molecule for secretion in CHO cells.

In other embodiments, host cells capable of expressing stabilized binding molecules can be screened to select for single cell isolates that are capable of expressing high levels of solubilized and properly-folded stabilized binding molecules (e.g. binding molecules exhibiting less than 10% aggregation). Such methods may employ fluorescence-activated cell sorting (FACS) techniques (see, for example, Brezinky et al., J Immunol Meth (2003). 277:141-155). In one embodiment, the single cell isolate is adapted to serum-free conditions to establish a stable producer cell line. The stable producer cell line may then be cultured to facilitate large-scale manufacture of a stabilized binding molecule of the invention.

In other embodiments, the methods of the invention are employed to improve the stability of a binding molecule that is expressed from a host cell in a large volume of culture media. In exemplary embodiments, the methods of the invention result in an increased stability (e.g. increased yield) when the binding molecule is expressed in at least 1 liter of culture media. In other embodiments, the methods of the invention are used to produce a stabilized binding molecule which has an increased stability (e.g. yield) when expressed from a host cell in at least 2 liters, at least 10 liters, at least 20 liters, at least 50 liters, at least 75 liters, at least 100 liters, at least 200 liters, or at least 500 liters of culture media. In an exemplary embodiment, the methods of the invention are used to produce at least 10 mg of a stabilized binding molecule for every liter of culture media.

X. Stabilized Binding Molecules Comprising Stabilized scFv Molecules

In one embodiment, a stabilized binding molecule of the invention is a fusion protein. For example, a stabilized scFv molecule of the invention may be linked to a second scFv molecule or a non-scFv molecule. In one embodiment, a non-scFv molecule to which a stabilized scFv molecule of the invention may be linked provides at least one additional binding site. For example, exemplary binding sites that can be included in a binding molecule of the invention include: the receptor binding portion of a ligand, the ligand binding portion of a receptor, the substrate binding portion of an enzyme, the enzyme binding portion of a substrate, or one or more antigen binding portions of an antibody. scFv molecules may be linked, e.g., to antibody molecules to form modified antibody molecules or to other polypeptides to form fusion proteins. Some examples are described below.

A. Modified Antibody Molecules

In one embodiment, a stabilized scFv molecule of the invention is linked to an antibody or fragment thereof to form a stabilized binding protein which is a modified antibody. In another embodiment, a stabilized scFv of the invention is linked to a modified antibody, i.e., non-naturally occurring antibody molecule, to form a stabilized binding protein. Preferred modified antibody constructs are described in more detail below. As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen). In addition, the term "modified antibody" includes multivalent forms of antibodies (e.g., trivalent, tetravalent, etc., antibodies that bind to three or more copies of the same antigen).

It will be understood that when discussing the binding molecules of the invention, the exemplary binding specificities described herein may be imparted by a stabilized scFv molecule of the invention, a binding molecule comprising an scFv molecule of the invention or both.

In one embodiment, the stabilized binding proteins of the present invention may be immunoreactive with one or more tumor antigens or antigens associated with immune disorders. For example, for neoplastic disorders, the binding site (i.e. the variable region or immunoreactive fragment or recombinant thereof) of the disclosed binding molecules binds to a selected tumor associated antigen at the site of the malignancy. Similarly, in one embodiment, a binding molecule may bind to at least one selected marker present on immune cells. Given the number of reported antigens associated with neoplasias and immune disorders, and the number of related antibodies, those skilled in the art will appreciate that the presently disclosed binding molecules may therefore be derived from any one of a number of whole antibodies. More generally, polypeptides useful in the present invention may be obtained or derived from any antibody (including those previously reported in the literature) that reacts with a molecule or marker associated with the selected condition. Further, the parent or precursor antibody, or fragment thereof, used to generate the stabilized binding molecules of the invention may be murine, human, chimeric, humanized, non-human primate or primatized.

As used herein, "tumor associated antigens" includes antigens which are generally associated with tumor cells, e.g., expressed on tumor cells. More generally, tumor associated antigens comprise antigens that provide for the localization of immunoreactive antibodies at a neoplastic cell irrespective of its expression on non-malignant cells. Such antigens may be relatively tumor specific, e.g., limited in expression to the surface of malignant cells. Alternatively, such antigens may be found on both malignant and non-malignant cells. For example, CD20 is a pan B antigen that is found on the surface of both malignant and non-malignant B cells that has proved to be an extremely effective target for immunotherapeutic antibodies for the treatment of non-Hodgkin's lymphoma. In this respect, pan T cell antigens such as CD2, CD3, CD5, CD6 and CD7 also comprise tumor associated antigens within the meaning of the present invention. Still other exemplary tumor associated antigens comprise but not limited to MAGE-1, MAGE-3, MUC-1, HPV 16, HPV E6 & E7, TAG-72, CEA, L6-Antigen, CD19, CD22, CD37, CD52, HLA-DR, EGF Receptor and HER2Receptor. In many cases immunoreactive antibodies for each of these antigens have been reported in the literature. Those skilled in the art will appreciate that each of these antibodies may serve as a precursor for antibodies of the invention in accordance with the present invention.

In one embodiment, the stabilized binding molecules of the present invention preferably associate with, and bind to, tumor or immune associated antigens as described above. Accordingly, as will be discussed in some detail below the stabilized binding molecules of the present invention may be derived, generated or fabricated from any one of a number of antibodies that react with tumor associated antigens. In certain embodiments the stabilized binding molecules of the invention are domain deleted antibodies that are derived using common genetic engineering techniques whereby at least a portion of one or more constant region domains are deleted or altered so as to provide the desired biochemical characteristics such as reduced serum half-life. More particularly, one skilled in the art may readily isolate the genetic sequence corresponding to the variable and/or constant regions of the subject stabilized binding molecule and delete or alter the appropriate nucleotides to provide polypeptides of the invention for use as monomeric subunits in accordance with the instant invention.

Previously reported antibodies that react with tumor associated antigens may be stabilized as described herein to provide the stabilized binding molecules of the present invention. Exemplary antibodies that may be used to provide antigen binding regions to generate or derive the disclosed stabilized binding molecules include, but are not limited to 2B8 and C2B8 (Zevalin® and Rituxan®, IDEC Pharmaceuticals Corp., San Diego), Lym 1 and Lym 2 (Techniclone), LL2 (Immunomedics Corp., New Jersey), HER2 (Herceptin®, Genentech Inc., South San Francisco), B1 (Bexxar®, Coulter Pharm., San Francisco), Campath® (Millennium Pharmaceuticals, Cambridge), abagovomab (Menarini, Italy), CEA-Scan™ (Immunomedics, Morris Plains, N.J.), capromab (Prostascint®, Cytogen Corp.), edrecolomab (Panorex®, Johnson & Johnson, New Brunswick, N.J.), igovomab (CIS Bio Intl., France), mitumomab (BEC2, Imclone Systems, Somerville, N.J.), nofetumomab (Verluma®, Boehringer Ingleheim, Ridgefield, Conn.), OvaRex (Altarex Corp., Waltham, Mass.), satumomab (Onoscint®, Cytogen Corp.), cetuximab (Erbitux®, Imclone Systems, New York, N.Y.), bevacizumab (AVASTIN®, Genentech Inc., S. San Francisco, Calif.), apolizumab (REMITOGEN™, Protein Design Labs, Fremont, Calif.), labetuzumab (CEACIDE™, Immunomedics Inc., Morris Plains, N.J.), pertuzumab (OMNI-TARG™, Genentech Inc., S. San Francisco, Calif.), MB1, BH3, B4, B72.3 (Cytogen Corp.), CC49 (National Cancer Institute) and 5E10 (University of Iowa). Other binding sites that can be incorporated into the subject binding molecules include those found in: Orthoclone OKT3 (CD3), ReoPro (GpIIb/gIIa), Zenapax (C25), Remicade (TNF-a), Simulect (CD25), Synagis (RSV), Mylotarg (CD33), and Campath (CD52). In preferred embodiments, the stabilized binding molecules of the present invention will bind to the same tumor associated antigens as the antibodies enumerated immediately above. In particularly preferred embodiments, the stabilized binding molecules will be derived from or bind the same antigens as 2B8, C2B8, CC49 and C5E10 and, even more preferably, will lack all or part of a CH2 domain.

In one embodiment, a binding molecule of the invention may have one or more binding sites derived from one or more of the following antibodies. tositumomab (BEXXAR®), muromonab (ORTHOCLONE®) and ibritumomab (ZEVALIN®), cetuximab (ERBITUX™), rituximab (MABTHERA®/RITUXAN®), infliximab (REMICADE®), abciximab (REOPRO®) and basiliximab (SIMULECT®), efalizumab (RAPTIVA®, bevacizumab (AVASTIN®), alemtuzumab (CAMPATH®), trastuzumab (HERCEPTIN®), gemtuzumab (MYLOTARG®), palivizumab (SYNAGIS®), omalizumab (XOLAIR®), daclizumab (ZENAPAX®), natalizumab (TYSABRI®) and ranibizumab (LUVENTIS®), adalimumab (HUMIRA®) and panitumumab (VECTIBIX®).

In one embodiment, a stabilized binding molecule of the invention binds to CD23 (U.S. Pat. No. 6,011,138). In a preferred embodiment, a stabilized binding molecule of the invention binds to the same epitope as the 5E8 antibody. In another embodiment, a binding molecule of the invention comprises at least one CDR (e.g., at least 1, 2, 3, 4, 5, or 6 CDRs) from an anti-CD23 antibody, e.g., the 5E8 antibody.

In one embodiment, a stabilized binding molecule of the invention binds to a TNF receptor. In one exemplary embodiment, a stabilized binding molecule of the invention binds to a LTβR. In another exemplary embodiment, a stabilized binding molecule of the invention binds to a TRAIL receptor. In another embodiment, a stabilized binding molecule of the invention comprises at least one CDR (e.g., at least 1, 2, 3, 4, 5, or 6 CDRs) from an anti-TRAIL-R2 antibody (e.g. murine or chimeric 14A2). In another embodiment, a stabilized binding molecule of the invention comprises at least one CDR from an anti-LTβR antibody. Examples of anti-LTβR antibodies include BKA11, CDH10, BCG6, AGH1, BDA8, CBE11 and BHA10.

In one embodiment, a stabilized binding molecule of the invention binds to the CRIPTO-I antigen (WO02/088170A2 or WO03/083041A2). In a preferred embodiment, a stabilized binding molecule of the invention binds to the same epitope as the B3F6 antibody. In another embodiment, a stabilized binding molecule of the invention comprises at least one CDR from an anti-CRIPTO-I antibody, e.g., the B3F6 antibody.

In one embodiment, the stabilized binding molecule will bind to the same tumor associated antigen as Rituxan®. Rituxan® (also known as, rituximab, IDEC-C2B8 and C2B8) was the first FDA-approved monoclonal antibody for treatment of human B-cell lymphoma (see U.S. Pat. Nos. 5,843,439; 5,776,456 and 5,736,137 each of which is incorporated herein by reference). Y2B8 (90Y labeled 2B8; Zevalin®; ibritumomab tiuxetan) is the murine parent of C2B8. Rituxan® is a chimeric, anti-CD20 monoclonal antibody which is growth inhibitory and reportedly sensitizes certain lymphoma cell lines for apoptosis by chemotherapeutic agents in vitro. The antibody efficiently binds human complement, has strong FcR binding, and can effectively kill human lymphocytes in vitro via both complement dependent (CDC) and antibody-dependent (ADCC) mechanisms (Reff et al., Blood 83: 435-445 (1994)). Those skilled in the art will appreciate that dimeric variants (homodimers or heterodimers) of C2B8 or 2B8, modified according to the instant disclosure, may be used in conjugated or unconjugated forms to effectively treat patients presenting with CD20+ malignancies. More generally, it must be reiterated that the stabilized binding molecule disclosed herein may be used in either a "naked" or unconjugated state or conjugated to a cytotoxic agent to effectively treat any one of a number of disorders.

In other preferred embodiments of the present invention, the stabilized binding molecule of the invention will be derived from, or bind to, the same tumor associated antigen as CC49. CC49 binds human tumor associated antigen TAG-72 which is associated with the surface of certain tumor cells of human origin, specifically the LS174T tumor cell line. LS174T [American Type Culture Collection (herein ATCC) No. CL 188] is a variant of the LS180 (ATCC No. CL 187) colon adenocarcinoma line. It will further be appreciated that numerous murine monoclonal antibodies have been developed which have binding specificity for TAG-72. One of these monoclonal antibodies, designated B72.3, is a murine IgG1 produced by hybridoma B72.3 (ATCC No. HB-8108). B72.3 is a first generation monoclonal antibody developed using a human breast carcinoma extract as the immunogen (see Colcher et al., Proc. Natl. Acad. Sci. (USA), 78:3199-3203 (1981); and U.S. Pat. Nos. 4,522,918 and 4,612,282 each of which is incorporated herein by reference). Other monoclonal antibodies directed against TAG-72 are designated "CC" (for colon cancer). As described by Schlom et al. (U.S. Pat. No. 5,512,443 which is incorporated herein by reference) CC monoclonal antibodies are a family of second generation murine monoclonal antibodies that were prepared using TAG-72 purified with B72.3. Because of their relatively good binding affinities to TAG-72, the following CC antibodies have been deposited at the ATCC, with restricted access having been requested: CC49 (ATCC No. HB 9459); CC 83 (ATCC No. FIB 9453); CC46 (ATCC No. HB 9458); CC92 (ATTCC No. HB 9454); CC30 (ATCC No. HB 9457); CC11 (ATCC No. 9455); and CC15 (ATCC No. HB 9460). U.S. Pat. No. 5,512,443 further teaches that the disclosed antibodies may be altered into their chimeric form by substituting, e.g., human constant regions (Fc) domains for mouse constant regions by recombinant DNA techniques known in the art. Besides disclosing murine and chimeric anti-TAG-72 antibodies, Schlom et al. have also produced variants of a humanized CC49 antibody as disclosed in PCT/US99/25552 and single chain constructs as disclosed in U.S. Pat. No. 5,892,019 each of which is also incorporated herein by reference. Those skilled in the art will appreciate that each of the foregoing antibodies, constructs or recombinants, and variations thereof, may be modified and used to provide polypeptides in accordance with the present invention.

In addition to the anti-TAG-72 antibodies discussed above, various groups have also reported the construction and partial characterization of domain-deleted CC49 and B72.3 antibodies (e.g., Calvo et al. Cancer Biotherapy, 8(1):95-109 (1993), Slavin-Chiorini et al. Int. J. Cancer 53:97-103 (1993) and Slavin-Chiorini et al. Cancer. Res. 55:5957-5967 (1995

Still other preferred embodiments of the present invention comprise binding sites that are derived from or bind to the same tumor associated antigen as C5E10. As set forth in co-pending application Ser. No. 09/104,717, C5E10 is an antibody that recognizes a glycoprotein determinant of approximately 115 kDa that appears to be specific to prostate tumor cell lines (e.g. DU145, PC3, or ND1). Thus, in conjunction with the present invention, stabilized binding molecules (e.g. CH2 domain-deleted antibodies) that specifically bind to the same tumor associated antigen recognized by C5E10 antibodies could be produced and used in a conjugated or unconjugated form for the treatment of neoplastic disorders. In particularly preferred embodiments, the stabilized binding molecule will be derived or comprise all or part of the antigen binding region of the C5E10 antibody as secreted from the hybridoma cell line having ATCC accession No. PTA-865. The resulting stabilized binding molecule could then be conjugated to a radionuclide as described below and administered to a patient suffering from prostate cancer in accordance with the methods herein.

In certain embodiments, the stabilized binding molecules of the invention have at least one of the binding specificities described herein, e.g., in Section C infra. In another embodiment, a stabilized binding molecule of the invention may bind to a target molecule of interest, e.g., described herein, e.g., in section B or C, infra.

Previously reported antibodies that react with antigens associated with immune-cell disorders (e.g., B-cell disorders) may be stabilized as described herein to provide the stabilized binding molecules of the present invention. Exemplary antibodies that may be used to provide antigen binding regions to generate or derive the disclosed stabilized binding molecules include, but are not limited to an anti-TNFα antibody (e.g., infliximab (Remicade®, Centocor, Horsham, Pa.); MAK195-F (Abbott Labs., Abbott Park, Ill.); adalimumab (Humira®, Abbott Labs, Abbott Park, Ill.); an anti-CD3 antibody (e.g., Orthoclone (OKT3®, OrthoBiotech, Bridgewater, N.J.); MEDI-500 (Medimmune, Gaithersburg, Md.); visilizumab (NUVION®, Protein Design Labs (Fremont, Calif., USA)), an anti-IgE antibody (e.g., omalizumab, XOLAIR®, Genentech, South San Francisco, Calif.), an anti-VLA-4 antibody (e.g., TYSABRI®, Biogenldec, Cambridge, Mass.), an anti-CD147 antibody (e.g., ABX-CBL (Abgenix, Fremont, Calif.)), an anti-CD25 antibody (e.g., basiliximab, Simulect® (East Hanover, N.J.); Inolimomab (OPI, France), an anti-CD18 antibody (e.g., odulimomab, Antilfa®, Pateur Meriuex, France), anti-NCA90 (e.g., sulesomab, Leukoscan®, Immunomedics, Morris Plains, N.J.), an anti-GpIIb/gIIa antibody (e.g., abciximab, ReoPro®, Centocor, Horsham, Pa.), an anti-C25 antibody (e.g., Zenapax), an anti-CD33 antibody (e.g., Mylotarg), and an anti-CD25 antibody (e.g., alemtuzumab, Campath® (Milleneum Pharmaceuticals, Cambridge, Mass.). In preferred embodiments, the stabilized binding molecules of the present invention will bind to the same immune-cell associated antigens as the antibodies enumerated immediately above.

In one embodiment, the term, "modified antibody" according to the present invention includes immunoglobulins, antibodies, or immunoreactive fragments or recombinants thereof, in which at least a fraction of one or more of the constant region domains has been deleted or otherwise altered so as to provide desired biochemical characteristics such as the ability to non-covalently dimerize, increased ability to localize at the site of a tumor, or reduced serum half-life when compared with a whole, unaltered antibody of approximately the same immunogenicity. In a preferred embodiment, the polypeptides of the present invention are domain deleted antibodies which comprise a polypeptide chain similar to an immunoglobulin heavy chain, but which lack at least a portion of one or more heavy chain domains. In one embodiment, one entire domain of the constant region of the stabilized binding protein will be deleted. In another embodiment, all or part of the CH2 domain will be deleted.

In one embodiment, the stabilized binding proteins of the invention are minibodies. Minibodies are dimeric molecules made up of two polypeptide chains each comprising a stabilized scFv molecule (a single polypeptide comprising one or more antigen binding sites, e.g., a VL domain linked by a flexible linker to a VH domain fused to a CH3 domain via a connecting peptide.

Minibodies can be made by constructing an scFv component and connecting peptide-CH3 component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis.

In another embodiment, a tetravalent minibody can be constructed. Tetravalent minibodies can be constructed in the same manner as minibodies, except that two scFv molecules are linked using a flexible linker, e.g., having an amino acid sequence $(G_4S)_4G_3AS$.

In one embodiment, tetravalent antibodies can be produced by combining a DNA sequence encoding an antibody with a scFv molecule. For example, in one embodiment, these sequences are combined such that the scFv molecule is linked at its N-terminus to the CH3 domain of the antibody via a flexible linker (e.g., a gly/ser linker such as $(Gly_4Ser)_3$.

In another embodiment a tetravalent antibody can be made by fusing n stabilized scFv molecule to a connecting peptide, which is fused to a CH1 domain to construct a stabilized scFv-Fab tetravalent molecule (Coloma and Morrison. 1997. Nature Biotechnology. 15:159; WO 95/09917).

In one embodiment a stabilized binding molecule of the invention comprises a tetravalent or bispecific tetravalent antibody with an scFv appended to the N-terminus of the light chain. In another embodiment of the invention, a binding molecule comprises a tetravalent or bispecific tetravalent CH2 domain-deleted antibody with an scFv appended to the N-terminus of the heavy chain. In one embodiment, the attachment of the scFv to the N-terminus results in reduced aggregation of the molecules as compared to molecules in which the scFv is attached at the carboxy-terminus.

Antibodies or fragments thereof for use in a stabilized binding molecule of the invention may be obtained using art recognized protocols, for example, antibodies are preferably raised in mammals by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., Nature, 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, Monoclonal Antibodies: Principles and Practice, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments (e.g., antigen binding sites) may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. Immunol. Today 21:371; Nagy et al. 2002. Nat. Med. 8:801; Huie et al. 2001. Proc. Natl. Acad. Sci. USA 98:2682; Lui et al. 2002. J. Mol. Biol. 315:1063, each of which is incorporated herein by reference. Several publications (e.g., Marks et al. Bio/Technology 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. Nat. Biotechnol. 18:1287; Wilson et al. 2001. Proc. Natl. Acad. Sci. USA 98:3750; or Irving et al. 2001 J. Immunol. Methods 248:31. In yet another embodiment, cell surface libraries can be screened for antibodies (Boder et al. 2000. Proc. Natl. Acad. Sci. USA 97:10701; Daugherty et al. 2000 J. Immunol. Methods 243:211. Such procedures provide alternatives to traditional hybridoma techniques for the isolation and subsequent cloning of monoclonal antibodies.

In another embodiment of the present invention a binding site of a binding molecule of the invention may be provided by a human or substantially human antibody. Human or substantially human antibodies may be made in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the binding molecules of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or synthetic to provide obtain polypeptides of the present invention.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

It will further be appreciated that the scope of this invention encompasses stabilized binding molecules comprising alleles, variants and mutations of art recognized antigen binding DNA sequences and a stabilized scFv molecule of the invention.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis. Exemplary antibodies or fragments thereof for use in the binding molecules of the invention include antibodies that recognize the targets set forth herein.

In certain embodiments, antigen binding fragments of antibodies can be produced using techniques well known in the art.

In one embodiment, a binding molecule of the invention may comprise a complete antibody molecule and a stabilized scFv molecule. In another embodiment, a binding molecule of the invention may comprise a portion of an antibody molecule and a a stabilized scFv molecule.

In one embodiment, a binding molecule of the invention comprises a fragment or portion of an antibody and a stabilized scFv molecule. For example, in one embodiment, a binding molecule of the invention may comprise a domain deleted antibody and a stabilized scFv molecule. Domain deleted antibodies are antibody molecules in which one or more domains are partially or entirely deleted. In especially preferred embodiments compatible stabilized binding molecules will comprise domain deleted constructs or variants wherein the entire CH2 domain has been removed (ΔCH2 constructs). For other preferred embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody.

Domain deleted constructs can be derived using a vector (e.g., from DEC Pharmaceuticals, San Diego) encoding an IgG1 human constant domain (see, e.g., WO 02/060955A2 and WO02/096948A2). It will be noted that these exemplary constructs were engineered to fuse the CH3 domain directly to a hinge region of the respective polypeptides of the invention. In other constructs it may be desirable to provide a peptide spacer between the hinge region and the synthetic CH2 and/or CH3 domains. For example, compatible constructs could be expressed wherein the CH2 domain has been deleted and the remaining CH3 domain (synthetic or unsynthetic) is joined to the hinge region with a 5-20 amino acid spacer. Such a spacer may be added, for instance, to ensure that the regulatory elements of the constant domain remain free and accessible or that the hinge region remains flexible. For example, a domain deleted B3F6 construct having a short amino acid spacer substituted for the CH2 domain and the lower hinge region (B3F6.ΔCH2 [gly/ser]) can be used. Other exemplary connecting peptides are known in the art (see, e.g., International PCT Application Nos. WO 2005/000898 and WO 2005/000899). These connecting peptides can be used in connection with the binding molecules of the invention. Preferably, the connecting peptides are used with a polypeptide lacking a CH2 heavy chain domain. Preferably, any connecting peptide compatible with the instant invention will be relatively non-immunogenic and not inhibit the non-covalent association of the polypeptides of the invention.

In one embodiment, a binding molecule of the invention comprises an immunoglobulin heavy chain having deletion or substitution of a few or even a single amino acid as long as it permits the desired covalent or non-covalent association between the monomeric subunits. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the stabilized binding molecule. Yet other preferred embodiments may comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

It is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In one embodiment, effector functions may be eliminated or reduced by using a constant region of an IgG4 antibody, which is thought to be unable to deplete target cells, or making Fc variants, wherein residues in the Fc region critical for effector function(s) are mutated using techniques known in the art, for example, U.S. Pat. No. 5,585,097. For example, the deletion or inactivation (through point mutations or other means) of a constant region domain may reduce Fc receptor binding of the circulating stabilized binding molecule thereby increasing tumor localization. In other cases it may be that constant region modifications consistent with the instant invention moderate compliment binding and thus reduce the serum half life and nonspecific association of a conjugated cytotoxin. Yet other modifications of the constant region may be used to modify disulfide linkages or oligosaccharide molecules that allow for enhanced localization due to increased antigen specificity or antibody flexibility. More generally, those skilled in the art will realize that antibodies modified as described herein may exert a number of subtle effects that may or may not be readily appreciated. However the resulting physiological profile, bioavailability and other biochemical effects of the modifications, such as tumor localization, biodistribution and serum half-life, may easily be measured and quantified using well know immunological techniques without undue experimentation.

In one embodiment, modified forms of antibodies can be made from a whole precursor or parent antibody using techniques known in the art. Exemplary techniques are discussed in more detail herein.

B. Modified Fusion proteins

In certain embodiments, a stabilized binding molecule of the invention is a modified fusion protein. In one exemplary embodiment, a binding molecule of the invention is a fusion protein comprising a stabilized scFv molecule linked to the ligand-binding region of a receptor, an adhesion molecule, a ligand, or an enzyme. In another exemplary embodiment, a binding molecule of the invention is fusion protein comprising a stabilized scFv molecule linked to a receptor binding portion of ligand. For example a binding molecule of the invention is fusion protein comprising a stabilized scFv molecule to one or more of the following molecules:

Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, and interferons such as interferon-α, β, or γ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IFNγ (EP0240975), and the TNF family of receptors (e.g., TNFα (e.g. TNFR-1 (EP 417, 563), TNFR-2 (EP 417,014) lymphotoxin beta receptor).

In another embodiment, an scFv molecule of the invention may bind to a cytokine or a cytokine receptor.

Adhesion Proteins

Adhesion molecules are membrane-bound proteins that allow cells to interact with one another. Various adhesion proteins, including leukocyte homing receptors and cellular adhesion molecules, of receptor binding portions thereof, can be incorporated in a binding molecule of the invention. Leucocyte homing receptors are expressed on leucocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

In another embodiment, an scFv molecule of the invention may bind to an adhesion protein or an adhesion protein receptor.

Chemokines

Chemokines, chemotactic proteins which stimulate the migration of leucocytes towards a site of infection or chemokine receptor binding portions thereof, can also be incorporated into a binding molecule of the invention. Exemplary chemokines include Macrophage inflammatory proteins (MIP-1-α and MIP-1-β), neutrophil chemotactic factor, and RANTES (regulated on activation normally T-cell expressed and secreted).

In another embodiment, an scFv molecule of the invention may bind to a chemokine or a receptor.

Growth Factors and Growth Factor Receptors

Growth factors or their receptors (or receptor binding or ligand binding portions thereof) or molecules which bind to them may be incorporated in the binding molecule of the invention. Exemplary growth factors include angiopoietin, Vascular Endothelial Growth Factor (VEGF) and its isoforms (U.S. Pat. No. 5,194,596); Epidermal Growth Factors (EGFs); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), neurotrophin-3, -4, -5, or -6 (NT-3, NT-4, NT-5, or NT-6), or a nerve growth factor such as NGF-13 platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); stem-cell factor (SCF), thrombopoietin (c-Mpl ligand), and the Wnt polypeptides (U.S. Pat. No. 6,159,462).

Exemplary growth factor receptors which may be used include EGF receptors (EGFRs); VEGF receptors (e.g. Flt1 or Flk1/KDR), PDGF receptors (WO 90/14425); HGF receptors (U.S. Pat. Nos. 5,648,273, and 5,686,292); IGF receptors (e.g. IGFR1 and IGFR2) and neurotrophic receptors including the low affinity receptor (LNGFR), also termed as p75$^{NTR}$ or p75, which binds NGF, BDNF, and NT-3, and high affinity receptors that are members of the trk family of the receptor tyrosine kinases (e.g. trkA, trkB (EP 455,460), trkC (EP 522,530)). In another embodiment, both IGFR1 and VEGF are targeted. In yet another embodiment, VLA4 and VEGF are targeted. In another embodiment, both LFA1 and VLA4 are targeted.

Other cell surface receptors and/or their ligands can also be targeted (e.g., the TNF family receptors or their ligands (as described in more detail herein).

In another embodiment, an scFv molecule of the invention may bind to a growth factor or growth factor receptor.

Hormones

Exemplary growth hormones or molecules which bind to them for use as targeting agents in a binding molecule of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH), calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

In another embodiment, an scFv molecule of the invention may bind to a hormone or a hormone receptor.

Clotting Factors

Exemplary blood coagulation factors for use as targeting agents in the binding molecules of the invention include the clotting factors (e.g., factors V, VH, VIII, X, IX, XI, XII and XIII, von Willebrand factor); tissue factor (U.S. Pat. Nos. 5,346,991, 5,349,991, 5,726,147, and 6,596,84); thrombin and prothrombin; fibrin and fibrinogen; plasmin and plasminogen; plasminogen activators, such as urokinase or human urine or tissue-type plasminogen activator (t-PA).

In another embodiment, an scFv molecule of the invention may bind to a clotting factor.

In other embodiments, stabilized binding protein of the invention is a modified immunoadhesin. As is well-known in the art, an immunoadhesin is a fusion protein that combines the target-binding region of a receptor, an adhesion molecule, a ligand, or an enzyme, with the Fc region of an antibody. Exemplary immunoadhesins are described, for example, in U.S. Pat. Nos. 5,116,964; 5,428,130; 5,714,147; and 6,406, 697, each of which is incorporated by reference herein. In one embodiment, a modified immunoadhesin of the invention is formed by linking a stabilized scFv molecule to an immunoadhesin.

Previously reported immunoadhesins may be stabilized as described herein to provide the modified immunoadhesins of the present invention. Exemplary immunoadhesins that may be used to generate or derive the disclosed modified immunoadhesin include, but are not limited to, abatecept (Orencia®, Bristol-Meyers Squibb, Princeton, N.J.), alefacept (Amevive®, Biogenldec, Cambridge, Mass.), etanercept (Enbrel®, Amgen, Thousand Oaks, Calif.), SMART™ Anti-Gamma Interferon (Protein Design Labs, Fremont, Calif.), SMART™ Anti-L-Selectin (Protein Design Labs. Fremont, Calif.), rilonacept (Regeneron Pharmaceuticals Inc., Tarrytown, N.Y.), regavirumab (TI-23, Teijin America, New York, N.Y.), R24 (National Cancer Institute (Bethesda, Md.), Oprelvekin (NEUMEGA®, Genetics Institute, Cambridge, Mass.), ONCOLYSIN B, ONCOLYSIN CD6, ONCOLYSIN M, and ONCOLYSIN S (all of ImmunoGen Inc., Cambridge, Mass., USA), ONCOLYM™ 131 (Techniclone Corp., Tustin, CAlif.), ImmuRAIT-LL2 (Immunomedics Inc., Morris Plains, N.J.), IL-4 RA (BAY 16-9996; Bayer Corp., Berkeley, Calif.), IC14 (ICOS Corporation, Bothell, Wash.), CYT-356-Y-90 (ONCORAD®PR, Cytogen Corp., Princeton, N.J.), COTARA™ (Techniclone Corp., Tustin, Calif.), CMB-401 (Wyeth Pharmaceuticals, Madison, N.J.), AVICIDIN® conjugate (NeoRx Corp., Seattle, Wash.) and anti-CD18 immunoadhesin (Genentech Inc., S. San Francisco, Calif.).

Another exemplary molecule that may be included in a binding molecule of the invention is immunoglobulin super family member 9 (IGSF9; Genomics. 2002. 79:663-70).

C. Binding Specificity

In one embodiment, a binding molecule of the invention binds to a target molecule that is present on the surface of a cell or that is soluble.

In one embodiment, at least one binding specificity of a binding molecule of the invention is catalytic. Catalytic binding specificities can be made using art recognized techniques (see, e.g., U.S. Pat. No. 6,590,080, U.S. Pat. No. 5,658,753). Catalytic binding specificities can work by a number of basic mechanisms similar to those identified for enzymes to stabilize the transition state, thereby reducing the free energy of activation. For example, general acid and base residues can be optimally positioned for participation in catalysis within catalytic active sites; covalent enzyme-substrate intermediates can be formed; catalytic antibodies can also be in proper orientation for reaction and increase the effective concentration of reactants by at least seven orders of magnitude (Fersht, A. R., et al., Am. Chem. Soc. 90 (1968):5833) and thereby greatly reduce the entropy of a chemical reaction. Finally, catalytic antibodies can convert the energy obtained upon substrate binding to distort the reaction towards a structure resembling the transition state.

In one embodiment, acid or base residues can be brought into the binding site by using a complementary charged molecule as an immunogen. This technique proved successful for elicitation of antibodies with a hapten containing a positively-charged ammonium ion (Shokat, et al., Chem. Int. Ed. Engl. 27 (1988):269-271).

In another approach, antibodies can be elicited to stable compounds that resemble the size, shape, and charge of the transition state of a desired reaction (i.e., transition state analogs). See U.S. Pat. No. 4,792,446 and U.S. Pat. No. 4,963,355 which describe the use of transition state analogues to immunize animals and the production of catalytic antibodies. Both of these patents are hereby incorporated by reference. In one embodiment, such molecules can be administered as part of an immunoconjugate, e.g., with an immunogenic carrier molecule, such as KLH.

Exemplary catalytic binding specificities can have, e.g., esterase activity (involving a charged transition state whose electrostatic and shape characteristics can be mimicked by a phosphonate structure; Jacobs, et al., J. Am. Chem. Soc. 109 (1987):2174-2176; Durfor, et al., J. Am. Chem. Soc. 110 (1988):8713-8714; Tramontano, et al., J. Am. Chem. Soc. 110 (1988):2282; Pollack, et al., J. Am. Chem. Soc. 111 (1989):5961-5962); peptidase or amidase activity (Janda, et al., Science 241 (1988):1188-1191; Iverson, et al., Science 243 (1989):1184-1188; Paul, et al., Science 244 (1989):1158-1162); Claisen rearrangement (Jackson, et al., J. Am. Chem. Soc. 110 (1988):4841-4842; Hilvert, et al., Proc. Natl. Acad. Sci. USA 85 (1988):4953-4955; Hilvert, et al., J. Am. Chem. Soc. 110 (1988):5593-5594); redox reactions (Shokat, et al., Angew. Chem. Int. Ed. Engl. 27 (1989):269-271); photochemical cleavage of a thymine dimer (Cochran, et al., J. Am. Chem. Soc. 110 (1988):7888-7890); stereospecific transesterification rearrangements (Napper, et al., Science 237 (1987):1041-1043); or a bimolecular amide synthesis (Benkovic, et al., Proc. Natl. Acad. Sci. USA 85 (1988):5355-5358; Janda, et al., Science 241 (1988):1188-1191).

In another approach, conventional binding specificities can be mutated to render them catalytic.

Methods of screening for catalytic antibody activity are well known in the art (e.g., Reymond, J. L. 2002. Journal of Immunological Methods 269:125; Mouratou et al. 2002. J. of Immunological Methods. 269:147. In yet another embodiment, catalytic B cells can be selected, e.g., as described in U.S. Pat. No. 6,590,080 using a molecule can be constructed which facilitates selection of catalytic B cells.

In another embodiment, catalytic binding specificities can be developed as part of a two step process. Catalytic antibodies can be selected only if displaying the following binding features: binding both the substrate and a reactive group in such a way that the two groups are in a reactive position towards each other. Second, the selected antibodies can be chemically engineered by covalently binding a reactive group into the binding pocket of the antibody. J Immunol Methods. 2002. 269:81-98.

In one embodiment, a catalytic binding specificity is specific for a prodrug. Such a binding specificity can be used to catalyze the conversion of a prodrug into a drug which is effective in vivo. Preferably, the reaction catalyzed is one that cannot be accomplished by natural enzymes in vivo. Examples of prodrug activation by antibodies are known in the art (see, e.g., Miyashita et al. 1993. Proc. Natl. Acad. Sci. USA 90:5337).

In one embodiment, a binding molecule of the invention comprises at least one binding specificity for a target cell and at least one binding specificity for a prodrug. For example, in a preferred embodiment, a stabilized binding molecule of the invention comprises at least one binding specificity for a tumor cell and at least one binding specificity for a prodrug which can be converted to cytotoxic drug. In one example, a stabilized binding molecule of the invention comprises a binding specificity for a carbamate prodrug 4-[N,N,-bis(2-chloroethyl)]aminophenyl-N-[(1S-(1,3-dicarboxy)propyl] carbamate and generates the corresponding cytotoxic nitrogen mustard (Wentworth et al. 1996. Proc Natl. Acad. Sci. USA. 93:799).

In one embodiment, binding molecule is administered prior to administration of the prodrug to allow accumulation at the site of the target cell. Exemplary prodrugs are known in the art. Prodrugs can also be synthesized by incorporating a portion designed to be released by catalytic action, e.g., by sequential retro-aldol/retro-Michael reactions catalyzed by an antibody with aldolase activity. (Shabat et al. 2001. Proc. Natl. Acad. Sci. USA 98:7428). Such drug masking portions can be made, e.g., by modification of hydroxyl or thiol groups of drugs.

In one embodiment, a binding molecule of the invention is multispecific, i.e., has at least one binding site that binds to a first target molecule or epitope of the target molecule and at least one second binding site that binds to a second, different target molecule or to a second, different epitope of the first target molecule. In certain embodiments, multispecific binding molecules of the invention (e.g. bispecific binding molecules) comprise at least one binding site from any of the antibodies described in herein, e.g., Section A, supra.

In one embodiment, a binding molecule of the invention is bispecific. Bispecific molecules can bind to two different target sites, e.g., on the same target molecule or on different target molecules. For example, in the case of antibodies, bispecific molecules can bind to two different epitopes, e.g., on the same antigen or on two different antigens. Bispecific molecules can be used, e.g., in diagnostic and therapeutic applications. For example, they can be used to immobilize enzymes for use in immunoassays. They can also be used in diagnosis and treatment of cancer, e.g., by binding both to a tumor associated molecule and a detectable marker (e.g., a chelator which tightly binds a radionuclide. Bispecific molecules can also be used for human therapy, e.g., by directing cytotoxicity to a specific target (for example by binding to a pathogen or tumor cell and to a cytotoxic trigger molecule, such as the T cell receptor or the Fcγ receptor. Bispecific antibodies can also be used, e.g., as fibrinolytic agents or vaccine adjuvants.

In one embodiment, the multispecific binding molecules of the invention include those with at least one arm (ie. binding site) directed against a cell-surface molecule, and at least one arm directed against a soluble molecule. In another embodiment, a multispecific antibody of the invention has two binding sites that bind to soluble molecules. In another embodiment, a multispecific antibody of the invention has two binding sites that bind to cell surface molecules.

The multispecific binding molecules of the invention may be monovalent for each specificity or multivalent for each specificity. In one embodiment, a bispecific binding molecule of the invention may comprise one binding site that reacts with a first target molecule and one binding site that reacts with a second target molecule (e.g. a bispecific antibody molecule, fusion protein, or minibody). In another embodiment, a bispecific binding molecule of the invention may comprise two binding sites that react with a first target molecule and two binding sites that react with a second target molecule (e.g. a bispecific scFv2 tetravalent antibody, tetravalent minibody, or diabody).

In certain embodiments, at least one binding site of a multispecific binding molecule of the invention is an antigen binding region of an antibody or an antigen binding fragment thereof.

In one embodiment, the multispecific binding molecules of the invention are bivalent antibodies or antibody variants with one arm containing at least one stabilized scFv directed to a first target molecule and a second arm containing at least one stabilized scFv directed to a second target molecule.

In one embodiment, the multispecific binding molecules of the invention comprise at least one stabilized scFv (e.g. 2, 3, or 4 scFvs) linked to the C-terminus of a heavy chain, wherein the scFvs have the same or different binding specificity. An exemplary binding molecule of this type (a "C-Hercules" antibody) is shown in FIG. 13. In another embodiment, the multispecific binding molecules of the invention comprise at least one stabilized scFv (e.g. 2, 3, or 4 scFvs) linked to the N-terminus of a heavy chain, wherein the scFvs have the same or different binding specificity. An exemplary binding molecule of this type (a "$N_H$-Hercules" antibody) is shown in FIG. 13. In another embodiment, the multispecific binding molecules of the invention comprise at least one stabilized scFv (e.g. 2, 3, or 4 scFvs) linked to the N-terminus of a light chain, wherein the scFvs have the same or different binding specificity. An exemplary binding molecule of this type (a "$N_L$-Hercules" antibody) is shown in FIG. 13. In another embodiment, the multispecific binding molecules of the invention comprise at least one stabilized scFv (e.g., 2, 3, or 4 scFvs linked to the N-terminus of the heavy chain or light chain and at least one stabilized scFv (e.g., 2, 3, or 4 scFvs) linked to the C-terminus of the heavy chain, wherein the scFvs have the same or different binding specificity.

Figure 42:
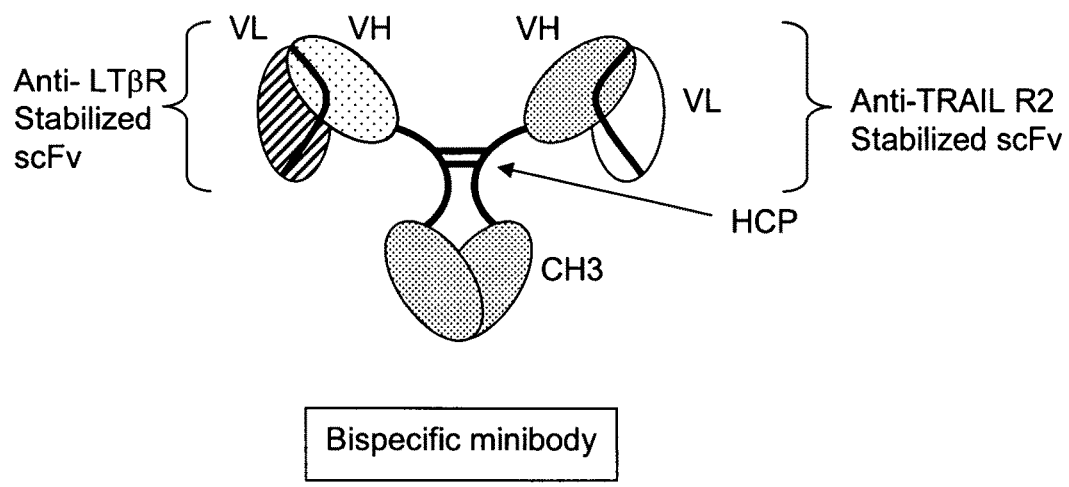
FIG. 42 depicts a schematic diagram of a stabilized two chain dimeric minibody comprising stabilized scFvs. The exemplary minibody contains a first chain portion comprising a stabilized scFv with binding specificity for TRAIL R2 antigen and a second chain portion comprising a stabilized scFv with binding specificity for the LTβR antigen. The orientation of the VH and VL domains in the scFv may be changed and the respective binding specificities may be altered.

In one embodiment, the multispecific binding molecules of the invention are bivalent minibodies with one arm containing at least one scFv fragment directed to a first target molecule and a second arm containing at least one scFv directed to a second target molecule wherein at least one of the scFv molecules is stabilized. An exemplary bispecific bivalent minibody construct is shown in FIG. 42. In FIG. 42 a CH3 domain is fused at its N-terminus to a connecting peptide which is fused at its N-terminus to a VH domain which is fused via its N-terminus to a (Gly4Ser)$_n$ flexible linker which is fused at its N-terminus to a VL domain.

Figure 43:
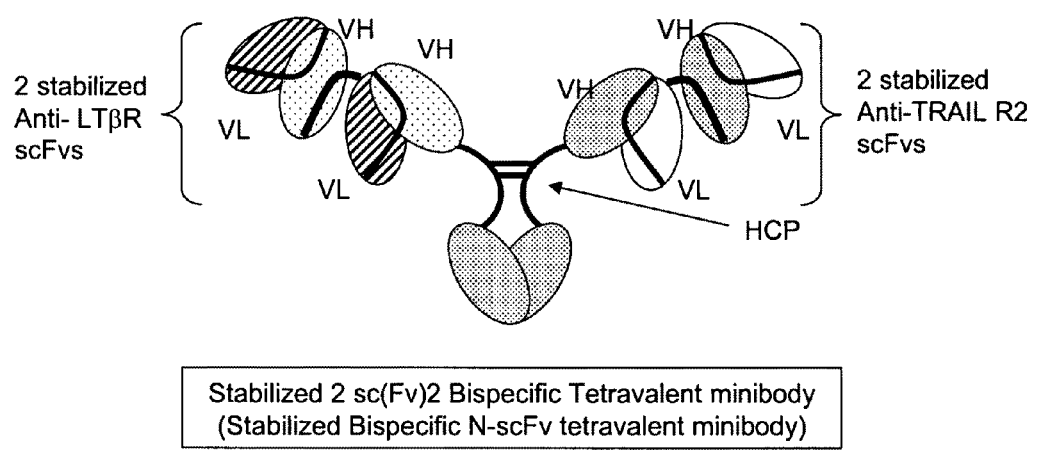
FIG. 43 depicts a schematic diagram of an exemplary stabilized bispecific two chain dimeric tetravalent minibody (stabilized Bispecific N-scFv tetravalent minibody) comprising stabilized scFv fragments of the invention appended to the amino termini. The exemplary stabilized bivalent tetravalent minibody contains a first chain portion with comprising 2 stabilized scFvs with binding specificity for TRAIL R2 antigen and a second chain portion comprising 2 stabilized scFvs with binding specificity for the LTβR antigen. Other configurations are also possible, for example, the bispecific tetravalent minibody can also be constructed such that each chain portion contains 2 stabilized scFv fragments with different specificities. In another embodiment, the orientation of the VH and VL domains in the scFv may be changed. In another embodiment, fewer than all of the scFvs are stabilized.
Figure 44:
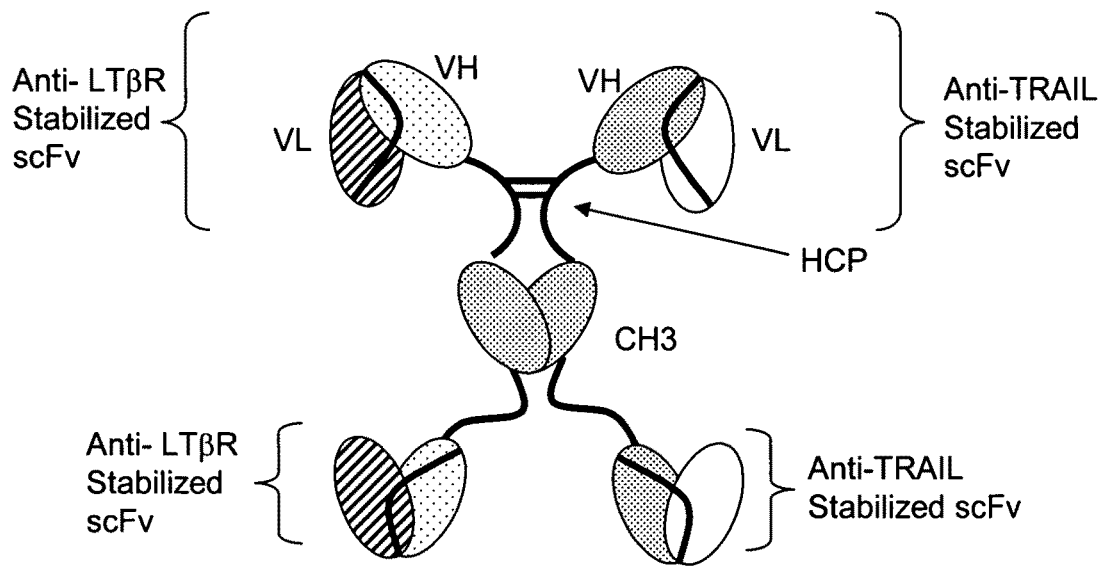
FIG. 44 depicts a schematic diagram of an exemplary stabilized bispecific two chain dimeric tetravalent minibody (stabilized Bispecific C-scFv tetravalent minibody) comprising stabilized scFv fragments appended to both carboxyl termini of a bivalent minibody. The exemplary stabilized bivalent tetravalent minibody contains a first chain portion with comprising 2 stabilized scFvs with binding specificity for TRAIL R2 antigen and a second chain portion comprising 2 stabilized scFvs with binding specificity for the LTβR antigen. Other configurations are also possible, for example, the bispecific two-chain dimeric tetravalent minibodies can also be constructed such that each chain contains 2 stabilized scFv fragments with different specificities. In another embodiment, the orientation of the VH and VL domains in the scFv may be changed. In another embodiment, fewer than all of the scFvs are stabilized.

In another embodiment, the multispecific binding molecules of the invention are scFv tetravalent minibodies, with each heavy chain portion of the scFv tetravalent minibody containing first and second scFv fragments wherein at least one of the scFv molecules is stabilized. Said second scFv fragment may be linked to the N-terminus of the first scFv fragment (e.g. bispecific $N_H$ scFv tetravalent minibodies or bispecific $N_L$ scFv tetravalent minibodies). An example of a bispecific N-scFv tetravalent minibody is shown in FIG. 43. Alternatively, the second scFv fragment may be linked to the C-terminus of said heavy chain portion containing said first scFv fragment (e.g. bispecific C-scFv tetravalent minibodies). An example of a bispecific C-scFv tetravalent minibody is shown in FIG. 44. In one embodiment, the first and second scFv fragments of may bind the same or different target molecule. Where the first and second scFv fragments of a first heavy chain portion of a bispecific tetravalent minibody bind the same target molecule, at least one of the first and second scFv fragments of the second heavy chain portion of the bispecific tetravalent minibody binds a different target molecule.

Figure 45:
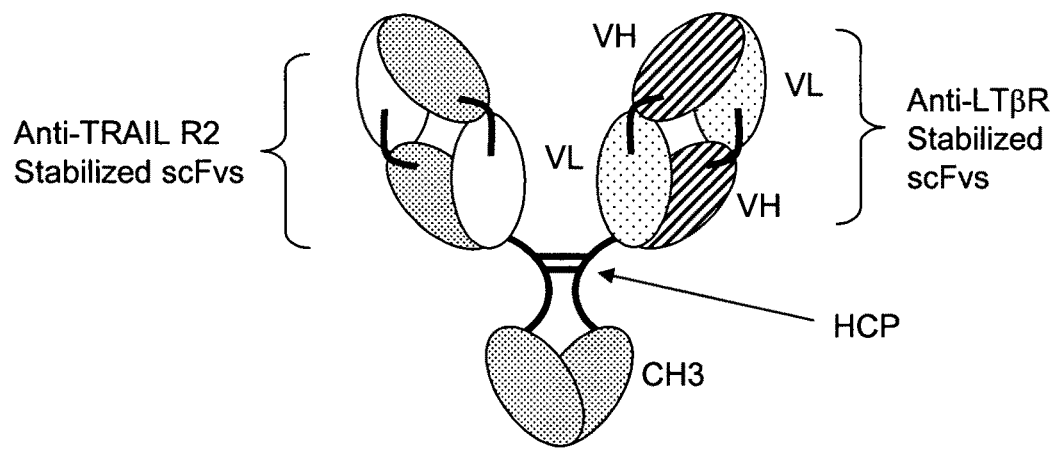
FIG. 45 shows a schematic diagram of a stabilized bispecific four chain dimeric diabody comprising stabilized scFvs of the invention. Other configurations are also possible, for example, the stabilized bispecific two-chain dimeric tetravalent minibody can also be constructed such that each arm contains stabilized scFv fragments with different specificities. The orientation of the VH and VL domains may be changed. In another embodiment, fewer than all of the scFvs are stabilized.

In another embodiment, the multispecific binding molecules of the invention are bispecific diabodies, with each arm of the diabody comprising tandem scFv fragments at least one of which is stabilized. In one embodiment, a bispecific diabody may comprise a first arm with a first binding specificity and a second arm with a second binding specificity (see, for example, FIG. 45). In another embodiment, each arm of the diabody may comprise a first scFv fragment with a first binding specificity and a second scFv fragment with a second binding specificity.

Figure 46:
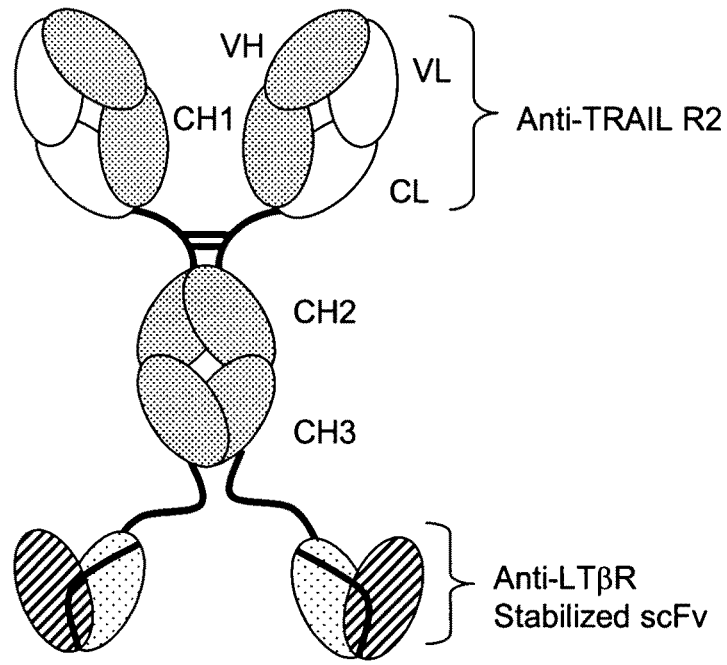
FIG. 46 shows a schematic diagram of a stabilized bispecific four chain dimeric tetravalent scFv antibody (stabilized C-scFv tetravalent antibody) comprising a stabilized scFv appended to the carboxyl terminus of CH3 and a hinge connecting peptide. The orientation of the VH and VL domains in the stabilized scFv may be changed. Alternatively, the stabilized scFv fragments can be appended to the amino termini of either the heavy or light chain portions to form $N_H$-scFv tetravalent antibodies or $N_L$-scFv tetravalent antibodies, respectively.

In another embodiment, the multispecific binding molecules of the invention are scFv2 tetravalent antibodies with each heavy chain portion of the scFv2 tetravalent antibody containing an scFv molecule, wherein at least one of the scFv molecules are stabilized. The scFv fragments may be linked to the N-termini of a variable region of the heavy chain portions (e.g. bispecific $N_H$ scFv2 tetravalent antibodies or bispecific $N_L$ scFv2 tetravalent antibodies). Alternatively, the scFv fragments may be linked to the C-termini of the heavy chain portions of the scFv2 tetravalent antibody (e.g. bispecific C-scFv2 tetravalent antibodies, see for example FIG. 46). Each heavy chain portion of the scFv2 tetravalent antibody may have variable regions and scFv fragments that bind the same or different target molecules. Where the scFv fragment and variable region of a first heavy chain portion of a bispecific scFc2 tetravalent antibody bind the same target molecule, at least one of the first and second scFv fragments of the second heavy chain portion of the bispecific tetravalent minibody binds a different target molecule.

Figure 47:
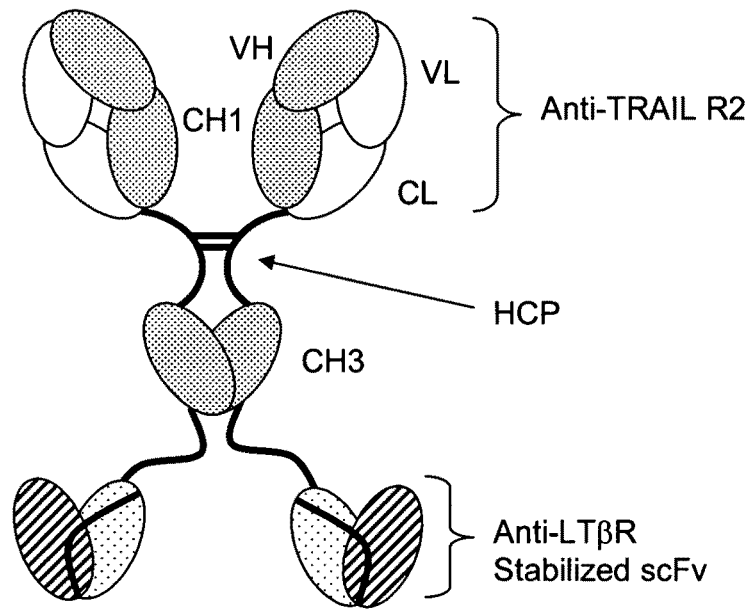
FIG. 47 shows a schematic diagram of a stabilized four-chain tetravalent scFv CH2 domain deleted bispecific antibody (stabilized C-scFv tetravalent CH2 domain deleted bispecific antibody) comprising a stabilized scFv appended to the carboxyl terminus of CH3 and a hinge connecting peptide. Each heavy chain portion of the bispecific antibody contains a Fv region with binding specificity for the TRAIL R2 antigen and a stabilized scFv region with binding specificity for the LTβR antigen. The orientation of the VH and VL domains in the stabilized scFv may be changed and the respective antigen binding specificities may be altered. In another embodiment, fewer than all of the scFvs are stabilized.
Figure 48:
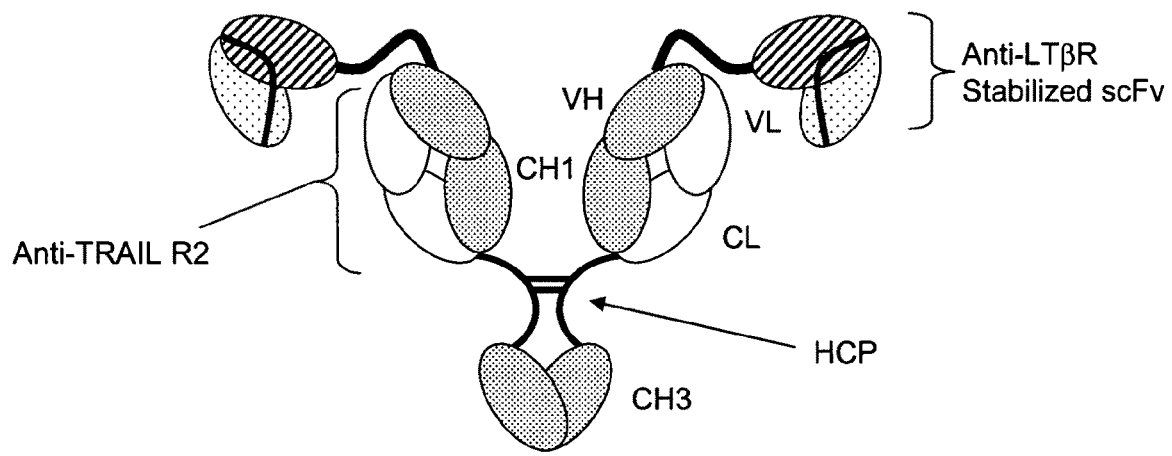
FIG. 48 shows a schematic diagram of a stabilized four-chain tetravalent scFv CH2 domain deleted bispecific antibody (stabilized $N_H$-scFv tetravalent CH2 domain deleted bispecific antibody) comprising a stabilized scFv appended to the amino terminus of VH and comprising a hinge connecting peptide. Each heavy chain portion of the bispecific antibody contains an Fv region with binding specificity for the TRAIL R2 antigen and a stabilized scFv region with binding specificity for the LTβR antigen. The orientation of the VH and VL domains in the stabilized scFv may be changed and the respective antigen binding specificities may be altered. In another embodiment, fewer than all of the scFvs are stabilized.
Figure 49:
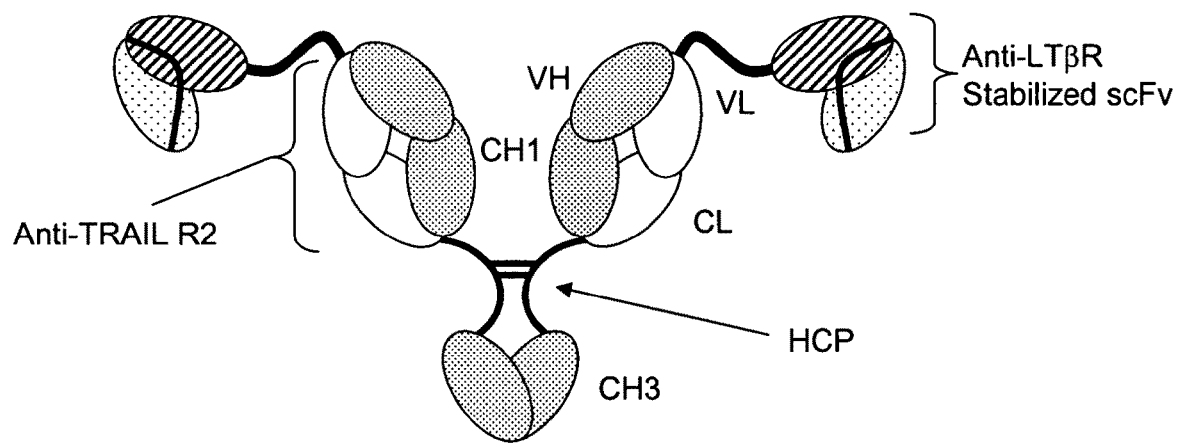
FIG. 49 shows a schematic diagram of a stabilized four-chain tetravalent scFv CH2 domain deleted bispecific antibody (stabilized $N_L$-scFv tetravalent CH2 domain deleted bispecific antibody) comprising a stabilized scFv appended to the amino terminus of VL and comprising a hinge connecting peptide. Each heavy chain portion of the bispecific antibody contains an Fv region with binding specificity for the TRAIL R2 antigen and a stabilized scFv region with binding specificity for the LTβR antigen. The orientation of the VH and VL domains in the stabilized scFv may be changed and the respective antigen binding specificities may be altered. In another embodiment, fewer than all of the scFvs are stabilized.

In another embodiment, the multispecific binding molecules of the invention are scFv2 tetravalent domain-deleted antibodies with each heavy chain portion of the scFv2 tetravalent antibody containing an scFv fragment at least one of which is stabilized. The scFv fragments may be linked to the N-termini of a variable region of the heavy chain portions (e.g. bispecific $N_H$ scFv2 tetravalent domain-deleted antibodies (see FIG. 48) or bispecific $N_L$ scFv2 tetravalent antibodies (see FIG. 49). Alternatively, the scFv fragments may be linked to the C-termini of the heavy chain portions of the scFv2 tetravalent domain-deleted antibody (e.g. bispecific C-scFv2 tetravalent domain deleted antibodies, see for example FIG. 47).

Exemplary cell-surface molecules to which a binding molecule of the invention may bind include receptors or tumor cell antigens that are overexpressed on the surface of a tumor or neoplastic cell, as well as any of the cytokine receptors, adhesion molecules, or growth factor receptors described in herein, e.g. section B supra. Exemplary soluble molecules include anti-tumor agents (e.g. toxins, chemotherapeutics, and prodrugs thereof), soluble enzymes (e.g. prodrug converting enzymes), cytokines, chemokines, hormones, growth factors, or clotting factors, e.g., as described herein, e.g. in section A supra.

Bispecific molecules which bind to both tumor cell antigens and anti-tumor agents or soluble enzymes can therefore localize the anti-cancer agent to a tumor cell expressing said tumor cell antigen, thereby maximizing the toxic effects of the anti-cancer agent on a tumor cell and minimizing a toxic effect of the anti-cancer agent on normal cells.

Exemplary bispecific binding molecules with at least one binding site for a tumor antigen and at least one binding site for a toxin include anti-saporin/anti-Id-1, anti-CD22/anti-saporin, anti-CD7/anti-saporin, anti-CD38/anti-saporin, anti-CEA/anti-ricin A chain, anti-interferon-.alpha.(IFN-.alpha.)/anti-hybridoma idiotype, anti-CEA/anti-vinca alkaloid). Exemplary bispecific binding molecules with at least one binding site for a cell-surface molecule and at least one binding site for a prodrug converting enzyme include for example, anti-CD30/anti-alkaline phosphatase (which catalyzes conversion of mitomycin phosphate prodrug to the chemotherapeutic mitomycin alcohol).

In other embodiments, the bispecific binding molecules bind to both tumor cell antigens and diagnostic agents, thereby localizing said diagnostic agent to a tumor cell expressing said tumor cell antigen and facilitating tumor detection in vitro or in vivo. Exemplary bispecific binding molecules include anti-CEA/anti-EOTUBE, anti-CEA/anti-DPTA, anti-CEA/anti-.beta.-galactosidase, and anti-p185HER2/anti-1-hapten).

In other embodiments, bispecific binding molecules of the invention bind to both soluble molecules (e.g. soluble antigens) and cell surface molecules on non-tumor cells (e.g. immune cells). For example, can be used to target soluble immune complexes to cell surface receptors on immune cells, thereby facilitating their clearance from the body by cell-mediated immune mechanisms. Exemplary bispecific molecules of this type include anti-low density lipoprotein (LDL)/anti-Fc receptor (e.g. Fc.gamma.RI, Fc.gamma.RII or Fc.gamma.RIII)) and bispecific binding molecules for use in therapy of infectious diseases (such as anti-CD3/anti-herpes simplex virus (HSV), anti-T-cell receptor: CD3 complex/anti-influenza, anti-Fc.gamma.R/anti-HIV.

In other embodiments, bispecific binding molecules of the invention are capable of binding to both cell surface receptors and soluble ligands thereof. In one embodiment, the ligand is the cognate ligand of a TNF family receptor.

Exemplary cell surface receptors to which the bispecific binding molecules can bind are tumor cell antigens or immune cell receptors. Exemplary cell surface receptors also include cytokine receptors, adhesion molecules, or growth factor receptors, e.g., as described in herein, e.g. in section B supra. Exemplary soluble ligands include cytokines, chemokines, hormones, growth factors, or clotting factors, e.g., as described in section B supra.

Exemplary bispecific binding molecules include anti-VLA4/anti-Mac-1, anti-VLA4/anti-VEGF, anti-VLA4/anti-angiopoietin, anti-VLA4/anti-TNFα, anti-IGFR1/anti-VEGF, anti-IGFR1/anti-angiopoietin, anti-IGFR1/anti-EGFR, anti-HGF-SF/anti-VEGF, anti-HGF-SF/anti-angiopoietin, and HGF-SF/any second antigen (See, e.g., Cao et al. Proc. Natl. Acad. Sci. 2001. 98:7443; Lu et al. 2004. J. Biol. Chem. 279:2856).

In other embodiments, the bispecific binding molecules of the invention include those with at least one arm (ie. binding site) directed against a first soluble molecule (e.g. soluble ligand), and at least one arm directed against a second soluble molecule (e.g. soluble ligand). Such bispecific binding molecules can be employed as diagnostic tools (e.g. anti-rabbit IgG/anti-ferritin, anti-horse radish peroxidase (HRP)/anti-hormone, anti-somatostatin/anti-substance P, anti-HRP/anti-FITC (see Nolan et al., supra)) or fibrinolytic agents (e.g. anti-fibrin/anti-tissue plasminogen activator (tPA), anti-fibrin/anti-urokinase-type plasminogen activator (uPA)).

In a preferred embodiment, the soluble molecule to which a bispecific binding molecule of the invention binds is a soluble ligand of the TNF family. Examples of TNF family ligands include, but are not limited to, LTA (which binds TNFR1/TNFRSF1A), TNF (which binds CD120b/TNFRSF1B), LTB (which binds LTBR/TNFRSF3), OX40L (which binds OX40/TNFRSF4), CD40L (which binds CD40/TNFRSF5), (which binds Fas/TNFRSF6 and DcR3/TNFRSF6B), CD27L (which binds CD27/TNFRSF7), CD30L (which binds CD30/TNFRSF8), 4-1-BB-L (which binds 4-1-BB/TNFRSF9), TRAIL (which binds TRAIL-R1/TNFRSF10A, TRAIL-R2/TNFRSF10B, TRAIL-R3/TNFRSF10C, and TRAIL-R4/TNFRSF10D), RANKL (which binds RANK/TNFRSF11A and Osteoprotegrin/TNFRSF11B), APO-3L (which binds APO-3/TNFRSF12 and DR3L/TNFRSF12L), APRIL (which binds TACI/TNFRSF13B), BAFF (which binds BAFFR/TNFRSF13A), LIGHT (which binds HVEM/TNFRSF14), NGF ligands (which bind LNGFR, e.g. NGF-β, NGF-2/NTF3, NTF5, BDNF, IFRD1), GITRL (which binds GITR/TNFRSF18), EDAR1 & XEDAR ligand, Fn14 ligand, and Troy/Trade ligand.

In other exemplary embodiments, the bispecific binding molecules of the invention have at least one binding site for a first cell-surface molecule and at least one binding site for a second cell-surface molecule. In one embodiment, the first and second cell-surface molecules are located on different cells (e.g. different cell types). For example, bispecific molecules may have at least one arm directed against a tumor cell antigen and at least one arm directed against cell-surface receptor on a non-tumor cell (e.g. an immune cell). Exemplary bispecific binding molecules of this type include those having at least one binding site for a tumor cell antigen and at least one binding site directed against a cytotoxic trigger molecule of an immune effector cell (such as anti-Fc.gamma.RI/anti-CD15, anti-p185.sup.HER2/Fc.gamma.RIII (CD16), anti-p185.sup.HER2/anti-VEGF, anti-CD3/anti-malignant B-cell (1D10), anti-CD3/anti-p185.sup.HER2, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, and anti-pan carcinoma associated antigen (AMOC-31)/anti-CD3)). Bispecific molecules which bind to both tumor cell antigens and cytotoxic trigger molecule are capable of effectively juxtaposing a tumor cell with an immune effector cell, thereby activating the effector cell to destroy the tumor cell by cell-mediated immune mechanisms.

In another embodiment, the first and second cell-surface molecules to which a bispecific binding molecule is capable of binding are located on the same cell or cell type. By crosslinking the first and second receptors on the same cell, the bispecific binding molecules of the invention may inhibit or enhance an activity (e.g. signal transduction activity) associated with one or both of the first and second receptors. In one embodiment the first and second cell surface molecules are of the same type (e.g., are in the same family of molecules). In another embodiment said first and second cell surface molecules are distinct types (e.g., are in different families of molecules). Exemplary cell surface receptors to which the bispecific binding molecules bind include tumor cell antigens or immune cell receptors. Exemplary cell surface receptors include any of the cytokine receptors, adhesion molecules, or growth factor receptors described in section B supra.

In one embodiment, exemplary target molecules to which a binding molecule of the invention binds include one or more epitopes of e.g., heparin sulfate, growth factors or their receptors (.e.g, epidermal growth factor receptor, insulin-like growth factor receptor, hepatocyte growth factor (HGF/SF) receptor (See, e.g., Cao et al. Proc. Natl. Acad. Sci. 2001. 98:7443; Lu et al. 2004. J. Biol. Chem. 279:2856).

In an exemplary embodiment, at least one of the molecules to which a bispecific binding molecule of the invention binds is a member of the TNF receptor (TNFR) family. In another exemplary embodiment, the first and second target molecules to which a bispecific binding molecule of the invention binds are both TNFR family members. In another embodiment, a binding molecule of the invention binds to a TNFR family ligand. In yet another embodiment, a binding molecule of the invention binds to one TNFR family member and an antigen expressed on the surface of a tumor cell, e.g., preferentially expressed on a tumor cell. The limiting factor in the treatment of tumors with monospecific TNFR binding molecules is that often only a subset of tumors appears to be sensitive to such therapies. Multispecific TNFR binding molecules can specifically activate TNFRs, and enhance receptor signaling by, for example, bringing the TNFRs into close proximity. The invention provides improved bispecific TNFR binding molecules which can target more than one TNFR or TNFR type and enhance signaling, thus providing an improved method of treating cancer. In one embodiment, the bispecific TNFR binding molecule increases the signal strength by binding to two or more TNFRs of the same type increasing the number of TNFRs being brought together. In another more preferred embodiment, the bispecific TNFR binding molecule is capable of binding to two different receptors of the TNF family.

In one embodiment, at least one of the TNFRs to which a bispecific TNFR binding molecule binds contains a death domain. The term "death domain" refers to a cytoplasmic region of a TNF family receptor which is involved TNF-mediated cell death or apoptotic signaling and cell-cytotoxicity induction mediated by these receptors. This region couples the receptor to caspase activation via adaptor proteins resulting in activation of the extrinsic death pathway.

Examples of TNF receptors which contain death domains include, but are not limited to, TNFR1 (TNFRSF1A), Fas (TNFRSF6), DR-3 (TNFRSF6B), LNGFR (TNFRSF16) TRAIL-R1 (TNFRSF10A), TRAIL-R2 (TNFRSF10B) and DR6 (TNFRSF21). The apoptotic signaling of these receptors is modulated upon binding of a cognate ligand and formation of any of the following receptor-ligand pairs: TNFR1/TNFα, Fas/FasL, DR-3/DR-3LG, TRAIL-R1/TRAIL, or TRAIL-R2/TRAIL.

Bispecific TNFR binding molecules that target TNF family receptors containing death domains are useful for the treatment of cancer since the TNFRs of this type are often overexpressed on tumor cells and stimulating of the receptor can activate tumor cell apoptosis. In preferred embodiments, the death-domain containing TNFR to which the bispecific TNFR binding molecule of the invention binds is TRAIL-R2. TRAIL-R2 is preferred for human tumor therapy since its activation does not trigger hepatocyte apoptosis and hence should have reduced toxicity.

While the activation of some of death domain containing receptors, e.g. TNFR1 or Fas, has been toxic in in vivo applications, it is likely that tethering these receptors to other TNF receptors may diminish toxicity and thus render a toxic antibody less toxic.

In one embodiment, a bispecific TNFR binding molecule of the invention comprises at least one binding site directed to a TNFR containing a death domain and at least one binding site directed to a TNFR lacking a death domain.

In certain exemplary embodiments, TNFRs lacking a death domain include TNFRs involved in tissue differentiation. Examples of TNFR receptors involved in tissue differentiation include LTβR, RANK, EDAR1, XEDAR, Fn14, Troy/Trade, and NGFR. TNFRs involved in tissue differentiation may influence tissue differentiation following binding of a cognate ligand. TNFR binding molecules that target TNFRs involved in tissue differentiation can affect tumors in several ways. First, they have the potential to directly slow tumor growth by altering cell cycle progression. Second, tissue differentiation in the context of tumor cell transformation may lead to cell cycle conflict and default apoptosis. Third, such conflicting input may render a cell more sensitive to chemotherapy.

In certain preferred embodiments, TNFR involved in tissue differentiation is lymphotoxin β receptor (LTβR). LTβR is involved in the control of the maturation status of various specialized stromal cells in the immune system and plays a critical role during the development of the stromal elements of the lymph node anlagen. It has been proposed that activation of a developmental program in epithelial or fibroblastoid cells in the context of a transformed cell is detrimental to their survival and this action may account for some of the anti-tumor activity of LTβR activation. These receptors can also initiate inflammatory programs that involve chemokine release or promote immunological anti-tumor responses. Such release could affect the inflammatory status of the tumor and/or invoke infiltration of lymphoid elements promoting an immunological reaction to the tumor. Thus, bispecific TNFR binding molecules which bind LTβR, alone or in combination with TNF receptors containing death domains (e.g. TRAIL-R2), are encompassed by the invention.

In certain exemplary embodiments, the TNFRs lacking a death domain include TNFRs involved in immune regulation. Such receptors include TNFR2, HVEM, CD27, CD30, CD40, 4-1BB, OX40, GITR, TACI, BAFF-R, BCMA, and RELT. Additional TNF family receptors involved in immune regulation include TRAIL-R3 and TRAIL-R4.

Other target TNF family receptors with a role in tumor formation can be identified using existing RNA databases of receptor expression in various cell types which allow one to define TNF family receptors that are present or ideally overexpressed on various tumors. Moreover, existing RNA databases provide an additional advantage in that the pair of TNF family receptors to which a bispecific TNFR binding molecule of the invention binds could be optimized by identifying those receptor pairs that are more uniquely expressed on a tumor type or subset of tumors but are not abundant on normal tissues, especially liver and vasculature. In such a manner receptor pairs (or more) are identified that could deliver a potent signal to the tumor and spare normal tissues.

Methods of producing multispecific molecules are well known in the art. For example, recombinant technology can be used to produce multispecific molecules, e.g., diabodies, single-chain diabodies, tandem scFvs, etc. Exemplary techniques for producing multispecific molecules are known in the art (e.g., Kontermann et al. Methods in Molecular Biology Vol. 248: Antibody Engineering: Methods and Protocols. Pp 227-242 US 2003/0207346 A1 and the references cited therein). In one embodiment, a multimeric multispecific molecules are prepared using methods such as those described e.g., in US 2003/0207346 A1 or U.S. Pat. No. 5,821,333, or US2004/0058400.

In another embodiment, a multispecific binding molecule of the invention is a multispecifc fusion protein. As used herein the phrase "multispecific fusion protein" designates fusion proteins (as hereinabove defined) having at least two binding specificities (i.e. combining a binding domains of a ligand or receptor). Multispecific fusion proteins can be assembled, e.g., as heterodimers, heterotrimers or heterotetramers, essentially as disclosed in WO 89/02922 (published Apr. 6, 1989), in EP 314, 317 (published May 3, 1989), and in U.S. Pat. No. 5,116,964 issued May 2, 1992. Preferred multispecific fusion proteins are bispecific. Examples of bispecific fusion proteins include CD4-scFv/TNFreceptor-IgG and CD4-scFv/L-selectin-IgG. The last mentioned molecule combines the lymph node binding function of the lymphocyte homing receptor (LHR, L-selectin), and the HIV binding function of CD4, and finds potential application in the prevention or treatment of HIV infection, related conditions, or as a diagnostic.

In another embodiment, the invention pertains to multispecific stabilized binding molecules, e.g., bispecific binding molecules, e.g., antibodies, which incorporate at least one binding site that binds to a known target and at least one binding site which recognizes an unknown target (for example, in one embodiment, the bispecific molecule incorporates binding sites selected from a semi-synthetic antibody phage display library) and a stabilized scFv of the invention.

In one embodiment of the invention, one of ordinary skill in the art could start with a single chain antibody of known specificity and build a Fab library using techniques known in the art or, alternatively, the skilled artisan could start with an Fab fragment of known specificity and build a stabilized single chain library using techniques known in the art. It is known in the art that libraries from nonimmunized sources and prepared by synthetic recombination of V-gene sequences (preferably recombination of VH with, DH and HT, and VL with JL sequences) can be used to isolate antibodies to any antigen. For example, patent application WO92/01047 teaches that antibody fragments can be displayed on the surface of bacteriophage and that they will bind antigen. Antibody fragments (e.g., Fab, Fv, scFv and VH) can be directly selected using this characteristic. Other methods known in the art include those taught, e.g., in U.S. Pat. Nos. 5,698,426; 6,291,159; 5,658,727; 5,667,988; and 5,969,108.

In another embodiment, scFv which recognize a known target can be dimerized with scFv isolated from a semi-synthetic human phage antibody display library. (see, e.g., Kruif and Logtenberg 1996. J. Biol. Chem. 271:7630).

In one embodiment, the subject multispecific molecule is expressed in an expression system used to express antibody molecules, for example mammalian cells, yeast such as *Picchia, E. coli*, Bacculovirus, etc. In one embodiment, the subject bispecific molecule is expressed in the NEOSPLA vector system (see, e.g., U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence.

In one embodiment, the subject multispecific molecules comprise a synthetic connecting peptide.

These multispecific molecules have one or more binding sites for a known target and express a library at one or more binding sites. Such multispecific molecules can be used, e.g., to identify molecules in close proximity to or associated with the known target. For example, the skilled artisan could use the subject multispecific molecules in an assay to select for those that induce a particular response, e.g., apoptosis or cellular activation, using screening methods well known in the art. The bispecific molecule identified as producing the response screened for can then be identified and its specificity determined. Using such methods it is possible to identify molecules in close association with particular targets of interest, e.g., T cell markers or other signaling molecules (such as CRIPTO-I, death domain molecules, or molecules involved in apoptosis). The proximity of the known target and the molecule newly identified as a "nearest neighbor" can be confirmed using immunoprecipitation or other techniques known to those of skill in the art. Using these methods it is possible to identify molecules as targets for modulating a particular cellular response.

Binding specificities comprising antigen recognition sites or entire variable regions of multispecific binding molecule, in particular multispecific antibodies or antibody variants of the invention may be derived from one or more parental antibodies. The parental antibodies can include naturally occurring antibodies or antibody fragments, antibodies or antibody fragments adapted from naturally occurring antibodies, antibodies constructed de novo using sequences of antibodies or antibody fragments known to be specific a target molecule. Sequences that may be derived from parental antibodies include heavy and/or light chain variable regions and/or CDRs, framework regions or other portions thereof.

In one exemplary embodiment of the invention, the parental antibodies used to construct a multispecific TNFR binding molecule are an anti-TRAIL-R2 antibody, for example 14A2, and an anti-LTβR antibody, for example CBE11 or BHA10. Multivalent, multispecific antibodies may contain a heavy chain comprising two or more variable regions and/or a light chain comprising one or more variable regions wherein at least two of the variable regions recognize different epitopes of LTβR.

Multispecific, e.g., bispecific TNFR binding molecules may be constructed in a variety different ways using a variety of different sequences derived from parental anti-LTβR antibodies, including murine or humanized BHA10 (Browning et al., *J. Immunol.* 154: 33 (1995); Browning et al. *J. Exp. Med.* 183:867 (1996)), murine or humanized CBE11 (U.S. Pat. No. 6,312,691 and WO 02/30986, respectively), and/or parental anti-TRAIL-R2 murine or chimeric 14A2. Examples of anti-LTβR antibodies which can be used for the bispecific TNFR binding molecules of the invention include consisting: BKA11, CDH10, BCG6, AGH1, BDA8, CBE11 and BHA10 or BHA10. The following hybridoma cell lines producing monoclonal anti-LT-β-R antibodies may be used to produce anti-LTβR antibodies from which to derive antibody construct sequences, which have been previously deposited with the American Type Culture Collection (ATCC) according to the provisions of the Budapest Treaty and have been assigned the indicated ATCC accession numbers:

| Cell Line | mAb Name | Accession No. |
| --- | --- | --- |
| a) AG.H1.5.1 | AGH1 | HB 11796 |
| b) BD.A8.AB9 | BDA8 | HB 11798 |
| c) BC.G6.AF5 | BCG6 | B 11794 |

-continued

| Cell Line | mAb Name | Accession No. |
|---|---|---|
| d) BH.A10 | BHA10 | B 11795 |
| e) BK.A11.AC10 | BKA11 | B 11799 |
| f) CB.E11.1 | CBE11 | B 11793 |
| g) CD.H10.1 | CDH10 | B 11797 |

Other examples of anti-TNF receptor antibodies which can be used in the multispecific TNFR binding molecules of the invention include antibodies directed to TNF receptors containing a death domain. A number of antibodies have been generated to death domain containing TNF receptors and are well known in the art. Such antibodies include anti-TNF-R1 monoclonal antibodies (R&D systems anti-TNF-R1; Tularik mAb #985, U.S. Pat. Nos. 6,110,690; 6,437,113), anti-Fas receptor mAb CH-11 (U.S. Pat. No. 6,312,691; WO 95/10540), anti-DR3 antibodies (U.S. Pat. No. 5,985,547; Johnson, et al. (1984) ImmunoBiology of HLA, ed. Dupont, B. O., Springer, N.Y.; U.S. Pat. Nos. 6,462,176; 6,469,166), and anti-TRAIL-R antibodies (U.S. Pat. Nos. 5,763,223; 6,072,047; 6,284,236; 6,521,228; 6,569,642; 6,642,358; and 6,417,328).

A number of antibodies have been also raised to TNF receptors involved in tissue differentiation and are known in the art. Examples of anti-TNF receptor antibodies specific to TNF receptors involved in tissue differentiation include: anti-RANK monoclonal antibodies (Immunex—U.S. Pat. Nos. 6,562,948; 6,537,763; 6,528,482; 6,479,635; 6,271,349; 6,017,729; Komed—WO 03/080671), anti-EDAR polyclonal (anti-human) and monoclonal (anti-mouse) antibodies (R&D Systems—MAB745, BAF157; Elomaa et al. (2001) Human Molecular Genetics. 10:953), anti-XEDAR monoclonal and polyclonal antibodies (R&D Systems—MAB1093 and AF1093), anti-Fn14 monoclonal antibodies (Nakayama et al. (2003) J. Immunology 170:341; ITEM-1, ITEM-2, and ITEM-4 clones available from eBioscience), anti-TROY antibody (T3323 from Sigma-Aldrich), and anti-NGFR (anti-rodent) antibodies (Chemicon USA).

A number of antibodies have been also raised to TNF receptors involved in immune regulation and are known in the art. Examples of anti-TNF receptor antibodies specific to TNF receptors involved in immune regulation include: anti-HVEM antibodies (HGSI—WO 03/086301), anti-CD40 antibodies (Biogen—WO 97/20063; Chiron—U.S. Pat. Nos. 5,677,165; 5,874,082; 6,004,552; 6,056,959; 6,315,998; US Application Publication No. 2002/0106371; US Application Publication Nos. 2003/0059427; US20030118588A1; 2003/0211100A1; US2002020142358A1; US Pat. Nos. 6,312,693; 6,051,228; Fanslow et al.—U.S. Pat. No. 5,801,227), anti-4-1BB (PCT Publication No. WO 03/084999; EP 0948353; U.S. Pat. No. 6,210,669; Genecraft—WO 03/083069), and anti-BAFF-R antibodies (rabbit polyclonal—ProSci catalog #3097), among many other antibodies raised to immune regulation receptors.

A variety of other multivalent antibody constructs may be developed by one of skill in the art using routine recombinant DNA techniques, for example as described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; Shaw et al. (1988) J. Natl. Cancer Inst. 80:1553-1559); Morrison (1985) Science 229:1202-1207; Oi et al. (1986) BioTechniques 4:214; U.S. Pat. No. 5,225,539; Jones et al. (1986) Nature 321:552-525; Verhoeyan et al. (1988) Science 239:1534; Beidler et al. (1988) J. Immunol. 141:4053-4060; and Winter and Milstein, Nature, 349, pp. 293-99 (1991)). Preferably non-human antibodies are "humanized" by linking the non-human antigen binding domain with a human constant domain (e.g. Cabilly et al., U.S. Pat. No. 4,816,567; Morrison et al., Proc. Natl. Acad. Sci. U.S.A., 81, pp. 6851-55 (1984)).

Other methods which may be used to prepare multivalent antibody constructs are described in the following publications: Ghetie, Maria-Ana et al. (2001) Blood 97:1392-1398; Wolff, Edith A. et al. (1993) Cancer Research 53:2560-2565; Ghetie, Maria-Ana et al. (1997) Proc. Natl. Acad. Sci. 94:7509-7514; Kim, J. C. et al. (2002) Int. J. Cancer 97(4):542-547; Todorovska, Aneta et al. (2001) Journal of Immunological Methods 248:47-66; Coloma M. J. et al. (1997) Nature Biotechnology 15:159-163; Zuo, Zhuang et al. (2000) Protein Engineering (Suppl.) 13(5):361-367; Santos A. D., et al. (1999) Clinical Cancer Research 5:3118s-3123s; Presta, Leonard G. (2002) Current Pharmaceutical Biotechnology 3:237-256; van Spriel, Annemiek et al., (2000) Review Immunology Today 21(8) 391-397.

XI. Expression of Binding Molecules

Following manipulation of the isolated genetic material to provide polypeptides of the invention as set forth above, the genes are typically inserted in an expression vector for introduction into host cells that may be used to produce the desired quantity of polypeptide that, in turn, provides the claimed binding molecules.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals. In particularly preferred embodiments the cloned variable region genes are inserted into an expression vector along with the heavy and light chain constant region genes (preferably human) synthetic as discussed above. Preferably, this is effected using a proprietary expression vector of IDEC, Inc., referred to as NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. As seen in the examples below, this vector has been found to result in very high level expression of antibodies upon incorporation of variable and constant region genes, transfection in CHO cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the polypeptides of the invention of the instant invention may be expressed using polycistronic constructs such as those disclosed in copending U.S. provisional application No. 60/331,481 filed Nov. 16, 2001 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a monomeric subunit of the binding molecule (e.g. a modified antibody) has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, the host cell line used for protein expression (e.g., of multivalent binding molecules) is of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). In one embodiment NS0 cells may be used. CHO cells are particularly preferred. Host cell lines are typically available from commercial services, the American Tissue Culture Collection or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding the polypeptide of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules. Where tetravalent forms of antibodies are desired, the subunits will then self-assemble into tetravalent antibodies (WO02/096948A2).

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

XII. Labeling or Conjugation of Binding Molecules

The binding molecules of the present invention may be used in non-conjugated form or may be conjugated to at least one of a variety of effector, i.e., functional, molecules, e.g., to facilitate target detection or for imaging or therapy of the patient. The polypeptides of the invention can be labeled or conjugated either before or after purification, when purification is performed. In particular, the polypeptides of the present invention may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), PEG, or detectable molecules useful in imaging. In another embodiment, a polypeptide of the invention can be conjugated to a molecule that decreases vascularization of tumors. In other embodiments, the disclosed compositions may comprise polypeptides of the invention coupled to drugs or prodrugs. Still other embodiments of the present invention comprise the use of polypeptides of the invention conjugated to specific biotoxins or their cytotoxic fragments such as ricin, gelonin, pseudomonas exotoxin or diphtheria toxin. The selection of which conjugated or unconjugated polypeptide to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy cells in solid tumors as well as lymphomas/leukemias in animal models, and in some cases in humans. Exemplary radioisotopes include: $^{90}$Y, $^{125}$I, $^{131}$I, $^{123}$I, $^{111}$I, $^{105}$Rh, $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

With respect to the use of radiolabeled conjugates in conjunction with the present invention, polypeptides of the invention may be directly labeled (such as through iodination) or may be labeled indirectly through the use of a chelating agent. As used herein, the phrases "indirect labeling" and "indirect labeling approach" both mean that a chelating agent is covalently attached to a binding molecule and at least one radionuclide is associated with the chelating agent. Such chelating agents are typically referred to as bifunctional chelating agents as they bind both the polypeptide and the radioisotope. Particularly preferred chelating agents comprise 1-isothiocycmatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

As used herein, the phrases "direct labeling" and "direct labeling approach" both mean that a radionuclide is covalently attached directly to a polypeptide (typically via an amino acid residue). More specifically, these linking technologies include random labeling and site-directed labeling. In the latter case, the labeling is directed at specific sites on the polypeptide, such as the N-linked sugar residues present only on the Fc portion of the conjugates. Further, various direct labeling techniques and protocols are compatible with the instant invention. For example, Technetium-99m labeled polypeptides may be prepared by ligand exchange processes, by reducing pertechnate (TcO$_4^-$) with stannous ion solution, chelating the reduced technetium onto a Sephadex column and applying the polypeptides to this column, or by batch labeling techniques, e.g. by incubating pertechnate, a reducing agent such as SnCl$_2$, a buffer solution such as a sodium-potassium phthalate-solution, and the antibodies. In any event, preferred radionuclides for directly labeling antibodies are well known in the art and a particularly preferred radionuclide for direct labeling is $^{131}$I covalently attached via tyrosine residues. Polypeptides according to the invention may be derived, for example, with radioactive sodium or potassium iodide and a chemical oxidizing agent, such as sodium hypochlorite, chloramine T or the like, or an enzymatic oxidizing agent, such as lactoperoxidase, glucose oxidase and glucose. However, for the purposes of the present invention, the indirect labeling approach is particularly preferred.

Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, 5,434,287 and 5,124,471 of Gansow also relate to polysubstituted DTPA chelates. These patents are incorporated herein in their entirety. Other examples of compatible metal chelators are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like. Cyclohexyl-DTPA or CHX-DTPA is particularly preferred and is exemplified extensively below. Still other compatible chelators, including those yet to be discovered, may easily be discerned by a skilled artisan and are clearly within the scope of the present invention.

Compatible chelators, including the specific bifunctional chelator used to facilitate chelation in co-pending application Ser. Nos. 08/475,813, 08/475,815 and 08/478,967, are preferably selected to provide high affinity for trivalent metals, exhibit increased tumor-to-non-tumor ratios and decreased bone uptake as well as greater in vivo retention of radionuclide at target sites, i.e., B-cell lymphoma tumor sites. However, other bifunctional chelators that may or may not possess all of these characteristics are known in the art and may also be beneficial in tumor therapy.

It will also be appreciated that, in accordance with the teachings herein, polypeptides may be conjugated to different radiolabels for diagnostic and therapeutic purposes. To this end the aforementioned co-pending applications, herein incorporated by reference in their entirety, disclose radiolabeled therapeutic conjugates for diagnostic "imaging" of tumors before administration of therapeutic antibody. "In2B8" conjugate comprises a murine monoclonal antibody, 2B8, specific to human CD20 antigen, that is attached to $^{111}$In via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}$In is particularly preferred as a diagnostic radionuclide because between about 1 to about 10 mCi can be safely administered without detectable toxicity; and the imaging data is generally predictive of subsequent $^{90}$Y-labeled antibody distribution. Most imaging studies utilize 5 mCi $^{111}$In-labeled antibody, because this dose is both safe and has increased imaging efficiency compared with lower doses, with optimal imaging occurring at three to six days after antibody administration. See, for example, Murray, *J. Nuc. Med.* 26: 3328 (1985) and Carraguillo et al., *J. Nuc. Med.* 26: 67 (1985).

As indicated above, a variety of radionuclides are applicable to the present invention and those skilled in the art can readily determine which radionuclide is most appropriate under various circumstances. For example, $^{131}$I is a well known radionuclide used for targeted immunotherapy. However, the clinical usefulness of $^{131}$I can be limited by several factors including: eight-day physical half-life; dehalogenation of iodinated antibody both in the blood and at tumor sites; and emission characteristics (e.g., large gamma component) which can be suboptimal for localized dose deposition in tumor. With the advent of superior chelating agents, the opportunity for attaching metal chelating groups to proteins has increased the opportunities to utilize other radionuclides such as $^{111}$In and $^{90}$Y. $^{90}$Y provides several benefits for utilization in radioimmunotherapeutic applications: the 64 hour half-life of $^{90}$Y is long enough to allow antibody accumulation by tumor and, unlike e.g., $^{131}$I, $^{90}$Y is a pure beta emitter of high energy with no accompanying gamma irradiation in its decay, with a range in tissue of 100 to 1,000 cell diameters. Furthermore, the minimal amount of penetrating radiation allows for outpatient administration of $^{90}$Y-labeled antibodies. Additionally, internalization of labeled antibody is not required for cell killing, and the local emission of ionizing radiation should be lethal for adjacent tumor cells lacking the target molecule.

Those skilled in the art will appreciate that these non-radioactive conjugates may also be assembled using a variety of techniques depending on the selected agent to be conjugated. For example, conjugates with biotin are prepared e.g. by reacting the polypeptides with an activated ester of biotin such as the biotin N-hydroxysuccinimide ester. Similarly, conjugates with a fluorescent marker may be prepared in the presence of a coupling agent, e.g. those listed above, or by reaction with an isothiocyanate, preferably fluorescein-isothiocyanate. Conjugates of the polypeptides of the invention with cytostatic/cytotoxic substances and metal chelates are prepared in an analogous manner.

Many effector molecules lack suitable functional groups to which antibodies can be linked. In one embodiment, an effector molecule, e.g., a drug or prodrug is attached to the antibody through a linking molecule. In one embodiment, the linking molecule contains a chemical bond that allows for the activation of cytotoxicity at a particular site. Suitable chemical bonds are well known in the art and include disulfide bonds, acid labile bonds, photolabile bonds, peptidase labile bonds, thioether bonds formed between sulfhydryl and maleimide groups, and esterase labile bonds. Most preferably, the linking molecule comprises a disulfide bond or a thioether bond. In accordance with the invention, the linking molecule preferably comprises a reactive chemical group. Particularly preferred reactive chemical groups are N-succinimidyl esters and N-sulfosuccinimidyl esters. In a preferred embodiment, the reactive chemical group can be covalently bound to the effector via disulfide bonding between thiol groups. In one embodiment an effector molecule is modified to comprise a thiol group. One of ordinary skill in the art will appreciate that a thiol group contains a sulfur atom bonded to a hydrogen atom and is typically also referred to in the art as a sulfhydryl group, which can be denoted as "—SH" or "RSH."

In one embodiment, a linking molecule may be used to join the effector molecule with the binding molecule. The linking molecule of the invention may be cleavable or non-cleavable. In one embodiment, the cleavable linking molecule is a redox-cleavable linking molecule, such that the linking molecule is cleavable in environments with a lower redox potential, such as the cytoplasm and other regions with higher concentrations of molecules with free sulfhydryl groups. Examples of linking molecules that may be cleaved due to a change in redox potential include those containing disulfides. The cleaving stimulus can be provided upon intracellular uptake of the binding protein of the invention where the lower redox potential of the cytoplasm facilitates cleavage of the linking molecule. In another embodiment, a decrease in pH triggers the release of the maytansinoid cargo into the target cell. The decrease in pH is implicated in many physiological and pathological processes, such as endosome trafficking, tumor growth, inflammation, and myocardial ischemia. The pH drops from a physiological 7.4 to 5-6 in endosomes or 4-5 in lysosomes. Examples of acid sensitive linking molecules which may be used to target lysosomes or endosomes of cancer cells, include those with acid-cleavable bonds such as those found in acetals, ketals, orthoesters, hydrazones, trityls, cis-aconityls, or thiocarbamoyls (see for example, Willner et al., (1993), *Bioconj. Chem.*, 4: 521-7; U.S. Pat. Nos. 4,569,789, 4,631,190, 5,306,809, and 5,665,358). Other exemplary acid-sensitive linking molecules comprise dipeptide sequences Phe-Lys and Val-Lys (King et al., (2002), *J. Med. Chem.*, 45: 4336-43). The cleaving stimulus can be provided upon intracellular uptake trafficking to low pH endosomal compartments (e.g. lysosomes). Other exemplary acid-cleavable linking molecules are the molecules that contain two or more acid cleavable bonds for attachment of two or more maytansinoids (King et al., (1999), *Bioconj. Chem.*, 10: 279-88; WO 98/19705).

Cleavable linking molecules may be sensitive to biologically supplied cleaving agents that are associated with a particular target cell, for example, lysosomal or tumor-associated enzymes. Examples of linking molecules that can be cleaved enzymatically include, but are not limited to, peptides and esters. Exemplary enzyme cleavable linking molecules include those that are sensitive to tumor-associated proteases such as Cathepsin B or plasmin (Dubowchik et al., (1999), *Pharm. Ther.*, 83: 67-123; Dubowchik et al., (1998), *Bioorg. Med. Chem. Lett.*, 8: 3341-52; de Groot et al., (2000), *J. Med. Chem.*, 43: 3093-102; de Groot et al., (1999)m 42: 5277-83). Cathepsin B-cleavable sites include the dipeptide sequences valine-citrulline and phenylalanine-lysine (Doronina et al., (2003), *Nat. Biotech.*, 21(7): 778-84); Dubowchik et al., (2002), *Bioconjug. Chem.*, 13: 855-69). Other exemplary enzyme-cleavable sites include those formed by oligopeptide sequences of 4 to 16 amino acids (e.g., Suc-β-Ala-Leu-Ala-Leu) which recognized by trouse proteases such as Thimet Oliogopeptidase (TOP), an enzyme that is preferentially released by neutrophils, macrophages, and other granulocytes.

In a further embodiment, the linking molecule is formed by reacting a binding molecule of the invention with a linking molecule of the formula:

wherein:
X is an attachment molecule;
Y is a spacer molecule; and
Z is a effector attachment moeity.

The term "binding molecule attachment molecule" includes molecules which allow for the covalent attachment of the connecting peptide to a binding molecule of the invention.

The attachment molecule may comprise, for example, a covalent chain of 1-60 carbon, oxygen, nitrogen, sulfur atoms, optionally substituted with hydrogen atoms and other substituents which allow the binding molecule to perform its intended function. The attachment molecule may comprise peptide, ester, alkyl, alkenyl, alkynyl, aryl, ether, thioether, etc. functional groups. Preferably, the attachment molecule is selected such that it is capable of reacting with a reactive functional group on a polypeptide comprising at least one antigen binding site, to form a binding molecule of the invention. Examples of attachment molecules include, for example, amino, carboxylate, and thiol attachment molecules.

Amino attachment molecules include molecules which react with amino groups on a polypeptide, such that a binding molecule of the invention is formed. Amino attachment molecules are known in the art. Examples of amino attachment molecules include, activated carbamides (e.g., which may react with an amino group on a binding molecule to form a linking molecule which comprises urea group), aldehydes (e.g., which may react with amino groups on a binding molecule), and activated isocyanates (which may react with an amino group on a binding molecule to from a linking molecule which comprises a urea group). Examples of amino attachment molecules include, but are not limited to, N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl, or 3-carboxy-4-nitrophenyl molecule.

Carboxylate attachment molecules include molecules which react with carboxylate groups on a polypeptide, such that a binding molecule of the invention is formed. Carboxylate attachment molecules are known in the art. Examples of carboxylate attachment molecules include, but are not limited to activated ester intermediates and activated carbonyl intermediates, which may react with a COOH group on a binding molecule to form a linking molecule which comprises a ester, thioester, or amide group.

Thiol attachment molecules include molecules which react with thiol groups present on a polypeptide, such that a binding molecule of the invention is formed. Thiol attachment molecules are known in the art. Examples of thiol attachment molecules include activated acyl groups (which may react with a sulfhydryl on a binding molecule to form a linking molecule which comprises a thioester), activated alkyl groups (which may react with a sulfhydryl on a binding molecule to form a linking molecule which comprises a thioester molecule), Michael acceptors such as maleimide or acrylic groups (which may react with a sulfhydryl on a binding molecule to form a Michael-type addition product), groups which react with sulfhydryl groups via redox reactions, activated di-sulfide groups (which may react with a sulfhydryl group on a binding molecule to form, for example, a linking molecule which comprises a disulfide molecule). Other thiol attachment molecules include acrylamides, alpha-iodoacetamides, and cyclopropan-1,1-dicarbonyl compounds. In addition, the thiol attachment molecule may comprise a molecule which modifies a thiol on the binding molecule to form another reactive species to which the linking molecule can be attached to form a binding molecule of the invention.

The spacer molecule, Y, is a covalent bond or a covalent chain of atoms which may contain one or more aminoacid residues. It may also comprise 0-60 carbon, oxygen, sulfur or nitrogen atoms optionally substituted with hydrogen or other substituents which allow the resulting binding molecule to perform its intended function. In one embodiment, Y comprises an alkyl, alkenyl, alkynyl, ester, ether, carbonyl, or amide molecule.

In another embodiment, a thiol group on the binding molecule is converted into a reactive group, such as a reactive carbonyl group, such as a ketone or aldehyde. The attachment molecule is then reacted with the ketone or aldehyde to form the desired compound of the invention. Examples of carbonyl reactive attachment molecules include, but are not limited to, hydrazines, hydrazides, O-substituted hydroxylamines, alpha-beta-unsaturated ketones, and $H_2C=CH-CO-NH-NH_2$. Other examples of attachment molecules and methods for modifying thiol molecules which can be used to form binding molecules of the invention are described Pratt, M. L. et al. J Am Chem Soc. 2003 May 21; 125(20):6149-59; and Saxon, E. Science. 2000 Mar. 17; 287(5460):2007-10.

The linking molecule may be a molecule which is capable of reacting with an effector molecule or a derivative thereof to form a binding molecule of the invention. For example, the effector molecule may be linked to the remaining portions of the molecule through a disulfide bond. In such cases, the linking molecule is selected such that it is capable of reacting with an appropriate effector moiety derivative such that the effector molecule is attached to the binding molecule of the invention. As described above, the linking molecule and/or the connecting peptide as a whole may be selected that the connecting peptide is cleaved in an appropriate environment.

Particularly preferred connecting peptide molecules include, for example, N-succinimidyl 3-(2-pyridyldithio) propionate (SPDP) (see, e.g., Carlsson et al., Biochem. J., 173, 723-737 (1978)), N-succinimidyl 4-(2-pyridyldithio) butanoate (SPDB) (see, e.g., U.S. Pat. No. 4,563,304), N-succinimidyl 4-(2-pyridyldithio)pentanoate (SPP) (see, e.g., CAS Registry number 341498-08-6), N-succinimidyl 4-(N-maleimidomethyl)cyclohexane-1-carboxylate (SMCC) (see, e.g., Yoshitake et al., Eur. J. Biochem., 101, 395-399 (1979)), and N-succinimidyl 4-methyl-4-[2-(5-nitro-pyridyl)-dithio] pentanoate (SMNP) (see, e.g., U.S. Pat. No. 4,563,304) The most preferred connecting peptide molecules for use in the inventive composition are SPP, SMCC, and SPDB. In a preferred embodiment, SPDB is used to link an effector molecule to a binding molecule of the invention.

Preferred cytotoxic effector molecules for use in the present invention are cytotoxic drugs, particularly those which are used for cancer therapy. As used herein, "a cytotoxin or cytotoxic agent" means any agent that is detrimental to the growth and proliferation of cells and may act to reduce, inhibit or destroy a cell or malignancy. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. Any cytotoxin that acts to retard or slow the growth of immunoreactive cells or malignant cells is within the scope of the present invention.

Exemplary cytotoxins include, in general, cytostatic agents, alkylating agents, antimetabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine.

Particularly preferred molecules for conjugation are maytansinoids. Maytansinoids were originally isolated from the east African shrub belonging to the genus *Maytenus*, but were subsequently also discovered to be metabolites of soil bacteria, such as *Actinosynnema pretiosum* (see, e.g., U.S. Pat. No. 3,896,111). Maytansinoids are known in the art to include maytansine, maytansinol, C-3 esters of maytansinol, and other maytansinol analogues and derivatives (see, e.g., U.S. Pat. Nos. 5,208,020 and 6,441,163). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues also are known in the art and described in, for example, Kupchan et al., J. Med. Chem., 21, 31-37 (1978). Methods for generating maytansinol and analogues and derivatives thereof are described in, for example, U.S. Pat. No. 4,151,042.

Suitable maytansinoids for use as antibody conjugates can be isolated from natural sources, synthetically produced, or semi-synthetically produced using methods known in the art. Moreover, the maytansinoid can be modified in any suitable manner, so long as sufficient cytotoxicity is preserved in the ultimate conjugate molecule.

Particularly preferred maytansinoids comprising a linking molecule that contains a reactive chemical group are C-3 esters of maytansinol and its analogs where the linking molecule contains a disulfide bond and the attachment molecule comprises a N-succinimidyl or N-sulfosuccinimidyl ester. Many positions on maytansinoids can serve as the position to chemically link the linking molecule, e.g., through an effector attachment molecule. For example, the C-3 position having a hydroxyl group, the C-14 position modified with hydroxymethyl, the C-15 position modified with hydroxy and the C-20 position having a hydroxy group are all useful. The linking molecule most preferably is linked to the C-3 position of maytansinol. Most preferably, the maytansinoid used in connection with the inventive composition is $N^{2'}$-deacetyl-$N^{2'}$-(–3-mercapto-1-oxopropyl)-maytansine (DM1) or $N^{2'}$-deacetyl-$N^{2'}$-(4-mercapto-4-methyl-1-oxopentyl)-maytansine (DM4).

Linking molecules with other chemical bonds also can be used in the context of the invention, as can other maytansinoids. Specific examples of other chemical bonds which may be incorporated in the linking molecules include those described above, such as, for example acid labile bonds, thioether bonds, photolabile bonds, peptidase labile bonds and esterase labile bonds. Methods for producing maytansinoids with linking molecules and/or effector attachment molecules are described in, for example, U.S. Pat. Nos. 5,208,020, 5,416,064, and 6,333,410.

The linking molecule (and/or the effector attachment molecule) of a maytansinoid typically and preferably is part of a larger connecting peptide molecule that is used to join the antibody to the maytansinoid. Any suitable connecting peptide molecule can be used in connection with the invention, so long as the linking molecule provides for retention of the cytotoxicity and targeting characteristics of the maytansinoid and the antibody, respectively. The linking molecule joins the maytansinoid to the antibody through chemical bonds (as described above), such that the maytansinoid and the antibody are chemically coupled (e.g., covalently bonded) to each other. Desirably, the linking molecule chemically couples the maytansinoid to the antibody through disulfide bonds or thioether bonds. Most preferably, the antibody is chemically coupled to the maytansinoid via disulfide bonds.

Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, caminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. As noted previously, one skilled in the art may make chemical modifications to the desired compound in order to make reactions of that compound more convenient for purposes of preparing conjugates of the invention.

One example of particularly preferred cytotoxins comprise members or derivatives of the enediyne family of anti-tumor antibiotics, including calicheamicin, esperamicins or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present only on the Fc portion of the constructs. Such site-directed linking methods have the advantage of reducing the possible effects of linkage on the binding properties of the constructs.

Among other cytotoxins, it will be appreciated that polypeptides can also be associated with a biotoxin such as ricin subunit A, abrin, diptheria toxin, botulinum, cyanginosins, saxitoxin, shigatoxin, tetanus, tetrodotoxin, trichothecene, verrucologen or a toxic enzyme. Preferably, such constructs will be made using genetic engineering techniques that allow for direct expression of the binding molecule-toxin construct. Other biological response modifiers that may be associated with the polypeptides of the invention of the present invention comprise cytokines such as lymphokines and interferons. In view of the instant disclosure it is submitted that one skilled in the art could readily form such constructs using conventional techniques.

Another class of compatible cytotoxins that may be used in conjunction with the disclosed polypeptides are radiosensitizing drugs that may be effectively directed to tumor or immunoreactive cells. Such drugs enhance the sensitivity to ionizing radiation, thereby increasing the efficacy of radiotherapy. A conjugate internalized by the tumor cell would deliver the radiosensitizer nearer the nucleus where radiosensitization would be maximal. The unbound radiosensitizer linked polypeptides of the invention would be cleared quickly from the blood, localizing the remaining radiosensitization agent in the target tumor and providing minimal uptake in normal tissues. After rapid clearance from the blood, adjunct radiotherapy would be administered in one of three ways: 1.) external beam radiation directed specifically to the tumor, 2.) radioactivity directly implanted in the tumor or 3.) systemic radioimmunotherapy with the same binding molecule. A potentially attractive variation of this approach would be the attachment of a therapeutic radioisotope to the radiosensitized immunoconjugate, thereby providing the convenience of administering to the patient a single drug.

In one embodiment, a molecule that enhances the stability or efficacy of the polypeptide can be conjugated. For example, in one embodiment, PEG can be conjugated to the polypeptides of the invention to increase their half-life in vivo. Leong, S. R., et al. 2001. *Cytokine* 16:106; 2002; *Adv. in Drug Deliv. Rev.* 54:531; or Weir et al. 2002. Biochem. Soc. Transactions 30:512.

As previously alluded to, compatible cytotoxins may comprise a prodrug. As used herein, the term "prodrug" refers to a precursor or derivative form of a pharmaceutically active substance that is less cytotoxic to tumor cells compared to the parent drug and is capable of being enzymatically activated or converted into the more active parent form. Prodrugs compatible with the invention include, but are not limited to, phosphate-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. In one embodiment, a cytotoxic agent, such as a maytansinoid, is administered as a prodrug which is released by the hydrolysis of disulfide bonds. Further examples of cytotoxic drugs that can be derivatized into a prodrug form for use in the present invention comprise those chemotherapeutic agents described above.

XIII. Administration of Binding Molecules

Methods of preparing and administering binding molecules of the invention to a subject are well known to or are readily determined by those skilled in the art. The route of administration of the binding molecules of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders.

Effective doses of the stabilized binding molecules of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

For passive immunization with a binding molecule of the invention, the dosage may range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention.

Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered may fall within the ranges indicated.

Binding molecules of the invention can be administered on multiple occasions. Intervals between single dosages can be, e.g., daily, weekly, monthly or yearly. Intervals can also be irregular as indicated by measuring blood levels of polypeptide or target molecule in the patient. In some methods, dosage is adjusted to achieve a certain plasma binding molecule or toxin concentration, e.g., 1-1000 μg/ml or 25-300 μg/ml. Alternatively, binding molecules can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies. In one embodiment, the binding molecules of the invention can be administered in unconjugated form, In another embodiment, the polypeptides of the invention can be administered multiple times in conjugated form. In still another embodiment, the binding molecules of the invention can be administered in unconjugated form, then in conjugated form, or vise versa.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of binding molecule, e.g., antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a polypeptide of the invention (e.g., in a vector). Doses for nucleic acids encoding polypeptides range from about 10 ng to 1 g, 100 ng to 100 mg, 1 μg to 10 mg, or 30-300 μg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. Intramuscular injection or intravenous infusion are preferred for administration of a binding molecule of the invention. In some methods, particular therapeutic binding molecules are injected directly into the cranium. In some methods, binding molecules are administered as a sustained release composition or device, such as a Medipad™ device.

Agents of the invention can optionally be administered in combination with other agents that are effective in treating the disorder or condition in need of treatment (e.g., prophylactic or therapeutic). Preferred additional agents are those which are art recognized and are standardly administered for a particular disorder.

Effective single treatment dosages (i.e., therapeutically effective amounts) of $^{90}$Y-labeled polypeptides of the invention range from between about 5 and about 75 mCi, more preferably between about 10 and about 40 mCi. Effective single treatment non-marrow ablative dosages of $^{131}$I-labeled antibodies range from between about 5 and about 70 mCi, more preferably between about 5 and about 40 mCi. Effective single treatment ablative dosages (i.e., may require autologous bone marrow transplantation) of $^{131}$I-labeled antibodies range from between about 30 and about 600 mCi, more preferably between about 50 and less than about 500 mCi. In conjunction with a chimeric modified antibody, owing to the longer circulating half life vis-à-vis murine antibodies, an effective single treatment non-marrow ablative dosages of iodine-131 labeled chimeric antibodies range from between about 5 and about 40 mCi, more preferably less than about 30 mCi. Imaging criteria for, e.g., the $^{111}$In label, are typically less than about 5 mCi.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$Cu, $^{81}$Rb, $^{81}$Kr, $^{87}$Sr, $^{113}$In, $^{127}$Cs, $^{129}$Cs, $^{132}$I, $^{197}$Hg, $^{203}$Pb, $^{206}$Bi, $^{177}$Lu, $^{186}$Re, $^{212}$Pb, $^{212}$Bi, $^{47}$Sc, $^{105}$Rh, $^{109}$Pd, $^{153}$Sm, $^{188}$Re, $^{199}$Au, $^{225}$Ac, $^{211}$At, and $^{213}$Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{123}$I, $^{99}$Tc, $^{43}$K, $^{52}$Fe, $^{67}$Ga, $^{68}$Ga, as well as $^{111}$In. Antibodies have also been labeled with a variety of radionuclides for potential use in targeted immunotherapy (Peirersz et al. *Immunol. Cell Biol.* 65: 111-125 (1987)). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

Whether or not the binding molecules of the invention are used in a conjugated or unconjugated form, it will be appreciated that a major advantage of the present invention is the ability to use these polypeptides in myelosuppressed patients, especially those who are undergoing, or have undergone, adjunct therapies such as radiotherapy or chemotherapy. In other preferred embodiments, the polypeptides (again in a conjugated or unconjugated form) may be used in a combined therapeutic regimen with chemotherapeutic agents. Those skilled in the art will appreciate that such therapeutic regimens may comprise the sequential, simultaneous, concurrent or coextensive administration of the disclosed antibodies and one or more chemotherapeutic agents. Particularly preferred embodiments of this aspect of the invention will comprise the administration of a toxin conjugated binding molecule, e.g., conjugated to a maytansinoid such as a D4 maytansinoid.

While the binding molecules may be administered as described immediately above, it must be emphasized that in other embodiments conjugated and unconjugated polypeptides may be administered to otherwise healthy patients as a first line therapeutic agent. In such embodiments the polypeptides may be administered to patients having normal or average red marrow reserves and/or to patients that have not, and are not, undergoing adjunct therapies such as external beam radiation or chemotherapy.

However, as discussed above, selected embodiments of the invention comprise the administration of binding molecules to myelosuppressed patients or in combination or conjunction with one or more adjunct therapies such as radiotherapy or chemotherapy (i.e. a combined therapeutic regimen). As used herein, the administration of polypeptides in conjunction or combination with an adjunct therapy means the sequential, simultaneous, coextensive, concurrent, concomitant or contemporaneous administration or application of the therapy and the disclosed binding molecules. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the present invention. Conversely, cytotoxin associated polypeptides could be administered intravenously followed by tumor localized external beam radiation. In yet other embodiments, the polypeptide may be administered concurrently with one or more selected chemotherapeutic agents in a single office visit. A skilled artisan (e.g. an experienced oncologist) would readily be able to discern effective combined therapeutic regimens without undue experimentation based on the selected adjunct therapy and the teachings of the instant specification.

In this regard it will be appreciated that the combination of the binding molecules (either conjugated or unconjugated) and the chemotherapeutic agent may be administered in any order and within any time frame that provides a therapeutic benefit to the patient. That is, the chemotherapeutic agent and polypeptide may be administered in any order or concurrently. Binding molecules and chemotherapeutic agents may be administered separately or may be administered in the form of one composition. In selected embodiments the polypeptides of the present invention will be administered to patients that have previously undergone chemotherapy. In yet other embodiments, the polypeptides and the chemotherapeutic treatment will be administered substantially simultaneously or concurrently. For example, the patient may be given the binding molecule while undergoing a course of chemotherapy. In preferred embodiments the binding molecule will be administered within 1 year of any chemotherapeutic agent or treatment. In other preferred embodiments the polypeptide will be administered within 10, 8, 6, 4, or 2 months of any chemotherapeutic agent or treatment. In still other preferred embodiments the polypeptide will be administered within 4, 3, 2 or 1 week of any chemotherapeutic agent or treatment. In yet other embodiments the polypeptide will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

Moreover, in accordance with the present invention a myelosuppressed patient shall be held to mean any patient exhibiting lowered blood counts. Those skilled in the art will appreciate that there are several blood count parameters conventionally used as clinical indicators of myelosuppresion and one can easily measure the extent to which myelosuppresion is occurring in a patient. Examples of art accepted myelosuppression measurements are the Absolute Neutrophil Count (ANC) or platelet count. Such myelosuppression or partial myeloablation may be a result of various biochemical disorders or diseases or, more likely, as the result of prior chemotherapy or radiotherapy. In this respect, those skilled in the art will appreciate that patients who have undergone traditional chemotherapy typically exhibit reduced red marrow reserves. As discussed above, such subjects often cannot be treated using optimal levels of cytotoxin (i.e. radionuclides) due to unacceptable side effects such as anemia or immunosuppression that result in increased mortality or morbidity.

More specifically conjugated or unconjugated polypeptides of the present invention may be used to effectively treat patients having ANCs lower than about 2000/mm$^3$ or platelet counts lower than about 150,000/mm$^3$. More preferably the polypeptides of the present invention may be used to treat patients having ANCs of less than about 1500/mm$^3$, less than about 1000/mm$^3$ or even more preferably less than about 500/mm$^3$. Similarly, the polypeptides of the present invention may be used to treat patients having a platelet count of less than about 75,000/mm$^3$, less than about 50,000/mm$^3$ or even less than about 10,000/mm$^3$. In a more general sense, those skilled in the art will easily be able to determine when a patient is myelosuppressed using government implemented guidelines and procedures.

As indicated above, many myelosuppressed patients have undergone courses of treatment including chemotherapy, implant radiotherapy or external beam radiotherapy. In the case of the latter, an external radiation source is for local irradiation of a malignancy. For radiotherapy implantation methods, radioactive reagents are surgically located within the malignancy, thereby selectively irradiating the site of the disease. In any event, the disclosed polypeptides may be used to treat disorders in patients exhibiting myelosuppression regardless of the cause.

In this regard it will further be appreciated that the polypeptides of the instant invention may be used in conjunction or combination with any chemotherapeutic agent or agents (e.g. to provide a combined therapeutic regimen) that eliminates, reduces, inhibits or controls the growth of neoplastic cells in vivo. As discussed, such agents often result in the reduction of red marrow reserves. This reduction may be offset, in whole or in part, by the diminished myelotoxicity of the compounds of the present invention that advantageously allow for the aggressive treatment of neoplasias in such patients. In other preferred embodiments the radiolabeled immunoconjugates disclosed herein may be effectively used with radiosensitizers that increase the susceptibility of the neoplastic cells to radionuclides. For example, radiosensitizing compounds may be administered after the radiolabeled binding molecule has been largely cleared from the bloodstream but still remains at therapeutically effective levels at the site of the tumor or tumors.

With respect to these aspects of the invention, exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), Ch1VPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas, in* HARRISON'S PRINCIPLES OF INTERNAL MEDICINE 1774-1788 (Kurt J. Isselbacher et al., eds., 13$^{th}$ ed. 1994) and V. T. DeVita et al., (1997) and the references cited therein for standard dosing and scheduling. These therapies can be used unchanged, or altered as needed for a particular patient, in combination with one or more polypeptides of the invention as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), ProMACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, cisplatin, etoposide and ifosfamide given alone or in combination. In relapsed or aggressive forms of certain neoplastic disorders the following protocols are often used: IMVP-16 (ifosfamide, methotrexate and etoposide), MIME (methylgag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the polypeptides of the instant invention may vary by subject or may be administered according to what is known in the art. See for example, Bruce A Chabner et al., *Antineoplastic Agents, in* GOODMAN & GILMAN'S THE PHARMACOLOGICAL BASIS OF THERAPEUTICS 1233-1287 ((Joel G. Hardman et al., eds., 9$^{th}$ ed. 1996).

In one embodiment, a binding molecule of the invention may be administered to a subject who has undergone, is undergoing, or will undergo a surgical procedure, e.g., to remove a primary tumor, a metastasis or precancerous growth or tissue as a preventative therapy.

In another embodiment, a binding molecule of the invention is administered in conjunction with a biologic. Biologics useful in the treatment of cancers are known in the art and a binding molecule of the invention may be administered, for example, in conjunction with such known biologics.

For example, the FDA has approved the following biologics for the treatment of breast cancer: Herceptin® (trastuzumab, Genentech Inc., South San Francisco, Calif.; a humanized monoclonal antibody that has antitumor activity in HER2-positive breast cancer); Faslodex® (fulvestrant, AstraZeneca Pharmaceuticals, LP, Wilmington, Del.; an estrogen-receptor antagonist used to treat breast cancer); Arimidex® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); Femara® (letrozole, Novartis Pharmaceuticals, East Hanover, N.J.; a nonsteroidal aromatase inhibitor approved by the FDA to treat breast cancer); and Nolvadex® (tamoxifen, AstraZeneca Pharmaceuticals, LP; a nonsteroidal antiestrogen approved by the FDA to treat breast cancer). Other biologics with which the binding molecules of the invention may be combined include: Avastin™ (bevacizumab, Genentech Inc.; the first FDA-approved therapy designed to inhibit angiogenesis); and Zevalin® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: Avastin™;Erbitux™ (cetuximab, ImClone Systems Inc., New York, N.Y., and Bristol-Myers Squibb, New York, N.Y.; is a monoclonal antibody directed against the epidermal growth factor receptor (EGFR)); Gleevec® (imatinib mesylate; a protein kinase inhibitor); and Ergamisol® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For use in treatment of Non-Hodgkin's Lymphomas currently approved therapies include: Bexxar® (tositumomab and iodine I-131 tositumomab, GlaxoSmithKline, Research Triangle Park, N.C.; a multi-step treatment involving a mouse monoclonal antibody (tositumomab) linked to a radioactive molecule (iodine I-131)); Intron® A (interferon alfa-2b, Schering Corporation, Kenilworth, N.J.; a type of interferon approved for the treatment of follicular non-Hodgkin's lymphoma in conjunction with anthracycline-containing combination chemotherapy (e.g., cyclophosphamide, doxorubicin, vincristine, and prednisone [CHOP])); Rituxan® (rituximab, Genentech Inc., South San Francisco, Calif., and Biogen Idec, Cambridge, Mass.; a monoclonal antibody approved for the treatment of non-Hodgkin's lymphoma; Ontak® (denileukin diftitox, Ligand Pharmaceuticals Inc., San Diego, Calif.; a fusion protein consisting of a fragment of diphtheria toxin genetically fused to interleukin-2); and Zevalin® (ibritumomab tiuxetan, Biogen Idec; a radiolaebeled monoclonal antibody approved by the FDA for the treatment of B-cell non-Hodgkin's lymphomas).

For treatment of Leukemia, exemplary biologics which may be used in combination with the binding molecules of the invention include Gleevec®; Campath®-1H (alemtuzumab, Berlex Laboratories, Richmond, Calif.; a type of monoclonal antibody used in the treatment of chronic Lymphocytic leukemia). In addition, Genasense (oblimersen, Genta Corporation, Berkley Heights, N.J.; a BCL-2 antisense therapy under development to treat leukemia may be used (e.g., alone or in combination with one or more chemotherapy drugs, such as fludarabine and cyclophosphamide) may be administered with the claimed binding molecules.

For the treatment of lung cancer, exemplary biologics include Tarceva™ (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include Velcade® Velcade (bortezomib, Millennium Pharmaceuticals, Cambridge Mass.; a proteasome inhibitor). Additional biologics include Thalidomid® (thalidomide, Clegene Corporation, Warren, N.J.; an immunomodulatory agent and appears to have multiple actions, including the ability to inhibit the growth and survival of myeloma cells and antiangiogenesis).

Other exemplary biologics include the MOAB IMC-C225, developed by ImClone Systems, Inc., New York, N.Y.

In addition, the claimed binding molecules may be administered in conjunction with vaccines or other agents (e.g., cytokines) to modulate anti-cancer immune responses. For example, Melacine® (Corixa Corporation, Seattle, Wash.) is an allogeneic tumor vaccine that has been reported to have promising results in the treatment of T3N0M0 resected melanoma. GMK® (Progenics Pharmaceutical, Inc., Tarrytown, N.Y.) is a ganglioside antigen administered as an adjuvant phase III agent in patients who are at high risk for melanoma recurrence. Anti-gastrin therapeutic Vaccine® (Aphton Corporation, Miami, Fla.) neutralizes hormones G17 and glyextened and is in phase III clinical trials for patients with colorectal, pancreatic, and stomach cancers. CeaVac® (Titan Pharmaceuticals, Inc., South San Francisco, Calif.) is an anti-idiotype antibody vaccine being studied in colorectal cancer. Finally, Theratope® (Biomira Inc., Edmonton, Alberta, Canada) is a synthetic carbohydrate therapeutic vaccine being investigated as a phase III agent in patients with metastatic breast cancer (Pharmaceutical Research and Manufacturers of America, 2000).

In another embodiment, a binding molecule of the invention may be administered in conjunction with an anti-angiogenic agent, e.g., Endostatin (an endogenous, tumor-derived, endothelial-specific inhibitor that halts microvascular endothelial cell production); anti-VEGF antibody; thalidomide; or matrix metalloproteinase inhibitors inhibit the synthesis and degradation of the basement membrane of blood vessels).

As previously discussed, the binding molecules of the present invention, immunoreactive fragments or recombinants thereof may be administered in a pharmaceutically effective amount for the in vivo treatment of mammalian disorders. In this regard, it will be appreciated that the disclosed binding molecules will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a binding molecule of the invention, conjugated or unconjugated to a therapeutic agent, shall be held to mean an amount sufficient to achieve effective binding to a target and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the polypeptides of the invention may be administered to a human or other animal in accordance with the aforementioned methods of treatment in an amount sufficient to produce a therapeutic or prophylactic effect. The polypeptides of the invention can be administered to such human or other animal in a conventional dosage form prepared by combining the binding molecule of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

XIV. Methods of Use

The molecules of the invention can be used in circumstances where it is desirable to use stabilized scFv molecules or compositions comprising such scFv molecules, e.g., for diagnostic or therapeutic purposes. Preferred embodiments of the present invention provide compounds, compositions, kits and methods for the diagnosis and/or treatment of disorders that would benefit from administration of a binding molecule of the invention, e.g., neoplastic disorders in a mammalian subject in need of such treatment. Preferably, the subject is a human.

In one embodiment, the subject binding molecules may be used in an assay to detect a tumor antigen in vitro, e.g., using an ELISA assay. Exemplary assays are known in the art, see, e.g., United States Application Number 20040077025.

In another embodiment, the subject binding molecules are useful for detecting the presence of tumor antigen bearing cells using imaging technology. For such applications, it may be desirable to conjugate the binding molecule to a detectable molecule, e.g., a radiolabel, as described further below.

In another embodiment, the subject binding molecules are useful for reducing or eliminating cells (e.g. by apoptosis) bearing an epitope (e.g., an epitope of Cripto or an epitope of a TNF receptor family member, eg. TRAIL-R2 or LTβR) recognized by a binding molecule of the invention. In another embodiment, the subject binding molecules are effective in reducing the concentration of or eliminating soluble target molecules in the circulation.

In another embodiment, a binding molecule of the invention reduces tumor size, inhibits tumor growth and/or prolongs the survival time of a tumor-bearing subject. Accordingly, this invention also relates to a method of treating tumors in a human or other animal by administering to such human or animal an effective, non-toxic amount of polypeptide. One skilled in the art would be able, by routine experimentation, to determine what an effective, non-toxic amount of polypeptide would be for the purpose of treating malignancies. For example, a therapeutically active amount of a polypeptide may vary according to factors such as the disease stage (e.g., stage I versus stage 1V), age, sex, medical complications (e.g., immunosuppressed conditions or diseases) and weight of the subject, and the ability of the binding molecule to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

For purposes of clarification "mammal" refers to any animal classified as a mammal, including humans, domestic and farm animals, and zoo, sports, or pet animals, such as dogs, horses, cats, cows, etc. Preferably, the mammal is human. "Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

In general, the disclosed compositions may be used to prophylactically or therapeutically. For example, a neoplasm comprising a marker that allows for the targeting of the cancerous cells by the binding molecule may be detected or inhibited (e.g., killed) using a binding molecule of the invention. In a preferred embodiment, the binding molecules of the invention are used to treat solid tumors. Exemplary cancers that may be treated include, but are not limited to, prostate, gastric carcinomas such as colon, skin, breast, ovarian, lung and pancreatic cancer. In another embodiment, the antibodies of the instant invention may be used to treat Kaposi's sarcoma, CNS neoplasias (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the ovary, Wilm's tumor or small cell lung carcinoma. It will be appreciated that appropriate polypeptides may be derived for tumor associated molecules related to each of the forgoing neoplasias without undue experimentation in view of the instant disclosure.

Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the compounds and methods of the present invention are particularly effective in treating a variety of B-cell lymphomas, including low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NEIL, high grade immunoblastic NHL, high grade lymphoblastic NHL, high grade small noncleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies bearing compatible tumor associated molecules.

In one embodiment, a binding molecule of the invention is capable of binding specifically to a tumor cell antigen and inhibiting growth of tumor cells in a patient. In certain embodiments, the tumor cells are brain, head, neck, prostate, breast, testicular, colon, lung, ovary, bladder, uterine, cervical, pancreatic and stomach tumor cells. In other embodiments, a binding molecule of the invention binds specifically to the tumor cell antigen and inhibits growth of tumor cells which overexpress the antigen. In one embodiment, the tumor cells are cell lines which overexpress the antigen, such as cell lines derived from brain, breast, testicular, colon, lung, ovary, bladder, uterine, cervical, pancreatic and stomach cancers.

In yet other embodiments the binding molecules of the present invention may be used to treat immune disorders that include, but are not limited to, allergic bronchopulmonary aspergillosis; Allergic rhinitis Autoimmune hemolytic anemia; Acanthosis nigricans; Allergic contact dermatitis; Addison's disease; Atopic dermatitis; Alopecia greata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus; Pemphigus foliaceus; Pemphigus vulgaris; Pigeon breeder's disease; Pneumonitis, hypersensitivity; Polyarteritis nodosa; Polymyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Serum sickness; Sezary syndrome; Sjogren's syndrome; Stevens-Johnson syndrome; Still's disease; Subacute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis and Wiskott-Aldrich syndrome.

In another embodiment, the binding molecules of the invention can be used for pretargeting applications. For example, the same advantages will be apparent in pretargeting applications for chemotherapeutic drug delivery.

For example, in pretargeting a tumor is pretargeted with a binding construct that has affinity for the tumor-associated antigen on the one hand and for, e.g., a radiolabeled hapten on the other. The radiolabeled hapten is administered later, preferably after the binding construct that has affinity for the tumor-associated antigen has cleared (see, e.g., Boerman et al. 2003. J. Nuclear Med. 44:400). In another example, an antibody which is non-toxic, but has been derivitized to react with a drug or prodrug that is toxic only when bound by the binding molecule. Given the biodistribution data in the instant examples, the binding molecules of the invention are well suited to use in pretargeting applications. In one embodiment, a clearing agent could be eliminated from the pretargeting methodology by using the instant binding molecules.

This invention is further illustrated by the following examples which should not be construed as limiting. The contents of all references, patents and published patent applications cited throughout this application are incorporated herein by reference.

EXAMPLES

Throughout the examples, the following materials and methods were used unless otherwise stated.

General Materials and Methods

In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., In Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Expression Constructs

In general, unless otherwise indicated, the expression constructs for scFvs in the following Examples included an N-terminal Gene III signal peptide as well as a C-terminal purification peptide comprising Myc and His tags and an Enterokinase cleavage site. DNA sequence for each peptide are set forth below:

```
N-terminal Gene III signal peptide DNA sequence
                                          (SEQ ID NO: 25)
ATGAAAAAACTGCTGTTCGCGATTCCGCTGGTGGTGCCGTTCTATAGCCA

TAGT

N-terminal Gene III signal peptide DNA sequence
                                          (SEQ ID NO: 26)
MKKLLFAIPLVVPFYSHS
```

```
C-terminal purification peptide DNA Sequence
                                          (SEQ ID NO: 27)
GACGACGACGACAAAAGCTTTCTAGAACAAAAACTCATCTCAGAAGAGGA

TCTGAATAGCGCCGTCGACCATCATCATCATCATCATTGA

C-terminal purification peptide DNA Sequence
                                          (SEQ ID NO: 58)
DDDDKSFLEQKLISEEDLNSAVDHHHHHH
```

Antibodies

BIIB Antibodies used in certain Examples (BIIB1-BIIB18) are a collection of therapeutic antibodies of various specificities. Seventeen of the 18 antibodies were expressed from either stable bulk or clonal CHO cell lines and 1 of the antibodies (BIIB13) was expressed using transient transfection in HEK293E cells. All 18 antibodies contain kappa light chains. The majority of the antibodies were human IgG1; however, BIIB2, BIIB5 and BIIB1 were human IgG4. Seventeen of the 18 antibodies were human or humanized. BIIB15 was PRIMATIZED® (Nakamura et al., 2000). The identity of the human germline for each antibody was assessed by ClustalW alignment (ClustalW WWW Service at the European Bioinformatics Institute, Thompson et al., 1994) of the BIIB $V_H$ or $V_\kappa$ sequences against the publicly available human germlines (Lefranc et al., 1999).

Fifteen of the 18 total antibodies were IgG1 subclass and the remaining 3 were IgG4 (BIIB2, BIIB5 and BIIB11). IgG1 and IgG4 $C_H1$ sequences have 10 amino acid differences (6 are conservative) and an alternate disulfide-bonding pattern with the light chain.

An IgG1 and an IgG4 construct with a duplicate Fv region was available to investigate the effect of IgG subclass on Fab stability. Two constructs were created which contained the $V_H$ region of BIIB7 grafted to either an IgG1 or an IgG4 heavy chain constant region.

Example 1

Preparation of Conventional BHA10 scFv and Fab Proteins

BHA10 scFv was subcloned from plasmid pXWU034, using the Polymerase Chain Reaction (PCR) with oligonucleotide primers shown in Table 2 below. The forward primer BHA10-01F contains a unique Sph I restriction endonuclease site (underlined sequence) followed by 18 bases of sequence complementary to the BHA10 N-terminal heavy variable domain gene. The reverse primer, BHA10-01R, contains 24 bases of sequence complementary to the BHA10 C-terminal light variable domain gene, 15 bases of sequence complementary to an Enterokinase Site, and adjacent Hind III and Xba I restriction endonuclease sites (endonuclease sites are underlined). Following PCR amplification, a PCR product corresponding to the expected size was resolved by agarose gel electrophoresis, excised, and purified using the Millipore Ultrafree-DA extraction kit according to manufacturer's instructions (Millipore; Bedford, Mass.). The purified PCR product was digested with Sph I, made blunt-end by digesting with DNA Polymerase I in the presence of dNTPs, and then digested with Hind III. The blunt-ended/Hind III digested PCR product was ligated to Sca I/Hind III digested pKJS216. pKJS216 is an *E. coli* vector that drives recombinant protein expression under the control of an inducible ara C promoter. A portion of the ligation mixture was used to transformed *E. coli* strain XL1-Blue. Ampicillin drug resistant colonies were screened and DNA sequence analysis confirmed the correct sequence of the final pIEH003 construct. DNA and amino acid sequences of BHA10 scFv are shown in FIGS. 1A and 1B, respectively.

TABLE 2

Oligonucleotides for PCR amplification of a conventional BHA10 scFv.

| Primers | Sequence |
|---|---|
| BHA10-01F (SEQ ID NO: 1) | 5'- CAGTAGCATGCAGGTCCAACTGGTGCAG -3' |
| BHA10-02R (SEQ ID NO: 2) | 5'-GTTCTAGAAAGCTTTTGTCGTCGTCGTCTTTGATCTC CACCTTGGTACCCTG -3' |

For expression of BHA10 scFv, freshly isolated colonies of *E. coli* strain W3110 (ATCC, Manassas, Va. Cat. #27325) transformed with plasmid pIEH003 were grown in 4×250 ml SB media (Teknova, Half Moon Bay, Ca. Cat. #S0140) containing 50 µg/ml carbenicillin in 1 L baffled flasks to $OD_{600}$≈0.8, induced by adding to 0.02% arabinose, and cultured overnight. Bacteria were collected by centrifugation. The pellets were solubilized and lysed using 40 mL B-PER protein extraction reagent (Cat#78243, Pierce). Solubilized scFv was applied to a 5 mL Ni-NTA-Superflow column (Cat#30410, Qiagen). Bound scFv was washed with 60 mM imidazole, pH 8.0 and eluted with 300 mM imidazole, pH 8.0. Eluted scFv was loaded onto a 6 mL Protein L agarose column (Cat#20510, Pierce). Bound protein was washed with phosphate buffered saline (PBS) and eluted with 0.1 M glycine, pH 3.0. Purified scFvs were dialyzed against PBS and stored at −20° C. Protein concentrations were determined using an $\epsilon_{280\,nm}$=2.1 ml mg$^{-1}$ cm$^{-1}$.

For enzymatic preparation of BHA10 Fab, BHA10 IgG was mixed with 4 µl of a concentrated papain stock (0.3 mg/mL, 30 Units/mg—Cat#108014, Roche) in 8.3 ml solution containing 2.4 mg/mL BHA10 IgG1, 100 mM Tris-HCl, 20 mM EDTA at pH 7.0. The reaction was allowed to proceed for 90 minutes at 25° C. The digest solution was diluted 1:5 with 20 mM acetate, pH 5.0 and loaded onto a 6 ml SP-Sepharose FF column equilibrated with dilution buffer. The column was washed with 2 column volumes of dilution buffer. Crude Fab fragments were eluted with 30 column volumes of a 0-200 mM NaCl linear gradient. A broad peak centering at 140 mM NaCl (~24 mL total) was collected and contained the majority of the digested IgG material. The eluted volume was reduced to 2 mL by concentration and loaded onto a preparative G300 SW Tosohaas SEC column (109 mL) equilibrated with PBS. Fab was eluted at 0.8 column volumes over 15 mL. Purified Fab was concentrated to between 2-11 mg/mL. Fab concentrations were determined using an $\epsilon_{280\,nm}$=1.5 mL mg$^{-1}$ cm$^{-1}$.

Example 2

Thermal Stability of Conventional BHA10 scFv Molecules

Differential Scanning calorimetry (DSC) was used to test whether an isolated BHA10 scFv is intrinsically less stable than its Fab counterpart. Scans were performed using an automated capillary differential scanning calorimeter (cap-DSC, MicroCal, LLC). Protein and reference solutions were sampled automatically from 96-well plates using the robotic attachment. Prior to each protein scan, 2 scans were performed with buffer in the sample cell and used for background subtraction. A single cleaning scan was performed using 5% Liquinox after every protein scan. After every scan, the instrument automatically rinsed both the reference and sample cells three times with 2 ml distilled deionized $H_2O$ containing 0.01% sodium azide. Scans were performed at 1° C./min using the medium feedback mode for enhanced peak resolution. The scan range was 20-95° C. All 96-well plates containing protein were stored within the instrument at 6° C.

Figure 2B:
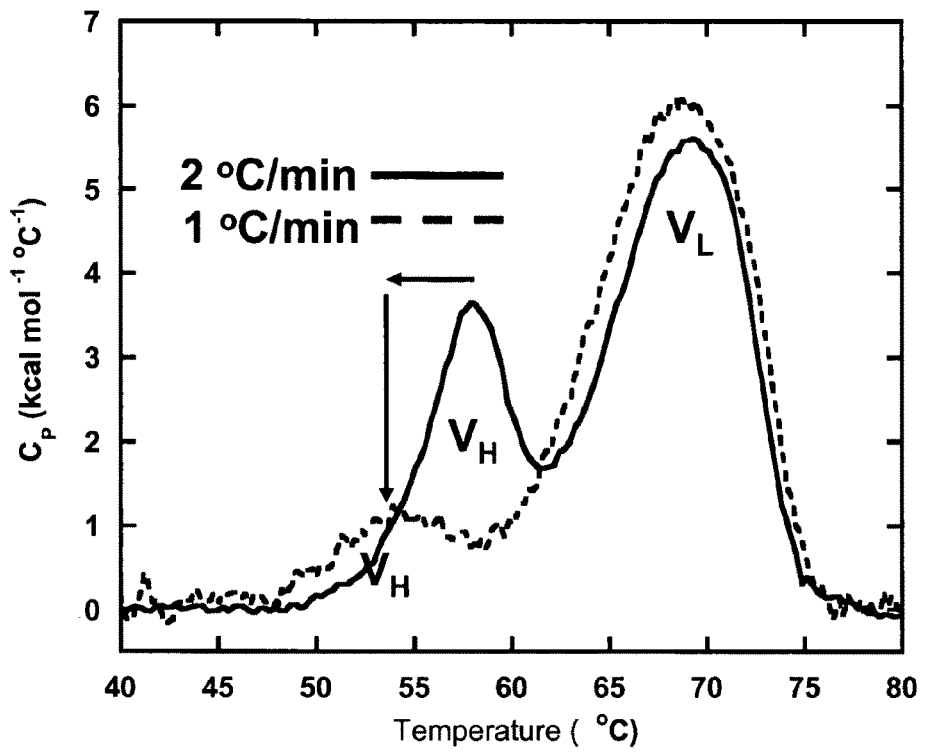
FIG. 2B depicts the results of DSC scans of the purified BHA10 scFv at scan rates of 1° C./min and 2° C./min.

FIG. 2 shows DSC measurements with purified BHA10 Fab and scFv antibody fragments. Within the calorimeter, the temperature is raised until the Fab or scFv unfolds. The temperature at which each protein unfolds (i.e., the $T_M$ value) can be indicative of the overall stability. All four domains of the BHA10 Fab ($V_H$, $V_L$, $C_H1$ and $C_L$) unfold cooperatively at 78° C. (FIG. 2A). The scFv domain lacks the $C_H1$ and $C_L$ domains. Without this scaffolding, the domains of the scFv unfold at much lower temperatures than the Fab and there is a significant decrease in the calorimetric enthalpy of the domains indicating the loss of stabilizing interactions. The $V_L$ domain unfolds with a $T_M$ of 68° C., while the $V_H$ domain unfolds at 58° C., 20° C. lower than what was observed for the unfolding transition of the BHA10 Fab (FIG. 2B). Additionally, there is a scan rate dependence of the $T_M$, suggesting that protein aggregation is occurring during the heating phase which artificially lowers the $T_M$ of the scFv as the scan rate is slowed (Sanchez-Ruiz et al., *Biochemistry*, 27: 1648-1652, 1988). The low apparent stability and the propensity to aggregate may be determining factors for the inability of CHO cells to produce significant quantities of stable, non-aggregated material which contain scFvs such as the conventional Hercules bispecific antibody molecules.

Example 3

Construction of BHA10 scFv Molecules with Improved Thermal Stability

Knowing that the BHA10 scFv domain, as evidenced in Example 2, is intrinsically unstable, it was hypothesized that engineering the scFv through the use of recombinant DNA technology to produce a modified scFv that is thermodynamically or functionally equivalent to a Fab under thermal challenge conditions should result man scFv domain that is useful for constructing a bispecific antibody. Moreover, it was also hypothesized that engineering of the isolated scFv domain by itself should impart whatever beneficial biophysical properties are gained when re-introduced as a component of a full bispecific molecule. Towards that end, an effort to improve the biophysical stability of the BHA10 scFv domain using an *E. coli* expression system and monitored improvements in stability by measuring binding of thermally resistant scFv domains to ligand in a thermal challenge assay was begun.

To stabilize the scFv domains two methods were applied: 1) introducing a disulfide bond between the $V_H$ and $V_L$ domain of the BHA10 scFv; and 2) optimizing the length of the $(Gly_4Ser)_n$ linker that connects the $V_H$ and $V_L$ domains of the BHA10 scFv.

A. Construction of Disulfide-Stabilized BHA10 scFvs

The BHA10 scFv producing bacterial expression vector, pIEH003, was utilized as the parental vector. The Quick-Change Site-Directed Mutagenesis Kit (Stratagene; La Jolla, Calif.) was used, according to the manufacturer's instructions, to introduce two cysteine residues, one in $V_H$ and a second in $V_L$ that could participate in forming a stabilizing disulfide bond. Primer pairs VH44-F and VH44-R (Table 3) were used to mutagenize the Gly residue (GGA) at position 44 (Kabat numbering system) of BHA10 variable heavy chain to a Cys residue (TGC). The mutagenesis product was digested with methylation sensitive enzyme Dpn I according to the kit protocol and transformed into the *E. coli* strain XL10-GOLD® (Stratagene; La Jolla, Calif.). *E. coli* colonies transformed to ampicillin drug resistance were screened for the correct sequence mutation by DNA sequence analysis. The resulting plasmid, pIEH004, was utilized for a subsequent reaction to mutate the Gln residue (CAG) at position 100 (Kabat numbering system) of BHA10 variable light chain to a Cys residue (TGC) using primer pairs VL100-F and VL100-R (Table 3). Forward (VH-144-F) and reverse (VH44-R) primers mutate Gly (GGA) to a Cys (TGC) at $V_H$ position 44 (TGC indicated by underlined sequence). Forward (VL100-F) and reverse (VL100-R) primers mutate Gln (CAG) to a Cys (TGC) at $V_L$ position 100 (TGC indicated by underlined sequence).

XL10-GOLD® *E. coli* colonies transformed to ampicillin drug resistance were screened for the correct sequence mutation by DNA sequence analysis and plasmid pIEH006 was identified as containing the double cysteine mutations at positions $V_H$44 and $V_L$100. DNA and amino acid sequences of VH44/VL100 disulfide-stabilized BHA10 scFv are shown in FIGS. 3A and 3B, respectively.

TABLE 3

Oligonucleotides for construction of VH44/VL100 disulfide-stabilized BHA10scFv.

| Primers | Sequence |
|---------|----------|
| VH44-F (SEQ ID NO: 5) | 5'- GCAGGCCCTGGACAGTGCCTTGAGTGGATGGGATG -3' |
| VH44-R (SEQ ID NO: 6) | 5'- CATCCCATCCACTCAAGGCACTGTCCAGGGGCCTGC -3' |
| VL100-F (SEQ ID NO: 7) | 5'- CCTATCCATTCACGTTCGGCTGCGGTACCAAGGTGG AGATC -3' |
| VL100-R (SEQ ID NO: 8) | 5'- GATCTCCACCTTGGTACCGCAGCCGAACGTGAATGG ATAGG -3' |

B. Construction of BHA10 scFv with Alternative (Gly4Ser)$_n$ Linkers

Plasmid pIEH003 encoding huBHA10 scFv with the conventional (Gly$_4$Ser)$_3$ linker was modified to contain a (Gly$_4$Ser)$_4$ or (Gly$_4$Ser)$_5$ linker by PCR amplification using the oligonucleotide primers described in Table 4.

BHA10 scFv (Gly$_4$Ser)$_4$ was assembled using a forward 5' PCR primer designated pXWU002-F1 and a reverse 3' PCR primer designated XWU002-R. The 5' VH PCR primer XW002-F1 included a Btg I restriction endonuclease site (underlined sequence) located at the carboxyl terminus of BHA10 VH followed by sequence encoding a (Gly$_4$Ser)$_4$ linker. The 3' VL PCR primer XW002-R included an Xba I site and a partial Enterokinase site. The partial BHA10 VH+ (Gly$_4$Ser)$_4$ linker+the BHA10 VL regions were amplified in a PCR reaction using the XW002-F1/XW002-R PCR primer set from plasmid DNA pIEH003 (described in Example 1). The partial BHA10 scFv-(Gly$_4$Ser)$_4$ linker gene fragment corresponding to the expected size was resolved by agarose gel electrophoresis, excised, and purified using the Millipore Ultrafree-DA extraction kit according to manufacturer's instructions (Millipore; Bedford, Mass.). The purified PCR product was digested and cloned into the Btg I/Xba I digested pIEH003 vector resulting in plasmid pXWU002 encoding BHA10 scFv containing a (Gly$_4$Ser)$_4$ linker. BHA10 scFv containing the (Gly$_4$Ser)$_5$ linker was constructed in similar fashion using PCR primers XW003-F and XW002-R to produce plasmid pXWU003. Forward 5' PCR primer (XWU003-F) contained a Btg I site (underlined sequence) followed by sequence encoding a few amino acid of the carboxyl terminus of BHA10 VH and sequence encoding a partial (Gly$_4$Ser)$_5$ linker. Correct sequences were confirmed by DNA sequence analysis. DNA and amino acid sequences of BHA10 scFv containing the (Gly$_4$Ser)$_4$ linker are shown in FIGS. 4A and 4B, respectively. DNA and amino acid sequences of BHA10 scFv containing the (Gly$_4$Ser)$_5$ linker are shown in FIGS. 5A and 5B, respectively.

TABLE 4

Oligonucleotides for construction of BHA10 scFv with (Gly$_4$Ser)$_4$ or (Gly$_4$Ser)$_5$ linkers.

| Primers | Sequence |
|---------|----------|
| XW002-F1 (SEQ ID NO: 11) | 5'- AAGGGACCACGGTCACCGTCTCCTCAGGCGGTGGA GGGTCCGGTGGGGGCGGATCTGGGGGCGGCGGATCCGGT GGTGGTGGTAG-3' |
| XW002-R (SEQ ID NO: 12) | 5'- TTTTGTTCTAGAAAACTTTTGTCGTCG-3' |
| XW003-F (SEQ ID NO: 13) | 5'- AAGGGACCACGGTCACCGTCTCCTCAGGAGGGGGC GGTTCAGGCGGTGGAGGGTCCGGTGGGGGCGGATCTGGG GGCGGCGGATC-3' |

Example 4

Characterization of BHA10 scFv Molecules with Improved Thermal Stability

A. Expression and Western Blot Analysis of Engineered BHA10 scFvs

For expression of engineered BHA10 scFvs, *E. coli* strain W3110 (ATCC, Manassas, Va. Cat. #27325) was transformed with plasmids pIEH003, pXWU002, pXWU003 and pIEH006 and ampicillin resistant colonies selected and grown in 10 ml SB media (Teknova, Half Moon Bay, Ca. Cat. #S0140) containing 50 μg/ml carbenicillin in a 50 ml conical centrifuge tube to OD$_{600}$≈0.8, induced by adding to 0.02% arabinose, and cultured overnight. Bacteria were collected by centrifugation and the pellets resuspended in 1/20 volume of an ice-cold iso-osmotic solution of 50 mM Tris-HCl, pH 8.0, 1 mM EDTA, and 20% sucrose (w/v) and chilled on ice. Equal volume of 50 mM Tris-HCl, pH 8.0, 1 mM EDTA, and 20% sucrose (w/v) containing 2 mg/ml Lysozyme (Sigma) was added to the bacterial suspension and incubated on ice with occasional mixing for 10 minutes. The bacterial suspension was centrifuged for 10 minutes at 8000×g, 4° C. and the periplasmic fraction retained.

Samples were mixed with native sample buffer or sample buffer containing the reducing agent dithiothreitol and heated at 90° C. for 3 minutes. Reduced and non-reduced samples were electrophoresed on an SDS-PAGE Tris-glycine polyacrylamide gel and electrophoretically transferred onto a nitrocellulose membrane (Invitrogen, Life Technologies, Carlsbad, Calif.). The membrane was blocked with PBS containing 5% (w/v) non-fat milk and 0.1% Triton X-100 and incubated with an anti-human kappa antibody (Roche Applied Science, Indianapolis, Ind.). The membrane was washed and then incubated with an anti-rabbit HRP antibody (Amersham Biosciences, Piscataway, N.J.). Immune complexes were detected using the ECL Western Blotting Analysis System according to the manufacturer (Amersham Biosciences, Piscataway, N.J.).

Figure 6:
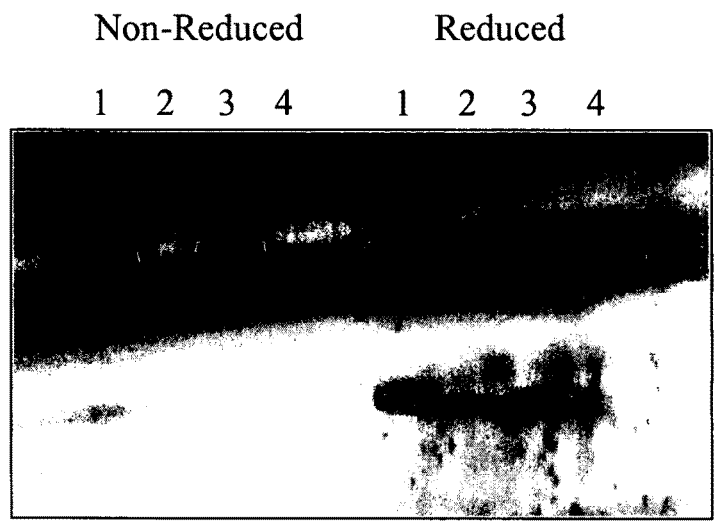
FIG. 6 depicts the results of a Western Blot analysis to compare the expression levels of a conventional BHA10 scFv (lane 1) and the stabilized BHA10 scFv molecules of the invention (lanes 2-4). Each sample was electrophoresed under both reducing (left panel) and non-reducing (right panel) conditions.

It was found that one of three disulfide pairs tested, namely $V_H44:V_L100$, produced suitable amounts of protein when expressed in E. coli (FIG. 6, lane 2). (The $V_H$ 44:$V_L$ 105 and $V_H$ 106:$V_L$43 disulfides tested did not produce as much intact scFv). Similarly, extending the length of the $(Gly_4Ser)_n$ linker to n=4 (lane 3) or n=5 (not shown) also produced suitable amounts of protein in E. coli. Combining both the $V_H44:V_L100$ and $(Gly_4Ser)_4$ linker modifications into BHA10 scFv using the methods described in Example 3 also led to suitable amounts of expressed protein (FIG. 6, lane 4). DNA and amino acid sequences of BHA10 scFv containing the combination of $V_H44:V_L100$ and $(Gly_4Ser)_4$ linker modifications are shown in FIGS. 7A and 7B, respectively. In both cases where the BHA10 scFv contains the $V_H44:V_L100$ mutations, the scFvs were found to migrate with increased mobility in the denaturing, non-reducing polyacrylamide gel, yet migrated similarly to conventional BHA10 scFv under denaturing, reducing conditions (FIG. 6, lanes 2 and 4). This analysis suggests that the BHA10 scFv variants containing the $V_H44:V_L100$ mutations are likely forming intact disulfide bonds and may be attaining a more compact structure.

B. Thermal Denaturation Assay.

The activities of the conventional and engineered BHA10 scFvs were then compared in a thermal challenge assay which can be used to determine the temperature at which 50% of scFv molecules retain their antigen binding activity following a thermal challenge event. The numerical value corresponding to this temperature is referred to as the "$T_{50}$" value and the units are in ° C. In this assay, the scFvs were subjected to a range of temperatures that encompass the thermal transition temperature of conventional BHA10 scFv.

E. coli strain W3110 (ATCC, Manassas, Va. Cat. #27325) was transformed with plasmids encoding the conventional and engineered BHA10 scFvs under the control of an inducible ara C promoter. Transformants were grown overnight in expression media consisting of SB (Teknova, Half Moon Bay, Ca. Cat. #S0140) supplemented with 1% glycine, 1% Triton X100, 0.02% arabinose, and 50 µg/ml carbenicillin at either 37° C. or 32° C. Bacteria was pelleted by centrifugation and supernatants harvested for further treatment. Including glycine and Triton X-100 in the media results in the release of periplasmic contents (native E. coli protein and scFv) into the media (Yang et al. Applied and Environmental Microbiology. (1998) 64:2869-2874). The presence of E. coli proteins in the supernatant is essential to the performance of this assay because the thermally denatured proteins act as a "sink", trapping transiently unfolded scFv molecules into irreversible inactive aggregates.

Each library was screened in duplicate using a thermal challenge assay with supernatant from one replicate subjected to treatment conditions and the second supernatant serving as untreated reference. Thermal denaturation assays can be run at a single or range of temperatures for measuring stability. Thermocycler machines capable of generating stable thermal gradients were used for treating sample supernatants (iCycler, Bio-Rad, Gaithersburg, Md.).

The challenge temperature varied depending on the properties of the parental BHA10 scFv variant and was generally two to three degrees Celsius higher than the experimentally determined $T_{50}$ value. Frozen Master plates were thawed and used to inoculate deep-well microtiter plates containing 250 µl of expression media per well, and cultures grown overnight at 32° C. As a control, cultures containing the parental plasmid were grown under the same conditions and processed simultaneously as the library. Bacteria were pelleted and 50-100 µl aliquots of test supernatant were placed in either PCR strip tubes (Applied Biosystems, Foster City, Calif., Cat. #N801-535) or 96-well plates (Applied Biosystems, Foster City, Calif., Cat. #N801-560) and the samples were heated for 60-90 minutes. Samples were transferred to 96-well v-bottomed plates (Corning, Corning, N.Y., Cat. #3357) and centrifuged in a refrigerated clinical centrifuge (IEC model 8R, Thermo Electron, Waltham, Ma) for 30 minutes, and 100 µl of the supernatant was transferred to standard microtiter plates (Corning, Corning, N.Y., Cat. #3357). An aliquot of the supernatant was reserved for the reference DELFIA. For most libraries, the plates containing the remainder of the supernatants were sealed (Nalge Nunc, Rochester, N.Y., Cat. #235205) and placed in an incubator set to the appropriate challenge temperature (Echo Therm, Torrey Pines Scientific, San Marcos, Calif.) for 90 minutes. For screens requiring multiple challenge temperatures (or for temperatures greater than 75° C.) the supernatants were transferred to 96-well PCR plates (Applied Biosystems, Foster City, Calif., Cat. #N801-560) and incubated for 90 minutes at the desired temperature.

After thermal challenge, the samples were centrifuged at 2,000 RPM to remove aggregated material. Soluble BHA10 scFv samples remaining in the treated, cleared supernatant were assayed for binding to cognate LTβR Ig antigen by DELFIA assay. 96-well plates (MaxiSorp, Nalge Nunc, Rochester, N.Y., Cat. #437111) were coated with fusion protein consisting of the ectodomain of the LTβ receptor (LTβR) fused to a human Fc region at 1 µg/ml in 0.1M sodium carbonate buffer, pH 9.5. Plates were coated overnight at 4° C., and blocked with DELFIA assay buffer (DAB, 10 mM Tris HCl, 150 mM NaCl, 20 µM EDTA, 0.5% BSA, 0.02% Tween 20, 0.01% $NaN_3$, pH 7.4) for one hour with shaking at room temperature. Plates were washed 3 times with DAB without BSA (Wash buffer), and test samples diluted in DAB were added to the plates in a final volume of 100 µl. The plates were incubated for one hour with shaking at room temperature, and then washed 3 times with Wash buffer to remove unbound and functionally inactivated scFv molecules. Bound BHA10 scFv was detected by addition of 100 µl per well of DAB containing 40 ng/ml of Eu-labeled anti-$His_6$ antibody (Perkin Elmer, Boston, Mass., Cat. #AD0109) and incubated at room temperature with shaking for one hour. The plates were washed 3 times with Wash buffer, and 100 µl of DELFIA enhancement solution (Perkin Elmer, Boston, Mass., Cat. #4001-0010) was added per well. Following incubation for 15 minutes, the plates were read using the Europium method on a Victor 2 (Perkin Elmer, Boston, Mass.).

Assay data was processed using Spotfire DecisionSite software (Spotfire, Somerville, Ma.) and expressed as the ratio of the DELFIA counts observed at challenge temperature to the reference temperature for each clone. Clones that reproducibly gave ratios greater than or equal to twice what was observed for the parental plasmid were considered hits. Plasmid DNAs from these positive clones were isolated by miniprep (Wizard Plus, Promega, Madison, Wis.) and retransformed back into E. coli W3110 for confirmation secondary thermal challenge assays.

For thermal gradients, the data was analyzed using Prism 4 software (GraphPad Software, San Diego, Calif.) using a sigmoidal dose response with variable slope as the model. The values obtained for the mid-point of the thermal denaturation curves are referred to as $T_{50}$ values, and are not construed as being equivalent to biophysically derived Tm values.

Figure 8:
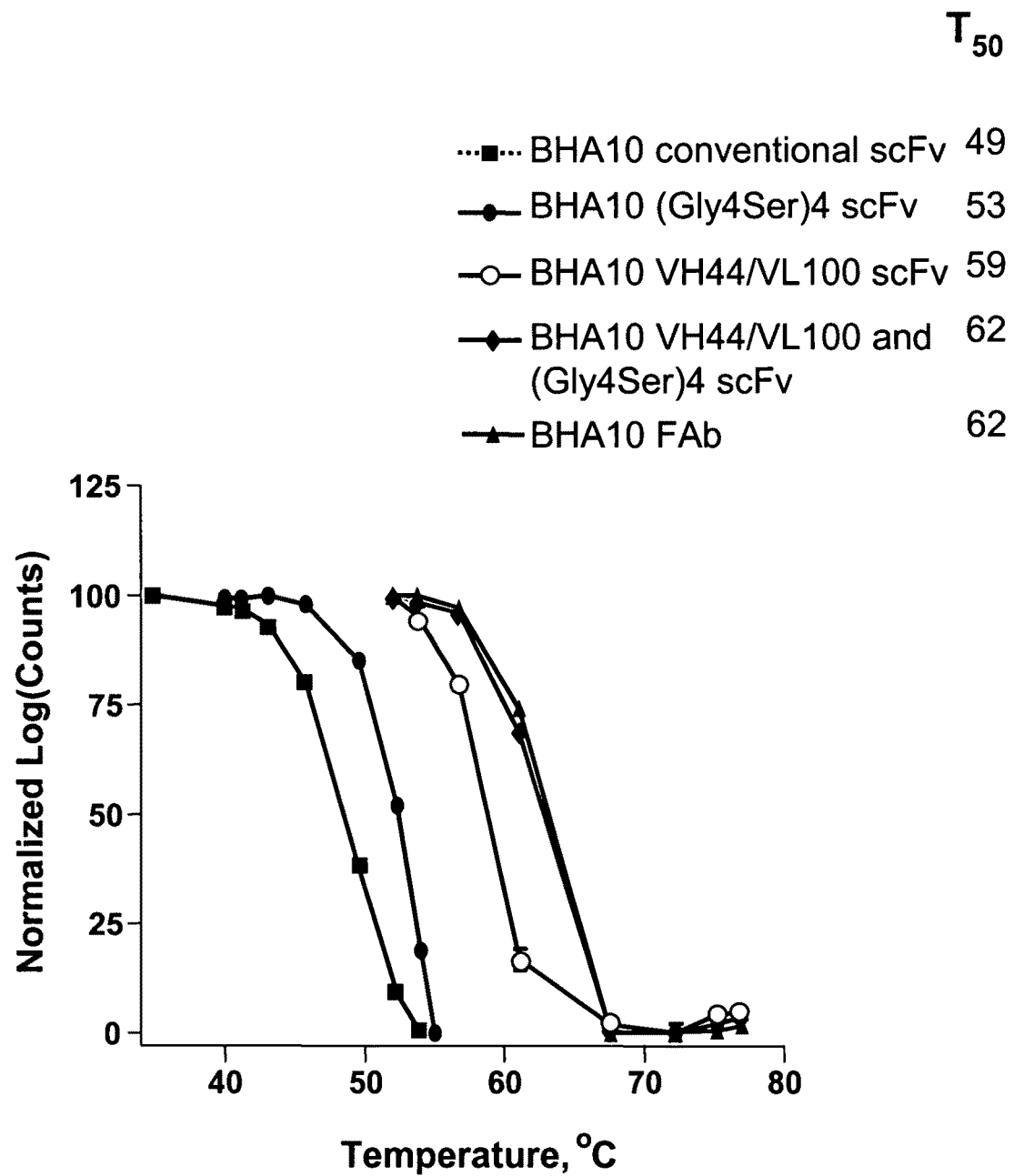
FIG. 8 depicts the results of a thermal challenge assay in which the thermal stabilities of the stabilized BHA10 scFv molecules of the invention were compared with that of a conventional BHA10 scFv molecule. The temperature at which 50% of the scFv molecules retain their binding activity (T50) is indicated in the figure legend.

The results of the thermal challenge assay are depicted in FIG. 8. As depicted in FIG. 8, all of the stabilized scFv molecules of the invention resulted in improvements in binding activity ($T_{50}$>49° C.) as compared with the conventional scFv. In particular, the $T_{50}$ values of BHA10 library position $V_L46$ scFv (S46L), library position $V_H16$ scFv (S16E and S16Q), and library positions $V_L49$: $V_L50$ scFv exhibited increases in thermal stability ranging from +3° C. to +12° C. relative to the conventional BHA10 scFv. In addition, the $T_{50}$ values of BHA10 library position $V_L3$ scFv (Q3A, Q3G, Q3S, Q3V, and Q3D), library position $V_H67$ scFv (V67I and V67L), library position $V_H48$ scFv (M48I and M48G), library position $V_H20$ scFv (V20I) and library position $V_H101$ scFv (P101D) exhibited increases in thermal stability ranging from +4° C. to +18° C. relative to the conventional BHA10 scFv. One of the stabilizing mutations ($V_L$ K13E) serendipitously resulted from a PCR error. Incorporation of one of these stabilizing mutations into pIEH009 was found to further improve thermal stability and even exceed that of BHA10 Fab under these conditions. Importantly, the non-covalent $V_L46$, $V_H101$ mutation, and $V_H55$ mutations derived from one or more of the four design methods ($V_L/V_H$ interface homology modeling, consensus scoring, computational modeling, and covariation analysis) resulted in an improvement in scFv thermal stability nearly approaching that observed with the disulfide mutations and validating the utility and novelty of these design tools. In particular, the $T_{50}$ of the pIEH006 construct, BHA10 $V_H44:V_L100$ scFv (59° C.), differed from BHA10 Fab (62° C.) by only 3° C., while the pIEH009 construct, BHA10 scFv $V_H44:V_L100/(Gly_4Ser)_4$ linker, was found to be functionally equivalent to BHA10 Fab under these conditions. These results demonstate that the stabilized scFvs of the invention have improved activity following a thermal challenge event.

c. Affinity Measurements

Isothermal titration calorimetry (ITC) was used to measure the affinity of sLTβR to the BHA10 Fab derived using enzymatic cleavage of the BHA10 IgG1 molecule. sLTβR was prepared as described previously (Eldredge et al., Biochemistry, (2006)). The Fab and sLTβR were concentrated to 6.0 and 2.0 mg/mL, respectively, using Amicon ultracentrifugal filter devices (MWCO 10,000). The concentrated stock solutions were simultaneously dialyzed against PBS prior to the ITC measurements. ITC was performed on a VP-ITC unit (MicroCal LLC, Northampton, Mass.) set to 30° C. Approximately 500 μL of a 7 μM sLTβR solution was placed into the sample cell and PBS dialysate was placed in the reference cell. A total of 234 μL of 70 μM BHA10 Fab was titrated into the sample cell in 7×10 4, 12×7 μL, followed by 8×10 injections. The reaction stoichiometry was 1:1. ITC curves were analysed using the Origin Software supplied by the manufacturer.

$K_D$ measurements of conventional BHA10 scFv, BHA10 $(Gly_4Ser)_4$ scFv, and BHA10 $V_H44:V_L100/(Gly_4Ser)_4$ scFv preparations as described in Examples 3 and expressed and purified using the methods described in Example 1 were performed using surface plasmon resonance (SPR) on a Biacore 3000 instrument (Biacore Inc., Piscataway, N.J.). All experiments were performed in HBS-EP buffer, pH 7.4. Biotinylated PENTA-His antibody (20 μg/mL, Cat#34440, Qiagen) was immobilized onto a streptavidin-coated CM5 chip at a flow rate of 10 μl/min for approximately 1 minute. 0.1 μM solutions of test scFvs were injected over the chip at a flow rate of 5 μl/min for 10 minutes and captured onto the surface via the immobilized PENTA-His antibody. To investigate binding between sLTβR and captured scFv, a concentration series of sLTβR (1, 2, 5, 10, 25, 50, 100, and 200 nM) was double injected at a flow rate of 30 μl/min onto the scFv-coated surface. Background was subtracted from test sample sensorgrams using sensorgram data from a flow cell containing buffer only and sensorgram data from the PENTA-His surface where scFv was injected followed by an injection of buffer instead of sLTβR. The curves were analyzed using the BiaEval 3.0 manufacturer's software. $K_D$ values were calculated by fitting kinetic association and dissociation curves to a 1:1 Langmuir binding model. Chip surfaces were regenerated by two consecutive 10 μL injections of 0.1 M glycine, pH 3.0.

Table 5 shows the results of the Biacore affinity assay. The binding affinity of recombinantly produced BHA10 scFv is essentially the same as the BHA10 Fab prepared as described in Example 1. Additionally, introduction of the $(G_4S)_4$ linker alone or in the presence of the stabilizing disulfide ($V_H44$: $V_L100$), or the combination of the two did not result in any significant loss of affinity towards antigen.

TABLE 5

Biacore affinity assay-binding to LTβR.

| Construct | Kd (nM) |
|---|---|
| BHA10 scFv | 3.7 |
| BHA10 $(Gly_4Ser)_4$ scFv | 2.5 |
| BHA10 $V_H44:V_L100/(Gly_4Ser)_4$ scFv | 4.3 |
| BHA10 Fab (CHO) | 1.9 ± 1.0* |

*Measured by isothermal titration calorimetry

D. Differential Scanning calorimetry Studies

Figure 9:
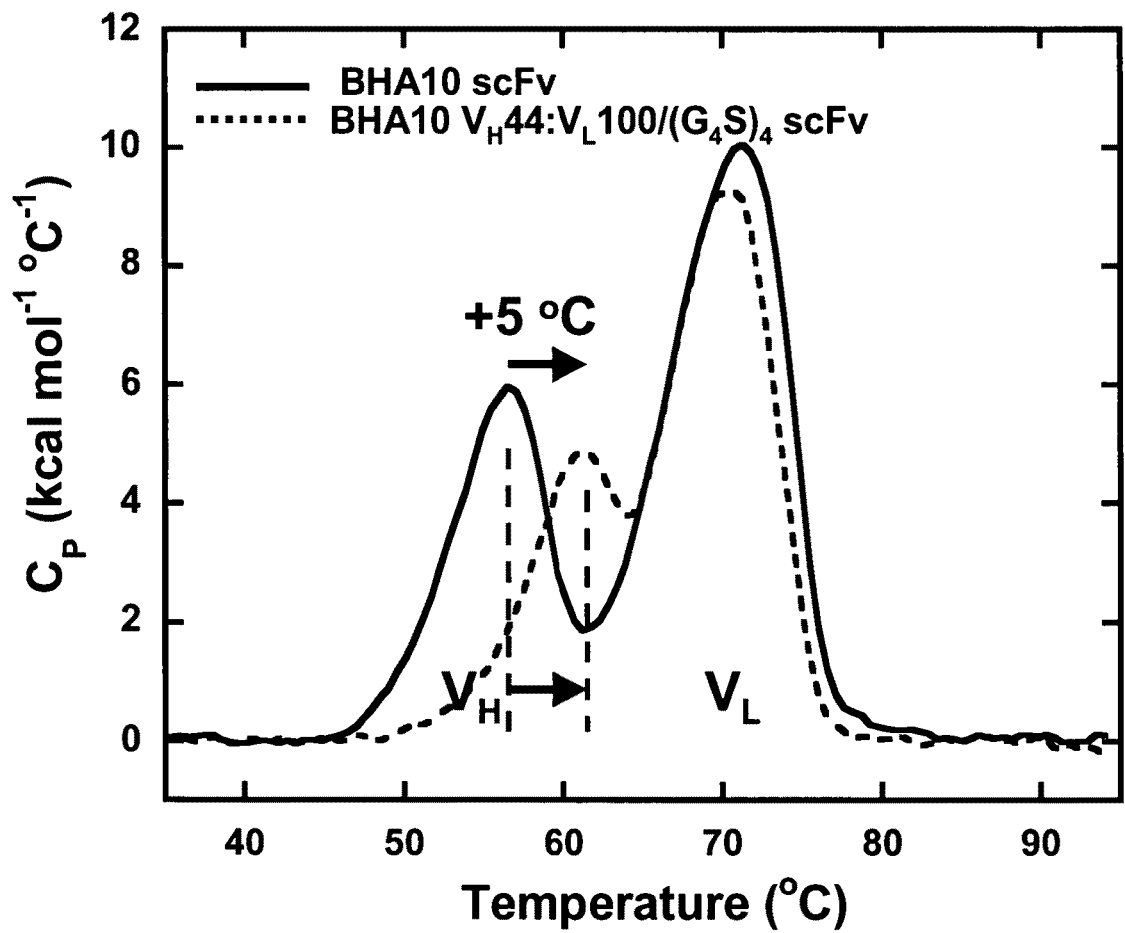
FIG. 9 depicts the results of Differential Scanning calorimetry (DSC) analyses performed with a conventional BHA10 scFv and a BHA10 V$_H$44:V$_L$100/(Gly$_4$Ser)$_4$ scFv.

Differential Scanning calorimetry (DSC) analyses were performed with BHA10 scFv, BHA10 $(Gly_4Ser)_4$ scFv, and BHA10 $V_H44:V_L100/(Gly_4Ser)_4$ scFv preparations. Experiments were performed as described above for the initial comparisons of the conventional scFv against the enzymatically produced Fab except they were performed at a scan rate of 4° C./min. BHA10 $V_H44:V_L100/(Gly_4Ser)_4$ scFv demonstrated superior thermostability properties compared to the wild-type scFv. In particular, the less stable of the two domains, the $V_H$ domain of BHA10 $V_H44:V_L100/(Gly_4Ser)_4$ scFv, denatured at approximately 5° C. higher than that of conventional BHA10 scFv (FIG. 9). Increases in the "melting temperature" or $T_M$ could be due to two separate factors, (i) an increase in the thermostability of the equilibrium folded state or (ii) a decreased tendency to aggregate. The ~5° C. temperature difference between the conventional BHA10 scFv and BHA10 $V_H44:V_L100/(Gly_4Ser)_4$ scFv was relatively independent of scan rate (between 0.2 and 4.0° C./min) suggesting the observed $T_M$ change was due to stabilization of the equilibrium folded state.

E. ANS Binding Studies

Figure 10:
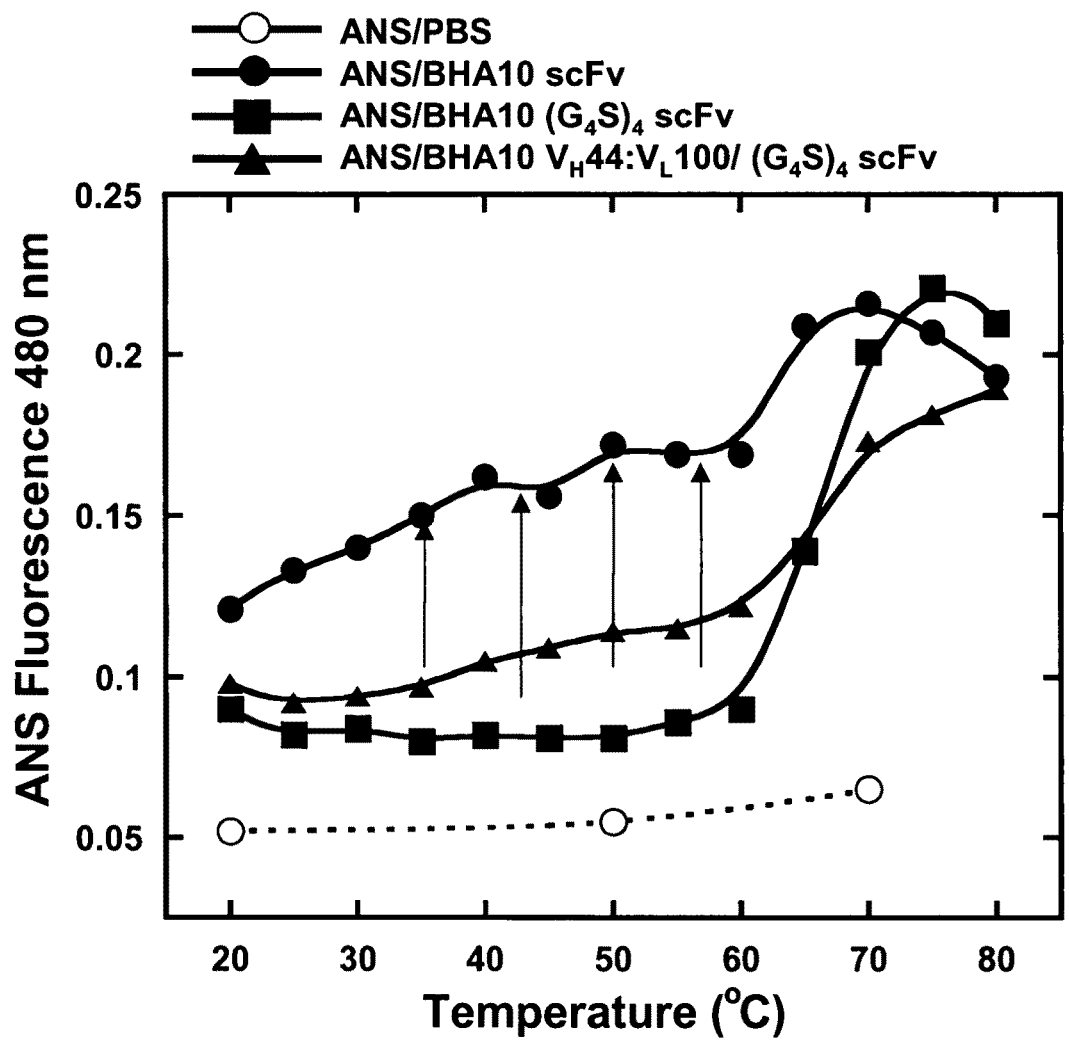
FIG. 10 shows results of binding of the hydrophobic fluorescent dye 1-anilino-8-naphthaline sulfonate (ANS) to conventional BHA10 scFv, BHA10 (Gly$_4$Ser)$_4$ scFv, and BHA10 V$_H$44:V$_L$100/(Gly$_4$Ser)$_4$ scFv.

The ability to bind the hydrophobic fluorescent dye 1-anilino-8-naphthaline sulfonate (ANS) is often a hallmark of interactions with significantly large hydrophobic regions either in a protein's native state or partially unfolded state that can occur upon increased treatment with temperature. The intrinsic fluorescence of the dye is quenched in solvent and significantly increases when exposed to large hydrophobic surface areas. The conventional BHA10 scFv intrinsically bound ANS at a much stronger level than the BHA10 $(Gly_4Ser)_4$ scFv, or BHA10 $V_H44:V_L100/(Gly_4Ser)_4$ scFv indicating the presence of hydrophobic exposure forced upon the scFv by an inadequately sized linker. Addition of the longer linker, specifically $(Gly_4Ser)_4$, appeared to mediate this effect. The apparent exposure of a hydrophobic surface by the conventional BHA10 scFv may lead to an increased level of aggregation in the presence of other proteins or molecules, or even in the presence of itself in isolation. Heating BHA10 scFv above its $T_M$ appeared to induce ANS binding for the conventional and engineered BHA10 scFvs. Interestingly, the conventional BHA10 scFv showed a gradual increase in ANS binding, as a function of increasing temperature, suggesting possible increases in hydrophobic exposure at temperatures below the $T_M$—such as temperatures used in bacterial and mammalian cell culture (i.e. 37° C.) (FIG. 10). In contrast, both BHA10 (Gly$_4$Ser)$_4$ and BHA10 V$_H$44: V$_L$100/(Gly$_4$Ser)$_4$ scFvs did not exhibit this property suggesting that the stabilizing mutations described in this invention decrease the tendency to self-associate or associate with other cell-culture protein components based on reduced exposure of hydrophobic surface areas.

Example 5

Identification of Stabilizing Mutations which confer Improved Intrinsic Protein Stability (i) Identification of Stabilizing Mutations A variety of sequence-based methods (e.g., consensus scoring, covariation analysis, VH/VL interface homology modeling) were used to identify stabilizing mutations which conferred improved protein stability to binding molecules of interest. These stabilizing mutations were used in the design and construction of antibody variable region expression libraries.

A. Covariation Analysis

A number of designs were developed for stabilizing the BHA10 scFv V$_H$ and V$_L$ domains based on the strong covariation exhibited by two or more residues within a single sequence. Covariation analysis was performed on the BHA10 scFv V$_H$ and V$_L$ domains using methods similar to those described in Example 17 infra in order to identify missing or violative covariations such that stabilizing mutations could be predicted and included in an antibody variable region expression library for experimental screening.

Figure 78:
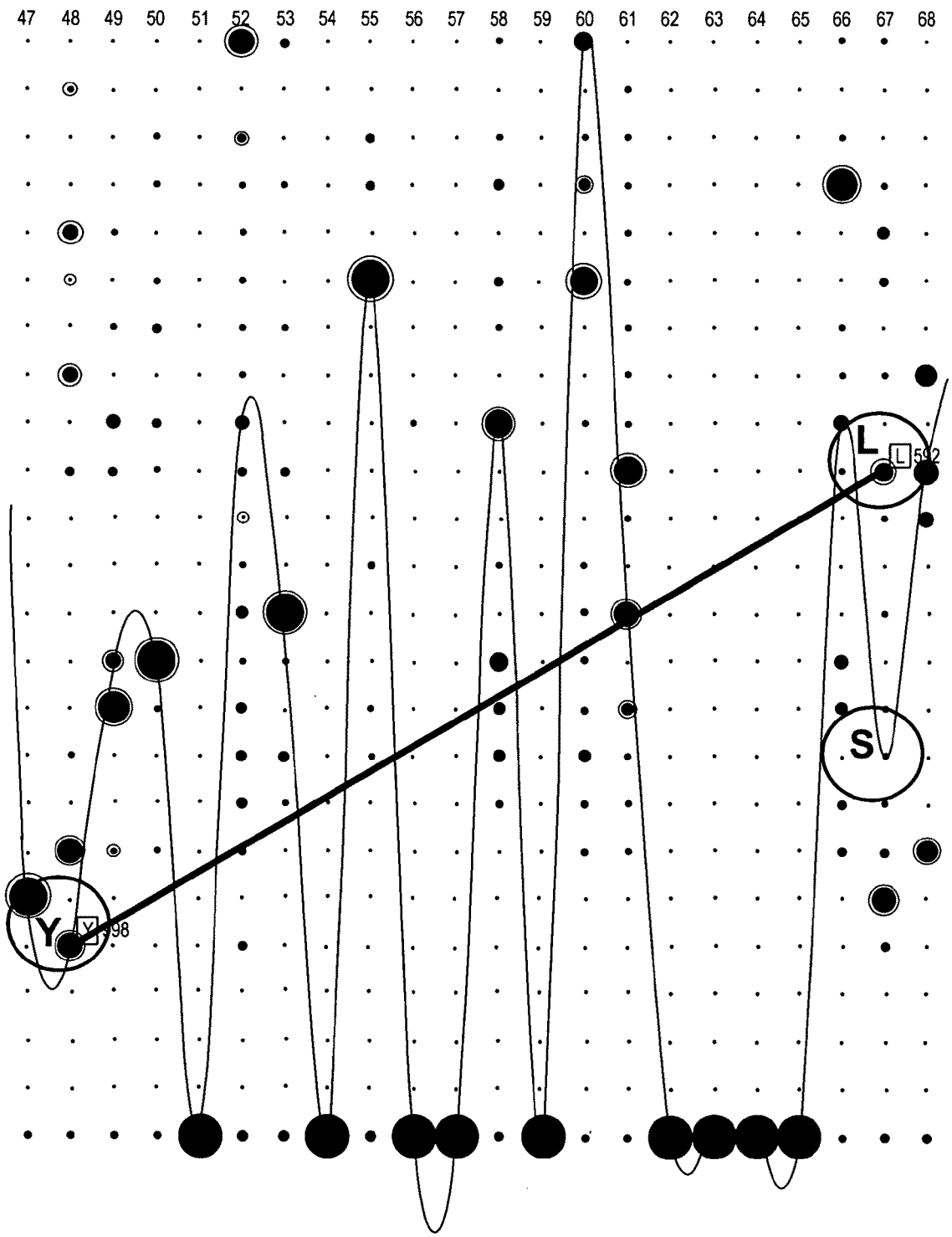
FIG. 78 shows a detail from the covariation analysis of BHA10 $V_L$ highlighting the covariation between Tyr at Kabat position 36 (residue position #48) and the mutation Ser→Leu at Kabat position 46 (residue position #67) as described in Example 7.

In a first example, mutation from Ser to Leu at position 46 (S46L; Kabat numbering system) within the BHA10 V$_L$ exhibited a positive connection to an existing Tyr at residue 36 which the Covariation Analysis Tool showed to covary strongly with Leu 46 (see FIG. 78). This mutation was also predicted to be stabilizing by residue frequency analysis.

In addition to S46L, a second mutation predicted by covariation to be stabilizing was a V55G mutation within the BHA10 V$_H$ domain. While residue frequency indicated that Val is infrequently observed at this position, this position is embedded within CDR2 and is variable. Therefore, without additional information, no changes at this position were previously attempted. Upon inspection by covariation analysis, however, the covariation data suggested that this position was strongly correlated with at least 10 other amino acids that already exist within the BHA10 V$_H$ domain. Mutation to Gly at position 55 satisfied all 10 covariations.

Another example of the utility of the Covariation Analysis Tool was the predicted negative effect of a BHA10 V$_H$ Q6E mutation. Single residue frequency analysis suggested that mutation to the much more commonly observed Glu at this position would lead to an increase in stability. However, the Covariation Analysis Tool indicated that single mutation to Glu violates several existing covariations present within the BHA10 V$_H$ sequence. To obtain an improvement in stability, one must replace several amino acids that preferentially stabilize Glu at this position.

Figure 79:
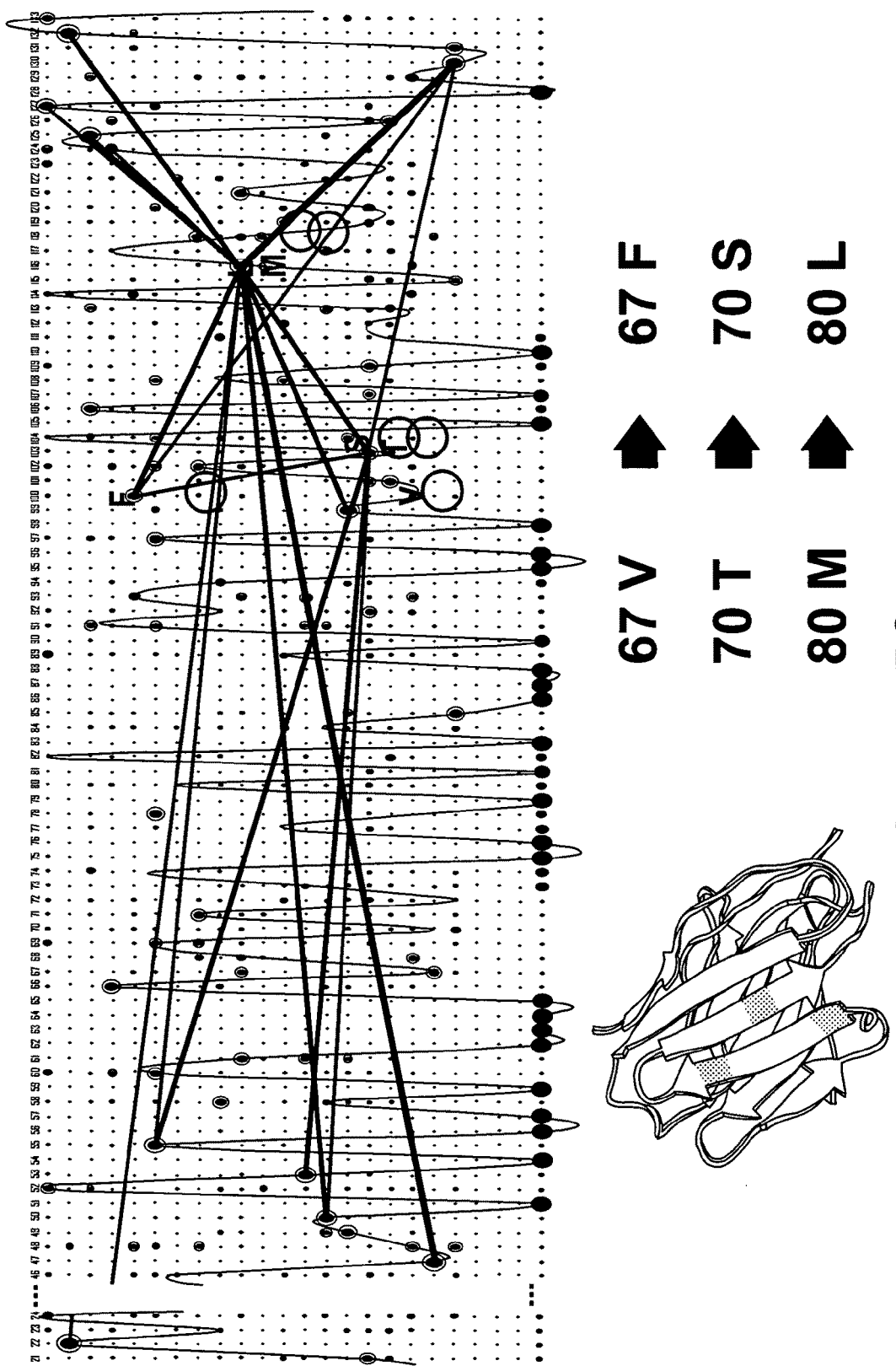
FIG. 79 shows a detail from the covariation analysis of BHA10 $V_H$ highlighting the conflicting covariation between Val at Kabat position 67 (residue position #100), Thr at Kabat position 70 (residue position #104), and the mutation Met→Leu at Kabat position 80 (residue position #116).

Yet, another example of the predictive value of the Covariation Analysis Tool is shown in FIG. 79. Met 80 was mutated to Leu as part of a single residue library design. It was thought that this single mutation would be highly stabilizing, as Leu is the most frequent amino acid observed at this position within the sequence database. However, covariation analyses indicate that two other amino acids must be mutated (V67F and T70S) in order to achieve covariation harmony.

B. Consensus Scoring

Consensus scoring was utilized as a method for identifying amino acid residues within the scFv V$_H$ and V$_L$ regions for mutagenesis to improve the intrinsic stability of the scFv. The scoring assesses the relative drift from consensus V$_H$ and V$_\kappa$ sequences due to hypersomatic mutations and evolutionary germline variations. Information derived from this analysis was then used to design a library to screen for scFv variants with improved stability.

The reference set of mammalian V$_H$ and V$_\kappa$ kappa sequences used to derive the consensus sequence for scoring and the individual amino acid frequencies at each residue position were collected, sorted, and culled as described previously (Demarest, et al., *J. Mol. Biol.* 335, 41-48 (2004); Demarest, et al., *Protein Eng. Des. Sel. In Press*, (2006). The mammalian reference sets were naively constructed to include V-genes from various mammals in order to obtain diversity via the evolutionary drift between species. The V$_H$ mammalian reference set contains 61 V$_H$ sequences primarily from NCBI and TIGR representing a total of 17 different mammalian species. The V$_\kappa$ mammalian reference set contains 53 V$_\kappa$ sequences from 13 different mammalian species.

Statistical analysis of the BHA10 V$_H$ and V$_L$ were performed using custom designed IgG databases and a modified PERL script (Demarest et al., 2004; Demarest et al., 2006). The amino acid frequency of every residue within the BHA10 V$_H$ and V$_L$ was calculated from the custom database. The residue frequency of each amino acid within the BHA10 VH and VL, $S_i(r)$, for each position, i, in an individual sequence was calculated by the number of times that particular residue-type (r=A, C, D . . . V, W, Y) is observed within the data set divided by the total number of sequences. FIG. 11 shows the BHA10 V$_H$ and V$_L$ residue frequencies divided by the residue frequency of the database consensus residues. By dividing by the consensus residue frequency, a stringent cutoff for the creation of libraries at residue positions where the BHA10 amino acid is infrequently observed among common V$_H$ or V$_L$ sequences is obtained. Library positions were determined by those whose residue frequency divided by the most frequent residue frequency ($S_i(r)/MFR_i(r)$) was <0.3. The residues listed to the right of the residue frequency calculations are those commonly found in human sequences as published (Chothia, et al., *J. Mol. Biol.* 278, 457-479, (1998)) and can be specifically targeted in a library format to screen for the most stabilizing amino acid. The CDRs of the BHA10 V$_H$ and V$_L$ were not considered for stability optimization due to potential interruption of the interaction with LTβR, but could be considered for second-generation designs.

C. VH/VL Interface Homology Modeling

As described in Example 15 infra, differential scanning calorimetry analyses were performed on 17 human antibodies. The top candidates, BIIB1-4 all had exquisite (i.e., very high and desired) stability properties. These highly stable antibodies may be used as a platform for improving the stability of scFvs or antibody domains with low intrinsic stability. In particular, emphasis was placed on the interface between V$_H$ and V$_L$ to provide a potentially greater level of stability properties.

Converting the BHA10 Fab to an scFv format resulted in a change in the DSC thermogram indicative of a fully cooperative unfolding event, as observed by a single, higher temperature unfolding transition (Fab), to a largely non-cooperative unfolding event, as observed by two individual, lower temperature unfolding transitions (scFv). In other words, in the Fab format, the interdomain contacts were strong enough to lock all the domains together into a single, higher temperature unfolding transition. Once the $C_H1$ and $C_L$ domains were removed, the $V_H$ and $V_L$ domains of the scFv no longer had the ability to drive the unfolding transition into a cooperative event. It is postulated that by stabilizing the interface, on may not only stabilize both the $V_H$ and $V_L$ domains simultaneously, but also promote the adherence of the $V_H/V_L$ interface and preclude aggregation.

The top 4 most stable BIIB antibodies (BIIB1-4) were used to design stabilizing mutations into the BHA10 scFv via a two-step procedure. First, a crystal structure of the humanized BHA10 Fab was utilized for structural analysis. Specifically, the crystal structure was employed to identify all the residues at the interface between $V_H$ and $V_L$ as well as the amount of surface area that each residue contributes to the interface (using MOLMOL software). The residues that bury significantly more surface area than others at the interface are considered to be more crucial to the interface. As an arbitrary limit prioritization, those that bury between 30 and 40 Å$^2$ are considered important. Those that bury >40 Å$^2$ are considered crucial. These two categories were given the highest priority in terms of homology modeling and mutagenesis. The amount of surface area each residue buries at the interface is listed in Table 6. Secondly, the amino acid types at the interface between $V_H$ and $V_L$ were compared with the amino acids that exist at the same positions in BIIB1-4 (i.e. the extremely stable antibodies). This method allowed identification of a number of outstanding mutations for stabilizing the BHA10 scFv.

Two mutations, S46L in the $V_L$ and P101D in the $V_H$ were experimentally validated as described in Example 8. In fact, these two mutations were the single most stabilizing mutations tested in the thermal challenge assay (e.g., see FIG. 50A and FIG. 50C). Both mutations stabilize both $V_H$ and $V_L$ domains simultaneously, suggesting that they help to build cooperativity among the domains.

TABLE 6

BHA10 $V_HV_L$ Surface Area Analysis.

| Position of VH/VL Interface Residue (Kabat #) | Region | BHA10 AA Type (Kabat) | Buried Surface Area (Å$^2$) | Residue Frequency within mammalian database | Corresponding AA from Stable Ab (BIIB) |
|---|---|---|---|---|---|
| VH 35 | FR2 | His | 16.4 | | His |
| VH 37 | FR2 | Val | 6.5 | | Val |
| VH 39 | FR2 | Gln | 37.4 | 98% | Gln |
| VH 44 | FR2 | Gly | 13.1 | | |
| VH 45 | FR2 | Leu | 97.8 | 97% | Leu |
| VH 47 | CDR2 | Trp | 78.5 | 97% | Trp |
| VH 50 | CDR2 | Trp | 24.1 | | |
| VH 59 | CDR2 | Gln | 28.8 | | |
| VH 61 | CDR2 | Asn | 26.4 | | |
| VH 90 | FR3 | Tyr | 37.3 | | Tyr |
| VH 100I | CDR3 | Glu | 101.8 | Highly Variable | Gly (BIIB1), Tyr (BIIB2) |
| VH 100J | CDR3 | Gly | 36.4 | Ala, Gly (MCR); Tyr (uncommon); | Phe (BIIB1), Ala (BIIB2) |
| VH 100K | CDR3 | Phe | 66.7 | Met (MCR); Phe (SMCR) | Phe (BIIB1); Met (BIIB2) |
| VH 101 | CDR3 | Pro | 43.3 | Asp (V. Cons); Ala (uncommon) | Asp* (BIIB1, BIIB2) |
| VH 103 | CDR3 | Trp | 78.9 | 98% | Trp |
| VH 104 | FR4 | Gly | 6.1 | | |
| VH 108 | Fr4 | Gln | 11.5 | | |
| VL 36 | FR2 | Tyr | 44.2 | 86% | Tyr (BIIB1, BIIB2) |
| VL 38 | FR2 | Gln | 34.5 | 92% | Gln (BIIB1, BIIB2) |
| VL 42 | FR2 | Lys | | | |
| VL 43 | FR2 | Ala | 47.7 | Ser = 50%; Ala = 35%; Pro = 10% | Ala (BIIB1, BIIB2) |
| VL 44 | FR2 | Pro | 69.7 | 100% | Pro (BIIB1, BIIB2) |
| VL 45 | FR2 | Lys | 3.5 | | |
| VL 46 | FR2 | Ser | 29.7 | Leu = 76%; Arg = 8%; Ser = 2% | Leu* (BIIB1, BIIB2) |
| VL 49 | FR2 | Ser | 14.8 | Tyr = 88%; Glu = 4%; Ser = 2% | Ser (BIIB1) |
| VL 50 | FR2 | Ser | 9.7 | | Gly (BIIB1) |
| VL 55 | CDR2 | Tyr | 59.6 | Ala = 34%; Glu = 28%; Tyr = 6% | Glu* (BIIB1) |
| VL 87 | FR3 | Phe | 35.1 | Tyr = 84%; Phe = 15% | Tyr* (BIIB1) |

TABLE 6-continued BHA10 $V_HV_L$ Surface Area Analysis.

| Position of VH/VL Interface Residue (Kabat #) | Region | BHA10 AA Type (Kabat) | Buried Surface Area (Å²) | Residue Frequency within mammalian database | Corresponding AA from Stable Ab (BIIB) |
|---|---|---|---|---|---|
| VL 89 | CDR3 | Gln | 14.7 | | Gln (BIIB1) |
| VL 91 | CDR3 | Tyr | 36.3 | | Phe (BIIB1) |
| VL 94 | CDR3 | Tyr | 68.4 | Thr = 20%; Tyr = 12% | Ala (BIIB1); Leu (BIIB2) |
| VL 95 | CDR3 | Pro | 38.8 | Pro = 90% | Pro (BIIB1); Leu (BIIB2) |
| VL 96 | FR4 | Phe | 76.6 | Tyr = 12%; Phe = 6% | Tyr* (BIIB1); Trp* (BIIB2) |
| VL 98 | FR4 | Phe | 102.5 | 100% | Phe |
| VL 99 | FR4 | Gly | 5.4 | | |
| VL 105 | FR4 | Glu | 6.2 | | |

(Residues positions labeled with '*' indicate good opportunities for stability design - via mutation to residues found in BIIB1, 2, 3, or 4).

D. Computational Analysis

Computational methods were used to analyze BHA10 for making recommendations on positions whereby amino acid substitutions might improve stability. These methods were composed of two steps: sequence-based analysis (step 1); and structure-based analysis (step 2). During the first step, a database of sequences of variable domains of antibodies was used. Amino acids present in low frequencies in their respective positions (less than in 10% of database sequences) or those that did not match the corresponding consensus amino acid were selected for substitutions to high-frequency or consensus amino acids (candidate mutations). During the second step a three-dimensional structure or model of an Fab fragment of the antibody was used. The candidate mutations were evaluated in their structural context and were prioritized for experimental testing based on structural properties, compatibility with complementarity determining regions (CDRs) conformations, role in $V_L/V_H$ interface packing, and folding of heavy and light chains.

BHA10 is unusual in having a serine in position 46 on the light chain. In the database, approximately 1% of $V_L$ (kappa subtype) sequences possess S46, whereas approximately 79% of $V_L$ (kappa subtype) sequences have L46. Also, human consensus KV1 has L46. Once identified as a candidate mutation, S46L substitution was evaluated in the context of a three-dimensional model of BHA10 Fab. Position 46 was found to reside at the $V_L/V_H$ interface making contacts with Y101 and W103 of $V_H$ and Y36 and Y55 of $V_L$. Structure-base analysis revealed that S46L substitution was compatible with the integrity $V_L/V_H$ interface, CDR conformations, and $V_L$ folding.

Serine is an infrequent amino acid at position 16 of the heavy chain. In the database, approximately 5% of $V_H$ sequences possess S16, 25% have A16, 21% have G16, 11% have E16, and approximately 10% are Q16. Also human consensus HV1 has A16. Once identified as candidate mutations, S16A, G, E, and Q substitutions were evaluated in the context of three-dimensional model of BHA10 Fab. Position 16 was found to reside in the loop proximal to the $V_H/C_H1$ interface making contacts with K13 and S16 of $V_H$. Structure-base analysis revealed that S16A, G, E, and Q substitutions were compatible with the integrity of the $V_L/V_H$ interface, CDR conformations, and $V_H$ folding. Also it was concluded that long hydrophilic sidechains of E16 and Q16 would be preferred. Accordingly, positions $V_L$ 46 and $V_H$ 16 were represented in the library design.

A complementary approach to computational analysis made use of structure-based protein engineering techniques, such as Rosetta (Kuhlman B. et al., PNAS 200198(19):10687-91) and DEEK (Hanf K. J., Ph.D. Thesis, MIT, 2002). Given a three dimensional structure of a protein interface, these methods can yield mutations in amino acid sequence that lead to improved ΔΔG for VH to VL binding (difference between bound and unbound states) and/or ΔΔG for VH and VL folding (difference between folded and reference unfolded states). Use of these methods revealed that S46L is a mutation that improves VH to VL binding, whereas S16E is a mutation that improves folding of the VH.

E. Combined Interface and Covariation Design Approaches

Covariation analysis was used to determine residue networks important for providing and supporting the interface between VH and VL and maintaining a strong affinity between $V_H/V_L$, thereby resulting in increased scFv stability. Residues directly involved in the interface between VH and VL of the BHA10 scFv were identified as described in Example 5C and are listed in Table 6 supra. Residues that covary strongly with the most highly buried residues listed in Table 6 supra were calculated using the covariation methodology described in Section III (a) supra. The HMM used for covariation analysis eliminates the ability to investigate residues in CDR2 and CDR3 of both the VH and VL domains that are buried at the interface. Nevertheless, it is believed that no strong covariations would arise from these residue positions as they are highly variable due to intense selective pressures that exist for antibodies to be able to recognize antigens with high affinity. Therefore, the residues that were used for determining whether a covariation network exists for supporting the interface between both VH and VL were:

| VH (kabat#) | VL (kabat#) |
|---|---|
| V37/I37 | Y36 |
| Q39 | Q38 |
| G44 | A43 |
| L45 | P44 |
| W47 | L46 |
| W50 | Y49 |
| Y91 | Y95 |
| W103 | F98 |

Residues whose appearance in the V-class sequence alignment correlated with the interface residues listed above were determined using a phi-value cutoff >0.25. No residue was considered as important for maintaining a strong interface between VH and VL if it was not correlated with at least 2 of the interface residues listed directly above. Tables 7 and 8 list those residues within the VH and VL domains, respectively, that demonstrate 2 or more correlations with interface residues. The larger the number of links, the greater the impact each of these amino acid positions is conceived to have for stabilizing the interface between VH and VL.

TABLE 7

Residues with VH with multiple strong correlations to structural residues observed at the interface of the BHA10 xray-crystal structure.

| Covar# | Amino Acid | Bha10Xray# | Kabat# | #Links |
|---|---|---|---|---|
| 67 | W | 47 | 47 | 6 |
| 48 | V(I**) | 37 | 37 | 5 |
| 61 | L | 45 | 45 | 5 |
| *66* | *E* | *46* | *46* | *5* |
| 71 | I | 51 | 51 | 5 |
| *85* | *Y* | *60* | *59* | *5* |
| 142 | L | 112 | 109 | 5 |
| 14 | P | 14 | 14 | 4 |
| 27 | G | 26 | 26 | 4 |
| 29 | F | 27 | 27 | 4 |
| *52* | *A* | *40* | *40* | *4* |
| 61 | L | 45 | 45 | 4 |
| 102 | I | 70 | 69 | 4 |
| 135 | W | 106 | 103 | 4 |
| 31 | F | 29 | 29 | 3 |
| *49* | *R* | *38* | *38* | *3* |
| 60 | G | 44 | 44 | 3 |
| 69 | G | 49 | 49 | 3 |
| 78 | G | 56 | 55 | 3 |
| 93 | L | 64 | 63 | 3 |
| 97 | G | 55 | 54 | 3 |
| 101 | T | 69 | 68 | 3 |
| 106 | D | 73 | 72 | 3 |
| 109 | S | 75 | 74 | 3 |
| 115 | Y | 80 | 79 | 3 |
| 120 | T(S*) | 85 | 82b | 3 |
| 6 | E | 8 | 8 | 2 |
| 43 | Y | 32 | 32 | 2 |
| 50 | Q | 39 | 39 | 2 |
| *53* | *P* | *41* | *41* | *2* |
| 92 | S | 63 | 62 | 2 |
| 124 | A | 89 | 85 | 2 |
| 131 | Y | 95 | 91 | 2 |
| 24 | A, V, G | 24 | 24 | 3* |
| 89 | A, N, P | 61 | 60 | 3* |

Residues in bold bury surface area at the interface. Residues in italics are those directly adjacent in primary sequence to residues that bury surface at the interface.
*Distinguishing subclass feature
**Covaries with many of the same residues as the primary residue, but at a lower correlation level due to weaker residue frequency.

TABLE 8

Residues with VL with multiple strong correlations to structural residues observed at the interface of the BHA10 xray-crystal structure.

| Covar# | Amino Acid | Bha10Xray# | Kabat# | #Links |
|---|---|---|---|---|
| *49* | *Q* | *37* | *37* | *7* |
| 48 | Y | 36 | 36 | 6 |
| 61 | P | 44 | 44 | 6 |
| 93 | P | 59 | 59 | 6 |
| 91 | G | 57 | 57 | 6 |
| 102 | G | 64 | 64 | 6 |
| 67 | L | 46 | 46 | 4 |
| 69 | I | 48 | 48 | 4 |
| 101 | S | 63 | 63 | 4 |
| 107 | S | 67 | 67 | 4 |
| 108 | G | 68 | 68 | 4 |
| 52 | K | 39 | 39 | 3 |
| *66* | *K* | *45* | *45* | *3* |
| 85 | R | 54 | 54 | 3 |
| 90 | S | 56 | 56 | 3 |
| 122 | Q | 79 | 79 | 3 |
| 129 | D | 85 | 85 | 3 |
| 135 | F | 98 | 98 | 3 |
| *68* | *L* | *47* | *47* | *2* |
| 92 | V | 58 | 58 | 2 |
| 117 | T | 74 | 74 | 2 |
| 120 | G | 77 | 77 | 2 |
| 126 | E | 83 | 83 | 2 |
| *133* | *Q* | *89* | *89* | *2* |
| 143 | L | 104 | 104 | 2 |

Residues in bold bury surface area at the interface. Residues in italics are those directly adjacent in primary sequence to residues that bury surface at the interface.
*Q50, A89, Y135 are conserved in both heavy and light chains and covariations do not appear to correlate with light chain positions.

Figure 87A:
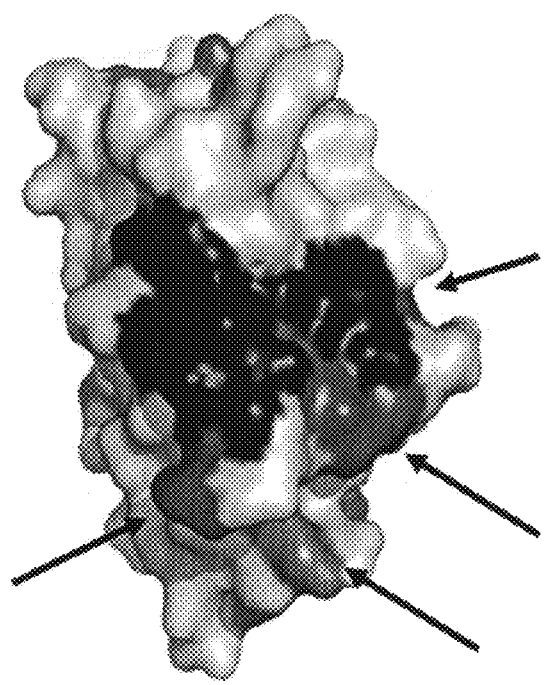
FIG. 87 depicts VH residues involved in Covariation networks that are important for interface maintenance (FIG. 87A) and interface residues involved in making direct contacts with the VH/VL interface and that are mapped directly to the surface of VH domain (FIG. 87B). Arrows indicate residue positions outside the actual interface that covariation analysis informs to be important for stabilizing the VH/VL interaction and for VH/VL stability. The location of hypervariable CDR3 residues that make direct contacts at the interface between VH and VL are enclosed within a box.
Figure 87B:
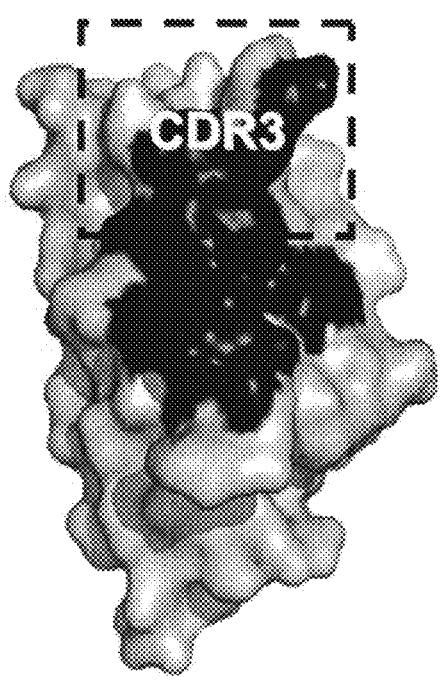
Figure 88A:
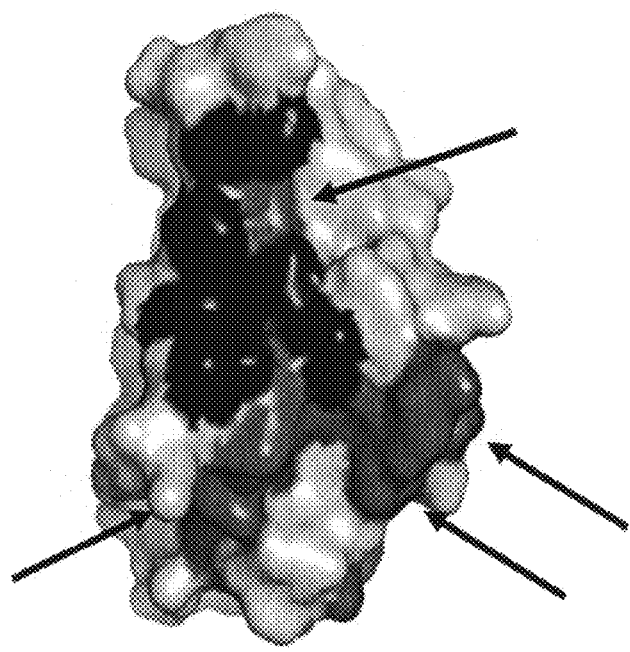
FIG. 88 depicts VL residues involved in Covariation networks important for interface maintenance (see FIG. 88A) and interface residues involved in making direct contacts with the VH/VL interface and that are mapped directly to the surface of VL (FIG. 88B). Arrows indicate residue positions outside the actual interface that covariation analysis informs to be important for stabilizing the VH/VL interaction and for VH/VL stability. The location of hypervariable CDR3 residues that make direct contacts at the interface between VH and VL are enclosed within a box.
Figure 88B:
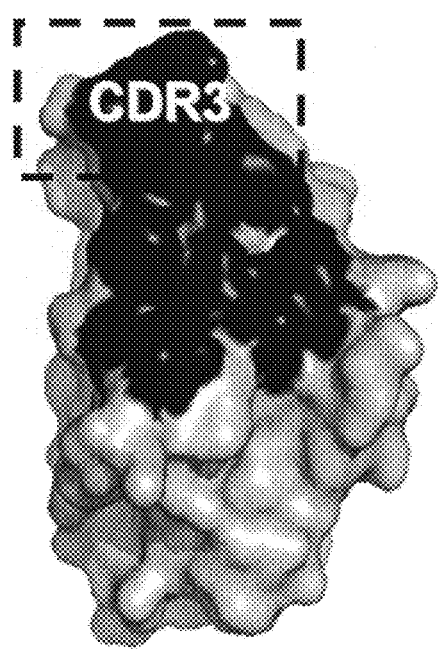

The residues from Tables 7 and 8 have been mapped to the surfaces of the BHA10 VH and VL, respectively, and compared with the actual residues that make direct contact at the interface between the two domains (see FIGS. 87 and 88). Two supported from this analysis. First, covariations do not provide information (at this stage) about networks involving CDR2 and CDR3 residues at the interface. Second, covariations suggest that not only are residues that make direct contacts within the interface important for its maintenance, but that many other residues outside the direct interface residues are important for scaffolding and supporting the positions of the interface residues. This point is illustrated by those residues that are illustrated on the surface of the covariation network but are absent on the surface obtained simply using the structures to calculate those residues that directly bury surface at the interface.

Violations of a few of these interface covariation networks were found to exist within the BHA10 or p5E8 (described below in Example 21) scFvs: VH or VL sequences. Mutation of the native/non-ideal amino acids at these positions to the ideally supportive interface amino acid residues described in Tables 7 and 8 were shown to be highly stabilizing to either the BHA10 or p5E8 scFvs: (a) BHA10 VL S46L, and (b)-Idec152 VH S49G (kabat and Xray#) E72D(73 for Xray). One of these residues (S46L$_{VL}$) was directly at the interface, one (S49G$_{VH}$) was directly adjacent to the interface, and one was distal to the interface (E72D$_{VH}$). However, all three were predicted based on Covariation Analysis to be stabilizing to the interface. Stabilization of the interface can be observed using DSC measurements as an increase in the thermal stability of both the V$_H$ and the V$_L$.

ii) Construction and Screening of BHA10 scFv Libraries with Improved Thermal Stability A) Construction of scFv Libraries Libraries designed to contain the desired amino acid replacements in the conventional BHA10 scFv (pXWU002) using the methods described in Examples 4, 5, and 6 were created using the QuikChange II Site-Directed Mutagenesis Kit following instructions provided by the manufacturer (Stratagene, La Jolla, Calif.) using oligonucleotides listed in Table 9. The DNA sequence of the conventional scFv is depicted in FIG. 1.

Individual transformed colonies were picked into deep-well 96 well dishes (Corning, Corning, N.Y., Cat. #3960) containing 400 μl/well LB plus 50 mg/ml carbenicillin and grown overnight at 37° C. Master plates were created by adding an equal volume of LB containing 20% glycerol to each well of the deep-well 96 well dishes and transferring 50 µl aliquots of the bacterial suspension to sterile microtiter plates (Corning, Corning, N.Y., Cat. #3359) and freezing for storage at −80° C.

TABLE 9

Oligonucleotides for stability engineering of BHA10 scFv.

| BHA10 Library Position | Sequence† | Design Method(s) |
|---|---|---|
| V$_L$ 49 and 50 (SEQ ID NO: 123) | 5'-GTACCGGTAGGAGGCMNNR KAAATCAGTGATTTAGG -3' | Consensus |
| Y$_L$ 46 (SEQ ID NO: 124) | 5'-GGGAAGGCTCCTAAATTACTG ATTTCCTCGGCC -3' | Consensus, Computation, V$_L$/V$_H$ Interface, Covariation |
| V$_H$ 16 (SEQ ID NO: 125) | 5'-GGACACCTTCACTGACBNCCC AGGCTTCTTCAC -3' | Consensus, Computation |
| V$_H$ 101 (SEQ ID NO: 126) | 5'-GATCCTGGGAAGGTTTTGACT ACTGGGGCCAAGGGAC -3' | V$_L$/V$_H$ Interface, |
| V$_H$ 20 (SEQ ID NO: 127) | 5'-GGGTCCTCAGTGAAGWTRTCC TGCAAGGCTTCTG -3' | Consensus |
| V$_H$ 48 (SEQ ID NO: 128) | 5'-CAGGGACTTGAGTGGVKKGG A TGGATTTATCCTG -3' | Consensus |
| V$_H$ 67 (SEQ ID NO: 129) | 5'-GAAGTTCAAGGGCAGGNYCA CAATCACTGCAGAC -3' | Consensus |
| V$_H$ 55 (SEQ ID NO: 130) | 5'-GGATGGATTTATCCTGGAAA TGGTCATGCTCAGTACAATGA G -3' | Covariation |
| V$_L$ 3 (SEQ ID NO: 131) | 5'-GGTGGTAGTGACATTVNSATG ACCCAGTCTCCTAGC -3' | Consensus |

†Positions targeted for mutagenesis are indicated by underline. Ambiguous bases are abbreviated as follows: W = A or T, V = A or C or G, Y = C or T, S = C or G, M = A or C, N = A or C or G or T, R = A or G, K = G or T, B = C or G or T (J Bio/Chem. 261(1): 13-7 (1986)).

B. Thermal Challenge Assay

The activities of the conventional and engineered BHA10 scFvs were then compared in a thermal challenge assay which can be used to determine the temperature at which 50% of scFv molecules retain their antigen binding activity following a thermal challenge event. The numerical value corresponding to this temperature is referred to as the T$_{50}$ value and the units are in ° C. In this assay, the scFvs were subjected to a range of temperatures that encompass the thermal transition temperature of conventional BHA10 scFv.

E. coli strain W3110 (ATCC, Manassas, Va. Cat. #27325) was transformed with plasmids encoding conventional and engineered BHA10 scFvs under the control of an inducible ara C promoter. Transformants were grown overnight in expression media consisting of SB (Teknova, Half Moon Bay, Ca. Cat. #S0140) supplemented with 1% glycine, 1% Triton X100, 0.02% arabinose, and 50 µg/ml carbenicillin at either 37° C. or 32° C. Bacteria was pelleted by centrifugation and supernatants harvested for further treatment. Including glycine and Triton X-100 in the media resulted in the release of periplasmic contents (native E. coli protein and scFv) into the media. The presence of E. coli proteins in the supernatant is essential to the performance of this assay because the thermally denatured proteins act as a "sink", trapping transiently unfolded scFv molecules into irreversible inactive aggregates.

Each library was screened in duplicate using a thermal challenge assay with supernatant from one replicate subjected to treatment conditions and the second supernatant serving as untreated reference. Thermal challenge assays can be run at a single or range of temperatures for measuring stability. Thermocycler machines capable of generating stable thermal gradients are used for treating sample supernatants (iCycler, Bio-Rad, Gaithersburg, Md.).

The challenge temperature varied depending on the properties of the parental BHA10 scFv variant and was generally two to three degrees Celsius higher than the experimentally determined T$_{50}$ value. Frozen Master plates were thawed and used to inoculate deep-well microtiter plates containing 250 µl of expression media per well, and cultures grown overnight at 32° C. As a control, cultures containing the parental plasmid were grown under the same conditions and processed simultaneously as the library. Bacteria were pelleted in the deep-well plates by centrifugation at 2000 rpm (IEC model 8R, Thermo Electron, Waltham, Ma) for 30 minutes, and 100 µl of the supernatant was transferred to standard microtiter plates (Corning, Corning, N.Y., Cat. #3357). An aliquot of the supernatant was reserved for the reference DELFIA. For most libraries, the plates containing the remainder of the supernatants were sealed (Nalge Nunc, Rochester, N.Y., Cat. #235205) and placed in an incubator set to the appropriate challenge temperature (Echo Therm, Torrey Pines Scientific, San Marcos, Ca) for 90 minutes. For screens requiring multiple challenge temperatures (or for temperatures greater than 75° C.) the supernatants were transferred to 96-well PCR plates (Applied Biosystems, Foster City, Calif., Cat. #N801-560) and incubated for 90 minutes at the desired temperature.

After thermal challenge, the aggregated material was removed by centrifugation and soluble BHA10 scFv samples remaining in the treated, cleared supernatant were assayed for binding to cognate LTβR Ig antigen by DELFIA assay. 96-well plates (MaxiSorp, Nalge Nunc, Rochester, N.Y., Cat. #437111) were coated with fusion protein consisting of the ectodomain of the LTβ receptor (LTβR) fused to a human Fc region at 1 µg/ml in 0.1M sodium carbonate buffer, pH 9.5. Plates were coated overnight at 4° C., and blocked with DELFIA assay buffer (DAB, 10 mM Tris HCl, 150 mM NaCl, 20 µM EDTA, 0.5% BSA, 0.02% Tween 20, 0.01% $NaN_3$, pH 7.4) for one hour with shaking at room temperature. Plates were washed 3 times with DAB without BSA (Wash buffer), and test samples diluted in DAB were added to the plates in a final volume of 100 µl. The plates were incubated for one hour with shaking at room temperature, and then washed 3 times with Wash buffer to remove unbound and functionally inactivated scFv molecules. Bound BHA10 scFv was detected by addition of 100 µl per well of DAB containing 40 ng/ml of Eu-labeled anti-$His_6$ antibody (Perkin Elmer, Boston, Mass., Cat. #AD0109) and incubated at room temperature with shaking for one hour. The plates were washed 3 times with Wash buffer, and 100 µl of DELFIA enhancement solution (Perkin Elmer, Boston, Mass., Cat. #4001-0010) was added per well. Following incubation for 15 minutes, the plates were read using the Europium method on a Victor 2 (Perkin Elmer, Boston, Mass.).

Assay data was processed using Spotfire DecisionSite software (Spotfire, Somerville, Ma.) and expressed as the ratio of the DELFIA counts observed at challenge temperature to the reference temperature for each clone. Clones that reproducibly gave ratios greater than or equal to twice what was observed for the parental plasmid were considered hits. Plasmid DNAs from these positive clones were isolated by miniprep (Wizard Plus, Promega, Madison, Wis.) and retransformed back into E. coli W3110 for confirmation secondary thermal challenge assays.

For thermal gradients, the data was analyzed using Prism 4 software (GraphPad Software, San Diego, Calif.) using a sigmoidal dose response with variable slope as the model. The values obtained for the mid-point of the thermal denaturation curves are referred to as $T_{50}$ values, and are not construed as being equivalent to biophysically derived Tm values.

Figure 12:
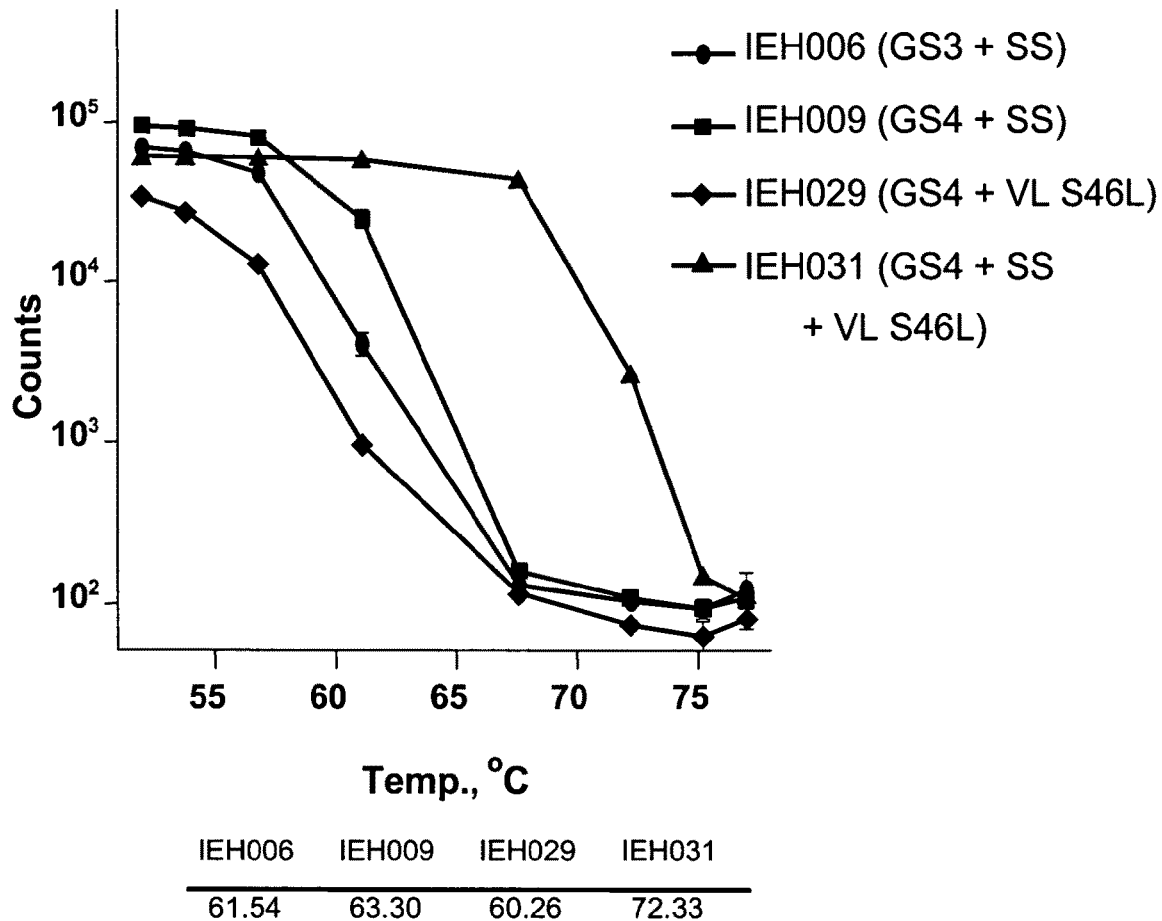
FIG. 12 depicts the results of a thermal challenge assay in which the effects of stabilizing BHA10 scFv mutations on thermal stability and the additivity of stabilizing mutations were assessed. (GS3 deonotes (G$_4$S)3 and GS4 denotes (G$_4$S) 4; SS denotes a disulfide bond).

Primary and confirmatory results from these assays are shown in Table 10. Several of the stabilized scFv molecules of the invention resulted in improvements in binding activity ($T_{50}$>49° C.) as compared with the conventional scFv. In particular, the $T_{50}$ values of BHA10 library position $V_L46$ scFv (S46L), library position $V_H16$ scFv (S16E and S16Q), and library positions $V_L49$: $V_L50$ scFv exhibited increases in thermal stability ranging from +3° C. to +12° C. relative to the conventional BHA10 scFv. stability ranging from +3° C. to +12° C. relative to the conventional BHA10 scFv. In addition, the $T_{50}$ values of BHA10 library position $V_L3$ scFv (Q3A, Q3G, Q3S, Q3V, and Q3D), library position $V_H67$ scFv (V67I and V67L), library position $V_H48$ scFv (M48I and M48G), library position $V_H20$ scFv (V20I) and library position $V_H101$ scFv (P101D) exhibited increases in thermal stability ranging from +4° C. to +18° C. relative to the conventional BHA10 scFv. One of the stabilizing mutations ($V_L$ K13E) serendipitously resulted from a PCR error. Incorporation of one of these stabilizing mutations into pIEH009 was found to further improve thermal stability and even exceed that of BHA10 Fab under these conditions (FIG. 12). Importantly, the non-covalent $V_L46$ mutation and $V_H55$ mutations derived from one or more of the four design methods ($V_L/V_H$ interface homology modeling, consensus scoring, computational modeling, and covariation analysis) resulted in an improvement in scFv thermal stability nearly approaching that observed with the disulfide mutations and validating the utility and novelty of these design tools.

FIG. 1B shows the amino acid sequences of conventional BHA10 scFv (SEQ ID NO: 4) and FIGS. 94A and B shows the amino acid sequence of stabilized BHA10 scFVs containing the S46L(VL) stabilizing mutation (SEQ ID NO: 137), and the V55G (VH) stabilizing mutation (SEQ ID NO: 138), respectively. The DNA sequence of wild-type BHA10 scFv (SEQ ID NO: 3) is depicted in FIG. 1A. The stabilizing mutation is indicated by the boxed residue. The leader sequence, gly/ser connecting peptide, and CH1 domain are indicating by the underlined, bolded, and italicized residues, respectively.

TABLE 10

BHA10 VH and VL library positions, library composition, and screening results.

| Position | Library | Hit Seq. Observed | $\Delta T_{50}$ ° C. |
| --- | --- | --- | --- |
| VL49 and 50 | 49 (Y or S) 50 (all AA's) | YT, YS, YR, YG, SR, SK | +3-4 |
| VH16 | Q, K, E, R, W, G, P, S, T, A | S16E S16Q | +8 +4 |
| VL46 | L | S46L | +10 |
| VH13 | na | K13E | +3 |
| VH101 | na | P101D | +18 |
| VH20 | F, M, L, I | V20I | +7 |
| VH48 | R, S, M, I, L, V, G | M48I M48G | +3-4 |
| VL3 | N, Q, K, H, E, D, R, W, G, P, S, T, A | Q3A, Q3S, Q3V, Q3D, Q3G, | +3-5 |
| VH55 | na | VH V55G | +12 |
| VH67 | T, P, I, L, V, A | V67I V67L | +5 +8 | na = not applicable

Table 11 shows the results of a comprehensive thermal stability analysis of the various individual and combined stabilizing mutations introduced into a conventional scFv. These results demonstrate that the improvements in activity are additive and that the methods described in this invention are capable of improving the thermal stability properties of scFvs even beyond that of native Fabs. Even in the absence of a covalent disulfide bond at positions $V_H44$-$V_L100$, stabilizing mutations were identified that upon combination exhibited increases in thermal stability ranging from +19° C. to +33° C. relative to the conventional BHA10 scFv.

TABLE 11

Characteristics of BHA10 constructs used to produce variant proteins and $T_{50}$ results from thermal challenge assay.

| Plasmid | Disulfide | Linker Length (aa) | Other Mutation | $T_{50}$ ° C. |
|---|---|---|---|---|
| pIEH003 | no | 15 | na | 49 |
| pIEH006 | VH44-VL100 | 15 | na | 59 |
| pXWU001 | Fab | na | Fab | 61 |
| pXWU002 | no | 20 | na | 51 |
| pXWU003 | no | 25 | na | 51 |
| pIEH009 | VH44-VL100 | 20 | na | 61 |
| pIEH029 | no | 20 | VL S46L | 61 |
| pIEH031 | VH44-VL100 | 20 | VL S46L | 71 |
| pIEH032 | no | 20 | VH S16E | 60 |
| pIEH034 | no | 20 | VH S16Q | 56 |
| pIEH058 | no | 20 | VH P101D | 67 |
| pIEH059 | no | 20 | VH V20I | 56 |
| pIEH060 | no | 20 | VH M48G | 54 |
| pIEH061 | no | 20 | VH M48I | 53 |
| pIEH062 | no | 20 | VL Q3A | 53 |
| pIEH063 | no | 20 | VL Q3S | 53 |
| pIEH065 | no | 20 | VL Q3V | 53 |
| pIEH066 | no | 20 | VL Q3D | 54 |
| pIEH067 | no | 20 | VL Q3G | 54 |
| pIEH068 | no | 20 | VH V67I | 55 |
| pIEH069 | no | 20 | VH V67L | 58 |
| pIEH070 | no | 20 | VH V55G | 64 |
| pIEH076 | no | 20 | VH S16E + VL S46L | 71 |
| pIEH078 | no | 20 | VH S16Q + VL S46L | 68 |
| pIEH080 | VH44-VL100 | 20 | VH S16E + VL S46L | 75 |
| pIEH081 | VH44-VL100 | 20 | VH S16Q + VL S46L | 72 |
| pIEH087 | no | 20 | VH S16E, V55G + VL S46L | 75 |
| pIEH094 | no | 20 | VH S16E, V55G, P101D + VL S46L | 82 | na = not applicable
aa = amino acids

Summary

Three stabilizing mutations ($V_L$_S46L, $V_H$_V55G, and $V_H$_P101D) were experimentally validated by thermal challenge ($T_{50}$) assay.

Figure 51A:
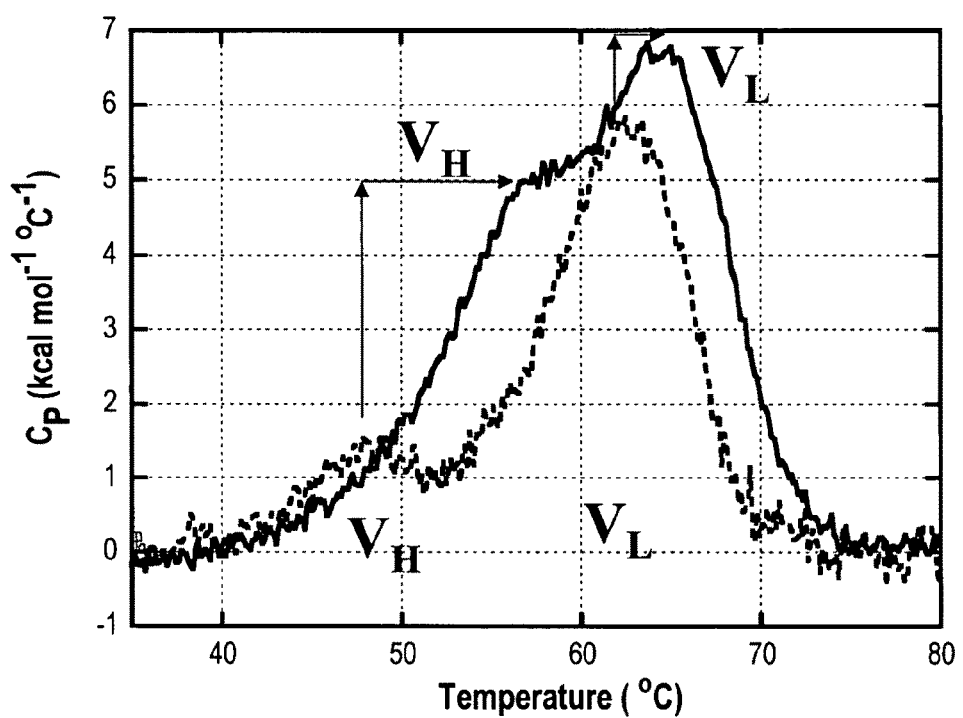
FIG. 51 depicts DSC curves of the wild-type VH-(GS)-4-VL-6His BHA10 scFv (grey line) versus BH10 scFvs containing the VL S46L (black line) (FIG. 51A) and VH V55G (black line) (FIG. 51B) stabilizing mutations.
Figure 51B:
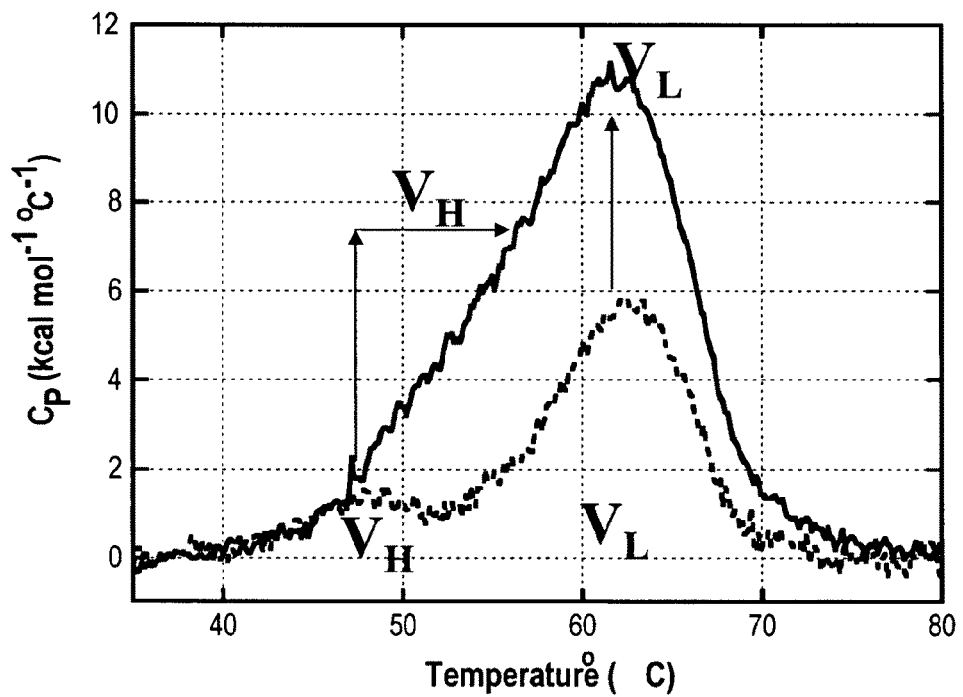

Both of the $V_L$_S46L and $V_H$_V55G mutations were predicted to be stabilizing to the individual VH and VL domains based on the covariation analyses described in Example 3 supra. As depicted in FIGS. 50A and B, both of these mutations led to significant increases in the $T_{50}$ of the BHA10 scFv. In particular, the VL_S46L mutation stabilizes the scFv by ~7-8° C. while the VH_V55G mutation stabilizes the scFv by ~12° C. Both of these mutations also significantly shrink the $T_M$ gap between $V_H$ and $V_L$ as determined by DSC (see FIG. 51). The DSC data shows that both mutations lead to significant increases in both the $T_M$ (midpoint of the thermal unfolding transitions) of both of the VH and VL domains and in the calorimetric enthalpy (i.e. area under the curve) for the scFv. Increases in these values provide experimental validation that these predicted stabilizing mutations are in fact stabilizing to the scFv. Furthermore, since these two mutations stabilize both $V_H$ and $V_L$ domains simultaneously, they are likely important in building cooperativity between the $V_H$ and $V_L$ domains. Accordingly, it is expected that strengthening the interface between $V_H$ and $V_L$ may not only help increase stability, but reduce the tendency to form aggregates as well.

Figure 52:
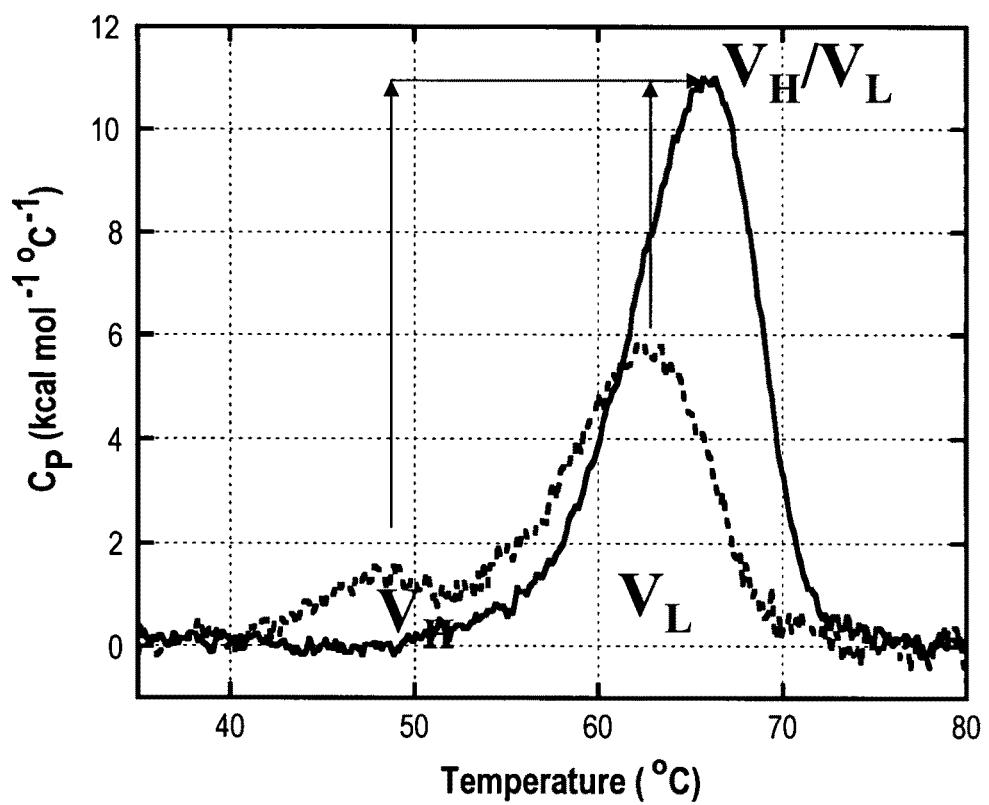
FIG. 52 depicts DSC curves of the wild-type VH-(GS)-4-VL-6His BHA10 scFv (grey line) versus a BH10 scFv containing the VH_P101D stabilizing mutation (black line).

The $V_L$_S46L stabilizing mutation and a third stabilizing mutation (VH_P101D) were also predicted to be stabilizing based on VH/VL interface homology modeling described in Example 4 supra. The VH_P101D stabilizing mutation stabilized the scFv by ~15° C. as measured by thermal challenge assay (FIG. 50C). In addition, DSC (see FIG. 52) shows that this stabilizing mutation leads to significant increases in $T_M$ both of the VH and VL domains and in the calorimetric enthalpy, indicating that this mutation is also likely cooperatively stabilize the scFv as a whole via the VH/VL interface.

Example 6

Biophysical Characterization of Stabilized BHA10 scFvs Comprising Stabilizing Mutations V region gene sequences from various plasmids listed in Table 11 were subcloned into a modified *E. coli* expression vector to drive recombinant protein expression under the control of an inducible ara C promoter. Variant BHA10 scFvs were expressed and purified using methods described above. An apparent cleavage site at the N-terminus of the $V_L$ domain led to a low level of $V_L$ in most scFv preparations as judged by SDS-Page analysis (FIG. 53).

The hydrodynamic properties of each scFv were investigated by size exclusion HPLC (Agilent Technologies) with static light scattering and refractive index detectors (MiniDAWN/ReX, Wyatt Technology). Each scFv was found to be predominantly monomeric; however, a few of the scFvs, including the wild-type (unstabilized) scFv, exhibited a low level of dimeric material (Table 12). None of the purified scFvs had detectable levels of oligomers larger than dimer.

TABLE 12

SEC/Light Scattering Results of scFvs

| Sample | Expressed Yield (mg/L)[a] | % Monomer | % Dimer | % Larger Aggregates |
|---|---|---|---|---|
| WT | n.d.[b] | 87 | 13 | 0 |
| GS4 | 0.6 ± 0.1 | 97 | 3 | 0 |
| 009 (ss) | n.d. | 99 | 1[c] | 0 |
| 072 $V_L$_S46L | 2.0 | 85 | 15 | 0 |
| 073 $V_L$_S46L + ss | *0.15 | 78 | 22 | 0 |
| 074 $V_H$_S16E | 2.4 ± 1.7 | 94 | 6 | 0 |
| 075 $V_H$_S16Q | 1.1 ± 0.5 | 96 | 4 | 0 |
| 076 $V_L$_S46L + $V_H$_S16E | 1.8 ± 0.4 | 80 | 20 | 0 |
| 077 $V_H$_P101D | 2.5 | 93 | 7 | 0 |
| 078 $V_L$_S46L + $V_H$_S16Q | 1.0 | 85 | 15 | 0 |
| 079 $V_H$_V55G | 2.0 | 92 | 8 | 0 |
| 080 $V_L$_S46L + $V_H$_S16E + ss | *0.21 | 76 | 24 | 0 |
| 087 $V_L$_S46L + $V_H$_S16E, V55G | 2.8 | 76 | 24 | 0 |
| 094 $V_L$_S46L + $V_H$_S16E, V55G, P101D | 2.5 | 79 | 21 | 0 |

[a]Proteins without standard error were expressed one time.

[b]n.d., not determined.

[c]These values were determined AFTER preparative SEC was performed to reduce aggregates The ultimate goal of the experiment was to investigate whether the designed mutations enhance stability and lead to a lower propensity for aggregation. The thermostability of each scFv was assessed using two separate methods. First, thermal unfolding of the scFvs was analyzed using DSC (FIG. 54A). Secondly, the thermostability of each scFv was investigated by heating the proteins in the presence of a fluorescent hydrophobic dye, 1-anilino-8-sulfonate (ANS, FIG. 54B). ANS generally binds to partially unfolded proteins or heat-denatured proteins in compact unfolded states. Upon association with exposed hydrophobic surface areas, the fluorescence of ANS increases significantly presumably due to sequestration of the quenching affects of solvent.

The temperature dependent ANS curves were fitted to a two-state protein unfolding transition as described below.

The buffer was PBS and the concentration of scFv used in every experiment was 750 nM. Fluorecence measurements were performed on a JASCO model 812 Circular Dichroism spectropolarimeter equipped with a peltier heating device and external water bath. Fluorescence was collected using an accessory containing a photomultiplier tube perpendicular to the light path. The accessory is equipped with an adjustable monochrometer set to 480 nm. The sensitivity was set to 600V. Heating was performed at a continuous rate of 120° C./min. The excitation monochrometer was set to 370 nm.

Thermal unfolding of every scFv in this study led to an increase in ANS fluorescence. The midpoint of thermal unfolding (i.e. the $T_M$) of each scFv protein domain was determined using DSC by fitting each unfolding peak to the Gibbs-Helmholtz equation using the Origin 7.0 software provided by the manufacturer (MicroCal, Inc). $T_M$s were also derived using ANS fluorescence by incorporation of the Gibbs-Helmholtz equation into the non-linear curve fitting routine in KaleighdaGraph™:

$$\Delta G_U°(T) = \Delta H_U°(T) - T\Delta S_U°(T), \quad (1)$$

where $\Delta G_U°(T)$ is the temperature-dependent change in Gibbs free energy upon unfolding, $\Delta H_U°(T)$ is the enthalpy change associated with unfolding, and $\Delta S_U°(T)$ is the entropy associated with unfolded. The equation can be expanded to:

$$\Delta G_U°(T) = \Delta H_U°\left(1 - \frac{T}{T_M}\right) - \Delta C_P°\left[(T_M - T) + T\ln\left(\frac{T}{T_M}\right)\right], \quad (2)$$

where $T_M$ is the midpoint of the unfolding curve and $\Delta C_P°$ is the change in the heat capacity between the folded and unfolded states. This equation can be used to derive the temperature-dependence of the ANS-fluorescence intensity by making the assumption that the fluorescence intensity is the sum of the intrinsic ANS fluorescence in the presence of folded and unfolded scFv, $$i_T(T) = i_F f_F + i_U f_U, \quad (3)$$

where $i_T(T)$ is the temperature-dependent total fluorescence signal, $i_F$ and $i_U$ are the fluorescence intensities of the folded and unfolded states, respectively, and $f_F$ and $f_U$ are the fractions of folded and unfolded scFv, respectively at the given temperature. The fractions folded are related to the equilibrium unfolding constant and free energy of unfolding:

$$K_U(T) = \frac{f_U}{f_F} = \exp\left(\frac{-\Delta G_U°(T)}{RT}\right). \quad (4)$$

By factoring $K_U(T)$ and $\Delta G_U°(T)$ into equation (3) and assuming that the fluorescence intensities of ANS in the presence of folded and unfolded scFv are linearly dependent on the temperature (i.e. $i_F = i_1 + i_2 T$ and $i_U = i_3 + i_4 T$) the following equation was obtained:

$$i_T(T) = \frac{i_F + i_U K_U}{1 + K_U} = \frac{i_1 + i_2(T) + (i_3 + i_4 T)\exp\left[-\frac{\Delta G_U°(T)}{RT}\right]}{1 + \exp\left[-\frac{\Delta G_U°(T)}{RT}\right]}. \quad (5)$$

To obtain the final equation utilized to fit the data, the relationship for $\Delta G_U°(T)$ in equation (2) is substituted into equation (5) assuming $\Delta C_P°$ is independent of temperature and proportional to the difference in solvent exposed surface area between the folded and unfolded states (Haynie & Friere, *Proteins: Struct. Funct. Genet.* 16: 115-140, (1993); Myers et al., Protein Sci. 4: 2138-2148 (1995)).

The thermostability measurements for all the scFvs derived from DSC and ANS-binding experiments were comparable. Unfolding of each scFv was irreversible; therefore, aggregation had an affect on the absolute $T_M$ measured by DSC or ANS-binding. Since the two techniques heated the samples differently and at different rates, the $T_M$s were not expected to be identical across the experimental formats (Sánchez-Ruiz et al., *Biochemistry*, 27:1648-1652 (1988)). However, the trend observed for each experimental technique was identical (see Table 13). The DSC experiments readily discriminated between the $V_H$ and $V_L$ unfolding transitions. The ANS-binding experiments were not capable of accurately discriminating 2 transitions (i.e. $V_H$ vs. $V_L$ unfolding); thus, only the apparent $T_M$ was provided for the ANS-binding experiments. The apparent $T_M$ observed by ANS-binding appeared to correlate well with the $T_M$ of the last domain to unfold, either $V_H$ or $V_L$ depending on the mutation, as determined by DSC. Due to aggregation of unfolded material in both assay formats, the $T_M$s were used as a guide to rank order the stability enhancements afforded by each mutation without additional interpretation of scFv free-energies of unfolding, etc.

TABLE 13

Thermostability measurements of each scFv.

| Construct | $V_H$ $T_M$ (° C.) DSC) | $V_L$ $T_M$ (° C.) DSC) | $V_H$ $T_M$ (° C.) ANS) | scFv $T_M$ (° C.) DSC)[a] | scFv $K_D$ (M) * $10^{-9}$ (Biacore) |
|---|---|---|---|---|---|
| Wild-type, $(G_4S)*3$ linker[b] | 55.4 | 68.7 | 65.6 | — | 2.7 |
| Wild-type, $(G_4S)*4$ linker | 57.7 | 67.4 | 67.0 | — | 2.1 |
| $V_H$_S16E | 60.7 | 68.1 | 66, 76 | — | 2.0 |
| $V_H$_S16Q | 59.4 | 68.4 | 69[c] | — | 1.9 |
| $V_L$_S46L | 65.6 | 74.2 | 71.0 | — | 4.0 |
| $V_H$_V55G | — | — | 75.4 | 68.4 | 2.2 |
| $V_H$_P101D | — | — | — | 71.9 | 5.2 |
| $V_H$_S16E, $V_L$_S46L | 71[d] | 74.5[d] | — | 72.2 | 3.4 |
| $V_H$_S16Q, $V_L$_S46L | 67.9[d] | 74.9[d] | 75.4 | — | 4.2 |
| $V_H$_S16E, $V_H$_V55G, $V_L$_S46L | — | — | 79.3 | 77.7 | 3.8 |
| $V_H$_S16E, $V_H$_V55G, $V_H$_P101D, $V_L$_S46L | 84.1 | 77 | 81.3 | — | n.d. |
| Wild-type, $(G_4S)*4$ linker w/ $V_H$44/$V_L$100 disulfide | 61 | 68 | n.d. | — | 3.3 |
| $V_H$_S16E, $V_L$_S46L | 69 | 77 | n.d. | — | 4.0 |
| $V_H$_S16Q, $V_L$_S46L | n.d. | n.d. | n.d. | n.d. | 3.3 |

[a]These particular mutations led to single, cooperative $V_H/V_L$ unfolding events.
[b]All subsequent scFvs were constructed with the $(G_4S)*4$ 20 amino acid linker.
[c]Multiple transitions complicated analysis.
[d]Unable to discriminate $V_H$ vs. $V_L$.

Summary

Figure 53:
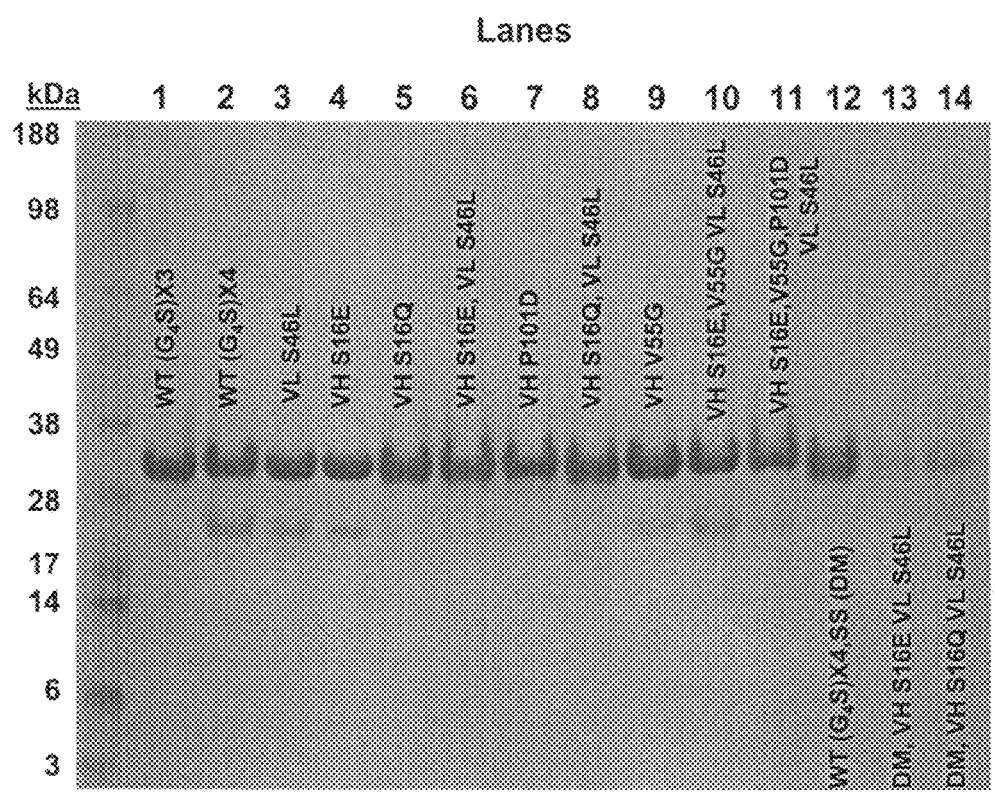
FIG. 53 depicts an SDS-PAGE analysis of the wild-type ("WT (G4S)X3") and stabilized mutant scFvs. All mutant scFvs contain a gly-ser connecting peptide of the formula $(Gly_4Ser)_4$ between the N-terminal VH and C-terminal VL ("(G4S)X4"). The identity of the scFv in each lane is depicted. Lanes 12-14 contain BHA10 scFv having a disulfide bond between VH44 and VL100. The (G4S)X4/disulfide stabilized scFv are denoted 'DM' for 'double mutant'. The final two lanes include designed mutations that also stabilized disulfide linked scFvs.
Figure 54A:
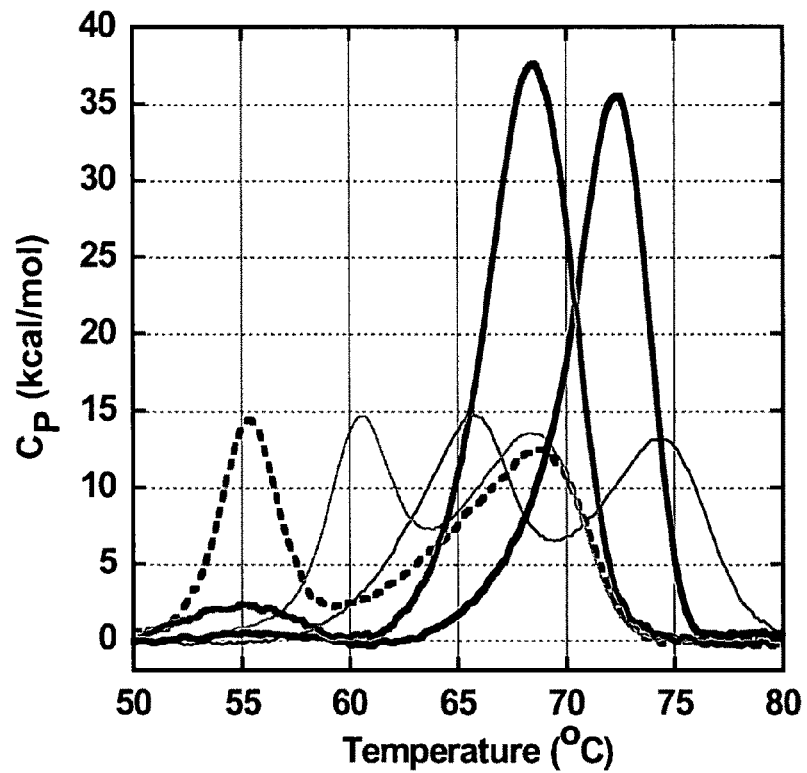
FIG. 54A depicts DSC curves of the wild-type ("VH-(GS)-4-VL-6His") BHA10 scFv (dashed line), VH S16E mutant scFv (thin grey line), VL S46L mutant scFv (thin black line), VH V55G mutant scFv (thick grey line), and VH P101D mutant scFv (thick black line).
Figure 54B:
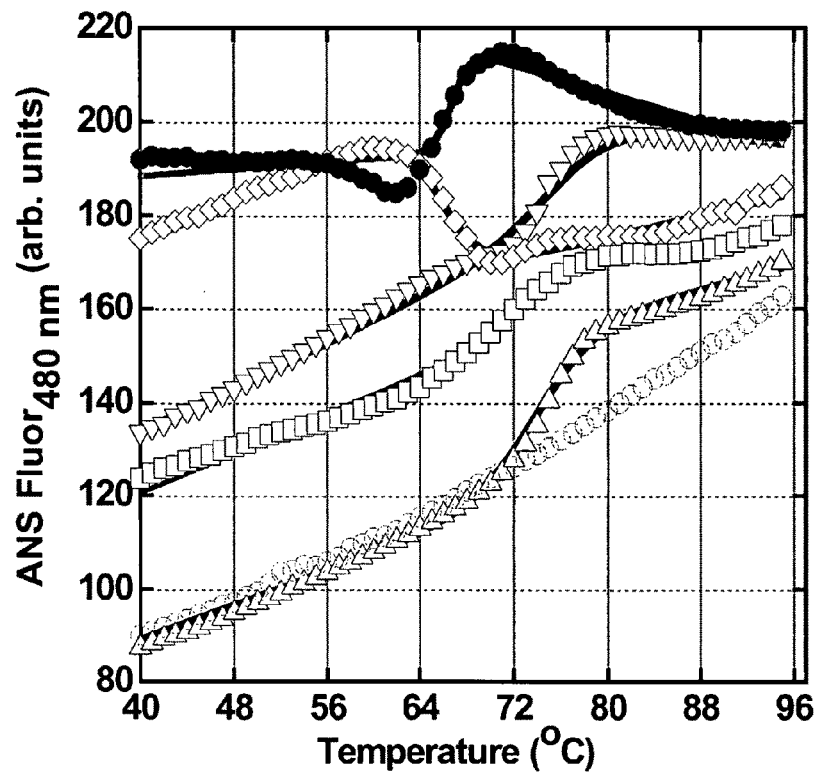
FIG. 54B depicts temperature dependent fluorescence of 10 mM ANS in PBS (open circles) or in the presence of the wild-type ("VH-(GS)-4-VL-6His") BHA10 scFv (closed grey circles), VH S16E mutant scFv (diamonds), VL S46L mutant scFv (squares), VH V55G mutant scFv (inverted triangles), and VH P101D mutant scFv (triangles). The lines through the curves are the fits to a two-state unfolding model.
Figure 55A:
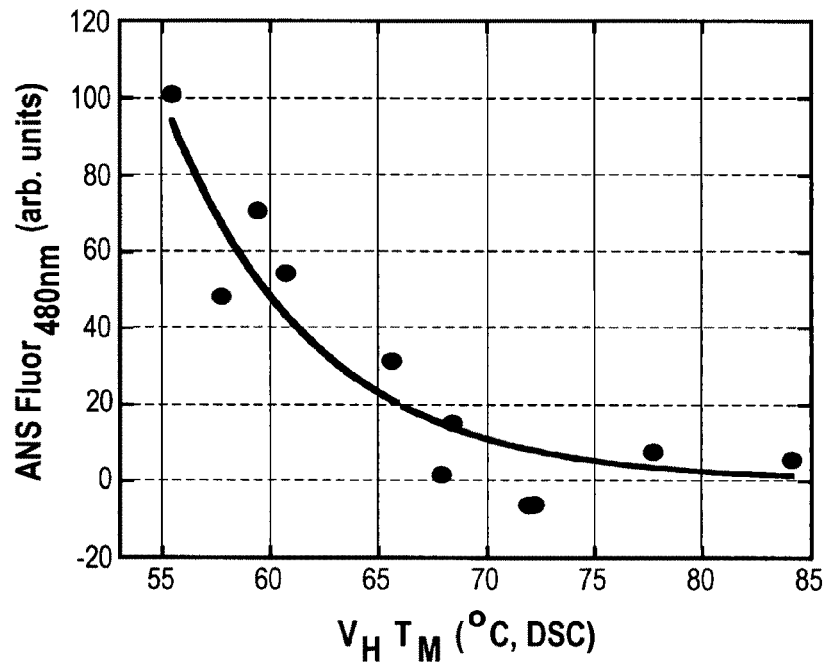
FIG. 55 depicts ANS fluorescence at 15° C. in the presence of wild-type and mutant scFvs. The ANS fluorescence induced by each scFv is plotted against the TM of the VH domain of the same scFv as determined by DSC (FIG. 55A) and the temperature-dependent increase in ANS fluorescence due to the unfolding transition of each scFv (FIG. 55B).
Figure 55B:
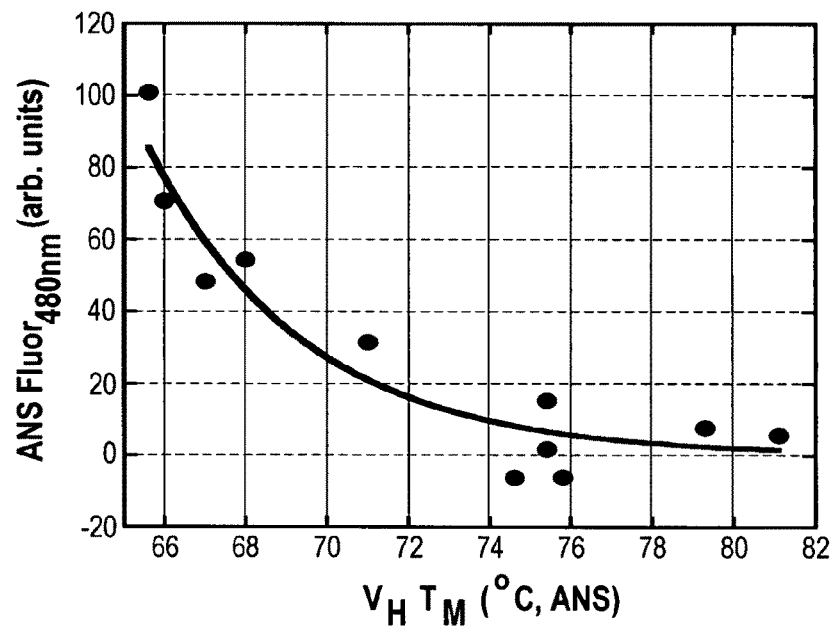

All designed single mutations picked from the library screens: $V_H$ S16E, S16Q, V55G, P101D, and $V_L$ S46L significantly stabilized the $V_H$ domain and in some instances, the $V_L$ domain as well (FIG. 53). The rationale behind testing these positions for stability enhancements often came from multiple forms of analysis. Consensus methods predicted that all of the mutations $V_H$ S16E, S16Q, V55G, P101D and $V_L$ S46L would stabilize the BHA10 scFv (Example 3). However, $V_H$ V55G and P101D (incidentally, the two most stabilizing mutations) are positioned within CDR2 and CDR3 of $V_H$, respectively, and were not considered for mutagenesis until further predictive evidence was compiled that suggested that mutation at these two positions could lead to stabilizing events. Both $V_H$ V55G and $V_L$ S46L were also predicted to be stabilizing based on Covariation Analyses. Finally, $V_H$ P101D and $V_L$ S46L were predicted to be potentially stabilizing to the $V_H/V_L$ interface based on the interface composition of highly stable human antibodies (Example 3).

Single mutations at the $V_H/V_L$ interface increased the stability of both domains, while $V_H$ mutations outside the interface only stabilized the $V_H$ domain itself. $V_H$ S16E, S16Q, and V55G were outside the interface and increased the apparent $T_M$ of the BHA10 $V_H$ by 3, 2, and 11° C., respectively. The $V_L$ stability was relatively unaffected by these mutations. $V_H$ V55G mutation appeared to increase the stability of the $V_H$ to match that of the $V_L$ domain, without leading to detectable increases in $V_L$ stability. Both mutations at the interface, $V_H$ P101D and $V_L$ S46L significantly increased the stability of both domains. The P101D mutation in particular led to the fully cooperative unfolding of the $V_H$ and $V_L$ domains suggesting that the interface and cooperativity of folding between $V_H$ and $V_L$ was significantly strengthened. Thus, mutations at the $V_H/V_L$ interface may provide the most effective means of forming a stabilized Fv region and provide a rationale for prioritizing stability designs to the $V_H/V_L$ interface of scFvs over designs directed towards at residues outside the Fv interface.

Combining $V_H$ mutations eventually led to a disconnect between the cooperativity of $V_H/V_L$ unfolding (Table 13). As the $V_H$ $T_M$ climbed above 75° C. (the result of combinations of $V_H$ mutations), the $T_M$ of the $V_L$ began to move towards lower temperatures. This suggests hyperstabilization of the $V_H$ domain without building in compensating mutations within the $V_L$ domain may lead to decreased folding cooperativity and a weakened interaction between the two domains. While the $T_M$s of the $V_H$ and $V_L$ domains (including the $T_M$ of the wild-type BHA10 scFv) were often quite different, evidence that mutations at the interface between the two domains could stabilize both domains simultaneously suggests that the two domains are interacting at some level with one another—although the apparent affinity between the isolated domains is not expected to be extremely high, except perhaps in the $V_H$ P101D stabilized variant (Brandts & Lin, *Biochemistry,* 29:6927-6940, (1990)).

Increasing the stability of the scFv led to decreased intrinsic binding of the hydrophobic, fluorescent dye ANS at ambient temperature (15° C., FIG. 55). The wild-type scFv binds weakly to ANS suggesting that the protein may permanently or transiently expose hydrophobic surface area to solvent. Stabilized scFvs appeared to completely lose the ability to bind ANS under ambient conditions—the fluorescence of ANS in the presence of the most stabilized scFvs was no greater than that of ANS alone in solvent. Plots of $V_{H}\_T_M$ (measured by DSC or temperature-dependent ANS-binding experiments) vs. ANS-fluorescence in the presence of folded protein at 15° C. demonstrate that scFv-dependent ANS fluorescence decreases as scFv stability increases (FIG. 55). Reduction of ANS-binding by scFv stabilization may indicate that less hydrophobic surface area gets exposed to solvent and that stabilized scFvs may have a lower intrinsic propensity for aggregation.

$K_D$ measurements of various individual and combined stabilizing BHA10 scFv mutations were performed using surface plasmon resonance (SPR) on a Biacore 3000 instrument. Table 13 shows the results of the Biacore affinity assay. The binding affinity of the variant BHA10 scFvs ranged from 1X-2.5X of the parent BHA10 scFv.

Example 7

Production of Stabilized Bispecific "Hercules" Antibodies

Both conventional BHA10 scFv and the stabilized BHA10 scFvs of the invention were used to construct a panel of bispecific antibodies referred to as "Hercules". Hercules bispecific antibodies comprise a fusion of chimeric 14A2 IgG antibody that binds to TRAIL R2 receptor with a BHA10 scFv that binds to LTβR. The Hercules antibodies were constructed both as N-terminal and C-terminal BHA10 scFv fusions (see FIG. 13). N-terminal scFv fusions can be engineered as light chain and/or heavy chain fusions ("$N_L$-Hercules" or "$N_H$-Hercules", respectively). The decision as to which amino terminal V region (heavy or light) is selected for adjoining the scFv is primarily driven by which chain is thought to tolerate a fused scFv which is capable of recognizing the first target antigen while not appreciably interfering with the binding of the Fab domain to the second target antigen.

It is also possible using the methods described in this invention to engineer tetravalent or bispecific antibodies consisting solely of stabilized scFvs fused directly to antibody hinge regions or to CH2 or CH3 domains as depicted, for example, in FIGS. 42-49. Said antibodies may comprise full-length Fc regions (see, for example, FIG. 46) or CH2-domain deleted Fc regions (see, for example, FIG. 42). In other exemplary embodiments, two or more stabilized scFv domains may be fused to the same terminus of a heavy or light chain (see, for example, FIG. 43).

A. Construction of "$N_H$-Hercules" with BHA10 Conventional, $(G_4S)_4$, $V_H44$:$V_L100$ and $V_H44$:V 100/$(Gly_4Ser)_4$ scFvs Four anti-LTβR (BHA10)×anti-TRAIL R2 (chi14A2) bispecific antibody designs were based on appending the conventional and variant BHA10 scFvs to the amino terminus of the anti-TRAIL R2 antibody heavy chain. The BHA10 scFvs DNAs described in Example 3 were used to construct a panel of $N_H$-Hercules bispecific antibodies by PCR amplification using the oligonucleotide primers described in Table 14. A $(Gly_4Ser)_5$ linker was used to connect the BHA10 scFvs to the mature amino terminus of chi heavy chain. The forward 5' VH PCR primer (scFvBHA10-F1) includes an Mlu I restriction endonuclease site (underlined sequence) for cloning followed by sequence encoding the last three amino acids of the heavy chain signal peptide and the amino terminus of BHA10 VH. Two reverse 3' PCR primers were used to generate the PCR products with internal reverse primer XWU005-R encoding the carboxyl terminus of BHA10 VL followed by the $(Gly_4Ser)_5$ linker, and reverse primer scFvBHA10-R1 encoding a partial anti-TRAIL R2 VH region and a Bgl II site (underlined sequence) for cloning.

TABLE 14

Oligonucleotides for PCR amplification of N- Hercules with conventional, $(Gly_4Ser)_4$, $V_H44$: $V_L100$ and $V_H44$: $V_L100/(Gly_4Ser)_4$ BHA10 scFvs

| | |
|---|---|
| scFvBHA10-F1 (SEQ ID NO: 134) | 5'-AGAGAGACGCGTGTCCTGTCCCAGGTCCAACTGGTGCAG-3' |

TABLE 14-continued Oligonucleotides for PCR amplification
of N- Hercules with conventional,
(Gly₄Ser)₄, V_H44: V_L100 and V_H44:
V_L100/(Gly₄Ser)₄ BHA10 scFvs

| | |
|---|---|
| XWU005-R<br>(SEQ ID<br>NO: 135) | 5'-<br>AGCCACCTCCCCCCGATCCACCGCCCCTGAACCGCCCC<br>CTCCAGAGCCCCCTCCACCGGACCCTCCACCGCCTTTGA<br>TCTCCACCTTG-3' |
| scFvBHA10-<br>R1<br>(SEQ ID<br>NO: 136) | 5'-<br>AGAGAG<u>AGATCTT</u>GACTGTCTCTCCAGGCTTCTTCAGCT<br>CAGGTCCAGACTGCACCAACTGGATCTGGGAGCCACCT<br>CCCCCCGATCCAC-3' |

Figure 14A:
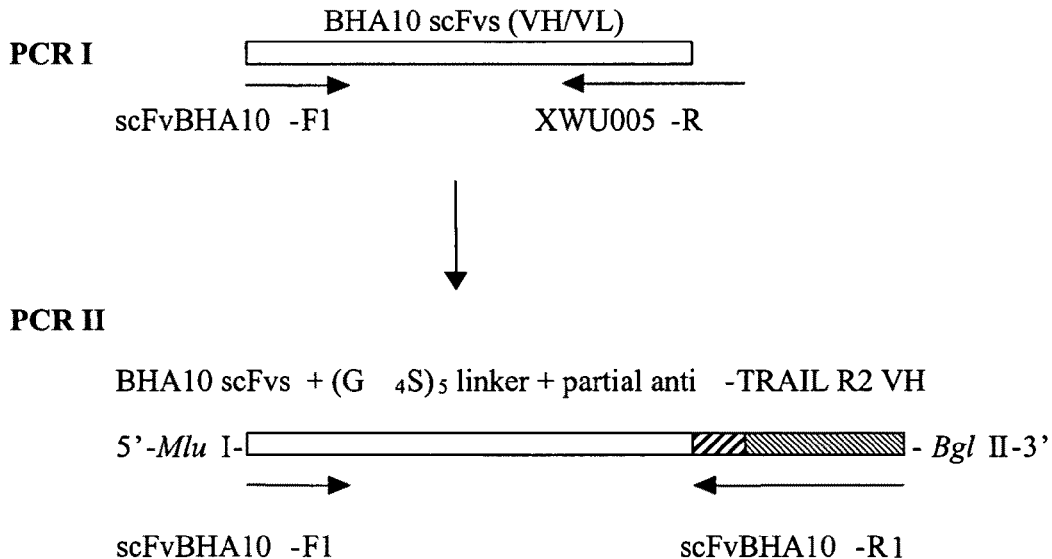
FIG. 14 is a schematic depicting the sequential PCR reactions used for fusing conventional and engineered BHA10 scFvs to the amino terminus (FIG. 14A) or carboxyl terminus (FIG. 14B) of a 14A2 heavy chain.

The BHA10 scFv+(Gly₄Ser)₅ linker+partial anti-TRAIL R2 VH gene sequences were amplified in two sequential PCR reactions through the common overlapping sequences encoding the (Gly₄Ser)₅ linker as represented in FIG. 14A to prepare conventional BHA10 scFv from plasmid DNA pXWU034, BHA10 scFv (Gly₄Ser)₄ from plasmid pXWU002, BHA10 scFv V_H44:V_L100 from plasmid pIEH006, and BHA10 scFv V_H44:V_L100/(Gly₄Ser)₄ from plasmid pIEH009. The PCR products from the panel of amplified BHA10 scFvs were purified by agarose gel electrophoresis using the Millipore Ultrafree-DA extraction kit according to manufacturer's instructions (Millipore; Bedford, Mass.). The purified PCR products were digested with Mlu I/Bgl II restriction endonucleases and ligated into an MluI/Bgl II digested, pN5KG1 vector containing the chi14A2 IgG1 previously modified to remove an internal Bgl II site present in the chi14A2 IgG1 coding sequence. The mammalian expression vector pN5KG1 contains a translation-impaired, modified (intron-containing) neomycin phosphotransferase gene to select for transcriptionally active integration events, and a murine dihydrofolate reductase gene to permit amplification with methotrexate (Barnett, et al., Antibody Expression and Engineering. (Imanaka, H. Y. W. a. T., ed), pp. 27-40, Oxford University Press, New York, N.Y., (1995)).

The resulting panel of constructs form fusion proteins of the variant BHA10 scFvs to the amino terminus of the anti-TRAIL R2 antibody VH domain through the 25 amino acid (Gly₄Ser)₅ linker. Fusion of the conventional BHA10 scFv gene sequence to the amino terminus of the anti-TRAIL R2 antibody heavy chain gene sequence produced plasmid pXWU005. Fusion of BHA10 scFv (Gly₄Ser)₄ gene sequence to the amino terminus of the anti-TRAIL R2 antibody heavy chain gene sequence produced plasmid pXWU026. Fusion of BHA10 scFv V_H44:V_L100 gene sequence to the amino terminus of the anti-TRAIL R2 antibody heavy chain gene sequence produced plasmid pXWU027. Fusion of BHA10 scFv V_H44:V_L100/(Gly₄Ser)₄ gene sequence to the amino terminus of the anti-TRAIL R2 antibody heavy chain gene sequence produced plasmid pXWU028. The ligation mixtures were used to transform *E. coli* strain TOP 10 competent cells (Invitrogen Corporation, Carlsbad, Calif.). *E. coli* colonies transformed to ampicillin drug resistance were screened for presence of inserts. DNA sequence analysis confirmed the correct sequence of the final constructs.

The chimeric 14A2 light chain used is common among all the N- and C-Hercules bispecific antibodies and the DNA (SEQ ID NO:28) and amino acid sequences (SEQ ID NO:29) are shown in FIGS. 15A and 15B. The chimeric 14A2 light chain is expressed with a signal peptide at the N-terminus having the following DNA and amino acid sequences:

(SEQ ID NO: 59)
ATGGCCTGGACTCCTCTCTTCTTCTTCTTTGTTCTTCATTGCTCAGGGT

CTTTCTCC (SEQ ID NO: 60)
MAWTPLFFFFVLHCSGSFS

The heavy chain DNA (SEQ ID NO:30) and amino acid sequences (SEQ ID NO:31) for conventional BHA10 scFv N_H-Hercules are shown in FIGS. 16 and 17, respectively. The heavy chain DNA (SEQ ID NO:32) and amino acid (SEQ ID NO:33) sequence for BHA10 scFv (Gly₄Ser)₄ N_H-Hercules are shown in FIGS. 18 and 19, respectively. Heavy chain DNA (SEQ ID NO:34) and amino acid (SEQ ID NO:35) sequences for BHA10 scFv V_H44:V_L100 N-Hercules are shown in FIGS. 20 and 21, respectively. Heavy chain DNA (SEQ ID NO:36) and amino acid (SEQ ID NO:37) sequences for BHA10 scFv V_H44:V_L100/(Gly₄Ser)₄ N-Hercules are shown in FIGS. 22 and 23, respectively. Each of the heavy chains was expressed with a signal peptide at the N-terminus having the following DNA and amino acid sequences:

(SEQ ID NO: 61)
ATGGGTTGGAGCCTCATCTTGCTCTTCCTTGTCGCTGTTGCTACGCGT

GTCCTGTCC (SEQ ID NO: 62)
MGWSLILLFLVAVATRVLS

B Construction of C-scFv "Hercules" with BHA10 Conventional, (G₄S)₄, V_H44:V_L100 and V_H44:V_L100/(Gly₄Ser)₄ scFvs Four anti-LTβR (BHA10)×anti-TRAIL R2 (chi14A2) bispecific antibody designs were based on appending the conventional and variant BHA10 scFvs to the carboxyl terminus of the anti-TRAIL R2 antibody heavy chain. The BHA10 scFvs DNAs described in Example 3 were used to construct a panel of C-Hercules bispecific antibodies by PCR amplification using the oligonucleotide primers described in Table 15. A Ser(Gly₄Ser)₃ linker was used to connect the BHA10 scFvs to the carboxyl terminus of chi14A2 heavy chain. The forward 5' VH PCR primer (XWU006-F1) includes a BamHI restriction endonuclease site (underlined sequence) for cloning followed by sequence encoding a portion of the Ser(Gly₄Ser)₃ linker peptide and the amino terminus of BHA10 VH. The reverse 3' VL PCR primer (XWU006-R1) primes BHA10 scFv light chain and includes a stop codon followed by a BamHI site (underlined sequence) for cloning. Forward 5' internal overlapping PCR primer (XWU006-F2) includes sequence encoding the (Gly₄Ser)₃ linker and contains a silent mutation indicated in bold type. Reverse 3' internal overlapping PCR primer (XWU006-R2) includes sequence encoding the (Gly₄Ser)₃ linker and contains a silent mutation indicated in bold type to remove a BamHI site located at BHA10 scFv (Gly₄Ser)₃ linker region.

TABLE 15

Oligonucleotides for PCR amplification of C-Hercules with BHA10 conventional, (G₄S)₄, V_H44: V_L100, and V_H44: V_L100/(Gly₄Ser)₄ scFvs.

| | |
|---|---|
| XWU006-F1<br>(SEQ ID<br>NO: 38) | 5'-<br>GGGGGT<u>GGATCC</u>GGTGGAGGGGGCTCCGGCGGTGGCGG<br>GTCCCAGGTCCAACTGGTGCAGTCTG -3' |

TABLE 15-continued

Oligonucleotides for PCR amplification of C-Hercules with BHA10 conventional, (G₄S)₄, V_H44: V_L100, and V_H44: V_L100/(Gly₄Ser)₄ scFvs.

XWU006-F2   5'- TGGGGGCGGCGGGTCCGGTGGTGGTGGTAG -3'
(SEQ ID
NO: 39)

XWU006-R2   5'- TACCACCACCACCGGACCCGCCGCCCCCAG -3'
(SEQ ID
NO: 40)

XWU006-R1   5'- GTTAACGGATCCTCATTTGATCTCCACCTTGG -3'
(SEQ ID
NO: 41)

Figure 14B:
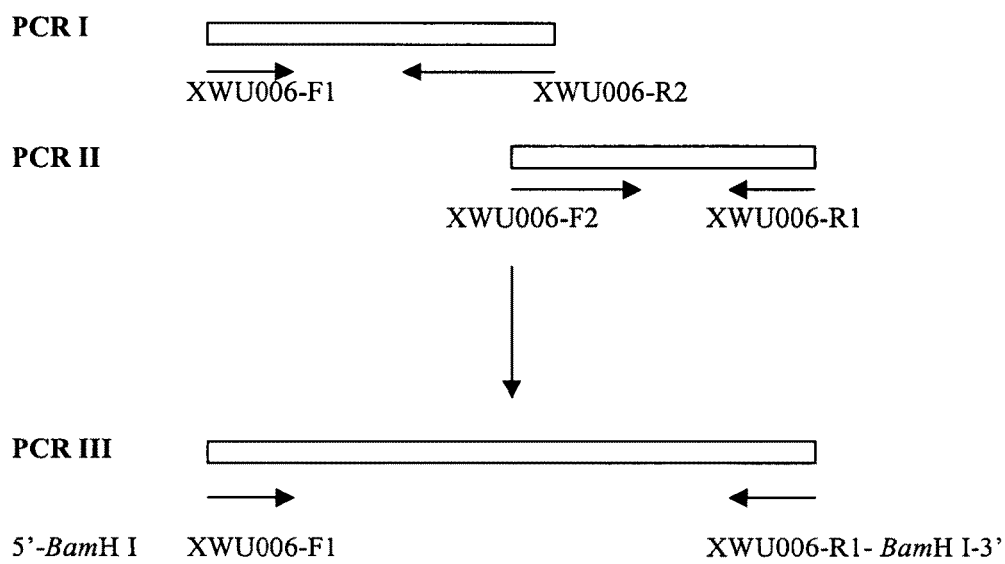

As represented in FIG. 14B, BHA10 scFv gene sequences were amplified in a two-step PCR reaction using the 5' VH XWU006-F1+3' VL XWU006-R1 PCR primer set and a set of internal overlapping PCR primers (XWU006-F2 and XWU006-R2) designed to eliminate a BamH I site within the BHA10 scFv (Gly₄Ser)₃ linker region. These PCR conditions were used to prepare conventional BHA10 scFv from plasmid pXWU034, BHA10 scFv (Gly₄Ser)₄ from plasmid pXWU002, BHA10 scFv $V_H44$:$V_L100$ from plasmid pIEH006, and BHA10 scFv $V_H44$:$V_L100$/(Gly₄Ser)₄ from plasmid pIEH009. The PCR products from the panel of amplified BHA10 scFvs were purified by agarose gel electrophoresis using the Millipore Ultrafree-DA extraction kit according to manufacturer's instructions (Millipore; Bedford, Mass.). The purified PCR products were digested with BamH I restriction endonuclease and ligated into a single BamH I site of the pN5KG1 vector previously engineered to contain several modifications. Briefly, the pN5KG1 vector containing chi14A2 IgG1 was modified to remove the stop codon at the 3' end of the heavy chain gene and introduce nucleotides coding for the amino acid sequence Ser-Gly-Gly-Gly immediately followed by a BamH I restriction endonuclease site (coding for Gly-Ser) for cloning. Lastly, an internal unwanted BamH I restriction endonuclease site in chi14A2 VL region was also eliminated.

The resulting panel of constructs form fusion proteins of the variant BHA10 scFvs to the carboxyl terminus of the anti-TRAIL R2 antibody heavy chain through the 16 amino acid Ser(Gly₄Ser)₃ linker. Fusion of the conventional BHA10 scFv gene sequence to the carboxyl terminus of the anti-TRAIL R2 antibody heavy chain gene sequence produced plasmid pXWU006. Fusion of BHA10 scFv (Gly₄Ser)₄ gene sequence to the carboxyl terminus of the anti-TRAIL R2 antibody heavy chain gene sequence produced plasmid pXWU034. Fusion of BHA10 scFv $V_H44$:$V_L100$ gene sequence to the carboxyl terminus of the anti-TRAIL R2 antibody heavy chain gene sequence produced plasmid pXWU035. Fusion of BHA10 scFv $V_H44$:$V_L100$/(Gly₄Ser)₄ gene sequence to the carboxyl terminus of the anti-TRAIL R2 antibody heavy chain gene sequence produced plasmid pXWU036.

The ligation mixtures were used to transform *E. coli* strain TOP 10 competent cells (Invitrogen Corporation, Carlsbad, Calif.). *E. coli* colonies transformed to ampicillin drug resistance were screened for presence of inserts. DNA sequence analysis confirmed the correct sequence of the final constructs. The chimeric 14A2 light chain used is common among all the N- and C-Hercules bispecific antibodies and DNA and amino acid sequences are shown in FIGS. 15A and 15B. Heavy chain DNA and amino acid sequences for conventional BHA10 scFv C-Hercules are shown in FIGS. 24 and 25, respectively. Heavy chain DNA and amino acid sequences for BHA10 scFv (Gly₄Ser)₄ C-Hercules are shown in FIGS. 26 and 27, respectively. Heavy chain DNA and amino acid sequences for BHA10 scFv $V_H44$:$V_L100$ C-Hercules are shown in FIGS. 28 and 29, respectively. Heavy chain DNA and amino acid sequences for BHA10 scFv $V_H44$:$V_L100$/(Gly₄Ser)₄ C-Hercules are shown in FIGS. 30 and 31, respectively. A summary of the C-terminal bispecific Hercules constructs is found in Table 16.

TABLE 16

Intermediate and expression plasmids encoding 'Hercules'

| Vector | Composition | Antibody |
| --- | --- | --- |
| pXWU002 | pIEH003 + BHA10 scFv (G₄S)₄ linker | BHA10 scFv with (G₄S)₄ linker |
| pXWU005 | pN5KG1 + BHA10 scFv N-Hercules | BHA10 scFv N-Hercules |
| pXWU006 | pN5KG1 + BHA10 scFv C-Hercules | BHA10 scFv C-Hercules |
| pXWU026 | pXWU005 + (G₄S)₄ linker | BHA10 scFv (G₄S)₄ N-Hercules |
| pXWU027 | pXWU005 + $V_H44$:$V_L100$ | BHA10 scFv $V_H44$:$V_L100$ N-Hercules |
| pXWU028 | pXWU005 + $V_H44$:$V_L100$/(Gly₄Ser)₄ | BHA10 scFv $V_H44$:$V_L100$/(Gly₄Ser)₄ N-Hercules |
| pXWU033 | Modified pXWU006 | Bam HI site removed in 14A2 VL of C-Hercules |
| pXWU034 | pXWU033 + (G₄S)₄ linker | BHA10 scFv (G₄S)₄ linker C-Hercules |
| pXWU035 | pXWU033 + $V_H44$:$V_L100$ | BHA10 scFv $V_H44$:$V_L100$ C-Hercules |
| pXWU036 | pXWU033 + $V_H44$:$V_L100$/(Gly₄Ser)₄ | BHA10 scFv $V_H44$:$V_L100$/(Gly₄Ser)₄ C-Hercules |

C. Transient Expression of Bispecific Antibodies in CHO Cells

Plasmid DNAs pXWU005, pXWU026, pXWU027, pXWU028; and pXWU006, pXWU034, pXWU035, and pXWU036 (Table 16) were used to transform CHO DG44 cells for transient production of antibody protein. Each 20 ug of plasmid DNA was combined with $4\times10^6$ cells in a volume of 0.4 mls of 1XPBS. The mixture was added to a 0.4 cm cuvette (BioRad) and placed on ice for 15 min. The cells were electroporated at 600 uF and 350 volts with a Gene Pulser electroporator (BioRad). The cells were placed in the CHO-SSFM II media containing 100 uM Hypoxanthine and 16 uM Thymidine into a T-25 flask and incubated at 37° for 4 days.

Figure 32:
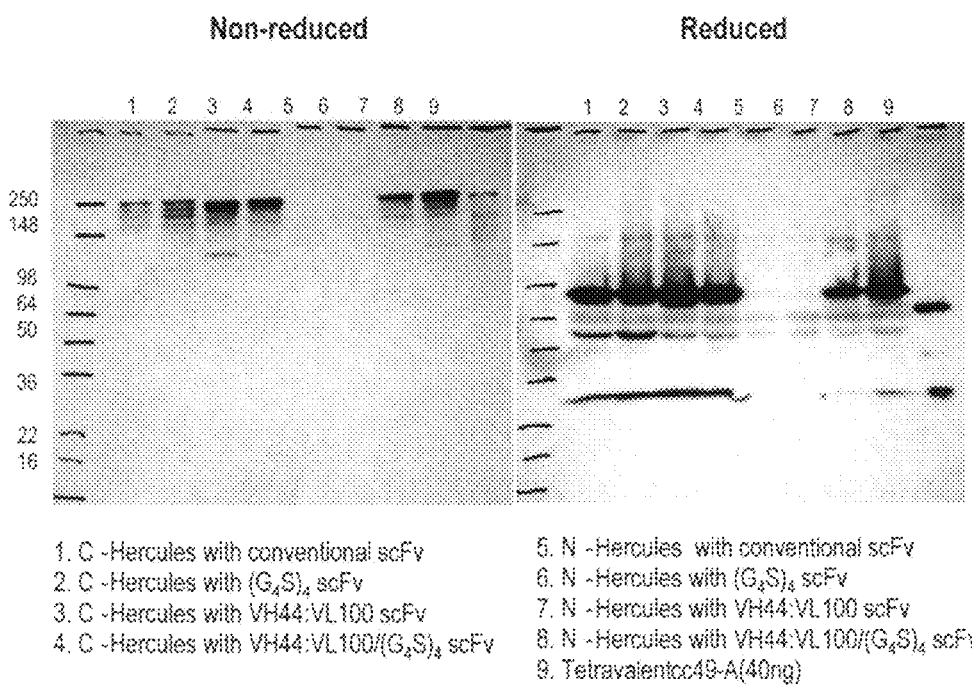
FIG. 32 shows results from Western Blot analyses of transiently expressed C- and N$_H$-Hercules bispecific antibodies in CHO cells. The left panel is analyzed under non-reducing conditions and the right panel under reducing conditions.

Supernatants containing Hercules proteins produced by this transient CHO expression system were collected and evaluated by Western Blot. FIG. 32 shows that the Hercules antibodies containing either the $V_H44$:$V_L100$ (ds=disulfide) or $V_H44$:$V_L100$/(Gly₄Ser)₄ linker stabilized BHA10 scFvs dramatically improved expression yields independent of whether the scFv was fused to the $N_H$- or C-terminus (lanes 3, 4, 7, 8). Surprisingly, no secreted protein was detected with wild type BHA10 scFv nor (Gly₄Ser)₄ linker BHA10 scFv N-terminal fusions indicating the benefit of scFv stabilization on expression (lanes 6 and 7). In addition, conventional BHA10 scFv and (Gly₄Ser)₄ linker BHA10 scFv C-terminal fusions displayed a significant amount of a ~55-60 molecular weight byproduct which is substantially reduced in the stabilized constructs suggesting that scFv stabilization may improve product quality.

D. Bispecific Binding ELISA Assay

Supernatants were tested for individual binding activity to recombinantly produced TRAIL R2 and LTβR receptors in ELISA assays. In both assays, receptor was immobilized onto plates and test samples incubated to permit binding to receptor. Bound samples were detected with labeled antibody.

96-well microtiter Immulon II plates (Fisher, Cat#14245-61) were coated with 100 µl/well of 2 µg/ml LTβR-Ig in Na$_2$CO$_3$/NaHCO$_3$ buffer pH 9.5, overnight at 4° C. and blocked with 200 µl dilution Buffer (0.5% Nonfat Dry Milk in PBS plus 0.01% Thimerosal) for 1 h at 37° C. In the next step, 100 µl individual 'Hercules' supernatant or purified protein in dilution buffer was added to duplicate wells and incubated for 1 h at 37° C. After washing with tap water, 100 µl of 100 ng/ml TRAIL-R2Fc 6×-His tagged fusion protein (R&D Systems, Minneapolis, Minn.) was added to the wells and incubated for 1 h at 37° C. After washing, 100p. 1 of a 1/2000 dilution of Penta-His HRP Conjugate (QIAGEN, Cat#34460) was added to each well and incubated for 1 h at 37° C. After washing, 100 µl/well of a HRPO Substrate combined TMB Peroxidase Substrate/Peroxidase Solution B (Kirdgaard and Perry Labs, Cat. 50-76-00) was added. The reaction was stopped with 100 µl of 2M H$_2$SO$_4$ after 5 to 10 min. The OD was measured at 450 nm and 540 nm using a Molecular Devices plate reader and binding curves were generated.

Figure 33A:
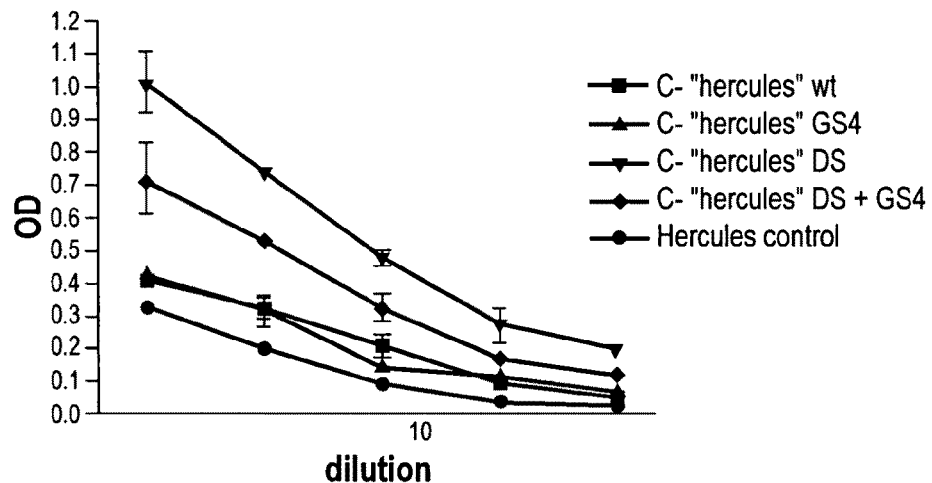
FIG. 33A depicts the results with stabilized C-Hercules antibodies.
Figure 33B:
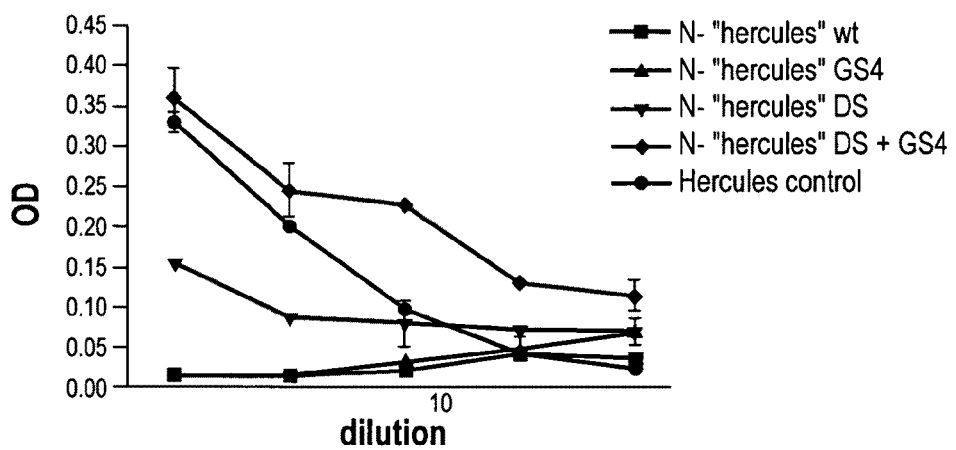
FIG. 33B depicts the results with stabilized N$_H$ Hercules antibodies. "wt" is conventional N$_H$ Hercules antibody. "GS4" is a stabilized N$_H$ Hercules antibody comprising a stabilized (Gly4Ser)$_4$ scFv. "ds" is a stabilized N$_H$ Hercules antibody comprising a stabilized scFv comprising the VH44/VL100 disulfide linker.
Figure 34A:
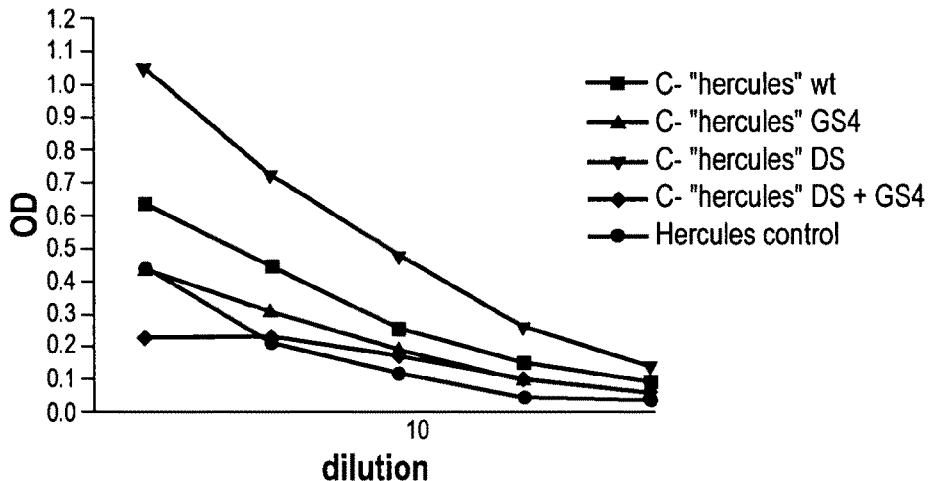
FIG. 34A depicts the results with stabilized C-terminal Hercules antibodies.
Figure 34B:
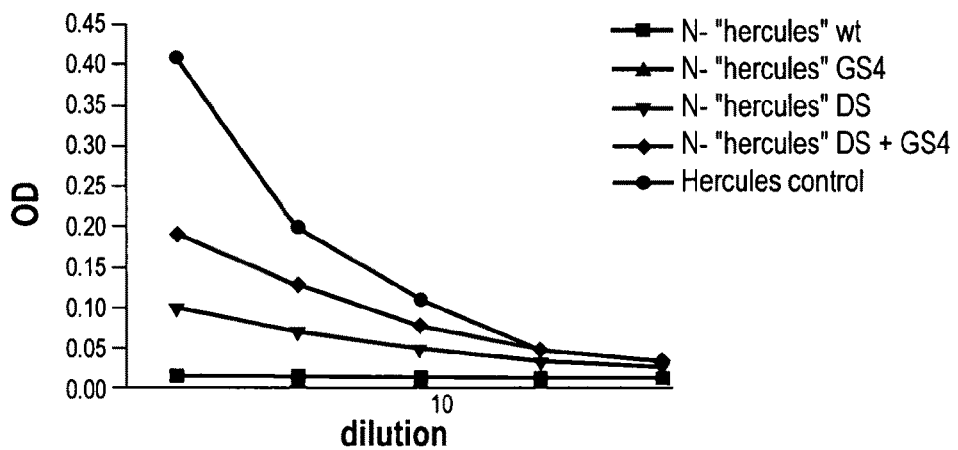
FIG. 34B depicts the results with stabilized $N_H$ Hercules antibodies. "wt" is conventional $N_H$ Hercules antibody. "GS4" is a stabilized $N_H$ Hercules antibody comprising a stabilized (Gly$_4$Ser)$_4$ scFv. "ds" is a stabilized $N_H$ Hercules antibody comprising a stabilized scFv comprising the VH44/VL100 disulfide linker.

FIGS. 33 and 34 show that both the N-terminal (FIG. 33A, 34A) and the C-terminal (FIG. 33B, 34B) Hercules antibodies containing either the $V_H44:V_L100$ (ds=disulfide) or $V_H44:V_L100/(Gly_4Ser)_4$ linker stabilized BHA10 scFv show improved binding to LTβR (FIG. 33) and TRAIL R2 (FIG. 34), respectively, compared to Hercules containing a conventional BHA10 scFv (wt).

E. Stable Expression of Bispecific Antibodies in CHO cells, Antibody Purification, and Characterization.

Plasmid DNAs pXWU027, pXWU028, and pXWU006, pXWU035, and pXWU036 (Table 16) were used to transform DHFR-deficient CHO DG44 cells for stable production of antibody protein. Transfected cells were grown in alpha minus MEM medium containing 2 mM glutamine supplemented with 10% dialyzed fetal bovine serum (Invitrogen Corporation) and enriched as a stable bulk culture pool using fluorescently labeled antibodies and reiterative fluorescent-activated cell sorting (FACS) (Brezinsky, et al. *J Immunol Methods*. 277(1-2):141-55 (2003)). FACS was also used to generate individual cell lines. Cell pools or cell lines were adapted to serum-free conditions and scaled for antibody production.

Figure 35:
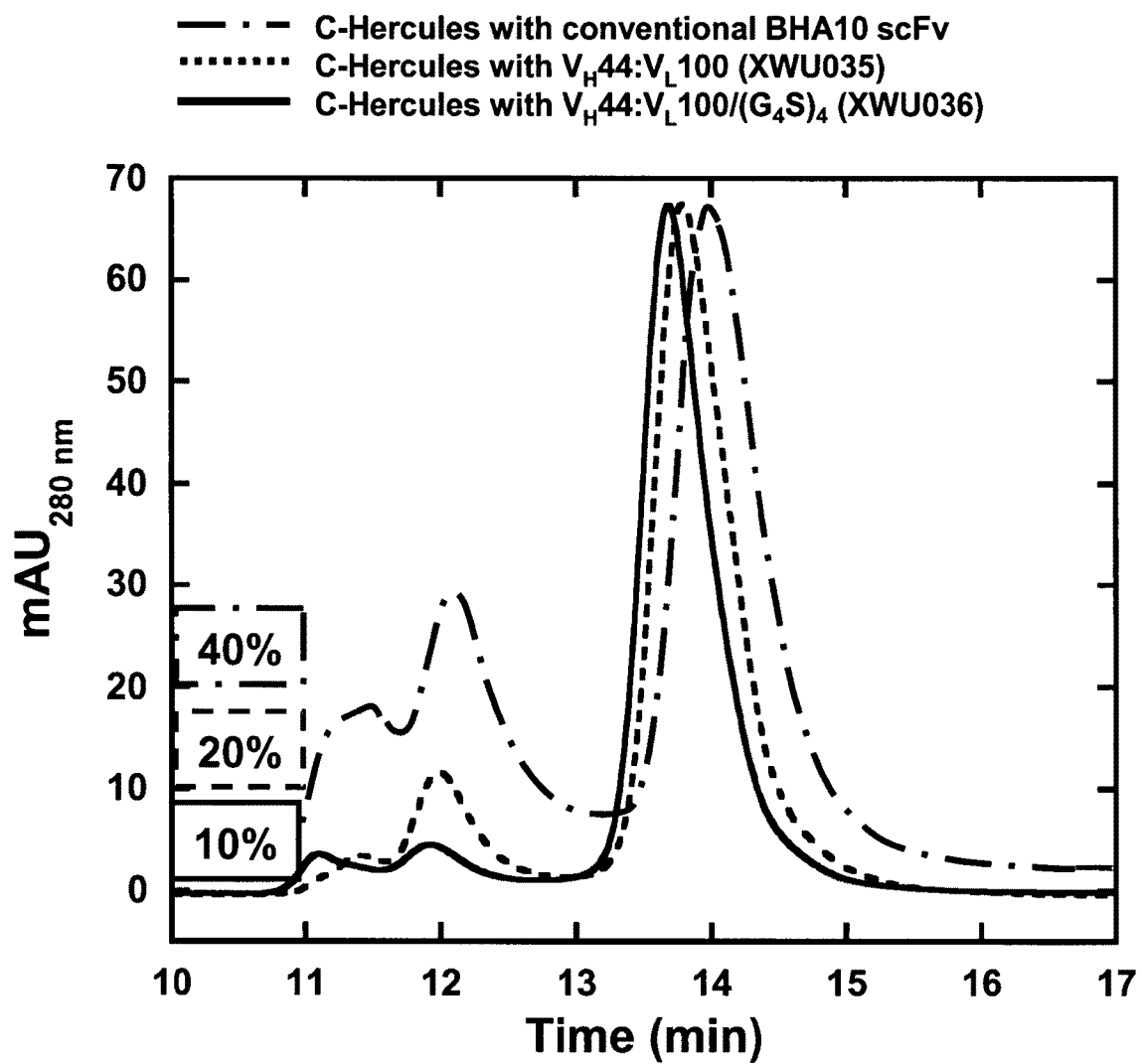
FIG. 35 shows the results of SEC analysis of stabilized C-Hercules bispecific antibodies following Protein A chromatography.

Supernatants from transfected CHO cell pools or cells lines expressing 1) C-terminal Hercules with the $V_H44:V_L100$ stabilized BHA10 scFv and 2) C-terminal Hercules with the $V_H44:V_L100/(Gly_4Ser)_4$ linker stabilized BHA10 scFv, as well as clonal CHO cell lines expressing 3) N-terminal Hercules with the $V_H44:V_L100$ stabilized BHA10 scFv and 4) N-terminal Hercules with the $V_H44:V_L100/(Gly_4Ser)_4$ linker stabilized BHA10 scFv were collected and purified using Protein A Sepharose FF (6 mL) column using a PBS, 10 mM EDTA running buffer. Hercules proteins were eluted using 0.1 M glycine, pH 3.0 and neutralized immediately to pH 7.5-8.5 using Tris base. In addition, C-Hercules containing the conventional BHA10 scFv was expressed and purified by Protein A chromatography for comparison. Protein A eluates from C-Hercules containing the conventional BHA10 scFv, C-terminal Hercules with the $V_H44:V_L100$ BHA10 scFv, and C-terminal Hercules with the $V_H44:V_L100/(Gly_4Ser)_4$ BHA10 scFv were examined for the presence of aggregates by analytical size exclusion chromatography (FIG. 35). The chromatogram profile of C-Hercules containing the conventional BHA10 scFv showed ~40% aggregates. In contrast, C-terminal Hercules with the $V_H44:V_L100$ BHA10 scFv reduced the aggregate level to 20% and further stabilization achieved through C-terminal Hercules with the $V_H44:V_L100/(Gly_4Ser)_4$ BHA10 scFv reduced the level of aggregates to 10%. The level of aggregation appeared to depend upon the properties of the scFv and not whether it was appended to the $N_H$- or C-terminus of the 14A2 IgG (data not shown). The protein A Hercules eluants were further purified by dialysis into 0.1 M acetate, pH 5.0, and purification by MonoS (GE Healthcare) cation exchange chromatography using an identical running buffer as the dialysate. Hercules proteins were eluted using a step gradient to 0.1 M acetate, pH 5.0, 0.5 M NaCl. The MonoS eluants were collected and passed through a TosoHaas preparative SEC column to remove aggregates.

Figure 36A:
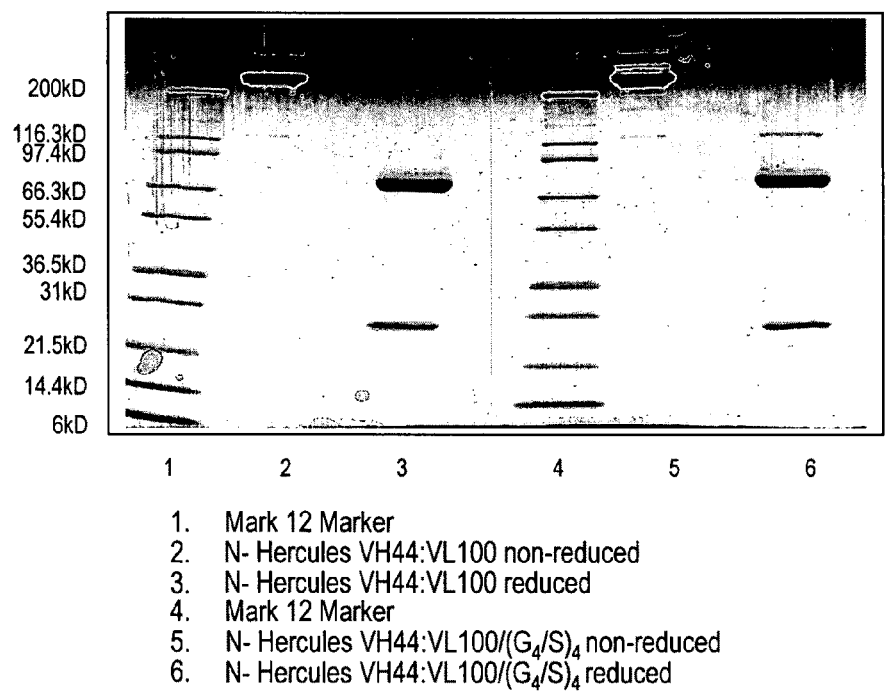
FIG. 36A depicts results with NH-Hercules bispecific antibodies.
Figure 36B:
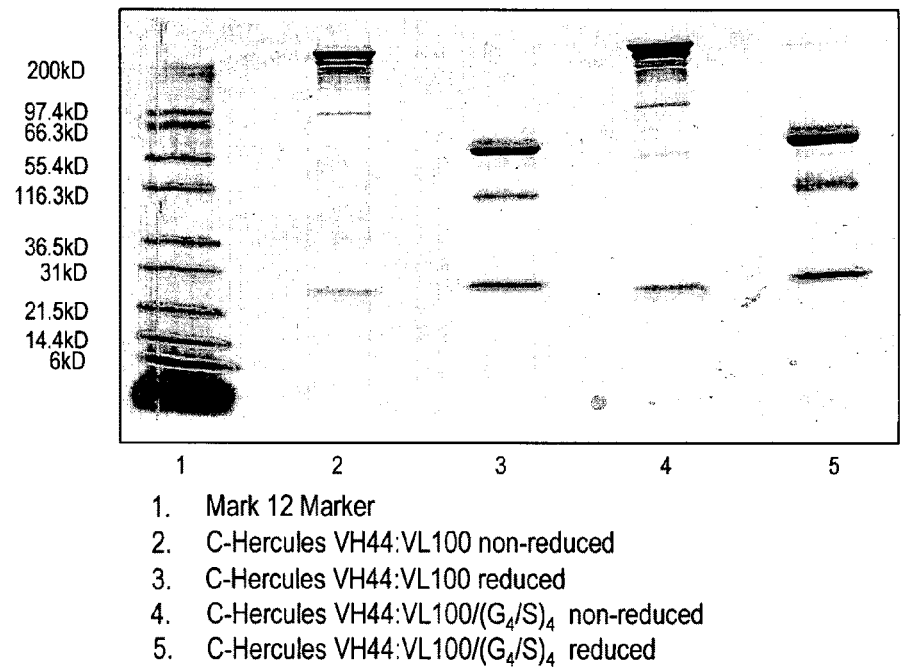
FIG. 36B depicts results with C-Hercules bispecific antibodies. 5 ug sample were loaded in each lane.

FIGS. 36A and 36B show SDS-PAGE gels of purified N-terminal Hercules with the $V_H44:V_L100$ stabilized BHA10 scFv and $N_H$-terminal Hercules with the $V_H44:V_L100/(Gly_4Ser)_4$ linker stabilized BHA10 scFv and C-terminal Hercules with the $V_H44:V_L100$ stabilized BHA10 scFv and C-terminal Hercules with the $V_H44:V_L100/(Gly_4Ser)_4$ linker stabilized BHA10 scFv, respectively. The reduced lanes show the expected sizes of the heavy and light chain proteins. Importantly, there is no significant level of degraded or unwanted lower molecular weight byproducts that has often been observed with Hercules containing wild type scFv domains.

Figure 37:
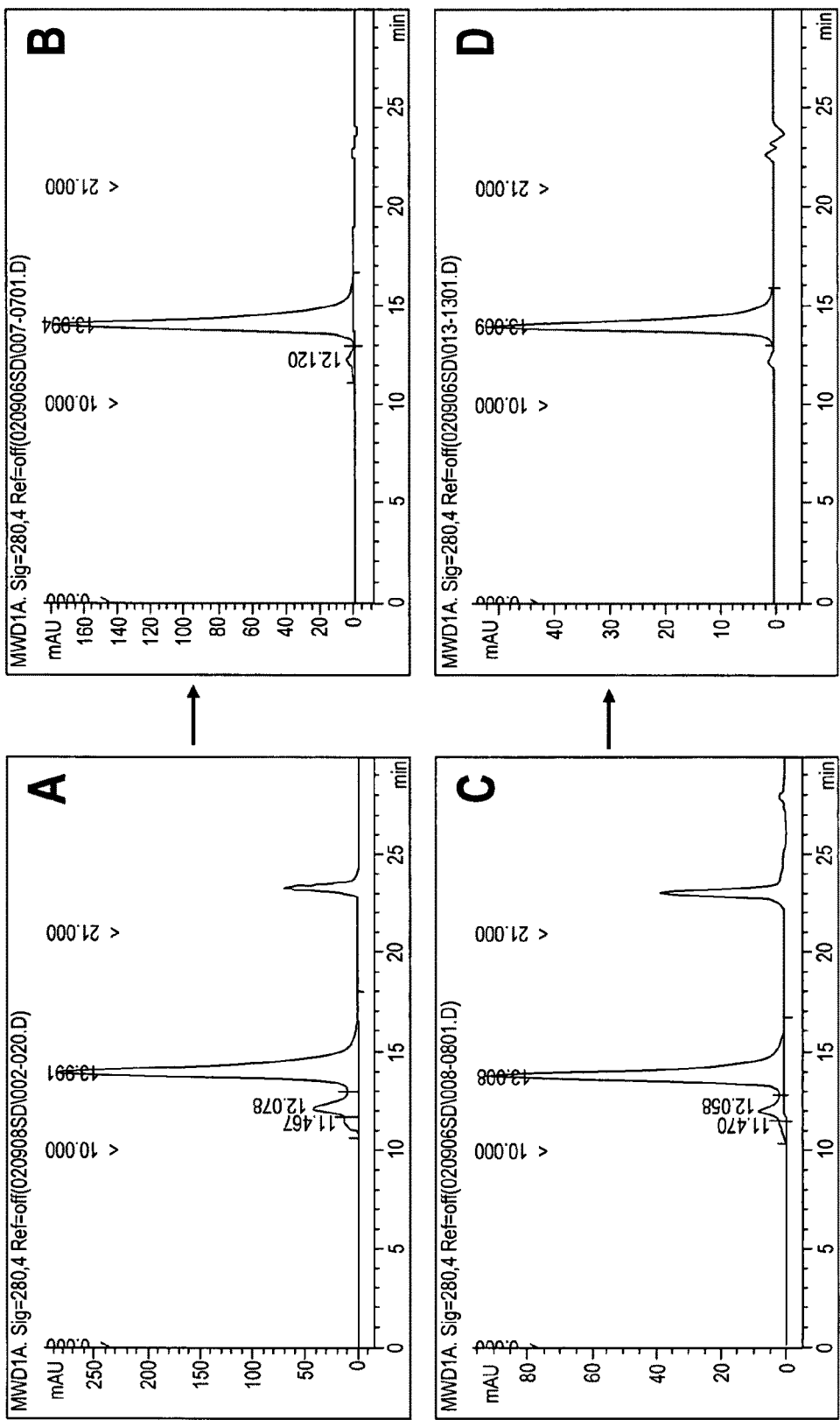
FIG. 37 shows the results of analytical SEC analysis of purified stabilized N-Hercules bispecific antibodies. Panel A shows the profile of N-Hercules with $V_H44$:$V_L100$ BHA10 scFv following Protein A chromatography and Panel B following preparative SEC. Panel C shows the profile of N-Hercules with $V_H44$:$V_L100$/(G$_4$S)$_4$ BHA10 scFv following Protein A chromatography and Panel D following preparative SEC.
Figure 38:
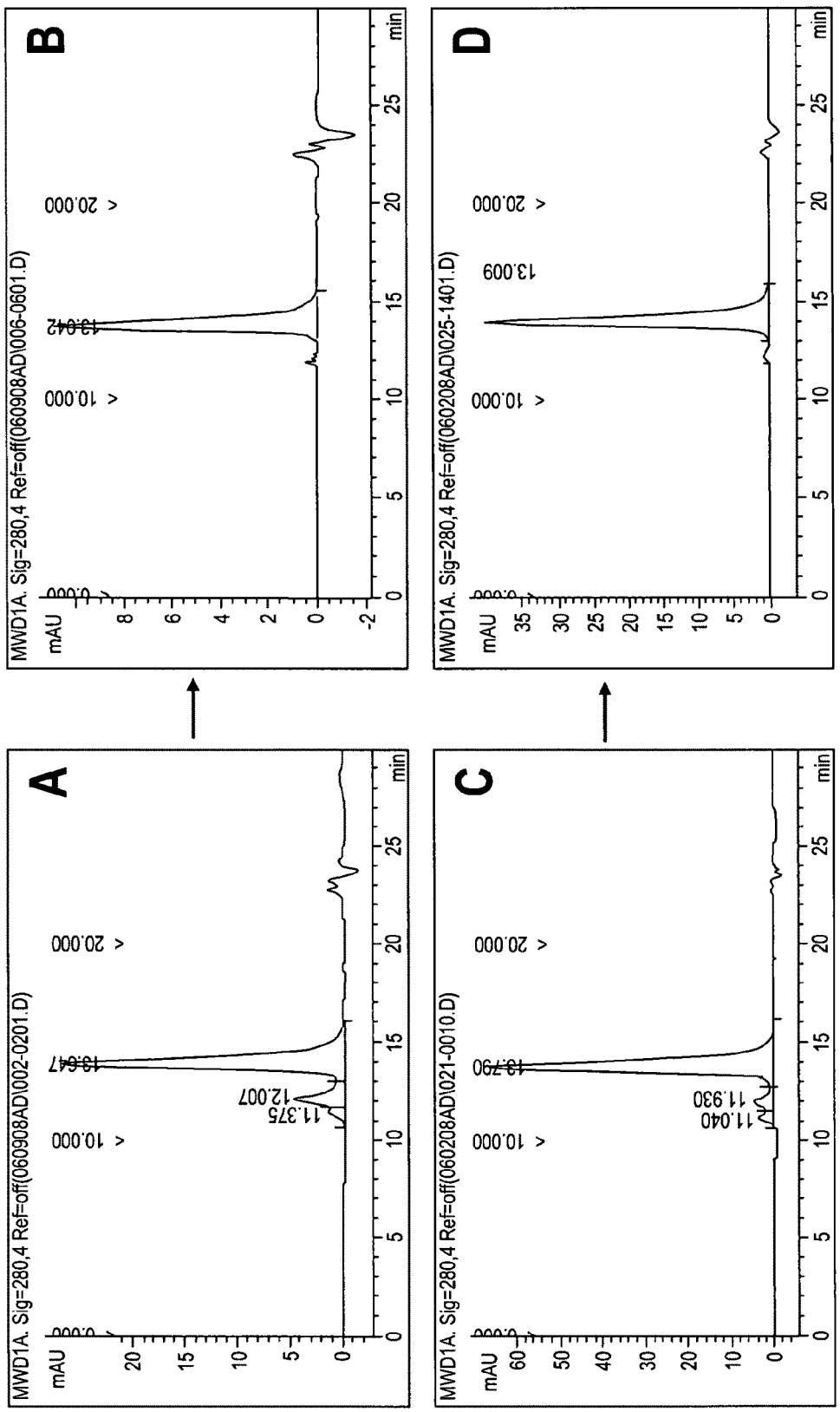
FIG. 38 shows the results of analytical SEC analysis of purified stabilized C-Hercules bispecific antibodies. Panel A shows the profile of C-Hercules with $V_H44$:$V_L100$ BHA10 scFv following Protein A chromatography and Panel B following preparative SEC. Panel C shows the profile of C-Hercules with $V_H44$:$V_L100$/(G$_4$S)$_4$ BHA10 scFv following Protein A chromatography and Panel D following preparative SEC.

FIG. 37 (Panels A and C) shows the analytical SEC elution profiles of $N_H$-terminal Hercules with the $V_H44:V_L100$ stabilized BHA10 scFv and $N_H$-terminal Hercules with the $V_H44:V_L100/(Gly_4Ser)_4$ linker stabilized BHA10 scFv, respectively, subsequent to the initial protein A purification step. FIG. 37 (Panels B and D) also shows the analytical SEC elution profiles of $N_H$-terminal Hercules with the $V_H44:V_L100$ stabilized BHA10 scFv and $N_H$-terminal Hercules with the $V_H44:V_L100/(Gly_4Ser)_4$ linker stabilized BHA10 scFv, respectively, following preparative SEC removal of residual non-monomeric protein contaminants. Similarly, FIG. 38 (Panels A and C) shows the analytical SEC elution profiles of C-terminal Hercules with the $V_H44:V_L100$ stabilized BHA10 scFv and C-terminal Hercules with the $V_H44:V_L100/(Gly_4Ser)_4$ linker stabilized BHA10 scFv, respectively, subsequent to the initial protein A purification step. FIG. 38 (Panels B and D) shows the analytical SEC elution profiles of C-terminal Hercules with the $V_H44:V_L100$ stabilized BHA10 scFv and C-terminal Hercules with the $V_H44:V_L100/(Gly_4Ser)_4$ linker stabilized BHA10 scFv, respectively, following preparative SEC removal of residual non-monomeric protein contaminants. These studies demonstrate that stabilization of the BHA10 scFv by addition of either the $V_H44:V_L100$ disulfide or the $V_H44:V_L100$ disulfide and $(Gly_4Ser)_4$ linker results in preparative quantities of >98% pure, monomeric Hercules bispecific antibody that is essentially free of higher order molecular weight species.

Figure 39:
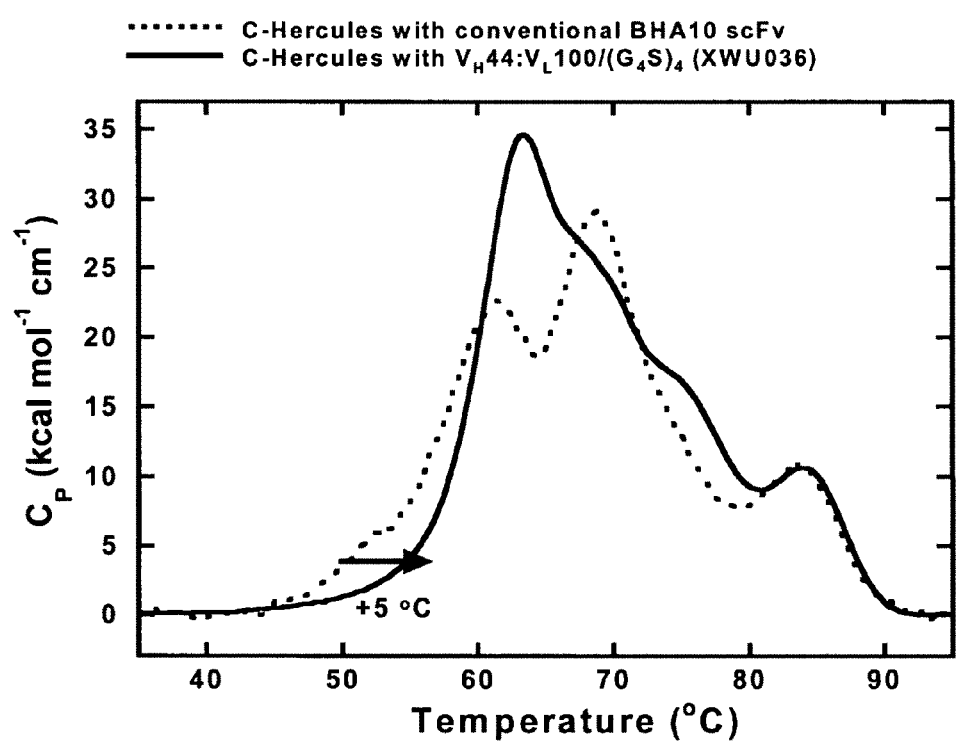
FIG. 39 shows results of Differential Scanning calorimetry (DSC) analyses performed with C-Hercules with $V_H44$:$V_L100$/(G$_4$S)$_4$ BHA10 scFv and C-Hercules with conventional BHA10 scFv.

DSC studies performed under identical conditions demonstrate that C-Hercules $V_H44:V_L100/(Gly_4Ser)_4$ BHA10 scFv is more thermostable than C-Hercules containing conventional BHA10 scFv (FIG. 39). The denaturation profile for C-Hercules containing conventional BHA10 scFv begins ~5° C. lower temperature than the profile observed for the C-Hercules $V_H44:V_L100/(Gly_4Ser)_4$BHA10 scFv. These results suggest that the scFv may limit the overall thermostability of the Hercules molecules. This correlates with a 5° C. $T_M$ observed increase for the $V_H44:V_L100/(Gly_4Ser)_4$ BHA10 scFv over that of the conventional BHA10 scFv.

Figure 40:
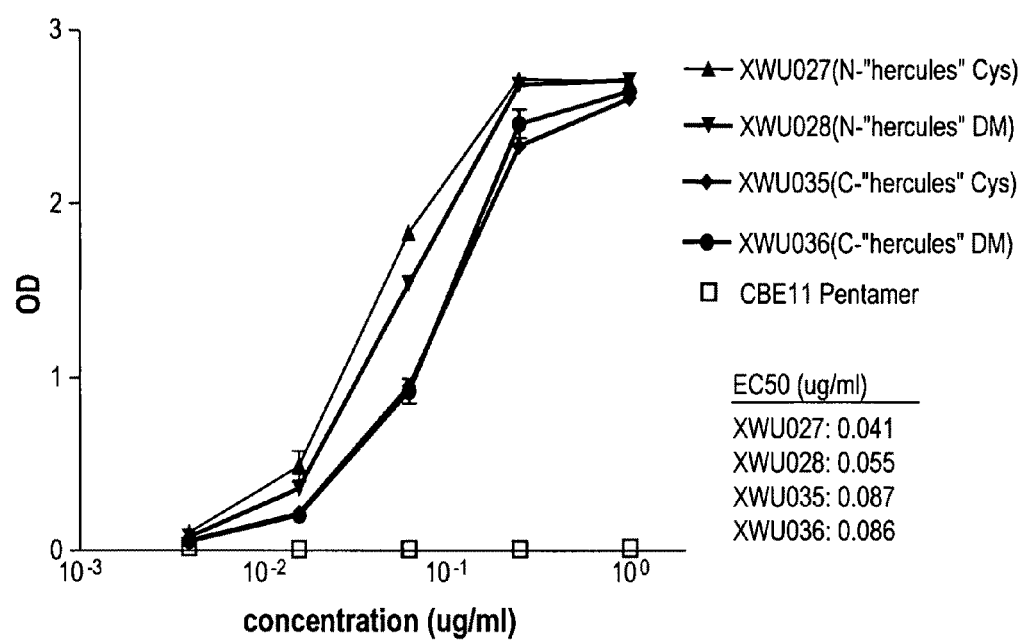
FIG. 40 depicts the results of an ELISA to evaluate the bispecific binding activity of the stabilized Hercules antibodies of the invention to TRAIL-R2 and LTβR Ig receptors. "N-"Hercules" Cys and C-"Hercules" Cys are Hercules antibodies comprising $N_H$- or C-terminal scFvs having the VH44/VL100 disulfide bond. "N-"Hercules"Cys and N-"Hercules" DM" are Hercules antibodies comprising the $N_H$- or C-terminal scFv comprising the VH44/VL100 disulfide and the (Gly4Ser)$_4$ linker. CBE11 pentamer is a control antibody with monospecific LTβR binding activity.

Purified versions of the stabilized Hercules constructs were then tested for bispecific binding activity to recombinantly produced TRAIL-R2 and LTβR receptors in an ELISA assay. In this assay LTβR Ig receptor was immobilized onto plates and test samples were then incubated to permit binding to receptor. Unbound samples were removed by washing followed by a second incubation step with TRAIL R2—(His)$_6$. Following a wash step, doubly-bound complexes were detected with a labeled anti-(His)$_6$ antibody. The results of this study and the effective concentration (EC50, in μg/ml) at which each construct are depicted in FIG. 40. FIG. 40 shows that both the N-terminal and C-terminal Hercules antibodies with either the V$_H$44:V$_L$100 (ds=disulfide) or V$_H$44:V$_L$100/(Gly$_4$Ser)$_4$ linker stabilized BHA10 scFv demonstrate clear bispecific binding to both LTβR and TRAIL R2. A multivalent (pentameric) version of an LTβR-binding antibody (CBE11) was used as a control to demonstrate that single recognition of LTβR alone does not induce signal in the binding assay.

Example 8

Scale-up Production of Stabilized Bispecific "Hercules" Antibodies in CHO Cells

DHFR-deficient CHO cell lines stably transfected with plasmid DNAs pXWU028 and pXWU036 (Table 16) were screened to select for single cell isolates that are capable of expressing high levels of solubilized and properly-folded Hercules molecules that were stabilized using the methods of the invention. The cell screening methods employed the fluorescence-activated cell sorting (FACS) analysis of Brezinky et al. (Brezinky et al., *J Immunol Meth* (2003). 277:141-155). Briefly, fluorescently tagged anti-Hercules antibodies were used to label CHO cells exhibiting transient expression of Hercules antibodies on their surface. Cells exhibiting a signature fluorescence intensity were then selected by tailoring the gating of the cell sorter apparatus to that signature. Single cells exhibiting high levels of productivity were thereby selected and adapted to serum-free conditions to establish stable producer cell lines. The producer cell lines were subsequently scaled-up for production and purification of the bispecific antibody protein.

80 L of N-terminal Hercules containing V$_H$44:V$_L$100/(Gly$_4$Ser)$_4$ BHA10 scFv (XWU028) supernatant from an 11 day bioreactor run was harvested and precleared by ultrafiltration. The bispecific antibody was captured by Protein A chromatography and eluted in 1218 mls volume. The Protein A fraction was further purified in two separate batches by anion exchange chromatography followed by preparative size exclusion chromatography. The first batch yielded 825.5 mg at a concentration of 4.85 mg/ml in PBS with 98.9% purity and an endotoxin load of 0.13 EU/mg. The second batch yielded 318 mg at a concentration of 10.3 mg/ml with a purity of 99.1% and an endotoxin load of 2.37 EU/mg. A total of 1143.5 mg highly purified, monomeric N-terminal Hercules containing V$_H$44:V$_L$100/(Gly$_4$Ser)$_4$ BHA10 scFv was recovered.

24 L of C-terminal Hercules containing V$_H$44:V$_L$100/(Gly$_4$Ser)$_4$ BHA10 scFv (XWU036) supernatant from an 11 day bioreactor run was harvested and precleared by ultrafiltration. The bispecific antibody was purified in two separate batches as described above using Protein A chromatography to capture crude product followed by anion exchange chromatography and preparative size exclusion chromatography. The first batch yielded 985.5 mg at a concentration of 13 mg/ml with 98.5% purity and an endotoxin load of 0.01 EU/mg. The second batch yielded 570 mg at a concentration of 11.42 mg/ml with a purity of 99% and an endotoxin load of 1.91 EU/mg. A total of 1555.5 mg highly purified, monomeric C-terminal Hercules containing V$_H$44:V$_L$100/(Gly$_4$Ser)$_4$ BHA10 scFv was recovered.

A CHO cell line producing the XWU054 bispecific antibody was isolated and found to produce 21.5 mg/L. This is within the expected range for research grade unamplified CHO cell lines and we would anticipate much higher productivity if we were to generate a Production Cell Line.

These scale-up production studies were conducted with non-amplified CHO cell lines and yet resulted in yields exceeding 1 gm of high quality, biophysically stable bispecific antibodies. Presumably a cell line amplification strategy would greatly enhance the cellular productivity of the transfected CHO cell lines enabling the development of processes suitable for commercial applications. These studies exemplify the utility of the methods described in this invention for enabling the scale-up production of stable bispecific antibodies in a cell line (e.g. CHO) suitable for manufacturing.

Example 9

Biological Activity of Bispecific "Hercules" Antibodies

Tumor cell lines WiDr, (ATCC CCL-218) a human colon carcinoma cell line, Me180, (ATCC HTB 33) a human cervical epithelial carcinoma cell line, and MDA231, (Dr. Dajun Yang, University of Michigan) a human breast carcinoma cell line were cultured in MEM-Earles with 10% FCS, 2 mM L-Glutamine, 1X non-essential amino acids, 0.5 mM sodium pyruvate, and Penicillin/Streptomycin. Tumor cell lines were rinsed once with PBS and cells released by digestion with trypsin. Cells were collected by centrifugation, resuspended in complete media, counted and 96-well tissue culture plates seeded at 5000 cells/well for WiDr and Me180 and 1500 cell/well for MDA231. Human IFNγ (Biogen Idec, Corp) is added to the cell suspensions to result in a final cytokine concentration of 80 U/ml for WiDr and MDA231 and 50 U/ml for Me180. 50 μl of the tumor cell/IFNγ suspension were mixed with 50 μl of 2× concentrated 3-fold serial dilutions of test antibodies prepared in complete media. The final concentrations of test antibodies typically ranged from 5000 pM to 0.07 pM. Cells were grown for 4 days (WiDr & Me180) or 3 days (MDA231) at 37° C. in a 5% CO$_2$ humidified chamber and cell killing assessed by the addition of 20 μL/well Promega CellTiter 96 AQueous One Solution Cell Proliferation Assay reagent (Promega Corporation, Madison, Wis.). Plates were read in a micotiter plate reader at 490 nM (Spectromax Plus, Molecular Devices, Sunnyvale Calif.). Data was graphed using Microsoft Excel (Microsoft Inc, Wash.).

Figure 41A:
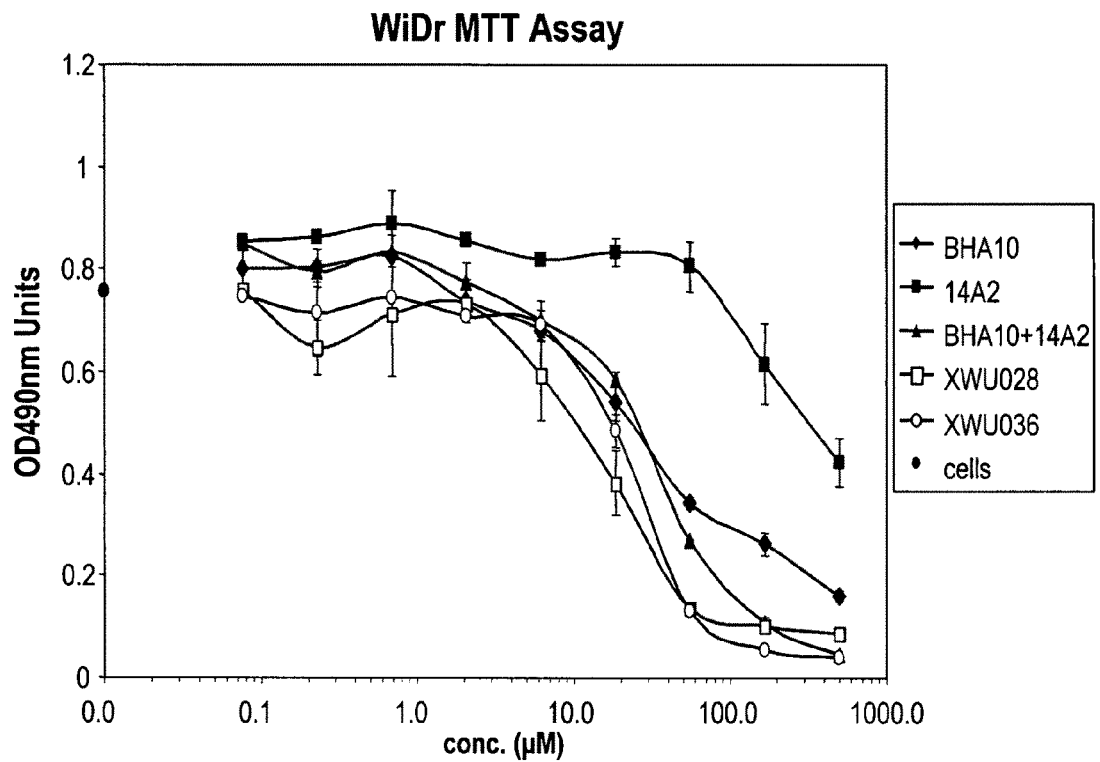
FIGS. 41A-41D depict effects on the growth of WiDr tumor cells, Me180 tumor cells, MDA231 tumor cells, and HUVEC cells, respectively.
Figure 41B:
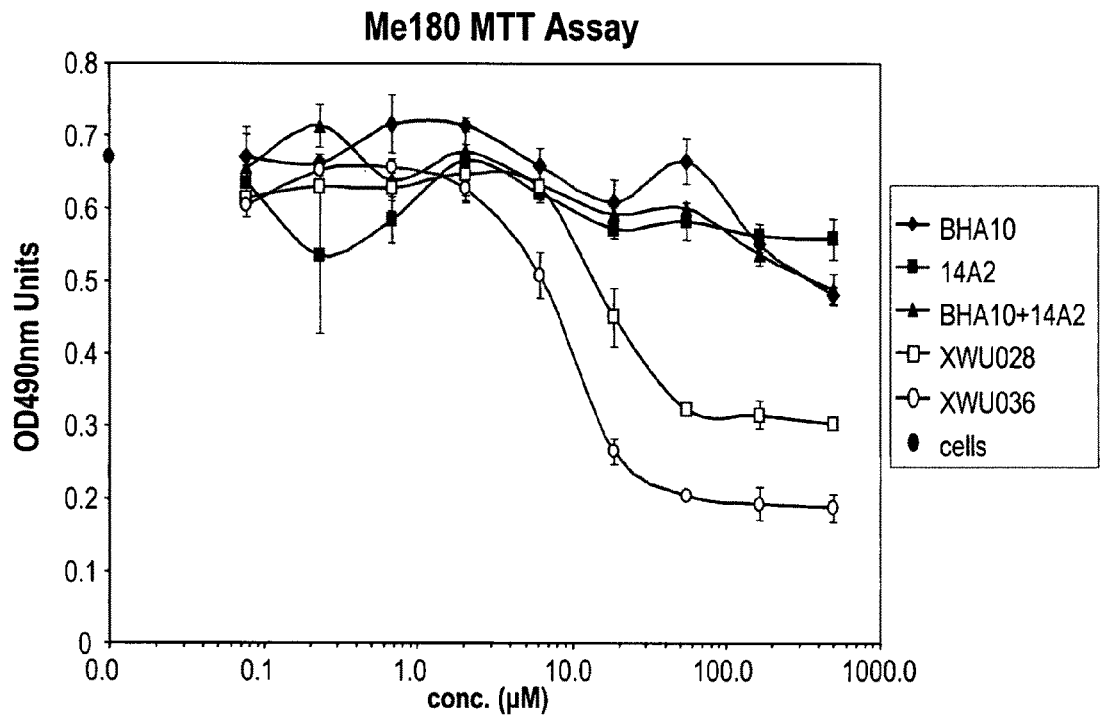
Figure 41C:
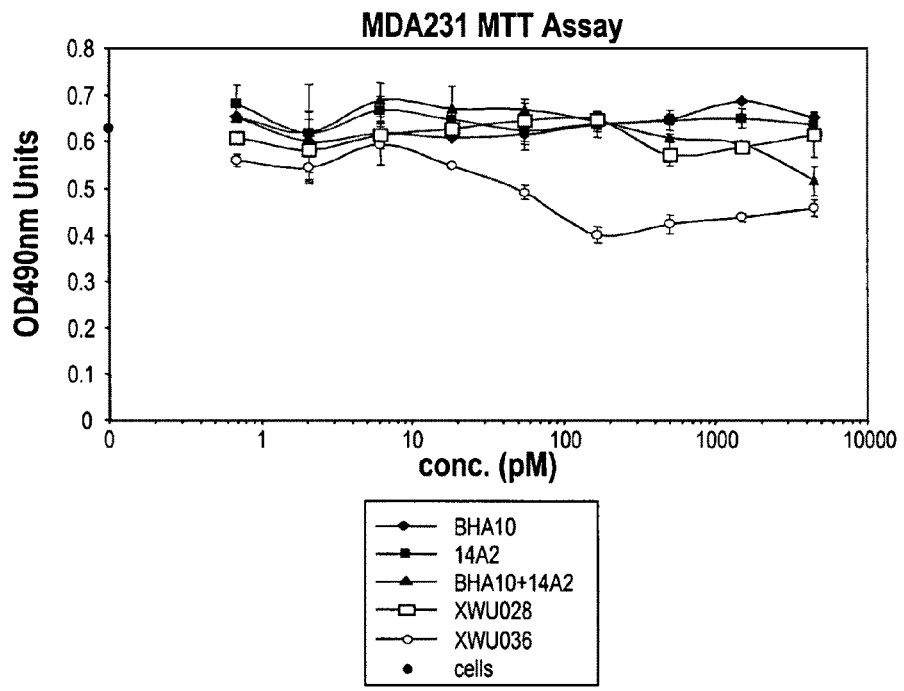
Figure 41D:
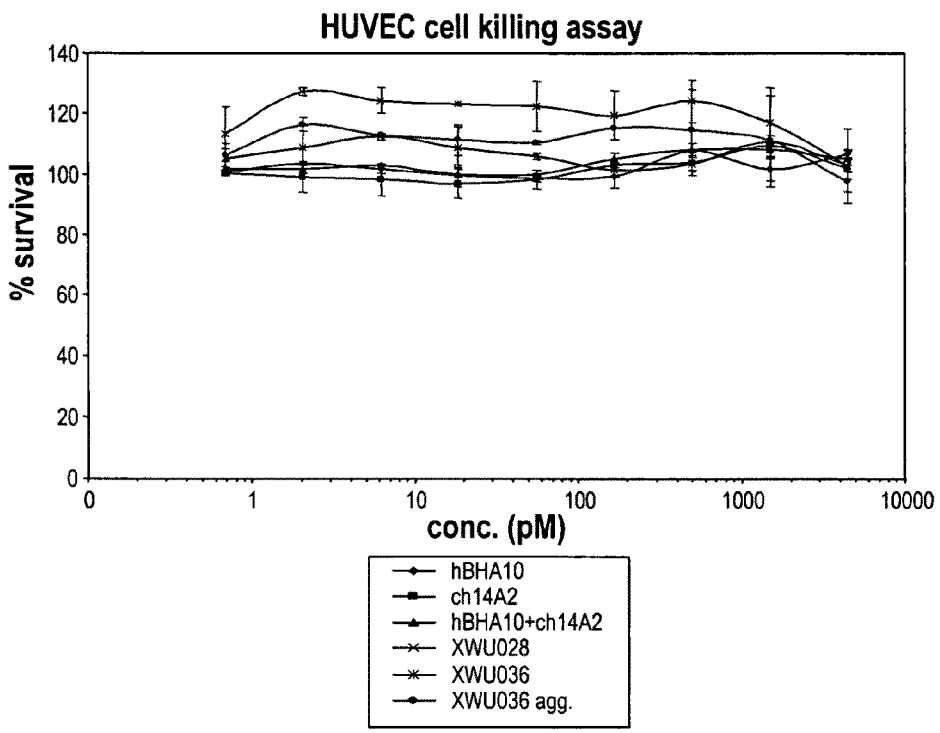

Results from these studies are shown in FIGS. 41A-41D. FIG. 41A shows that 14A2 IgG antibody had modest activity in inhibiting growth of WiDr tumor cells and in combination with BHA10 IgG exhibited a slight increase in anti-tumor cell activity compared to BHA10 IgG alone. In contrast, both of the bispecific Hercules antibodies showed enhanced tumor cell killing of the WiDr cells. FIG. 41B shows that both the 14A2 IgG and BHA10 IgG antibodies had modest, if not negligible, activity in inhibiting growth of Me180 tumor cells as single agents or in combination. In contrast, both of the bispecific Hercules antibodies showed tumor cell killing of the Me180 cells. FIG. 41C shows that both the 14A2 IgG and BHA10 IgG antibodies had negligible activity in inhibiting growth of MDA231 tumor cells as single agents and perhaps some activity when used in combination. In contrast, the bispecific Hercules antibody XWU036 (C-terminal Hercules with the V$_H$44:V$_L$100/(Gly$_4$Ser)$_4$ linker stabilized BHA10 scFv) showed tumor cell killing of the MDA231 cells. FIG. 41D shows that none of the antibodies demonstrate any activity towards control cultured human umbilical vein endothelial cells (HUVEC) demonstrating that the cell killing activity of the bispecific antibodies is not indescriminant. HUVEC shows positive staining for LTβR and TRAIL-R2 by FACS analysis (data not shown) indicating presence of receptors and that the activity of the bispecific antibody may be dependent on triggering specific or unique pathway components in tumor cells.

Example 10

Stability Studies of Bispecific "Hercules" Antibodies

Real-time stability studies of the N- and C-terminal bispecific antibody samples XWU028 (BHA10 scFv $V_H44$: $V_L100/(Gly_4Ser)_4$ N-Hercules) and XWU036 (BHA10 scFv $V_H44:V_L100/(Gly_4Ser)_4$ C-Hercules) stored at 2-8° C. for three months were conducted. Protein quality was assessed for (1) aggregation, (2) precipitation, (3) polypeptide cleavage or proteolysis, and (4) post-translational modifications such as deamidation or oxidation.

High and low concentration N- and C-terminal bispecific antibody samples used for the studies were XWU028 at 1.8 mg/mL (Low) and 10.3 mg/mL (High) and XWU036 at 5.0 mg/mL (Low) and 11.4 mg/mL (High). Antibodies were formulated in PBS. For the stability study, initial (T=0), intermediate (T=1 wk, 2 wk, 1 mo, 2 mo) and final (T=3 mo) time point samples were analyzed immediately following sample collection. In addition, initial (T=0) samples were frozen and stored at −70° C. until thawed for secondary analyses at the end of the 3-month study. BHA10 IgG (8.7 mg/mL) was used as control and was similarly handled.

A. Protein Aggregation and Precipitation Analysis

Figure 56A:
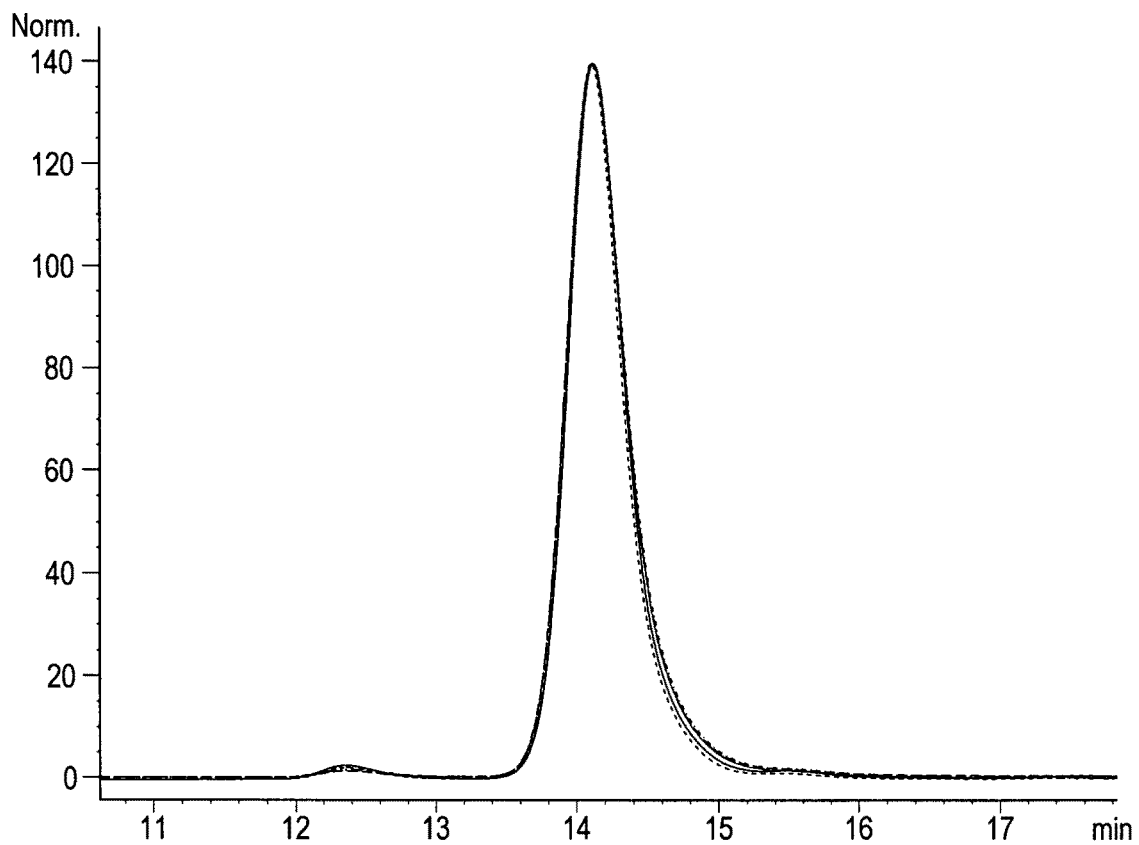
FIG. 56A), stabilized C-Hercules (XWU036; (BHA10 scFv $V_H44$:$V_L100$/$(Gly_4Ser)_4$ C-Hercules.
Figure 56B:
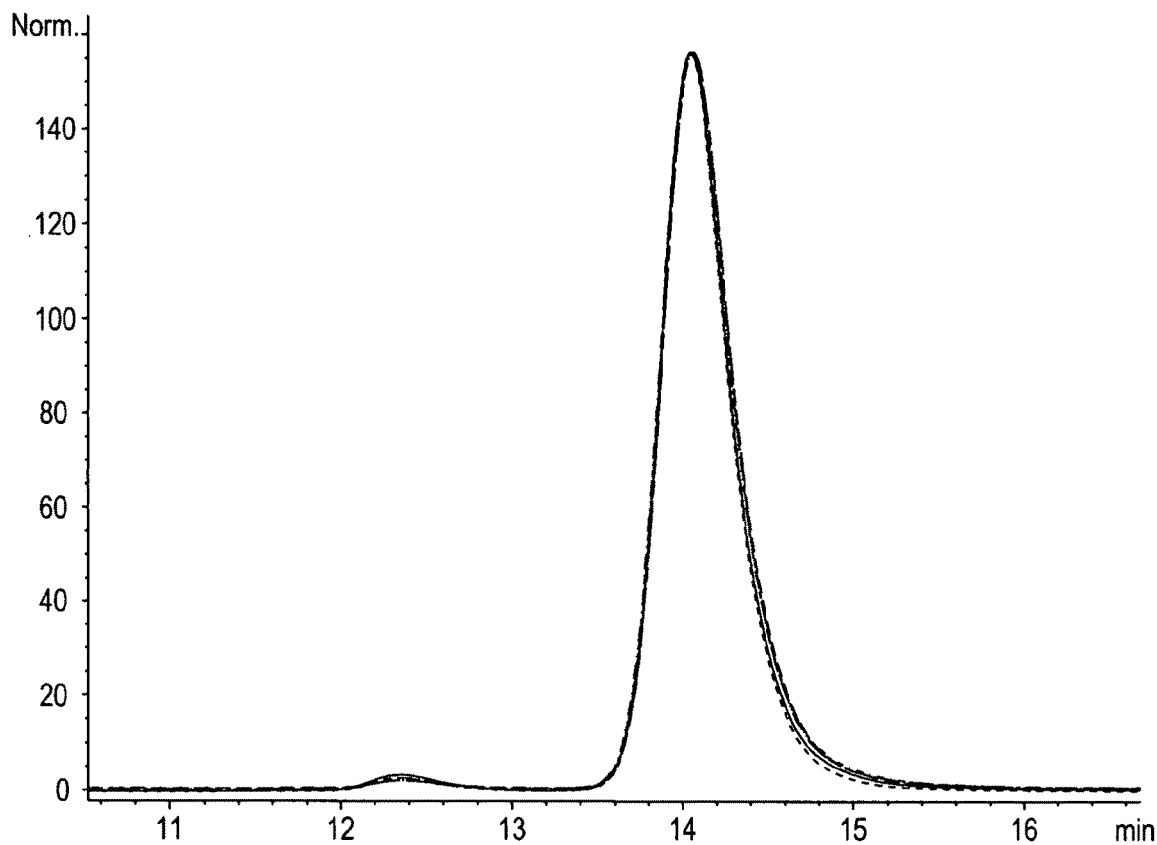
FIG. 56B) and the wild-type BHA10 antibody (FIG. 56C) at six time points (T=0, T=1 week, T=2 weeks, T=1 mo, T=2 mo, and T=3 mo) and low temperatures (2-8° C.). The x-axis is time (minutes) and the y-axis is mAU (absorbance units) at 280 nm. No significant changes in the elution profile were observed over the time course.
Figure 56C:
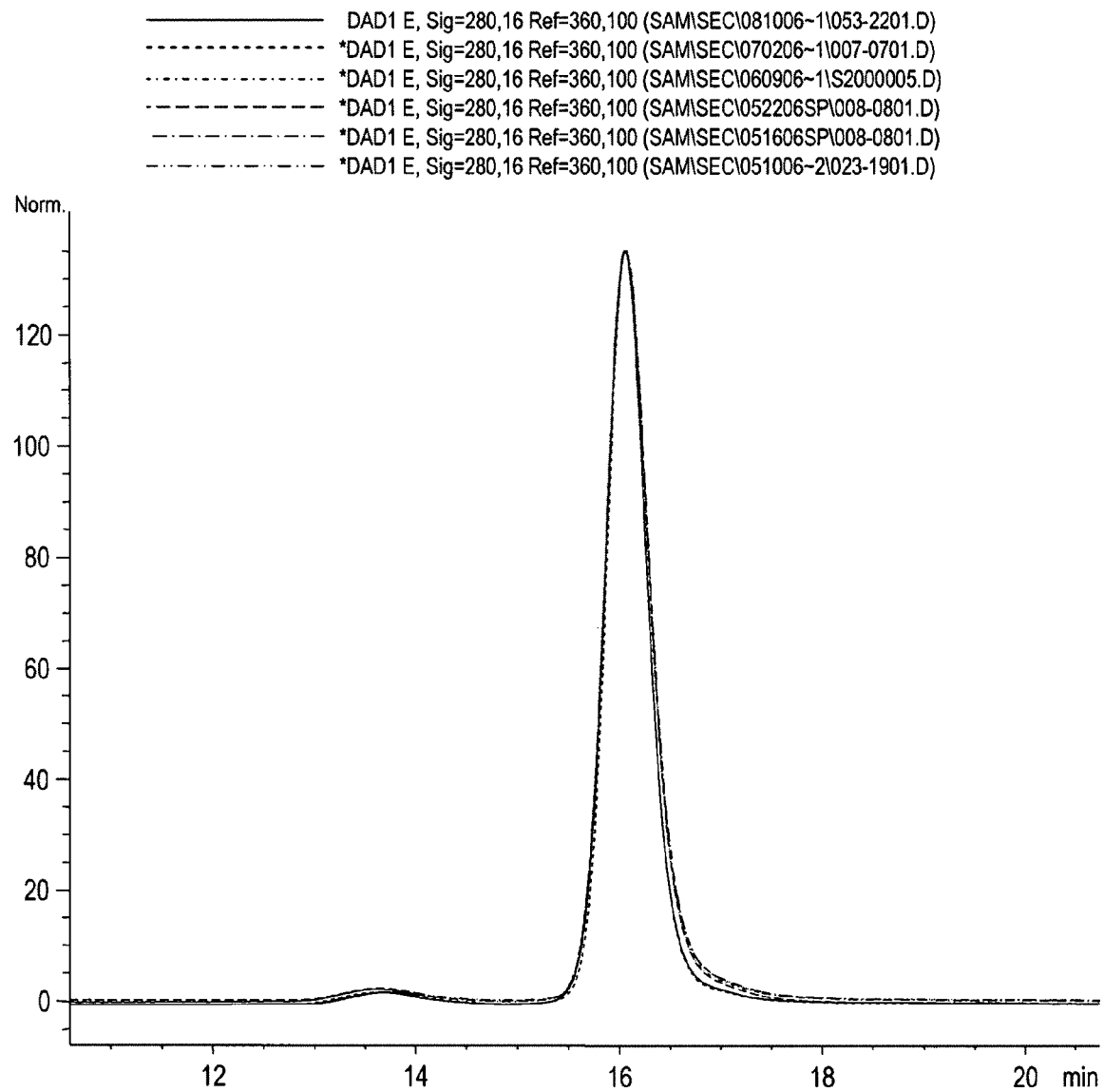
FIG. 56 depicts size-exclusion chromatography (SEC) of high concentrations of stabilized N-Hercules (XWU028; BHA10 scFv $V_H44$:$V_L100$/$(Gly_4Ser)_4$N-Hercules.

Protein aggregation or precipitation was monitored using analytical size exclusion chromatography (SEC) linked to inline light scattering and refractive index detectors (Wyatt Technologies, MiniDawn and rEX, respectively). SEC/Light scattering analysis showed no evidence of aggregation or material loss that might occur through precipitation. The SEC elution profiles of the initial, T=0, and final, T=3 mo, time points for XWU028, XWU036, and the BHA10 antibody were nearly identical (FIGS. 56A, 56B, and 56C, respectively). XWU028 and XWU036 samples both accumulated ~1% aggregated material by the completion of the study; however detection of these aggregates was near the lower limit of detection determined for this method (Table 17). Aggregate formation was independent of protein concentration. Based on the molecular masses determined using light scattering detection, it is possible that that the low levels of aggregates in the test samples are likely a product of monomeric species converting to dimers. Neither of the bispecific antibodies samples, XWU028 or XWU036, accumulated detectable levels of high-order aggregates, even though this type of aggregate would have easily been observed using these methods. The BHA10 antibody demonstrated no increase in aggregates over the 3-month course of the study (Table 17).

TABLE 17

Percent monomer detected using analytical size exclusion chromatography.

|  | T = 0 | T = 1 week | T = 2 week | T = 1 mo | T = 2 mo | T = 3 mo |
|---|---|---|---|---|---|---|
| SEQID#49 Low | 99.0 | 98.7 | 98.4 | 98.3 | 98.2 | 97.9 |
| SEQID#49 High | 99.1 | 99.0 | 98.9 | 98.6 | 98.2 | 98.1 |
| SEQID#51 Low | 98.8 | 97.5 | 97.5 | 97.4 | 97.2 | 96.7 |
| SEQID#51 High | 98.9 | 98.8 | 98.7 | 98.5 | 98.1 | 96.7 |
| BHA10 IgG | 97.4 | 97.5 | 97.5 | 97.5 | 97.3 | 97.5 |

B. Proteolysis and Post-Translational Modification Analyses

Figure 57:
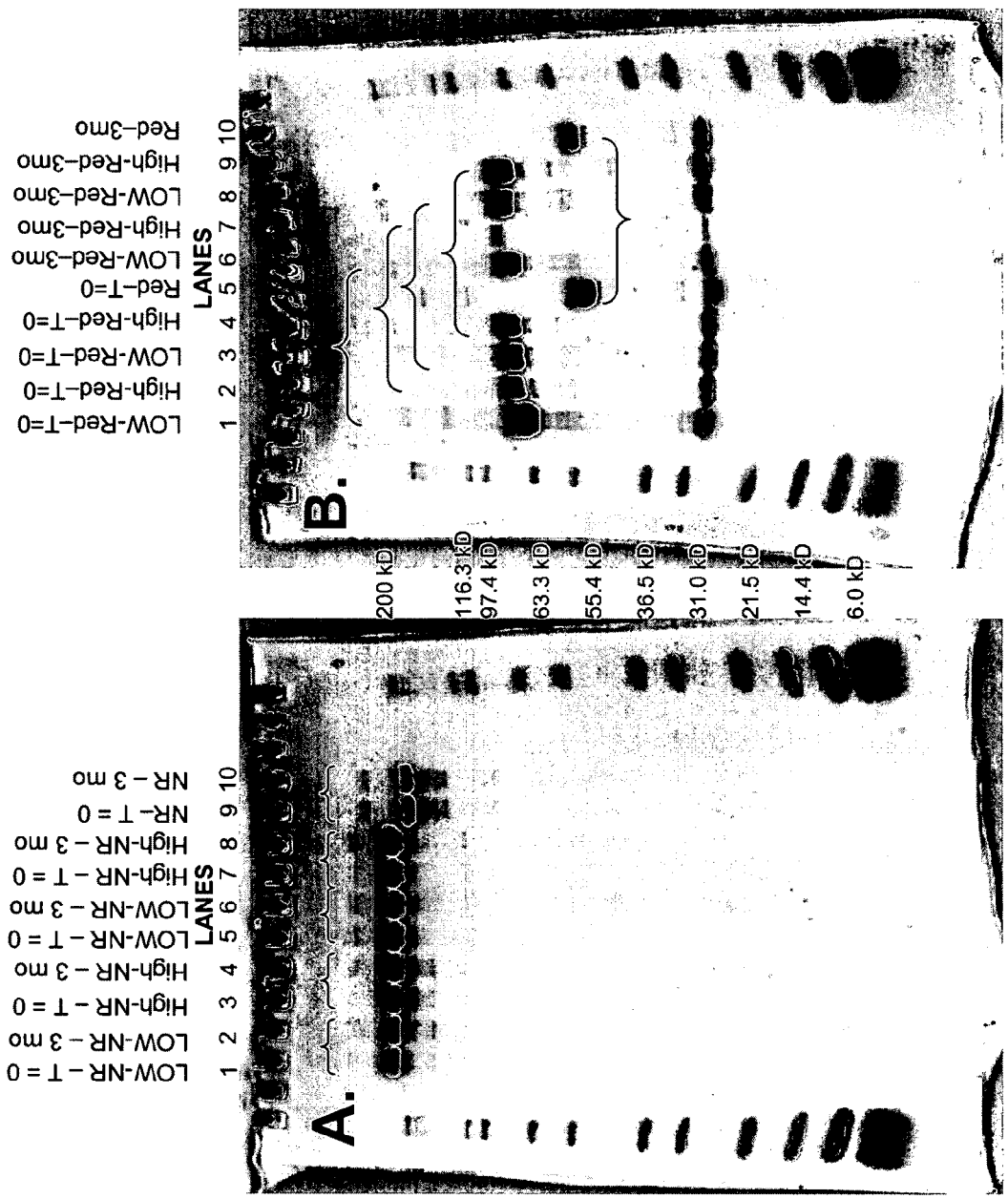
FIG. 57 depicts SDS-PAGE analysis of XWU028 and XWU036 before and after 3 months storage at 2-8° C. Panel A. Samples were unreduced (designated as "NR"). The expected MW, ~200 kDa, is observed for the bispecific samples. BHA10 runs at its expected MW of ~150 kDa. Lanes 1-4 are XWU028 samples. Lanes 5-8 are XWU036 samples. Lanes 9-10 are BHA10 IgG samples. Panel B. Samples were reduced with DTT (designated as "Red" for reduced). The expected MWs of the heavy chain, ~75 kDa, and the light chain, ~25 kDa, are observed for the bispecific samples under reducing conditions. The BHA10 heavy and light chains run at their expected MWs of 50 kDa and 25 kDa, respectively, under reducing conditions. Lanes 1, 2, 6, and 7 are XWU028 samples. Lanes 3, 4, 8, and 9 are XWU036 samples. Lanes 5 and 10 are BHA10 IgG samples.
Figure 58A:
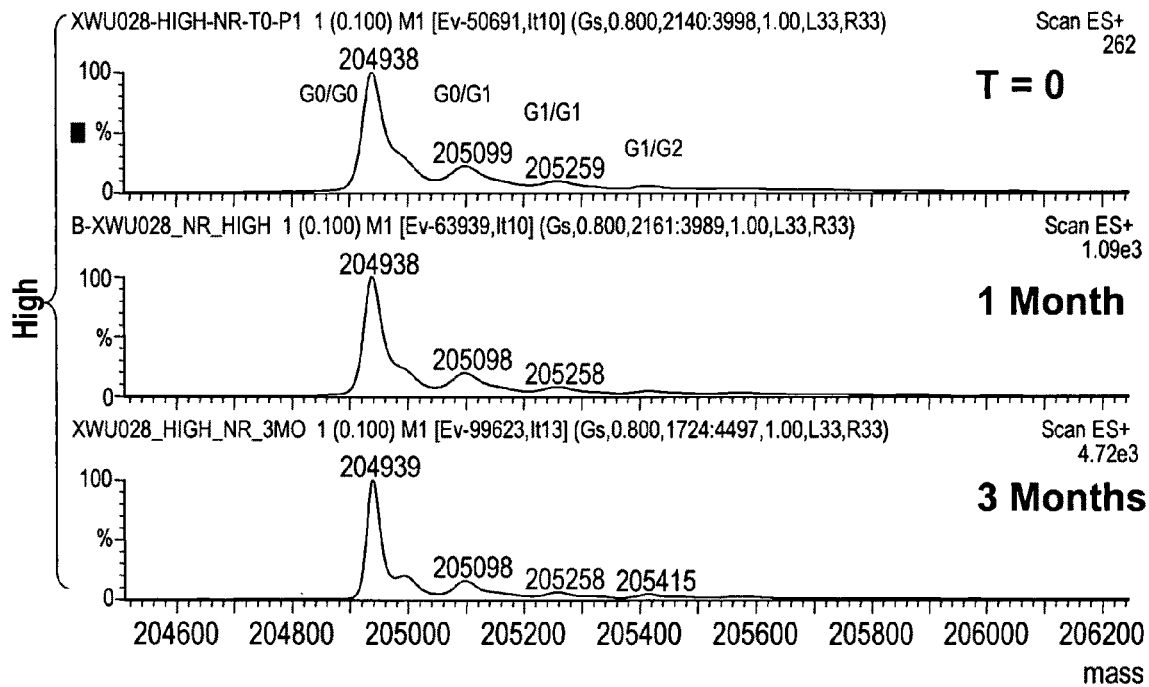
FIG. 58 depicts intact mass analyses of XWU028 (Panel A) and XWU036 (Panel B) at T=0, T=1 mo, and T=3 mo. Multiple peaks are observed for each protein due to various levels of sialylation of the N-linked carbo-hydrates in the CH2. The carbohydrate distribution of the bispecifics is typical of standard IgG1 proteins.
Figure 58B:
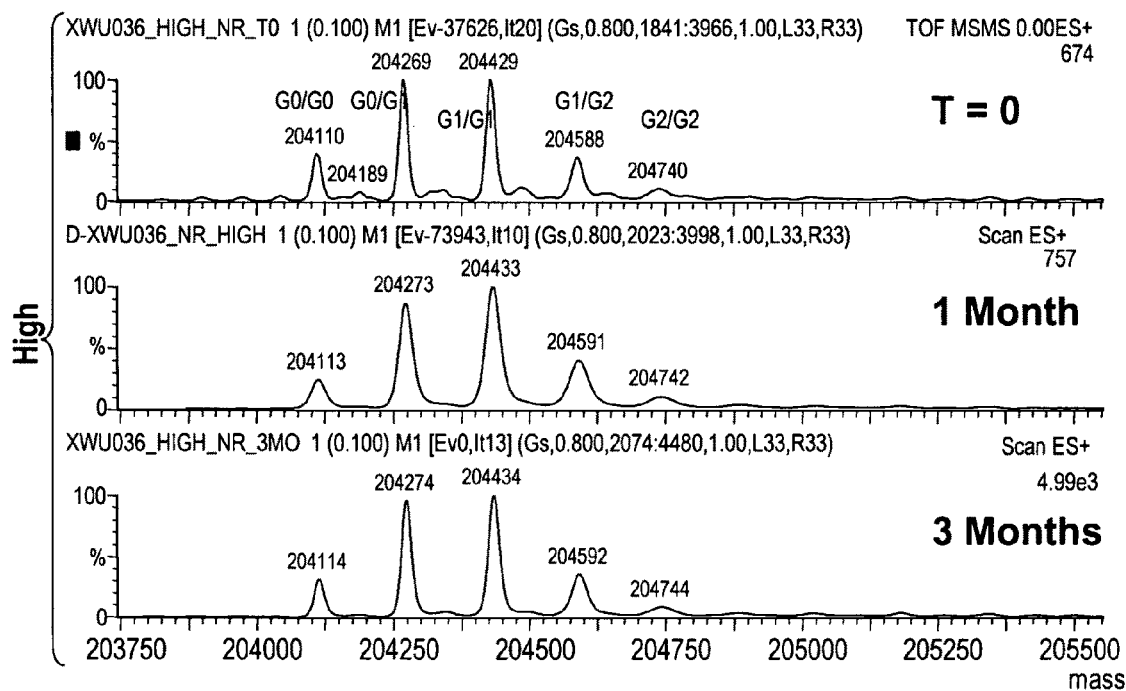

Proteolysis was monitored using SDS-PAGE and liquid chromatography/mass spectroscopy (LC/MS) intact mass analysis (Agilent LC/MSD TOF coupled to an Agilent 1100 LC system via an electrospray interface). For SDS-PAGE analysis, 5 ug of protein was loaded per lane. Reduced samples were prepared in 1× Tris-glycine sample buffer containing 5% β-mercaptoethanol. XWU028 and XWU036 showed no evidence of proteolysis over the 3-month storage period at 2-8° C. as determined by non-reducing and reducing SDS-PAGE analysis (FIGS. 57A and B). Similarly, XWU028 and XWU036 showed no evidence of lower molecular weight proteolytic products over the 3-month storage period at 2-8° C. as determined by LC/MS analysis (FIG. 58).

Post-translational modifications were monitored using LC/MS. T=0, T=1 mo, and T=3 mo samples were analyzed in both the non-reduced and reduced form. Reduced samples were prepared by treating in 50 mM DTT/4M guanidine hydrochloride for 1 hour at 37° C. HPLC Buffer A consists of 0.03% TFA in water and HPLC buffer B contains 0.025% TFA in acetonitrile. Flow rate was kept constant at 100 μl per minute. 7.5 μg of each sample (reduced and non-reduced) was injected onto a 2.1×50 mm C4 column and analyzed by Agilent ESI-TOF. A bind-and-elute method was used for non-reduced samples while a gradient method was used for reduced samples. Spectra were obtained using the Analyst and deconvoluted using the MaxEnt1 software packages included with the instrumentation. Deconvoluted mass spectra of XWU028 and XWU036 (high concentrations) at T=0, T=1 mo, and T=3 mo are shown in FIG. 58. Neither XWU028, nor XWU036, demonstrated any detectable changes in their mass spectra, indicating absence of post-translational modification that could potentially adversely affect bispecific antibody function or stability.

Taken together, the data indicate that both the N- and C-terminal bispecific antibodies containing stabilized scFv domains are stable under extended storage conditions such as those required for biological drug products. These results are particularly encouraging because these stability studies were conducted with the N- and C-terminal bispecific antibodies prepared in a simple buffer (PBS) and not with solutions prepared with optimal formulations.

Example 11

In Vivo Pharmacokinetic Activity and Serum Stability of Bispecific "Hercules" Antibodies A single bolus injection of 10 mg/kg (1 mg/ml) of N-terminal Hercules (XWU028) or C-terminal Hercules (XWU036) diluted in phosphate-buffered saline (PBS) was administered intraperitoneally into male CB 17-scid mice. Mice were sacrificed at 0, 0.5, 2, 6, 24, 48, 72, 96, 168, 240, and 336 hours post-injection using three mice per timepoint for each bispecific antibody. Serum samples were prepared for analysis by ELISA assay to quantify levels of the bispecific antibodies. ELISA plates were coated with goat-anti-human IgG, blocked with PBS/1% BSA, and dilutions of serum containing the bispecific antibodies were serially diluted in PBS/1% BSA, added to the plates and incubated. Captured antibodies were detected with a goat-anti-human kappa chain-HRP-linked antibody. Results of the pharmacokinetic study are shown in Table 18. N-terminal Hercules (XWU028) has an elimination half-life ($t_{1/2}$) of 10.3 days with a peak serum concentration of 85.67 m/ml. C-terminal Hercules (XWU036) has a longer elimination half-life ($t_{1/2}$) of 15.1 days with a peak serum concentration of 105.67 μg/ml. Both molecules have similar volumes of distribution (Vd) though these values have not been adjusted for bioavailability.

TABLE 18

Pharmacokinetic Parameters

| Parameter | Units | N-terminal Hercules (XWU028) Value | C-terminal Hercules (XWU036) Value |
|---|---|---|---|
| T1/2 | hr | 247.9386 | 362.3607 |
| Cmax | ug/ml | 85.67 | 105.67 |
| Vd* | L/kg | 0.1707 | 0.1748 |
| Cl* | ml/min/kg | 0.008 | 0.0056 |

*not adjusted for bioavailability

Figure 59A:
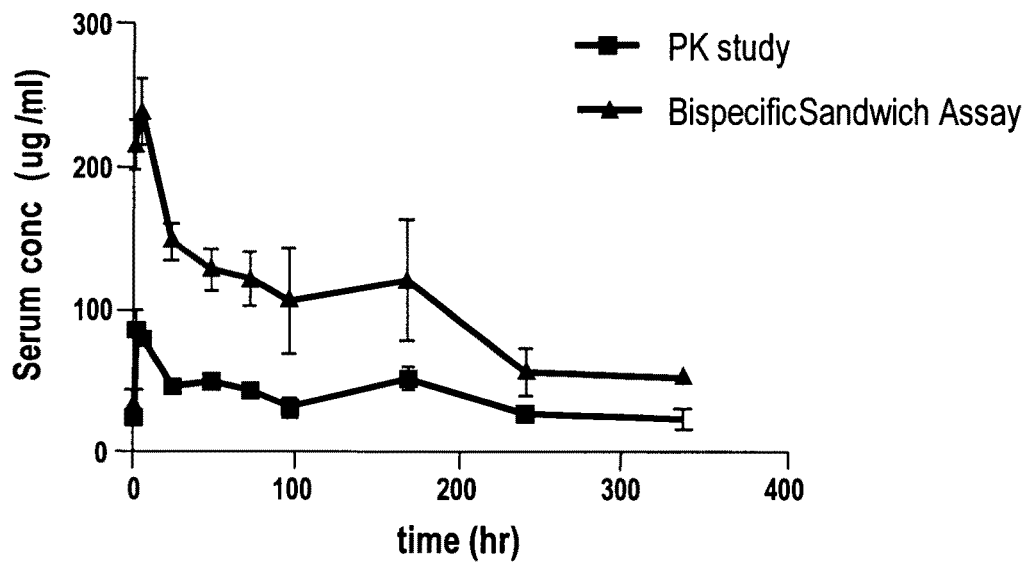
FIG. 59 depicts the results of a sandwich ELISA assay measuring bispecific binding of serum samples containing N-terminal Hercules (XWU028.
Figure 59B:
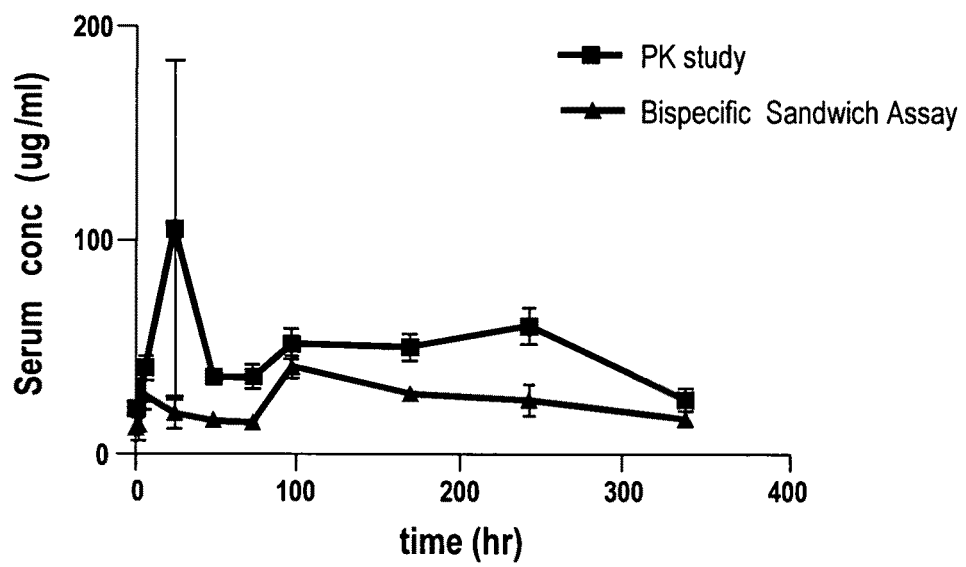

Serum samples were also analyzed in the bispecific binding ELISA described in Example 7. In this assay, the serum samples containing N-terminal Hercules (XWU028) or C-terminal Hercules (XWU036) described above were tested for bispecific binding activity to recombinantly produced TRAIL-R2 and LTβR receptors in an ELISA assay. FIGS. 59A and B show that serum samples from N- and C-terminal Hercules treated mice contain antibodies that bispecifically bind to both TRAIL-R2 and LTβR and closely parallel the elimination profiles observed from the PK study indicating that the bispecific antibodies are remaining intact under physiological conditions for extended periods of time.

Example 12

Figure 60:
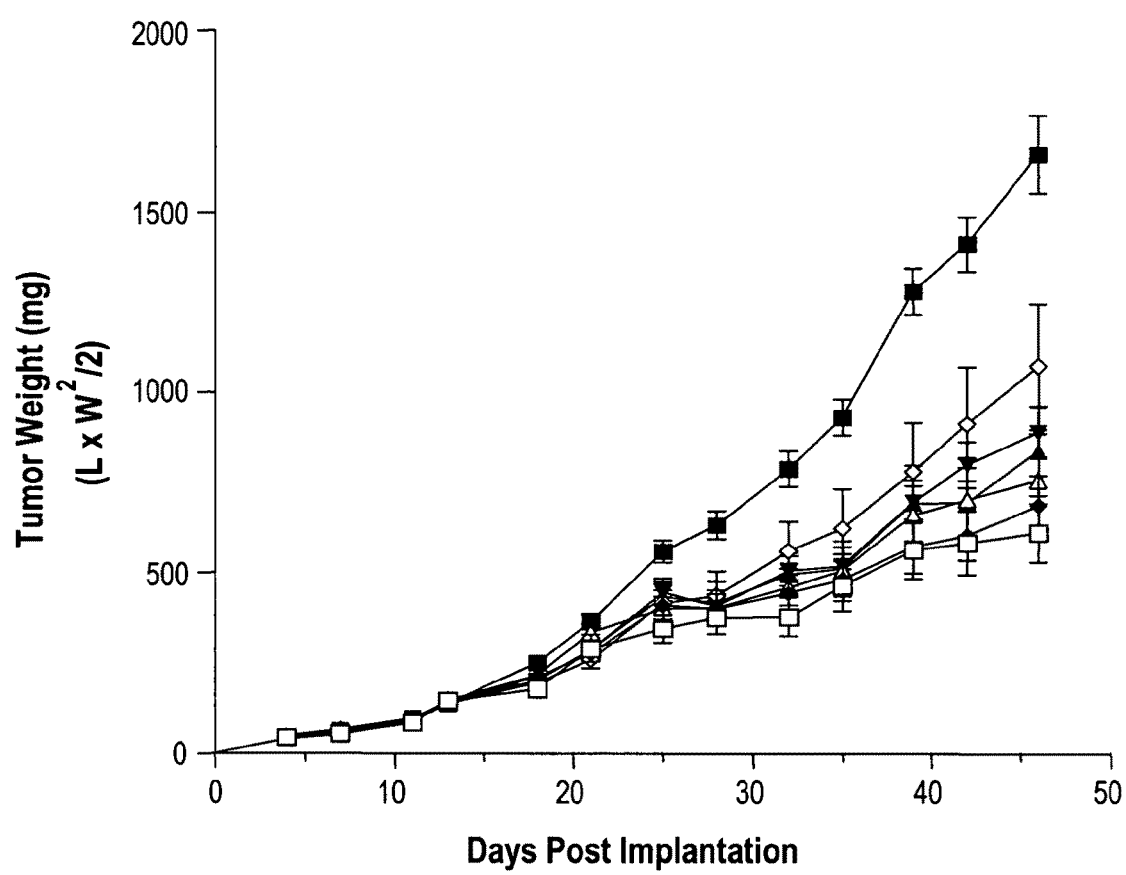
FIG. 60 depicts the results of an experiment evaluating the relative in vivo activity of stabilized bispecific antibodies (XWU028 (diamonds) and XWU036 (open squares)), and monospecific antibodies administered alone ((hCBE11 (closed triangle), hBHA10 (inverted triangle) and ch14A2 (diamond)) and in combination (open triangle) against a tumor xenograft mouse model. Dosing began at day 13. hCBE11 v. VC:P<0.001; hBHA10 v. VC:P<0.001; ch14A2 v. VC:P<0.01; Hercules-II XWU028 v. VC.:P<0.001; Hercules-II XWU028 v.hBHA10:P<0.05; Hercules-II XWU028 v. ch14A2:P<0.005; Hercules-II XWU036 v. VC:P<0.001; Hercules-II XWU036 v. hBHA10:P<0.01; Hercules-II XWU036 v. ch14A2:P<0.05; combo v. V.C.:P<0.001

In Vivo Biological Activity of Bispecific "Hercules" Antibodies (A) In Vivo Biological Activity of Bispecific "Hercules" Antibodies in a Colon Cancer Tumor Model WiDr human colon carcinoma (2×10E6 cells per mouse) cells were implanted subcutaneously into 125 athymic nude mice. The tumors were grown until they reached approximately 100 mg, at which point a total of 70 mice were selected for the study, divided into 7 groups of 10 mice. IP treatments were administered, beginning on day 13 post-implantation, as follows: Group 1=pyrogen-free PBS; Group 2=CBE11, 2 mg/kg, 1×/wk; Group 3=hBHA10, 2 mg/kg, 2×/wk; Group 4=ch14A2, 2 mg/kg, 2×/wk; Group 5=Hercules-II XWU028, 2 mg/kg, 1×/wk; Group 6=Hercules-II XWU036, 2 mg/kg, 1×/wk; Group 7=hBHA10+ch14A2, 1 mg/kg each, 2×/wk. Tumor sizes and body weights were recorded bi-weekly. Study was terminated when average tumor size of vehicle group reached approximately 2000 mg. Tumor volume was calculated using the formula: ($L \times W^2/2$). Interim analyses of mice treated with the XWU028 and XWU036 showed significant anti-tumor activity ($p<0.001$) for both bispecific antibodies compared to PBS vehicle control (FIG. 60).

For XWU028, significant anti-tumor responses ($p<0.05$) were observed compared to responses with single hBHA10 or ch14A2 mAb treatment. For XWU036, a significant anti-tumor response ($p<0.05$) was observed compared to the response with ch14A2 mAb treatment and, notably, a greater significant response ($p<0.01$) compared to hBHA10 mAb. Importantly, the bispecific antibodies showed superior in vivo anti-tumor activity though administered only once per week suggesting that the stability enhancements described in this invention result in improved antibody properties and physical stability under physiological conditions.

Figure 86:
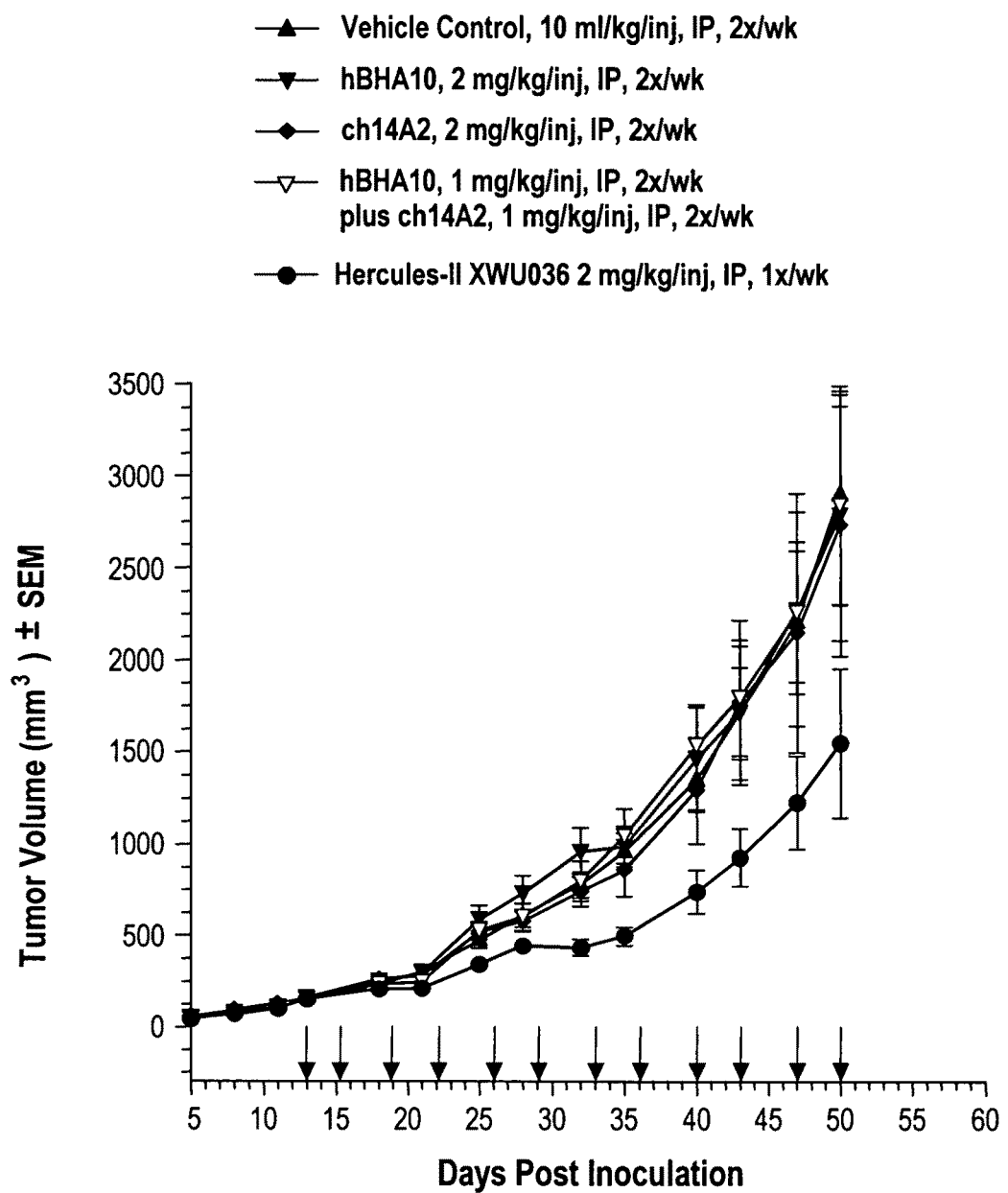
FIG. 86 depicts the results of an experiment evaluating the relative in vivo activity of stabilized bispecific "Hercules-II" antibodies (XWU036 (closed circle)) and monospecific antibodies administered alone (hBHA10 (inverted closed triangle) and ch14A2 (closed diamond)) and in combination (open inverted triangle) against a tumor xenograft mouse model of human breast cancer (MDA-MB-231).

(B) In Vivo Biological Activity of Bispecific "Hercules" Antibodies in a Breast Cancer Tumor Model MDA-MB-231 human breast carcinoma cells were implanted subcutaneously into 135 athymic nude mice (2×10E6 cells per mouse). The tumors were grown until day 13 at which point 75 tumor-bearing mice with an average size of approximately 168 mg were assigned to treatment (N=10) and vehicle control (N=15) groups. Mice received antibodies and vehicle IP starting at day 13. Exemplary groups are shown as follows: Group 1=pyrogen-free PBS; 1×/wk; Group 2=hBHA10, 2 mg/kg, 2×/wk; Group 3=ch14A2, 2 mg/kg, 2×/wk; Group 4=Hercules-II XWU036, 2 mg/kg, 1×/wk; Group 5=hBHA10+ch14A2, 1 mg/kg each, 2×/wk. Tumor sizes and body weights were recorded bi-weekly. Study was terminated when average tumor size of vehicle group reached approximately 2800 mg. Tumor volume was calculated using the formula: ($L \times W^2/2$). XWU036 demonstrated statistically significant ($p<0.001$) anti-tumor activity compared to either single treatment with hBHA10 or ch14A2 mAbs or to treatment with a mixture of the two antibodies. Importantly, the bispecific antibody XWU036 demonstrated good anti-tumor activity in vivo administered on a once per week dosing schedule suggesting that the stability enhancements described in this invention result in improved antibody properties and physical stability under physiological conditions (see FIG. 86).

Example 13

Production of Stabilized Bispecific "Hercules" Antibodies Containing Non-Covalent Stabilizing scFv Mutations BHA10 scFvs of the invention containing non-covalent stabilizing mutations alone and in combination with a $V_H44$-$V_L100$ disulfide bond were used to construct stabilized bispecific C-Hercules antibodies comprising a fusion of chimeric 14A2 IgG antibody that binds to TRAIL R2 receptor with a BHA10 scFv that binds to LTβR. The bispecific antibodies were constructed as C-terminal BHA10 scFv fusions using methods essentially as described in Example 7.

A. Construction of C-Hercules Bispecific Antibody with BHA10 VH S16E+$V_L$ S46L and $V_H44$-$V_L100$/V S16E+$V_L$ S46L scFvs PCR was used to amplify variant BHA10 scFv gene fragments from plasmid DNAs pIEH-050 (parent plasmid of the high expression plasmid pIEH076) and pIEH-052 (parent plasmid of the high expression plasmid pIEH080) containing the BHA10 $V_H$ S16E+$V_L$ S46L and $V_H44$-$V_L100$/$V_H$ S16E+$V_L$ S46L scFvs, respectively using the oligonucleotide primers described in Table 19. The variant BHA10 scFv gene fragments were gel isolated. Due to a BamHI site in the linker region of plasmids pIEH-050 and pIEH-052, the gene fragments were digested with pPuM I and Kpn I restriction endonucleases and ligated to the modified plasmid pN5KG1 digested with the same restriction endonucleases resulting in a fusion product of the stabilized anti-LTBR (BHA10) scFvs to the carboxyl terminus of the anti-TRAILR2 (14A2) antibody CH3 domain through a 16 amino acid Ser(Gly$_4$Ser)$_3$ linker. Correct sequences were confirmed by DNA sequence analysis.

TABLE 19

Oligonucleotides for PCR amplification of BHA10 V$_H$ S16E + V$_L$ S46L and V$_H$44-V$_L$100/V$_H$ S16E + V$_L$ S46L scFvs.

| | |
|---|---|
| pXWU006-F1 (SEQ ID NO: 56) | 5'-GGGGGTGGATCCGGTGGAGGGGCTCCGGCGGTGGCGG GTCC CAGGTCCAACTGGTGCAGTCTG -3' |
| XWU006-R1 (SEQ ID NO: 57) | 5'-GTTAAC<u>GGATCCTC</u>ATTTGATCTCCACCTTGG -3' |

Fusion of BHA10 scFv V$_H$ S16E+V$_L$ S46L gene sequence to the carboxyl terminus of the anti-TRAIL R2 antibody heavy chain gene sequence produced plasmid pXWU054. Fusion of BHA10 scFv V$_H$44-V$_L$100N$_H$S16E+V$_L$ S46L gene sequence to the carboxyl terminus of the anti-TRAIL R2 antibody heavy chain gene sequence produced plasmid pXWU055.

The ligation mixtures were used to transform E. coli strain TOP 10 competent cells (Invitrogen Corporation, Carlsbad, Calif.). E. coli colonies transformed to ampicillin drug resistance were screened for presence of inserts. DNA sequence analysis confirmed the correct sequence of the final constructs. The chimeric 14A2 light chain DNA (SEQ ID NO:28) and amino acid sequences (SEQ ID NO:29) are shown in FIGS. 15A and 15B. The heavy chain DNA (SEQ ID NO:52) and amino acid sequence (SEQ ID NO:53) for C-Hercules BHA10 scFv V$_H$ 516E+V$_L$ S46L bispecific antibody are shown in FIGS. 61 and 62, respectively. The heavy chain DNA (SEQ ID NO: 54) and amino acid sequence (SEQ ID NO:55) for C-Hercules BHA10 scFv V$_H$44-V$_L$100/V$_H$ S16E+V$_L$ S46L bispecific antibody are shown in FIGS. 63 and 64, respectively. The heavy chains employed the same signal peptide as used previously.

B. Stable Expression of Bispecific Antibodies in CHO cells, Antibody Purification, and Characterization.

Figure 65:
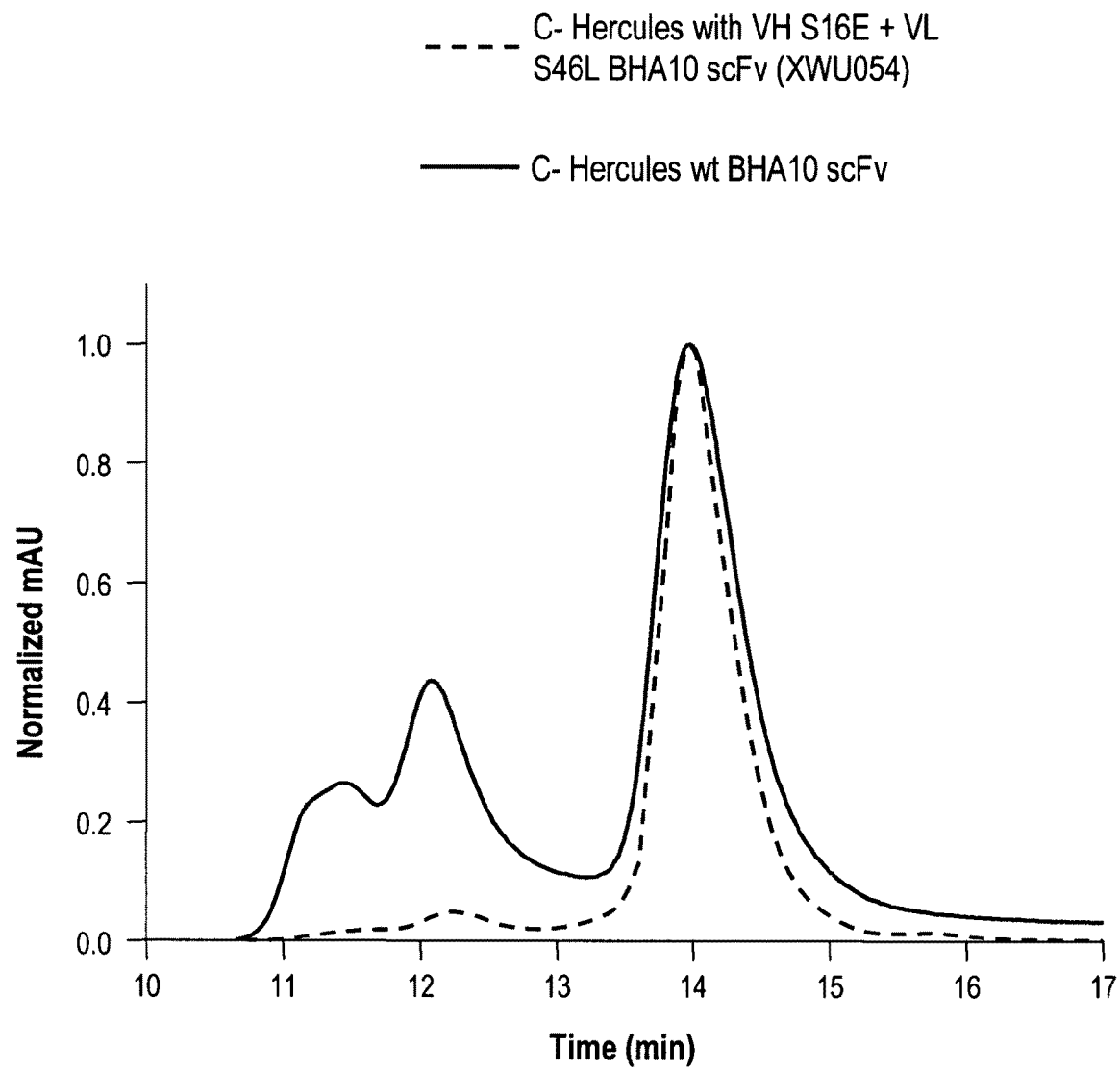
FIG. 65 depicts the results of analytical size exclusion chromatography (SEC) of Protein A eluates from supernatants containing C-Hercules with the stabilized $V_H$ S16E+$V_L$ S46L BHA10 scFv (XWU054) and C-Hercules with conventional ("WT") BHA10 scFv.

DHFR-deficient CHO cell lines stably transfected with plasmid DNAs pXWU054 and pXWU055 and adapted to serum-free conditions were scaled for production of bispecific antibody protein and proteins purified as described in Example 8. Protein A eluates from supernatants containing C-Hercules with the stabilized V$_H$ S16E+V$_L$ S46L BHA10 scFv and C— bispecific antibody with the stabilized V$_H$44-V$_L$100N$_H$ S16E+V$_L$ S46L BHA10 scFv were examined for the presence of aggregates by analytical size exclusion chromatography (FIG. 65). The chromatogram profile of C-Hercules containing the conventional BHA10 scFv showed ~40% aggregates. In contrast, C-terminal Hercules with the stabilized V$_H$ S16E+V$_L$ S46L BHA10 scFv significantly reduced aggregates to levels comparable to that observed with standard IgGs.

FIGS. 66A and 66B show SDS-PAGE gels of purified C-terminal Hercules with the V$_H$ S16E+V$_L$ S46L BHA10 scFv and C-terminal Hercules with the V$_H$44:V$_L$100N$_H$ S16E+V$_L$ S46L BHA10 scFv, respectively. The reduced lanes show the expected sizes of the heavy and light chain proteins. Importantly, there is no significant level of degraded or unwanted lower molecular weight byproducts that has often been observed with Hercules containing wild type scFv domains.

Figure 67A:
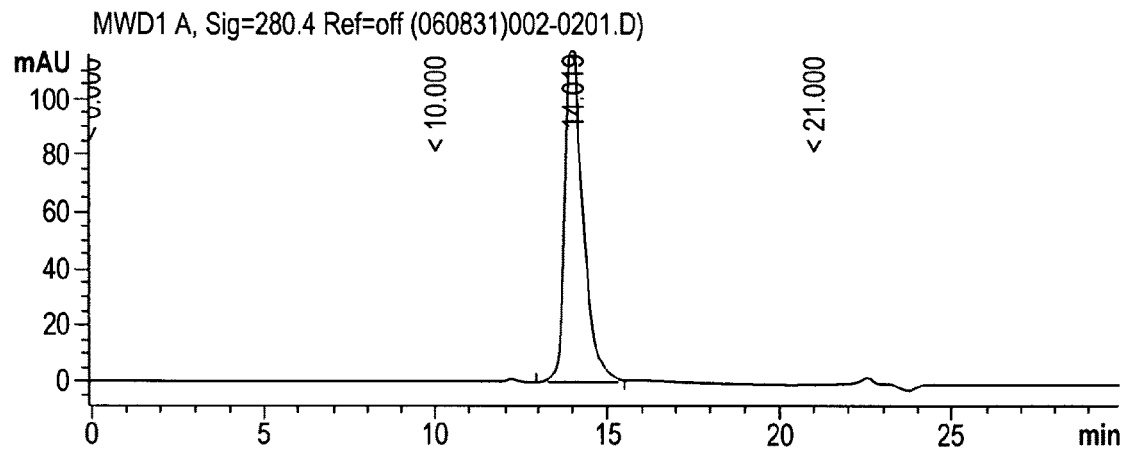
FIG. 67 shows the analytical SEC elution profiles of C-terminal Hercules with the $V_H$ S16E+$V_L$ S46L BHA10 scFv (FIG. 67A) and C-terminal Hercules with the $V_H44$:$V_L100$/$V_H$ S16E+$V_L$ S46L BHA10 scFv (FIG. 67B) subsequent to the initial protein A purification step.
Figure 67B:
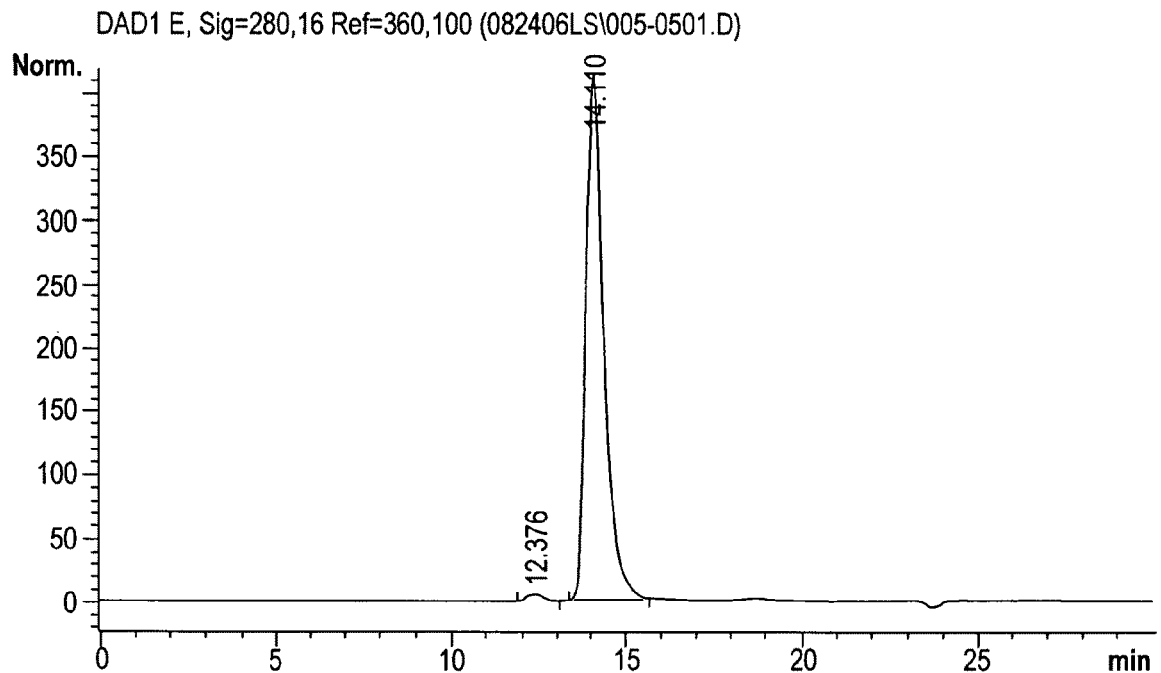

FIGS. 67A and 67B show the analytical SEC elution profiles of C-terminal Hercules with the V$_H$ S16E+V$_L$ S46L BHA10 scFv and C-terminal Hercules with the V$_H$44: V$_L$100N$_H$ S16E+V$_L$ S46L BHA10 scFv, respectively, subsequent to the initial protein A purification step. These studies demonstrate that stabilization of the BHA10 scFv by addition of V$_H$ S16E+V$_L$ S46L mutations alone and in combination with the V$_H$44:V$_L$100 disulfide results in preparative quantities of >98% pure, monomeric Hercules bispecific antibody that is essentially free of higher order molecular weight species.

Example 14

Biological Activity of Bispecific "Hercules" Antibodies Containing Non-Covalent Stabilizing scFv Mutations In vitro biological activity of C-terminal Hercules with the V$_H$S16E+V$_L$ S46L BHA10 scFv (XWU054) and C-terminal Hercules with the V$_H$44:V$_L$100/V$_H$ S16E+V$_L$ S46L BHA10 scFv (XWU055) were tested in the tumor cell proliferation assay as described in Example 7.

Figure 68A:
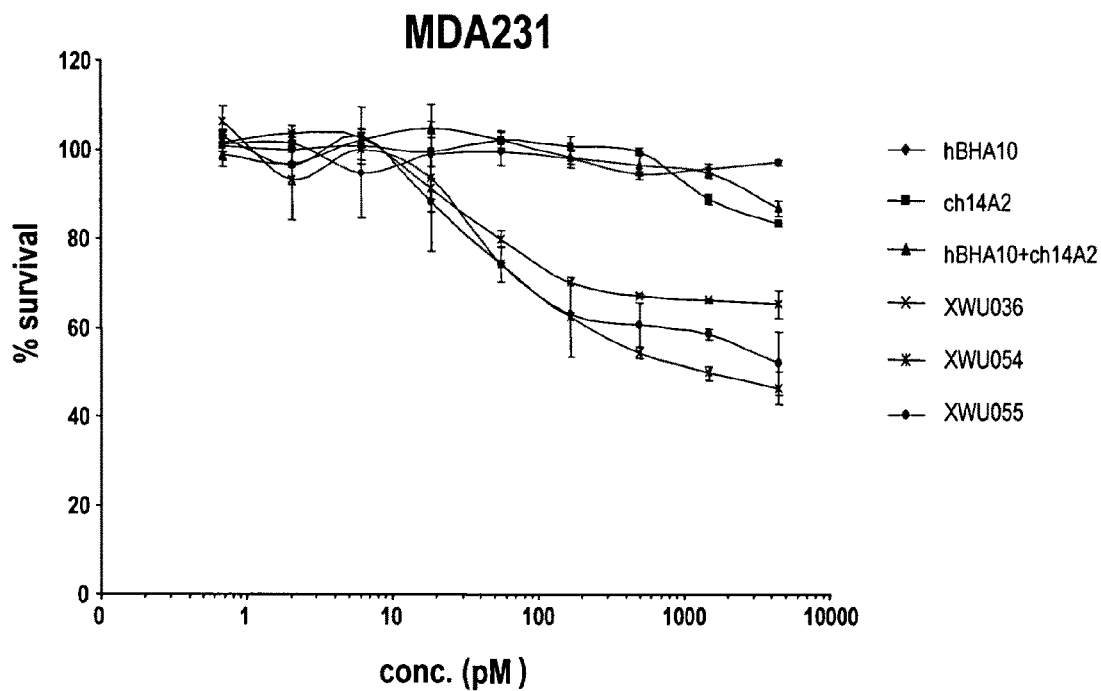
FIG. 68 shows the results of in vitro tumor cell proliferation assays of the activity of C-terminal Hercules with the $V_H$ S16E+$V_L$ S46L BHA10 scFv (XWU054) and C-terminal Hercules with the $V_H44$:$V_L100$/$V_H$ S16E+$V_L$ S46L BHA10 scFv (XWU055). Both MDA231 (FIG. 68A) and WiDr cells (FIG. 68B) were administered antibody. Activity for both Hercules antibodies was compared with stabilized XWU036 bispecific antibody and corresponding monospecific antibodies (hBHA10 and ch14A2) administered alone or in combination.
Figure 68B:
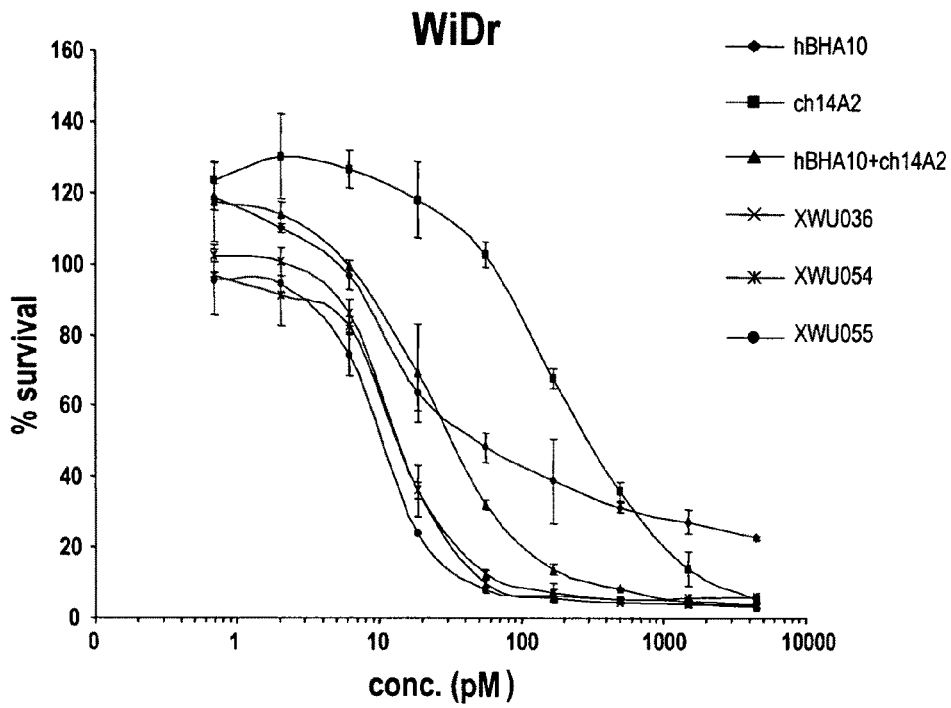

Results from these studies are shown in FIG. 68. FIG. 68B shows that 14A2 IgG antibody had moderate activity in inhibiting growth of WiDr tumor cells and in combination with BHA10 IgG exhibited a slight increase in anti-tumor cell activity compared to BHA10 IgG alone. In contrast, both of the bispecific Hercules antibodies (XWU054 and XWU055) showed enhanced tumor cell killing of the WiDr cells comparable to that observed with the XWU036 molecule (C-terminal Hercules with the V$_H$44:V$_L$100/(Gly$_4$Ser)$_4$ linker stabilized BHA10 scFv) described in Example 10. FIG. 68A shows that both the 14A2 IgG and BHA10 IgG antibodies had negligible activity in inhibiting growth of MDA231 tumor cells as single agents as well as when used in combination. In contrast, the bispecific Hercules antibodies (XWU054 and XWU055) showed enhanced tumor cell killing of the MDA231 cells comparable to that observed with the XWU036 molecule (C-terminal Hercules with the V$_H$44: V$_L$100/(Gly$_4$Ser)$_4$ linker stabilized BHA10 scFv) described in Example 10.

Example 15

Utilization of Differential Scanning calorimetry (DSC) to Measure Thermal Stability of Human or Humanized Antibody Sequences To assess the range of apparent stabilities of antibodies, differential scanning calorimetry (DSC) was performed on a set of 17 human or humanized BIIB antibodies.

The BIIB antibodies were dialyzed exhaustively against a 20 mM sodium citrate, 150 mM sodium chloride buffer at pH 6.0. Dialysates were used within the reference cell of a calorimeter to define the baseline of each antibody scan. Subsequent to dialysis, the concentrations of BIIB1-17 were measured by 280 nm absorbance (Pace et al., *Protein Sci.* 4, 2411-2423, 1995). Antibody solutions used for DSC were universally prepared at 1 mg/mL by diluting the concentrated stocks with their dialysates.

Scans were performed using an automated capillary differential scanning calorimeter (capDSC, MicroCal, LLC). Protein and reference solutions were sampled automatically from 96-well plates using the robotic attachment. Prior to each protein scan, 2 scans were performed with buffer in the sample cell and used for background subtraction. A single cleaning scan was performed using 5% Liquinox after every protein scan. After every scan, the instrument automatically rinsed both the reference and sample cells with 3X-2 mL distilled deionized H$_2$O containing 0.01% sodium azide. Scans were performed at 1° C./min using the medium feedback mode for enhanced peak resolution. The scan range was 20-95° C. All 96-well plates containing protein were stored within the instrument at 6° C.

Scans were analyzed using the Origin software supplied by the manufacturer. Subsequent to background subtraction, non-zero baselines were corrected using a third order polynomial. The unfolding transitions of each IgG1 domain were deconvoluted by fitting the multi-peak curves to 3 separate transitions. Recombinant IgG1 and IgG4 Fcy domains were utilized to identify the C$_H$2 and C$_H$3 peaks within each transition. The remaining transition(s) was assumed to correspond to the unfolding of the Fab portion of the antibody.

Figure 69A:
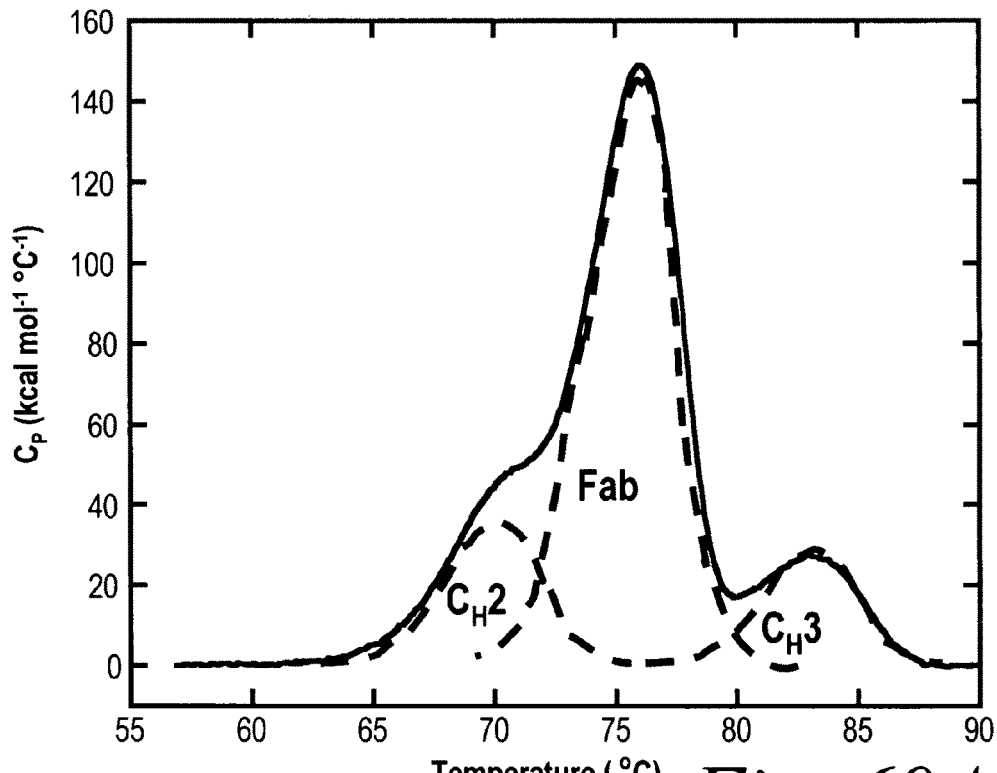
FIG. 69A depicts a DSC unfolding curve of BIIB7 IgG1 taken under conditions identical to those used for the remaining 18 BIIB human(ized) antibodies (solid line). The individual Fab, $C_H2$ and $C_H3$ transitions apparent within the DSC curve are labeled and sketched with dotted lines.

Most of the Fab portions of the 17 antibodies unfolded in apparent single transitions with midpoints of thermal unfolding (T$_M$s) ranging from 57 to 82° C. depending on the unique properties of each individual Fv. Only three antibodies, BIIB15, BIIB16, and BIIB17 exhibited 4 transitions. A typical IgG1 DSC trace is shown in FIG. 69A. The C$_{Pmax}$ (i.e. the height of a DSC peak) for Fab portions is generally significantly greater than that of the C$_H$2 or C$_H$3 domains. This is reasonable considering the Fab protein mass within an antibody is 4-fold greater than that of either the C$_H$2 or the C$_H$3 domains, and the Fab portion of the antibody also contains buried surface area between 4 domains as opposed to the C$_H$2 and C$_H$3 domains whose transitions each involve the disruption of only a single homodimeric interface. In general, the transitions observed for the C$_H$2 and C$_H$3 domains of each IgG1 antibody superimposed well upon one another. The same is true for the C$_H$2 and C$_H$3 domains of the 3 IgG4s. For these reasons, the Fab transitions of each IgG1 or IgG4 molecule were readily identified. One antibody (BIIB18) was not studied by DSC. BIIB18 expressed poorly and never resulted in soluble/non-aggregated material. This antibody was included in the sequence analyses described in Example 16.

Figure 69B:
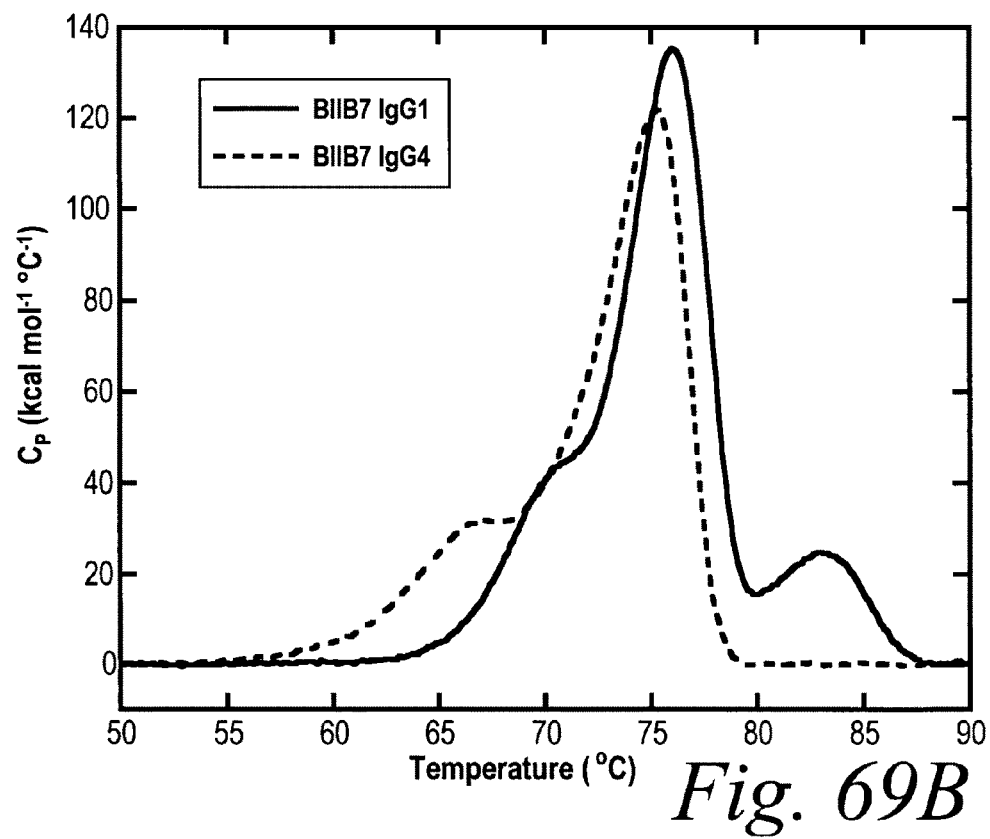
FIG. 69B depicts the DSC unfolding curves of the BIIB7 antibody in both the IgG1 and IgG4 formats.

One of the antibodies, BIIB7, was analyzed in both the human IgG1 and IgG4 format. The apparent Fab thermostabilities of BIIB7 in the IgG1 and IgG4 format as measured by the midpoints of their thermal unfolding transitions (T$_M$) were very similar (see FIG. 69B). Variation in the constant domain subclass did not affect the Fab T$_M$ or Fab calorimetric unfolding enthalpy.

The overlapping transitions corresponding to the C$_H$2 and C$_H$3 domains of the IgG4 Fc occur at significantly lower temperatures than those of IgG1 and artificially make the Fab transitions look ~1-2° C. lower for IgG4. Once the IgG transitions are completely deconvoluted, the Fab T$_M$s are much closer than they appear in the DSC traces ($\Delta$T$_M$<1° C.). The fact that the Fab DSC curves of BIIB7 in the IgG1 and IgG4 formats were highly similar suggests that the thermostability of the IgG1 Fabs and IgG4 Fabs can be directly compared.

DSC measurements with 17 of the humanized BIIB antibodies indicate that the Fv regions heavily influenced the apparent stability of their respective Fabs. For example, FIG. 70 demonstrates the very different DSC curves obtained for BIIB1, BIIB4, BIIB6 and BIIB16. All four antibodies are IgG1, and the only sequence differences between them reside in the Fv region. The position and magnitude of the C$_H$2 and C$_H$3 DSC transitions of all 17 antibodies are independent of the Fab to which they are attached (see FIG. 70). The range of Fab T$_M$s for the top 17 antibodies in Table 20 was between 57.2 and 81.6° C. (±24.4° C.), with BIIB1 exhibiting the highest apparent Fab stability and BIIB17 the lowest.

Figure 70:
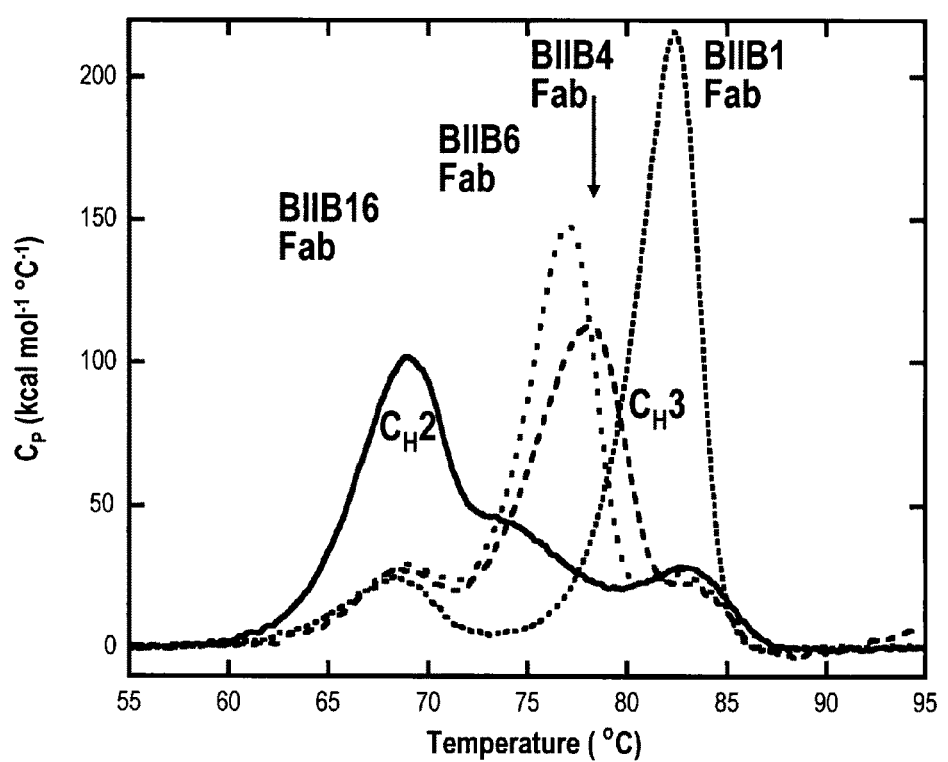
FIG. 70 depicts thermal unfolding curves of four human (ized) IgG1 antibodies, BIIB16, BIIB6, BIIB4 and BIIB1. The unfolding transitions of the $C_H2$ and $C_H3$ domains for all four IgG1 constructs are identical, while the Fab unfolding transitions are highly variable.

The three antibodies with the lowest measurable Fab T$_M$ values, BIIB15, BIIB16, and BIIB17, demonstrate a disconnect between domain unfolding transitions within the Fab (See FIG. 70 for BIIB16's DSC curve). The expected Fab peak was split into two separate transitions. The lower T$_M$ transitions were listed in Table 20, but a second transition, which may represent the unfolding of the C$_H$1/C$_L$ structural unit, occurred with T$_M$s of 74, 72 and 70° C. for BIIB15, BIIB16 and BIIB17, respectively. BIIB18 was included in the study as an example of an antibody which would not express and whose V$_H$ sequence diverged significantly from consensus (see Example 16).

The DSC analyses clearly showed that the unique properties of individual Fv-regions can highly attenuate the apparent T$_M$ of an entire Fab portion of an antibody. In the extreme cases of BIIB15, BIIB16 and BIIB17, the apparent Fv stabilities were low enough that the unfolding transitions of the domains within the Fab portion became uncoupled from one another. In order to maintain an apparent single transition for the unfolding of all four domains of the Fab, there may be a minimum overall T$_M$ limit (>70° C. for IgG1s under the scan conditions described here), otherwise multiple transitions appear. It would be convenient to assign the low temperature unfolding transitions of BIIB15, BIIB16, and BIIB17 to the Fv and the second, higher temperature transitions, to the C$_H$1/C$_L$ domain. However, Ewert and coworkers have shown that V$_H$/V$_L$ domain unfolding is not always coupled and can depend on subclass, V$_H$/V$_L$ stability, and V$_H$/V$_L$ complementarity (Ewert et al., *J. Mol. Biol.* 325: 531-553, 2003). In fact, very few of their V$_H$/V$_L$ scFv constructs with consensus-derived frameworks exhibited cooperative unfolding. Therefore, it is likely that, as the transitions uncouple, the unfolding scenario may be more complicated than a simple split into two transitions representing the Fv-region and C$_H$1/C$_L$-regions.

The apparent stabilities as measured by DSC for the BIIB7 IgG1 and IgG4 Fabs were highly similar even though there are substantial inherent differences in C$_H$1 sequence and disulfide-bonding between the two subclasses. There are many possible explanations for this such as (1) the biophysical properties of the Fv set the thermostability ceiling of the BIIB7 Fab regardless of whether the C$_H$1 is IgG1 or IgG4, (2) the apparent stability of the C$_H$1/C$_L$ region is identical between IgG1 and IgG4, or (3) the C$_H$1/C$_L$ structural unit does not unfold within the timeframe of the DSC experiment. The fact that the BIIB7 Fab unfolded at a single T$_M$ and with a similar calorimetric enthalpy in both the IgG1 and IgG4 formats suggests a potential stability dependence upon the Fv and not the constant regions

TABLE 20

BIIB IgG Fab T$_M$-values, V$_H$ and V$_κ$ scores and germlines.

| IgG | Fab T$_M$ (° C.) | V$_H$ sub-class | V$_H$ germline[a] | V$_H$ score | V$_H$ subclass score | Δscore | V$_κ$ sub-class | V$_κ$ germline[a] | V$_κ$ score |
|---|---|---|---|---|---|---|---|---|---|
| BIIB1 | 81.6 | VH1 | X92340VH1 | 58.8 | 70.1 +/− 3.1 | +3.7 | VK1 | M64855VK1 | 78.2 |
| BIIB2 | 78.5 | VH1 | X92340VH1 | 72.2 | 70.1 +/− 3.1 | +2.1 | VK1 | M64855VK1 | 72.8 |

TABLE 20-continued

BIIB IgG Fab T$_M$-values, V$_H$ and V$_\kappa$ scores and germlines.

| IgG | Fab T$_M$ (° C.) | V$_H$ sub-class | V$_H$ germline[a] | V$_H$ score | V$_H$ subclass score | Δscore | V$_\kappa$ sub-class | V$_\kappa$ germline[a] | V$_\kappa$ score |
|---|---|---|---|---|---|---|---|---|---|
| BIIB3 | 78.2 | VH1 | AB019438VH1 | 72.6 | 70.1 +/− 3.1 | +2.5 | VK2 | X12684VK2 | 82.4 |
| BIIB4 | 77.7 | VH3 | M99649VH3 | 96.1 | 92.2 +/− 4.5 | +3.9 | VK2 | X12684VK2 | 83.9 |
| BIIB5 | 77.1 | VH2 | X56365VH4 | 69.8 | 68.1 +/− 5.5 | +1.7 | VK1 | X59316VK1 | 83.0 |
| BIIB6 | 76.8 | VH3 | M99649VH3 | 97.7 | 92.2 +/− 4.5 | +5.6 | VK1 | M64855VK1 | 77.4 |
| BIIB7 | 75.9 | VH1 | AB019438VH1 | 72.7 | 70.1 +/− 3.1 | +2.6 | VK3 | X72812VK3 | 83.2 |
| BIIB8 | 75.6 | VH1 | Z14300VH1 | 58.0 | 70.1 +/− 3.1 | +2.9 | VK1 | X59316VK1 | 79.8 |
| BIIB9 | 74.7 | VH3 | Z12358VH3 | 95.2 | 92.2 +/− 4.5 | +3.0 | VK4 | Z00023VK4 | 88.8 |
| BIIB10 | 74.7 | VH4 | X56365VH4 | 69.3 | 68.1 +/− 5.5 | +0.8 | VK1 | X59316VK1 | 84.0 |
| BIIB11 | 58.1 | VH1 | AB019438VH1 | 71.3 | 70.1 +/− 3.1 | +1.2 | VK4 | Z00023VK4 | 94.4 |
| BIIB12 | 71.2 | VH1 | AB019438VH1 | 67.9 | 70.1 +/− 3.1 | −2.2 | VK4 | Z00023VK4 | 92.5 |
| BIIB13 | 70.8 | VH3 | M99657VH3 | 91.1 | 92.2 +/− 4.5 | −1.3 | VK4 | Z00023VK4 | 93.1 |
| BIIB14 | 70.6 | VH7 | L10057VH7 | 65.1 | 70.2 +/− 3.2 | −5.1 | VK- | — | 56.6 |
| BIIB15 | 68.5 | VH3 | M99660VH3 | 92.4 | 92.2 +/− 4.5 | +0.2[b] | VK1 | M64858VK1 | 81.6 |
| BIIB16 | 68.0 | VH3 | M99649VH3 | 95.6 | 92.2 +/− 4.5 | +3.3[b] | VK3 | X72812VK3 | 82.0 |
| BIIB17 | 57.2 | VH3 | J00239VH3 | 89.4 | 92.2 +/− 4.5 | −3.0 | VK2 | X63397VK2 | 84.8 |
| BIIB18 | —[c] | VH3 | M99400VH3 | 80.0 | 92.2 +/− 4.5 | −12.3[b] | VK2 | X63397VK2 | 84.5 |

[a]Lefranc et al., 1999;
[b]Unusual insertion/deletion in CDR1 or CDR2.
[c]Did not express Example 16

Utilization of Consensus Scoring to identify Antibody Variable Region with Sub-Optimal Stability Consensus scoring was utilized as a method for identifying which of the BIIB antibodies contained significantly large numbers of non-optimal amino acids within their Fv regions. The scoring assesses the relative drift from consensus V$_H$ and V$_\kappa$ sequences due to hypersomatic mutations and evolutionary germline variations. The DSC measurements for the 17 antibodies were used to qualify the ability of the consensus scoring approach for predicting poor antibody stability.

The reference set of mammalian V$_H$ and V$_\kappa$ kappa sequences used to derive the consensus sequence for scoring and the individual amino acid frequencies at each residue position were collected, sorted, and culled as described previously (Demarest et al., J. Mol. Biol. 335: 41-48, 2004). The mammalian reference sets were naively constructed to include V-genes from various mammals in order to obtain diversity via the evolutionary drift between species. The V$_H$ mammalian reference set contains 61 V$_H$ sequences primarily from NCBI and TIGR representing a total of 17 different mammalian species. The V$_\kappa$ mammalian reference set contains 53 V$_\kappa$ sequences from 13 different mammalian species.

Human V$_H$ and V$_\kappa$ sequences for building a reference set (or for use as test sequences) were gathered from the NCBI database using the search criteria "homo sapiens antibody variable heavy chain" and "homo sapiens antibody kappa variable light chain", respectively. A total of 182 human V-gene sequences, 114 V$_H$ and 68 V$_\kappa$, were semi-randomly selected from the NCBI database for comparison against mammalian V$_H$ and V$_\kappa$ databases. The subclass distribution of human V$_H$ and V$_\kappa$ sequences obtained by semi-random cherry-picking of the NCBI database yielded the expected subclass representation based on natural germline V$_H$ or V$_\kappa$ usage (Guigou et al., 1990) suggesting little bias in the way sequences were chosen from the NCBI.

The sequences were then categorized into their individual variable domain subclasses (V$_H$1-V$_H$7 and V$_\kappa$1-V$_\kappa$4) by ClustalW alignment against the subclass consensus sequences obtained from Aho's Amazing Atlas of Antibody Anatomy website. The subclasses were additionally confirmed by alignment against the publicly available human germline sequences (Lefranc et al., Nucleic Acids Res. 27, 209-212, 1999). No more than 5 human sequences from any one multi-sequence NCBI submission were included within the reference sets to reduce potential bias introduced by primer sets or antigen-based V-gene usage. The sequence gathering was performed naively; therefore, there was a natural abundance of V$_H$3 and V$_\kappa$1 sequences after subclass grouping. The average score and standard deviation (described below and in Table 20) were calculated for each subclass using 25 V$_H$1, 3 V$_H$2, 44 V$_H$3, 34 V$_H$4, 5 V$_H$5, 3 V$_H$7, 29 V$_\kappa$1, 4 V$_\kappa$2, 19 V, 3 and 16 V$_\kappa$4 human sequences. Only 2 of the 18 antibodies (BIIB5 and BIIB14) contained V$_H$ domains with minimal subgroup sequence populations (i.e. V$_H$2, V$_H$5 or V$_H$7). Four of the 18 antibodies (BIIB3, BIIB4, BIIB17 and BIIB18) contained V$_\kappa$2 subclass variable domains whose subclass was underrepresented in sequence space and whose scoring accuracy was ill defined. No natural V$_H$6 sequences were found within the human V$_H$ sequence reference set. This was not a concern as none of the BIIB antibody constructs contained a V$_H$6 domain.

The variable domain sequences of the 18 BIIB antibodies and the 182 human V$_H$ and V$_\kappa$ sequences obtained from the NCBI were scored against the reference set of mammalian antibody sequences. All V$_H$ and V$_\kappa$ sequences were truncated prior to CDR3 (two residues after the consensus YYC residues) to reduce the unpredictability introduced by the hypervariable nature of the V-(D-)J-C joining region. Residue frequencies (p$_i$(r)), at every position within the mammalian database were calculated by summing the number of times each amino acid (A, C, D . . . V, W, Y,-) occurs at each residue position within the database divided by the total number of sequences. Scores were evaluated for each human V$_H$ and V$_\kappa$ test sequence using the following formula:

$$\text{score} = \sum_i \frac{h_i(r)}{c_i(r)}$$

wherein $c_i(r)$ equals the consensus residue frequency at each position of the mammalian variable domain databases and $h_i(r)$ equals the test residue frequency of each amino acid of the human variable domain test sequence. Perfect consensus scores for the consensus sequences of the mammalian databases were 104 for $V_H$ and 100 for $V_\kappa$.

Figure 71:
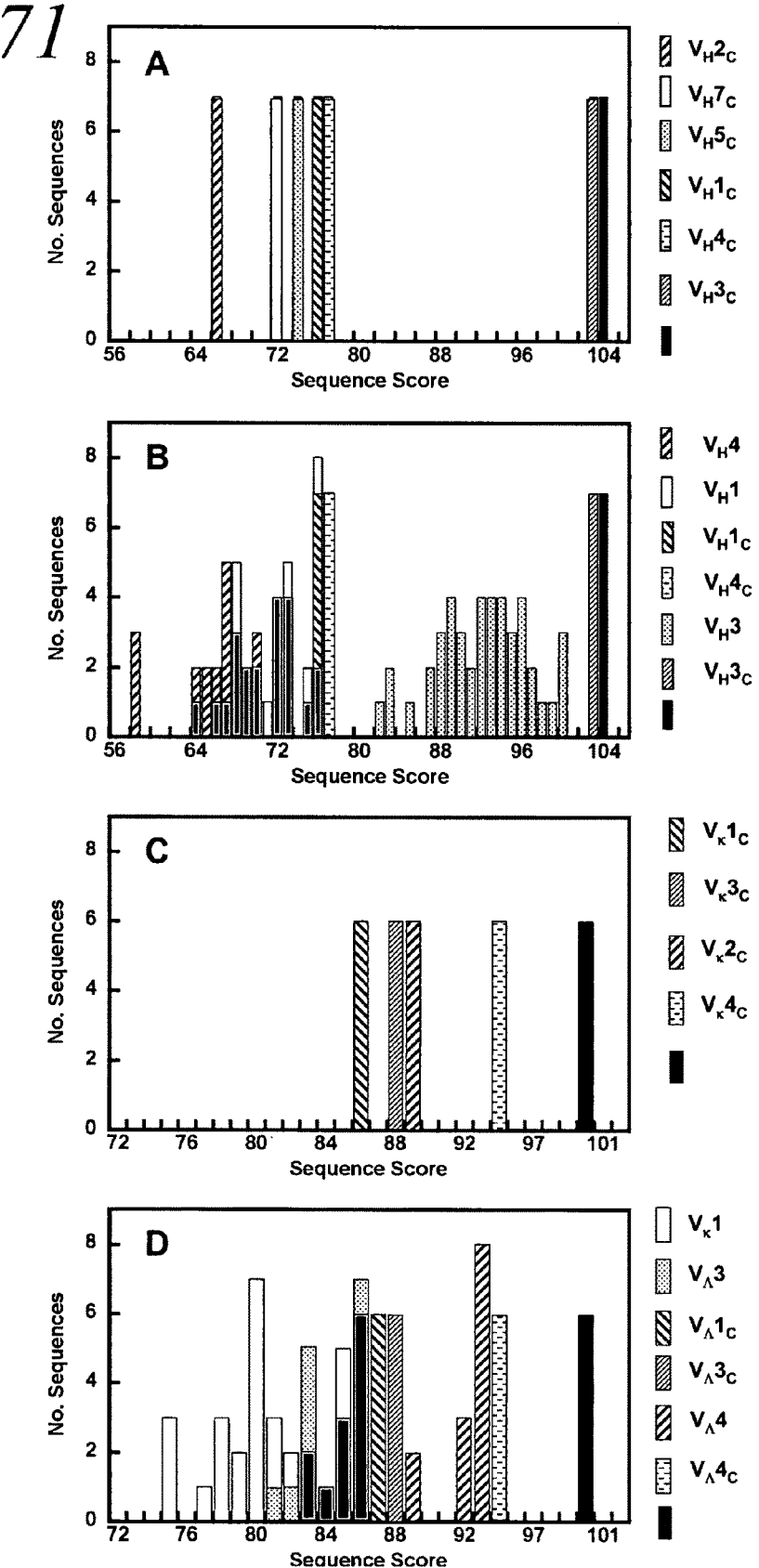
FIG. 71 depicts consensus scoring results for 182 human antibody variable domain reference sequences and the individual subclass consensus sequences. A. $V_H$ subclass sequence scores derived by residue frequency analysis against a mammalian $V_H$ database. B. Distribution of scores from reference $V_H$ sequence selected from NCBI. $V_H$ sequence scores are clustered according to subclass. C. $V_\kappa$ subclass consensus sequence scores derived by residue frequency analysis against a mammalian $V_\kappa$ database. D. Distribution of scores from reference $V_\kappa$ sequence selected from NCBI. $V_\kappa$ sequence scores are clustered according to subclass.

A. Scoring Random $V_H$ and $V_\kappa$ Sequences Using a Mammalian V-Gene Database $V_H$ and $V_\kappa$ subclass consensus sequences were scored against the mammalian databases consensus and plotted in FIGS. 71A and 71C, respectively. The $V_H3$-subclass consensus scored only 1 point lower than the hypothetical "perfect" score of the mammalian database consensus and differed from the mammalian database consensus by a total of three residues. Thus, it is apparent that the mammalian database is biased towards $V_H3$-like sequences. All other human $V_H$ subclass consensus sequences scored significantly lower. A bias towards $V_\kappa 4$ sequences was observed for the mammalian $V_\kappa$ database (FIG. 71C). The human or humanized BIIB sequence scores were analyzed based on the performance of human NCBI sequences of comparable subclass. Distributions of the individual $V_H$ sequence scores are shown in FIG. 71B, and distributions of the individual $V_\kappa$ sequence scores are shown in FIG. 71D.

B. Scoring Results for BIIB1 through BIIB18

$V_H$ and $V_\kappa$ scores for all 18 BIIB antibodies were calculated and compared to the relative numbers derived from the NCBI human V-gene sequence reference set (Table 20). Also included in Table 20 is the difference between the BIIB V-gene score and the average subclass score. It is the difference between these scores that was used for examining potential stability trends. BIIB1 through 18 were labeled in descending order of their measured Fab stabilities. The V-gene subclass and the closest individual human germline for the BIIB $V_H$ and $V_\kappa$ genes were determined by ClustalW analysis.

Figure 72A:
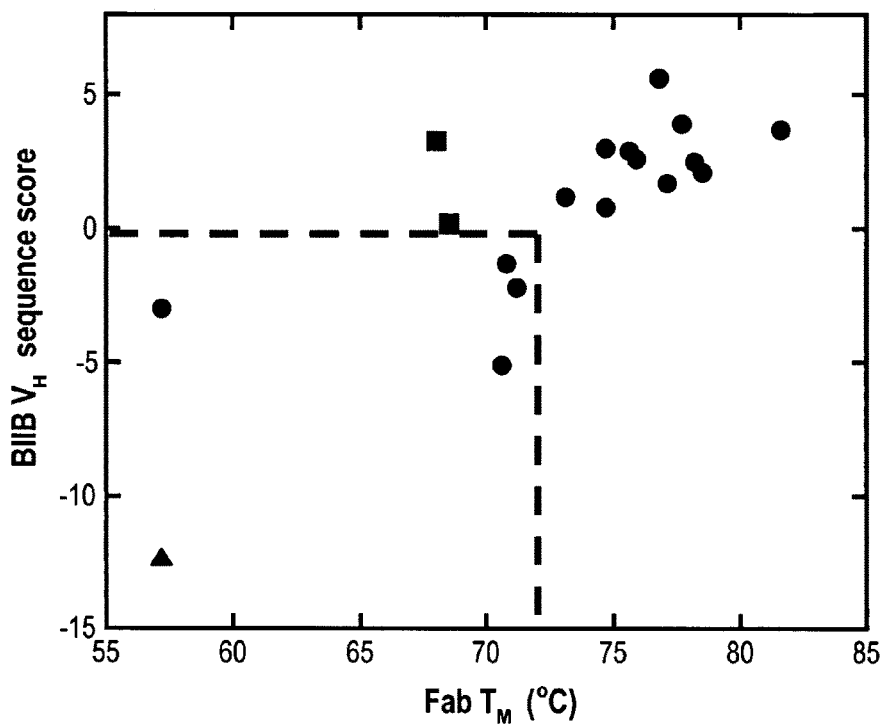
FIG. 72A depicts BIIB1-18 $V_H$ scores plotted against the Fab $T_M$s. The identity of each point can be found in Table 20. The $V_H$S of BIIB15 and BIIB16 contain unusual insertions/deletions in their CDRs. The results for BIIB15 and BIIB16 are displayed as squares. BIIB18's $T_M$ was artificially labeled as 57.2° C. (to match the lowest measured $T_M$ from BIIB17) since its own $T_M$ was immeasurable due to the lack of expression. BIIB18's $T_M$ is likely much lower based on its extremely low sequence score and its inability to express. The Fab results for BIIB18 are displayed as a triangle. The remaining BIIB antibody $V_H$ results are displayed as circles.
Figure 72B:
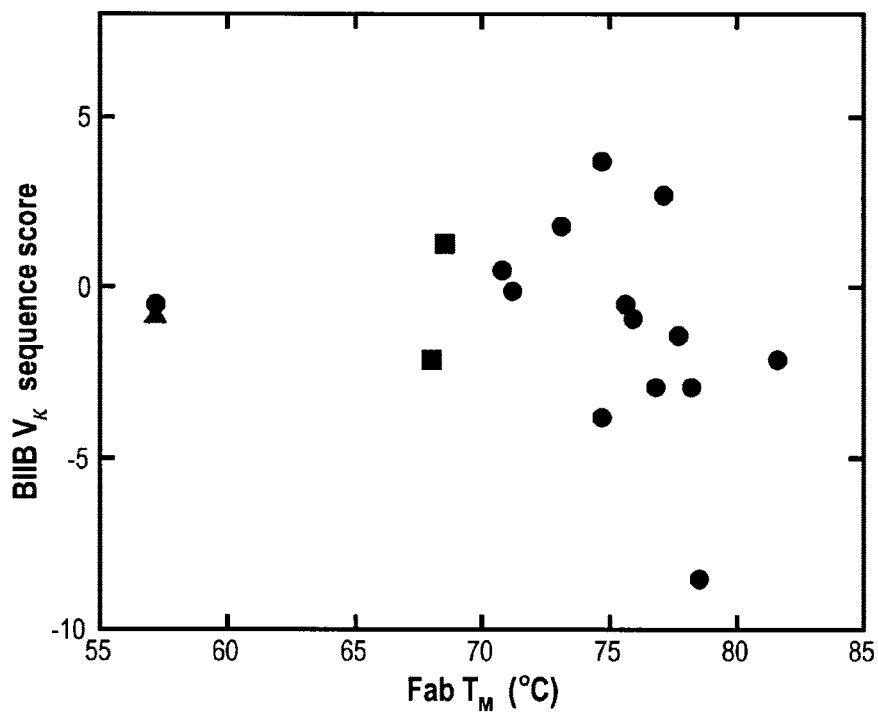
FIG. 72B depicts BIIB1-18 $V_\kappa$ scores plotted against the Fab $T_M$s. The symbols are the same as described for plot (A), except the scores are for $V_\kappa$.

Consensus-based scores were derived for the 18 BIIB antibodies and compared to the experimentally determined Fab thermal unfolding profiles. BIIB antibodies with greatest difference between the BIIB V-gene score and their average subclass score (ie. lowest sequence scores) was correlated with the low Fab $T_M$s measured in Example 15 (Table 20, FIG. 72A). There was no apparent trend correlating V, scores with the $T_M$s measured by DSC (FIG. 72B). In fact, the lowest scoring V, sequence belonged to BIIB2 which had the second highest apparent Fab stability.

Unusual CDR amino acid insertions and deletions were found in BIIB15 and BIIB16, as well as in BIIB18, which had the worst $V_H$ score of all the BIIB antibodies and never expressed at appreciable levels. $V_H$ scoring did not suggest potential stability problems for BIIB15 and BIIB16; however, their Fab $T_M$s were two of the lowest tested (FIG. 72A). BIIB15 contained an unusually long CDR1 (13 amino acids in length and 2 longer than any $V_H3$-like domain in our mammalian database or $V_H3$ domain in our set of human sequences) and BIIB16 contained an unusually short CDR2 (15 amino acids in length and 1 amino acid shorter than the significant majority of the other $V_H3$CDR2s in both our mammalian $V_H$ database and our reference set of human $V_H$s).

C. Utility of Small Mammalian Sequence Databases for Residue Frequency Analysis and Stability Prediction of the BIIB Fabs Scoring the BIIB $V_H$ domains against the mammalian database of $V_H$ sequences proved to be a useful tool for determining the abundance of non-optimal amino acids within each $V_H$ domain, which may in turn limit the overall stability of a Fab. The scores were useful for picking out Fabs with low stability and the potential for reduced in vitro longevity and increased aggregation rates. Based on the subclass biases observed for the mammalian V-gene databases, one might question whether it would be best to use strictly human V-gene databases for performing the consensus scoring as opposed to the mammalian database used here. However, based on the significant number of stability determining variables that the scoring does not reflect, such as the exact residue positions of non-consensus amino acids, the strength of the $V_H/V_L$ interaction, the nature of the V-(D-)J-C joining and the incidence of hypersomatic insertions or deletions, it is difficult to believe that an all-human $V_H$ database would provide a significant improvement. A strictly human database used for scoring may also require a significantly greater number of sequences to match the evolutionary diversity naively included within the mammalian database. One piece of data that indicates the mammalian database approach works well is that the human subclass consensus $V_H$ sequences scored in ascending order of their genomic subclass abundance and apparent subclass usage (Guigou et al., 1990; Teale and Medina, 1992; Tomlinson et al., 1992). The mammalian $V_H$ database appears to weight the overall contributions of the human $V_H$ subclasses appropriately. The fact that each $V_H$ and $V_\kappa$ subclass consensus sequence generally scored higher than the vast majority of the individual and unique human sequences picked from the NCBI suggests that the mammalian database is capturing consensus information for all subclasses, even though a bias exists towards $V_H3$. Therefore, due to the existence of other stability-influencing factors that the scoring does not incorporate, the trend observed in FIG. 72A is unlikely to improve by fine-tuning of the $V_H$ sequence database used for scoring.

Unusual insertions or deletions in $V_H$ domains appear to have significant effects on stability not reflected by consensus scoring. The unusually long (13 amino acids) CDR1 of BIIB15 and the unusually short (15 amino acids) CDR2 of BIIB16 are likely carry-overs of humanization from the original mouse sequence. In fact, the BIIB16 $V_H$ sequence aligns closely with two mouse $V_H$ sequences in our mammalian database that also contained a 15 amino acid CDR2. Forcing the unusually small CDR onto the human framework may have adversely affected the stability of this antibody. BIIB18 not only displayed the lowest $V_H$ score of all the BIM sequences but also contained an extraordinarily long CDR2 (22 residues compared to the usual 19 amino acid maximum). Thus, it is not surprising considering the multiple possible problems inherent within the sequence of BIIB 18 that it never reached expression levels allowing for anything other than extremely crude biological assays with unpurified supernatants. The results for BIIB15, BIIB16 and BIIB18 suggest that unusual $V_H$ insertions or deletions may have a greater effect on antibody thermostability than most single point mutations. The exceptionally poor behavior of BIIB18 was not predicted based on a perfunctory glance over its sequence as its Fv contained all the "essential" amino acids strictly conserved within the V-gene folds. Having the ability to pick out troublesome antibodies using a somewhat finer comb is the real the utility of the scoring approach.

No trends were apparent when comparing the measured Fab stabilities against the $V_\kappa$ scores. Combining the $V_\kappa$ scores with the $V_H$ scores simply reduced the trending observed for the $V_H$ scores alone. Unlike the $V_H$ scoring results, the human $V_\kappa$ consensus scores were not in line with the natural abundance of $V_\kappa$ germlines and gene usage (Guigou et al., 1990; Meindl et al., 1990; Cox et al., 1994); even though the consensus scores themselves all scored better than their individual human kappa subclass sequences (FIG. 72B). It is only speculation that these deviations from the expected order of $V_\kappa$ consensus scores may deter the mammalian databases' ability to accurately predict low stability $V_\kappa$ domains. Also, there were not enough $V_\kappa 2$ sequences for defining the $V_\kappa 2$ subclass average score. After subclass distributions were determined for the 68 human $V_\kappa$ sequences, only 4 were $V_\kappa 2$ (which reflects $V_\kappa 2$ usage pretty well). Even with these drawbacks, the $V_\kappa$ results still suggest that the greater sequence diversity of $V_H$ genes may, more often than not, make $V_H$ domains the stability-determining component of Fabs (Demarest et al., 2006); although examples of the opposite are available in the literature (Röthlisberger et al., 2006).

D. Stability Dependence Upon $V_H$ or $V_L$ Germline and $V_H/V_L$ Pairing

Many of the 18 antibodies contained overlapping germlines V-genes whose CDRs and hypersomatic mutations varied and whose $V_H$ or $V_\kappa$ pairing was the same or different. This allowed for a comparison of antibody Fab stabilities against the individual germlines from which they were derived. The two most stable Fabs, BIIB1 and BIIB2, have the same $V_H 1$ and $V_\kappa 1$ germline combinations. $V_H$ and $V_\kappa$ pairings do not appear to have clear intrinsic biases based on a study by Winter and coworkers, but are believed to be "receptor driven" (de Wildt et al., 1999b). BIIB1 and BIIB2 bind relatively dissimilar antigens, CCL2 and VLA4; therefore, the combination either occurred randomly or was the result of humanization. There was a clear abundance of non-optimal amino-acids within the $V_H$ domains of the least stable Fabs, BIIB17 and BII18 (i.e. low sequence scores and BIIB18 contained an unusual insertion). Both of these antibodies also contained the same $V_\kappa 2$ germline, potentially suggesting light chain protein stability issues on top of the $V_H$-based issues identified by the scoring. An interesting future study would be to determine whether this particular $V_\kappa 2$ was a contributor to the poor biophysical behavior of these two antibodies. $V_\kappa 2$ subclass in general was not associated with poor Fab stabilities as BIIB3 and BIIB4 also contain a $V_\kappa 2$ subclass gene. The AB019438$V_H 1$ germline (Lefranc et al., 1999) cropped up four times. The $T_M$-values for these Fabs (BIIB12, BIIB11, BIIB7 and BIIB3) ranged from 71.2 to 78.2. Interestingly, their $V_H$ sequence scores correlated with their apparent Fab stabilities (BIIB12<BIIB11<BIIB7 A positive $V_H$ scoring correlation was also found in the BIIB1 and BIIB2 antibodies described above with the same $V_H 1$ germline. The apparent imprecision of the $V_H$ scoring, however, was emphasized by a negative stability correlation observed for BIIB4 and BIIB6 which both contained the M99649$V_H 3$ germline.

While usage of $V_H$ germline families in adult humans appears to be fairly random, the $V_H 3$ family contains the most members in humans. $V_H 3$ or $V_H 3$-like genes stochastically appeared more often in the human reference set and the mammalian database. Ewert and Plückthun's results demonstrated that a consensus-derived human $V_H 3$ sequence was the most stable of the consensus-derived $V_H$ domains (Ewert and Pluckthun, 2003). This result may not be entirely unexpected considering the $V_H 3$ subclass has more germline sequences to contribute to the creation of an optimal consensus compared to the other subclasses. Our stability data shows that IgGs containing $V_H 3$ germlines do not in general exhibit higher Fab $T_M$-values. There are $V_H 3$ and $V_H 1$ subclass genes at both the top and bottom of the stability list. While many other factors contribute to the overall stability of the Fab, especially the properties of the $V_\kappa$ counterpart within the Fv, one might expect a trend towards higher Fab stabilities for those containing $V_H 3$ subclass germlines if the $V_H 3$ domains in general were more stable than the other subclasses. This does not appear to be the case from the limited stability studies described here.

Example 17

Covariation Analysis of Ig-Fold Polypeptides

A. Collecting and Filtering Ig-Fold Structures

Structures of Ig-Fold proteins or Ig-Fold domains from multidomain proteins were gathered from the ASTRAL database, which contains domain structures matching the SCOP hierarchy. Immunoglobulin specific Ig-domains were found under the following classifications within the SCOP hierarchy: "All beta proteins"→"Immunoglobulin-like beta-sandwich"→"Immunoglobulin". Under immunoglobulin, four sets of structures were available: "V set," "C1 set," "C2 set," and "I set." Four custom download scripts were separately run to obtain "V-class", "C1-class", "I-class", and "C2-class" pdb files.

Once the structure files for each subfamily were downloaded, some filtering performed to remove erroneously categorized, incomplete, redundant, or domain-swapped structures (Liu Y, et al., Protein Sci. (2002), 1285-1299). There were 4 main filtering steps, described below:

Step #1. Removal Sequences that have Breaks

Structures from each subclass were visually inspected, using SwissPDB Viewer, for breaks in sequence (either unresolved densities or missing sections due to domain swapping). The PDB files of faulty structures were manually removed from the V-, C1-, C2-, and I-class structure datasets.

Step #2. Removal of 100% Identical Sequences

PDB format structures were converted to FASTA format amino acid sequences, and filtered to remove any sequences that were either 100% identical to, or perfect match substrings of, remaining sequences.

Step #3. Removal of Sequences of Aberrant Length

Figure 74:
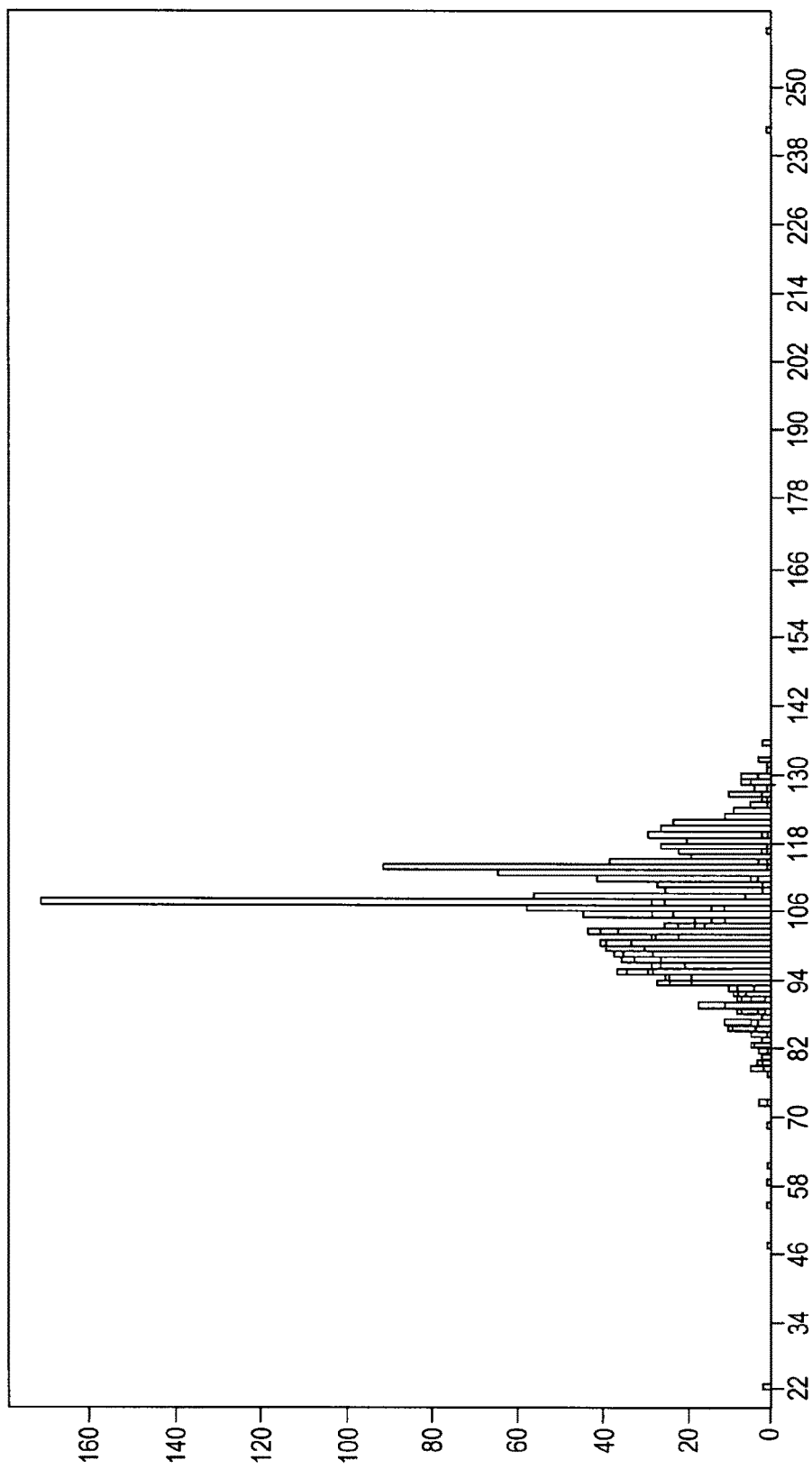
FIG. 74 depicts a histogram of the sequence lengths of V-, I-, C1-, and C2-class Ig-Folds obtained from SCOP.

PDB structures with aberrantly long or short amino acid sequences were removed from the structure datasets. The length cutoff criteria were determined by examining the histogram of all sequence lengths (FIG. 74). The histograms appeared somewhat normally distributed. Sequences outside two standard deviations from the mean were removed from each subfamily dataset. The overall mean number of residues for the immunoglobulin superfamily was 106.10 and the standard deviation was 12.19. Consequently, the global cutoffs used were <=81 and >=131 residues. A breakdown of the mean lengths and standard deviations is shown in Table 21.

TABLE 21

Sequence Length Criteria of Structure Datasets

| Subclass | Average Length | Standard Deviation |
|---|---|---|
| C1 | 99.44 | 8.79 |
| C2 | 88.07 | 15.14 |
| I | 95.5 | 4.94 |
| V | 111.95 | 10.62 |
| Overall | 106.10 | 12.19 |

Step #4. Removal of Misfolded Sequences

The structures were visually inspected, using SwissPDB Viewer, for misfolding.

Any structures that did not conform to the two beta-sheet sandwich topology were discarded. Since only five C2-class domains were obtained from SCOP, C2-subclass Ig-Folds were not pursued further. Hereafter, C1-class is referred to as C-class.

B. Obtaining Sequence Alignments from Structure Alignments

For each separate class, the Ig-Fold structures were superimposed upon one another using Secondary Structure Matching (SSM) within the Schrödinger structalign package (See Schrödinger Prime program documentation for instructions on creating superpositions). Superpositions were performed on an 'all-to-all' or an 'all-to-one' basis. Each algorithm led to similar quality alignments, so 'all-to-one' was chosen for the superpositions. Some superimpositions were corrected to insure that the core regions of each structure were superimposed instead of the loops. The superimpositions were then used to generate structure-based sequence alignments of all the V-class, I-class, and C-class sequences within each structural alignment. Alignment of each sequence onto another was performed using the Schrödinger package by matching amino acids from one sequence to that of second sequence based on the shortest distance between α-carbons of the polypeptide backbones.

C. Construction of a Curated Ig-Fold Sequence Database

A number of defined steps were created to generate a curated Ig-Fold dataset for calculating robust covariation statistics:

Step #1. Construction of HMM Profiles

Three Hidden Markov Model (HMM) profiles were built, each based upon the structure-based sequence alignments for one of the three Ig-Fold classes. The profiles were created with the HMMER software package (version 1.8), using the commands "hmmbuild" and "hmmcalibrate" with standard options. These HMMs were then used to detect and align additional Ig-Fold sequences in the NR-database maintained at the NCBI.

Step #2. Searching NR Using the New V-, I-, and C-Class HMM Profiles.

The three class-specific HMMs were used to search for similar sequences in a local NR database. The NR database is a large file containing ~3 million non-redundant protein sequences. For each of the V-, I-, and C-class HMMs, the HMMER command "hmmsearch" was used to search NR. Each output ranked NR sequences by their scores relative to the HMM used, and provided information about the number of regions hit by the HMM and the positions of the hit regions within each NR sequence. For each Ig-Fold class-specific HMM search, hit NR sequences above a recommended criterion score threshold were retained as candidate members of the Ig-Fold class whose HMM was used. For those hit regions that were subsequences of an NR sequence, the exact NR subsequence hit was extracted from the full NR sequence using a custom program.

Step #3. Validation of Ig-Fold Class Assignment Using PFAM.

PFAM is a protein family and domain classification tool, created and maintained at the Wellcome Trust Sanger Institute (Fin, et al., Nuc. Acids. Res., (2006), 34: D247-D251), that can be applied to individual protein sequences. A Pfam tool 'pfamverify' was applied to each Ig-Fold candidate sequence obtained in step 2 above, to confirm that it was correctly classified by the Ig-Fold class-specific HMMs created from the structure-based sequence alignments. PFAM's Ig-clan HMM profiles (including V-, I-, C1-, C2-, and less specific Ig HMMs) were downloaded from the PFAM website. Each sequence from NR was scored by the Ig-clan HMMs, revealing how well each sequence conforms to each PFAM HMM. Sequences whose scores lay below recommended cutoffs (TC1—defined at the PFAM website) for the V-, I-, or C-classes were removed from the respective sequence sets. Thus, the candidate class-specific Ig-Fold sequences found in step 2 were retained only if their PFAM scores validated their Ig-Fold class assignments.

Step #4. Aligning the New Ig-Fold Sequences.

The Ig-Fold sequences that were pulled from NR with HMM searches and that survived step 3 above, were next aligned to our custom HMMs of their assigned class. Since these HMMs had been based upon careful structural alignments, this process insured a structure-guided alignment of the new sequences. The HMMER package was utilized to generate 'mapali' alignments in fasta output format, to be used in the Sequence Covariation Tool described below. The alignments were also output in 'Stockholm' output format, and inspected for aberrant or misaligned sequences, which were manually omitted. The resulting alignments, consisting of the original structurally-aligned sequences and the added HMM-aligned sequences from NR, contained the following numbers of sequences: ~50,000 V-class; ~10,000 C-class; ~10,000 I-class.

Step #5. Removing Redundant or Similar Sequences.

We expected these alignments to be biased towards frequently observed sequences, with under-representation of rare sequences and a consequent masking of sequence diversity. For example, we expected a large bias in the V-class Ig-Fold sequence alignment towards murine and human immunoglobulin variable domains. Since over-representation of particular sequence types limits the usefulness of covariation analyses, a filtering tool was created and applied to reduce the alignment redundancy. The tool used a novel heuristic algorithm to find sequences with >80% identity to one another, and removed them from the alignments. In brief, percent identities were calculated for all sequence pairs. The identity values were then grouped into bins of percent identity (i.e. 99% bin, 98% bin, 97% bin, etc.). During the reduction of each bin, the sequences of each bin were ranked by decreasing non-gap residue count, and then by their Henikoff sequence weight (Henikoff S and Henikoff J G, J. Mol. Biol., (1994), 243: 184-199). After this step, the remaining number of sequences in each alignment were: 2,786 V-class; 1,587 I-class; and 518 C-class.

Step #6. Removal of Gaps to Create the Final Alignments

In the final alignments, columns that were not match states in the HMM profile used to find these sequences (see HMMER manual) were removed. Therefore, while many of the sequences contain more amino acids than the final alignment length, the lengths were truncated to avoid calculations on the less informative gap regions of the alignment. The final numbers of residues (including gaps) within the alignments were 144 for the V-class, 60 for the I-class, and 111 for the C-class.

D. General Description of the Final Alignments a) V-Class

After the final 80% filter was applied, the 2,786 V-class sequences could be divided into three categories: (1) Immunoglobulin variable gene class, 49%, which include both the $V_H$ and $V_L$ domains of diverse immunoglobulins; (2) T-Cell Receptor V-class genes, 16%, which contained the hypervariable domains; and (3) Other V-class genes, 35%. The Immunoglobulin V-class genes come from a huge variety of species ranging from cartilaginous fish to primates. There was a bias towards human V-class sequences (537 of the 1272 sequences). However, other vertebrate species were only minimally represented: mouse (33), cow (5), camel (23), llama (31), macaque (17), chicken (6), etc. The T-cell receptor set of sequences was nearly as diverse ranging from fish to primate and did not contain a bias towards human sequences. The "Other" category comprised a large number of diverse sequences with no real subcategories comprising over 1-2% of the remaining sequences. The "Other" category contained an even wider array of species including chordates (primarily), cartilaginous fish, cephalopods, and insects.

b) C-Class

After the final 80% filter was applied, the 518 C-class sequences could be divided into three categories: (1) Immunoglobulin constant domains, 44%; (2) MHC-type Ig-Folds, 21%; and (3) Other C-class Ig-Folds, 35%. The Immunoglobulin constant domain category contained diverse sequences ranging from cartilaginous fish to primates. The C-class immunoglobulin subcategory was not biased by primate or even mammalian sequences (only 3 human sequences remained unfiltered: IgE-$C_H4$, a kappa $C_L$, and a lambda $C_L$). The MHC subcategory also ranged from cartilaginous fish to primates and also showed little bias towards one evolutionary group. The "Other" C-class category contained many unknown proteins, a very small subcategory of various beta-2-microglobulins, and many other proteins that were not observed with a frequency deserved of a subcategory.

c) I-Class

The I-class did not have any clear subcategories. Titan or titan-like molecules cropped up commonly as did cell-adhesion or cell-adhesion-like molecules.

E. Calculation of Covariation Statistics

Correlation strength (in terms of a $\phi$-value) and significance (in terms of a $\chi^2$-value) of covariations between all possible pairs of amino acids in the alignments was calculated based on art-recognized methods, but included the following variations: 1) Gaps were included as a distinct residue type; (2) the Henikoff weighing scheme was not performed; (3) Sequence Average Identities (SAT) were not used to filter out covarying pairs; (4) $\chi^2$ values were calculated using event based counts (number of occurrences), rather than frequencies; and (5) covarying pairs were not reported by the program unless they were observed a minimum number of times. Two bodies of statistics were created, the first (and smaller set) with an event cutoff of 10 and a second (much larger set) with an event cutoff of 6 events. The ability to calculate these parameters on any given sequence alignment was encoded into a Java executable and tested with Java Runtime Engine (JRE) version 1.4.2.

Figure 75:
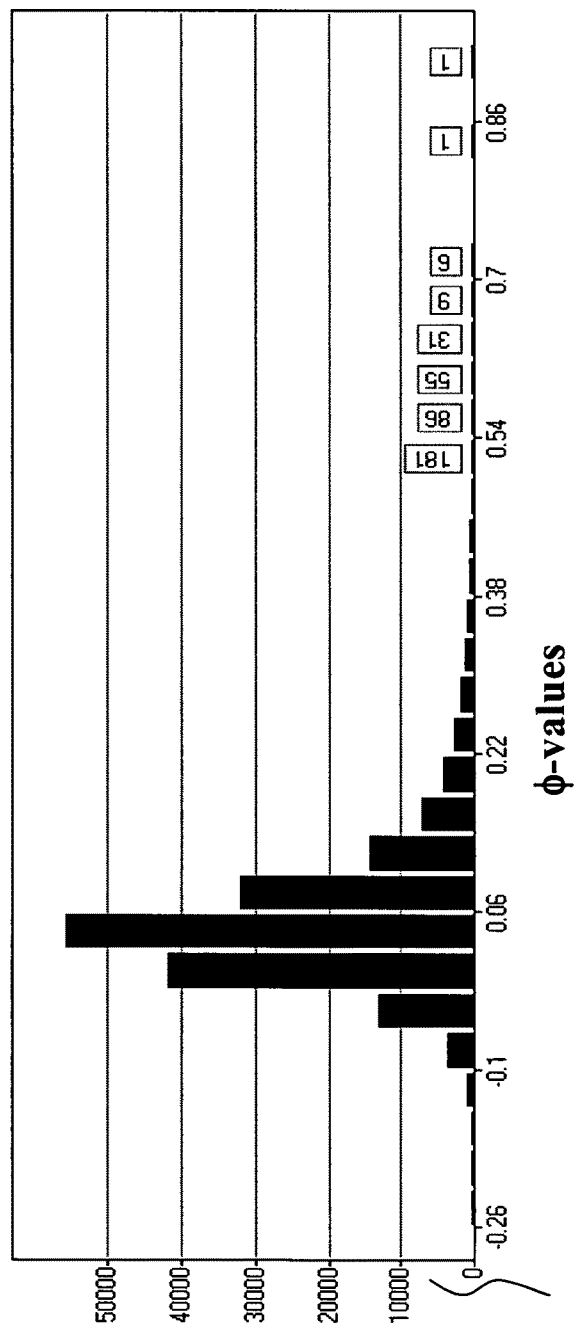
FIG. 75 depicts a histogram of f-value correlation coefficients calculated for every residue combination within the C-class dataset.

Based on the number of positions within the alignment and a total of 23 possible residues at each position (including gaps, B, and Z ambiguous residues), there were 2.4 million correlations calculated for the C-class, 700 thousand calculated for the I-class, and 4.1 million calculated for the V-class. FIG. 75 shows the $\phi$ values calculated for the V-class with high $\chi^2$ significance. $\phi$ values range from −1 to +1. As positive $\phi$ values move away from 0 (i.e. toward+1), the strength of the correlation (i.e. the covariation) between two amino acids at defined positions within the alignments increases. Negative correlations (i.e. the presence of one amino acid at one site in the alignment forcing the absence of another specific amino acid at a second site) increase as $\phi$ values move towards −1. Cutoffs for what is a real covariation are somewhat arbitrary, but those with a $\phi$ value >0.5 are strongly correlated with one another. Thus, according to FIG. 75, only 370 of the possible 2.4 million correlations within the C-class are strong. However, correlations above 0.3 have been reported as important and would increase the number of positive correlations observed for all three classes by ~10-fold. These correlations represent the very small, but important piece of the dataset that is used for further analyses, generating protein designs, or prediction of functional residue positions.

F. Validation of Covariation Statistics

There were several criteria used to validate that the strong covariations that were derived from the Ig-Fold database were significant and meaningful apart from the statistical strengths based on the calculations. The first was to analyze whether there was a trend between residues that covaried with one another and their proximity inside Ig-Folds of known structure. Previous studies in the literature have demonstrated that a correlation between covarying positions and their proximity to one another do exist—although they are very weak—in agreement with our results. A second criterion looked at whether the Ig-Fold covariation calculations generated known connections between amino acid positions that have already been reported to exist within known Ig-Fold subsets. One clear test case was at N-terminus of human/murine IgG variable heavy chain folds (part of the V-class). Residues 6-10 are known to adopt very specific conformations based on the conservation of covarying pairs of amino acids (Ewert S, et al., *Methods*, (2004), 24: 184-199). Two of the three reported pairs of covarying amino acids were found to have $\phi$ values above 0.3—well above the apparent background of the dataset.

Example 18

Preparation of a PRIMATIZED® p5E8 Tetravalent Antibody Comprising a Conventional p5E8 scFv PRIMATIZED® p5E8G1 is a chimeric macaque/human (PRIMATIZED®) monoclonal antibody containing macaque heavy and light variable regions fused to human gamma 1 and kappa constant regions, respectively. PRIMATIZED® p5E8G1 binds to human CD23, the low affinity receptor for IgE (FcεR11) (Mavromatis and Cheson. 2003. J. Clin. Oncol. 21:1874; US Patent Application 20030059424). A tetravalent PRIMATIZED® p5E8 antibody was constructed using a similar strategy as that described in Examples 1-8. The PRIMATIZED® p5E8 scFv used for constructing the tetravalent antibody is comprised of p5E8 VL and VH region sequences tethered by a short linker in the VL→$(Gly_4Ser)_3$ linker→VH orientation and is described in greater detail in Example 19. Correct sequences were confirmed by DNA sequence analysis. Plasmid DNA was used to transform CHO DG44 cells for stable production of antibody protein. FIG. 80 shows the DNA sequence of heavy chain C-terminal tetravalent PRIMATIZED® p5E8 antibody comprising a conventional scFv. FIG. 81 shows the amino acid sequence of heavy chain C-terminal tetravalent PRIMATIZED® p5E8 antibody comprising a conventional scFv. FIG. 82A shows the DNA sequence of PRIMATIZED® p5E8 light chain. FIG. 82B shows the amino acid sequence of PRIMATIZED® p5E8 light chain.

Example 19

Preparation of PRIMATIZED® p5E8 scFv and Fab Proteins

PRIMATIZED® p5E8 scFvs in both orientations (VL→$(Gly_4Ser)_3$ linker→VH (VL/VH) and VH→$(Gly_4Ser)_3$ linker→VL (VH/VL)) were subcloned by PCR amplification from plasmids described in U.S. Patent Application 20050163782. Oligonucleotides used in the construction are shown in Table 22.

PRIMATIZED p5E8 scFvs (VL/VH) was constructed by PCR using the forward primer P5E8-VL01F which contains 29 bases encoding part of the gpIII leader sequence followed by 15 bases of sequence complementary to the p5E8 N-terminal light variable domain gene and the reverse primer, P5E8-VH01R, which contains 15 bases of sequence complementary to the p5E8 C-terminal heavy variable domain followed by a unique adjacent Sal I endonuclease site (endonuclease site is underlined). Similarly, PRIMATIZED p5E8 scFvs (VH/VL) was constructed by PCR using the forward primer P5E8-VH01F which contains 29 bases encoding part of the gpIII leader sequence followed by 18 bases of sequence complementary to the p5E8 N-terminal variable heavy domain gene and the reverse primer, P5E8-VL01R, which contains 12 bases of sequence complementary to the p5E8 C-terminal variable light domain gene followed by a unique adjacent Sal I endonuclease site (endonuclease site is underlined).

TABLE 22

Oligonucleotides for PCR amplification of a conventional PRIMATIZED ® p5E8 scFvs.

| Primers | Sequence |
|---|---|
| P5E8-VL01F (SEQ ID NO: 71) | 5'- CGCTGGTGGTGCCGTTCTATAGCCATAGTGAC ATCCAGATGACC -3' |
| P5E8-VL01R (SEQ ID NO: 72) | 5'- GTGGTCGACTTTGATTTCCAC -3' |
| P5E8-VH01F (SEQ ID NO: 73) | 5'- CGCTGGTGGTGCCGTTCTATAGCCATAGTGAGG TGCAGCTGGTGGAG -3' |
| P5E8-VH01R (SEQ ID NO: 74) | 5'- GTGGTCGACTGAGGAGACGGTGAC -3' |
| P5E8-Leader01 (SEQ ID NO: 75) | 5'- GGCATATGAAAAAACTGCTGTTCGCGATTCCGCTG GTGGTGCCGTTCTATAG -3' |

Following PCR amplification, primer P5E8-Leader01 was added to both reactions for a second PCR reaction. Primer P5E8-Leader01 contains a unique Nde I endonuclease site followed by 25 bases encoding the N-terminal portion of the gpIII leader sequence, followed by 22 bases complementary to the 5' ends of P5E8-VL01F and P5E8-VH01F and PCR amplified again. PCR products corresponding to the expected sizes were resolved by agarose gel electrophoresis, excised, and purified using the Millipore Ultrafree-DA extraction kit according to manufacturer's instructions (Millipore; Bedford, Mass.). The purified PCR products were subsequently digested with Nde I and Sal I and cloned into the Nde I/Sal I sites of a modified E. coli expression vector designed to drive recombinant protein expression under the control of an inducible ara C promoter. The expression vector contained a modification encoding a unique Nde I site overlapping the start codon of the BHA10 scFv. Individual ligation reactions were performed with each of the gel purified PCR products and the digested expression vector and a portion of each of the ligation mixtures were used to transform E. coli strain XL1-Blue. Ampicillin drug resistant colonies were screened and DNA sequence analysis confirmed the correct sequence of the final p5E8 (VH/VL) encoding pIEH-162 and p5E8 (VL/VH) encoding pIEH-163 constructs. DNA and amino acid sequences of p5E8 (VL/VH) scFv are shown in FIGS. 83A and 83B, respectively. DNA and amino acid sequences of p5E8 (VH/VL) scFv are shown in FIGS. 84A and 84B, respectively.

For expression of conventional p5E8 scFvs, freshly isolated colonies of E. coli strain W3110 (ATCC, Manassas, Va. Cat. #27325) transformed with plasmids pIEH-162 and pIEH-163 were cultivated and either culture supernatants or periplasm extracts were prepared as described in Example 4.

PRIMATIZED® p5E8 Fab was prepared by enzymatic digestion of PRIMATIZED® p5E8 IgG following methods described in Example 1. Purified Fab was concentrated to between 2-11 mg/mL. Fab concentrations were determined using an $\epsilon_{280\,nm} = 1.5$ mL mg$^{-1}$ cm$^{-1}$.

Example 20

Thermal Stability of Conventional p5E8 scFv Antibodies

Figure 85:
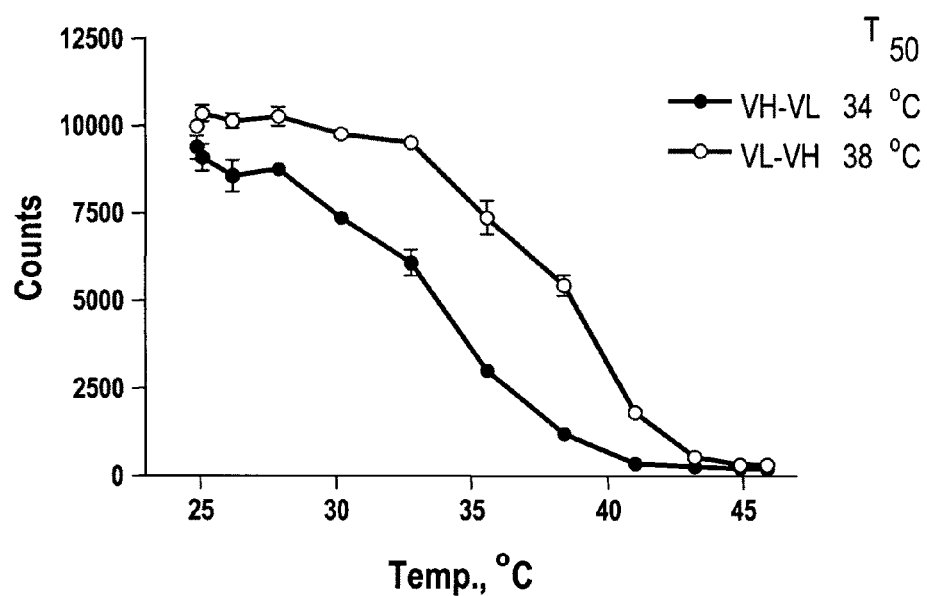
FIG. 85 depicts T50 curves of conventional p5E8 (VH/VL) scFv (filled circles) versus conventional p5E8 (VL/VH) scFv (open circles).

Since an excellent correlation has been observed between T50 values obtained using the thermal challenge assay described in Examples 4 and 5 and Tm values calculated by DSC analysis ($r^2 = 0.93$), a thermal challenge assay was employed to evaluate the relative thermal stabilities of the p5E8 (VL/VH) and p5E8 (VH/VL) scFvs. The thermal challenge assay was utilized as described in Examples 4 and 5 except that soluble CD23 antigen at 1 ug/ml was used to coat the plates and the concentration of the Eu-labelled anti-6 His antibody (Perkin Elmer, Boston, Mass., Cat. #AD0109) was increased to 250 ng/ml. Results from this assay determined the T50 value of p5E8 (VL/VH) to be 38° C. and p5E8 (VH/VL) to be slightly lower at 34° C. (FIG. 85). Given the remarkably low T50 values of both scFvs and the observation that of the two p5E8 (VL/VH) was slightly more thermally stabile, p5E8 (VL/VH) was selected for further stability engineering.

Example 21

Construction of p5E8 scFv Molecules with Improved Thermal Stability

Individual variants and libraries designed to contain the desired amino acid replacements in the conventional p5E8 (VL/VH) scFv using the methods described in Examples 3 and 5 were created as previously described using oligonucleotides listed in Table 23.

In Table 23, each oligonucleotide name gives reference to amino acid substitutions at position(s) in VH or VL according to Kabat numbering system. "Rationale" refers to the design method employed. Said methods are described in detail in Example 5 supra. Mutagenic residues are shown as capital letters. Oligonucleotide pairs for introducing VH/VL disulfides are boxed. Abbreviations are: "COMP"—Computational Analysis, "COVAR"—Covariation Analysis, "CONS"—Consensus Scoring, "INTER-VH/VL" Interface Design, "SS"-VH/VL disulfide bond, and "TBD"—to be determined.

TABLE 23

Oligonucleotides and rationale for construction of variant p5E8 (VL/VH) scFvs.

| Oligo_names | Rationale | Sequence$^\dagger$ | SEQ ID NO: |
|---|---|---|---|
| VH_E6Q | COMP | gaggtgcagctggtgCagtctgggggcggcttg | 76 |
| VH_L11SDG | COMP | gagtctgggggcggcRRCgcaaagcctgggggg | 77 |

TABLE 23-continued

Oligonucleotides and rationale for construction of variant p5E8 (VL/VH) scFvs.

| Oligo_names | Rationale | Sequence† | SEQ ID NO: |
|---|---|---|---|
| VH_A12VK_K13QER | COVAR | gtctgggggcggcttgRHGMAGcctgggggtccctg | 78 |
| VH_N32S | CONS | gttcaggttcaccttcAGCaactactacatggac | 79 |
| VH_D35bHSN | INTER | caataactactacatgMRCtgggtccgccaggctc | 80 |
| VH_Q43KR | COVAR | cgccaggctccagggARGggctggagtgggtc | 81 |
| VH_S49GA | COVAR | gggctggagtgggtcGSCcgtattagtagtagtg | 82 |
| VH_I51M | COMP | gagtgggtctcacgtatGagtagtagtggtgatc | 83 |
| VL_Q37A | COMP | ggtattatttaaattggtatGCCcagaaaccaggaaaag | 84 |
| VH_D55GS | CONS | gtattagtagtagtggtRGCccacatggtacgcag | 85 |
| VH_P56STD | CONS | gtagtagtggtgatRVCacatggtacgcagac | 86 |
| VH_W58YN | INTER | gtggtgatcccacaWACtacgcagactccgtg | 87 |
| VH_E72DN | COVAR | gattcaccatctccagaRACaacgccaagaacacac | 88 |
| VH_A74S | COVAR | catctccagagagaacAGCaagaacacactgtttc | 89 |
| VH_F79YSV | COVAR | gccaagaacacactgKHCcttcaaatgaacagc | 90 |
| VH_Q81E | COMP | gaacacactgtttcttGaaatgaacagcctgagag | 91 |
| VH_A84G | COMP | caaatgaacagcctgagaGGCgaggacacggctgtc | 92 |
| VH_V89AGT | COMP | gagctgaggacacggctRSCtattactgtgcg | 93 |
| VH_S94RK | CONS | gtctattactgtgcgARGttgactacagggtctg | 94 |
| VH_V107T | COVAR | TBD | |
| VH_L108AGS | COMP | TBD | |
| VH_T110VS | COVAR | TBD | |
| VL_L11G | COVAR | cagtctccatcttccGGCtctgcatctgtaggg | 95 |
| VL_V15AGS | COMP | ccctgtctgcatctRSCggggacagagtcacc | 96 |
| VL_V19L | COVAR | ctgtaggggacagaCTGaccatcacttgcagg | 97 |
| VL_I21L | COVAR | ggggacagagtcaccCTGacttgcagggcaag | 98 |
| VL_T22S | COMP | gacagagtcaccatcAGCtgcagggcaagtcag | 99 |
| VL_D28SG | CONS | gcagggcaagtcagRGCattaggtattatttaaattg | 100 |
| VL_R30SL | CONS | gcaagtcaggacattMKCtattatttaaattgg | 101 |
| VL_K39A | COVAR | aattggtatcagcagGCCccaggaaaagctcc | 102 |
| VL_K45ER | INTER | ccaggaaaagctcctSRCctcctgatctatgttg | 103 |
| VL_V50n | INTER | ctaagctcctgatctatNNKgcatccagtttgcaaag | 104 |
| VL_L54R | CONS | ctatgttgcatccagtCGCaaagtggggtccc | 105 |
| VL_V58S | COVAR | cagtttgcaaagtgggTCCcatcaaggttcagc | 106 |
| VL_E70D | COVAR | cagtggatctgggacaGACttcactctcaccgtc | 107 |
| VL_V75I | COMP | gagttcactctcaccATcagcagcctgcagcc | 108 |
| VL_P80AG | COMP | cagcagcctgcagRGCgaagattttgcgac | 109 |
| VL_F83AGST | COMP | ctgcagcctgaagatRSCgcgacttattactg | 110 |
| VL_T85D | COVAR | cctgaagattttgcgGACtattactgtctacag | 111 |

TABLE 23-continued

Oligonucleotides and rationale for construction of variant p5E8 (VL/VH) scFvs.

| Oligo_names | Rationale | Sequence† | SEQ ID NO: |
|---|---|---|---|
| VL_L89AQ | INTER | gcgacttattactgtSMRcaggtttatagtacc | 112 |
| VL_R96LY | INTER | gtttatagtacccctMWAacgttcggccaaggg | 113 |
| VL_F98W | INTER | gtacccctcggacgTGGggccaagggaccaag | 114 |
| VL_I106AGS | COMP | TBD | |
| VH_L45C | SS | gctccagggcaggggTGCgagtgggtctcacg | 115 |
| VL_F98C | SS | gtacccctcggacgTGCggccaagggaccaag | 116 |
| VH_D101C | SS | cttgactacagggtctTGCtcctggggccagggag | 117 |
| VL_L46C | SS | ggaaaagctcctaagTGCctgatctatgttgc | 118 |
| VH_S102C | SS | gactacagggtctgacTGCtggggccagggagtc | 119 |
| VL_L46C | SS | ggaaaagctcctaagTGCctgatctatgttgc | 120 |
| VH_G44C | SS | caggctccagggcagTGCctggagtgggtctcac | 121 |
| VL_Q100C | SS | cctcggacgttcggcTGCgggaccaaggtggaaatc | 122 |

†Positions targeted for mutagenesis are indicated by underline. Ambiguous bases are abbreviated as follows: W = A or T, V = A or C or G, Y = C or T, S = C or G, M = A or C, N = A or C or G or T, R = A or G, K = G or T, B = C or G or T (J Biol Chem. 261(1): 13-7 (1986)).

Individual transformed colonies were picked into deep-well 96 well dishes, processed, and screened according to the methods detailed in Example 5. Transformants were grown overnight in expression media consisting of SB (Teknova, Half Moon Bay, Ca. Cat. #S0140) supplemented with 0.6% glycine, 0.6% Triton X100, 0.02% arabinose, and 50 μg/ml carbenicillin at either 37° C. or 32° C.

After thermal challenge, the aggregated material was removed by centrifugation and assayed in the soluble CD23 DELFIA as described in Example 3. Assay data was processed using Spotfire DecisionSite software (Spotfire, Somerville, Ma.) and expressed as the ratio of the DELFIA counts observed at challenge temperature to the reference temperature for each clone. Clones that reproducibly gave ratios greater than or equal to twice what was observed for the parental plasmid were considered hits. Plasmid DNAs from these positive clones were isolated by mini-prep (Wizard Plus, Promega, Madison, Wis.) and retransformed back into E. coli W3110 for confirmation secondary thermal challenge assays as well as for DNA sequence determination.

Primary and confirmatory results from these assays are shown in Table 24. Several of the stabilized scFv molecules of the invention resulted in improvements in binding activity ($T_{50}$>38° C.) as compared with the conventional p5E8 scFv. In particular, the $T_{50}$ values of p5E8 library position $V_H6$ (E6Q), library position $V_H49$ (S49G and S49A), library position $V_H43$ (Q43K), library positions $V_H72$ (E72D and E72N), and library position $V_H79$ (F79S), exhibited increases in thermal stability ranging from +4° C. to +5° C. relative to the conventional p5E8 scFv. The $T_{50}$ values of p5E8 library position $V_L50$ (V50D and V50S), library position $V_L75$ (V75I), library position $V_L80$ (P80S), and library positions $V_L83$ (F83A, F83G, F83S and F83T), exhibited increases in thermal stability ranging from +3° C. to +7° C. relative to the conventional p5E8 scFv.

In addition, the $T_{50}$ values of p5E8 library position $V_H32$ (N32S) and library position $V_H79$ (F79Y) exhibited increases in thermal stability of +2° C. relative to the conventional p5E8 scFv.

Stabilizing mutations were identified using an assortment of the design methods described in Example 5—the $V_H6$ (E6Q), $V_L75$ (V75I), $V_L80$ (P80S) and $V_L83$ (F83A, F83G, F83S and F83T) mutations were derived using Computational Analysis, the $V_H32$ (N32S) mutation was derived using Consensus Scoring, and the four mutations $V_H49$ (S49G and S49A), $V_H43$ (Q43K), $V_H72$ (E72D and E72N), the $V_H79$ (F79S and F79Y) mutations were derived using Covariation Analysis, and the $V_L50$ (V50D and V50S) mutations were derived using VH/VL interface analysis, validating the utility and novelty of these design tools. Combining $V_H43Q$ and $V_H32S$ mutations with $V_H49G$, $V_H72D$, or $V_H49A$ stabilizing mutations enhanced the thermal stability ($T_{50}$) of p5E8 up to 53° C., an increase of 15° C. relative to the conventional p5E8 scFv.

TABLE 24 p5E8 VH and VL library positions, library composition, and screening results.

| Position | Library | Hit Seq. Observed | ΔT$_{50}$ ° C. |
|---|---|---|---|
| VH6 | Q | E6Q | +4 |
| VH32 | S | N32S | +2 |
| VH49 | S, A | S49G, S49A | +5, +5 |
| VH43 | K, R | Q43K | +4 |
| VH72 | D, N | E72D, E72N | +5, +4 |
| VH79 | S, V, Y | F79S, F79Y | +4, +2 |
| VL50 | all amino acids | V50D, V50S | +4, +3 |
| VL75 | I | V75I | +5 |
| VL80 | S, G | P80S | +4 |
| VL83 | S, A, G, T | F83S, F83A, F83G, F83T | +4, +6, +7, +6 |

Table 25 shows the results of a comprehensive thermal stability analysis of the various individual and combined stabilizing mutations introduced into a conventional scFv. Stabilizing mutations were identified that upon combination exhibited increases in thermal stability ranging from +10° C. to +15° C. relative to the conventional p5E8 scFv. These results demonstrate, as similarly shown in Example 5, that improvements in activity are additive and that the methods described in this invention are capable of improving the thermal stability properties of a second test scFv demonstrating the general usefulness of the methods.

TABLE 25

Characteristics of p5E8 constructs used to produce variant proteins and $T_{50}$ results from thermal challenge assay.

| Plasmid | Disulfide | Linker Length (aa) | Other Mutation | $T_{50}$ ° C. |
|---|---|---|---|---|
| pIEH162 | no | 15 | na | 34 |
| pIEH163 | no | 15 | na | 38 |
| pIEH164 | no | 20 | na | 37 |
| pIEH165 | no | 20 | na | — |
| pIEH171 | no | 15 | VH E6Q | 42 |
| pIEH172 | no | 15 | VH N32S | 40 |
| pIEH173 | no | 15 | VH S49G | 43 |
| pIEH174 | no | 15 | VH E72D | 43 |
| pIEH175 | no | 15 | VH Q43K | 42 |
| pIEH176 | no | 15 | VH S49A | 45 |
| pIEH177 | no | 15 | VH E72N | 42 |
| pIEH178 | no | 15 | VH F79S | 42 |
| pIEH179 | no | 15 | VH F79Y | 40 |
| pIEH187 | no | 15 | VL V75I | 43 |
| pIEH188 | no | 15 | VL P80S | 42 |
| pIEH189 | no | 15 | VL F83S | 42 |
| pIEH190 | no | 15 | VL F83A | 44 |
| pIEH191 | no | 15 | VL F83G | 45 |
| pIEH192 | no | 15 | VL F83T | 44 |
| pIEH182 | VH45-VL98 | 15 | na | TBD |
| pIEH183 | VH101-VL46 | 15 | na | TBD |
| pIEH184 | VH102-VL46 | 15 | na | TBD |
| pIEH193 | VH44-VL100 | 15 | na | TBD |
| pIEH195 | no | 15 | VL V50D | 43 |
| pIEH196 | no | 15 | VL V50S | 41 |
| pIEH197 | no | 15 | VH E6Q, S49G | 51 |
| pIEH198 | no | 15 | VH E6Q, N32S, S49G | 53 |
| pIEH199 | no | 15 | VH E6Q, E72N | 48 |
| pIEH-200 | no | 15 | VH E6Q, N32S, E72N | 50 |
| pIEH-201 | no | 15 | VH E6Q, N32S, E72D | 50 |
| pIEH-202 | no | 15 | VH E6Q, E72D | 48 |
| pIEH-203 | no | 15 | VH E6Q, N32S, S49A | 51 |
| pIEH-204 | no | 15 | VH E6Q, S49A | 48 | na = not applicable
aa = amino acids
TBD = to be determined

Example 22

Production of Stabilized p5E8 Tetravalent Antibodies

Stabilized p5E8 scFvs of the invention are used to construct tetravalent antibodies as both N-terminal and C-terminal scFv fusions similar in configuration as shown in FIG. 13.

A. Construction of $N_H$-p5E8 Tetravalent Antibody

The p5E8 scFvs DNAs described in Example 21 are used to construct an $N_H$-p5E8 tetravalent antibody similar to that described in Example 7 supra. A $(Gly_4Ser)_5$ linker is used to connect the p5E8 scFv to the mature amino terminus of PRIMATIZED® p5E8 IgG heavy chain. The organization of the molecule is a p5E8 scFv-(Gly4Ser)$_5$ linker-PRIMATIZED® p5E8 IgG heavy chain. This molecule assembles with the light chain to form the tetravalent antibody. The correct sequence would be confirmed by DNA sequence analysis. The construct could be used for transfecting CHO cells as described in Example 8 for scaled-up production of a $N_H$-p5E8 Tetravalent Antibody. Transfected CHO cells can be screened for binding to immobilized CD23 antigen by DELFIA assay. 96-well plates. For example, (MaxiSorp, Nalge Nunc, Rochester, N.Y., Cat. #437111) can be coated with soluble CD23 antigen at 1 ug/ml in 0.1M sodium carbonate buffer, pH 9.5. Plates are coated overnight at 4° C., and blocked with DELFIA assay buffer (DAB, 10 mM Tris HCl, 150 mM NaCl, 20 mM EDTA, 0.5% BSA, 0.02% Tween 20, 0.01% NaN3, pH 7.4) for one hour with shaking at room temperature. Plates are washed 3 times with DAB without BSA (Wash buffer), and test samples diluted in DAB added to the plates in a final volume of 100 ul. The plates are incubated for one hour with shaking at room temperature, and then washed 3 times with Wash buffer to remove unbound material. Bound antibody is detected by addition of 100 ul per well of DAB containing 250 ng/ml of Eu-labeled anti-human antibody (Perkin Elmer, Boston, Mass., Cat. #1244-330) and incubated at room temperature with shaking for one hour. The plates are washed 3 times with Wash buffer, and 100 ul of DELFIA enhancement solution (Perkin Elmer, Boston, Mass., Cat. #4001-0010) is added per well. Following incubation for 15 minutes, the plates are read using the Europium method on a Victor 2 plate reader (Perkin Elmer, Boston, Mass.).

B. Construction of C-p5E8 Tetravalent Antibody

The p5E8 scFvs DNAs described in Example 21 supra are used to construct a C-p5E8 tetravalent antibody as described in Example 7 supra. A Ser(Gly$_4$Ser)$_3$ linker peptide is used to connect the p5E8 scFv to the carboxy terminus of PRIMATIZED® p5E8 IgG heavy chain. The organization of the molecule is a PRIMATIZED® p5E8 IgG heavy chain-Ser (Gly$_4$Ser)$_3$ linker-p5E8 scFv. This molecule assembles with the light chain to form the tetravalent antibody. The correct sequence would be confirmed by DNA sequence analysis. The construct could be used for transfecting CHO cells as described in Example 8 for scaled-up production of a C-p5E8 Tetravalent Antibody. Transfected CHO cells can be screened as described above.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for producing a stabilized antibody or antigen binding fragment thereof, which comprises a stabilized $V_H$ domain and a stabilized $V_L$ domain derived from a $V_H$ domain and a $V_L$ domain of a wild-type candidate antibody, wherein said method comprises:
   (a) providing a curated reference set of amino acid sequences which belong to immunoglobulin superfamily polypeptides;
   (b) aligning said reference set of amino acid sequences to generate an aligned set;
   (c) calculating covariation between two or more amino acid positions in the aligned set to generate a covariation dataset;
   (d) identifying non-covarying amino acids in said wild-type candidate antibody $V_H$ domain or said wild-type candidate antibody $V_L$ domain, wherein said non-covarying amino acids fail to satisfy one or more covariations observed in the covariation dataset;
   (e) substituting one or more of said non-covarying amino acids in the wild-type candidate antibody $V_H$ domain or wild-type candidate antibody $V_L$ domain with one or more replacement amino acids, wherein each replacement amino acid is an amino acid found at the corresponding amino acid position in the aligned set which satisfies one or more covariations in the covariation dataset, and wherein the replacement amino acid establishes one or more covariations in the candidate antibody;
   (f) expressing in a host cell the antibody or antigen binding fragment thereof comprising at least one substitution, and
   (g) testing at least one biophysical property of the antibody or antigen binding fragment thereof comprising at least one substitution to determine whether at least one biophysical property is improved with respect to the wild-typed candidate antibody, thereby making a stabilized antibody and antigen binding fragment thereof with an improved biophysical property.

2. The method of claim 1, wherein said biophysical property is selected from the group consisting of thermal stability, pH unfolding profile, stable removal of glycosylation, solubility, biochemical function, and combinations thereof.

3. The method of claim 1, wherein said stabilized antibody or antigen binding fragment thereof is a domain antibody, a humanized antibody, a human antibody, a non-human monoclonal antibody, a chimeric antibody, a bispecific antibody, a scFv molecule, a scFv-containing antibody, or a domain-deleted antibody comprising a stabilized $V_H$ domain and a stabilized $V_L$ domain derived from a $V_H$ domain and a $V_L$ domain of a wild-type candidate antibody.

4. The method of claim 1, wherein said amino acids in the covariation dataset in (b) are part of a structural feature selected from the group consisting of a disulfide bond, a salt bridge, a portion of a ligand binding pocket or surface, a network of van der Waals interactions, a network of hydrogen bond interactions, a network of charge-charge interactions, and a combination of two or more of said structural features.

5. The method of claim 1, wherein each amino acid sequence of said aligned set in (b) has less than 95% identity with the other sequences in said aligned set.

6. The method of claim 1, wherein the construction of said curated reference set of amino acid sequences comprises:
   (a) collecting a set of Ig-fold three-dimensional structures, wherein said structures contain an Ig fold selected from the group of Ig fold classes consisting of a V-class fold, an I-class fold, a C1-class fold, a C2-class fold, and a combination of said Ig fold classes;
   (b) filtering said set of Ig-fold structures by discarding Ig-fold structures containing sequences with breaks, 100% sequence identity, aberrant length, or displaying misfolded topologies;
   (c) constructing structure alignments, wherein said filtered set of Ig-fold structures are superimposed upon one another;
   (d) obtaining sequence alignments from said structure alignments, wherein amino acids from the sequence of one structure are matched to amino acids from the sequence of a second structure based on the shortest distance between α-carbons of the polypeptide backbones;
   (e) constructing Hidden Markov Models (HMMs) based upon the structure-based sequence alignments for one of the Ig-fold classes;
   (f) searching a protein sequence database using one or more of said Ig-fold class-specific HMMs, wherein sequences in the protein sequence database matching said HMMs are retrieved; and,
   (g) validating the Ig-fold class assignment of the protein sequences retrieved in (f) using an annotated database of protein domains, wherein the candidate Ig-fold protein sequences found in (f) are retained only if their assignment to a Ig-fold class in the annotated database of protein domain is statistically significant.

7. The method of claim 1, wherein said aligning further comprises:
   (aa) removing redundant or highly similar amino acid sequences from the sequence alignment obtained in (b); and
   (bb) removing columns in the alignment that are not match states in the HMM profile.

8. The method of claim 1, wherein the calculation of (c) comprises one or more features selected from the group consisting of (i) identification of gaps as a distinct amino acid type, (ii) a weighing function, wherein said weighing function is not a Henikoff diversity weighing function, (iii) a filtering function for covarying pairs wherein said function does not use Sequence Average Identities (SAI), (iv) an event cut-off, wherein covarying pairs are not reported unless they are observed a minimum number of times, and wherein said event cut-off is about 2 or more events, and (v) a combination of two or more of said features.

9. The method of claim 1, wherein the calculation of (c) comprises a calculation of the statistical significance of variation using a $\chi^2$ analysis.

10. The method of claim 9, wherein values of said $\chi^2$ are calculated using an event based count formula.

11. The method of claim 10, wherein said event based count formula is:

$$\chi^2 = \frac{[c(i,j) - (p(i) \cdot p(j) \cdot c(t))]^2}{p(i) \cdot p(j) \cdot c(t)}$$

wherein
p(i) and p(j) are the amino acid frequencies of any two amino acid types of interest at positions i and j, respectively, in the aligned set of sequences;
c(i,j) is the number of times p(i) and p(j) are observed in the same sequence; and,
c(t) is the number of total sequences in the alignment;
and wherein amino acid frequencies are defined as the number of times an amino acid type is observed at a specific position in an alignment divided by the total number of sequences in the alignment.

12. The method of claim 11, wherein the calculation of (c) comprises a calculation of the correlation coefficient (φ) performed using the formula:

$$\phi(a_i b_j) = \frac{(a_i b_j * \overline{a_i} \overline{b_j}) - (a_i \overline{b_j} * \overline{a_i} b_j)}{\sqrt{(a_i b_j + \overline{a_i} b_j) * (a_i \overline{b_j} + \overline{a_i} \overline{b_j}) * (a_i b_j + a_i \overline{b_j}) * (\overline{a_i} b_j + \overline{a_i} \overline{b_j})}}$$

wherein
$a_i b_j$ is the number of times amino acids of type a or b are found in the same sequence at positions i and j, respectively;
$\vec{a}_i \vec{b}_j$ is the number of times both amino acid types are absent from the same sequence;
$a_i \vec{b}_j$ is the number of times amino acid a is found present while amino acid b is absent; and,
$\vec{a}_i b_j$ is the number of times amino acid a is absent while amino acid b is present;
and wherein the correlation coefficient (φ) measures the statistical strength of the covariation.

13. The method of claim 11, wherein the calculation of covariation includes the generation of covariation scores only for covariations that satisfy a threshold level of statistical significance.

14. The method of claim 13, wherein the covariation scores are generated only for covariations above or below a threshold $\chi^2$ value or φ value.

15. The method of claim 14, wherein amino acid positions of the candidate sequence are assigned positive specific covariation scores for positive covariations with φ correlation coefficients of about +0.25 to about 1.0.

16. The method claim 14, wherein amino acid positions of the candidate sequence are assigned negative specific covariation scores for negative covariations with φ correlation coefficients of about −0.25 to about −1.0.

17. The method of claim 1, further comprising:
   (aa) providing structural models of a template antibody $V_H$ or $V_L$ domain and the candidate antibody $V_H$ or $V_L$ domain;
   (bb) identifying protein-protein interface amino acids in the template antibody $V_H$ or $V_L$ domain that are important for stability;
   (cc) identifying scaffolding amino acids which covary with the interface amino acids of (bb);
   (dd) substituting one or more interface amino acids or scaffolding amino acids in the candidate antibody $V_H$ or $V_L$ domain with the corresponding interface amino acids or scaffolding amino acids identified in (bb) and (cc).

18. The method of claim 17, wherein the template antibody $V_H$ or $V_L$ domain contains an Ig superfamily fold.

19. The method of claim 17, wherein the protein-protein interface amino acids are located at the $V_H/V_L$ interface of a candidate $V_H$ or $V_L$ domain.

20. The method of claim 1, further comprising:
   (1) calculating consensus-based scores for one or more amino acid positions of said candidate antibody $V_H$ or $V_L$ domain;
   (2) combining said consensus-based scores with the data in the covariation dataset; and,
   (3) selecting amino acid substitutions predicted to stabilize the candidate antibody $V_H$ domain or $V_L$ domain, wherein said selection is based on the combination of consensus-based scores and covariation data.

21. The method of claim 20, wherein the calculation of consensus-based scores comprises the steps of:
   (i) providing a curated reference set of polypeptide sequences which belong to the Immunoglobulin superfamily;
   (ii) aligning said reference set sequences to generate an aligned set; and,
   (iii) calculating the test amino acid frequency for each amino acid position within the candidate antibody VH or $V_L$ domain, wherein said frequency is calculated by summing the number of times the amino acid at said amino acid position is present at the corresponding position in the aligned set, and dividing the summed value by the total number of sequences within the reference set.

22. The method of claim 21, comprising the further steps of:
   (a) calculating a consensus sequence, wherein the amino acid at each position within the sequence corresponds to the most common amino acid at said position in the aligned set;
   (b) calculating the consensus amino acid frequency for each amino acid position within the consensus polypeptide sequence, wherein said sequence is calculated by summing the number of times the amino acid at said amino acid position is present at the corresponding position in the aligned set, and dividing the summed value by the total number of sequences within the reference set; and,
   (c) dividing the test amino acid frequency by the consensus amino acid frequency to give a consensus score.

* * * * *